(12) United States Patent
Singh et al.

(10) Patent No.: US 8,791,267 B2
(45) Date of Patent: Jul. 29, 2014

(54) BIARYL PDE4 INHIBITORS FOR TREATING INFLAMMATORY, CARDIOVASCULAR AND CNS DISORDERS

(75) Inventors: Jasbir Singh, Naperville, IL (US); Mark E. Gurney, Grand Rapids, MI (US); Alex Burgin, Kingston, WA (US); Vincent Sandanayaka, Northboro, MA (US); Alexander Kiselyov, San Diego, CA (US); Adalie Motta, Naperville, IL (US); Gary Schiltz, Naperville, IL (US); Georgeta Hategan, Naperville, IL (US); Timothy Hagen, Lisle, IL (US)

(73) Assignee: Decode Genetics EHF (IS)

( * ) Notice: Subject to any disclaimer, the term of this patent is extended or adjusted under 35 U.S.C. 154(b) by 0 days.

(21) Appl. No.: 13/430,164

(22) Filed: Mar. 26, 2012
(Under 37 CFR 1.47)

(65) Prior Publication Data

US 2012/0183522 A1 Jul. 19, 2012

Related U.S. Application Data

(63) Continuation of application No. 12/275,163, filed on Nov. 20, 2008, now abandoned.

(60) Provisional application No. 60/989,551, filed on Nov. 21, 2007.

(51) Int. Cl.
C07D 213/72 (2006.01)
A61K 31/435 (2006.01)

(52) U.S. Cl.
USPC .......................................... 546/297; 514/277

(58) Field of Classification Search
None
See application file for complete search history.

(56) References Cited

U.S. PATENT DOCUMENTS

| | | | |
|---|---|---|---|
| 2,535,015 A * | 12/1950 | Johnson, Jr. et al. | 514/734 |
| 3,144,479 A * | 8/1964 | Obendorf | 560/47 |
| 4,287,366 A * | 9/1981 | Yamaguchi et al. | 568/33 |
| 5,023,363 A | 6/1991 | Maignan et al. | |
| 5,272,147 A | 12/1993 | Bell et al. | |
| 5,594,141 A | 1/1997 | Yuan et al. | |
| 5,763,450 A | 6/1998 | Guerry et al. | |
| 5,877,190 A | 3/1999 | Dhainaut et al. | |
| 5,919,801 A | 7/1999 | Dhainaut et al. | |
| 6,090,817 A | 7/2000 | Manley | |
| 6,221,604 B1 | 4/2001 | Upadhya et al. | |
| 6,747,048 B2 | 6/2004 | Zhang et al. | |
| 7,138,425 B2 * | 11/2006 | Courtney et al. | 514/418 |
| 2005/0070578 A1 | 3/2005 | Baxter | |
| 2005/0075342 A1 | 4/2005 | Abe et al. | |
| 2006/0046980 A1 | 3/2006 | Erion et al. | |
| 2007/0078136 A1 | 4/2007 | Vaccaro et al. | |
| 2007/0254913 A1 | 11/2007 | Dunn et al. | |
| 2008/0045536 A1 | 2/2008 | Vaccaro et al. | |
| 2009/0130076 A1 | 5/2009 | Singh et al. | |
| 2009/0130077 A1 | 5/2009 | Singh et al. | |
| 2009/0131530 A1 | 5/2009 | Singh et al. | |
| 2009/0136473 A1 | 5/2009 | Singh et al. | |
| 2009/0186909 A1 | 7/2009 | Negoro et al. | |
| 2009/0324569 A1 | 12/2009 | Singh et al. | |

FOREIGN PATENT DOCUMENTS

| | | |
|---|---|---|
| CN | 1629139 | 6/2005 |
| EP | 0249963 | 12/1987 |
| EP | 0675118 | 10/1995 |
| EP | 0834508 | 4/1998 |
| EP | 0894794 A1 | 2/1999 |
| EP | 1227086 | 7/2002 |
| EP | 1609785 A1 | 12/2005 |
| EP | 1726580 A1 | 11/2006 |

(Continued)

OTHER PUBLICATIONS

Buu-Hoi, Ng. Ph. et al J. Org Chem 1956, vol. 21, pp. 136-138.*
Kogan, T. et al. J. Med. Chem., 1998, vol. 41, pp. 1099-1111.*
CAPLUS 1987:598287.*
Chapman, G. et al., J. Chem Soc. Perkin 1, 2002.*
Shiota et al., Regioselective Reactions of Organozinc Reagents with 2,4-Dichloroquinoline and 5,7-Dichloropyrazolo[1,5-a]pyrimidine, Journal of Organic Chemistry (1999), 64(2), pp. 453-457.

(Continued)

*Primary Examiner* — Heidi Reese
(74) *Attorney, Agent, or Firm* — Heslin Rothenberg Farley & Mesiti P.C.

(57) ABSTRACT

The present invention relates to a genus of biaryl compounds containing at least one further ring. The compounds are PDE4 inhibitors useful for the treatment and prevention of stroke, myocardial infarct and cardiovascular inflammatory diseases and disorders. The compounds have general formula I:

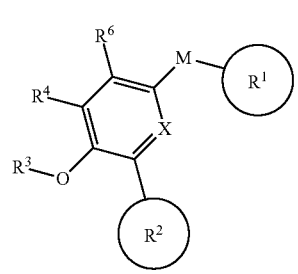

A particular embodiment is

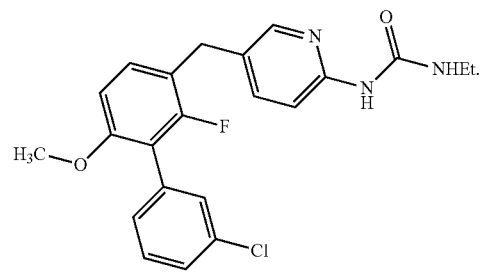

22 Claims, No Drawings

(56) References Cited

FOREIGN PATENT DOCUMENTS

| | | |
|---|---|---|
| JP | H06 24138 A | 2/1994 |
| WO | WO 96/06089 | 2/1996 |
| WO | WO 9606089 A1 * | 2/1996 |
| WO | WO 96/16058 | 5/1996 |
| WO | 97/00679 A1 | 1/1997 |
| WO | WO 97/03967 A1 | 2/1997 |
| WO | 97/15555 A2 | 5/1997 |
| WO | WO 97/32853 | 9/1997 |
| WO | WO 99/31062 | 6/1999 |
| WO | WO 00/14083 | 3/2000 |
| WO | WO 01/16122 | 3/2001 |
| WO | WO 02/072009 | 9/2002 |
| WO | WO 03/062205 | 7/2003 |
| WO | WO 03/093261 A1 | 11/2003 |
| WO | WO 03/094845 | 11/2003 |
| WO | 2004/007439 A1 | 1/2004 |
| WO | WO 2004/084824 | 10/2004 |
| WO | WO 2004/092140 | 10/2004 |
| WO | WO 2004/093799 | 11/2004 |
| WO | WO 2005/047270 | 5/2005 |
| WO | WO 2005/051298 | 6/2005 |
| WO | 2005/063729 A1 | 7/2005 |
| WO | 2005/086661 A2 | 9/2005 |
| WO | WO 2005/095359 A1 | 10/2005 |
| WO | WO 2006/056854 | 6/2006 |
| WO | WO 2006/066978 | 6/2006 |
| WO | WO 2006/083477 | 8/2006 |
| WO | WO 2006/128056 | 11/2006 |
| WO | WO 2007/067614 A1 | 6/2007 |
| WO | WO 2007/079186 | 7/2007 |
| WO | 2007/123225 A1 | 11/2007 |
| WO | WO 2007/136116 A2 | 11/2007 |
| WO | WO 2008/001959 | 1/2008 |
| WO | 2008/021849 A2 | 2/2008 |
| WO | WO 2008/099902 | 8/2008 |
| WO | WO 2008/116185 A2 | 9/2008 |
| WO | WO 2009/022007 A1 | 2/2009 |
| WO | WO 2009/067597 | 5/2009 |
| WO | WO 2009/067600 | 5/2009 |
| WO | WO 2009/067604 | 5/2009 |
| WO | WO 2009/067618 | 5/2009 |
| WO | WO 2009/067621 | 5/2009 |
| WO | WO 2010/059836 | 5/2010 |
| WO | WO 2010/059838 | 5/2010 |

OTHER PUBLICATIONS

Cortes et al., Alkaloids from Annonaceae . . . , Journal of Natural Products, (1985), vol. 48, No. 1, pp. 76-85.
Mazzocchi, et al., Synthesis of diphenyl ether models of thyroid hormones. Diphenyl ethers linked to the 3-oxo-2-azabicyclo[2.2.1]heptane ring system as substrates for conformational analysis, Journal of Organic Chemistry (1981), 46(22), pp. 4530-4536.
Parenti, et al., Three-Dimensional Quantitative Structure-Activity Relationship Analysis of a Set of *Plasmodium falciparum* Dihydrofolate Reductase Inhibitors Using a Pharmacophore Generation Approach, J. Med. Chem., (2004), 47, pp. 4258-4267.
Wilgus et al, The Chemistry of Thioether-Substituted Hydroquinones and Quinones, Journal of Organic Chemistry, (1964), 29(3), pp. 594-600.
Bradsher et al., Aromatic cyclodehydration. XXXI. New polycyclic aromatic systems containing the quinolizinium nucleus, Journal of the American Chemical Society (1956), 78, 2459-62.
Chiellini et al, Synthesis and Biological Activity of Novel Thyroid Hormone Analogues: 5'-Aryl Substituted GC-1 Derivatives Bioorganic & Medicinal Chemistry, 10,2, 333-346, 2002.
Yogi, et al., Synthesis of Imido-Substituted 3,8-Diphenyl-1,2-diazacycloocta-2,4,6,8-te traenes and their Thermolysis, Bulletin of the Chemical Society of Japan, vol. 60, Feb. 1987, pp. 731-735.
Buu-Hoi, et al., The Pfitzinger Reaction with Ketones Derived from o-Hydroxydiphenyl, Journal of Organic Chemistry, vol. 21, No. 1, 1956, pp. 136-138.

Fusco et al., Rearrangement of arylhydrazones of aromatic and arylaliphatic carbonyl compounds to biphenyl derivatives. 3, Journal of Organic Chemistry, vol. 46, No. 1, 1981, pp. 83-89.
Babu et al, In(III)-Mediated Chemoselective Dehydrogenative Interaction of ClMe2SiH with Carboxylic Acids: Direct Chemo- and Regioselective Friedel—Crafts Acylation of Aromatic Ethers, Organic Letters, vol. 9, No. 3, Jan. 12, 2007, pp. 405-408.
International Search Report and Written Opinion for international application PCT/US2008/084193, completed Jun. 11, 2009.
International Search Report and Written Opinion for international application PCT/US2008/084230, completed Mar. 11, 2009.
International Preliminary Report on Patentability for corresponding international application PCT/US2008/084193, issued May 25, 2010.
International Preliminary Report on Patentability for international application PCT/US2008/084230, completed May 25, 2010.
International Search Report and Written Opinion for international application PCT/US2008/084199, mailed Feb. 25, 2009.
International Search Report and Written Opinion for international application PCT/US2008/084225, mailed Feb. 25, 2009.
International Preliminary Report on Patentability for international application PCT/US2008/084199, issued May 25, 2010.
International Preliminary Report on Patentability for international application PCT/US2008/084225, issued May 25, 2010.
International Search Report and Written Opinion for international application PCT/US2009/065162, mailed Mar. 4, 2010.
International Preliminary Report on Patentability for international application PCT/US2009/065162, issued May 24, 2011.
International Search Report and Written Opinion for international application PCT/US2009/065164, mailed Oct. 13, 2010.
International Preliminary Report on Patentability for international application PCT/US2009/065164, issued May 24, 2011.
Hamblin, JN, et al. Pyrazolopyridines as a novel structural class of potent and selective PDE4 inhibitors. Bioorganic and Medicinal Chemistry Letters, vol. 18, pp. 4237-4241. May 17, 2008.
Chemical Abstracts Service, Columbus, Ohio. Smirnov, LD, et al. Chemistry of 2-aryl substituted 3-hydroxypyridines 1-Aminomethylation of 2-phenyl- and 2-(4'-alkylpheny1)-3-hydroxypyridines. Retrieved from STN Database accession No. 1971:76279; & Izvestiya Akademii Nauk SSSR, Seriya Khimicheskaya, (8), 1845-51 CODEN: IASKA6; ISSN:0002-3353, 1970.
Chemical Abstracts Service, Columbus, Ohio. Livermore, RA, et al. Reactions in the diethyl peroxide-nitric oxyide system. III. The pressure dependence of the combination of ethoxyl radicals with nitric oxide. Retrieved from STN Database accession No. 1966:446901; & Journal of the Chemical Society [section] B: Physical Organic, (7), 640-3 CODEN: JCSPAC; ISSN: 0045-6470, 1966.
Chemical Abstracts Service, Columbus, Ohio. Smirnov, LD, et al. Synthesis and study of some electrophilic reactions of 2-phenyl-3-hydroxypyridine N-oxides. Retrieved from STN Database accession No. 1973:442297; & Izvestiya Akademii Nauk SSSR, Seriya Khimicheskaya, (4), 861-4 CODEN: IASKA6; ISSN:0002-3353, 1973.
Feenstra, RW, et al. New 1-aryl-4-(biarylmethylene)piperazines as potential atypical antipsychotics sharing dopamine D2-receptor and serotonin 5-HT1A-receptor affinities. Bioorganic and Medicinal Chemistry Letters. vol. 11, pp. 2345-2349. Aug. 23, 2001.
Hcaplus 1958:25397, "Cyclohexane-1,3-diones. II. New synthesis of substituted p-terphenyls", Ames, et al. (1957).
Second Written Opinion for International Application PCT/US2008/084230, Jun. 2010.
Matthews , C. et al. , Biochemistry $3^{rd}$ Edition, Addison-Wesley 2000, except pp. 1-3.
Silverman, R. "The Organic Chemistry of Drug Design and Drug Action," 2004, Elsevier, pp. 29-32.
Kogan, T. et al., J. Med. Chem., vol. 41, 1998, pp. 1099-1111.
Sakagami, ZCAPLUS 1991.
Zhang et al., Expert Opin. Ther. Targets, vol. 9, 2005, pp. 1283-1305.
Chapman, G. et al., J. Chem. Soc. Perkin Trans I, 2002, pp. 581-582.

(56) References Cited

OTHER PUBLICATIONS

Database CA [Online] Chemical Abstracts Service, Columbus, Ohio, US; Asano, Yukiyasu et al: "Preparation of 6-5 bicyclic heterocyclic derivatives as thyroid hormone receptor ligands", XP002699358, retrieved from STN Database accession No. 2008:10485 ; & WO 2008/001959 A1 (Sanwa Kagaku Kenkyusho Co., Ltd., Japan) Jan. 3, 2008.

Database CAPLUS [Online] Chemical Abstracts Service, Columbus, Ohio, US; 2006, Pandey, V. K., Trivedi, Noopur, Mukesh: "Synthesis and biological activity of 1,2-disubstituted benzimidazoles", XP002699359, retrieved from STN Database accession No. 2007:101815.

Database CAPLUS [Online] Chemical Abstracts Service, Columbus, Ohio, US; Bentley, Jonathan Mark; Dawson, Claire Elisabeth; Guba, Wolfgan;: "Preparation of morpholines as 5HT2C agonists for treating obesity, diabetes and other diseases", XP002699360, retrieved from STN Database accession No. 2006:733208, 2006.

Database CAPLUS [Online] Chemical Abstracts Service, Columbus, Ohio, US; 1998, Sato, Susumu; Kuribayashi, Takeshi; Ushiyama, Shigeru: "Preparation of aryl C-glycosides and sulfated esters as antiinflammatory agents and selectin receptors", XP002699361, retrieved from STN Database accession No. 1998:509207.

Database CAPLUS [Online] Chemical Abstracts Service, Columbus, Ohio, US; Uehara, Fumiaki; Aritomo, Keiichi; Shoda, Aya;: "Preparation of 6- pyrimidinyl-3-substituted-4-pydrimidones that inhibit tau protein kinase 1 useful against neurodegenerative diseases like Alzheimer's disease", XP002699362, Database accession No. 2003:261819, 2003.

Chemical Abstracts Service, Columbus, Ohio. Alami M. et al. Preparation of dihydro-iso-CA-4 and analogues as potent cytotoxic compounds and inhibitors of tubulin polymerization. Retrieved from STN Database accession No. 2009:1536640; & WO 2009/147217 A1 (Centre National De La Recherche Scientifique, Fr.) Dec. 10, 2009.

Chemical Abstracts Service, Columbus, Ohio. Chen, Yongheng et al. Preparation of pyrimidines as adenosine A2A receptor antagonists. Retrieved from STN Database accession No. 2008:1157507; & WO 2008/116185 A2 (Neurocrine Biosciences, Inc. USA) Sep. 25, 2008.

Database CA [Online] Chemical Abstracts Service, Columbus, Ohio, US; Lu, Zhaoqiang et al: "Synthesis and structural characterization of novel, fluorinated poly(phthalazinone ether)s containing perfluorophenylene moieties", retrieved from STN Database accession No. 2004:99191 ; & Lu, Zhaoqiang et al: "Synthesis and structural characterization of novel, fluorinated poly (phthalazinone ether)s containing perfluorophenylene moieties", Journal of Polymer Science, Part A: Polymer Chemistry ( 2004 ), 42(4), 925-932 CODEN: JPACEC; ISSN: 0887-624X.

Database CA [Online] Chemical Abstracts Service, Columbus, Ohio, US; Hay, Allan S.: "Polymers derived from phenolphthaleins", retrieved from STN Database accession No. 1994:108013 ; & US 5 237 062 A (Hay, Allan S.) Aug. 17, 1993.

Database CA [Online] Chemical Abstracts Service, Columbus, Ohio, US; Asano, Yukiyasu et al: "Preparation of 6-5 bicyclic heterocyclic derivatives as thyroid hormone receptor ligands", retrieved from STN Database accession No. 2008:10485 ; & WO 2008/001959 A1 (Sanwa Kagaku Kenkyusho Co., Ltd., Japan) Jan. 3, 2008.

Database CA [Online] Chemical Abstracts Service, Columbus, Ohio, US; Maignan, Jean et al: "Preparation of aromatic carboxylic acids and their derivatives for use in cosmetics and pharmaceuticals", retrieved from STN Database accession No. 1988:111954 ; & DE 37 11 546 A1 (Oreal S. A., Fr.) Oct. 15, 1987.

Database CA [Online] Chemical Abstracts Service, Columbus, Ohio, US; Ruminski, Jan K. et al: "Synthesis and reactivity of 2-aroylbenzoic acids. Part I. 2-[(2'-Hydroxy-5'-biphenylyl)carbonyl]benzoic acid", retrieved from STN Database accession No. 1983:88914 ; & Ruminski, Jan K. et al: "Synthesis and reactivity of 2-aroylbenzoic acids. Part I. 2-[(2'-Hydroxy-5'-biphenylyl)carbonyl]benzoic acid", Polish Journal of Chemistry ( 1981), 55(5), 995-1005 CODEN: PJCHD; ISSN: 0137-5083.

Database CA [Online] Chemical Abstracts Service, Columbus, Ohio, US; Kita, Jun-Ichiro et al: "Acid-addition salts of optically active piperidine compound and process for producing the same", retrieved from STN Database accession No. 1998:485054 ; & WO 98/29409 A1 (Ube Industries, Ltd., Japan; Tanabe Seiyaku Co., Ltd.) Jul. 9, 1998.

Database CA [Online] Chemical Abstracts Service, Columbus, Ohio, US; Nakanishi, Michio et al: "Benzophenone derivatives", retrieved from STN Database accession No. 1963:3135 ; & JP 37 000085 B (Yoshitomi Pharmaceutical Industries, Ltd.) Jan. 16, 1962.

Chapman, Glen M. et al., Synthesis of novel poly(dithienylpyridines), Journal of Materials Chemistry, 2002, 12(8), 2292-2298.

Gerencser, Janos et al., Synthesis of Isoplagiochin A +, The Journal of Organic Chemistry, 1997, 62(11), 3666-3670.

\* cited by examiner

BIARYL PDE4 INHIBITORS FOR TREATING INFLAMMATORY, CARDIOVASCULAR AND CNS DISORDERS

CROSS-REFERENCE TO RELATED APPLICATIONS

This application is a continuation application of U.S. patent application Ser. No. 12/275,163, filed Nov. 20, 2008, which claims priority from U.S. provisional application 60/989,551, filed Nov. 21, 2007, the entire disclosures of which are incorporated herein by reference. The application is related to, but does not claim priority from, four other US non-provisional applications filed on Nov. 20, 2008: Ser. Nos. 12/275,152; 12/275,165; 12/275,164; and 12/275,168. Their disclosures are incorporated herein by reference.

FIELD OF THE INVENTION

The present invention relates to a chemical genus of biaryl inhibitors of phosphodiesterase-4 (PDE4) useful for the treatment and prevention of stroke, myocardial infarct, cardiovascular inflammatory diseases and central nervous system disorders.

BACKGROUND OF THE INVENTION

PDE4 is the major cAMP-metabolizing enzyme found in inflammatory and immune cells. PDE4 inhibitors have proven potential as anti-inflammatory drugs, especially in inflammatory pulmonary diseases such as asthma, COPD and rhinitis. They suppress the release of cytokines and other inflammatory signals and inhibit the production of reactive oxygen species. A large number of PDE4 inhibitors have been developed for a variety of clinical indications (Torphy and Page. 2000. TIPS 21, 157-159; Burnouf and Pruniaux. 2002. Curr. Pharm. Design 8, 1255-1296; Lipworth. 2005. Lancet 365, 167-175). To quote from a recent article in the British Journal of Pharmacology, "PDE4 inhibitors have been in development as a novel anti-inflammatory therapy since the 1980s with asthma and chronic obstructive pulmonary disease (COPD) being primary indications. Despite initial optimism, none have yet reached the market. In most cases, the development of PDE4 inhibitors of various structural classes, including cilomilast, filaminast, lirimilast, piclamilast, tofimilast . . . has been discontinued due to lack of efficacy. A primary problem is the low therapeutic ratio of these compounds, which severely limits the dose that can be given. Indeed, for many of these compounds it is likely that the maximum tolerated dose is either sub-therapeutic or at the very bottom of the efficacy dose-response curve. Therefore, the challenge is to overcome this limitation." [Giembycz, Brit. J. Pharmacol. 155, 288-290 (2008)]. Many of the PDE4 inhibitors of the prior art have not reached the market because of the adverse side effect of emesis (Giembycz 2005. Curr. Opin. Pharm. 5, 238-244). Analysis of all known PDE4 inhibitors suggests that they are competitive with cAMP and bind within the active site (Houslay et al. 2005. DDT 10, 1503-1519); this may explain their narrow therapeutic ratio. The compounds of the present invention are non-competitive inhibitors of cAMP while being gene-specific inhibitors (PDE4D), and, based on the target rationale and in vitro potency, a person of skill in the art would expect the compounds to be useful as anti-inflammatory agents for the treatment, amelioration or prevention of inflammatory diseases and of complications arising therefrom and useful as CNS agents for amelioration of the cognitive decline in Alzheimer's disease, Parkinson's disease, the treatment of schizophrenia and depression, and neuroprotective in Huntington's disease.

SUMMARY OF THE INVENTION

The present invention relates to compounds exhibiting PDE4 enzyme inhibition, having the general formula I

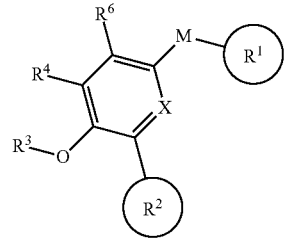

In these compounds, $R^1$ is an optionally substituted carbocycle or optionally substituted heterocycle of three or fewer rings;

$R^2$ is an optionally substituted carbocycle or optionally substituted heterocycle of two or fewer rings;

$R^3$ is chosen from H, —C(=O)NH$_2$, —(C$_1$-C$_6$)alkyl, halo (C$_1$-C$_6$)alkyl, —(C$_1$-C$_6$)alkyl-R$^{30}$, —(C$_2$-C$_6$)alkyl-R$^{31}$, and saturated 4- or 5-membered heterocycle optionally substituted with methyl;

$R^{30}$ is chosen from —C(=O)NH$_2$ and 4- or 5-membered heterocycle optionally substituted with methyl;

$R^{31}$ is chosen from (C$_1$-C$_4$)alkoxy, amino, hydroxy, (C$_1$-C$_6$) alkylamino and di(C$_1$-C$_6$)alkylamino;

$R^4$ is chosen from H and F;

$R^6$ is chosen from H, (C$_1$-C$_6$)alkyl and halogen;

X is N, N→O, or C—R$^5$;

$R^5$ is chosen from H, halogen, OH, (C$_1$-C$_6$)alkyl, (C$_1$-C$_6$) alkoxy, CF$_3$, CN, NH$_2$, CH$_2$OH, CH$_2$NH$_2$ and C≡CH; and M is chosen from direct bond, —C(R$^{20}$)(R$^{21}$)—, —O—, —NR$^{22}$—, —S(O)$_n$—, —C(=O)—, —C(R$^{20}$)(R$^{21}$)C(R$^{20}$)(R$^{21}$)—, —C(R$^{20}$)=C(R$^{21}$)—, —C(R$^{20}$)(R$^{21}$)—O—, —C(R$^{20}$)(R$^{21}$)—NR$^{22}$—, —C(R$^{20}$)(R$^{21}$)—S(O)$_n$—, —C(R$^{20}$)(R$^{21}$)—C(=O)—, —O—C(R$^{20}$)(R$^{21}$)—, —NR$^{22}$—C(R$^{20}$)(R$^{21}$)—, —S(O)$_n$—C(R$^{20}$)(R$^{21}$)—, —C(=O)—C(R$^{20}$)(R$^{21}$)— and

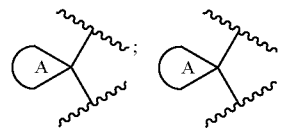

is a five or six-membered ring optionally substituted with methyl;

n is zero, one or two; and $R^{20}$, $R^{21}$ and $R^{22}$ are selected independently in each occurrence from H and (C$_1$-C$_4$)alkyl.

The present invention also relates to two subgenera of compounds of formula I. The first, in which X is N or N→O, is represented by the formulae:

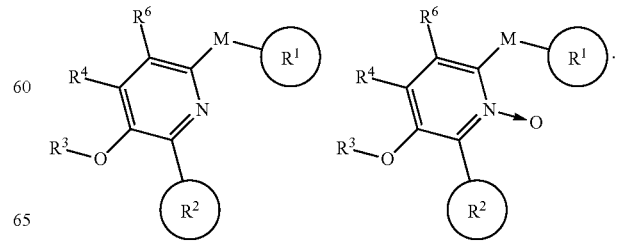

The second, in which X is CR⁵ is represented by the formula:

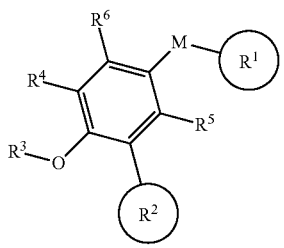

The present invention also relates to pharmaceutical compositions comprising a pharmaceutically acceptable carrier and a therapeutically effective amount of at least one compound of the general formula I described above. When the compound is present as a salt, the salt should be a pharmaceutically acceptable salt.

In a third aspect, the invention relates to methods for the treatment or prophylaxis of a disease or condition mediated by phosphodiesterase-4. The methods comprise administering to a mammal a therapeutically effective amount of a compound having the general formula I. The disease or condition may be related to allergic, acute or chronic inflammation. The disease may be, for example, atherosclerosis, thrombosis, stroke, acute coronary syndrome, stable angina, peripheral vascular disease, critical leg ischemia, intermittent claudication, abdominal aortic aneurysm or myocardial infarction.

Selective PDE4 inhibitors of the invention are expected to be useful in improving cognition and thus useful for treating learning disorders, memory loss and other cognitive dysfunctions. Selective PDE4 inhibitors of the invention are also useful for treating asthma and Chronic Obstructive Pulmonary Disease (COPD). Compounds of the invention, which inhibit tumor growth and metastases, also find utility in the treatment and prevention of cancer, including esophageal cancer, brain cancer, pancreatic cancer, and colon cancer.

These and other embodiments of the present invention will become apparent in conjunction with the description and claims that follow.

DETAILED DESCRIPTION OF THE INVENTION

Throughout this specification the substituents are defined when introduced and retain their definitions.

Unless otherwise specified, alkyl is intended to include linear, branched, or cyclic hydrocarbon structures and combinations thereof. A combination would be, for example, cyclopropylmethyl. Lower alkyl refers to alkyl groups of from 1 to 6 carbon atoms. Examples of lower alkyl groups include methyl, ethyl, propyl, isopropyl, butyl, s- and t-butyl and the like. Preferred alkyl groups are those of $C_{20}$ or below; $C_1$ to $C_8$ are more preferred. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like.

$C_1$ to $C_{20}$ hydrocarbon includes alkyl, cycloalkyl, polycycloalkyl, alkenyl, alkynyl, aryl and combinations thereof. Examples include benzyl, phenethyl, cyclohexylmethyl, camphoryl and naphthylethyl. Hydrocarbon refers to any substituent comprised of hydrogen and carbon as the only elemental constituents.

Unless otherwise specified, the term "carbocycle" is intended to include ring systems in which the ring atoms are all carbon but of any oxidation state. Thus $(C_3-C_{10})$ carbocycle refers to both non-aromatic and aromatic systems, including such systems as cyclopropane, benzene, cyclopentene and cyclohexene; $(C_8-C_{12})$ carbopolycycle refers to such systems as norbornane, decalin, indane and naphthalene. Carbocycle, if not otherwise limited, refers to monocycles, bicycles and polycycles.

Alkoxy or alkoxyl refers to groups of from 1 to 8 carbon atoms of a straight, branched or cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons. For the purpose of this application, alkoxy and lower alkoxy include methylenedioxy and ethylenedioxy. Alkoxyalkyl refers to ether groups of from 3 to 8 atoms of a straight, branched, cyclic configuration and combinations thereof attached to the parent structure through an alkyl. Examples include methoxymethyl, methoxyethyl, ethoxypropyl, and the like. Alkoxyaryl refers to alkoxy substituents attached to an aryl, wherein the aryl is attached to the parent structure. Arylalkoxy refers to aryl substituents attached to an oxygen, wherein the oxygen is attached to the parent structure. Substituted arylalkoxy refers to a substituted aryl substituent attached to an oxygen, wherein the oxygen is attached to the parent structure.

Oxaalkyl refers to alkyl residues in which one or more carbons (and their associated hydrogens) have been replaced by oxygen. Examples include methoxypropoxy; 3,6,9-trioxadecyl; 2,6,7-trioxabicyclo[2.2.2]octane and the like. The term oxaalkyl is intended as it is understood in the art [see Naming and Indexing of Chemical Substances for Chemical Abstracts, published by the American Chemical Society, 196, but without the restriction of 127(a)], i.e. it refers to compounds in which the oxygen is bonded via a single bond to its adjacent atoms (forming ether bonds); it does not refer to doubly bonded oxygen, as would be found in carbonyl groups. Similarly, thiaalkyl and azaalkyl refer to alkyl residues in which one or more carbons has been replaced by sulfur or nitrogen, respectively. Examples include ethylaminoethyl and methylthiopropyl.

Unless otherwise specified, acyl refers to formyl and to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons. The double bonded oxygen, when referred to as a substituent itself is called "oxo".

Aryl and heteroaryl mean (i) a phenyl group (or benzene) or a monocyclic 5- or 6-membered heteroaromatic ring containing 1-4 heteroatoms selected from O, N, or S; (ii) a bicyclic 9- or 10-membered aromatic or heteroaromatic ring system containing 0-4 heteroatoms selected from O, N, or S; or (iii) a tricyclic 13- or 14-membered aromatic or heteroaromatic ring system containing 0-5 heteroatoms selected from O, N, or S. Aryl, as understood herein, includes residues in which one or more rings are aromatic, but not all need be. Thus aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquino line, quinoxaline, pyrimidine, pyrazine, tetrazole and pyrazole.

Arylalkyl refers to a substituent in which an aryl residue is attached to the parent structure through alkyl. Examples are benzyl, phenethyl and the like. Heteroarylalkyl refers to a substituent in which a heteroaryl residue is attached to the parent structure through alkyl. In one embodiment, the alkyl group of an arylalkyl or a heteroarylalkyl is an alkyl group of from 1 to 6 carbons. Examples include, e.g., pyridinylmethyl, pyrimidinylethyl and the like.

Heterocycle means a cycloalkyl or aryl carbocycle residue in which from one to three carbons is replaced by a heteroatom selected from the group consisting of N, O and S. The nitrogen and sulfur heteroatoms may optionally be oxidized, and the nitrogen heteroatom may optionally be quaternized. Unless otherwise specified, a heterocycle may be non-aromatic or aromatic. It is to be noted that heteroaryl is a subset of heterocycle in which the heterocycle is aromatic. Examples of heterocyclic residues that fall within the scope of the invention include pyrazole, pyrrole, indole, quinoline, isoquino line, tetrahydroisoquinoline, benzo furan, benzodioxan, benzodioxole (commonly referred to as methylenedioxyphenyl, when occurring as a substituent), morpholine, thiazole, pyridine (including 2-oxopyridine), pyridine N-oxide, pyrimidine, thiophene (i.e. thiene), furan, oxazole, oxazoline, oxazolidine, isoxazolidine, isoxazole, dioxane, azetidine, piperazine, piperidine, pyrrolidine, pyridazine, azepine, pyrazolidine, imidazole, imidazo line, imidazolidine, imidazolopyridine, pyrazine, thiazolidine, isothiazole, 1,2-thiazine-1,1-dioxide, quinuclidine, isothiazolidine, benzimidazole, thiadiazole, benzopyran, benzothiazole, benzotriazole, benzoxazole, tetrahydrofuran, tetrahydropyran, benzothiene, thiamorpholine, thiamorpholine sulfoxide, thiamorpholine sulfone, oxadiazole, triazole, tetrazole, isatin (dioxoindole), phthalimide (dioxoisoindole), pyrrolopyridine, triazolopyridine and the dihydro and tetrahydro congeners of the fully unsaturated ring systems among the foregoing.

An oxygen heterocycle is a heterocycle containing at least one oxygen in the ring; it may contain additional oxygens, as well as other heteroatoms. Oxygen heterocycles found in the examples of the invention include tetrahydrofuran, benzodioxole, morpholine, isoxazole and 2,6,7-trioxabicyclo[2.2.2]octane. A sulphur heterocycle is a heterocycle containing at least one sulphur in the ring; it may contain additional sulphurs, as well as other heteroatoms. A nitrogen heterocycle is a heterocycle containing at least one nitrogen in the ring; it may contain additional nitrogens, as well as other heteroatoms.

As used herein, the term "optionally substituted" may be used interchangeably with "unsubstituted or substituted". The term "substituted" refers to the replacement of one or more hydrogen atoms in a specified group with a specified radical. For example, substituted alkyl, aryl, cycloalkyl, heterocyclyl etc. refer to alkyl, aryl, cycloalkyl, or heterocyclyl wherein up to three H atoms in each residue are replaced with halogen, haloalkyl, alkyl, acyl, alkoxyalkyl, hydroxyalkyl, carbonyl (i.e. oxo), phenyl, heteroaryl, benzenesulfonyl, hydroxy, alkoxy, haloalkoxy, oxaalkyl, carboxy, alkoxycarbonyl [—C(=O)O-alkyl], alkoxycarbonylamino [—NHC(=O)O-alkyl], alkoxycarbonylaminoalkyl [-alkyl-NHC(=O)O-alkyl], carboxyalkylcarbonylamino [—NHC(=O)-alkyl-COOH], carboxamido [—C(=O)NH$_2$], aminocarbonyloxy [—OC(=O)NH$_2$], alkylaminocarbonyl [—C(=O)NH-alkyl], dialkylaminocarbonyl [—C(=O)N(alkyl)$_2$], aminocarbonylalkyl [-alkyl-C(=O)NH$_2$], cyano, acetoxy, nitro, amino, alkylamino, dialkylamino, aminoalkyl, (alkyl)(aryl)aminoalkyl, alkylaminoalkyl (including cycloalkylaminoalkyl), dialkylaminoalkyl, dialkylaminoalkoxy, alkyl(hydroxyalkyl)amino, heterocyclylalkoxy, mercapto, alkylthio, alkylsulfonyl, alkylsulfonylamino, alkylsulfinyl, alkylsulfonyl, arylthio, arylsulfonyl, arylsulfonylamino, arylsulfinyl, arylsulfonyl, acylaminoalkyl, acylaminoalkoxy, acylamino, amidino, aryl, benzyl, heterocyclyl, heterocyclylalkyl, phenoxy, benzyloxy, heteroaryloxy, heterocyclylamino, hydroxyimino, alkoxyimino, oxaalkyl, aminosulfonyl, trityl, amidino, guanidino, ureido, —NHC(=O)NHalkyl, —NHC(=O)NH-heterocyclyl, -alkyl-NHC(=O)N(alkyl)$_2$, heterocyclylalkylcarbonylamino, benzyloxyphenyl, and benzyloxy. Although oxo is included among the substituents referred to in "optionally substituted", it will be appreciated by persons of skill in the art that, because oxo is a divalent radical, there are circumstances in which it will not be appropriate as a substituent (e.g. on phenyl). Additional substituents that are considered within the scope of the term, particularly for $R^1$, are the are the residues of amino acids, amino acid amides, protected residues of aminoacids and their amides, and N-methylated (mono- or di-, as appropriate) amino acids and amino acid amides.

For the purpose of $R^1$, the substituents alkyl, acyl, alkoxyalkyl, hydroxyloweralkyl, phenyl, heteroaryl, benzenesulfonyl, loweralkoxy, haloalkoxy, oxaalkyl, alkoxycarbonyl, alkoxycarbonylamino, carboxamido, alkylaminocarbonyl, amino, alkylamino, (alkyl)(aryl)aminoalkyl, alkylaminoalkyl, heterocyclylalkoxy, alkylthio, sulfonylamino, alkylsulfinyl, alkylsulfonyl, acylaminoalkyl, acylaminoalkoxy, acylamino, amidino, aryl, benzyl, heterocyclyl, heterocyclylalkyl, heterocyclylalkoxy, phenoxy, benzyloxy, heteroaryloxy, heterocyclylamino, oxaalkyl, amino sulfonyl, amidino, guanidino, ureido, benzyloxyphenyl, and benzyloxy may be further substituted with one or two substituents from the list of substituents above. Substituents that are considered within the scope of the term, particularly for $R^1$, are the are the residues of amino acids, amino acid amides and protected residues of amino acids and their amides, as well as the following specific residues: —CH$_3$, —CH$_2$CF$_3$, —CF$_3$, —CHO, —COOH, —CN, halogen, —OH, —OEt, —C(=O)NH$_2$, —C(=O)NHEt, —C(=O)NMe$_2$, —COOCH$_3$, —COOEt, —CH$_2$NHC(=O)NH$_2$, —CH(CH$_3$)NHC(=O)NH$_2$, —CH$_2$NHC(=O)H, —CH$_2$NHC(=O)CH$_3$, —CH$_2$C(=O)NH$_2$, —CH$_2$COOH, —CH$_2$COOEt, —CH$_2$NHC(=O)OEt, —CH$_2$NHC(=O)O—C$_6$H$_5$, —CH$_2$NHC(=O)C(=O)NH$_2$, —CH$_2$NHC(=O)NHEt, —C(CH$_3$)$_2$OH, —CH$_2$NHC(=O)N(CH$_3$)$_2$, —CH$_2$NHC(=O)NHCH$_3$, —CH$_2$NH$_2$, —CH(CH$_3$)NH$_2$, —C(CH$_3$)$_2$NH$_2$, —CH$_2$OH, —CH$_2$CH$_2$OH, —CH$_2$NHSO$_2$CH$_3$, —CH$_2$OC(=O)NHEt, —OCH$_3$, —OC(=O)NH$_2$, —OCH$_2$CH$_2$N(CH$_3$)$_2$, —OCH$_2$CH$_2$OCH$_3$, —NHC(=O)NH$_2$, —NHC(=O)NHEt, —NHCH$_3$, —NHEt, —NH(tBoc), —NHCH$_2$COOH ("residue of glycine"), —N(CH$_3$)CH$_2$COOH ("residue of N-methylglycine"), —NHC(=O)NHCH$_2$CH$_2$Cl, —NHSO$_2$NH$_2$, —NHEt, —N(CH$_3$)$_2$, —NH$_2$, —NH(CH$_3$)C(=O)NH$_2$, —NHSO$_2$CH$_3$, —N(SO$_2$CH$_3$)$_2$, —NHC(=O)OCH$_3$, —NHC(=O)OtBu, —NHC(=O)CH$_3$, —SO$_2$NH$_2$, —NHC(=O)CH$_2$CH$_2$COOH, —NHC(=O)NHCH$_2$COOH, —CH$_2$NHCHO, —NHC(=O)NHCH$_2$COOEt, —NHC(=O)NH(CH$_2$)$_2$COOEt, —NHC(=O)NH(CH$_2$)$_2$COOEt, —N(CH$_3$)CH$_2$CH$_2$OH, —NHC(=O)OEt, —N(Et)C(=O)OEt, —NHC(=O)NH(CH$_2$)$_2$COOH, —NHC(=O)CH$_2$N(CH$_3$)$_2$, —NHC(=O)NH(CH$_2$)$_3$COOH, —NHC(=O)

CH₂NH₂, —NHC(=O)CH₂CH₂NH₂, —NHC(=O)CH₂NH(tBoc),

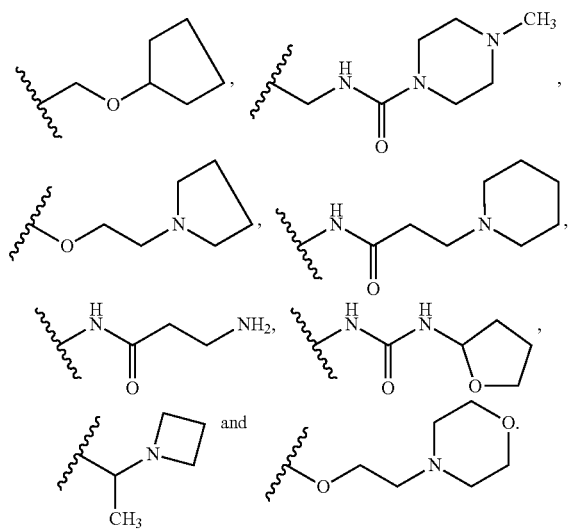

The term "a residue of an amino acid, amino acid amide", etc. refers to an amino acid etc. minus the functional groups that are considered part of the bond to the parent structure. For example, in the molecule P-143 illustrated below:

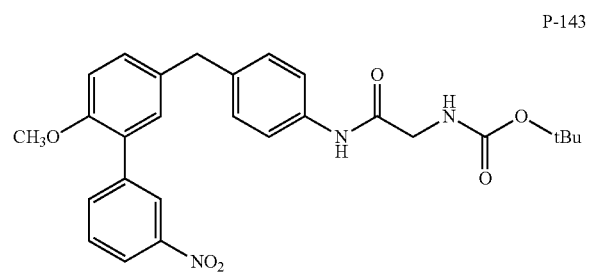

P-143 after one subtracts the hydrogen that connects (BOC)glycinamide to the phenyl ring, the structure of A that remains is:

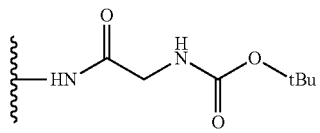 [SMILES: *NC(=O)CNC(=O)OC(C)(C)C]

This is not sensu stricto a protected amino acid amide, since it lacks the hydrogen on the C-terminal amide. This and similar structures that lack atoms at the points of attachment (e.g. the OH of COOH or the H of NH₂) are referred to herein as "residues" of their respective parents.

The terms "haloalkyl" and "haloalkoxy" mean alkyl or alkoxy, respectively, substituted with one or more halogen atoms. The terms "alkylcarbonyl" and "alkoxycarbonyl" mean —C(=O)alkyl or —C(O)alkoxy, respectively.

The term "halogen" means fluorine, chlorine, bromine or iodine. In one embodiment, halogen may be fluorine or chlorine.

Substituents R″ are generally defined when introduced and retain that definition throughout the specification and in all independent claims.

In the characterization of some of the substituents, it is recited that certain substituents may combine to form rings. Unless stated otherwise, it is intended that such rings may exhibit various degrees of unsaturation (from fully saturated to fully unsaturated), may include heteroatoms and may be substituted with lower alkyl or alkoxy.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, and chlorine include $^{2}H$, $^{3}H$, $^{13}C$, $^{14}C$, $^{15}N$, $^{35}S$, $^{18}F$, and $^{36}Cl$, respectively. Compounds that contain those radioisotopes and/or other radioisotopes of other atoms are within the scope of this invention. Tritiated, i.e. $^{3}H$, and carbon-14, i.e., $^{14}C$, radioisotopes are particularly preferred for their ease in preparation and detectability. Compounds that contain isotopes $^{11}C$, $^{13}N$, $^{15}O$ and $^{18}F$ are well suited for positron emission tomography. Radiolabeled compounds of formula I of this invention and prodrugs thereof can generally be prepared by methods well known to those skilled in the art. Conveniently, such radio labeled compounds can be prepared by carrying out the procedures disclosed in the Examples and Schemes by substituting a readily available radiolabeled reagent for a non-radio labeled reagent.

As used herein (particularly in the claims), and as would be understood by the person of skill in the art, the recitation of "a compound" is intended to include salts, solvates, co-crystals and inclusion complexes of that compound as well as any stereoisomeric form, or a mixture of any such forms of that compound in any ratio. Thus, in accordance with some embodiments of the invention, a compound as described herein, including in the contexts of pharmaceutical compositions, methods of treatment, and compounds per se, is provided as the salt form. Thus, for example, the recitation "a compound of formula I" as depicted above, in which $R^{1}$ is imidazolyl, would include imidazolium salts. In a particular embodiment, the term "compound of formula I" refers to the compound or a pharmaceutically acceptable salt thereof.

The compounds described herein may contain asymmetric centers and may thus give rise to enantiomers, diastereomers, and other stereoisomeric forms. Each chiral center may be defined, in terms of absolute stereochemistry, as (R)- or (S)-. The present invention is meant to include all such possible isomers, in any ratio from racemic to optically pure forms. Optically active (R)- and (S)-isomers may be prepared using chiral synthons or chiral reagents, or resolved using conventional techniques. The prefix "rac" refers to a racemate. When the compounds described herein contain olefinic double bonds or other centers of geometric asymmetry, and unless specified otherwise, it is intended that the compounds include both E and Z geometric isomers. The representation of the configuration of any carbon-carbon double bond appearing herein is selected for convenience only, and unless explicitly stated, is not intended to designate a particular configuration. Thus a carbon-carbon double bond depicted arbitrarily as E may be Z, E, or a mixture of the two in any proportion. Likewise, all tautomeric forms are also intended to be included.

The term "solvate" refers to a compound of Formula I in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions. Inclusion complexes are described in Remington: The Science and Practice of Pharmacy 19th Ed. (1995) volume 1, page 176-177, which is incorporated herein by reference. The most commonly employed inclusion complexes are those with cyclodextrins, and all cyclodextrin complexes, natural and synthetic, are specifically encompassed within the claims.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable anions for the compounds of the present invention include acetate, benzenesulfonate (besylate), benzoate, bicarbonate, bisulfate, carbonate, camphorsulfonate, citrate, ethanesulfonate, fumarate, gluconate, glutamate, glycolate, bromide, chloride, isethionate, lactate, maleate, malate, mandelate, methanesulfonate, mucate, nitrate, pamoate, pantothenate, phosphate, succinate, sulfate, tartrate, trifluoroacetate, p-toluenesulfonate, acetamidobenzoate, adipate, alginate, aminosalicylate, anhydromethylenecitrate, ascorbate, aspartate, calcium edetate, camphorate, camsylate, caprate, caproate, caprylate, cinnamate, cyclamate, dichloroacetate, edetate (EDTA), edisylate, embonate, estolate, esylate, fluoride, formate, gentisate, gluceptate, glucuronate, glycerophosphate, glycolate, glycollylarsanilate, hexylresorcinate, hippurate, hydroxynaphthoate, iodide, lactobionate, malonate, mesylate, napadisylate, napsylate, nicotinate, oleate, orotate, oxalate, oxoglutarate, palmitate, pectinate, pectinate polymer, phenylethylbarbiturate, picrate, pidolate, propionate, rhodanide, salicylate, sebacate, stearate, tannate, theoclate, tosylate and the like. The desired salt may be obtained by ion exchange of whatever counter ion is obtained in the synthesis of the quat. These methods are well known to persons of skill. Although pharmaceutically acceptable counter ions will be preferred for preparing pharmaceutical formulations, other anions are quite acceptable as synthetic intermediates. When the compounds contain an acidic side chain, suitable pharmaceutically acceptable base addition salts for the compounds of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine.

The graphic representations of racemic, ambiscalemic and scalemic or enantiomerically pure compounds used herein are taken from Maehr J. Chem. Ed. 62, 114-120 (1985): solid and broken wedges are used to denote the absolute configuration of a chiral element; wavy lines and single thin lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration.

Terminology related to "protecting", "deprotecting" and "protected" functionalities occurs throughout this application. Such terminology is well understood by persons of skill in the art and is used in the context of processes that involve sequential treatment with a series of reagents. In that context, a protecting group refers to a group, which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry, such as Protective Groups in Organic Synthesis by T. W. Greene [John Wiley & Sons, New York, 1991], which is incorporated herein by reference.

A comprehensive list of abbreviations utilized by organic chemists appears in the first issue of each volume of the Journal of Organic Chemistry. The list, which is typically presented in a table entitled "Standard List of Abbreviations", is incorporated herein by reference.

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here. The starting materials, are either commercially available, synthesized as described in the examples or may be obtained by the methods well known to persons of skill in the art.

PDE4 inhibitors have been shown to be effective therapeutic agents in clinical studies. For example, administration of cilomilast and roflumilast (PDE4 inhibitors) to patients suffering from asthma and COPD showed initially excellent results, although the effect of cilomilast disappeared on long-term trial [Lipworth, *Lancet* 365, 167-175 (2005)]. Genetic studies have clearly demonstrated an association between PDE4D and ischemic stroke (Gretarsdottir et al. 2003. Nature Genetics. 35, 1-8). L-454,560, a selective PDE4 inhibitor has been shown to improve learning in a rat model in vivo [Huang et al. *Biochemical Pharmacology* 73, 1971-1981 (2007)]. This suggests that selective PDE4 inhibitors will be useful in treating learning disorders, memory loss (e.g. Alzheimer's disease) and other cognitive dysfunctions. Rolipram, another selective PDE4 inhibitor, has been shown to enhance cognition in multiple rodent models [Blokland et al., Current Pharmaceutical Design 12, 2511-2523 (2006)] as well as in primates [Rutten et al., 2008, Psychopharmacology 196, 643-648 (2008)]. Rolipram also improves the outcome in two separate studies in mice in vivo in models accepted by persons of skill in the art as predictive of utility in schizophrenia [Kanes et al., *Neuroscience* 144, 239-246 (2007); Davis and Gould, *Behav. Neurosci.* 119, 595-602 (2005)]. Rolipram has also been shown to exhibit a neuroprotective effect in a rat model of Huntington's disease [DeMarch et al. Neurobiol. Dis. 25, 266-273 (2007)]. This suggests that PDE4 modulators will be useful for treating many CNS disorders. Selective PDE4 inhibitors (e.g. rolipram) are also useful for treating bone loss [Yao et al., *J. Musculoskelet. Neuronal Interact.* 7, 119-130 (2007)].

Additionally, a PDE4 inhibitor, YM976, was shown to ameliorate the effects of experimentally-induced interstitial cystitis in rats, resulting in a decrease in the frequency of urination and an increase in the volume of urine at each time of urination [Kitta et al., *BJU Int.* 102, 1472-1476 (2008)]. Another PDE4 inhibitor, IC485, was shown to be equally efficacious as tolteradine tartrate, a marketed drug for treating overactive bladder, in a rodent model of obstructive bladder [Kaiho et al. BJU Int. 101, 615-20 (2008)]. These findings suggest that PDE4 inhibitors will be useful in treating symptoms of bladder overactivity, inflammation and pain.

In addition to the foregoing studies demonstrating utility in in vivo models, a number of authors have suggested connections between PDE4 inhibition and putative utilities as antidepressants [Houslay et al., Drug Discov Today 10, 1503-1519 (2005); Polesskaya et al., Biol. Psychiatr. 61, 56-64 (2007); anon. *Current Opin. Invetig. Drugs* 5, 34-39 (2004)] and as anxiolytics [Zhang et al., *Neuropsychopharmacology* Aug. 15, 2007 Epub; Cherry et al., *Biochim. Biophys. Acta* 1518, 27-35 (2001)]. Rolipram has been shown in human clinical trials to ameliorate depression [Hebenstreit et al., Pharmacopsychiat. 22, 156-160 (1989)]. Other possible utilities may include Pick's disease and epilepsy.

Furthermore, the compounds, compositions and methods of the present invention may be useful in treating cancer. Phosphodiesterase activity has been shown to be associated with hematological malignancies [Lerner et al., *Biochem. J.* 393, 21-41 (2006); Ogawa et al., *Blood* 99, 3390-3397 (2002)]. The compounds may also be administered to overcome cognitive impairment induced by one or more of the following agents, alcohol, amphetamine, antipsychotic medication, anti-retroviral therapy, MDMA (3,4-methylenedioxy-N-methylamphetamine, cannabis, cocaine, delta-9 tetrahydrocannabinol, dexamphetamine, haloperidol, heroin and other opiates, ketamine and metamphetamine.

Furthermore, the compounds, compositions and methods of the present invention, particularly when radio labeled as described above or labeled by methods well-known in the art with florescent and spin labels, may be employed as imaging agents and in other ways for diagnosis and/or treatment. Moreover, immobilization of compounds of the invention on solid support could be of utility for affinity purification and modification of compounds of the invention with chemically active groups may be used for protein labeling.

For many of the utilities outlined above, it may be advantageous to administer compounds of the general formula I together with cholinesterase inhibitors (e.g. tacrine, huperzine, donepezil); NMDA antagonists (e.g. lanicemine, remacemide, neramexane, memantine); calpain inhibitors (e.g. CEP-3122); antioxidants (e.g. vitamin E, coenzyme Q10) and agents that have shown clinical efficacy but whose mechanism is unclear (e.g. dimebon). Compounds of formula I may also be administered together with one or more of the following agents to improve cognition: amisulpride, atomoxetine, bromocryptine, buspirone, caffeine, chlorpromazine, clonidine, clozapine, diazepam, flumazenil, fluoxetine, galantamine, guanfacine, methylphenidate, idazoxan, modafinil, olanzapine, paroxetine, pergolide, phenserine, quetiapine, risperidone, rivastigmine, SGS742 and sulpiride.

The terms "methods of treating or preventing" mean amelioration, prevention or relief from the symptoms and/or effects associated with disorders. The term "preventing" as used herein refers to administering a medicament beforehand to forestall or obtund an acute episode. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended in applicants' claims. As used herein, reference to "treatment" of a patient is intended to include prophylaxis.

The term "mammal" is used in its dictionary sense. Humans are included in the group of mammals, and humans would be the preferred subjects of the methods.

The cognitive impairment to be treated may arise from one or more of the following disorders, which may not in themselves be necessarily associated with PDE4 abnormality: acute pain, AD/HD—Attention deficit hyperactivity disorder, AIDS dementia complex, alcoholism, amphetamine addiction, amygdalo-hippocampectomy, anorexia nervosa, anterior parietal damage, antisocial behavior, antisocial personality disorder, anxiety, autism, basal ganglia lesions, bipolar disorder, borderline personality disorder, camptocormia, capgras syndrome, carcinoid syndrome, carotid endarterectomy surgery, chronic drug misuse, chronic fatigue syndrome, chronic occupational solvent encephalopathy, chronic pain, brain ischemia, coronary artery bypass surgery, critical illness requiring intensive care, dementia Alzheimer-type (DAT), dementia Lewy Body type, dementia of frontal type, dementia caused by ischemia, dental pain, developmental dyslexia, diabetes, dorsolateral frontal cortical compression, Down's Syndrome, drug abuse, dysexecutive syndrome, fibromyalgia, frontal lobe damage, frontal lobe excision, frontal variant frontotemporal dementia, gluten ataxia, hallucinosis, head injury, hearing loss, heart disease, heart failure, heavy social drinking, hepatic encephalopathy, heroin addiction, herpes encephalitis, hippocampal atrophy, HIV/AIDS, Huntington's disease, hydrocephalus, hypercortisolemia, hyperostosis frontalis interna, hypertension, idiopathic pain, insomnia, Korsakoff syndrome, late paraphrenia, lead exposure, left ventricular systolic dysfunction, orbitofrontal cortex lesion, liver failure, long term health effects of diving, Machado-Joseph disease, mad hatter's disease, manic depression, melancholia, mercury poisoning, mild cognitive impairment (MCI), mild cognitive impairment (MCI) of aging, motor neuron disease, multiple sclerosis, multiple system atrophy, narcolepsy, neuronal migration disorders, normal pressure hydrocephalus, obsessive compulsive disorder, organophosphate pesticide exposure, panic disorder, paraphrenia, Parkinson's disease, periventricular brain insult, personality disorder, gasoline sniffing, phenylketonuria, postconcussion syndrome, premature birth needing intensive care, premenstrual dysphoric disorder, progressive supranuclear palsy, psychopathy, psychosis, questionable dementia, renal cancer, Roifman syndrome, schizoaffective disorder, schizophrenia, seasonal affective disorder, self harm, semantic dementia, specific language impairment, social withdrawal in schizophrenia, solvent encephalopathy, spina bifida, Steele-Richardson-Olzsewski syndrome, stiff person syndrome, striatocapsular infarct, subarachnoid hemorrhage, substance abuse, tardive dyskinesia, temporal lobe excision, temporal lobe lesion, tinnitus, Tourette's syndrome, transient cerebral ischemia, traumatic brain injury, trichotillomania, tuberous sclerosis, and white matter lesions.

While it may be possible for compounds of formula I to be administered as the raw chemical, it will often be preferable to present them as part of a pharmaceutical composition. In accordance with an embodiment of the present invention there is provided a pharmaceutical composition comprising a compound of formula I or a pharmaceutically acceptable salt thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof. Furthermore, when reference is made in an independent claim to a compound or a pharmaceutically acceptable salt thereof, it will be understood that claims which depend from that independent claim which refer to such a compound also include pharmaceutically acceptable salts of the compound, even if explicit reference is not made to the salts in the dependent claim.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. Such methods include the step of bringing into association a compound of formula I or a pharmaceutically acceptable salt or solvate thereof ("active ingredient") with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein. The pharmaceutical compositions may include a "pharmaceutically acceptable inert carrier", and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or non-aqueous techniques, "Pharmaceutically acceptable carrier" also encompasses controlled release means.

Pharmaceutical compositions may also optionally include other therapeutic ingredients, anti-caking agents, preservatives, sweetening agents, colorants, flavors, desiccants, plasticizers, dyes, and the like. Any such optional ingredient must be compatible with the compound of formula I to insure the stability of the formulation. The composition may contain other additives as needed, including for example lactose, glucose, fructose, galactose, trehalose, sucrose, maltose, raffinose, maltitol, melezitose, stachyose, lactitol, palatinite, starch, xylitol, mannitol, myoinositol, and the like, and hydrates thereof, and amino acids, for example alanine, glycine and betaine, and peptides and proteins, for example albumen.

Examples of excipients for use as the pharmaceutically acceptable carriers and the pharmaceutically acceptable inert carriers and the aforementioned additional ingredients include, but are not limited to binders, fillers, disintegrants, lubricants, anti-microbial agents, and coating agents.

The dose range for adult humans is generally from 0.005 mg to 10 g/day orally. Tablets or other forms of presentation provided in discrete units may conveniently contain an amount of compound of formula I which is effective at such dosage or as a multiple of the same, for instance, units containing 5 mg to 500 mg, usually around 10 mg to 200 mg. The precise amount of compound administered to a patient will be the responsibility of the attendant physician. However, the dose employed will depend on a number of factors, including the age and sex of the patient, the precise disorder being treated, and its severity.

A dosage unit (e.g. an oral dosage unit) can include from, for example, 1 to 30 mg, 1 to 40 mg, 1 to 100 mg, 1 to 300 mg, 1 to 500 mg, 2 to 500 mg, 3 to 100 mg, 5 to 20 mg, 5 to 100 mg (e.g. 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg) of a compound described herein.

For additional information about pharmaceutical compositions and their formulation, see, for example, Remington: The Science and Practice of Pharmacy, $20^{th}$ Edition, 2000. The agents can be administered, e.g., by intravenous injection, intramuscular injection, subcutaneous injection, intraperitoneal injection, topical, sublingual, intraarticular (in the joints), intradermal, buccal, ophthalmic (including intraocular), intranasaly (including using a cannula), or by other routes. The agents can be administered orally, e.g., as a tablet or cachet containing a predetermined amount of the active ingredient, gel, pellet, paste, syrup, bolus, electuary, slurry, capsule, powder, granules, as a solution or a suspension in an aqueous liquid or a non-aqueous liquid, as an oil-in-water liquid emulsion or a water-in-oil liquid emulsion, via a micellar formulation (see, e.g. WO 97/11682) via a liposomal formulation (see, e.g., EP 736299, WO 99/59550 and WO 97/13500), via formulations described in WO 03/094886 or in some other form. The agents can also be administered transdermally (i.e. via reservoir-type or matrix-type patches, microneedles, thermal poration, hypodermic needles, iontophoresis, electroporation, ultrasound or other forms of sonophoresis, jet injection, or a combination of any of the preceding methods (Prausnitz et al. 2004, Nature Reviews Drug Discovery 3:115)). The agents can be administered locally, for example, at the site of injury to an injured blood vessel. The agents can be coated on a stent. The agents can be administered using high-velocity transdermal particle injection techniques using the hydrogel particle formulation described in U.S. 20020061336. Additional particle formulations are described in WO 00/45792, WO 00/53160, and WO 02/19989. An example of a transdermal formulation containing plaster and the absorption promoter dimethylisosorbide can be found in WO 89/04179. WO 96/11705 provides formulations suitable for transdermal administration. The agents can be administered in the form a suppository or by other vaginal or rectal means. The agents can be administered in a transmembrane formulation as described in WO 90/07923. The agents can be administered non-invasively via the dehydrated particles described in U.S. Pat. No. 6,485,706. The agent can be administered in an enteric-coated drug formulation as described in WO 02/49621. The agents can be administered intranasaly using the formulation described in U.S. Pat. No. 5,179,079. Formulations suitable for parenteral injection are described in WO 00/62759. The agents can be administered using the casein formulation described in U.S. 20030206939 and WO 00/06108. The agents can be administered using the particulate formulations described in U.S. 20020034536.

The agents, alone or in combination with other suitable components, can be administered by pulmonary route utilizing several techniques including but not limited to intratracheal instillation (delivery of solution into the lungs by syringe), intratracheal delivery of liposomes, insufflation (administration of powder formulation by syringe or any other similar device into the lungs) and aerosol inhalation. Aerosols (e.g., jet or ultrasonic nebulizers, metered-dose inhalers (MDIs), and dry-Powder inhalers (DPIs)) can also be used in intranasal applications. Aerosol formulations are stable dispersions or suspensions of solid material and liquid droplets in a gaseous medium and can be placed into pressurized acceptable propellants, such as hydrofluoroalkanes (HFAs, i.e. HFA-134a and HFA-227, or a mixture thereof), dichlorodifluoromethane (or other chlorofluorocarbon propellants such as a mixture of Propellants 11, 12, and/or 114), propane, nitrogen, and the like. Pulmonary formulations may include permeation enhancers such as fatty acids, and saccharides, chelating agents, enzyme inhibitors (e.g., protease inhibitors), adjuvants (e.g., glycocholate, surfactin, span 85, and nafamostat), preservatives (e.g., benzalkonium chloride or chlorobutanol), and ethanol (normally up to 5% but possibly up to 20%, by weight). Ethanol is commonly included in aerosol compositions as it can improve the function of the metering valve and in some cases also improve the stability of the dispersion. Pulmonary formulations may also include surfactants which include but are not limited to bile salts and those described in U.S. Pat. No. 6,524,557 and references therein. The surfactants described in U.S. Pat. No. 6,524,557, e.g., a $C_8$-$C_{16}$ fatty acid salt, a bile salt, a phospholipid, or alkyl saccharide are advantageous in that some of them also reportedly enhance absorption of the compound in the formulation. Also suitable in the invention are dry powder formulations comprising a therapeutically effective amount of active compound blended with an appropriate carrier and adapted for use in connection with a dry-Powder inhaler. Absorption enhancers which can be added to dry powder formulations of the present invention include those described in U.S. Pat. No. 6,632,456. WO 02/080884 describes new methods for the surface modification of powders. Aerosol formulations may include U.S. Pat. No. 5,230,884, U.S. Pat. No. 5,292,499, WO 017/8694, WO 01/78696, U.S. 2003019437, U.S. 20030165436, and WO 96/40089 (which includes vegetable oil). Sustained release formulations suitable for inhalation are described in U.S. 20010036481A1, 20030232019A1, and U.S. 20040018243A1 as well as in WO 01/13891, WO 02/067902, WO 03/072080, and WO 03/079885. Pulmonary formulations containing microparticles are described in WO 03/015750, U.S. 20030008013, and WO 00/00176. Pulmonary formulations containing stable glassy state powder are described in U.S. 20020141945 and U.S. Pat. No. 6,309,671. Other aerosol formulations are described in EP 1338272A1 WO 90/09781, U.S. Pat. No. 5,348,730, U.S. Pat. No. 6,436,367, WO 91/04011, and U.S. Pat. No. 6,294,153 and U.S. Pat. No. 6,290,987 describes a liposomal based formulation that can be administered via aerosol or other means. Powder formulations for inhalation are described in U.S. 20030053960 and WO 01/60341. The agents can be administered intranasally as described in U.S. 20010038824.

Solutions of medicament in buffered saline and similar vehicles are commonly employed to generate an aerosol in a nebulizer. Simple nebulizers operate on Bernoulli's principle and employ a stream of air or oxygen to generate the spray particles. More complex nebulizers employ ultrasound to create the spray particles. Both types are well known in the art and are described in standard textbooks of pharmacy such as Sprowls' American Pharmacy and Remington's The Science and Practice of Pharmacy. Other devices for generating aerosols employ compressed gases, usually hydro fluorocarbons and chlorofluorocarbons, which are mixed with the medicament and any necessary excipients in a pressurized container, these devices are likewise described in standard textbooks such as Sprowls and Remington.

The agent can be incorporated into a liposome to improve half-life. The agent can also be conjugated to polyethylene glycol (PEG) chains. Methods for pegylation and additional formulations containing PEG-conjugates (i.e. PEG-based hydrogels, PEG modified liposomes) can be found in Harris and Chess, Nature Reviews Drug Discovery 2:214-221 and the references therein. The agent can be administered via a nanocochleate or cochleate delivery vehicle (BioDelivery Sciences International). The agents can be delivered transmucosally (i.e. across a mucosal surface such as the vagina, eye or nose) using formulations such as that described in U.S. Pat. No. 5,204,108. The agents can be formulated in microcapsules as described in WO 88/01165. The agent can be administered intra-orally using the formulations described in U.S. 20020055496, WO 00/47203, and U.S. Pat. No. 6,495,120. The agent can be delivered using nanoemulsion formulations described in WO 01/91728A2.

In general, compounds of formula I may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

The present invention relates to compounds exhibiting PDE4 enzyme inhibition, having the general formula I

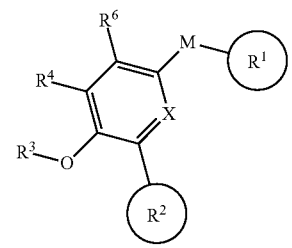

In one embodiment, X is $CR^5$, $R^2$ is pyrazolyl or substituted phenyl and $R^3$ is other than H. In another embodiment, M is chosen from direct bond, —$CH_2$—, —CH(OH)—, —C[($CH_3$)(OH)]—, —C[($CH_3$)($NH_2$)]—, —C(=O)—, —O—, —NH—, —N($CH_3$)—, —S(O)$_n$—, —$CH_2$NH—, —$CH_2CH_2$—, —CH=CH—, —$CH_2$S(O)$_n$—, —$CH_2$O— and

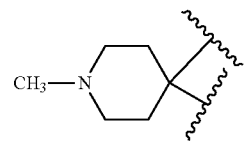

There are two subgenera of compounds of formula I. The first, in which X is N or N→O, is represented by the formulae:

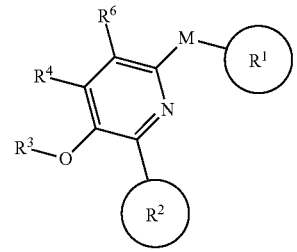

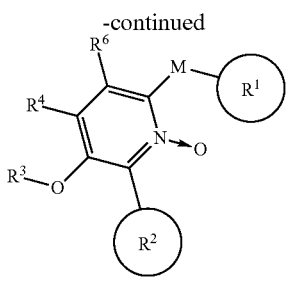

The second, in which X is CR⁵ is represented by the formula:

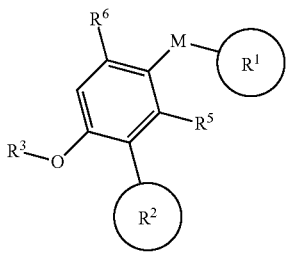

In one embodiment, $R^1$ is a substituted phenyl. In another embodiment, $R^1$ is phenyl and $R^2$ is pyrazolyl or substituted phenyl. In another embodiment, $R^1$ is substituted phenyl and $R^2$ is pyrazolyl or substituted phenyl.

In another embodiment, $R^1$ is an unsubstituted heterocycle. In another embodiment, $R^1$ is a substituted heterocycle. In both heterocycle embodiments, the heterocycle may be chosen from pyrazole, pyrrole, indole, quinoline, isoquinoline, tetrahydroisoquinoline, benzo furan, benzodioxan, benzodioxole, morpholine, thiazole, pyridine, pyridine N-oxide, pyrimidine, thiene, furan, oxazole, oxazoline, oxazolidine, isoxazolidine, isoxazole, dioxane, azetidine, piperazine, piperidine, pyrrolidine, pyridazine, azepine, pyrazolidine, imidazole, imidazoline, imidazolidine, purine, imidazolopyridine, pyrazine, thiazolidine, isothiazole, 1,2-thiazine-1,1-dioxide, 2,6,7-trioxabicyclo[2.2.2]octane, quinuclidine, isothiazolidine, benzimidazole, thiadiazole, benzopyran, benzothiazole, benzotriazole, benzoxazole, benzoxadiazole, tetrahydrofuran, tetrahydropyran, benzothiene, thiamorpholine, thiamorpholine sulfoxide, thiamorpholine sulfone, oxadiazole, triazole, tetrazole, isoindole, pyrrolopyridine, triazolopyridine and the dihydro and tetrahydro congeners thereof, whether specifically named or not. For example, a dihydro congener of indole would be indoline or dihydroindole; a tetrahydro congener of pyridine would be piperidine. In a further embodiment, $R^1$ is an optionally substituted heterocycle chosen from pyrazole, benzodioxole, morpholine, thiazole, pyridine, pyridine N-oxide, pyrimidine, thiene, oxazolidine, isoxazole, azetidine, piperazine, pyrrolidine, imidazole, imidazolidine, imidazolopyridine, pyrazine, 1,2-thiazine-1,1-dioxide, benzimidazole, thiadiazole, benzotriazole, benzoxazole, oxadiazole, triazole, tetrazole, isoindole, pyrrolopyridine, triazolopyridine and their dihydro and tetrahydro congeners.

In an embodiment, the substituted phenyl or substituted heterocycle is substituted with a substituent chosen from halogen, haloalkyl, alkyl, acyl, alkoxyalkyl, hydroxyalkyl, carbonyl, phenyl, heteroaryl, benzenesulfonyl, hydroxy, alkoxy, haloalkoxy, oxaalkyl, carboxy, alkoxycarbonyl, alkoxycarbonylalkyl, alkoxycarbonylamino, carboxyalkyl, alkoxycarbonylaminoalkyl, carboxyalkylcarbonylamino, carboxamido, aminocarbonyloxy, alkylaminocarbonyl, dialkylaminocarbonyl, amino carbonylalkyl, cyano, acetoxy, nitro, amino, alkylamino, dialkylamino, aminoalkyl, (alkyl)(aryl)aminoalkyl, alkylamino alkyl, dialkylaminoalkyl, dialkylaminoalkoxy, alkyl(hydroxyalkyl)amino, heterocyclylalkoxy, mercapto, alkylthio, alkylsulfonyl, alkylsulfonylamino, alkylsulfinyl, alkylsulfonyl, arylthio, arylsulfonyl, arylsulfonylamino, arylsulfinyl, arylsulfonyl, acylaminoalkyl, acylaminoalkoxy, acylamino, amidino, aryl, benzyl, heterocyclyl, heterocyclylalkyl, phenoxy, benzyloxy, heteroaryloxy, heterocyclylamino, hydroxyimino, alkoxyimino, oxaalkyl, aminosulfonyl, trityl, amidino, guanidino, ureido, —NHC(=O)NHalkyl, —NHC(=O)NH-heterocyclyl, -alkyl-NHC(=O)N(alkyl)₂, heterocyclylalkylcarbonylamino, benzyloxyphenyl, benzyloxy, the residues of amino acids, amino acid amides, protected residues of aminoacids, protected residues of amino acid amides, N-methylated amino acids and N-methylated amino acid amides. Exemplary amino acids are glycine, alanine and proline.

In another embodiment, the substituted phenyl or substituted heterocycle is substituted with a substituent chosen from —CH₃, —CH₂CF₃, —CF₃, —CHO, —COOH, —CN, halogen, —OH, —OEt, —C(=O)NH₂, —C(=O)NHEt, —C(=O)NMe₂-COOCH₃, —COOEt, —CH₂NHC(=O)NH₂, —CH(CH₃)NHC(=O)NH₂, —CH₂NHC(=O)H, —CH₂NHC(=O)CH₃, —CH₂C(=O)NH₂, —CH₂COOH, —CH₂COOEt, —CH₂NHC(=O)OEt, —CH₂NHC(=O)O—C₆H₅, —CH₂NHC(=O)C(=O)NH₂, —CH₂NHC(=O)NHEt, —C(CH₃)₂OH, —CH₂NHC(=O)N(CH₃)₂, —CH₂NHC(=O)NHCH₃, —CH₂NH₂, —CH(CH₃)NH₂, —C(CH₃)₂NH₂, —CH₂OH, —CH₂CH₂OH, —CH₂NHSO₂CH₃, —CH₂C(=O)NHEt, —OCH₃, —OC(=O)NH₂, —OCH₂CH₂N(CH₃)₂, —OCH₂CH₂OCH₃, —NHC(=O)NH₂, —NHC(=O)NHEt, —NHCH₃, —NHEt, —NH(tBoc), —NHCH₂COOH, —N(CH₃)CH₂COOH, —NHC(=O)NHCH₂CH₂Cl, —NHSO₂NH₂, —NHEt, —N(CH₃)₂, —NH₂, —NH(CH₃)C(=O)NH₂, —NHSO₂CH₃, —N(SO₂CH₃)₂, —NHC(=O)OCH₃, —NHC(=O)OtBu, —NHC(=O)CH₃, —SO₂NH₂, —NHC(=O)CH₂CH₂COOH, —NHC(=O)NHCH₂COOH, —CH₂NHCHO, —NHC(=O)NHCH₂COOEt, —NHC(=O)NH(CH₂)₃COOEt, —NHC(=O)NH(CH₂)₂COOEt, —N(CH₃)CH₂CH₂OH, —NHC(=O)OEt, —N(Et)C(=O)OEt, —NHC(=O)NH(CH₂)₂COOH, —NHC(=O)CH₂N(CH₃)₂, —NHC(=O)NH(CH₂)₃COOH, —NHC(=O)CH₂NH₂, —NHC(=O)CH₂CH₂NH₂, —NHC(=O)CH₂NH(tBoc),

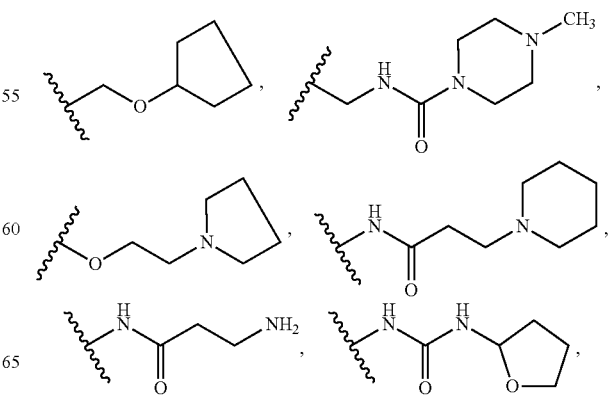

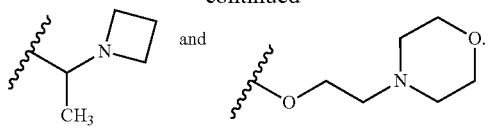

One embodiment of compounds of the first genus are those in which $R^3$ is methyl or fluoromethyl; $R^6$ is H; and M is —CH$_2$— or —CH$_2$O—.

In an embodiment, $R^2$ is chosen from optionally substituted phenyl, optionally substituted monocyclic unsaturated heterocycle, unsubstituted bicyclic unsaturated heterocycle and fluoro-substituted bicyclic unsaturated heterocycle. In a further embodiment, $R^2$ is chosen from optionally substituted phenyl, indole, benzodioxole, benzoxadiazole, benzodioxan, benzimidazole, oxadiazole, pyrazole, pyridine and pyridine N-oxide. In a further embodiment, $R^2$ is chosen from meta-substituted phenyl, indole, benzodioxole, 2,2-difluorobenzodioxole, benzooxadiazole, benzimidazole, 5-(pyridin-4-yl)[1,2,4]oxadiazole, 5-(pyridin-4-yl)[1,3,4]oxadiazole, benzodioxan, 4-chloropyrazole, 4-(pyridin-4-yl)pyrazole, 6-chloropyridine, 3-(trifluoromethyl)pyrazole, and pyridine N-oxide.

In another embodiment, $R^2$ is substituted phenyl:

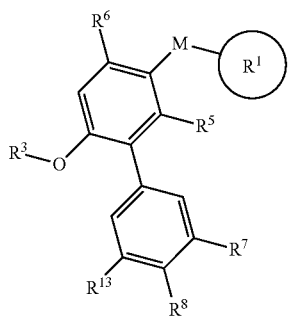

wherein $R^7$ is chosen from hydrogen, halogen, nitro, cyano, halo($C_1$-$C_6$)alkyl, hydroxy, ($C_1$-$C_6$)alkoxy, ($C_1$-$C_6$)oxaalkyl, carboxy, ($C_1$-$C_6$)alkoxycarbonyl, aminocarbonyl (—CONH$_2$), ($C_1$-$C_6$)alkylamino carbonyl, acyl, hydroxy($C_1$-$C_6$)alkyl, halo($C_1$-$C_6$)alkoxy, amino($C_1$-$C_6$)alkyl, amino, ($C_1$-$C_6$)alkylamino, di[($C_1$-$C_6$)alkyl]amino, mercapto, ($C_1$-$C_6$)alkylthio, ($C_1$-$C_6$)alkylsulfinyl, ($C_1$-$C_6$)alkylsulfonyl, ($C_1$-$C_6$)alkylsulfonamido, acylamino, amidino, phenyl, benzyl, heterocyclyl, phenoxy, benzyloxy, and heteroaryloxy; and $R^8$ and $R^{13}$ are chosen independently from H and F. In a further embodiment, $R^8$ and $R^{13}$ are H and $R^7$ is chosen from hydrogen, fluoro, chloro, bromo, nitro, cyano, acetyl, trifluoromethyl, methoxy, trifluoromethoxy, oxadiazolyl, tetrazolyl, methylthio, methanesulfinyl, methanesulfonyl, methansulfonamido, amino, methoxymethyl, hydroxyethyl, and morpholinyl.

In another embodiment, $R^1$ is chosen from optionally substituted phenyl, optionally substituted five membered heteroaryl, optionally substituted six-membered heteroaryl, optionally substituted 4-7 membered non-aryl heterocycle, and optionally substituted fused bicycle.

For example, $R^1$ may be chosen from optionally substituted phenyls; optionally substituted five membered heteroaryls selected from thiazoles, thiadiazoles, pyrazoles, oxadiazole, isoxazoles, triazoles, imidazoles, thiophenes, tetrazoles and oxazoles; optionally substituted six membered hereroaryls selected from pyridines, pyrimidines, pyridazinones, pyrimidinone, pyridinone, pyrazines and diazines; optionally substituted 5- and 6-membered non-aryl heterocyclics selected from tetrahydrothiophenes, piperazine, oxazolidinones, imidazolidinones, morpholines, piperidines, pyrrolidinones, pyrrolidinediones, pyrrolidines, piperidinones, piperidinediones and trioxa-bicyclo[2.2.2]octanes; and optionally substituted fused bicycles selected from benzoxazolones, indoles, isoindolinediones, 2H-pyrrolopyridinediones, purines, indolinediones, triazolopyridinones, benzimidazoles, benzoxadiazoles, quinolines and quinolones; wherein the substituents are chosen independently from hydrogen, halogen, halo($C_1$-$C_6$)alkyl, hydroxyl, ($C_1$-$C_6$)alkoxy, carboxy, ($C_1$-$C_6$)alkoxycarbonyl, aminocarbonyl (—CONH$_2$), ($C_1$-$C_6$)alkylaminocarbonyl, cyano, carbonyl(oxo), acyl, hydroxy($C_1$-$C_6$)alkyl, halo($C_1$-$C_6$)alkoxy, amino($C_1$-$C_6$)alkyl, ($C_1$-$C_6$)alkoxy($C_1$-$C_6$)alkyl, nitro, amino, ($C_1$-$C_6$)alkylamino, di[($C_1$-$C_6$)alkyl]amino, mercapto, ($C_1$-$C_6$)alkylthio, sulfoxide, sulfone, sulfonate, sulfonimide, acylamino, amidino, phenyl, benzyl, heteroaryl, phenoxy, benzyloxy, heteroaryloxy, aminocarbonyl($C_1$-$C_6$)alkyl, ($C_1$-$C_6$)alkoxycarbonyl($C_1$-$C_6$)alkyl, carboxy($C_1$-$C_6$)alkyl, formylamino($C_1$-$C_6$)alkyl, carboxy($C_1$-$C_6$)alkylamino, —(CH$_2$)$_p$—NR$^{12}$CO—(CH$_2$)$_q$—NR$^9$R$^{10}$, —NHSO$_2$R$^{11}$, —OCH$_2$CH$_2$NR$^9$R$^{10}$—NHSO$_2$NR$^9$R$^{10}$, —SO$_2$NR$^9$R$^{10}$, —(CH$_2$)$_p$—NHCOR$^9$, OCONR$^9$R$^{10}$ and NR$^{12}$COOR$^{11}$;

$R^3$ is chosen from —CH$_3$, —CH$_2$CH$_3$, —CF$_3$, —CHF$_2$ and —CH$_2$F;

$R^5$ is chosen from H, —F, —OH, —CH$_3$, —OCH$_3$, —CF$_3$, —CN, —NH$_2$ and —C≡CH;

$R^2$ is
(a) phenyl and $R^7$ is chosen from H, halogen, nitro, acetyl, hydroxyethyl, —NH$_2$, —SCH$_3$, methoxycarbonyl, —SOCH$_3$, —SO$_2$CH$_3$, —OCH$_3$, —OCF$_3$, —CN, —CF$_3$, —CH$_2$OCH$_3$; or
(b) benzoxadiazole, benzodioxole, 2,2-difluorobenzodioxole, benzoxadiazole, benzodioxan, benzimidazole, oxadiazole, pyrazole, pyridine and pyridine N-oxide;

$R^9$ is chosen from H, ($C_1$-$C_6$)alkyl, halo($C_1$-$C_6$)alkyl, ($C_1$-$C_6$)alkoxycarbonyl, carboxy($C_1$-$C_6$)alkyl, ($C_1$-$C_6$)alkoxycarboxy($C_1$-$C_6$)alkyl;

$R^{10}$ is H, ($C_1$-$C_6$)alkyl, or taken together, or $R^9$ and $R^{10}$ together form a heterocycle optionally substituted with ($C_1$-$C_6$)alkyl;

p is 0 or 1, q is 0, 1 or 2, $R^{11}$ is linear ($C_1$-$C_6$)alkyl, $R^{12}$ is H or ($C_1$-$C_6$)alkyl; or two adjacent substituents together form an optionally substituted fused heterocyclic ring. When $R^5$ is H, $R^3$ is —CH$_3$ and $R^1$ is substituted or unsubstituted pyrazole, compounds that have been tested and found active are those in which $R^8$ is —NO$_2$ or $R^8$ represents two adjacent substituents that form an optionally substituted, fused heterocycle. When $R^5$ is H, $R^3$ is —CH$_3$, $R^2$ is —CF$_3$, and $R^1$ is

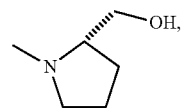

the compound does not appear to be active in initial screening. When $R^5$ is H, $R^3$ is —$CH_3$, $R^2$ is —$NO_2$, and $R^1$ is

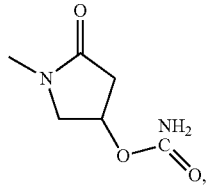

the compound does not appear to be active in initial screening. And, when $R^5$ is H, $R^3$ is —$CH_3$, $R^2$ is —$OCH_3$ or —$COCH_3$, and $R^1$ is

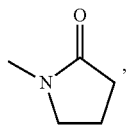

the compound does not appear to be active in initial screening.

One embodiment of compounds of the second genus has the formula

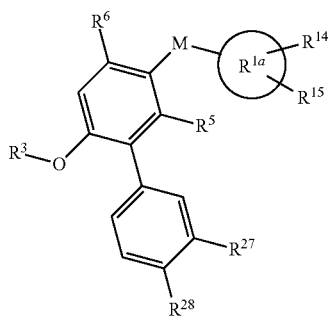

wherein
$R^{1a}$ is phenyl, five-membered heteroaryl, six-membered heteroaryl, 4-7 membered non-aryl heterocycle or fused bicycle;
$R^{14}$ is chosen from H, —$CH_2NHC(=O)NH_2$, —$NHC(=O)NH_2$, —$NHC(=O)NHEt$, —$CH_3$, —$CH_2CF_3$, —$CH_2NHC(=O)CH_3$, —$NHCH_3$, —$NHEt$, —$NH$(tBoc), —$CHO$, —$NHC(=O)NHCH_2CH_2Cl$, —$NHSO_2NH_2$, —$NHEt$, —$N(CH_3)_2$, —$NH_2$, —$COOH$, —$C(=O)NH_2$, —$CH_2C(=O)NH_2$, —$CH_2COOH$, —$CH_2COOEt$, —$CN$, —$OCH_3$, —$OC(=O)NH_2$, —$NH(CH_3)C(=O)NH_2$, halogen, —$CH_2NHC(=O)OEt$, —$NHSO_2CH_3$, —$N(SO_2CH_3)_2$, —$NHC(=O)OCH_3$, —$OH$, —$CH_2NHC(=O)N(CH_3)_2$, —$CH_2NH_2$, —$CH_2OH$, —$CH_2CH_2OH$, —$SO_2NH_2$, —$NHC(=O)NHCH_2COOH$, —$CH_2NHCHO$, —$NHC(=O)NHCH_2COOEt$, —$COOCH_3$, —$COOEt$, —$NHC(=O)NH(CH_2)_3COOEt$, —$NHC(=O)NH(CH_2)_2COOEt$, —$NH(Et)C(=O)OEt$, —$NHC(=O)NH(CH_2)_2COOH$, —$CH_2NHSO_2CH_3$, —$OEt$, —$NHC(=O)CH_2N(CH_3)_2$, —$NHC(=O)NH(CH_2)_3COOH$, —$NHC(=O)CH_2NH_2$, —$NHC(=O)CH_2CH_2NH_2$, —$NHC(=O)CH_2NH(tBoc)$, —$OCH_2CH_2N(CH_3)_2$, —$OCH_2CH_2OCH_3$, 3'-nitro-6-methoxybiphenyl-3-ylmethyl, tetrahydroimidazol-2-on-1-yl, 3-methyltetrahydroimidazol-2-one-1-yl, pyrazol-1-yl,

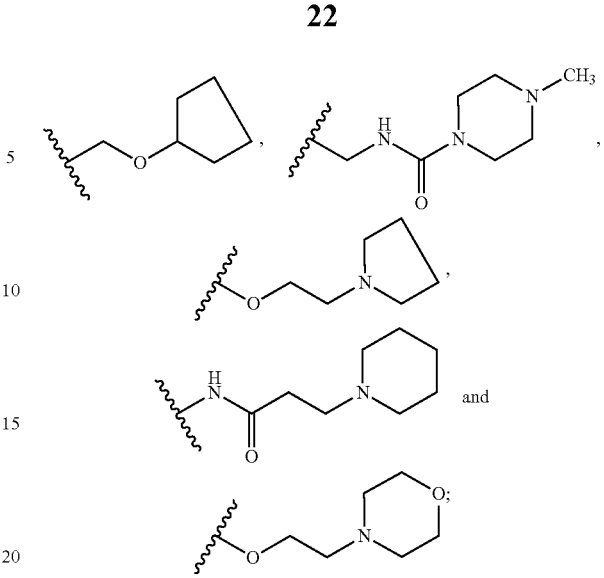

$R^{15}$ is chosen from H, $NO_2$, OH, $NH_2$, and —$NHSO_2NH_2$; or $R^{15}$ together with $R^{14}$ forms methylene dioxy;
$R^{27}$ is chosen from hydrogen, halogen, nitro, cyano, halo($C_1$-$C_6$)alkyl, hydroxy, ($C_1$-$C_6$)alkoxy, ($C_1$-$C_6$)oxaalkyl, carboxy, ($C_1$-$C_6$)alkoxycarbonyl, aminocarbonyl (—$CONH_2$), ($C_1$-$C_6$)alkylaminocarbonyl, acyl, hydroxy($C_1$-$C_6$)alkyl, halo($C_1$-$C_6$)alkoxy, amino($C_1$-$C_6$)alkyl, amino, ($C_1$-$C_6$)alkylamino, di[($C_1$-$C_6$)alkyl]amino, mercapto, ($C_1$-$C_6$)alkylthio, ($C_1$-$C_6$)alkylsulfinyl, ($C_1$-$C_6$) alkylsulfonyl, ($C_1$-$C_6$)alkylsulfonamido, acylamino, amidino, phenyl, benzyl, heterocyclyl, phenoxy, benzyloxy, and heteroaryloxy;
$R^{28}$ is chosen from H and F, or
$R^{27}$ together with $R^{28}$ forms a five-membered ring.

In further embodiments $R^{27}$ and $R^{28}$ represent a fused heterocycle at 3- and 4-positions so that the residue formed from $R^{27}$ and $R^{28}$ together with the phenyl to which they are attached is chosen from:

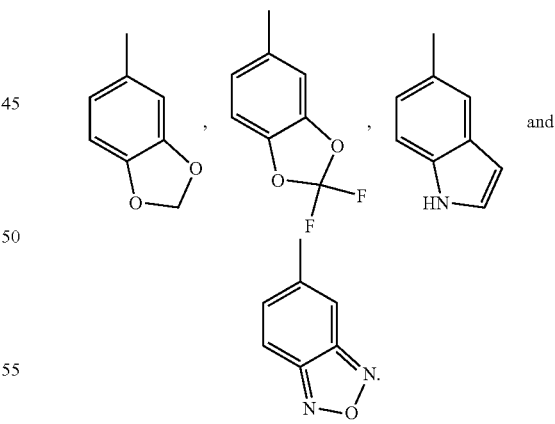

In other embodiments, $R^{27}$ is chosen from halogen, nitro, acetyl, hydroxyethyl, amino, methylthio, trifluoromethyl, methoxymethyl, methoxycarbonyl, trifluoromethoxy, cyano and 1,3,4-thiadiazol-2-yl, or taken together $R^7$ and $R^8$ are methylenedioxy or difluoromethylenedioxy. In the foregoing embodiments, $R^{1a}$ may be chosen from a benzene ring, a triazole, a pyridine or pyridine-N-oxide, a pyrazole, a tetrahydrothiophene, an imidazole, a pyrimidine, a thiadiazole, and an imidazopyridine.

In an embodiment of the invention, $R^5$ is fluoro, H, CN or OH. In other embodiments, $R^3$ is methyl or fluoromethyl.

Another embodiment of compounds of the invention have the formula

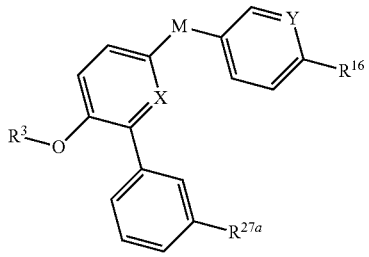

In these compounds $R^3$ is methyl or fluorinated methyl; Y is CH or N; $R^{27a}$ is chosen from halogen, cyano, acetyl, methylthio, nitro and trifluoromethyl; and $R^{16}$ is chosen from —NR$^{17}$C(=O)NR$^{18}$R$^{19}$ and

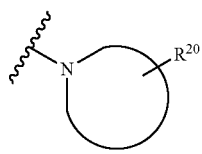

wherein

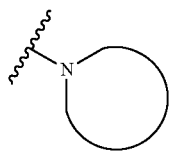 [SMILES: *N(C)C]

is a 4-7 membered ring heterocycle attached through its nitrogen; $R^{17}$, and $R^{18}$ are independently chosen from H, (C$_1$-C$_6$) alkyl and halo(C$_1$-C$_6$)alkyl; $R^{19}$ is chosen from H, (C$_1$-C$_6$) alkyl, halo(C$_1$-C$_6$)alkyl, —[(C$_1$-C$_6$)alkyl]COOH, and —[(C$_1$-C$_6$)alkyl]COO(C$_1$-C$_6$)alkyl; and $R^{20}$ is chosen from a carboxylic acid, a carboxamide, a carboxylic ester, a primary, secondary or tertiary alcohol and a primary, secondary or tertiary amine. Examples of a carboxylic acid, a carboxamide, a carboxylic ester, a primary, secondary or tertiary alcohol and a primary, secondary or tertiary amine include —COOH, —CONH$_2$, —CONHCH$_3$, —CON(CH$_3$)$_2$, —COOCH$_3$, —CH$_2$OH, —CH(CH$_3$)OH, —C(CH$_3$)$_2$OH, —CH$_2$NH$_2$, —CH(CH$_3$)NH$_2$ and —C(CH$_3$)$_2$NH$_2$. In a further embodiment, X is CH, CF or N→O; M is —CH$_2$— or —S—; $R^{27a}$ is chosen from chloro, cyano, acetyl and methylthio; and $R^{16}$ is chosen from —NR$^{17}$C(=O)NR$^{18}$R$^{19}$,

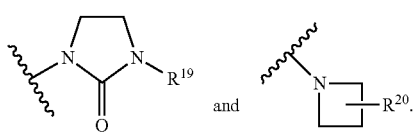

In a further embodiment, Y is CH; M is —CH$_2$—; $R^{27a}$ is chloro; and $R^{16}$ is —NR$^{17}$C(=O)NR$^{18}$R$^{19}$. In yet a further embodiment, $R^{16}$ is —NR$^{17}$C(=O)NR$^{18}$R$^{19}$ and $R^{17}$, $R^{18}$ and $R^{19}$ are all hydrogen.

Examples of the foregoing substituents on phenyl, five-membered heteroaryl, six-membered heteroaryl, 4-7 membered non-aryl heterocycle or fused bicycles ($R^{1a}$) may be described by the formula VI:

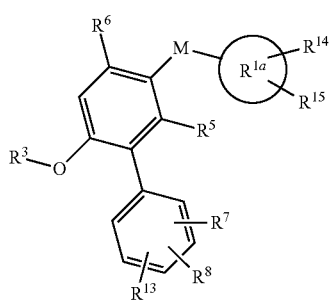

in which
$R^{14}$ is chosen from H, —CH$_2$NHC(=O)NH$_2$, —NHC(=O)NH$_2$, —NHC(=O)NHEt, —CH$_3$, —CH$_2$CF$_3$, —CH$_2$NHC(=O)CH$_3$, —NHCH$_3$, —NHEt, —NH(tBoc), —CHO, —NHC(=O)NHCH$_2$CH$_2$Cl, —NHSO$_2$NH$_2$, —NHEt, —N(CH$_3$)$_2$, —NH$_2$, —COOH, —C(=O)NH$_2$, —CH$_2$C(=O)NH$_2$, —CH$_2$COOH, —CH$_2$COOEt, —CN, —OCH$_3$, —OC(=O)NH$_2$, —NH(CH$_3$)C(=O)NH$_2$, halogen, —CH$_2$NHC(=O)OEt, —NHSO$_2$CH$_3$, —N(SO$_2$CH$_3$)$_2$, —NHC(=O)OCH$_3$, —OH, —CH$_2$NHC(=O)N(CH$_3$)$_2$, —CH$_2$NH$_2$, —CH$_2$OH, —CH$_2$CH$_2$OH, —SO$_2$NH$_2$, —NHC(=O)NHCH$_2$COOH, —CH$_2$NHCHO, —NHC(=O)NHCH$_2$COOEt, —COOCH$_3$, —COOEt, —NHC(=O)NH(CH$_2$)$_3$COOEt, —NHC(=O)NH(CH$_2$)$_2$COOEt, —NH(Et)C(=O)OEt, —NHC(=O)NH(CH$_2$)$_2$COOH, —CH$_2$NHSO$_2$CH$_3$, —OEt, —NHC(=O)CH$_2$N(CH$_3$)$_2$, —NHC(=O)NH(CH$_2$)$_3$COOH, —NHC(=O)CH$_2$NH$_2$, —NHC(=O)CH$_2$CH$_2$NH$_2$, —NHC(=O)CH$_2$NH(tBoc), —OCH$_2$CH$_2$N(CH$_3$)$_2$, —OCH$_2$CH$_2$OCH$_3$, 3'-nitro-6-methoxybiphenyl-3-ylmethyl, tetrahydroimidazol-2-on-1-yl, 3-methyltetrahydroimidazol-2-one-1-yl, pyrazol-1-yl,

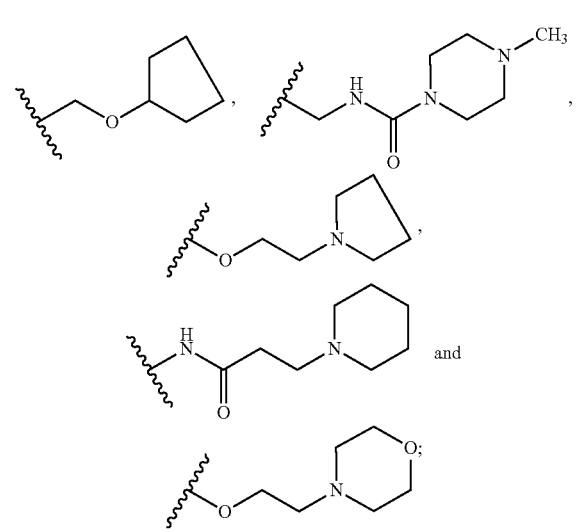

$R^{15}$ is chosen from H, NO$_2$, OH, NH$_2$, and —NHSO$_2$NH$_2$; or $R^{15}$ together with $R^N$ forms methylene dioxy.

In certain embodiments, $R^3$ is chosen from —$CH_3$, —$CH_2CH_3$, —$CF_3$, —$CHF_2$ and —$CH_2F$. In certain embodiments, $R^5$ is chosen from H, —F, —OH, —$CH_3$, —$OCH_3$, —$CF_3$, —CN, —$NH_2$ and —C≡CH. In certain embodiments, $R^7$, is chosen from H, halogen, nitro, acetyl, hydroxyethyl, —$NH_2$, —$SCH_3$, methoxycarbonyl, —$SOCH_3$, —$SO_2CH_3$, —$OCH_3$, —$OCF_3$, —CN, —$CF_3$, —$CH_2OCH_3$ and oxadiazole, and a fused heterocycle at 3- and 4-positions.

In certain embodiments of the compounds I, $R^5$ may be fluoro, H, CN or OH. In certain embodiments of the compounds I, $R^3$ may be methyl or fluoromethyl. (Fluoromethyl is intended to include $CHF_2$, $CH_2F$ and $CF_3$.)

All of the compounds, except for those identified in paragraph [0071], falling within the foregoing parent genus I and its subgenera are useful as PDE4 inhibitors, but not all the compounds are novel. In particular, certain known species fall within the genus I, although no utility in inhibiting PDE4 has been suggested for these species. It may be found upon examination that compounds that have been excluded from the claims are patentable to the inventors in this application; it may also be found that additional species and genera not presently excluded are not patentable to the inventors in this application. In either case, the exclusion of species and genera in applicants' claims are to be considered artifacts of patent prosecution and not reflective of the inventors' concept or description of their invention. The invention, in a composition aspect, is all active compounds of formula I except those that are in the public's possession. In particular, a search of the literature indicates that certain compounds in which X is N, $R^3$ is methyl, M is $CH_2$, $R^2$ is a five-membered ring heterocycle, and $R^1$ is a substituted tetralin are known. Similarly certain compounds in which X is N, $R^3$ is methyl, M is $CH_2$, $R^1$ is a five-membered ring heterocycle, and $R^2$ is a substituted tetralin are known.

In general, the compounds of the present invention may be prepared by the methods illustrated in the general reaction schemes as, for example, described below, or by modifications thereof, using readily available starting materials, reagents and conventional synthesis procedures.

Generally compounds of the Formula I, where $R^2$ is a substituted aryl/heteroaryl and the two biaryl groups are linked by a C—C bond, may be prepared from appropriately functionalized alkoxy-aryl ether derivatives containing desirable functionalities W, where W may for example be CH, N, COH, CF, etc (Route A, Scheme A1). The biaryl portion can be constructed first, typically via Suzuki or Stille coupling (G1->G2). In such case either Y=halogen or OSO2R(OTf, ONf) and the other reagent would be R2-B(OR)$_2$ or R2-SnR3' or vise versa, where R2-halogen is coupled with G1 containing boronate/boronic acid or trialkyltin as Y. When A is a carbon derived substituent, e.g. CH3, CH$_2$OH, CO2R", CN etc. these groups are converted to provide intermediate G3 where D is either a halogen or OTf, ONf, or OCOOR" (carbonate) such that substituent (R1) is introduced by employing a transition-metal catalyzed coupling reactions such as Suzuki, Stille or Negishi reaction. An alternative route to compounds of type G4 involves essentially reversing the order of incorporation of R1 and R2 fragments. The route B, as highlighted in Scheme A1, allows formation of G6, where the R2 fragment is introduced at later stage in the sequence, analogous to chemistries employed for G1-G2, for examples Suzuki, Stille coupling.

One may attach R1, which may be aryl, heterocyclic, acyclic, aliphatic, or any other desirable variety of functionality, to the central aromatic ring (Ar) by a wide rage of tether groups M. The central aromatic ring (Ar) may be a biaryl ring system with a R2 group already attached, or the R2 group may be attached subsequent to that of R1. The linker group M may be a linear chain of one or more atoms consisting of C, N, O, or S. The linker group M may also consist of functionalities including, but not limited to amide, sulfonamide, sulfone, or ketone. It is evident to one skilled in the art that many of these exemplified functional groups may be attached in more than one way, for example, Ar—CH2-O—R1 or Ar—O—CH2-R1. Considering those compounds with M groups such as S or O, the heteroatom may originally be in the Ar or the R1 group. Some examples of how the two groups can then be joined are nucleophilic aromatic substitution, metal-promoted coupling, and nucleophilic displacement (Scheme A2). Chemical reactivity of the Ar and R1 groups should of course be considered when determining which partner contains the linker heteroatom, and which shall serve as the reaction partner. For

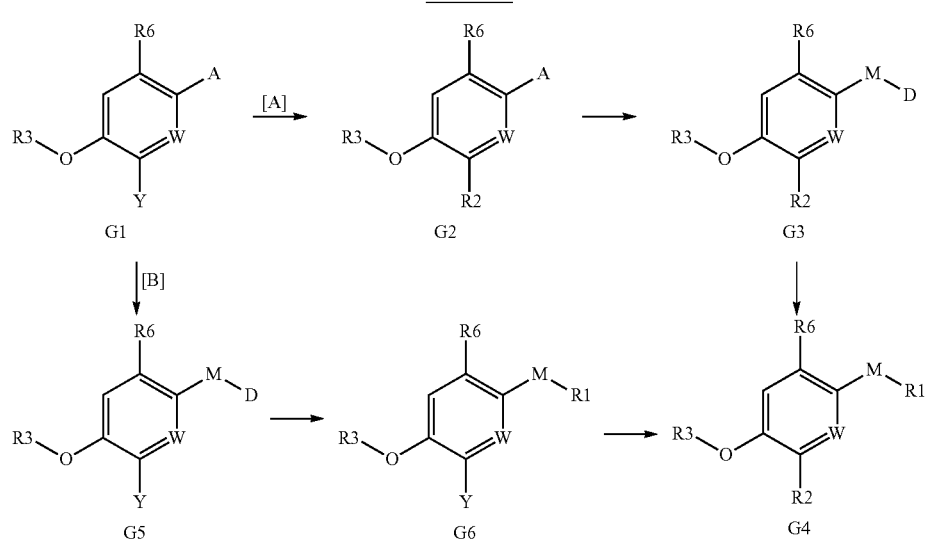

Scheme A1 example, it is well understood that in aromatic ring systems an electron-withdrawing group para- or ortho- to a leaving group (e.g. halogen) allows susceptibility of the aromatic halogen for nucleophilic displacement. Thus, Ar1 group containing NO2, CO2R, ketone, CN etc. would allow formation of aryl-M-aryl(heteroaryl) intermediates. The linker group M may also be subject to further elaboration. For example, sulfides may be oxidized to sulfoxides and sulfones and amines may be subjected to alkylation or reductive amination. Well known synthetic transformations can be used to create tether groups M such as ether amide, sulfonamide, and the like. The functional group location in the precursor Ar and R1 groups can be used to dictate the nature and type of the linkage (e.g. alternative ethers), as mentioned above.

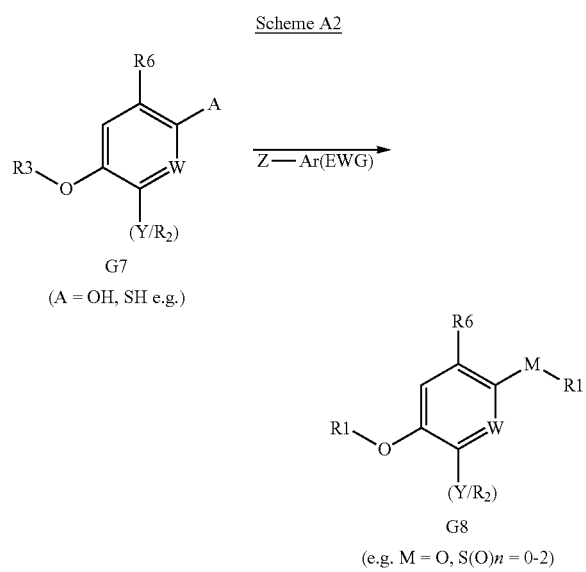

The key fragments Ar and R1 could also be joined using non transition-metal catalyzed C—C bond forming coupling reactions. When A=H, Fridele-Crafts acylation or alkylation can be employed to combine the Ar and R1 groups. Given the chemical reactivity of the aromatic para-methoxy group in the Ar ring, Friedel-Crafts acylation would typically involve a suitably elaborated R1-COCl (acid chloride) group to form compound G10. In this case J=CO, which can be reduced to the secondary alcohol (typically with hydride-based reducing agents). If a R'MgX or other such organometallic agent is used, the J=CO group can be transformed into the tertiary alcohol with simultaneous addition of an R' group. In another variation, the J=CO group can be converted into the imine or oxime using standard procedures and addition of an R'MgX-type reagent results in the tertiary amine derivative. If desired, the J=CO group can be reduced, using a number of well established methods, to the CH2 group (M). In another variation, when A=H, an aldehyde group can be introduced using either Vilsmeier reaction or using Lewis acid (TiCl4, BF3.OEt2 etc.) mediated reaction with dichloromethylmethyl. The aldehyde functionality can subsequently be transformed into a suitable transition-metal catalyzed coupling reaction partner. Alternatively the aldehye could be used for Wittig reaction forming olefin or CH2CH2 linkage to incorporate R1. In yet another variation, substituent "A" can be various types of carbonyl (aldehyde or ketone) or imine groups. In one example, addition of a suitably elaborated organometallic R1 group (e.g. R1-MgX) to aldehyde G9 (A=CHO) would result in G10 with J=C(H)OH. Reduction of this alcohol gives rise to G11 with M=CH2. Similar types of transformations could be employed by one skilled in the art if G9 contained A=ketone or imine.

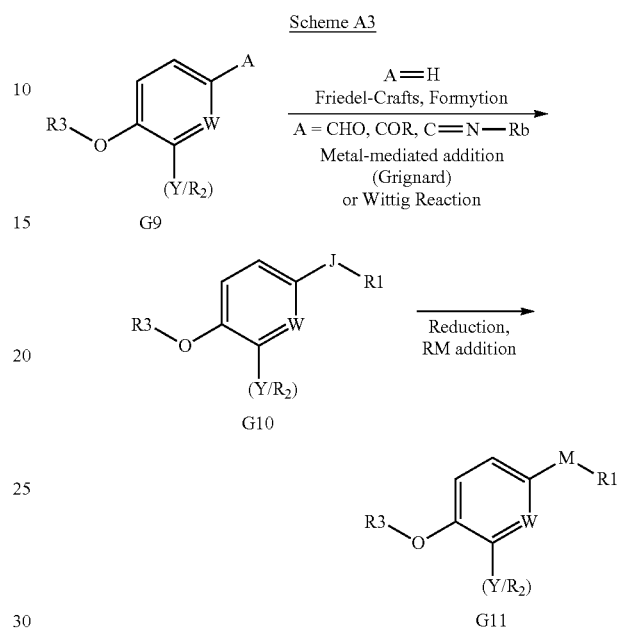

Alternatively, the C—C bond forming reaction between the Ar and R1 groups could be accomplished by displacement of a leaving group on the R1 by a nucleophile present in the tether region M (Scheme G4) of G12. The activating group could be either removed to provide Z=H (Z=CO2R—decarboxylation of or Z=CN, decyanation) or these could be further transformed to other functional groups e.g. Z=CH2)H or CH2NH2. When M-Z is CH2-halide or CH2-O-sulfonate, R1 fragment can be introduced via formation of ether linkage. This allows attachment of R1 to the central aromatic ring by spacers (M) of varying lengths and compositions. (Scheme A4)

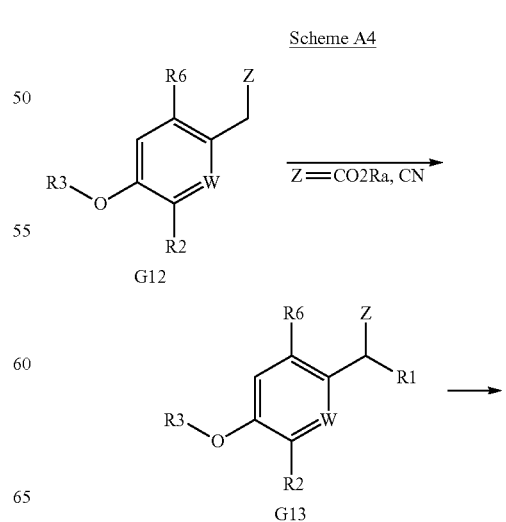

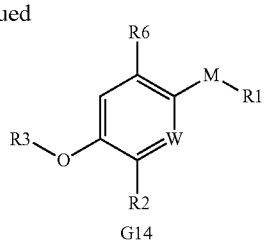

G14

The R1 group could also be assembled form an acyclic intermediate to form a heterocylic or heteroaromatic ring. Examples of these chemistries include formation of 5-membered heteroaryls such as oxadiazole, thiadiazole, triazole (G17) form acyl hydrazide (G16); thiazole from 2-halo-ketone or dipolar cycloaddition reactions from olefin or acetylic group to form 5-membered heterocycles or 5-membered heteroaryls (G18) [Scheme A5]. Alternatively the 6-membered heteroaryl or heterocyclic rings could be formed using Diels-Alder or hetero-Diels-Alder chemistries using appropriately substituted alkyl aryl ether bearing either a dienophile or a diene functionalities. The necessary acyclic precursors could be synthesized by standard methods according to previously described intermediates (e.g. aldehyde, alkyl halide) schemes.

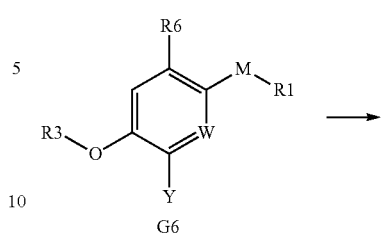

Scheme A6

G6

G19

The diverse selection of substituents present in R1 and R2 could be formed by standard functional group transformations that are well know in the art. Some of these include

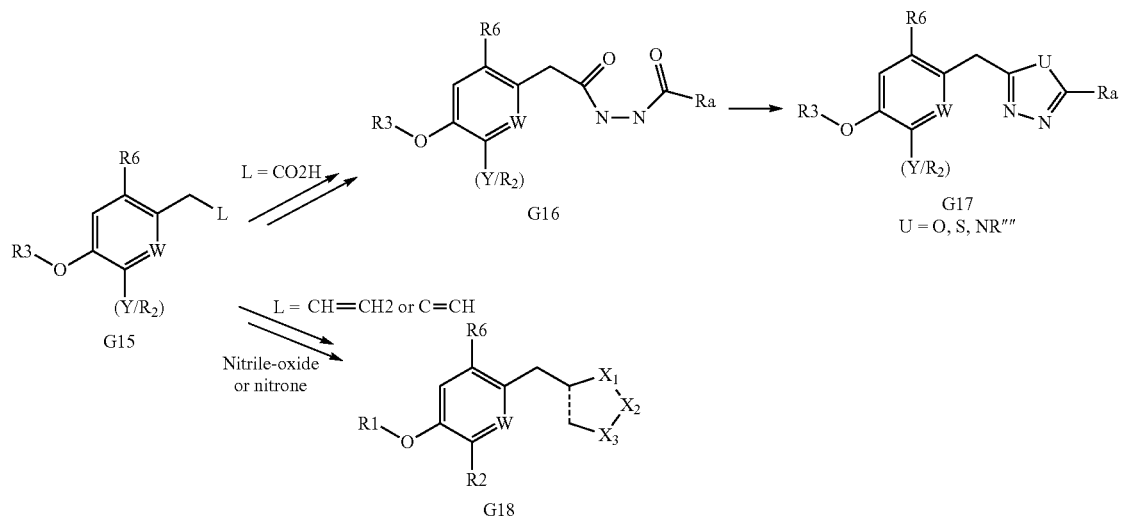

Scheme A5

G15

G16

G17
U = O, S, NR''''

G18

----- single or double bond
e.g. isoxazole, isoxazoline etc.

When the R2 group is linked to the Ar group thru a heteroatom (N), these biaryl systems could be prepared by organometallic mediated aza-coupling reactions or other nucleophilic aromatic substitution-based procedures (Scheme G6). The Ar—(N)R2 biaryl may be formed from intermediate G6 where R1 group is already in place. Alternatively, the (N)R2 ring can be added to the central Ar ring first, R1 can be attached through a variety of means using approaches described in previous schemes. Examples of (HN)R2 heteroaryl or heterocyclic rings include, but not limited to, imidazole, pyrrole, pyrazole, pyrrolidine, or triazole. The R2 functional group can be fully elaborated prior to addition of the (N)R2 to the Ar, or suitably elaborated after formation of the key C—N bond.

formation of amide, sulfonamide, ureas, imidazolone, oxazolones, carbamates from the R2, R3, or Ar ring fragments bearing appropriate amine, carboxylic acid, alcohol, or phenol groups. A particularly useful aromatic ring functionalization technique, in which either the R2 or R1 rings can be employed, is the nucleophilic displacement of ortho-halo N-containing aromatic rings (G20, scheme A7). Examples of ring substrates useful in this type of transformation include 2-halo-pyridine, 2-halo-pyrimidine and 2-halo-imidazole. Additionally, other leaving groups besides halogens (X) may be used such as sulfonate esters (OTf, ONf). These displacement reactions can be carried out using alkali or tertiary amine bases, or could be mediated through the use of an organometallic reagent such as palladium or aluminum reagents. Examples of nucleophiles (R″) useful in this type of transformation include amines (primary, secondary, acyclic, or cyclic), alcohols, phenols, NH-containing heterocycle groups (imidazole, or pyrrazole) groups capable of performing nucleophilic displacement.

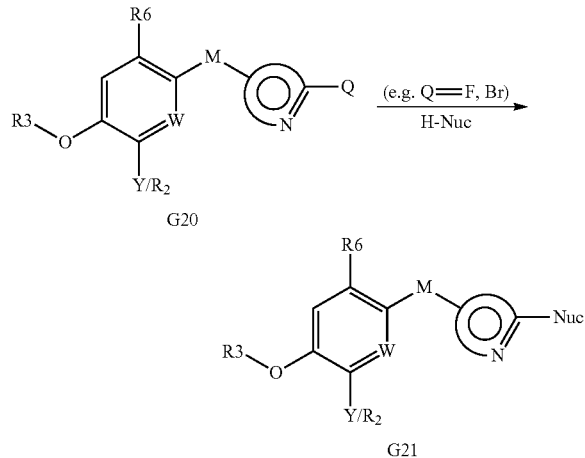

Scheme A7

When R1 group contains additional functional groups, such as amine, ester/acid/alcohols many of which may have be masked or protected during the previous chemistries, these could be used for further functional group manipulations. A wide variety of modifications of R1 functionalities may be achieved using well established synthetic procedures including, but not limited to, alkylation, reductive amination, nucleophilic displacement, cyclization, saponification, and oxidation/reduction. Additionally, like these functional group manipulations, Ar1 mono-cyclic may be further transformed to a bi-cyclic ring. Examples of such ring transformations may be represented by elaboration of pyridine derivatives to imidazo[1,2-a]pyridine and imidazo[1,5-a]pyridine. These functional group manipulations and bicyclic ring elaborations may be accomplished at any chemically suitable point in the synthesis prior to or post incorporation of R2 or other synthetic transformations.

These above transformations could be carried out from alkylated phenols containing or lacking fluoro substituents in the central Ar ring. Several of these approaches are also applicable to 3-alkoxy pyridines as the Ar ring starting materials. The non-limiting specific examples described in later schemes are meant to serve as examples of the broad scope of possible reactions. Similarly, analogs where W=CH2OH, COOH, CN, CONH2 etc. (or suitably protected precursors) could be derived by following similar chemistries (schemes A1-A7) and these functional groups could be derived form an ester or amide derived starting material.

The following examples of compounds of the invention were prepared.

TABLE 1

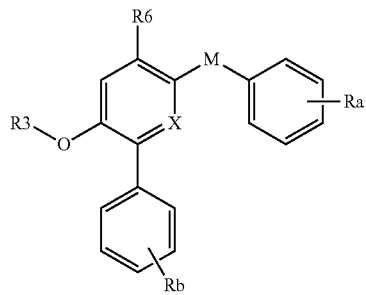

| Example | X | R3 | M | Rb | Ra |
|---------|------|-------|-------|----------|----------|
| P-001 | C—H | CH3 | CH2 | 3-NO2 | 4-F |
| P-002 | C—H | CH3 | CH2 | 3-CO2CH3 | 4-F |
| P-003 | C—H | CH3 | CH2 | 3,4-OCH2O | 4-F |
| P-004 | C—H | CH3 | CH2 | 3,4-NON | 4-F |
| P-013 | C—H | CH3 | CH2 | 3,4-NON | 3,4-NON |
| P-021 | N | CH3 | CH2 | 3-NO2 | 3,4-OCH2O |
| P-023 | N | CH3 | CH2 | 3-NO2 | 4-F |
| P-049 | C—F | CH3 | C=O | 3-NO2 | 4-F |
| P-050 | C—F | CH3 | CH2 | 3-NO2 | 4-F |
| P-051 | C—F | CH3 | CH(OH) | 3-NO2 | 4-F |
| P-054 | N—O | CH3 | CH2 | 3-NO2 | 4-F |
| P-057 | N | CHF2 | CH2 | 3-NO2 | 4-F |
| P-065 | N | CH3 | CH2 | 3-CF3 | 4-F |
| P-067 | C—H | CHF2 | CH2 | 3-NO2 | 4-F |
| P-079 | C—H | CF3 | CH(OH) | 3-NO2 | 4-F |
| P-080 | C—H | CF3 | CH2 | 3-NO2 | 4-F |
| P-093 | C—H | CH3 | CH(OH) | 3-NO2 | 4-F |
| P-094 | C—H | CH3 | CH2 | 3-NO2 | 4-F |
| P-095 | C—OCH3 | CH3 | C=O | 3-NO2 | 4-F |
| P-096 | C—OH | CH3 | C=O | 3-NO2 | 4-F |
| P-097 | C—OCH3 | CH3 | CH2 | 3-NO2 | 4-F |
| P-098 | C—F | CH3 | CH2 | 3-NH2 | 4-F |
| P-099 | C—OH | CH3 | CH2 | 3-NO2 | 4-F |
| P-102 | C—H | CH3 | CH2 | 3-NO2 | 3-OH |
| P-103 | C—H | CH3 | CH2 | 3-NO2 | 3-CH2OH |
| P-105 | C—H | CH3 | CH2 | 3-NO2 | 2-OH |

TABLE 1-continued

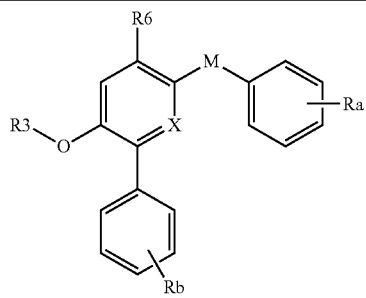

| Example | X | R3 | M | Rb | Ra |
|---|---|---|---|---|---|
| P-107 | C—F | CH3 | CH2 | 3-NO2 | 4-NHCOCH3 |
| P-112 | C—H | CH3 | CH2 | 3-NO2 | 4-NHCOOC(CH3)3 |
| P-113 | C—H | CH3 | CH2 | 3-NO2 | 4-NH2 |
| P-114 | C—H | CH3 | CH2 | 3-NO2 | 4-NHCOCH3 |
| P-116 | C—F | CHF2 | CH2 | 3-NO2 | 4-F |
| P-117 | C—H | CH3 | CH(OH) | 3-[2-Oxadiazole] | 4-F |
| P-118 | C—H | CH3 | CH2 | 3-[2-Oxadiazole] | 4-F |
| P-119 | C—H | CH3 | CH2 | 3-NO2 | 2-OH, 4-F |
| P-121 | C—H | CH3 | CH2 | 3-NO2 | N(SO2CH3)2 |
| P-122 | C—H | CH3 | CH2 | 3-NO2 | NHCOCH2CH2COOH |
| P-123 | C—H | CH3 | CH2 | 3-NO2 | 4-NHSO2CH3 |
| P-133 | C—H | CH3 | CH2 | 3-NO2 | 2-CH2NH2 |
| P-134 | C—H | CH3 | CH2 | 3-NO2 | 2-CH2OH |
| P-135 | C—H | CH3 | CH2 | 3-NO2 | 3-CH2OH, 4-F |
| P-136 | C—F | CH3 | CH2 | 3-NO2 | 4-NH2 |
| P-137 | C—OH | CH3 | CH(OH) | 3-NO2 | 4-CN |
| P-138 | C—OH | CH3 | CH2 | 3-NO2 | 4-CN |
| P-139 | C—F | CH3 | CH2 | 3-Br | 4-F |
| P-140 | C—H | CH3 | CH2 | 3-COCH3 | 4-F |
| P-141 | C—H | CH3 | CH2 | 3,4-OCF2O | 4-F |
| P-142 | C—H | CH3 | CH2 | 3-NO2 | 4-OH |
| P-143 | C—H | CH3 | CH2 | 3-NO2 | 4-NHCOCH2NHCOOC(CH3)3 |
| P-144 | C—H | CH3 | CH2 | 3-NO2 | 4-NHCOCH2N(CH3)2 |
| P-145 | C—H | CH3 | CH2 | 3-NO2 | 4-NHCOCH2NH2 |
| P-146 | C—H | CH3 | CH2 | 3-NO2 | 4-NHCOCH2CH2N(CH2)5 |
| P-147 | C—F | CH3 | CH2 | 3-NO2 | 4-NHCOCH2N(CH3)2 |
| P-148 | C—F | CH3 | CH2 | 3-NO2 | 4-CH2NH2 |
| P-151 | C—H | CH3 | CH2 | 3-SCH3 | 4-F |
| P-157 | C—OH | CH3 | CH2 | 3-NO2 | 4-N(CH3)2 |
| P-158 | C—H | CH3 | CH2 | 3-NO2 | 2-CH2NHCHO |
| P-159 | C—H | CH3 | CH2 | 3-NO2 | 4-NHCOCH2CH2NH2 |
| P-160 | C—H | CH3 | CH2 | 3-NO2 | 3-CH2NHCOOC(CH3)3 |
| P-161 | C—H | CH3 | CH2 | 3-NO2 | 3-CH2NH2 |
| P-163 | C—CN | CH3 | CH2 | 3-NO2 | 4-F |
| P-164 | C—H | CH3 | CH2 | 3-NO2 | 4-OCH2CH2N(CH3)2 |
| P-165 | C—H | CH3 | CH2 | 3-NO2 | 4-OCH2CH2-N(pyrrolidine) |
| P-166 | C—H | CH3 | CH2 | 3-NO2 | 4-OCH2CH2-N(piperidine) |
| P-167 | C—F | CH3 | CH2 | 3-NH2 | 4-NHCOCH3 |
| P-168 | C—F | CH3 | CH2 | 3-Br | 4-NHCOCH3 |
| P-170 | C—H | CH3 | CH2 | 3-COCH3, 4-OCH3 | 4-F |
| P-171 | C—H | CH3 | CH2 | 3-NO2 | 4-OCH2CH2-N(morpholine) |
| P-173 | C—OH | CH3 | CH2 | 3-NO2 | 4-(N-pyrazole) |
| P-175 | C—F | CH3 | CH2 | 3-NO2 | 4-CH2NHCOCH2N(CH3)2 |
| P-176 | C—NH2 | CH3 | CH2 | 3-NO2 | 4-F |
| P-180 | C—OH | CH3 | CH2 | 3-NO2 | 4-CHO |
| P-181 | C—F | CH3 | CH2 | 3-NO2 | 4-NHCONH2 |
| P-183 | C—OH | CH3 | CH2 | 3-NO2 | 4-CH2OH |
| P-187 | C—F | CH3 | CH2 | 3-Cl | 4-F |
| P-189 | C—H | CH3 | CH2—S | 3-NO2 | 4-F |
| P-190 | C—OH | CH3 | CH2 | 3-NO2 | 4-NHCOCH3 |
| P-191 | C—H | CH3 | CH2—SO2 | 3-NO2 | 4-F |
| P-192 | C—H | CH3 | CH2—SO | 3-NO2 | 4-F |
| P-193 | C—H | CH3 | O | 3-NO2 | 4-F |
| P-194 | C—F | CH3 | CH2—O | 3-Br | 4-NHCOCH3 |
| P-199 | C—F | CH3 | CH2—O | 3-Br | 4-NH2 |
| P-200 | C—F | CH3 | CH2 | 3-Br | 4-NHSO2CH3 |
| P-202 | C—F | CH3 | CH2—O | 3-Br | 4-NHSO2CH3 |
| P-216 | C—F | CH3 | CH2 | 3-Cl | 4-OH |
| P-217 | C—F | CH3 | CH2 | 3-Cl | 3-OH |
| P-219 | C—F | CH3 | CH2 | 3-Cl | 4-OCH2CH2-N(morpholine) |
| P-220 | C—F | CH3 | CH2 | 3-Cl | 3-OCH2CH2-N(morpholine) |
| P-221 | C—F | CH3 | CH2 | 3-Cl | 4-OCONH2 |
| P-222 | C—F | CH3 | CH2 | 3-Cl | 3-OCONH2 |

TABLE 1-continued

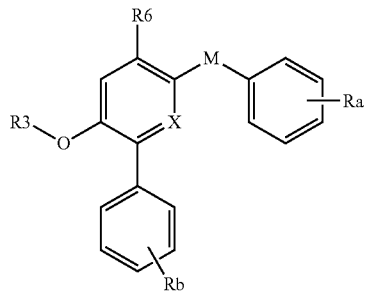

| Example | X   | R3     | M      | Rb     | Ra                   |
|---------|-----|--------|--------|--------|----------------------|
| P-227   | C—F | CH3    | CH2    | 3-Cl   | 4-NHSO2CH3           |
| P-228   | C—F | CH3    | CH2    | 3-Cl   | 4-NHCOCH3            |
| P-230   | C—H | CH3    | O      | 3-Cl   | 4-F                  |
| P-231   | C—F | CH3    | CH2—O  | 3-Cl   | 3-NHCOCH3            |
| P-232   | C—F | CH3    | CH2—O  | 3-Cl   | 3-NH2                |
| P-233   | C—F | CH3    | CH2    | 3-Cl   | 3-NHCOCH3            |
| P-234   | C—F | CH3    | CH2    | 3-Cl   | 3-NH2                |
| P-237   | C—F | CH3    | CH2    | 3-NO2  | 4-CH2NHCONH2         |
| P-238   | C—F | CH3    | CH2    | 3-Cl   | 4-NHCOCH2N(CH3)2     |
| P-239   | C—F | CH3    | CH2    | 3-Cl   | 4-NHSO2NH2           |
| P-240   | C—H | CH3    | CH2    | 3-Cl   | 4-CONH2              |
| P-241   | C—H | CH3    | CH2    | 3-Cl   | 4-N(CH3)2            |
| P-242   | C—F | CH3    | CH2    | 3-Cl   | 3,4-OCH2O            |
| P-243   | C—F | CH3    | CH2    | 3-Cl   | 4-NHCONH2            |
| P-246   | C—H | CH3    | CH2    | 3-Cl   | 4-NHSO2CH3           |
| P-247   | C—H | CH3    | CH2    | 3-Cl   | 4-NHCH2CH3           |
| P-249   | C—F | CH3    | CH2    | 3-COCH3| 4-NHSO2CH3           |
| P-250   | C—F | CH3    | CH2    | 3-Cl   | 4-NHCONHCH2CH3       |
| P-254   | C—F | CH3    | O      | 3-Cl   | 4-NHSO2CH3           |
| P-255   | C—H | CH3    | CH2    | 3-Cl   | 3-NH2                |
| P-256   | C—F | CH3    | CH2    | 3-Cl   | 3-OH, 4-NH2          |
| P-257   | C—F | CH3    | CH2    | 3-Cl   | 3-OH, 4-NO2          |
| P-260   | C—H | CH3    | NH     | 3-NH2  | 4-NH2                |
| P-261   | C—F | CH3    | CH2    | 3-COCH3| 4-NH2                |
| P-262   | C—F | CH3    | CH2    | 3-Cl   | 3-OH, 4-NHCONH2      |
| P-264   | C—F | CH3    | CH2    | 3-Cl   | 3-OH, 4-NHSO2CH3     |
| P-265   | C—F | CH3    | CH2    | 3-Cl   | 3-OSO2CH3, 4-NHSO2CH3|
| P-266   | C—H | CH3    | CH2    | 3-Cl   | 4-SO2NH2             |
| P-267   | C—H | CH3    | NH     | 3-COCH3| 4-NHSO2CH3           |
| P-268   | C—H | CH3    | NH     | 3-COCH3| 4-NHCONH2            |
| P-269   | C—F | CH3    | CH2    | 3-COCH3| 4-NHCONH2            |
| P-270   | C—H | CH3    | CH2    | 3-Cl   | 3-NHCONH2            |
| P-271   | C—H | CH3    | CH2    | 3-Cl   | 3-NHSO2CH3           |
| P-273   | C—F | CH3    | CH2    | 3-Cl   | 4-NHCOCH2NH2         |
| P-274   | C—F | CH3    | CH2    | 3-Cl   | 3-F, 4-CN            |
| P-275   | C—F | CH3    | CH2    | 3-Cl   | 3-F, 4-CH2NH2        |
| P-276   | C—F | CH3    | CH2    | 3-Cl   | 3-OH, 4-NHSO2NH2     |
| P-280   | C—H | CH3    | NH     | 3-Cl   | 4-NH2                |
| P-282   | C—H | CH3    | CH2    | 3-Cl   | 3-CONH2              |
| P-283   | C—F | CH3    | O      | 3-COCH3| 4-NH2                |
| P-286   | C—F | CH3    | CH2    | 3-Cl   | 3-F, 4-CH2NHSO2CH3   |
| P-287   | C—F | CH3    | CH2    | 3-Cl   | 3-F, 4-CH2NHCONH2    |
| P-288   | C—H | CH3    | N(CH3) | 3-Cl   | 4-NH2                |
| P-289   | C—F | CH3    | CH2    | 3-Cl   | 4-NHCOCH2NHCH3       |
| P-293   | C—H | CH3    | N(CH3) | 3-Cl   | 4-NHCONH2            |
| P-294   | C—H | CH3    | NH     | 3-Cl   | 4-NHCONH2            |
| P-295   | C—F | CH3    | CH2    | 3-Cl   | 3-OH, 4-CN           |
| P-296   | C—F | CH3    | CH2    | 3-Cl   | 3-OH, 4-CH2NH2       |
| P-299   | C—F | CH3    | CH2    | 3-Cl   | 3-OH, 4-CH2NHSO2CH3  |
| P-300   | C—F | CH3    | CH2    | 3-Cl   | 3-F, 4-CH2NHCOCH3    |
| P-301   | C—F | CH3    | CH2    | 3-Cl   | 3-OH, 4-CH2NHCONH2   |
| P-302   | C—F | CH3    | CH2    | 3-Cl   | 3-OH, 4-CH2NHCOCH3   |
| P-303   | C—F | CH3    | CH2    | 3-Cl   | 4-N(CH3)2            |
| P-304   | C—F | CH3    | CH2    | 3-COCH3| 4-SO2NH2             |
| P-305   | C—F | CH3    | CH2    | 3-COCH3| 4-CONH2              |
| P-311   | C—F | CH3    | CH2    | 3-Cl   | 4-NHCH3              |
| P-312   | C—F | CH3    | CH2    | 3-COCH3| 4-NHSO2NH2           |
| P-313   | C—F | CHF2   | CH2    | 3-Br   | 4-NHCOCH3            |
| P-316   | C—F | CHF2   | CH2    | 3-NO2  | 4-NHCONH2            |
| P-317   | C—F | CHF2   | CH2    | 3-Br   | 4-NH2                |
| P-319   | C—F | CH3    | CH2    | 3-COCH3| 4-COOCH3             |
| P-320   | C—F | CH3    | CH2    | 3-COCH3| 4-COOH               |
| P-322   | C—F | CH2CH3 | CH2    | 3-Br   | 4-NHCOCH3            |

TABLE 1-continued

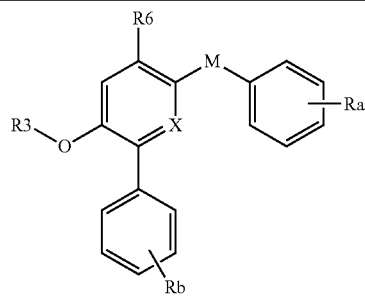

| Example | X   | R3       | M          | Rb              | Ra                   |
|---------|-----|----------|------------|-----------------|----------------------|
| P-323   | C—F | CHF2     | CH2        | 3-Br            | 4-NHCONH2            |
| P-324   | C—F | CH3      | CH2        | 3-Cl            | 3-OH, 5-NH2          |
| P-326   | C—F | CH3      | CH2        | 3-COCH3         | 4-N(CH3)2            |
| P-329   | C—F | CH3      | CH2        | 3-COCH3         | 3-F, 4-CH2NHCOCH3    |
| P-330   | C—F | CH3      | CH2        | 3-COCH3         | 3-F, 4-CH2NHCONH2    |
| P-331   | C—F | CH3      | CH2        | 3-COCH3         | 4-NHCH3              |
| P-334   | C—F | CH2CH3   | CH2        | 3-COCH3         | 4-NH2                |
| P-335   | C—F | CH2CH3   | CH2        | 3-COCH3         | 4-NHCONH2            |
| P-338   | C—F | CH3      | CH2        | 3-COCH3         | 4-N(CH3)CONH2        |
| P-340   | C—F | CH3      | CH2        | 3-CH(OH)CH3     | 4-NHCONH2            |
| P-347   | C—F | CH3      | CH2        | 3-Br            | 4-NHCONH2            |
| P-348   | C—F | CH3      | CH2        | 3-Br            | 4-NHCONHCH2COOH      |
| P-349   | C—F | CH3      | CH2        | 3-Br            | 4-NHCONHCH2CH2COOH   |
| P-376   | N   | CH3      | CH2        | 3-Cl            | 4-NHCONH2            |
| P-378   | C—H | CH3      | CH2        | 3-Cl            | 4-NHCONH2            |
| P-380   | C—H | CH3      | CH2        | N1-(3-Cl Pyrrazole) | 4-F              |
| P-381   | C—F | CH3      | CH2        | N-Pyrrolidine   | 4-NHCOCH3            |
| P-385   | C—H | CH3      | CH2        | N-morpholine    | 4-F                  |
| P-390   | C—F | CH3      | CH2        | N-morpholine    | 4-NHCOCH3            |
| P-394   | C—H | CH3      | CH2        | 3-CN            | 4-NHCONH2            |
| P-404   | C—F | CH3      | CH2        | 3-Cl            | 4-(N1-tetrazole)     |
| P-413   | C—F | CH3      | CH2        | 3-CN            | 4-NHCONH2            |
| P-418   | C—F | CH3      | CH=CH      | 3-Cl            | 4-F                  |
| P-419   | C—F | CH3      | CH=CH      | 3-Cl            | 4-F                  |
| P-420   | C—H | CHF2     | CH2        | 3-Cl            | 4-NHCONH2            |
| P-421   | CH  | H        | CH2        | 3-Cl            | 4-NHCONH2            |
| P-434   | C—F | CH3      | C=O        | 3-Cl            | 4-NHCONH2            |
| P-441   | C—F | CH3      | C(CH3)(OH) | 3-Cl            | 4-NHCONH2            |
| P-447   | C—H | CH3      | S          | 3-Cl            | 4-NH2                |
| P-448   | C—H | CH3      | S          | 3-Cl            | 4-NHCONH—Et          |
| P-449   | C—H | CH3      | SO         | 3-Cl            | 4-NHCONH—Et          |
| P-450   | C—H | CH3      | SO2        | 3-Cl            | 4-NHCONH—Et          |
| P-451   | C—F | H        | CH2        | 3-NO2           | 4-F                  |
| P-453   | C—F | CH3      | CH2        | 3-Br            | 4-NH2                |
| P-454   | C—H | CH3      | CH2        | 3-Cl            | 4-NH(2-Thiazolyl)    |
| P-466   | C—F | CH3      | CH2        | 3-Cl            | 4-NH(2-Thiazolyl)    |
| P-467   | C—H | CH3      | CH2        | 3-Cl            | 4-NH(N-Methyl 2-imidazolyl) |
| P-468   | C—F | H        | CH2        | 3-Cl            | 4-NHCOCH3            |
| P-476   | C—H | CH3      | CH2        | 3-Cl            | 4-NHCH3              |
| P-477   | C—H | CH3      | CH2        | 3-Cl            | 3-NHCOCH3            |
| P-453   | C—F | CH3      | CH2        | 3Br             | 4-NH2                |
| P-494   | C—H | H        | CH2        | 3-NO2           | 4-F                  |
| P-496   | C—F | H        | CH2        | 3-Br            | 4-F                  |
| P-497   | C—F | CH3      | CH2        | 3-Br            | 4-F                  |
| P-498   | C—H | CH3      | CH2        | 3-NO2           | 4-OH                 |
| P-501   | C—H | CH3      | CH2        | 3-NO2           | 2-CH2NHCOH           |
| P-502   | C—F | CH3      | CH2        | 3-NO2           | 4-CH2NHCOCH2NMe2     |
| P-505   | C—F | CH3      | CH2—NH     | 3-Cl            | 4-NHACc              |
| P-508   | C—F | H        | CH2        | 3-NO2           | 4-NHCONH2            |
| P-516   | C—H | CD3      | CH2        | 3-Cl            | 4-NHCONH2            |
| P-530   | C—F | CH3      | C(CH3)(OH) | 3-Cl            | 4-NHAc               |
| P-532   | C—F | CH3      | CD2        | 3-Cl            | 4-NHCONH2            |
| P-537   | C—F | CH3      | CD(OH)     | 3-Cl            | 4-NO2                |
| P-538   | C—F | CH3      | CD(OH)     | 3-Cl            | 4-NH2                |
| P-539   | C—F | CH3      | CD(OH)     | 3-Cl            | 4-NHCONH2            |
| P-540   | C—H | CH3      | S          | 3-Cl            | 4-NHCONH2            |
| P-541   | C—H | CH2CH3   | CH2        | 3-Cl            | 4-NHCONH2            |
| P-542   | C—H | H2NCH2CH2— | CH2      | 3-Cl            | 4-NHCONH2            |
| P-543   | C—H | 2-(Tetarhydro-furanyl)CH2 | CH2 | 3-Cl    | 4-NHCONH2            |
| P-547   | C—H | CH3      | CD2        | 3-Cl            | 4-NHCONH2            |

TABLE 1-continued

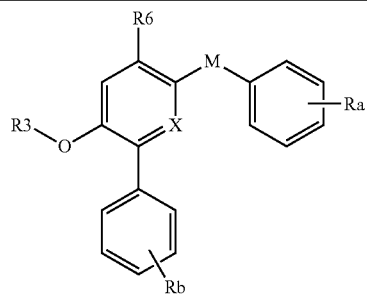

| Example | X | R3 | M | Rb | Ra |
|---|---|---|---|---|---|
| P-548 | C—H | (Me)CNCH2CH2— | CH2 | 3-Cl | 4-NHCONH2 |
| P-550 | C—H | CH3 | CH2 | 3-Cl | 4-NHCONH2 |
| P-553 | C—H | 3-(thiatenyl) | CH2 | 3-Cl | 4-NHCONH2 |
| P-554 | C—H | 3-(azetidinyl) | CH2 | 3-Cl | 4-NHCONH2 |
| P-555 | C—H | 3-(oxetanyl) | CH2 | 3-Cl | 4-NHCONH2 |
| P-556 | C—H | 3-(N-methyl pyrrolidinyl) | CH2 | 3-Cl | 4-NHCONH2 |
| P-557 | C—H | H2NCOCH2- | CH2 | 3-Cl | 4-NHCONH2 |
| P-558 | C—H | CH3 | C(=O) | 3-Cl | |
| P-560 | C—F | CH3 | C(CH3)(OH)-enantiomer-A | 3-Cl | 4-NHCOAc |
| P-561 | C—F | CH3 | C(CH3)(OH)-enantiomer-B | 3-Cl | 4-NHCOAc |
| P-562 | C—H | 3-(Oxetanyl) | CH2 | 3-Cl | 4-NH2 |
| P-563 | C—H | ((S)-1-pyrrolidin-2-CH2— | CH2 | 3-Cl | 4-NHCONH2 |
| P-564 | C—H | CH3 | C[(CH2CH2)N(CH3))CH2CH2)] | 3-Cl | 4-F |
| P-565 | C—H | 3-(N-emthyl pyrrolidine) | CH2 | 3-Cl | 4-NHCONH2 |
| P-566 | C—H | CH3 | CH2 | 3-Cl | NHCONH(2-Tetrahydrofuran) |
| P-575 | C—F | CH3 | CH2—O | 3-Cl | 4-NO2 |
| P-576 | C—F | CH3 | CH2—O | 3-Cl | 4-NH2 |
| P-578 | C—H | CH3 | CO | 3,4-OCH2CH2O— | 4-NH2 |
| P-579 | C—H | CH3 | CO | 3-F | 4-NH2 |
| P-580 | C—H | CH3 | CO | 3,4-F2 | 4-NH2 |
| P-583 | C—H | CH3 | CD(OH) | 3-Cl | 4-NO2 |
| P-584 | C—H | CH3 | CD(OH) | 3-Cl | 4-NHCONH2 |
| P-589 | C—F | CH3 | CH2—O | 3-Cl | 4-NHCONH2 |
| P-594 | C—F | CH3 | CH—O | 3-Cl | 4-NHAc |
| P-620 | C—F | H | CH2 | 3-Br | 4-NHAc |

Except Examples P-093 and P-094 where R6 = F, for all other Examples in Table 1 R6 = H.

TABLE 2

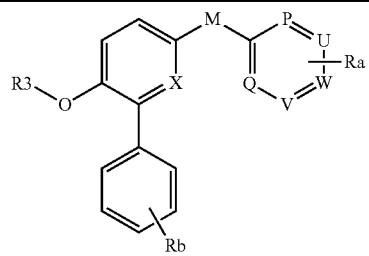

| Example | X | R3 | M | Rb | P | Q | U | V | W | Ra |
|---|---|---|---|---|---|---|---|---|---|---|
| P-008 | C—H | CH3 | CH2 | 3-NO2 | CH | CH | CH | CH | N | — |
| P-009 | C—H | CH3 | CH2 | 3-NO2 | N | CH | NH | CH | CO | — |
| P-011 | C—H | CH3 | CH2 | 3,4-NON | CH | CH | CH | CH | N | — |
| P-012 | C—H | CH3 | CH2 | 3,4-NON | N | NH | CH | CH | CO | — |
| P-015 | C—H | CH3 | O | 3-NO2 | N | CH | NH | CH | CO | — |
| P-016 | C—OH | CH3 | C=O | 3-NO2 | CH | CH | CH | CH | N | — |
| P-017 | C—OH | CH3 | CH2 | 3-NO2 | CH | CH | CH | CH | N | — |
| P-018 | C—H | CH2CH2OCH3 | CH2 | 3-NO2 | N | CH | N | CH | CO | (U)—CH2CH2OCH3 |

TABLE 2-continued

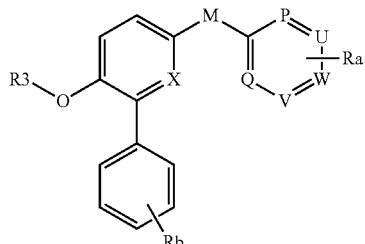

| Example | X | R3 | M | Rb | P | Q | U | V | W | Ra |
|---|---|---|---|---|---|---|---|---|---|---|
| P-019 | N | CH3 | CH2 | 3-NO2 | CH | CH | CH | CH | N | — |
| P-020 | C—H | CONH2 | CH2 | 3-NO2 | N | CH | NH | CH | CO | — |
| P-106 | C—OH | CH3 | CH2 | 3-NO2 | CH | CH | N | CH | CH | — |
| P-109 | C—OH | CH3 | CH2 | 3-NO2 | C | CH | N | CH | CH | (P)—Cl |
| P-110 | C—H | CH3 | CH2 | 3-NO2 | CH | CH | N | CH | C | (W)—NHCO2—tBu |
| P-111 | C—H | CH3 | CH2 | 3-NO2 | CH | CH | N | CH | C | (W)—NH2 |
| P-124 | C—OH | CH3 | C=O | 3-NO2 | CH | CH | N | CH | C | (W)—OCH3 |
| P-125 | C—OH | CH3 | CH2 | 3-NO2 | CH | CH | N | CH | C | (W)—OCH3 |
| P-126 | C—OH | CH3 | CH2 | 3-NO2 | CH | CH | N | CH | C | (W)—Cl |
| P-150 | C—OH | CH3 | CH2 | 3-NO2 | CH | CH | N | CH | C | (W)—OCH2CH2N(CH3)2 |
| P-152 | C—F | CH3 | CH2 | 3-NO2 | CH | CH | N | CH | C | (W)—Cl |
| P-177 | C—OH | CH3 | CH2 | 3-NO2 | CH | CH | N | CH | C | (W)—NHCH2CO2H |
| P-178 | C—OH | CH3 | CH2 | 3-NO2 | CO | CH | NH | CH | CH | — |
| P-182 | C—OH | CH3 | CH2 | 3-NH2 | C | CH | N | CH | CH | (P)—Cl |
| P-185 | C—OH | CH3 | CH2 | 3-NH2 | CO | CH | NH | CH | CH | — |
| P-224 | C—H | CH3 | CH2—O | 3-NO2 | CH | N | CH | CH | CH | — |
| P-225 | C—F | CH3 | CH2 | 3-Cl | CH | CH | N | CH | C | (W)—OCH3 |
| P-226 | C—F | CH3 | CH2 | 3-Cl | CH | CH | N | CH | C | (W)—Cl |
| P-252 | C—F | CH3 | CH2 | 3-Cl | CH | CH | N | CH | C | (W)—NH2 |
| P-258 | C—F | CH3 | CH2 | 3-Cl | CH | CH | N | CH | C | (W)—NHSO2CH3 |
| P-259 | C—F | CH3 | CH2 | 3-Cl | CH | CH | N | CH | C | (W)—NHCONH2 |
| P-272 | C—F | CH3 | CH2 | 3-Cl | CH | CH | N | CH | C | (W)—NHSO2NH2 |
| P-277 | C—F | CH3 | CH2 | 3-COCH3 | CH | CH | N | CH | C | (W)—NH2 |
| P-278 | C—F | CH3 | CH2 | 3-Cl | CH | CH | N | N | C | (W)—NH2 |
| P-279 | C—F | CH2CH3 | CH2 | 3-Cl | CH | CH | N | CH | C | (W)—NHCONH2 |
| P-281 | C—F | CH3 | CH2 | 3-COCH3 | CH | CH | N | N | C | (W)—NH2 |
| P-284 | C—F | CH3 | CH2 | 3-COCH3 | CH | CH | N | N | C | (W)—NHSO2CH3 |
| P-290 | C—F | CH3 | CH2 | 3-COCH3 | CH | CH | N | CH | C | (W)—NHCONH2 |
| P-291 | C—F | CH3 | CH2 | 3-Cl | CH | CH | N | N | C | (W)—NHCONH2 |
| P-292 | C—F | CH3 | CH2 | 3-Cl | CH | CH | N | N | C | (W)—NHSO2CH3 |
| P-297 | C—F | CH3 | CH2 | 3-COCH3 | CH | CH | N | CH | C | (W)—NHSO2CH3 |
| P-298 | C—F | CH3 | CH2 | 3-Cl | CH | CH | N | N | C | (W)—NHSO2NH2 |
| P-307 | C—F | CH3 | CH2 | 3-COCH3 | CH | CH | N | CH | C | (W)—NHSO2NH2 |
| P-308 | C—F | CH3 | CH2 | 3-Cl | CH | CH | CH | N—O | C | (W)—NHCONH2 |
| P-309 | C—F | CH3 | CH2 | 3-Cl | CH | CH | N | N—O | C | (W)—NHCONH2 |
| P-314 | C—F | CH3 | CH2 | 3-COCH3 | CH | CH | N | N | C | (W)—NHSO2NH2 |
| P-315 | C—F | CH3 | CH2 | 3-COCH3 | CH | CH | N | N | C | (W)—NHCONHEt |
| P-318 | C—F | CH3 | CH2 | 3-Cl | CH | CH | CH | N | C | (W)—NHEt |
| P-321 | C—F | CH3 | CH2 | 3-COCH3 | CH | CH | N | CH | C | (W)—CO2CH3 |
| P-325 | C—F | CH3 | CH2 | 3-COCH3 | CH | CH | N | N | C | (W)—N(CH3)2 |
| P-327 | C—F | CH3 | CH2 | 3-COCH3 | CH | CH | N | CH | C | (W)—CO2H |
| P-328 | C—F | CH3 | CH2 | 3-COCH3 | CH | CH | N | CH | C | (W)—CONH2 |
| P-332 | C—F | CH3 | CH2 | 3-COCH3 | CH | CH | N | CH | C | (W)—(CH3)2 |
| P-336 | C—F | CH3 | CH2 | 3-COCH3 | CH | CH | N | CH | C | (W)—NHCH3 |
| P-337 | C—F | CH3 | CH2 | 3-COCH3 | CH | CH | N | CH | C | (W)—NHCONHEt |
| P-339 | C—F | CH3 | CH2 | 3-COCH3 | CH | CH | N | CH | C | (W)—NHEt |
| P-344 | C—F | CH3 | CH2 | 3-Cl | CH | CH | N | CH | C | (W)—CH2NH2 |
| P-345 | C—F | CH3 | CH2 | 3-COCH3 | CH | CH | N | CH | C | (W)—NHCOCH3 |
| P-355 | C—F | CH3 | CH2 | 3-Cl | CH | CH | N | CH | C | (W)—CN |
| P-356 | C—F | CH3 | CH2 | 3-Cl | CH | CH | N | CH | C | (W)—NHCONHEt |
| P-357 | C—F | CH3 | CH2 | 3-Cl | CH | CH | N | CH | C | (W)—NHCO2Et |
| P-358 | C—F | CH3 | CH2 | 3-Cl | CH | CH | N | CH | C | (W)—NHCONHCH2CO2H |
| P-359 | C—F | CH3 | CH2 | 3-Cl | CH | CH | N | CH | C | (W)—N(Et)CO2Et |
| P-360 | C—F | CH3 | CH2 | 3-Cl | CH | CH | N | CH | C | (W)—NHCONHCH2CH2CO2Et |
| P-361 | C—F | CH3 | CH2 | 3-COCH3 | CH | CH | N | CH | C | (W)-1N-2-imidazolidinone |
| P-362 | C—F | CH3 | CH2 | 3-COCH3 | CH | CH | N | N | C | (W)—NHCONH2 |
| P-365 | C—F | CH3 | CH2 | 3-Cl | CH | CH | N | CH | C | (W)—NHCONHCH2CH2CO2H |
| P-366 | C—F | CH3 | CH2 | 3-COCH3 | CH | CH | N | N | C | (W)—NHCONHCH2Cl |
| P-367 | C—F | CH3 | CH2 | 3-Cl | CH | CH | N | CH | C | (W)—CH2NHCO2Et |
| P-368 | C—F | CH3 | CH2 | 3-Cl | CH | CH | N | CH | C | (W)—CH2NHCONH2 |
| P-371 | C—F | CH3 | CH2 | 3-Cl | CH | CH | N | CH | C | (W)—CH2NHCON(CH3)2 |
| P-372 | C—F | CH3 | CH2 | 3-Cl | CH | CH | N | CH | C | (W)—CH2NHCONHEt |
| P-373 | C—F | CH3 | CH2 | 3-Cl | CH | CH | N | CH | C | (W)—CH2NHCO(4-Me-1N-Piperazine) |

TABLE 2-continued

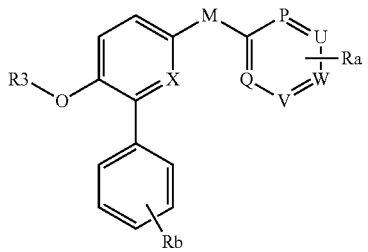

| Example | X | R3 | M | Rb | P | Q | U | V | W | Ra |
|---|---|---|---|---|---|---|---|---|---|---|
| P-374 | C—F | CH3 | CH2 | 3-Cl | CH | CH | N | CH | C | (W)—CH2-1N(-2-imidazolidinone) |
| P-375 | C—F | CH3 | CH2 | 3-Cl | CH | CH | N | CH | C | (W)—CH2-1N((N3-methyl-(2-imidazolidinone) |
| P-377 | C—F | CH3 | CH2 | 3-Cl | CH | CH | N | CH | C | (W)—N(morpholine) |
| P-379 | N | CH3 | CH2 | 3-Cl | CH | CH | N | CH | C | (W)—NH2 |
| P-382 | C—F | CH3 | CH2 | 3-Cl | CH | CH | N | CH | C | (W)—CON(CH3)2 |
| P-383 | C—F | CH3 | CH2 | 3-Cl | CH | CH | N | CH | C | (W)—CO—N(Piperidine-4-CO2Et) |
| P-384 | C—F | CH3 | CH2 | 3-Cl | CH | CH | N | CH | C | (W)—CO—N(Piperidine-4-COOH) |
| P-386 | N | CH3 | CH2 | 3-Cl | CH | CH | N | CH | C | (W)—NHCONHEt |
| P-387 | C—F | CH3 | CH2 | 3-Cl | CH | CH | N | CH | C | (W)—NHCOCH3 |
| P-388 | C—F | CH3 | CH2 | 3-Cl | CH | CH | N | CH | C | (W)-1N-2-imidazolidinone |
| P-392 | C—F | CH3 | CH2 | 3-Cl | CH | CH | N | N | C | (W)—Cl |
| P-393 | C—F | CH3 | CH2 | 3-Cl | CH | CH | N | N | C | (W)—N-[3-OH-Azetidine] |
| P-395 | C—F | CH3 | CH2 | CN | CH | CH | N | N | C | (W)—NH2 |
| P-397 | C—F | CH3 | CH2 | 3-Cl | CH | CH | N—O | CH | C | (W)—NHCONHEt |
| P-398 | C—F | CH3 | CH2 | CN | CH | CH | N | CH | C | (W)—NHCO2Et |
| P-399 | C—F | CH3 | CH2 | CN | CH | CH | N | N | | (W)—NHCONHEt |
| P-400 | C—H | CH3 | CH2 | CN | CH | CH | N | CH | C | (W)—NHCONHEt |
| P-401 | C—F | CH3 | CH2 | 3-Cl | CH | CH | N | CH | C | (W)—CONH2 |
| P-402 | C—F | CH3 | CH2 | 3-Cl | CH | CH | N | CH | C | (W)—Br |
| P-403 | C—F | CH3 | CH2 | 3-Cl | CH | CH | N | CH | C | (W)—NHCH2CO2H |
| P-405 | C—F | CH3 | CH2 | CN | CH | CH | N | CH | C | (W)—NHCONHEt |
| P-406 | C—F | CH3 | CH2 | 3-Cl | CH | CH | N | N | C | (W)—O—[(S)—(N—Me-3-pyrrolidine)] |
| P-407 | C—F | CH3 | CH2 | 3-Cl | CH | CH | N | CH | C | (W)-4-OH-3-pyrdine |
| P-408 | C—F | CH3 | CH2 | 3-Cl | CH | CH | N | CH | C | (W)—OH |
| P-409 | C—F | CH3 | CH2 | 3-Cl | CH | CH | N | CH | C | (W)—N(COCH3)CH2CO2H |
| P-410 | C—F | CH3 | CH2 | 3-Cl | CH | CH | N | CH | C | (W)-4-Br-3-pyrdine |
| P-411 | C—F | CH3 | CH2 | 3-Cl | CH | CH | N | CH | C | (W)—NHCH2CH2OH |
| P-412 | C—F | CH3 | CH2 | 3-Cl | CH | CH | N | CH | C | (W)-1N-1,2,4-triazole |
| P-414 | C—F | CH3 | CH2 | 3-Cl | CH | CH | N | CH | C | (W)—CO-1N-pyrrolidine-3-CO2H) |
| P-415 | C—F | CH3 | CH2 | CN | CH | CH | N | CH | C | (W)—CONH2 |
| P-416 | C—F | CH3 | CH2 | 3-Cl | C | CH | N | N | CH | (P)—Cl |
| P-417 | C—F | CH3 | CH2 | CN | CH | CH | N | N | C | (W)—N-[3-OH-Azetidine] |
| P-422 | C—F | CH3 | CH2 | 3-Cl | CH | CH | N | CH | C | (W)-1N-tetrazole |
| P-423 | C—F | CH3 | CH2 | 3-Cl | CH | CH | N | CH | C | (W)-1N-piperazine |
| P-426 | C—F | CH3 | CH2 | 3-Cl | CH | CH | N | CH | C | (W)-1N-(S)-Proline |
| P-427 | C—F | CH3 | CH2 | 3-Cl | CH | CH | N | N | C | (W)-1N-(piperidine-3-CO2H) |
| P-428 | C—F | CH3 | CH2 | 3-Cl | CH | CH | N | CH | C | (W)-1H-5-tetrazolyl |
| P-431 | C—F | CH3 | CH2 | 3-Cl | CH | CH | N | CH | C | (W)-1N-(piperazine-4-CO2Et) |
| P-432 | C—F | CH3 | CH2 | 3-Cl | CH | CH | N | CH | C | (W)-1N-(piperazine-4-CONH2) |
| P-433 | C—F | CH3 | CH2 | 3-Cl | CH | CH | C | CH | N | (U)—CN |
| P-437 | C—F | CH3 | CH2 | 3-Cl | CH | CH | C | CH | N | (U)—CH2NH2 |
| P-438 | C—F | CH3 | CH2 | 3-Cl | CH | CH | N | N | C | (W)-1N-(pyrrolidine-3-CO2H) |
| P-439 | C—F | CH3 | O | CN | CH | CH | N | CH | C | (W)—NH2 |
| P-440 | C—F | CH3 | O | CN | CH | CH | N | CH | C | (W)—NHCONHEt |
| P-442 | C—F | CH3 | CH2 | 3-Cl | CH | CH | N | N | C | (W)-1N-(pyrrolidine-3-CO2Me |
| P-446 | C—F | CH3 | CH2 | 3-Cl | CH | CH | CH | N | C | (W)—N(azetidine-4-COOH) |
| P-455 | C—F | CH3 | CH2 | 3-Cl | CH | CH | N | N | C | (W)-sarcosine |

TABLE 2-continued

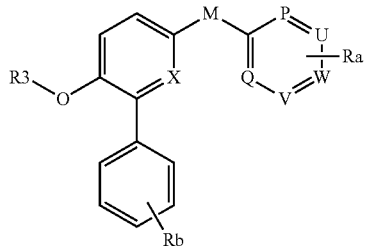

| Example | X | R3 | M | Rb | P | Q | U | V | W | Ra |
|---|---|---|---|---|---|---|---|---|---|---|
| P-456 | C—F | CH3 | CH2 | 3-Cl | CH | CH | CH | N | C | (W)—F |
| P-457 | C—F | CH3 | CH2 | 3-Cl | CH | CH | CH | N | C | (W)—N(azetidine-3-OH) |
| P-458 | C—F | CH3 | CH2 | 3-Cl | CH | CH | N | N | C | (W)—N(CH3)CH2CH2OH |
| P-459 | C—F | CH3 | CH2 | 3-Cl | CH | CH | CH | N | C | (W)—CH2NHCOCO2Et |
| P-460 | C—F | CH3 | CH2 | 3-Cl | CH | CH | CH | N | C | (W)—CH2NHCONH—Me |
| P-461 | C—F | CH3 | CH2 | 3-Cl | CH | CH | CH | N | C | (W)—N1(N3-ethyl-imidazolidin-2-one) |
| P-462 | C—F | CH3 | CH2 | 3-Cl | CH | CH | CH | N(—O) | C | (W)—CH2NHCONH—Et |
| P-463 | C—F | CH3 | CH2 | 3-Cl | CH | CH | CH | N(—O) | C | (W)—CH2—N-Oxazolidin-2-one |
| P-464 | C—F | CH3 | CH2 | 3-Cl | CH | CH | N | N | C | (W)—N(azetidine-(W)—COOH) |
| P-465 | C—F | CH3 | CH2 | 3-Cl | CH | CH | CH | N | C | (W)—CH2—N-Oxazolidin-2-one |
| P-469 | C—F | CH3 | CH2 | 3-Cl | CH | CH | CH | N | C | (W)—N-Oxazolidin-2-one |
| P-470 | C—F | CH3 | CH2 | 3-Cl | CH | CH | CH | N | C | (W)—N1(N3-Methyl-imidazolidin-2-one) |
| P-471 | C—F | CH3 | CH2 | 3-Cl | CH | CH | CH | N | C | (W)—NHCH2CONH2 |
| P-472 | C—F | CH3 | CH2 | 3-Cl | CH | CH | CH | N | C | (W)—CONHSO2CH3 |
| P-473 | C—F | CH3 | CH2 | 3-Cl | CH | CH | CH | N | C | (W)—N(CH3)2 |
| P-478 | C—F | CH3 | CH2 | 3-Cl | N | CH | CH | CH | C | (W)—NH2 |
| P-488 | C—H | H | CH2 | 3-NO2 | N | CH | NH | CH | C(=O) | — |
| P-499 | C—H | H | CH2 | 3-NO2 | CH | CH | NH | CH | C | (W)—OCH3 |
| P-500 | C—H | H | CH2 | 3-NO2 | CH | CH | N | CH | C | (W)—Cl |
| P-507 | C—F | H | CH2 | 3-Cl | CH | CH | N | CH | C | (W)—NHCONH2 |
| P-513 | C—F | CH3 | CH2 | C-Tetrazole | CH | CH | N | CH | C | (W)—NHCONH—Et |
| P-514 | C—F | CH3 | CH2 | 3-Cl | CH | CH | N | CH | C | (W)—[N(CH2CH2)2N]—CONHEt |
| P-515 | C—F | CH3 | CH2 | 3-Cl | CH | CH | C | CH | N | (U)—N-Piperazinyl |
| P-518 | C—F | CH3 | CH2 | 3-Cl | CH | CH | C | CH | N | (U)—[N(CH2CH2)2N]—CONH2 |
| P-519 | C—F | CH3 | CH2 | 3-Cl | CH | CH | C | CH | N | (U)—[N(CH2CH2)2N]—CONH—Et |
| P-520 | C—F | CH3 | CH2 | 3-Cl | CH | CH | N | CH | C | (W)—CH2NHCOO—Ph |
| P-521 | C—F | CH3 | CH2 | 3-Cl | CH | CH | N | CH | C | (W)—CH2NHCOCOCNH2 |
| P-523 | C—F | CH3 | CH2 | 3-Cl | CH | CH | N | CH | C | (W)—O—CH2—[(S)-2-Pyrrolidine] |
| P-531 | C—F | CH3 | CH2—O | 3-CN | CH | CH | C | CH | N | (U)—CH2NHCONH—Et |
| P-533 | C—F | CH3 | CH2 | 3-Cl | CH | CH | N | CH | C | (W)—O—CH2—[(S)-2-]**** |
| P-567 | C—F | CH3 | CH2 | 3-Cl | CH | CH | N | CH | C | (W)—CH2OH |
| P-568 | C—H | CH3 | CH2 | 3-Cl | CH | CH | N | CH | C | (W)—N-Azetidine |
| P-569 | C—F | CH3 | CH2 | 3-Cl | CH | CH | N | CH | C | (W)—N-Azetidine |
| P-570 | C—H | CH3 | CH2 | 3-Cl | CH | CH | N | CH | C | (W)—CH2OCO—NH—Et |
| P-571 | C—F | CH3 | CH2 | 3-Cl | CH | CH | N | CH | C | (W)—N-Azetidine-2-Carboxamide |
| P-572 | C—H | CH3 | CH2 | 3-Cl | CH | CH | N | CH | C | (W)—N-morpholine |
| P-573 | C—F | CH3 | CH2 | 3-Cl | CH | CH | N | CH | C | (W)—N-imidazole |
| P-574 | C—F | CH3 | CH2—O | 3-Cl | N | CH | CH | CH | C | (W)—Br |
| P-577 | C—F | CH3 | CH2 | 3-Cl | CH | CH | N | CH | C | (W)—N-[(2,5-dimethyl)pyrrolidine] |
| P-581 | C—F | CH3 | CH2 | 3-Cl | CH | CH | N | CH | C | (W)—N-(pyrrolidine(2-C(Me2)OH)] |
| P-582 | C—F | CH3 | CH2 | 3-Cl | CH | CH | N | CH | C | (W)—N-(pyrrolidine) |
| P-585 | C—F | CH3 | CH2—O | 3-Cl | CH | CH | N | CH | C | (W)—Cl |
| P-586 | C—F | CH3 | CH2—O | 3-Cl | CH | CH | N | CH | C | (W)—N-Azetidine |
| P-587 | C—F | CH3 | CH2 | 3-Cl | CH | CH | N | CH | C | (W)—C(CH3)2OH |
| P-588 | C—F | CH3 | CH2 | 3-Cl | CH | CH | N | CH | C | (W)—OCH2CH2NMe2 |
| P-590 | C—H | CH3 | CH2 | 3-Cl | CH | CH | N | CH | C | (W)—CN |
| P-591 | C—H | CH3 | CH2 | 3-Cl | CH | CH | N | CH | C | (W)—CH2NH2 |
| P-592 | C—H | CH3 | CH2 | 3-Cl | CH | CH | N | CH | C | (W)—CH2NHCOOPh |
| P-593 | C—H | CH3 | CH2 | 3-Cl | CH | CH | N | CH | C | (W)—CH2NHCONHCH3 |
| P-595 | C—F | CH3 | CH2 | 3-Cl | CH | CH | N | CH | C | (W)—C(CH3)2NH2 |
| P-596 | C—H | CF2H | CH2 | 3-Cl | CH | CH | N | CH | C | (W)—CH2NH2 |
| P-597 | C—H | CH3 | CH2 | 3-Cl | CH | CH | N | CH | C | (W)—CH2NHCONH—Et |

TABLE 2-continued

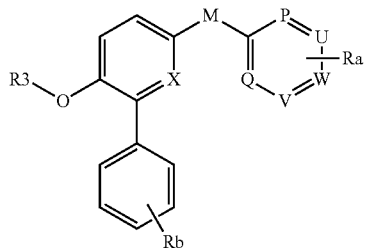

| Example | X | R3 | M | Rb | P | Q | U | V | W | Ra |
|---|---|---|---|---|---|---|---|---|---|---|
| P-598 | C—H | CF2H | CH2 | 3-Cl | CH | CH | N | CH | C | (W)—CH2NHCONH—Me |
| P-599 | C—F | CH3 | CH2 | 3-Cl | CH | CH | N | CH | C | (W)—CH2OH |
| P-600 | C—H | CH3 | CH2 | 3-Cl | CH | CH | N | CH | C | (W)—C(CH3)2NH2 |
| P-601 | C—F | CH3 | CH2 | 3-Cl | CH | CH | N | CH | C | (W)—N[pyrrolidine(3-hydrohyl)] |
| P-602 | C—H | CH3 | CH2 | 3-Cl | CH | CH | N | CH | C | (W)—N[pyrrolidine(3-hydrohyl)] |
| P-603 | C—H | CH3 | CH2—O | 3-Cl | CH | CH | CH | C | N | (V)—Cl |
| P-604 | C—F | CH3 | CH2—O | 3-Cl | CH | CH | CH | C | N | (V)—Cl |
| P-605 | C—H | CH3 | CH2 | 3-Cl | CH | CH | N | CH | C | (W)—C(CH3)2OH |
| P-606 | C—F | CH3 | CH2 | 3-Cl | CH | CH | N | CH | C | (W)—CH(CH3)NH2 |
| P-607 | C—H | CH3 | CH2—O | 3-Cl | CH | CH | CH | C | N | (V)—N(pyrrolidine) |
| P-608 | C—F | CH3 | CH2—O | 3-Cl | CH | CH | CH | C | N | (V)—N(pyrrolidine) |
| P-609 | C—H | CH3 | CH2 | 3-Cl | CH | CH | N | CH | C | (W)—CH(CH3)-N(azetidine) |
| P-610 | C—H | CF2H | CH2 | 3-Cl | CH | CH | N | CH | C | (W)—C(CH3)2OH |
| P-611 | C—H | CF2H | CH2 | 3-Cl | CH | CH | N | CH | C | (W)—NH2 |
| P-612 | C—F | CH3 | CH2 | 3-Cl | CH | CH | N | CH | C | (W)—N[(S)proline-2-amide)] |
| P-613 | C—F | CH3 | CH2 | 3-Cl | CH | CH | N | CH | C | (W)—CH(CH3)NHCONH2 |
| P-614 | C—H | CF2H | CH2 | 3-Cl | CH | CH | N | CH | C | (W)—N-Azetidine |
| P-615 | C—F | CH3 | CH2 | 3-Cl | CH | CH | N | CH | C | (W)—N[Azetidine-2-(R)-carboxamide)] |
| P-616 | C—H | CF2H | CH2 | 3-Cl | CH | CH | N | CH | C | (W)—NHCONH2 |
| P-617 | C—F | CH3 | CH2 | 3-Cl | CH | CH | N | CH | C | (W)—N[Azetidine-2-(S)-carboxamide)] |
| P-618 | C—H | CF2H | CH2 | 3-Cl | CH | CH | N | CH | C | (W)—NHCOCH2NMe2 |
| P-619 | C—F | CH3 | CH2 | 3-Cl | CH | CH | N | N | C | (W)—NHCONH—Et |
| P-621 | C—H | CF2H | CH2 | 3-Cl | CH | CH | N | CH | C | (W)—N(CH3)CH2CONH2 |
| P-622 | C—H | CH3 | CH2 | 3-Cl | CH | CH | N | CH | C | (W)—N(CH3)CH2CONH2 |

Ar1 = Het(6)-Ra

TABLE 3

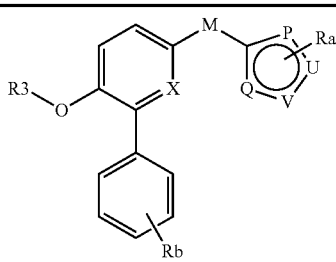

| Ex. No. | Core | R3 | M | Rb | P | Q | U | V | Ra |
|---|---|---|---|---|---|---|---|---|---|
| P-062 | C—H | CH3 | CH2 | 3,4-OCH2O | C(CH3) | C(CH3) | N | O | — |
| P-073 | C—H | CH3 | CH(OH) | 3,4-OCH2O | N(CH3) | CH | N | CH | — |
| P-075 | C—H | CH3 | CH2 | 3,4-OCH2O | N(CH3) | CH | N | CH | — |
| P-087 | C—H | CH3 | CH2 | 3-NO2 | C(CH3) | C(CH3) | N | N | (U)—CH2CO2CH2CH3 |
| P-088 | C—H | CH3 | CH2 | 3-NO2 | C(CH3) | C(CH3) | N | N | (U)—CH2CH2OH |
| P-089 | C—H | CH3 | CH2 | 3-NO2 | C(CH3) | C(CH3) | NH | N | |
| P-090 | C—H | CH3 | CH2 | 3-NO2 | C(CH3) | C(CH3) | N | N | (U)—CH2CF3 |
| P-100 | C—H | CH3 | CH2 | 3-NO2 | C(CH3) | C(CH3) | N | N | (U)—CH2COOH |
| P-101 | C—H | CH3 | CH2 | 3-NO2 | C(CH3) | C(CH3) | N | N | (U)—CH2CONH2 |
| P-115 | C—H | CH3 | CH2 | 3,4-OCF2O | N | CH | N | CH | (P)—CH3 |
| P-128 | C—F | CH3 | C=O | 3-NO2 | S | CH | CH | CH | — |
| P-129 | C—OH | CH3 | C=O | 3-NO2 | O | CH | N | CH | — |
| P-130 | C—OH | CH3 | CH2 | 3-NO2 | O | CH | N | CH | — |

TABLE 3-continued

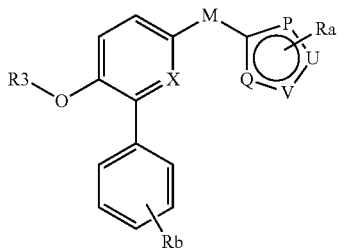

| Ex. No. | Core | R3 | M | Rb | P | Q | U | V | Ra |
|---|---|---|---|---|---|---|---|---|---|
| P-174 | C—OH | CH3 | CH2 | 3-NO2 | C | C | N | O | (P)—CH3, (Q)—CH3 |
| P-201 | C—H | CHF2 | CH2 | 3,4-OCH2O | N | CH | N | CH | (P)—CH3 |
| P-306 | C—H | CH3 | CH2 | 3-Cl | O | N | C | N | (U)—NH2 |
| P-310 | C—F | CH3 | CH2 | 3-Cl | S | CH | C | CH | (U)—OCH2CH3 |
| P-333 | C—F | CH3 | CH2 | 3-Cl | S | N | C | N | (U)—NH2 |
| P-341 | C—F | CH3 | CH2 | 3-Cl | N | CH | C | S | (U)—NH2 |
| P-342 | C—F | CH3 | CH2 | 3-Cl | S | N | C | N | (U)—NHCOOCH3 |
| P-343 | C—F | CH3 | CH2 | 3-Cl | S | N | C | N | (U)—NHCONHCH2CH3 |
| P-346 | C—F | CH3 | CH2 | 3-Cl | N | CH | C | S | (U)—NHCONHCH2CH3 |
| P-350 | C—F | CH3 | CH2 | 3-Cl | S | N | C | N | (U)—NHCONHCH2COOCH2CH3 |
| P-351 | C—F | CH3 | CH2 | 3-Cl | S | N | C | N | (U)—NHCONHCH2CH2COOCH2CH3 |
| P-352 | C—F | CH3 | CH2 | 3-Cl | S | N | C | N | (U)—NHCONH2 |
| P-353 | C—F | CH3 | CH2 | 3-Cl | S | N | C | N | (U)—NHCONHCH2COOH |
| P-354 | C—F | CH3 | CH2 | 3-Cl | S | N | C | N | (U)—NHCONHCH2CH2COOH |
| P-363 | C—F | CH3 | CH2 | 3-Cl | S | N | C | N | (U)—NHCONH(CH2)3COOCH2CH3 |
| P-364 | C—F | CH3 | CH2 | 3-Cl | S | N | C | N | (U)—NHCONH(CH2)3COOH |
| P-369 | C—F | CH3 | CH2 | 3-Cl | S | CH | C | N | (U)—NH2 |

TABLE 4

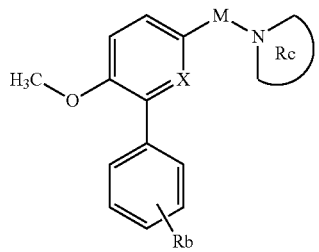

| Ex. No. | X | M | Rb | N(Rc) |
|---|---|---|---|---|
| P-005 | C—H | CH2 | 3-NO2 | 1N-1,2,4-Triazole |
| P-006 | C—H | CH2 | 3,4-NON | 1N-Imidazole |
| P-007 | C—H | CH2 | 3-NO2 | 1N-Benzotriazole |
| P-010 | C—H | CH2 | 3-NO2 | N(Indole) |
| P-014 | C—H | CH2 | 3,4-NON | 1N-Benzimidazole |
| P-022 | C—H | CH2 | 3-CO2CH3 | 1N-1,2,4-Triazole |
| P-024 | N | CH2 | 3-NO2 | 1N-1,2,4-Triazole |
| P-026 | N | CH2 | 3-NO2 | N(Morpholine) |
| P-029 | C—H | CH2 | 3-NO2 | N(2-Pyrrolidinone) |
| P-031 | N | CH2 | 3-NO2 | N(2-Pyrrolidinone) |
| P-033 | N | CH2 | 3-NO2 | 1N-imidazolidin-2-one |
| P-034 | C—H | CH2 | 3-NO2 | 1N-2-imidazolidin-2-one |
| P-035 | C—H | CH2 | 3-NO2 | N-1,4-Butanesultam |
| P-036 | C—H | CH2 | 3-NO2 | N-Succinimide |
| P-037 | C—H | CH2 | 3,4-OCH2O | 1N-Imidazole |
| P-039 | C—H | CH2 | 3-NO2 | N-Saccharin |
| P-040 | C—H | CH2 | 3-NO2 | N-Glutarimide |
| P-041 | C—H | CH2 | 3-NO2 | N-Isatin |
| P-042 | C—H | CH2 | 3-NO2 | N-Phthalimide |
| P-044 | C—H | CH2 | 3,4-OCH2O | 1N-1,2,4-Triazole |
| P-045 | C—H | CH2 | 3,4-OCH2O | 1N-2-Pyrrolidinone |
| P-046 | C—H | CH2 | 3-CO2CH3, 4-F | 1N-1,2,4-Triazole |
| P-048 | C—H | CH2 | 3-CO2CH3, 2-F | 1N-1,2,4-Triazole |
| P-052 | C—H | CH2 | 3,4-OCH2O | N-Phthalimide |
| P-053 | C—H | CH2 | 3,4-OCH2O | 1N-Succinimide |
| P-055 | C—H | CH2 | 3-NO2 | N-3,4-Pyridinedicarboximide |
| P-056 | C—H | CH2 | 3-NO2 | 9N-2-Amino-6-chloropurine |

TABLE 4-continued

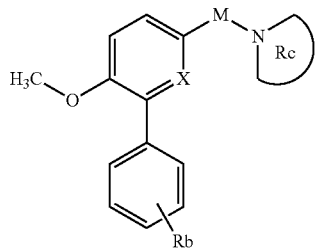

| Ex. No. | X | M | Rb | N(Rc) |
|---|---|---|---|---|
| P-058 | C—H | CH2 | 3-F | 1N-1,2,4-Triazole |
| P-059 | C—H | CH2 | 3-NO2 | 9N-Guanine |
| P-060 | C—H | CH2 | 3,4-F2 | 1N-1,2,4-Triazole |
| P-061 | C—H | CH2 | 3,4,5-F3 | 1N-1,2,4-Triazole |
| P-063 | C—H | CH2 | 3-CF3 | 1N-1,2,4-Triazole |
| P-064 | N | CH2 | 3-CF3 | 1N-1,2,4-Triazole |
| P-066 | C—H | CH2 | 3-NO2 | 4N-1,2,4-Triazole |
| P-068 | N | CH2 | 3-CF3 | N-L-4-Hydroxyproline methyl ester |
| P-069 | C—H | CH2 | 3-NO2 | N-L-4-Hydroxyproline methyl ester |
| P-070 | C—H | CH2 | 3-NO2 | N-(S)-3-Pyrrolidinol |
| P-071 | C—H | CH2 | 3-NO2 | N-(R)-3-Pyrrolidinol |
| P-072 | C—H | CH2 | 3-NO2 | N-D-Prolinol |
| P-074 | C—H | CH2 | 3,4-OCH2O | 1N-Pyrazole |
| P-076 | C—H | CH2 | 3-NO2 | 3N-2-Oxazolidinone |
| P-077 | C—H | CH2 | 3-NO2 | 1N-Pyrazole |
| P-078 | C—H | CH2 | 3-CF3 | N-(R)-3-Pyrrolidinol |
| P-081 | C—H | CH2 | 3-CN | 1N-1,2,4-Triazole |
| P-082 | C—H | CH2 | 3-COCH3 | 1N-1,2,4-Triazole |
| P-083 | C—H | CH2 | 3-CF3 | 3N-2-Oxazolidinone |
| P-084 | C—H | CH2 | 3-OCF3 | 1N-1,2,4-Triazole |
| P-085 | C—H | CH2 | 3-SCH3 | 1N-1,2,4-Triazole |
| P-086 | C—H | CH2 | 3-OCH3 | 1N-1,2,4-Triazole |
| P-104 | C—H | CH2 | 3-NO2 | N-2-Pyridone |
| P-108 | C—H | CH2 | 3-CH2OCH3 | 1N-1,2,4-Triazole |
| P-131 | C—H | CH2 | 3-NO2 | N-(S)-5-(Hydroxymethyl)-pyrrolidin-2-one |
| P-132 | C—H | CH2 | 3-NO2 | N-(R)-5-(Hydroxymethyl)-pyrrolidin-2-one |
| P-153 | C—H | CH2 | 3-NO2 | 1N-5-(Hydroxymethyl)-imidazole |
| P-154 | C—H | CH2 | 3-NO2 | 1N-4-(Hydroxymethyl)-imidazole |
| P-155 | C—H | CH2 | 3-NO2 | N-(S)-5-(Aminomethyl)-pyrrolidin-2-one |
| P-156 | C—H | CH2 | 3-NO2 | N-(R)-5-(Aminomethyl)-pyrrolidin-2-one |
| P-162 | C—H | CH2 | H | 1N-2-Pyrrolidinone |
| P-169 | C—H | CH2 | 3-SOCH3 | 1N-1,2,4-Triazole |
| P-172 | C—H | CH2 | 3-COCH3 | 1N-2-Pyrrolidinone |
| P-179 | C—H | CH2 | 3-COCH3 | N-2-Pyridone |
| P-184 | C—H | CH2 | 3-OCH3 | 1N-2-Pyrrolidinone |
| P-186 | C—H | CH2 | 3-[2-Oxadiazole] | 1N-2-Pyrrolidinone |
| P-188 | C—H | CH2 | 3-NO2 | 1N-2-piperidinone |
| P-195 | C—H | CH2 | 3-NO2 | 1N-5-Carbonitrile-pyridin-2-one |
| P-196 | C—H | CH2 | 3-NO2 | 1N-4-Carbonitrile-pyridin-2-one |
| P-197 | C—H | CH2 | 3-NO2 | 2N-6-Methyl pyridazin-3-one |
| P-198 | C—H | CH2 | 3-NO2 | 1N-5-Amino-pyridin-2-one |
| P-203 | C—F | CH2NH | 3-Cl | N-(4-(acetamido)-phenyl) |
| P-204 | C—H | CH2 | 3-NO2 | 2N-6-Methoxyl pyridazin-3-one |
| P-205 | C—H | CH2 | 3-NO2 | 2N-Pyridazinone |
| P-206 | C—H | CH2 | 3-NO2 | 1N-3-Methoxy-pyridin-2-one |
| P-207 | C—H | CH2 | 3-NO2 | 1N-4-Carboxamide-pyridin-2-one |
| P-208 | C—H | CH2 | 3-NO2 | 1N-Pyridin-2-one-5-urea |
| P-209 | C—H | CH2 | 3-Cl | N-Pyrrolidin-2-one |
| P-210 | C—H | CH2 | 3-NO2 | 1N-Pyridin-2-one-4-carboxylic acid |
| P-211 | C—H | CH2 | 3-NO2 | 1N-Pyridin-2-one-5-acetamide |
| P-212 | C—H | CH2 | 3-NO2 | 1N-Pyridin-2-one-5-carboxamide |
| P-215 | C—H | CH2 | 3-NO2 | 1N-4-Amino-pyridin-2-one |
| P-218 | C—H | CH2 | 3-Cl | N-Pyrrolidin-2-one |
| P-223 | C—H | CH2 | 3,4-F2 | N-Pyrrolidin-2-one |
| P-229 | C—OH | CH2 | 3-NO2 | N-Pyrrolidin-2-one |
| P-235 | C—H | CH2 | 3-Cl | 1N-5-Bromo-2-pyrimidinone |
| P-236 | C—H | CH2 | 3-NO2 | 1N-6-Amino-pyridin-2-one |
| P-244 | C—H | CH2CH2 | 3-NO2 | CH2-1N-Pyrrolidin-2-one |
| P-245 | C—H | CH2 | SCH3 | 1N-Pyrrolidin-2-one |
| P-248 | C—H | CH2 | 3-NO2 | N-(S)-4-Hydroxy-pyrrolid-2-one |
| P-253 | C—H | CH2 | 3-NO2 | N-[(S)-Pyrrolid-2-one-4-carbamate |
| P-370 | C—F | CH2 | 3-Cl | 1N-Piperazine-4-carboxamide |
| P-424 | C—F | CH2 | 3-Cl | 1N-4-(4-Aminophenyl) pyrazole |
| P-435 | C—F | CH2 | 3-Cl | 1N-4-(4-Ureaphenyl) pyrazole |
| P-436 | C—F | CH2 | 3-Cl | 1N-4-(4-Ethylureaphenyl) pyrazole |

TABLE 4-continued

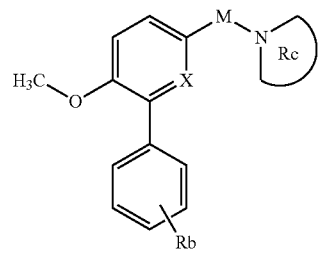

| Ex. No. | X | M | Rb | N(Rc) |
|---|---|---|---|---|
| P-479 | C—F | CH2 | 3-Cl | N1-imidazol-4-yl]-pyridine |
| P-481 | C—H | CH2 | 3,4(=N—O—N=) | 1N-(12,4)Triazole |
| P-482 | C—H | CH2 | 3-NO2 | 1N-Benztriazole |
| P-483 | C—H | CH2 | 3-NO2 | 1N-benzimidazole |
| P-486 | C—H | CH2 | 3,4-(CHCHN(H)) | 1N-(12,4)Triazole |
| P-492 | C—H | CH2 | 3-NO2 | N-Glutarmide |
| P-493 | C—H | CH2 | 3-NO2 | N-(R)-prolinol |
| P-495 | C—H | CH2 | 3-SO2CH3 | 1N-(12,4)Triazole |
| P-503 | C—H | CH2 | 3-NO2 | 1N-Pyrrolidin-2-one |
| P-504 | C—OH | CH2 | 3-NO2 | 1N-Pyrrolidin-2-one |
| P-511 | C—F | CH2 | 3-Cl | 1N[4(4-nitrophenyl)pyrazole] |
| P-512 | C—F | CH2 | 3-Cl | 1N[4{4-(NHCO2Et)phenyl}pyrazole] |
| P-517 | C—F | ch2 | 3-Cl | 1N[3{3-pyridyl)imidazole] |
| P-524 | C—H | bond | 3-Cl | 1N(7-aminobenzimidazole) |
| P-527 | C—F | CH2 | 3-Cl | 1N[4{2-pyridyl)imidazole] |
| P-528 | C—H | CH2 | 3-Cl | 1N[4{4-pyridyl)imidazole] |
| P-534 | C—F | CH2 | 3-Cl | 1N[imidazole-4-carboxamide] |
| P-535 | C—F | CH2 | 3-Cl | 1N[imidazole-5-carboxamide] |
| P-536 | C—F | CH2 | 3-Cl | 1N[4-nitro-imidazole] |
| P-544 | C—F | CH2 | 3-Cl | 1N[3(2-pyridinyl)pyrazole] |
| P-545 | C—F | CH2 | 3-Cl | 1N[3(2-pyrazinyl)pyrazole] |
| P-546 | C—F | CH2 | 3-Cl | 1N[4(6-pyrimidinyl)pyrazole] |
| P-549 | C—F | CH2 | 3-Cl | 1N[2(3-pyridinyl)imidazole] |
| P-551 | C—F | CH2 | 3-Cl | 1N[3-trifluoromethyl-5-(2-pyridinyl)-pyrazole] |
| P-552 | C—F | CH2 | 3-Cl | 1N[3-trifluoromethyl-5-(3-pyridinyl)-pyrazole] |
| P-559 | C—F | CH2 | 3-Cl | 1N[2(2-thienyl)imidazole] |
| P-529 | C—H | bond | 3-Cl | 1N[(7-NHCONHEt)benzimidazole] |
| P-623 | C—F | CH2 | 3-Cl | 4N-Piperazin-2-one |

TABLE 5

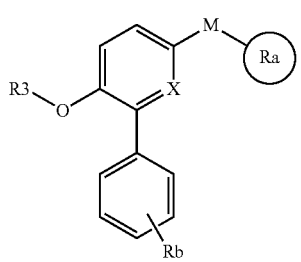

| Ex. No. | X | R3 | M | Rb | Ra |
|---|---|---|---|---|---|
| P-038 | N | CH3 | CH2 | 3-NO2 | O-Cyclopentane |
| P-091 | C—H | CH3 | CH2 | 3-CF3 | 3-O-2-Cylopentene-1-one |
| P-092 | C—H | CH3 | CH2 | 3-NO2 | 3-O-2-Cylopentene-1-one |
| P-127 | C—F | CH3 | CH2 | 3-NO2 | 2-Tetrahydrothiophene |
| P-120 | C—H | CH3 | CH2 | 3-NO2 | 1-(4-Methyl-2,6,7-trioxa-bicyclo[2.2.2]octane) |

TABLE 6

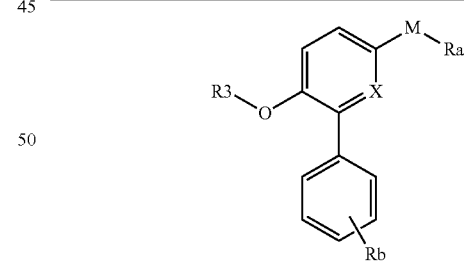

| Ex. No. | X | R3 | M | Rb | Ra |
|---|---|---|---|---|---|
| P-025 | N | CH3 | CH2 | 3-NO2 | OCH3 |
| P-030 | N | CH3 | CH2 | 3-NO2 | OCH(CH3)2 |
| P-149 | C—OH | CH3 | CH2 | 3-NO2 | OH |
| P-027 | C—H | CH3 | CH2 | 3-NO2 | CONHCH3 |
| P-491 | N | CH3 | CH2 | 3-NO2 | OH |

TABLE 7
All of the Examples in the table below, R3 = CH3
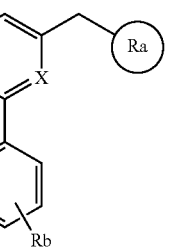
| Ex. No. | X | Rb | Ra |
|---|---|---|---|
| P-028 | C—H | 3-NO2 Phenyl | 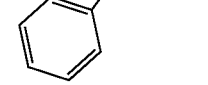 |
| P-032 | C—H | 3-NO2 Phenyl | 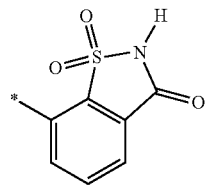 |
| P-043 | C—H | 3-NO2 Phenyl | 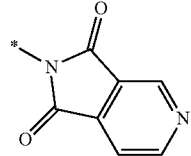 |
| P-047 | C—H | 3-NO2 Phenyl | 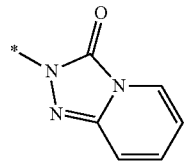 |
| P-213 | C—H | 3-NO2 Phenyl | 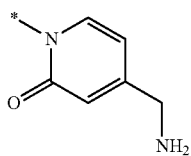 |
| P-214 | C—H | 3-NO2 Phenyl | 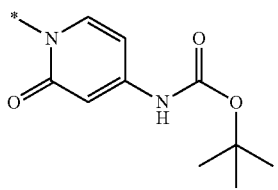 |
| P-251 | C—F | 3-Cl Phenyl | 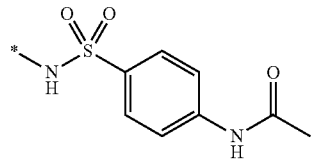 |
TABLE 7-continued
All of the Examples in the table below, R3 = CH3
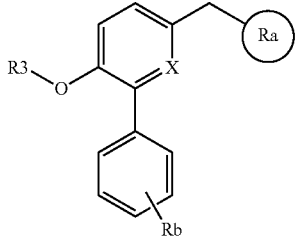
| Ex. No. | X | Rb | Ra |
|---|---|---|---|
| P-263 | C—F | 3-Cl Phenyl | 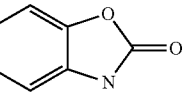 |
| P-285 | C—F | 3-Cl Phenyl | 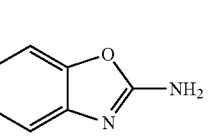 |
| P-425 | C—F | 3-Cl Phenyl | 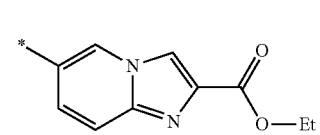 |
| P-429 | C—F | 3-Cl Phenyl | 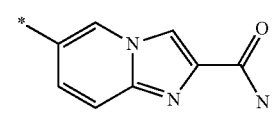 |
| P-430 | C—F | 3-Cl Phenyl | 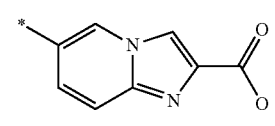 |
| P-445 | C—F | 3-Cl Phenyl | 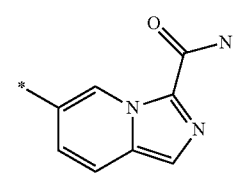 |
| P-480 | C—F | 3-Cl Phenyl | 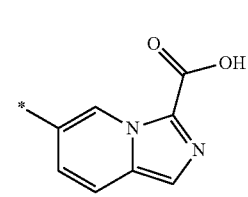 |

TABLE 8

| Ex. No. | X | Rb | Ra |
|---|---|---|---|
| P-389 | C—F | 4-(1H-pyrazol-1-yl)pyridin-4-yl | 4-F Phenyl |
| P-391 | C—H | 6-chloropyridin-2-yl | 4-F Phenyl |
| P-396 | C—F | 3-(trifluoromethyl)-1H-pyrazol-1-yl | 4-F Phenyl |
| P-475 | C—H | pyridin-3-yl N-oxide | 4-F Phenyl |
| P-380 | C—F | 4-chloro-1H-pyrazol-1-yl | 4-F Phenyl |
| P-396 | C—H | 3-(difluoromethyl)-1H-pyrazol-1-yl | 4-F Phenyl |
| P-525 | C—H | 5-(pyridin-4-yl)-1,3,4-oxadiazol-2-yl | 4-F Phenyl |

TABLE 8-continued

| Ex. No. | X | Rb | Ra |
|---|---|---|---|
| P-526 | C—H | 5-(pyridin-4-yl)-1,3,4-oxadiazol-2-yl | 4-F Phenyl |
| P-474 | C—H | 3-pyridinyl | 4-F Phenyl |
| P-475 | C—H | 3-pyridinyl N-oxide | 4-F Phenyl |

In another aspect the present invention provides a pharmaceutical composition comprising a pharmaceutically acceptable carrier and a therapeutically effective amount of at least one compound as described above.

Methods of the invention parallel the compositions and formulations. The methods comprise administering to a patient in need of treatment a therapeutically effective amount of a compound according to the invention. The present invention also provides a method for inhibiting phosphodiesterase 4.

In-vitro assay for PDE4 enzymes. The in-vitro activity of PDE4 enzymes and the in-vitro potency of therapeutic agents described in the present invention were measured using a real-time, enzyme-coupled spectrophotometric assay. By using three different coupling enzymes, the product of the PDE4 reaction is coupled to the oxidation of the reduced form β-nicotinamide adenine dinucleotide (NADH), which dissipation can be monitored spectrophotmetrically at 340 nM.

Assay description. Buffer A containing 50 mM Tris, pH 8.0, 16 mM MgCl$_2$ and 80 mM KCl is prepared and stored at room temperature. Buffer B containing 50 mM Tris, pH 8.0 is prepared and stored at room temperature. Stock solutions of the following reagents are prepared in Buffer B and stored at −20° C.: Adenosine-5'-triphosphate (ATP), cyclic adenosine-5'-monophosphate (cAMP), phosphoenolpyruvate (PEP) and NADH. An assay mix is prepared by mixing Buffer A, trichloroethylphosphine (TCEP), ATP, PEP, NADH, myokinase (MK), pyruvate kinase (PK), lactate dehydroganese (LDH) and PDE4 to a final volume of 20 mL, which is enough for a single 96-well assay plate. Assay mix (180 μL) and test article (10 μL) in 1:1 DMSO/H2O mixture is pre-incubated at room temperature for 10 min. The enzymatic reaction is initiated by addition of cAMP (10 μL). Final concentration of all components in the assay (200 μL/well) are as follows: 10 mM MgCl$_2$, 50 mM KCl, 5 mM TCEP, 2.5% DMSO, 0.4 mM NADH, 1 mM PEP, 0.04 mM ATP, 5 units MK, 1 unit PK, 1 unit LDH and appropriate amount of PDE4. Reaction progress curves are monitored in a plate reader capable of measuring light absorbance at 340 nM. A decrease in light absorbance at 340 nm is due to oxidation of NADH. Positive controls containing no test article and negative controls containing no test article and no cAMP are included on every assay plate. Reaction rates are determined from the slopes of the linear portions of the progress curves. All data is percent normalized with respect to controls and presented as percent inhibition.

The results of testing of representative species are shown below in Tables 9 and 10. The activities are designated A=<5 µM, B=5-20 µM, C=20-40 µM.

TABLE 9

| CmpdNo | hPDE4D |
|---|---|
| P-001 | A |
| P-002 | A |
| P-003 | A |
| P-004 | A |
| P-005 | A |
| P-006 | A |
| P-007 | A |
| P-008 | A |
| P-009 | A |
| P-010 | A |
| P-011 | A |
| P-012 | B |
| P-014 | B |
| P-015 | A |
| P-017 | A |
| P-018 | B |
| P-019 | A |
| P-020 | B |
| P-021 | A |
| P-022 | A |
| P-023 | A |
| P-024 | A |
| P-025 | B |
| P-026 | B |
| P-027 | A |
| P-028 | A |
| P-029 | A |
| P-030 | B |
| P-033 | B |
| P-034 | A |
| P-035 | A |
| P-036 | A |
| P-037 | A |
| P-038 | B |
| P-040 | B |
| P-041 | B |
| P-042 | A |
| P-043 | A |
| P-044 | A |
| P-045 | C |
| P-046 | A |
| P-047 | B |
| P-048 | A |
| P-049 | A |
| P-050 | A |
| P-051 | A |
| P-052 | A |
| P-053 | B |
| P-054 | A |
| P-055 | A |
| P-057 | A |
| P-058 | A |
| P-060 | A |
| P-061 | A |
| P-062 | A |
| P-063 | A |
| P-064 | B |
| P-065 | A |
| P-066 | A |
| P-067 | A |
| P-070 | A |
| P-071 | A |
| P-072 | B |
| P-073 | A |
| P-074 | A |
| P-075 | A |
| P-076 | A |
| P-077 | A |
| P-078 | B |

TABLE 9-continued

| CmpdNo | hPDE4D |
|---|---|
| P-079 | A |
| P-080 | A |
| P-081 | A |
| P-082 | A |
| P-083 | B |
| P-084 | A |
| P-085 | A |
| P-086 | A |
| P-087 | A |
| P-088 | A |
| P-089 | A |
| P-090 | A |
| P-091 | A |
| P-092 | A |
| P-093 | A |
| P-094 | A |
| P-095 | C |
| P-097 | A |
| P-098 | A |
| P-099 | A |
| P-101 | A |
| P-102 | A |
| P-103 | A |
| P-104 | A |
| P-105 | A |
| P-106 | A |
| P-107 | A |
| P-108 | A |
| P-109 | A |
| P-111 | A |
| P-112 | A |
| P-113 | A |
| P-114 | A |
| P-115 | A |
| P-116 | A |
| P-117 | A |
| P-118 | A |
| P-119 | A |
| P-120 | A |
| P-121 | A |
| P-122 | A |
| P-123 | A |
| P-125 | A |
| P-126 | A |
| P-127 | A |
| P-128 | A |
| P-130 | A |
| P-131 | B |
| P-132 | C |
| P-133 | B |
| P-134 | A |
| P-135 | A |
| P-136 | A |
| P-137 | A |
| P-138 | A |
| P-139 | A |
| P-140 | A |
| P-141 | A |
| P-142 | A |
| P-143 | A |
| P-144 | A |
| P-145 | A |
| P-146 | A |
| P-147 | A |
| P-148 | A |
| P-149 | A |
| P-150 | B |
| P-151 | A |
| P-152 | A |
| P-153 | A |
| P-154 | A |
| P-155 | C |
| P-156 | A |
| P-157 | A |
| P-158 | B |
| P-159 | A |
| P-160 | B |
| P-161 | B |

TABLE 9-continued

| CmpdNo | hPDE4D |
|---|---|
| P-162 | B |
| P-163 | A |
| P-164 | A |
| P-165 | A |
| P-166 | A |
| P-167 | A |
| P-168 | A |
| P-169 | B |
| P-170 | A |
| P-171 | A |
| P-172 | A |
| P-173 | A |
| P-174 | A |
| P-175 | A |
| P-176 | A |
| P-177 | A |
| P-178 | A |
| P-179 | B |
| P-180 | A |
| P-181 | A |
| P-182 | B |
| P-183 | A |
| P-184 | B |
| P-185 | B |
| P-186 | C |
| P-187 | A |
| P-188 | A |
| P-189 | B |
| P-190 | A |
| P-192 | B |
| P-193 | A |
| P-194 | A |
| P-195 | B |
| P-196 | A |
| P-197 | B |
| P-199 | A |
| P-200 | A |
| P-201 | B |
| P-203 | A |
| P-204 | B |
| P-205 | A |
| P-206 | A |
| P-207 | B |
| P-208 | B |
| P-209 | B |
| P-211 | B |
| P-212 | B |
| P-213 | B |
| P-215 | B |
| P-216 | A |
| P-217 | A |
| P-218 | A |
| P-219 | A |
| P-220 | A |
| P-221 | A |
| P-222 | A |
| P-223 | B |
| P-224 | B |
| P-225 | A |
| P-226 | A |
| P-227 | A |
| P-228 | A |
| P-229 | A |
| P-230 | B |
| P-231 | A |
| P-232 | A |
| P-233 | A |
| P-234 | A |
| P-235 | B |
| P-236 | C |
| P-237 | A |
| P-238 | A |
| P-240 | A |
| P-241 | A |
| P-242 | A |
| P-243 | A |
| P-244 | A |
| P-245 | B |
| P-246 | B |
| P-247 | A |
| P-248 | A |
| P-249 | A |
| P-250 | A |
| P-251 | A |
| P-252 | A |
| P-254 | B |
| P-255 | A |
| P-256 | A |
| P-257 | A |
| P-258 | A |
| P-259 | A |
| P-260 | A |
| P-261 | A |
| P-262 | A |
| P-263 | A |
| P-264 | A |
| P-266 | A |
| P-267 | A |
| P-268 | A |
| P-269 | A |
| P-270 | A |
| P-271 | B |
| P-273 | A |
| P-274 | A |
| P-275 | A |
| P-277 | A |
| P-278 | A |
| P-279 | A |
| P-280 | A |
| P-281 | A |
| P-282 | A |
| P-283 | A |
| P-284 | A |
| P-285 | A |
| P-286 | A |
| P-287 | A |
| P-288 | A |
| P-289 | A |
| P-290 | A |
| P-291 | A |
| P-292 | A |
| P-293 | A |
| P-294 | A |
| P-295 | A |
| P-296 | A |
| P-297 | A |
| P-299 | A |
| P-300 | A |
| P-301 | A |
| P-302 | A |
| P-303 | A |
| P-304 | A |
| P-305 | A |
| P-306 | B |
| P-310 | A |
| P-311 | A |
| P-313 | A |
| P-315 | A |
| P-316 | A |
| P-317 | A |
| P-318 | A |
| P-322 | A |
| P-323 | A |
| P-325 | A |
| P-326 | A |
| P-328 | A |
| P-329 | A |
| P-330 | A |
| P-331 | A |
| P-332 | A |
| P-333 | A |
| P-334 | A |
| P-335 | A |
| P-336 | A |
| P-337 | A |
| P-338 | A |

TABLE 9-continued

| CmpdNo | hPDE4D |
|---|---|
| P-339 | A |
| P-340 | A |
| P-341 | A |
| P-342 | A |
| P-343 | A |
| P-344 | A |
| P-345 | A |
| P-346 | A |
| P-347 | A |
| P-352 | A |
| P-355 | A |
| P-356 | A |
| P-357 | A |
| P-359 | A |
| P-361 | A |
| P-362 | A |
| P-366 | A |
| P-367 | A |
| P-368 | A |
| P-369 | A |
| P-370 | A |
| P-371 | A |
| P-372 | A |
| P-373 | A |
| P-374 | A |
| P-375 | A |
| P-376 | A |
| P-377 | A |
| P-378 | A |
| P-379 | A |
| P-380 | A |
| P-381 | A |
| P-382 | A |
| P-385 | B |
| P-386 | A |
| P-387 | A |
| P-388 | A |
| P-389 | B |
| P-390 | B |
| P-391 | A |
| P-392 | A |
| P-393 | A |
| P-394 | A |
| P-395 | A |
| P-396 | A |
| P-397 | A |
| P-398 | A |
| P-399 | A |
| P-400 | A |
| P-401 | A |
| P-402 | A |
| P-404 | A |
| P-405 | A |
| P-406 | A |
| P-407 | A |
| P-410 | A |
| P-411 | A |
| P-412 | A |
| P-413 | A |
| P-415 | A |
| P-416 | A |
| P-417 | A |
| P-418 | B |
| P-419 | B |
| P-420 | A |
| P-421 | A |
| P-422 | A |
| P-423 | B |
| P-424 | A |
| P-429 | A |
| P-431 | A |
| P-432 | A |
| P-433 | A |
| P-434 | A |
| P-435 | A |
| P-437 | A |
| P-439 | A |
| P-440 | A |
| P-441 | A |
| P-445 | A |
| P-447 | A |
| P-448 | A |
| P-449 | A |
| P-450 | A |
| P-451 | A |
| P-453 | A |
| P-454 | A |
| P-456 | A |
| P-457 | A |
| P-458 | A |
| P-460 | A |
| P-461 | A |
| P-462 | A |
| P-463 | A |
| P-465 | A |
| P-466 | A |
| P-467 | A |
| P-468 | A |
| P-469 | A |
| P-470 | A |
| P-471 | A |
| P-473 | A |
| P-474 | A |
| P-475 | B |
| P-476 | A |
| P-477 | A |
| P-478 | A |
| P-479 | A |
| P-481 | A |
| P-483 | A |
| P-486 | C |
| P-488 | A |
| P-491 | C |
| P-492 | C |
| P-493 | C |
| P-494 | A |
| P-495 | C |
| P-496 | A |
| P-497 | A |
| P-499 | A |
| P-500 | A |
| P-501 | B |
| P-502 | A |
| P-503 | B |
| P-504 | A |
| P-505 | B |
| P-507 | A |
| P-508 | A |
| P-513 | B |
| P-514 | A |
| P-515 | A |
| P-516 | A |
| P-517 | A |
| P-518 | A |
| P-519 | A |
| P-520 | A |
| P-521 | A |
| P-523 | A |
| P-524 | A |
| P-525 | A |
| P-526 | B |
| P-527 | A |
| P-528 | A |
| P-530 | A |
| P-531 | A |
| P-532 | A |
| P-533 | A |
| P-534 | A |
| P-535 | A |
| P-536 | A |
| P-537 | A |
| P-538 | A |
| P-539 | A |
| P-540 | A |
| P-541 | A |
| P-542 | C |

TABLE 9-continued

| CmpdNo | hPDE4D |
|---|---|
| P-543 | A |
| P-544 | A |
| P-545 | A |
| P-546 | A |
| P-547 | A |
| P-548 | B |
| P-549 | A |
| P-550 | A |
| P-552 | A |
| P-553 | A |
| P-554 | B |
| P-555 | A |
| P-556 | B |
| P-557 | A |
| P-558 | A |
| P-559 | A |
| P-560 | B |
| P-561 | A |
| P-562 | A |
| P-563 | A |
| P-564 | B |
| P-565 | B |
| P-566 | A |
| P-567 | A |
| P-568 | A |
| P-569 | A |
| P-570 | A |
| P-571 | A |
| P-572 | A |
| P-573 | A |
| P-574 | A |
| P-575 | B |
| P-576 | A |
| P-577 | A |
| P-578 | A |
| P-579 | A |
| P-580 | A |
| P-581 | A |
| P-582 | A |
| P-583 | A |
| P-584 | B |
| P-585 | A |
| P-586 | A |
| P-587 | A |
| P-588 | A |
| P-589 | A |
| P-590 | A |
| P-591 | A |
| P-592 | A |
| P-593 | A |
| P-594 | A |
| P-595 | A |
| P-596 | A |
| P-597 | A |
| P-598 | A |
| P-599 | A |
| P-600 | A |
| P-601 | A |
| P-602 | A |
| P-603 | A |
| P-604 | A |
| P-605 | A |
| P-606 | A |
| P-607 | A |
| P-608 | A |
| P-609 | A |
| P-610 | A |
| P-611 | A |
| P-612 | A |
| P-613 | A |
| P-614 | A |
| P-615 | A |
| P-616 | A |
| P-617 | A |
| P-618 | A |
| P-619 | A |
| P-620 | A |
| P-621 | A |
| P-622 | A |
| P-623 | A |

TABLE 10

PDE4B Activity, where A < 5 uM, B = 5-20 uM, C = 21-40 uM.

| Cmpd No | hPDE4B |
|---|---|
| P-001 | A |
| P-002 | A |
| P-004 | B |
| P-006 | A |
| P-007 | B |
| P-008 | A |
| P-009 | A |
| P-010 | A |
| P-011 | A |
| P-012 | B |
| P-014 | B |
| P-015 | C |
| P-017 | A |
| P-019 | A |
| P-020 | C |
| P-021 | B |
| P-022 | B |
| P-023 | B |
| P-024 | C |
| P-025 | C |
| P-027 | B |
| P-028 | A |
| P-029 | A |
| P-030 | C |
| P-031 | C |
| P-033 | B |
| P-034 | A |
| P-035 | A |
| P-036 | B |
| P-037 | A |
| P-038 | C |
| P-040 | B |
| P-041 | A |
| P-042 | B |
| P-043 | B |
| P-044 | A |
| P-045 | B |
| P-046 | B |
| P-047 | A |
| P-049 | A |
| P-050 | A |
| P-051 | B |
| P-053 | C |
| P-054 | A |
| P-055 | B |
| P-057 | A |
| P-058 | B |
| P-060 | B |
| P-061 | B |
| P-062 | A |
| P-063 | B |
| P-066 | A |
| P-067 | A |
| P-070 | C |
| P-071 | C |
| P-072 | C |
| P-073 | C |
| P-074 | B |
| P-075 | A |
| P-076 | A |
| P-077 | A |
| P-079 | A |
| P-081 | B |
| P-082 | B |
| P-083 | B |

TABLE 10-continued

PDE4B Activity, where A < 5 uM, B = 5-20 uM, C = 21-40 uM.

| Cmpd No | hPDE4B |
|---|---|
| P-084 | B |
| P-085 | A |
| P-086 | B |
| P-087 | A |
| P-088 | A |
| P-089 | A |
| P-090 | A |
| P-091 | C |
| P-092 | A |
| P-093 | B |
| P-094 | A |
| P-099 | A |
| P-101 | A |
| P-102 | A |
| P-103 | A |
| P-104 | A |
| P-105 | A |
| P-106 | A |
| P-107 | A |
| P-109 | A |
| P-111 | A |
| P-112 | A |
| P-113 | A |
| P-114 | A |
| P-115 | A |
| P-116 | A |
| P-117 | C |
| P-118 | A |
| P-119 | A |
| P-120 | B |
| P-122 | B |
| P-123 | A |
| P-125 | A |
| P-126 | A |
| P-127 | A |
| P-128 | A |
| P-130 | A |
| P-131 | B |
| P-133 | B |
| P-134 | B |
| P-135 | A |
| P-136 | A |
| P-138 | A |
| P-140 | A |
| P-142 | A |
| P-143 | A |
| P-144 | A |
| P-145 | A |
| P-146 | B |
| P-147 | A |
| P-148 | A |
| P-149 | B |
| P-150 | B |
| P-152 | A |
| P-153 | B |
| P-154 | A |
| P-155 | B |
| P-156 | A |
| P-159 | A |
| P-161 | B |
| P-162 | B |
| P-164 | B |
| P-165 | B |
| P-166 | A |
| P-168 | A |
| P-171 | A |
| P-172 | A |
| P-173 | A |
| P-174 | A |
| P-175 | A |
| P-176 | A |
| P-177 | A |
| P-178 | A |
| P-179 | B |
| P-180 | A |
| P-181 | A |
| P-182 | C |
| P-183 | A |
| P-184 | B |
| P-185 | C |
| P-186 | C |
| P-187 | A |
| P-188 | A |
| P-190 | A |
| P-192 | B |
| P-193 | A |
| P-195 | C |
| P-196 | B |
| P-197 | B |
| P-199 | A |
| P-200 | A |
| P-201 | C |
| P-204 | C |
| P-205 | A |
| P-206 | A |
| P-207 | A |
| P-208 | B |
| P-209 | A |
| P-211 | B |
| P-212 | B |
| P-213 | A |
| P-215 | B |
| P-216 | A |
| P-217 | A |
| P-218 | A |
| P-221 | A |
| P-222 | A |
| P-223 | B |
| P-224 | B |
| P-225 | A |
| P-226 | B |
| P-227 | A |
| P-228 | A |
| P-229 | A |
| P-230 | C |
| P-233 | A |
| P-234 | A |
| P-235 | B |
| P-236 | C |
| P-237 | A |
| P-240 | B |
| P-242 | A |
| P-243 | A |
| P-244 | A |
| P-245 | A |
| P-246 | A |
| P-248 | A |
| P-249 | A |
| P-250 | A |
| P-251 | A |
| P-252 | A |
| P-253 | C |
| P-254 | A |
| P-255 | A |
| P-256 | B |
| P-258 | A |
| P-259 | A |
| P-260 | B |
| P-261 | A |
| P-262 | A |
| P-263 | A |
| P-264 | B |
| P-266 | A |
| P-267 | A |
| P-268 | B |
| P-269 | A |
| P-270 | B |
| P-274 | A |
| P-275 | B |
| P-277 | A |

TABLE 10-continued

PDE4B Activity, where A < 5 uM, B = 5-20 uM, C = 21-40 uM.

| Cmpd No | hPDE4B |
|---|---|
| P-278 | A |
| P-279 | A |
| P-280 | A |
| P-281 | A |
| P-282 | B |
| P-283 | A |
| P-284 | A |
| P-285 | B |
| P-287 | A |
| P-290 | A |
| P-291 | A |
| P-292 | B |
| P-295 | C |
| P-296 | C |
| P-297 | B |
| P-299 | B |
| P-300 | A |
| P-301 | A |
| P-302 | A |
| P-303 | A |
| P-304 | A |
| P-305 | B |
| P-310 | A |
| P-311 | A |
| P-313 | A |
| P-315 | A |
| P-316 | A |
| P-317 | A |
| P-318 | A |
| P-323 | A |
| P-324 | C |
| P-325 | A |
| P-328 | A |
| P-329 | A |
| P-330 | A |
| P-331 | A |
| P-332 | A |
| P-333 | A |
| P-334 | A |
| P-335 | A |
| P-336 | A |
| P-337 | A |
| P-338 | A |
| P-339 | A |
| P-341 | A |
| P-342 | A |
| P-343 | A |
| P-344 | A |
| P-345 | A |
| P-346 | B |
| P-347 | A |
| P-352 | A |
| P-355 | A |
| P-356 | A |
| P-357 | A |
| P-359 | B |
| P-361 | A |
| P-362 | A |
| P-366 | A |
| P-367 | A |
| P-368 | A |
| P-369 | A |
| P-370 | B |
| P-371 | A |
| P-372 | A |
| P-373 | B |
| P-374 | A |
| P-375 | A |
| P-376 | A |
| P-378 | A |
| P-379 | A |
| P-382 | A |
| P-386 | A |
| P-387 | A |
| P-388 | A |
| P-392 | A |
| P-393 | A |
| P-394 | A |
| P-395 | A |
| P-397 | A |
| P-398 | A |
| P-399 | A |
| P-400 | A |
| P-401 | A |
| P-402 | A |
| P-404 | A |
| P-405 | A |
| P-406 | A |
| P-411 | A |
| P-412 | A |
| P-413 | A |
| P-415 | A |
| P-416 | C |
| P-417 | A |
| P-420 | A |
| P-421 | A |
| P-422 | A |
| P-429 | A |
| P-432 | A |
| P-433 | A |
| P-437 | A |
| P-439 | A |
| P-440 | B |
| P-441 | B |
| P-445 | B |
| P-447 | A |
| P-448 | A |
| P-451 | A |
| P-453 | A |
| P-456 | A |
| P-457 | A |
| P-458 | A |
| P-460 | A |
| P-461 | A |
| P-462 | A |
| P-463 | A |
| P-465 | A |
| P-467 | A |
| P-468 | A |
| P-469 | A |
| P-470 | A |
| P-471 | A |
| P-473 | A |
| P-478 | A |
| P-479 | B |
| P-481 | B |
| P-488 | B |
| P-494 | A |
| P-496 | A |
| P-498 | A |
| P-499 | B |
| P-500 | B |
| P-502 | A |
| P-503 | B |
| P-504 | B |
| P-507 | B |
| P-508 | B |
| P-513 | C |
| P-515 | A |
| P-516 | A |
| P-517 | B |
| P-518 | A |
| P-519 | A |
| P-521 | A |
| P-523 | A |
| P-524 | A |
| P-526 | B |
| P-527 | B |
| P-530 | C |
| P-531 | A |

TABLE 10-continued

PDE4B Activity, where A < 5 uM, B = 5-20 uM, C = 21-40 uM.

| Cmpd No | hPDE4B |
|---|---|
| P-532 | A |
| P-533 | A |
| P-534 | A |
| P-535 | A |
| P-536 | A |
| P-539 | C |
| P-540 | A |
| P-541 | A |
| P-542 | C |
| P-544 | A |
| P-545 | A |
| P-547 | A |
| P-549 | B |
| P-550 | A |
| P-553 | A |
| P-555 | A |
| P-559 | A |
| P-560 | B |
| P-562 | A |
| P-563 | B |
| P-564 | C |
| P-565 | C |
| P-566 | A |
| P-567 | A |
| P-568 | A |
| P-569 | A |
| P-570 | A |
| P-571 | A |
| P-573 | A |
| P-575 | A |
| P-576 | A |
| P-578 | A |
| P-579 | A |
| P-582 | A |
| P-583 | B |
| P-585 | A |
| P-587 | A |
| P-588 | A |
| P-590 | A |
| P-591 | A |
| P-592 | A |
| P-593 | A |
| P-594 | A |
| P-596 | A |
| P-597 | A |
| P-598 | A |
| P-599 | A |
| P-600 | C |
| P-603 | A |
| P-604 | A |
| P-605 | A |
| P-606 | A |
| P-610 | A |
| P-611 | A |
| P-612 | A |
| P-619 | A |
| P-620 | C |
| P-621 | A |
| P-623 | B |

The activity of PDE4 inhibitors described in the present invention was also measured using in an ex-vivo assay measuring leukotriene E4 (LTE4) in human whole blood after Sephadex stimulation. The anti-inflammatory activity of therapeutic agents of the present invention is demonstrated by the inhibition of eosinophil activation as measured by sephadex bead stimulated LTE4 production in whole human blood. For each sample, 356 μA of heparinized human whole blood (Vacutainer tube #6480) is added to wells of a 96 well plate. Then, 4 μl of a series of compound dilutions (in DMSO) are added in triplicates, suspension mixed and allowed to incubate at 37° C. for 15 min with gentle shaking. After that, blood samples are stimulated by adding 40 μL of Sephadex G-15 beads (Sigma-Aldrich, Sweden). The beads are predissolved in PBS (0.16 g/mL PBS). After mixing, the suspension is incubated at 37° C. for 90 min. Then, 8 μL of 15% EDTA/PBS is added to each sample, mixed and plate centrifuged for 5 min at 115×g at 21° C. and supernatants taken. In each plate, 10 positive controls and 10 negative controls are used, containing DMSO instead of compound solution. The positive controls are stimulated with Sephadex as described for the samples, and in the negative controls (unstimulated), Sephadex solution is replaced by PBS. $LTE_4$ levels in the resulting plasma samples are determined using a commercial enzyme-linked immunoassay (Cayman Chemical Company, Ann Arbor, Mich.) according to the manufacturer's instructions. Examples P-050, P-075, P-107, P-113, P-136, P-139, P-140, P-156, P-163, P-168, P-175, P-181, P-187, P-200, P-221, P-222, P-227, P-237, P-239, P-242, P-243, P-250, P-269, P-287, P-312, P-315, P-318, P-325, P-328, P-330, P-332, P-336, P-337, P-338, P-339, P-342, P-356, P-378, P-382, P-403, P-405, P-409, P-415, P-420 and P-439 all showed IC50<1 μM in this ex-vivo assay, whereas example P-358 had IC50>1 μM. Persons of skill in the art accept that positive results in PDE4 models are predictive of therapeutic utility as discussed above.

The following specific non-limiting examples are illustrative of the synthesis of compounds of the invention.

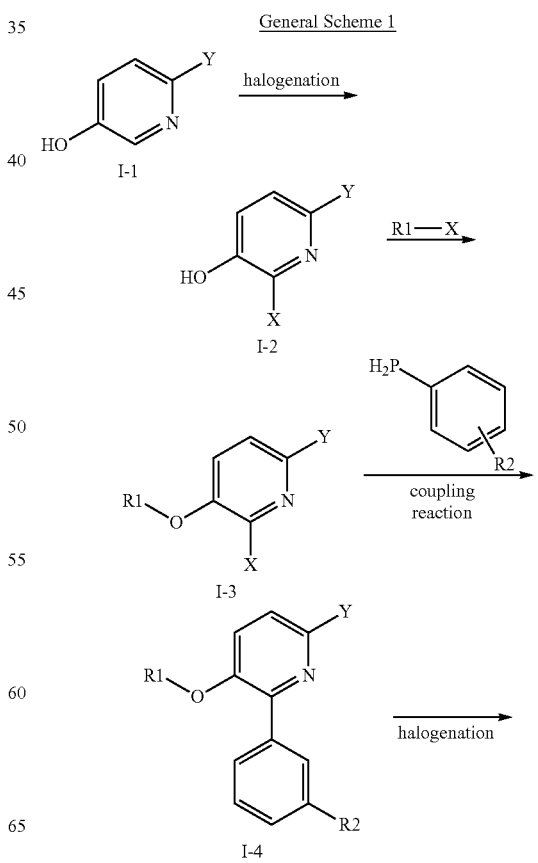

General Scheme 1

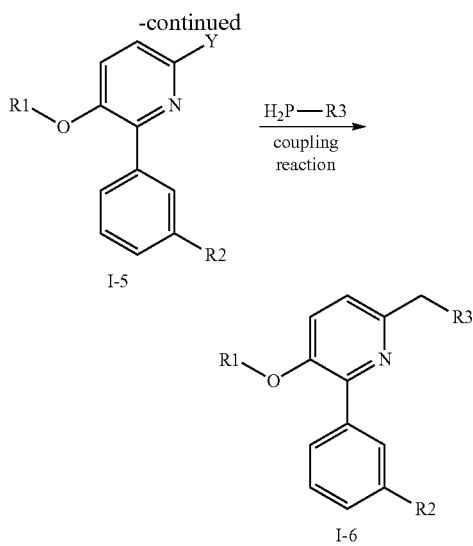

Y = CH3, CH2OH, CH2Br, CH2OCO2CH3
X = Br, I, Cl
R1 = H, Me, CHF2, CF3
P = halogen, boronate
R2 = Cl, CF3, CH3CO, CN, NO2, Br, fused heterocycle
R3 = substituted aryl groups Example 1

Preparation of P-065

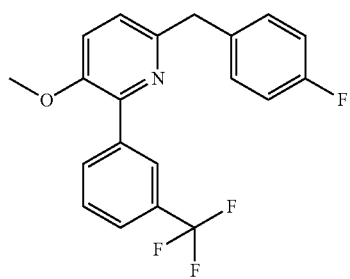

Synthesis of 2-bromo-6-methyl-pyridin-3-ol (I-2, X=Br, Y=CH₃): To 6-methyl-pyridin-3-ol (I-1, Y=CH₃, 5.0 g, 45.82 mmol) in pyridine (15 mL) was added bromine (3.66 g, 22.91 mmol). The reaction was stirred at room temperature under N₂ for 20 h. The crude reaction mixture was poured on to crushed ice-water (300 mL), stirred for 3 h. The mixture was extracted with ethyl acetate (5×100 mL) and the combined organic extracts were washed with brine, dried over Na₂SO₄, filtered, and concentrated to afford 6.3 g (73%) of 2-bromo-6-methyl-pyridin-3-ol (I-2, X=Br, Y=CH₃) as light yellow solid.

Synthesis of 2-bromo-3-methoxy-6-methyl-pyridine (I-3, X=Br, Y=R₁=CH₃): To the 2-bromo-6-methyl-pyridin-3-ol (I-2) 6.0 g, 31.91 mmol) and K₂CO₃ (8.82 g, 63.82 mmol) in acetone (100 mL) was added MeI (6.79 g, 479.87 mmol). The reaction was stirred at 45° C. under N₂ for 20 h. The reaction was cooled to room temperature, filtered and concentrated. The residue was purified by silica gel column chromatography using 1:1 dichloromethane-hexanes as eluent to afford 2.34 g (36%) of 2-bromo-3-methoxy-6-methyl-pyridine (I-3, X=Br, Y=R₁=CH₃) as off-white solid.

Synthesis of 3-methoxy-6-methyl-2-(3-trifluoromethyl-phenyl)-pyridine (I-4, Y=R₁=CH₃, R₂=CF₃): To the 2-bromo-3-methoxy-6-methyl-pyridine synthesized above (1.2 g, 5.94 mmol), 3-trifluoromethylphenylboronic acid (1.69 g, 8.91 mmol), PPh₃ (0.31 g, 1.19 mmol), K₂CO₃ (2.46 g, 17.82 mmol) and Pd(OAc)₂ (0.13 g, 0.59 mmol) was added DME (15 mL), and EtOH—H₂O (1:1, 6 mL). Ar gas was bubbled through the stirred reaction for 5 min. The reaction was stirred at 80° C. under Ar for 20 h. The reaction was cooled to room temperature, concentrated, and H₂O and dichloromethane (40 mL each) were added. The organic layer was separated and the aqueous layer was extracted with dichloromethane (2×25 mL). The combined organic extracts were dried with Na₂SO₄, filtered, and concentrated. The residue was purified by silica gel column chromatography using 1:1 dichloromethane-hexanes then dichloromethane to afford 1.36 g (86%) of 3-methoxy-6-methyl-2-(3-trifluoromethyl-phenyl)-pyridine (I-4, Y=R₁=CH₃, R₂=CF₃) as a light yellow solid.

Synthesis of 6-bromomethyl-3-methoxy-2-(3-trifluoromethyl-phenyl)-pyridine (I-5, R₁=CH₃, R₂=CF₃, Y=CH₂Br). To the 3-methoxy-6-methyl-2-(3-trifluoromethyl-phenyl)-pyridine synthesized above (1.3 g, 4.86 mmol) and NBS (1.04 g, 5.83 mmol) in CCl₄ (25 mL) was added benzoyl peroxide (0.12 g, 0.49 mmol). The reaction was stirred at 80° C. under N₂ for 20 h. The reaction was cooled to room temperature and concentrated. The residue was dissolved in mixture of dichloromethane and hexanes (1:1, 8 mL) and purified by silica gel column chromatography using 1:1 dichloromethane-hexanes to afford 0.74 g (44%) of 6-bromomethyl-3-methoxy-2-(3-trifluoromethyl-phenyl)-pyridine as off-white solid.

Synthesis of 6-(4-fluoro-benzyl)-3-methoxy-2-(3-trifluoromethyl-phenyl)-pyridine (P-065): To the 6-bromomethyl-3-methoxy-2-(3-trifluoromethyl-phenyl)-pyridine synthesized above (0.2 g, 0.58 mmol), 4-fluorophenylboronic acid (0.12 g, 0.87 mmol), PPh₃ (0.03 g, 0.12 mmol), K₃PO₄ (0.37 g, 1.73 mmol) and Pd(OAc)₂ (0.013 g, 0.058 mmol) was added DME (4.0 mL), and EtOH—H₂O (1:1, 1.0 mL). The reaction was stirred at 80° C. for 20 h. The reaction was cooled to room temperature, concentrated. The residue was purified by silica gel column chromatography using 1:1 dichloromethane-hexanes then dichloromethane to afford 0.056 g (22%) of 6-(4-fluoro-benzyl)-3-methoxy-2-(3-trifluoromethyl-phenyl)-pyridine (P-065) as a clear viscous liquid. ¹H NMR (CDCl₃, 400 MHz): 8.24 (s, 1H), 8.14 (d, J=8.0 Hz, 1H), 7.6-7.64 (m, 1H), 7.52-7.65 (m, 1H), 7.2-7.34 (m, 4H), 6.96-7.05 (m, 2H), 4.14 (s, 2H), 3.85 (s, 3H); MS (APCI+): 362.1 (M+1), LC-MS: 97.2%.

The following compounds were prepared according to general scheme 1, analogous to the preparation of P-065.

| |
|---|
| P-005 |
| P-010 |
| P-014 |
| P-019 |
| P-021 |
| P-022 |
| P-023 |
| P-024 |
| P-026 |
| P-028 |
| P-029 |
| P-031 |
| P-033 |
| P-034 |
| P-084 |
| P-035 |

-continued
P-036
P-044
P-045
P-046
P-048
P-053
P-054
P-057
P-058
P-060
P-061
P-063
P-064
P-068
P-069
P-070
P-071
P-072
P-076
P-078
P-081
P-082
P-083
P-085
P-086
P-104
P-108
P-131
P-132
P-153
P-154
P-155
P-156
P-162
P-169
P-184
P-188
P-195
P-196
P-197
P-198
P-204
P-205
P-206
P-207
P-208
P-209
P-210
P-211
P-212
P-213
P-214
P-215
P-218
P-229
P-233
P-235
P-236
P-245
P-248
P-253
P-370
P-376
P-379
P-386
P-422
P-424
P-435
P-436
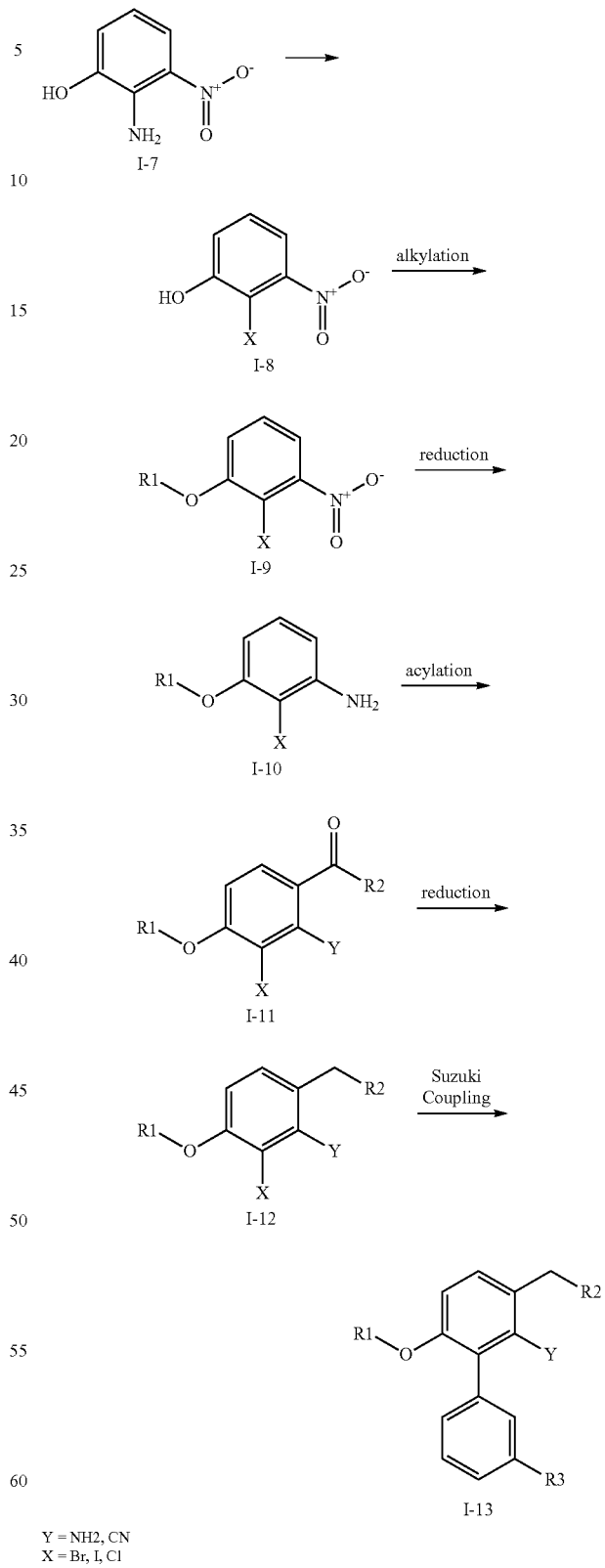
General Scheme 2.
Y = NH2, CN
X = Br, I, Cl
R1 = H, Me, CHF2, CF3
R3 = Cl, CH3CO, CN, NO2, Br, fused heterocycle
R2 = substituted aryl groups

Example 2

Preparation of P-176

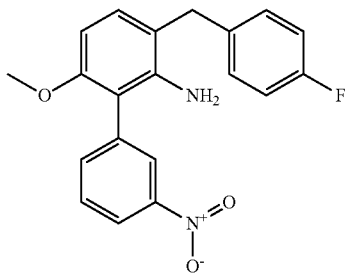

P-176

Synthesis of 2-bromo-3-nitro-phenol (I-8, X=Br): (Prepared by a modification of reported procedure, J. Org. Chem. 1988, 53, pp 1170-1176). To 2-amino-3-nitro-phenol (24.9 mmol, 1.0 eq.) in 24 mL of water and 12 mL of 1,4-dioxane at reflux, was added 13 mL of HBr (48% aq.) over 10 minutes. The resulting solution was refluxed for an additional 15 minutes, and cooled 0-5° C. A solution of sodium nitrite (24.4 mmol, 0.98 eq.) in 20 mL of water was added over 10 minutes, and stirred for 15 minutes. The reaction mixture was then heated to 60° C. for 15 minutes, and allowed to cool naturally to room temperature, and stirred for 16 hours. The reaction mixture was then extracted with two portions of diethyl ether, and the combined ethereal layers washed with brine, dried over magnesium sulfate, filtered through a layer of celite and concentrated. The residue was diluted with dichloromethane (with ~0.1% MeOH), and purified via silica gel plug filtration with dichloromethane to yield 2-bromo-3-nitro-phenol (I-8, X=Br) as a pale orange-brown solid. Yield: 50%. $^1$H NMR (400 MHz; CDCl$_3$): 6.07 (s, 1H), 7.25 (dd, J=8.4, 1.2 Hz, 1H), 7.37 (t, J=8.0 Hz, 1H), 7.48 (dd, J=8.0, 1.6 Hz, 1H) ppm.

Synthesis of 2-bromo-3-nitro-anisole (I-9, X=Br, R$_1$=CH$_3$): To a solution of 2-bromo-3-nitro-phenol synthesized above (11.5 mmol, 1.0 eq.) in DMF at room temperature was added cesium carbonate (13.8 mmol, 1.2 eq.), followed by iodomethane (33.7 mmol, 2.9 eq.), and the resultant mixture was stirred at room temperature for 16 hours. The reaction mixture was poured into water, stirred for 2 hours, filtered, the cake washed with two portions of water, and the resultant solid dried to afford 2-bromo-3-nitro-anisole (I-9, X=Br, R$_1$=CH$_3$) as a pale orange solid. Yield: 97%; $^1$H NMR (400 MHz; CDCl$_3$): 3.97 (s, 3H), 7.07 (dd, J=8.4, 1.2 Hz, 1H), 7.32 (dd, J=8.0, 1.6 Hz, 1H), 7.40 (t, J=8.0 Hz, 1H) ppm.

Synthesis of 2-bromo-3-methoxy-aniline (I-10, X=Br, R$_1$=CH$_3$): (Prepared by a modification of reported procedure WO Patent: WO2006/7700). To a solution of 2-bromo-3-nitro-anisole synthesized above (10.3 mmol, 1.0 eq.) in absolute ethanol and glacial acetic acid at room temperature was added iron powder (42.1 mmol, 4.1 eq). The resultant mixture was heated to reflux for 1.5 hours, and then cooled to room temperature. The reaction mixture was diluted with water, and solid sodium carbonate was added until the pH was 6-7. Dichloromethane was added, and the mixture was filtered through celite. The dried (sodium sulfate) organics were concentrated to afford 2-bromo-3-methoxy-aniline (I-10, X=Br, R$_1$=CH$_3$) as an oil. Yield: 90%; $^1$H NMR (400 MHz; CDCl$_3$): 3.87 (s, 3H), 4.16 (br s, 2H), 6.31 (dd, J=8.0, 1.2 Hz, 1H), 6.42 (dt, J=8.0, 0.8, 0.4 Hz, 1H), 7.05 (t, J=8.0 Hz, 1H) ppm.

Synthesis of 2-amino-3-bromo-4-methoxy-phenyl)-(4-fluoro-phenyl)-methanone (I-11, X=Br, Y=NH$_2$, R$_1$=CH$_3$, R$_2$=4-fluorophenyl): To a solution of boron trichloride (1.0 M in heptane; 10.0 mmol; 1.1 eq.) at 0° C. in tetrachloroethane was added a solution of 2-bromo-3-methoxy-aniline synthesized above (9.09 mmol; 1 eq.) in tetrachloroethane over 1 minute. The resultant mixture was stirred at the same temperature for 10 minutes, and to it was added a solution of 4-fluorobenzonitrile (18.2 mmol; 2 eq.) in tetrachloroethane and aluminum chloride (10.0 mmol; 1.1 eq.). The reaction was heated to 110° C. for 5 hours, and allowed to cool to room temperature and stir for 16 hours. The reaction mixture was added 10 mL of 3N HCl, and the resultant mixture was heated to 90° C. for 1 hour, and cooled to room temperature. The pH was adjusted with 6N NaOH to 11-12, and extracted with dichloromethane. The organics were washed with a brine solution, dried over magnesium sulfate, and filtered. The filtrate was concentrated, and the residue purified via silica gel chromatography using 10% hexanes in dichloromethane as eluent to afford 2-amino-3-bromo-4-methoxy-phenyl)$_{4-4}$-fluoro-phenyl)-methanone (I-11, X=Br, Y=NH$_2$, R$_1$=CH$_3$, R$_2$=4-fluorophenyl) in 65% yield.; $^1$H NMR (400 MHz; CDCl$_3$): 3.95 (s, 3H), 6.25 (d, J=8.8 Hz, 1H), 6.85 (br s, 2H), 7.11-7.16 (M, 2H), 7.42 (d, J=8.8 Hz, 1H), 7.60-7.64 (m, 2H) ppm.

Synthesis of 2-bromo-6-(4-fluoro-benzyl)-3-methoxy-aniline (I-12, X=Br, Y=NH$_2$, R$_1$=CH$_3$, R$_2$=4-fluorophenyl): To a solution of trifluoroacetic acid (21.6 mmol; 10 eq.) in dichloromethane at −15° C. was added in portions sodium borohydride (8.06 mmol; 3.7 eq.) while maintaining internal bath temperature between −15° and −20° C. (caution, strong gas evolution) The reaction mixture was allowed to warm to 0-5° C., and a solution of the above ketone (2.16 mmol; 1.0 eq) in dichloromethane was added over approximately 5 minutes. The resultant mixture was allowed to stir at room temperature for 16 hours, and was quenched with 5% aq. NaHCO$_3$, and extracted with ethyl acetate. The combined organics were washed with water, brine, and dried over magnesium sulfate, and concentrated. (TLC analysis indicated a mixture of starting ketone and desired methylene product) The residue was taken into THF, and treated with BH$_3$.THF (15 mmol) at room temperature for 1 hour. The excess borane was quenched with methanol, and the mixture concentrated. Three additional portions of methanol were added, and the mixture concentrated. The residue was purified via flash chromatography on silica gel using 1:1 dichloromethane-hexanes as eluent to give 2-bromo-6-(4-fluoro-benzyl)-3-methoxy-aniline (I-12, X=Br, Y=NH$_2$, R$_1$=CH$_3$, R$_2$=4-fluorophenyl) in 40% yield.; $^1$H NMR (400 MHz; CDCl$_3$): 3.86 (s, 2H), 3.87 (s, 3H), 4.07 (br s, 2H), 6.33 (d, J=8.4 Hz, 1H), 6.93 (d, J=8.4 Hz, 1H), 7.98 (ddd, J=8.8, 8.4, 2.0 Hz, 2H), 7.12 (ddd, J=8.0, 6.4, 1.0 Hz, 2H) ppm.

Synthesis of 3-(4-fluoro-benzyl)-6-methoxy-3'-nitro-biphenyl-2-ylamine (P-176): A mixture of 2-bromo-6-(4-fluoro-benzyl)-3-methoxy-aniline synthesized above (0.403 mmol; 1.0 eq.), 4-fluorophenylboronic acid (0.605 mmol; 1.5 eq), and 2 M K$_2$CO$_3$ (650 mL, 3.2 eq) in dioxane was degassed with nitrogen for 10 minutes, and tetrakis(triphenylphosphine)palladium was added, and the resultant mixture degassed for an additional 5 minutes. The reaction was stirred at 70° C. for 16 hours, and cooled to room temperature. The reaction was diluted with water, and extracted with two portions of ethyl acetate. The combined organics were washed with three portions of water, brine, dried over magnesium sulfate, and filtered through celite. The residue was purified via flash chromatography on silica gel using 20% acetone in hexane as eluent to give 3-(4-fluoro-benzyl)-6-methoxy-3'-nitro-biphenyl-2-ylamine (P-176) in 46% yield.; $^1$H NMR (400 MHz; CDCl$_3$): 3.70 (s, 3H), 3.86 (s, 2H), 6.42 (d, J=8.4 Hz, 1H), 6.97-7.02 (m, 2H), 7.04 (d, J=8.4 Hz, 1H), 7.17 (dd, J=5.2, 3.2 Hz, 2H), 7.60-7.67 (m, 2H), 8.18-8.20 (m, 2H) ppm; LC/MS (86.9%); (ESI+). Found 353.6 (M+1). Calcd 352.4 m/z.

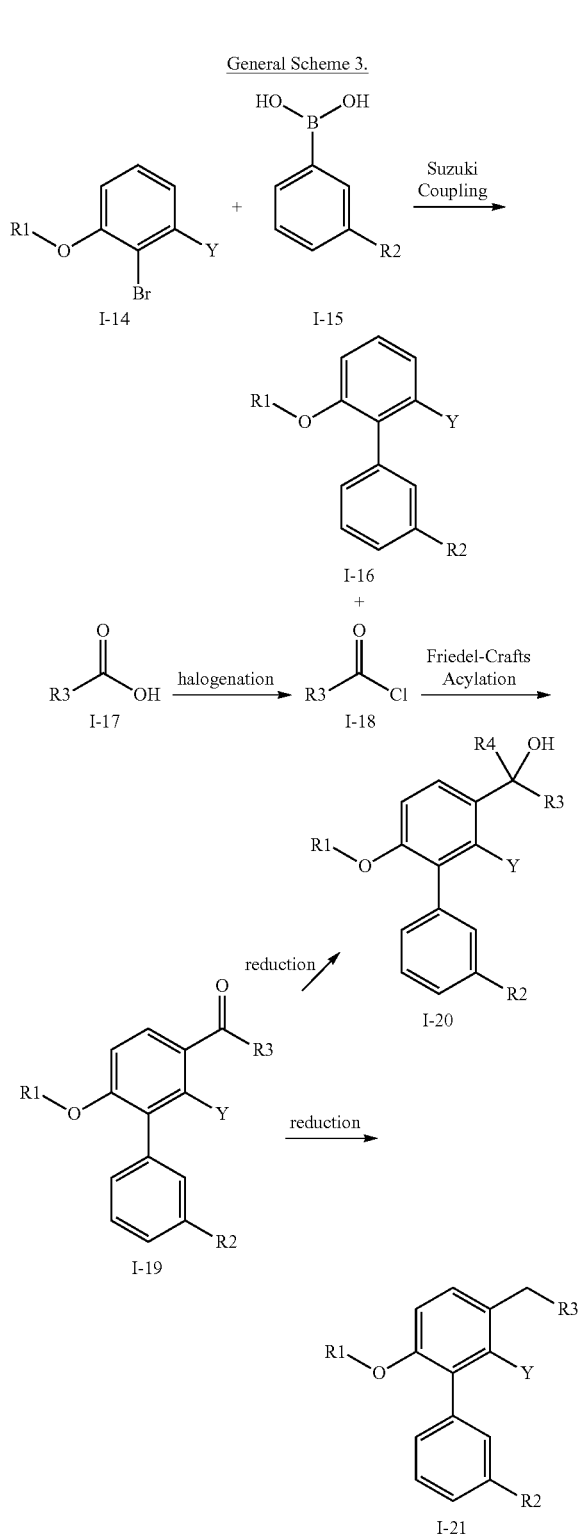

Y = H, F, OH
R1 = H, Me, CHF2, CF3
R2 = Cl, CH3CO, CN, NO2, Br, NH2, fused heterocycle
R3 = substituted aryl groups
R4 = H, Me Example 3

Preparation of P-404

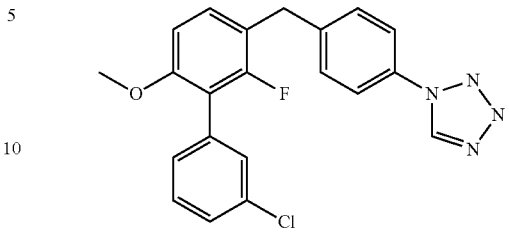

P-404

Synthesis of 3'-chloro-6-fluoro-2-methoxy-biphenyl (I-16, $R_1$=$CH_3$, $R_2$=Cl, Y=F): To 2-bromo-3-fluoroanisole (1.0 g, 4.88 mmol), 3-chlorophenylboronic acid (0.91 g, 5.88 mmol), PPh₃ (0.64 g, 2.44 mmol), K₂CO₃ (0.27 g, 1.95 mmol) and Pd(OAc)₂ (0.13 g, 0.58 mmol) was added dioxane (8 mL), and EtOH—H₂O (1:1, 4 mL). Ar gas was bubbled through the stirred reaction for 5 min. The reaction was heated at 180° C. using microwave oven (Biotage Intiator II) for 20 min. The reaction was cooled to room temperature, combined with another 0.5 g scale run, concentrated. The residue was purified by silica gel column chromatography using 1:1 dichloromethane-hexanes to afford 1.33 g (77%) 3'-chloro-6-fluoro-2-methoxy-biphenyl (I-16, $R_1$=$CH_3$, $R_2$=Cl, Y=F) as a viscous liquid.

Synthesis of N-[4-(3'-chloro-2-fluoro-6-methoxy-biphenyl-3-carbonyl)-phenyl]-acetamide (I-19, $R_1$=$CH_3$, $R_2$=Cl, Y=F, $R_3$=4-acetylaminophenyl): To a stirred suspension of 4-acetylaminobenzoic acid (Aldrich, 1.32 g, 5.58 mmol) in anhydrous THF (20 mL) was added SOCl₂ (1.19 g, 10.04 mmol) and DMF (4 drops). The reaction mixture was stirred at room temperature for 3 h, concentrated under vacuum to afford 4-acetylaminobenzoyl chloride (I-18, $R_3$=4-acetylaminophenyl) as a light yellow solid.

To a stirred solution of nitrobenzene (12 mL) was added AlCl₃ (2.23 g, 16.73 mmol) portion wise over 10 min, then the solution was stirred at room temperature for 20 min. A solution of 4-acetylaminobenzoyl chloride synthesized above (1.32 g, 5.58 mmol) in dichloromethane (4 mL) was added one portion to this reaction mixture, stirred for 72 h. The reaction mixture was poured on to crushed ice-water (250 mL), Extracted with dichloromethane (2×60 mL). The combined organic layers were washed with brine (60 mL), dried (Na₂SO₄), filtered and then purified by silica gel column chromatography using dichloromethane then 3% methanol-dichloromethane to afford 1.97 g (89%) N-[4-(3'-chloro-2-fluoro-6-methoxy-biphenyl-3-carbonyl)-phenyl]-acetamide (I-19, $R_1$=$CH_3$, $R_2$=Cl, Y=F, $R_3$=4-acetylaminophenyl) as light brown solid.

Synthesis of (4-amino-phenyl)-(3'-chloro-2-fluoro-6-methoxy-biphenyl-3-yl)-methanone hydrochloride (I-19, R3=4-aminophenyl). To a stirred suspension of N-[4-(3'-chloro-2-fluoro-6-methoxy-biphenyl-3-carbonyl)-phenyl]-acetamide synthesized above (1.75 g, 4.44 mmol) in ethanol (40 mL) was added con. HCl (40 mL). The reaction was refluxed for 2 h, cooled to room temperature, filtered, washed with water than hexanes to afford 0.82 g (48%) of (4-amino-phenyl)-(3'-chloro-2-fluoro-6-methoxy-biphenyl-3-yl)-methanone hydrochloride as light yellow solid.

Synthesis of (3'-chloro-2-fluoro-6-methoxy-biphenyl-3-yl)-(4-tetrazol-1-yl-phenyl)-methanone: To a stirred suspension of (4-amino-phenyl)-(3'-chloro-2-fluoro-6-methoxy-biphenyl-3-yl)-methanone hydrochloride synthesized above (0.4 g, 1.02 mmol) and sodium azide (0.2 g, 3.06 mmol) in glacial acetic acid (10 mL) was added trimethylorthoformate (0.32 g, 3.06 mmol). The reaction was stirred at room temperature for 3 h, diluted with cold water (60 mL), than basified with ammonium hydroxide solution (28%). Extracted with dichloromethane (2×40 mL), the combined dichloromethane solution was washed with brine (40 ml), dried with $Na_2SO_4$, filtered, and concentrated to afford 0.38 g (90%) of (3'-chloro-2-fluoro-6-methoxy-biphenyl-3-yl)-(4-tetrazol-1-yl-phenyl)-methanone as light yellow solid.

Synthesis of 1-[4-(3'-chloro-2-fluoro-6-methoxy-biphenyl-3-ylmethyl)-phenyl]-1H-tetrazole (P-404): To (3'-chloro-2-fluoro-6-methoxy-biphenyl-3-yl)-(4-tetrazol-1-yl-phenyl)-methanone synthesized above (0.1 g, 0.24 mmol) in TFA (1.5 mL) was added triethylsilane (0.28 g, 2.4 mmol). The reaction mixture was stirred at room temperature for 20 h. The reaction mixture was cooled to 0° C., diluted with water (3 mL), basified with ammonium hydroxide solution (28%), filtered, washed with water dried to afford 0.08 g (81%) of 1-[4-(3'-chloro-2-fluoro-6-methoxy-biphenyl-3-ylmethyl)-phenyl]-1H-tetrazole (P-404) as off-white solid. $^1$H NMR (DMSO-$d_6$, 400 MHz): 7.2-7.4 (m, 6H), 7.04-7.12 (s, 3 H), 6.7 (d, J=8.4 Hz, 1H), 3.95 (s, 2H), 3.77 (s, 3H) ppm; MS (APCI+): 365.1 (M−28), LC-MS: 95.9%.

The following compounds were prepared by incorporation of various R3 groups analogous to the preparation of P-404.

| | | | |
|---|---|---|---|
| P-434 | P-003 | P-187 | P-152 |
| P-441 | P-004 | P-051 | P-124 |
| P-099 | P-013 | P-256 | P-125 |
| P-137 | P-032 | P-257 | P-106 |
| P-138 | P-095 | P-262 | P-109 |
| P-157 | P-096 | P-263 | P-126 |
| P-173 | P-097 | P-264 | P-150 |
| P-180 | P-049 | P-265 | P-177 |
| P-183 | P-050 | P-276 | P-178 |
| P-190 | P-116 | P-285 | P-182 |
| P-001 | P-098 | P-016 | P-185 |
| P-002 | P-139 | P-017 | P-163 |

General Scheme 4.

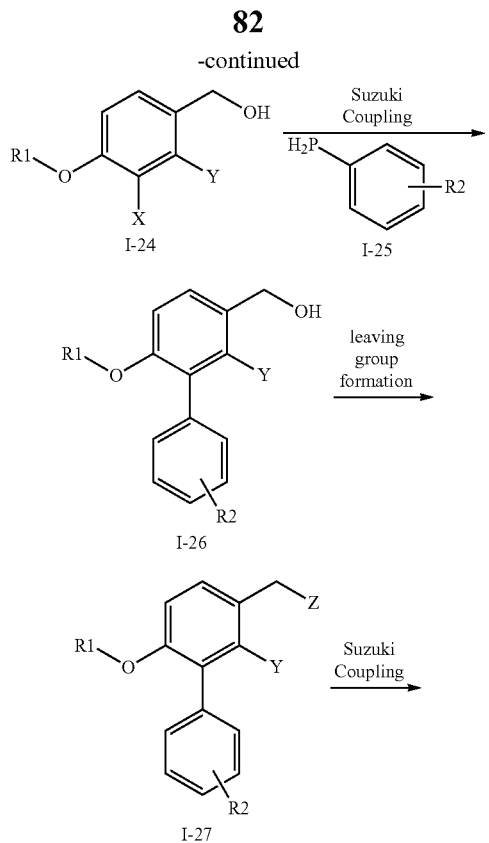

Y = H, F, OH, NH2, CN, OCH3, OEt
X = (Br, I, Cl), boronate
Z = Br, Cl, OCO$_2$CH$_3$
R1 = H, Me, CHF2, CF3
P = halogen, (boronate)
R2 = Cl, CH3CO, CN, NO2, Br, fused heterocycle
R3 = substituted aryl groups

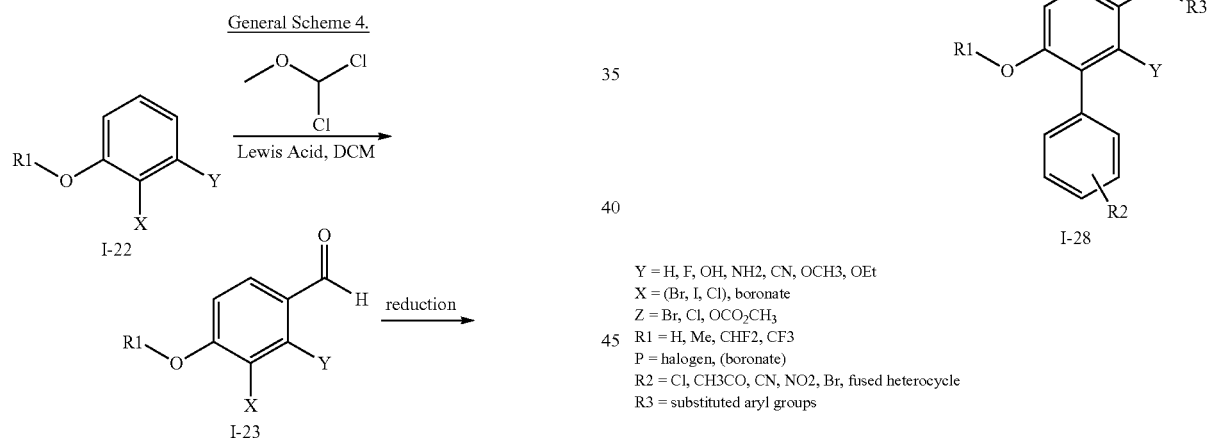

Scheme 5.

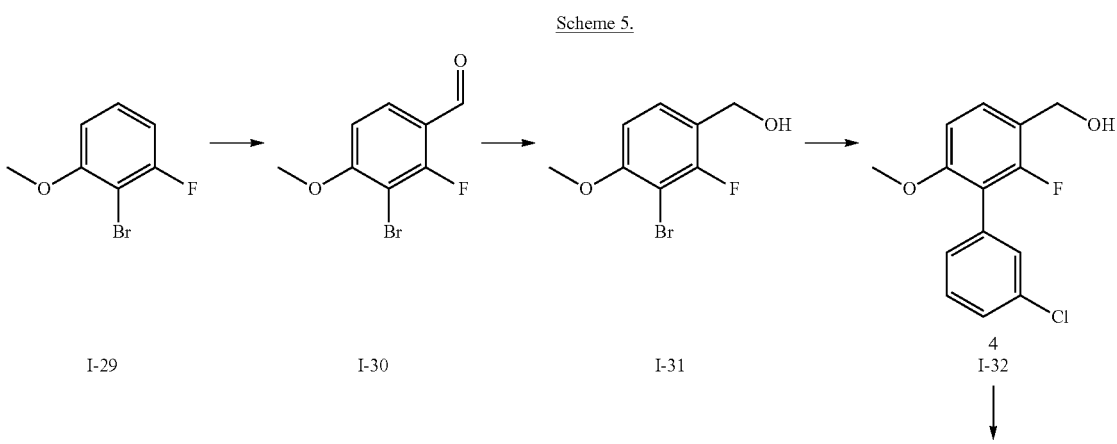

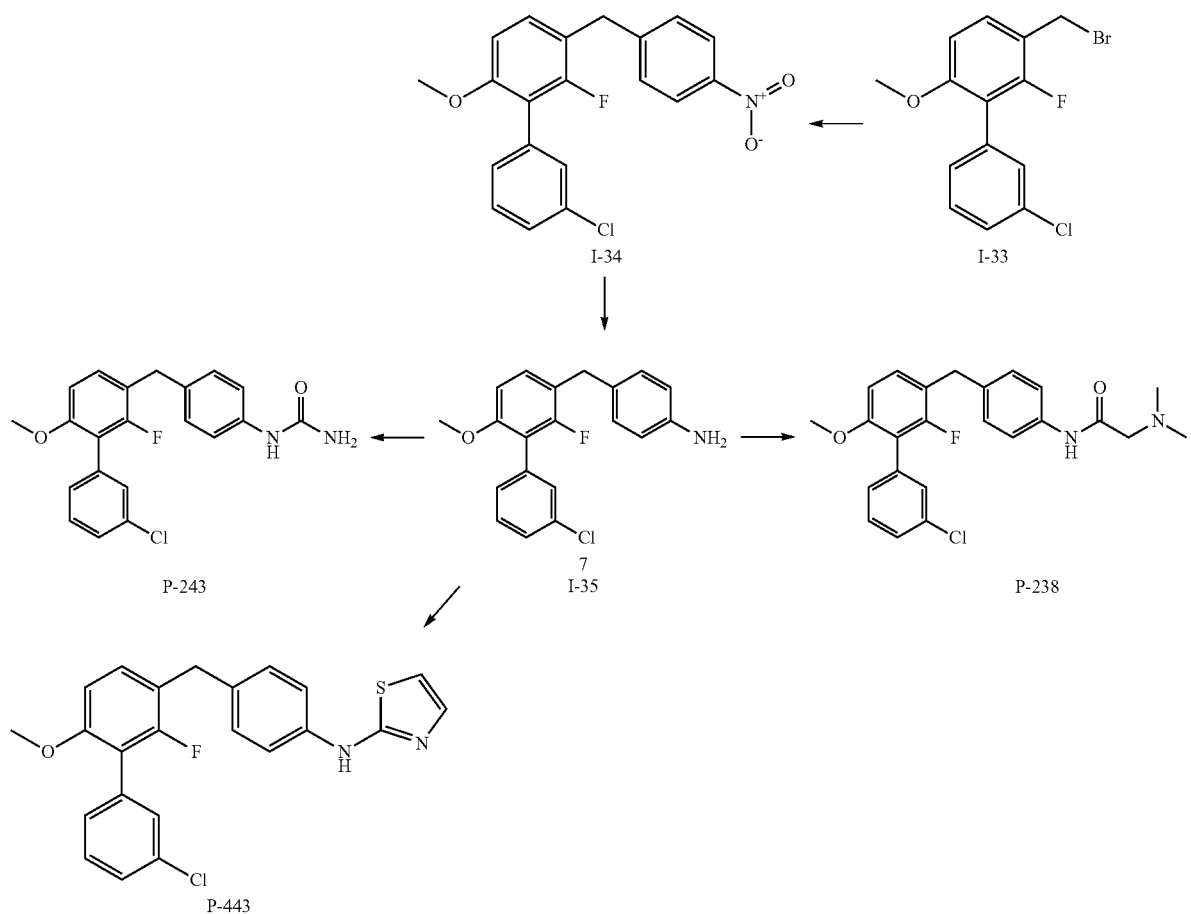

Example 4

Preparation of P-443

Synthesis of 3-bromo-2-fluoro-4-methoxy-benzaldehyde (I-30). In a 3-necked 250 mL round-bottomed flask equipped with nitrogen lines and a stir bar was placed 2-bromo-1-fluoro-3-methoxy-benzene (I-29, 2.0 g, 9.75 mmol) and dichloromethane (48 mL). The solution was cooled in an ice water bath for 15 minutes and then titanium tetrachloride (5.02 mL, 45.8 mmol) and dichloromethyl methyl ether (1.32 mL, 14.6 mmol) were added and the reaction mixture was allowed to warm to room temperature and react for 2 hours. The reaction mixture was slowly added to ice water (250 mL) and extracted with dichloromethane (2×100 mL). The organic portions were combined, washed with a saturated sodium bicarbonate solution (75 mL), water (75 mL) and brine (75 mL), dried (MgSO$_4$) and concentrated. The crude material was triturated with hexanes (15 mL) to produce 1.67 g of 3-bromo-2-fluoro-4-methoxy-benzaldehyde (I-30) as an off-white solid in 74% yield. MS (ESI+): 233.2 (M+)

Synthesis of (3-bromo-2-fluoro-4-methoxy-phenyl)-methanol (I-31). In a 100 mL round bottomed flask equipped with a stir bar was placed 3-bromo-2-fluoro-4-methoxy-benzaldehyde (I-30, 1.67 g, 7.17 mmol), methanol (12 mL), dichloromethane (12 mL) and sodium borohydride. The reaction mixture was allowed to stir at room temperature for 17 hours, quenched with water (10 mL) and 1M HCl (5 mL) and extracted with dichloromethane (2×30 mL). The organic portions were combined, washed with brine (30 mL), dried (MgSO$_4$) and concentrated. The crude material was triturated with hexanes (15 mL) to produce 955 mg (57%) of (3-bromo-2-fluoro-4-methoxy-phenyl)-methanol (I-31) as a white solid.

Synthesis of (3'-chloro-2-fluoro-6-methoxy-biphenyl-3-yl)-methanol (I-32). Into a 100 mL round bottom flask was added (3-bromo-2-fluoro-4-methoxy-phenyl)-methanol (I-31, 1.04 g, 4.0 mmol), 3-chlorophenylboronic acid (0.76 g, 4.8 mmol), Pd(PPh$_3$)$_4$ (0.45 g, 0.41 mmol), Na$_2$CO$_3$ (6 mL, 2M aq), toluene, (32 mL), and EtOH (11 mL). The reaction was degassed with N$_2$, then stirred at 80° C. for 24 hours. Water was added and the product was extracted with ethyl acetate. The combined organics were concentrated and filtered through a SiO$_2$ plug eluting with 50% ethyl acetate/hexanes. The solid was triturated with ether and filtered. The filtrate was concentrated and triturated with ether and filtered. The filter cakes were combined and purified by flash column chromatography eluting with 20% acetone/hexanes to give (3'-chloro-2-fluoro-6-methoxy-biphenyl-3-yl)-methanol (I-32, 0.79 g, 67%) as a white solid.

Synthesis of 3-bromomethyl-3'-chloro-2-fluoro-6-methoxy-biphenyl (I-33). Into a 250 mL round bottom flask was added (3'-Chloro-2-fluoro-6-methoxy-biphenyl-3-yl)-methanol synthesized above (1.21 g, 4.54 mmol), dichloromethane (20 mL), $PPh_3$ (1.19 g, 4.54 mmol), and the solution was cooled to 0° C. NBS (0.81 g, 4.54 mmol) was added and the reaction stirred for 2 hours at 0° C. The organics were washed with $H_2O$ and concentrated. The residue was purified by flash column chromatography eluting with 8% ethyl acetate/hexanes to give 3-bromomethyl-3'-chloro-2-fluoro-6-methoxy-biphenyl (I-33, 956 mg, 64%) as an off-white solid.

Synthesis of 3'-chloro-2-fluoro-6-methoxy-3-(4-nitrobenzyl)-biphenyl (I-34). In a 40 mL vial equipped with a stir bar was placed 3-bromomethyl-3'-chloro-2-fluoro-6-methoxy-biphenyl (I-33, 400 mg, 1.21 mmol), 4-nitrophenylboronic acid (420 mg, 1.45 mmol), potassium phosphate (tribasic) (514 mg, 2.42 mmol), dimethoxyethane (3.5 mL) and 50% aqueous ethanol (3.5 mL). After degassing with nitrogen for 15 minutes, tetrakis(triphenylphosphine)palladium(0) (140 mg, 0.121 mmol) was added. The mixture was heated to 60° C. for 18 hours and then the palladium catalyst was removed by filtering through Celite. To the filtrate were added water (50 mL) and a saturated ammonium chloride solution (50 mL). After extracting with ethyl acetate (3×50 mL), the organic portions were combined, washed with brine (75 mL), dried ($MgSO_4$) and concentrated. The crude material was purified by silica gel chromatography utilizing 20% ethyl acetate/hexanes as eluent to produce 342 mg (76%) of 3'-chloro-2-fluoro-6-methoxy-3-(4-nitro-benzyl)-biphenyl (I-34) as a yellow solid. MS (APCI–): 370.1 (M–1).

Synthesis of 4-(3'-chloro-2-fluoro-6-methoxy-biphenyl-3-ylmethyl)-phenylamine (I-35): In an 18 mL vial equipped with a stir bar was placed iron powder (179 mg, 3.20 mmol), ethanol (5.0 mL) and water (1.2 mL). The mixture was heated to 85° C. in an oil bath and then the above product 3'-Chloro-2-fluoro-6-methoxy-3-(4-nitro-benzyl)-biphenyl (6) (340 mg, 0.914 mmol) was added and the reaction was continued at 85° C. for 2 hours. The reaction mixture was cooled to room temperature and filtered through Celite. To the filtrate was added water (50 mL) and extractions were performed with ethyl acetate (2×60 mL). The organic portions were combined, washed with brine (50 mL), dried ($MgSO_4$) and concentrated to produce 245 mg of 4-(3'-chloro-2-fluoro-6-methoxy-biphenyl-3-ylmethyl)-phenylamine (I-35) as a yellow, viscous oil in 79% yield. MS (APCI+): 342.0 (M+1).

Synthesis of [4-(3'-chloro-2-fluoro-6-methoxy-biphenyl-3-ylmethyl)-phenyl]-thiazol-2-yl-amine. (P-443): In an 8 mL vial equipped with a stir bar was placed 4-(3'-chloro-2-fluoro-6-methoxy-biphenyl-3-ylmethyl)-phenylamine (I-35) synthesized above (100 mg, 0.293 mmol), 2-bromothiazole (52.1 μL, 0.585 mmol), 10% aqueous ethanol (1.5 mL) and concentrated hydrochloric acid (48.8 μL, 0.585 mmol). The mixture was heated to 90° C. for 18 hours and then cooled to room temperature. After water (30 mL) and 5% aqueous potassium carbonate (30 mL) were added, the aqueous portion was extracted with ethyl acetate (2×35 mL) and the organic portions were combined, washed brine (30 mL), dried (magnesium sulfate) and concentrated. The crude material was purified by column chromatography utilizing 3% acetone/dichloromethane as the eluent to produce 57 mg of [4-(3'-chloro-2-fluoro-6-methoxy-biphenyl-3-ylmethyl)-phenyl]-thiazol-2-yl-amine. (P-443) as white solid in 45% yield. $^1$H NMR (400 MHz, $CDCl_3$) δ 3.75 (s, 3H), 3.94 (s, 2H), 6.62 (d, J=4 Hz, 1H), 6.70 (dd, J=8, 1 Hz, 1H), 7.10 (t, J=9 Hz, 1H), 7.20-7.22 (m, 2H), 7.26-7.40 (m, 8H) ppm; MS (APCI+): 425.0 (M+1), LC-MS: 89%

Example 5

Preparation of P-238

Synthesis of N-[4-(3'-chloro-2-fluoro-6-methoxy-biphenyl-3-ylmethyl)-phenyl]-2-dimethylamino-acetamide (P-238). In a 8 ml vial was charged with 4-(3'-chloro-2-fluoro-6-methoxy-biphenyl-3-ylmethyl)-phenylamine (I-35) (70 mg, 0.2 mmol, HCl salt), N,N-dimethylglycine/HCl salt (31 mg, 0.3 mmol, 1.5 eq.) EDCI (80 mg, 0.4 mmol, 2 eq.), HOBt (41 mg, 0.3 mmol, 1.5 eq.), $Et_3N$ (0.2 ml, 1.43 mmol, 5.3 eq.), N,N-dimethylforamide (2 ml). The resulting mixture was stirred at rt overnight. The mixture was poured into water and extracted with EtOAc. Evaporation of solvent gave a residue, which was purified by chromatography on silica gel using dichloromethane in methanol (33:1) as eluent to give the free base product, which was converted into HCl salt by treating with 2N HCl in ether. 65 mg of N-[4-(3'-chloro-2-fluoro-6-methoxy-biphenyl-3-ylmethyl)-phenyl]-2-dimethylamino-acetamide (P-238) as HCl salt in 75% yield. $^1$H NMR ($CDCl_3$, 400 MHz): 9.04 (br s, 1H), 7.46-7.52 (m, 2H), 7.37-7.43 (m, 1H), 7.24-7.36 (m, 3H), 7.14-7.23 (m, 2H), 7.01-7.12 (m, 1H), 6.64-6.74 (m, 1H), 3.86-3.98 (m, 2H), 3.73 (s, 3H), 3.05 (s, 2H), 2.36 (s, 6H) ppm; LCMS: 96%.

Example 6

Preparation of P-243

Synthesis of [4-(3'-chloro-2-fluoro-6-methoxy-biphenyl-3-ylmethyl)-phenyl]-urea (P-243). A mixture of 4-(3'-chloro-2-fluoro-6-methoxy-biphenyl-3-ylmethyl)-phenylamine (I-35) (100 mg, 0.26 mmol, 1 eq.), sodium cyanate (74 mg, 0.52 mmol, 2 eq.) in HOAc (1 ml) and water (1 ml) was sonicated at rt for 20 min. then was shaken at rt overnight. The mixture was diluted with water. The precipitate was collected by filtration and washed with water. After dried, 71 mg of crude product containing a less polar by product (presumably the corresponding acetamide) was obtained. Trituration of the crude product with acetone/hexane gave 56 mg of [4-(3'-chloro-2-fluoro-6-methoxy-biphenyl-3-ylmethyl)-phenyl]-urea (P-243) as white solid in 56% yield. $^1$H NMR (DMSO-$d_6$, 400 MHz): 8.42 (s, 1H), 7.40-7.47 (m, 2H), 7.36 (m, 1H), 7.23-7.32 (m, 4H), 7.07 (m, 2H), 6.92 (m, 1H), 5.76 (s, 2H), 3.83 (s, 2H), 3.72 (s, 3H) ppm.

Scheme 6.
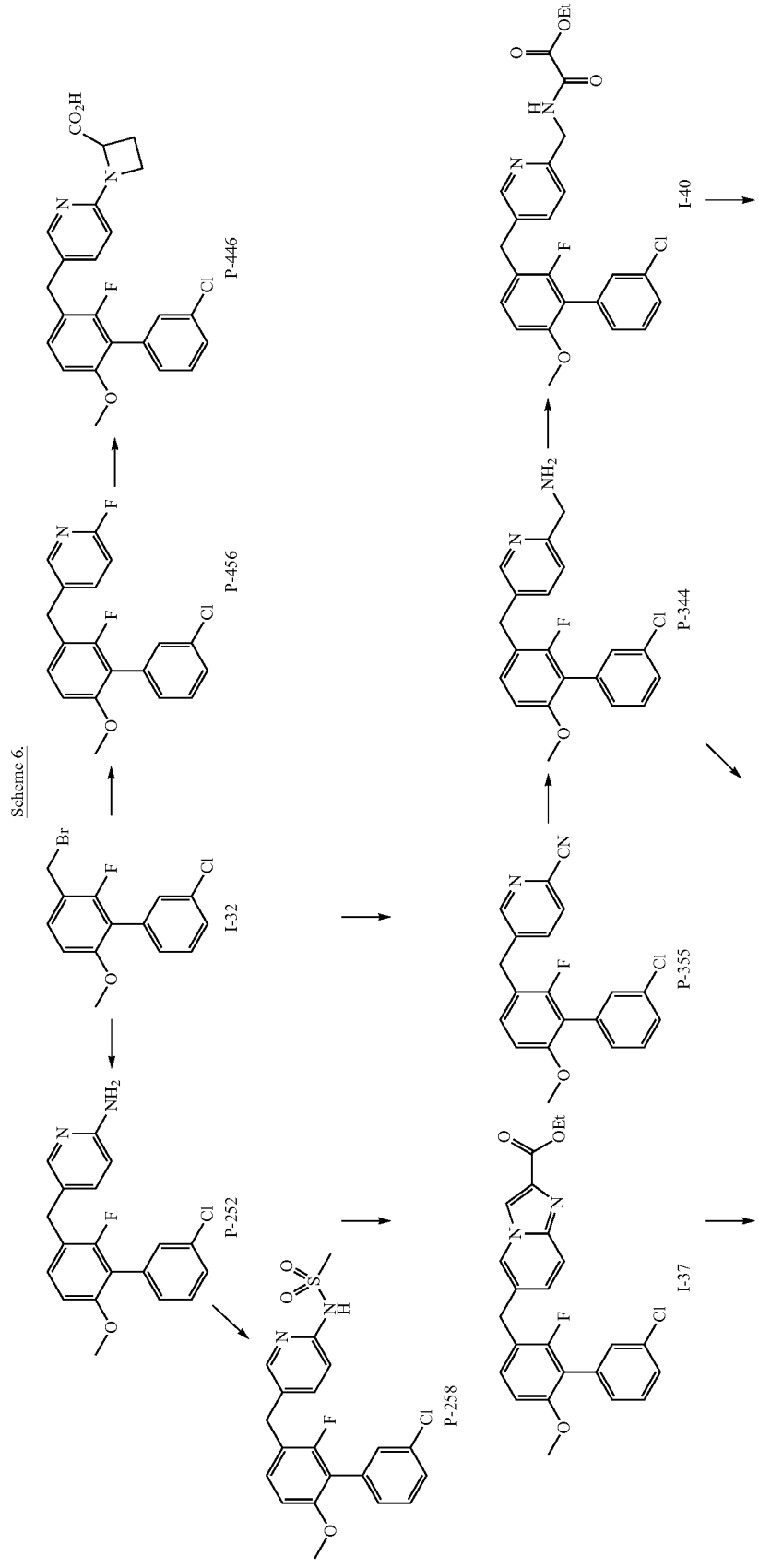

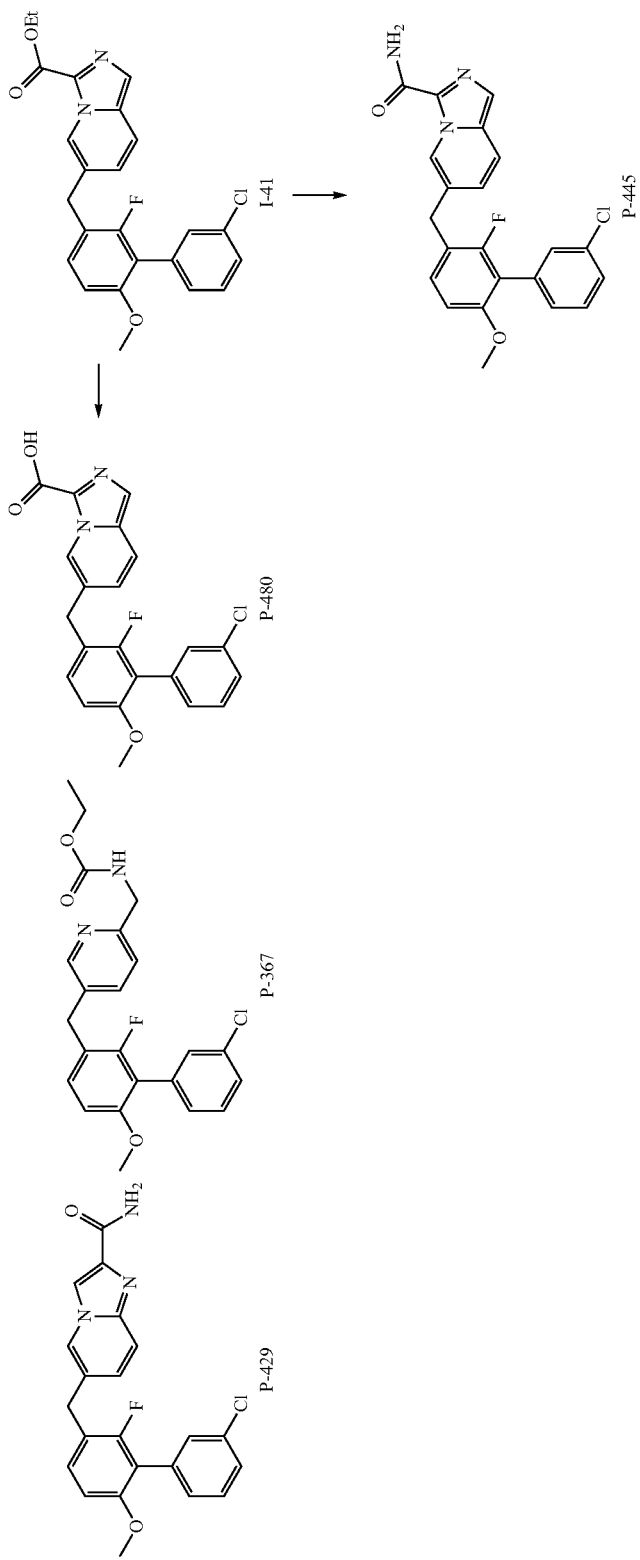

Example 7

Preparation of P-252

Synthesis of 5-(3'-Chloro-2-fluoro-6-methoxy-biphenyl-3-ylmethyl)-pyridin-2-ylamine P-252. A solution of I-145 (1.20 g, 3.70 mmol) and 2-aminopyridine-5-boronic acid pinacol ester (894 mg, 4.06 mmol) in N,N-dimethylformamide (8 mL) was degassed using a nitrogen stream for 10 min. To the solution was added potassium carbonate (1.54 g, 11.1 mmol), allylpalladium(II)chloride dimer (203 mg, 0.555 mmol), and bis(diphenylphosphino)pentane (489 mg, 1.11 mmol) under nitrogen and the suspension was stirred at 65° C. under nitrogen for 15 h. To the reaction was added ethyl acetate (50 mL) and water (50 mL) and the biphasic suspension was filtered through celite (~15 g). The celite was washed with ethyl acetate (2×20 mL), and water (2×20 mL) and the filtrate was separated. The aqueous layer was extracted with ethyl acetate (100 mL) and the organic extracts were combined. The organic solution was washed with water (200 mL) and brine (200 mL), dried over sodium sulfate, filtered, and the solvent removed under vacuum. The residue was purified by flash silica gel column chromatography (10-33% acetone in dichloromethane), triturated in diethyl ether (5 mL), filtered, washed with hexanes (5 mL) and diethyl ether (2 mL) to give P-252 (190 mg, 15% yield) as a beige powder. $^1$H NMR (400 MHz, CDCl$_3$): 7.97 (d, J=2.4 Hz, 1H), 7.39-7.27 (m, 5H), 7.07 (t, J=8.6 Hz, 1H), 6.69 (dd, J=8.8 Hz, 1.2 Hz, 1H), 6.45 (d, J=8.8 Hz, 1H), 4.32 (s, 2H), 3.82 (s, 2H), 3.75 (s, 3H) ppm. LCMS=96.6% purity. MS (APCI+)=343.0 (M+1).

Example 8

Preparation of P-258

Synthesis of N-[5-(3'-chloro-2-fluoro-6-methoxy-biphenyl-3-ylmethyl)-pyridin-2-yl]-methanesulfonamide (P-258). To a solution of 5-(3'-chloro-2-fluoro-6-methoxy-biphenyl-3-ylmethyl)-pyridin-2-ylamine (P-252) synthesized above (70 mg, 0.18 mmol) in pyridine (2 ml) was added methanesulfonyl chloride (23 mg, 0.20 mmol) at 0 C under nitrogen, and stirred at room temperature for 20 h. The reaction mixture was diluted with water, neutralized with 6N HCl, extracted with ethyl acetate, washed with water and brine, and dried over Na2SO4. After it was concentrated in vacuo, the residue was purified by a chromatography on silica gel to yield N-[5-(3'-chloro-2-fluoro-6-methoxy-biphenyl-3-ylmethyl)-pyridin-2-yl]-methanesulfonamide (P-258) (25 mg, 32%). $^1$H NMR (400 MHz, CDCl$_3$) 8.15 (s, 1H), 7.58 (dd, J=8.8, 2.1 Hz, 1H), 7.38 (s, 1H), 7.34 (t, J=6.6 Hz, 3H), 7.24-7.31 (m, 2H), 7.11 (t, J=8.5 Hz, 1H), 6.73 (d, J=8.5 Hz, 1H), 3.89 (s, 2H), 3.77 (s, 3H), 3.09 (s, 3H) ppm.

Example 9

Preparation of P-429

Synthesis of 6-(3'-chloro-2-fluoro-6-methoxy-biphenyl-3-ylmethyl)-imidazo[1,2-a]pyridine-2-carboxylic acid ethyl ester (I-37). Into a 20 mL vial with stir bar was added 5-(3'-chloro-2-fluoro-6-methoxy-biphenyl-3-ylmethyl)-pyridin-2-ylamine (P-252, 565 mg, 1.65 mmol), ethyl bromopyruvate (0.52 mL, 4.12 mmol), and 5 mL of DME. The reaction was stirred at room temperature for 18 hours, then basified with NaHCO$_3$ (aq. sat). The product was extracted with ethyl acetate and concentrated. Purification by flash column chromatography (5% acetone/dichloromethane) provided a tan solid which was triturated with ether to obtain 6-(3'-chloro-2-fluoro-6-methoxy-biphenyl-3-ylmethyl)-imidazo[1,2-a]pyridine-2-carboxylic acid ethyl ester (I-37) (198 mg, 27%) as an off-white solid.

Synthesis of 6-(3'-chloro-2-fluoro-6-methoxy-biphenyl-3-ylmethyl)-imidazo[1,2-a]pyridine-2-carboxylic acid amide (P-429). Into an 8 mL vial was added 6-(3'-chloro-2-fluoro-6-methoxy-biphenyl-3-ylmethyl)-imidazo[1,2-a]pyridine-2-carboxylic acid ethyl ester (I-37) synthesized above (37 mg, 0.084 mmol) and 2 mL of 7N NH$_3$/MeOH. After stirring for 20 hours at 60° C., the reaction was concentrated. Trituration with ether provided 6-(3'-chloro-2-fluoro-6-methoxy-biphenyl-3-ylmethyl)-imidazo[1,2-a]pyridine-2-carboxylic acid amide (P-429) (24.5 mg, 71%) as a white solid. $^1$H-NMR (400 MHz, DMSO-d$_6$): 8.42 (s, 1H), 8.30 (s, 1H), 7.64 (br s, 1H), 7.53 (d, J=4.6 Hz, 1H), 7.42 (m, 5H), 7.30 (m, 1H), 7.23 (dd, 1H, J=9.6, 1.6 Hz), 6.97 (d, 1H), 8.4 Hz), 3.95 (s, 2H), 3.74 (s, 3H) ppm. LC/MS=83.4%, 410.0 (APCI+).

Example 10

Preparation of P-456

Synthesis of 5-(3'-chloro-2-fluoro-6-methoxy-biphenyl-3-ylmethyl)-2-fluoro-pyridine (P-456). A flask was charged with 3-Bromomethyl-3'-chloro-2-fluoro-6-methoxy-biphenyl (I-32, 3.3 g, 10 mmol), 2-fluoro-pyridine-5-boronic acid (1.4 g, 10 mmol), toluene (40 mL), 2M aq. Na$_2$CO$_3$ (10 mL, 20 mmol), ethanol (10 mL) and Pd(PPh$_3$)$_4$ (577 mg, 0.5 mmol). The reaction mixture was bubbled with nitrogen gas for 5 minutes. Then the yellow reaction mixture was stirred at 80° C. After overnight stirring the reaction mixture was cooled to room temperature and concentrated in-vacuo. The residue was diluted in EtOAc (20 mL) and washed with water (30 mL). The aqueous layer was extracted with EtOAc (2×20 mL). The combined organic layers were washed with brine (50 mL), dried over Na2SO4 and concentrated in-vacuo. The crude was purified by silica gel column chromatography, eluted with hexane/EtOAc (9:1) to produce 3.23 g (93% yield) of 5-(3'-chloro-2-fluoro-6-methoxy-biphenyl-3-ylmethyl)-2-fluoro-pyridine (P-456) as a colorless solid. $^1$H NMR (400 MHz, DMSO-d$_6$) 3.73 (s, 3H), 3.98 (s, 2H), 6.95 (d, J=8.6 Hz, 1H), 7.11 (dd, J=8.4, 2.8 Hz, 1H), 7.25-7.51 (m, 5H), 7.82 (td, J=8.2, 2.4 Hz, 1H), 8.14 (s, 1H), 8.32 (s, 1H) ppm.

Example 11

Preparation of P-446

Synthesis of 1-[5-(3'-chloro-2-fluoro-6-methoxy-biphenyl-3-ylmethyl)-pyridin-2-yl]-azetidine-2-carboxylic acid (P-446). A vial was charged with D,L-azetidine-2-carboxylic acid (56 mg, 0.56 mmol) and DMF (1 mL). Then NaH (60% dispersion in mineral oil, 33 mg, 0.84 mmol) was added slowly (gas evolution). After 2 min. of stirring at room temperature was added 5-(3'-chloro-2-fluoro-6-methoxy-biphenyl-3-ylmethyl)-2-fluoro-pyridine (P-456). The heterogeneous white reaction mixture was stirred and heated at 120° C. After overnight stirring the reaction mixture was cooled to rt and was diluted in EtOAc (5 mL). The mixture was poured into a reparatory funnel with 0.5M HCl (1 mL) and water (5 mL). The aqueous layer was extracted with EtOAc (3×5 mL). The combined organic layers were washed with brine (15 mL), dried over Na2SO4 and concentrated in-vacuo. The crude was purified by silica gel column chromatography, eluted with dichloromethane in methanol (9:1) to produce 7.7 mg (6% yield) of 1-[5-(3'-chloro-2-fluoro-6-methoxy-biphenyl-3-ylmethyl)-pyridin-2-yl]-azetidine-2-carboxylic acid (P-446) as a cream solid.

Example 12

Preparation of P-445

Synthesis of N-[5-(3'-chloro-2-fluoro-6-methoxy-biphenyl-3-ylmethyl)-pyridin-2-ylmethyl]-oxalamic acid ethyl ester (I-40). Into a 20 mL vial was added [5-(3'-chloro-2-fluoro-6-methoxy-biphenyl-3-ylmethyl)-pyridin-2-ylmethyl]-carbamic acid ethyl ester (P-367) (152 mg, 0.43 mmol), dichloromethane (4 mL), TEA (0.11 mL, 0.85 mmol). The solution was cooled to 0° C. and Ethyl chlorooxoacetate (71 uL, 0.64 mmol) was added. After 20 minutes at room temperature, the organic solution was washed with $H_2O$ and brine, and then concentrated. Ethyl acetate was added to the residue, which produced a solid and was filtered. The solid was triturated with ether and dried to give N-[5-(3'-chloro-2-fluoro-6-methoxy-biphenyl-3-ylmethyl)-pyridin-2-ylmethyl]-oxalamic acid ethyl ester (I-40) (69 mg, 35%) as a gray-blue solid.

Synthesis of 6-(3'-chloro-2-fluoro-6-methoxy-biphenyl-3-ylmethyl)-imidazo[1,5-a]pyridine-3-carboxylic acid ethyl ester (I-41). Into a 4 mL vial was added the above compound (12) (44 mg, 0.096 mmol), dichloromethane (1 mL), pyridine (31 uL, 0.48 mmol), and $POCl_3$ (13 uL, 0.14 mmol). The reaction was stirred for 18 hours at room temperature and then $H_2O$ was added. The product was extracted with dichloromethane and then concentrated. Purification using FCC eluting with 20% acetone/hexane provided a yellow semi-solid which was triturated with hexane to give 6-(3'-chloro-2-fluoro-6-methoxy-biphenyl-3-ylmethyl)-imidazo[1,5-a]pyridine-3-carboxylic acid ethyl ester (I-41) (8.2 mg, 19%) as a tan solid.

Synthesis of 6-(3'-chloro-2-fluoro-6-methoxy-biphenyl-3-ylmethyl)-imidazo[1,5-a]pyridine-3-carboxylic acid amide (P-445). Into a 4 mL vial was added I-41 (7 mg, 0.016 mmol) and 2 mL of 7N $NH_3$/MeOH. The reaction was stirred at 60° C. for 18 hours, and then concentrated to afford 6-(3'-chloro-2-fluoro-6-methoxy-biphenyl-3-ylmethyl)-imidazo[1,5-a]pyridine-3-carboxylic acid amide (P-445) (6.6 mg, 99%) as a tan solid. $^1$H NMR (400 MHz, DMSO-$d_6$) 9.29 (s, 1H), 7.82 (br s, 1H), 7.71 (d, J=9.3 Hz, 1H), 7.52 (s, 1H), 7.49-7.33 (m, 5H), 7.33-7.26 (m, 1H), 6.95 (s, 2H), 3.97 (s, 2H), 3.74 (s, 3H) ppm. LC/MS=88.6%, 410.0 (APCI+).

Scheme 7.

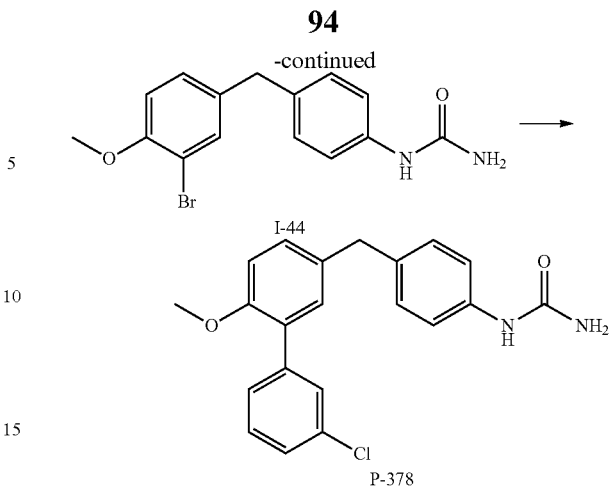

Example 13

Preparation of P-378

Synthesis of [4-(3-bromo-4-methoxy-benzyl)-phenyl]-urea (I-44). To a 40 mL vial equipped with a teflon screw cap and a magnetic stir bar was added 2-bromo-4-bromomethyl-1-methoxybenzene (649 mg, 2.32 mmol), [4-(4,4,5,5-tetramethyl-[1,3,2]dioxaborolan-2-yl)-phenyl]-urea (577 mg, 2.20 mmol) and potassium phosphate (933 mg, 4.40 mmol). To the vial was then added dimethoxyethane (15 mL), ethanol (3.7 mL) and water (3.7 mL). To this stirring solution was added tetrakis(triphenylphosphine) palladium (127 mg, 0.11 mmol) and the solution was degassed by bubbling $N_2$ gas through the solution for 20 min. The vial was capped and placed in an oil bath with stirring at 65° C. for 12.5 h. The cooled reaction mixture was concentrated under a stream of $N_2$ gas to a total volume of ~5 mL and then diluted with ethyl acetate (20 mL) and water (10 mL). Upon shaking a white solid precipitates. The solid is filtered and dried to afford 272 mg (34%) of [4-(3-bromo-4-methoxy-benzyl)-phenyl]-urea (I-44) as a white solid.

Synthesis of [4-(3'-chloro-6-methoxy-biphenyl-3-ylmethyl)-phenyl]-urea (P-378). To a 20 mL vial equipped with a magnetic stir bar and a screw cap was added [4-(3-bromo-4-methoxy-benzyl)-phenyl]-urea (I-44) synthesized above compound (250 mg, 0.746 mmol), dimethoxyethane (5 mL), ethanol (1 mL) and water (1 mL). To this mixture were added 3-chlorophenylboronic acid (140 mg, 0.895 mmol), potassium phosphate (316 mg, 1.49 mmol) and tetrakis(triphenylphosphine) palladium (30 mg, 0.0254 mmol). The stirring reaction mixture was degassed by bubbling $N_2$ gas through the solution for 10 min. The vial was capped and placed in an oil bath with stirring at 80° C. for 16 h. The cooled reaction mixture was concentrated to dryness, then diluted with water (5 mL) and ethyl acetate (15 mL). The aqueous layer was extracted with ethyl acetate (2×5 mL) and the combined organic extracts were dried ($Na_2SO_4$), filtered and concentrated under a stream of $N_2$ gas. The residue was purified by flash chromatography on silica gel (35 g) utilizing 9:1 dichloromethane/acetone as eluent. Fractions pure by TLC were combined and concentrated to give 139 mg (51%) of [4-(3'-chloro-6-methoxy-biphenyl-3-ylmethyl)-phenyl]-urea (P-378) as an off-white solid. $^1$H NMR (400 MHz, DMSO-$d_6$) δ 3.74 (s, 3H), 3.83 (s, 2H), 5.75 (br s, 2H), 7.03 (d, J=8.4 Hz, 1H), 7.08 (m, 2H), 7.15 (d, J=2.4 Hz, 1H), 7.18

(dd, J=8.4, 2.4 Hz, 1H), 7.28 (m, 2H), 7.36-7.41 (m, 3H), 7.48 (m, 1H), 8.40 (br s, 1H) ppm. MS (APCI+): 367.0 (M$^+$+1); LC-MS: 95.9% purity.

The following compounds were prepared analogous to the Examples shown above.

P-008
P-011
P-067
P-102
P-103
P-105
P-110
P-111
P-112
P-113
P-114
P-119
P-121
P-122
P-123
P-134
P-135
P-140
P-141
P-142
P-143
P-144
P-145
P-146
P-151
P-159
P-164
P-165
P-166
P-170
P-171
P-189
P-191
P-192
P-194
P-199
P-202
P-216
P-217
P-219
P-220
P-221
P-222
P-225
P-226
P-231
P-232
P-233
P-234
P-240
P-242
P-252
P-258
P-259
P-261
P-266
P-272
P-274
P-275
P-277
P-278
P-279
P-281
P-284
P-286
P-287
P-290
P-291
P-292
P-295
P-296
P-297
P-298

-continued

P-299
P-300
P-301
P-302
P-304
P-305
P-308
P-309
P-312
P-313
P-314
P-315
P-316
P-317
P-318
P-319
P-320
P-321
P-322
P-323
P-324
P-325
P-327
P-328
P-329
P-330
P-331
P-334
P-335
P-336
P-337
P-338
P-339
P-340
P-344
P-345
P-347
P-348
P-349
P-355
P-356
P-357
P-358
P-359
P-360
P-361
P-362
P-365
P-366
P-367
P-368
P-371
P-372
P-373
P-374
P-375
P-377
P-378
P-381
P-382
P-383
P-384
P-385
P-387
P-388
P-390
P-391
P-392
P-394
P-395
P-399
P-400
P-401
P-402
P-403
P-407
P-408
P-409
P-410

P-411
P-412
P-413
P-414
P-415
P-420
P-421
P-423
P-428
P-431
P-432
P-433
P-437
P-269
P-239

General Scheme 8.

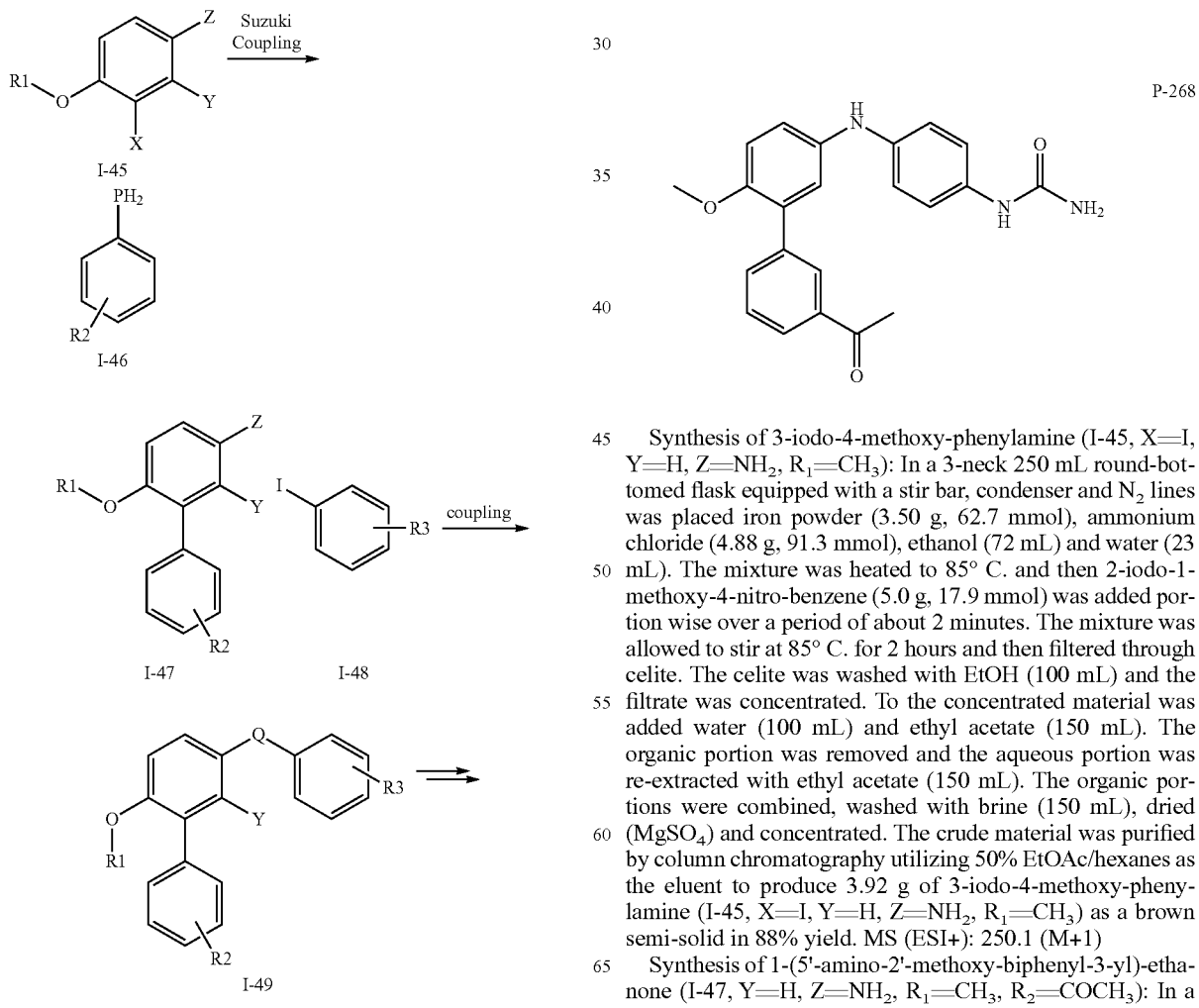

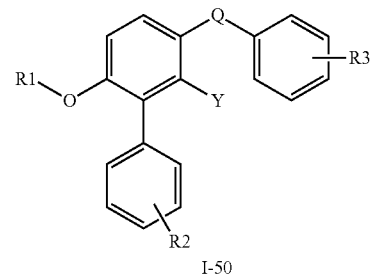

Y = H, F
X = Br, I, Cl, boronate
Z = OH, NH2, NO2
R1 = H, Me, CHF2, CF3
P = halogen, boronate
Q = O, NR', S
R2 = Cl, CH3CO, CN, NO2, Br, fused heterocycle
R3 = substituted groups Example 14

Preparation of P-268

Synthesis of 3-iodo-4-methoxy-phenylamine (I-45, X=I, Y=H, Z=NH$_2$, R$_1$=CH$_3$): In a 3-neck 250 mL round-bottomed flask equipped with a stir bar, condenser and N$_2$ lines was placed iron powder (3.50 g, 62.7 mmol), ammonium chloride (4.88 g, 91.3 mmol), ethanol (72 mL) and water (23 mL). The mixture was heated to 85° C. and then 2-iodo-1-methoxy-4-nitro-benzene (5.0 g, 17.9 mmol) was added portion wise over a period of about 2 minutes. The mixture was allowed to stir at 85° C. for 2 hours and then filtered through celite. The celite was washed with EtOH (100 mL) and the filtrate was concentrated. To the concentrated material was added water (100 mL) and ethyl acetate (150 mL). The organic portion was removed and the aqueous portion was re-extracted with ethyl acetate (150 mL). The organic portions were combined, washed with brine (150 mL), dried (MgSO$_4$) and concentrated. The crude material was purified by column chromatography utilizing 50% EtOAc/hexanes as the eluent to produce 3.92 g of 3-iodo-4-methoxy-phenylamine (I-45, X=I, Y=H, Z=NH$_2$, R$_1$=CH$_3$) as a brown semi-solid in 88% yield. MS (ESI+): 250.1 (M+1)

Synthesis of 1-(5'-amino-2'-methoxy-biphenyl-3-yl)-ethanone (I-47, Y=H, Z=NH$_2$, R$_1$=CH$_3$, R$_2$=COCH$_3$): In a 3-neck 100 mL round-bottomed flask equipped with a condenser, stir bar and N$_2$ lines was placed 3-iodo-4-methoxyphenylamine synthesized above (2.92 g, 11.7 mmol), 3-acetylylphenylboronic acid (2.11 g, 12.9 mmol), potassium carbonate (4.85 g, 35.1 mmol), triphenylphosphine (921 mg, 3.51 mmol), 1,4-dioxane (23 mL), 50% aqueous ethanol (23 mL) followed by palladium (II) acetate (263 mg, 1.17 mmol). The mixture was heated to 90° C. for 16 hours and then cooled to room temperature. The palladium catalyst was removed via filtration and to the filtrate was added 1M HCl (50 mL) and water (50 mL). The aqueous portion was Extracted with ethyl acetate (2×75 mL), the organic portions were combined, washed with brine (75 mL), dried (MgSO$_4$) and concentrated. The crude material was purified by column chromatography utilizing 50% EtOAc/hexanes as the eluent to produce 1.18 g of (5'-amino-2'-methoxy-biphenyl-3-yl)-ethanone (I-47, Y═H, Z═NH$_2$, R$_1$═CH$_3$, R$_2$═COCH$_3$) as a pale orange oil in 42% yield. MS (APCI+): 242.0 (M+1).

Synthesis of 1-[2'-methoxy-5'-(4-nitro-phenylamino)-biphenyl-3-yl]-ethanone (I-49, Y═H, Q═NH, R$_1$═CH$_3$, R$_2$═COCH$_3$, R$_3$═NO$_2$): To a 40 mL vial equipped with a stir bar was placed 1-iodo-4-nitrobenzene (1.26 g, 5.07 mmol), cesium carbonate (2.20 g, 6.76 mmol), (±)-2,2'-bis(diphenylphosphino)-1,1'-binaphthalene (316 mg, 0.507 mmol), and a solution of (5'-amino-2'-methoxy-biphenyl-3-yl)-ethanone (I-47, Y═H, Z═NH$_2$, R$_1$═CH$_3$, R$_2$═COCH$_3$) synthesized above (816 mg, 3.38 mmol) in toluene (13.5 mL). The mixture was stirred for 10 minutes and then tris(dibenzylideneacetone)dipalladium(0) (310 mg, 0.338 mmol) and the mixture was heated to 110° C. for 16 hours. The reaction was cooled to room temperature and then filtered through Celite. The filtrate was treated with water (40 mL), 1M HCl (40 mL) and then Extracted with ethyl acetate (2×75 mL). The organic portions were combined, washed with brine (75 mL), dried (MgSO$_4$) and concentrated. The crude material was purified by column chromatography utilizing 35% EtOAc/hexanes as the eluent to produce 277 mg of 1-[2'-methoxy-5'-(4-nitro-phenylamino)-biphenyl-3-yl]-ethanone (I-49, Y═H, Q═NH, R$_1$═CH$_3$, R$_2$═COCH$_3$, R$_3$═NO$_2$) as a dark orange solid in 23% yield.

Synthesis of 1-[5'-(4-amino-phenylamino)-2'-methoxy-biphenyl-3-yl]-ethanone hydrochloride: In an 18 mL vial equipped with a stir bar was placed iron powder (148 mg, 2.66 mmol), ammonium chloride (207 mg, 3.87 mmol), absolute EtOH (3.1 mL) and water (1.0 mL). The mixture was heated to 85° C. and then was added -[2'-methoxy-5'-(4-nitro-phenylamino)-biphenyl-3-yl]-ethanone (I-49, Y═H, Q═NH, R$_1$═CH$_3$, R$_2$═COCH$_3$, R$_3$═NO$_2$) synthesized above (275 mg, 0.759 mmol) was added and the mixture was heated for 2 hours. The reaction was cooled to room temperature, filtered through Celite and Extracted with ethyl acetate (2×40 mL). The organic portions were combined, washed with brine (40 mL), dried (MgSO$_4$) and concentrated. The crude material was purified by column chromatography utilizing 75% EtOAc/hexanes as the eluent to produce 207 mg of the free base as a dark orange oil in 82% yield. The free base was treated with 4.0 M HCl in 1,4-dioxane (1.0 mL) and stirred for 3 hours at room temperature. The reaction mixture was treated with diethyl ether (4 mL) and the solid was collected via suction filtration. After washing the solid with diethyl ether (3×2 mL), 100 mg of 1-[5'-(4-amino-phenylamino)-2'-methoxy-biphenyl-3-yl]-ethanone hydrochloride was isolated as a brown solid in 44% yield. MS (APCI−): 366.9 (M−2); LC-MS: 85%

Synthesis of [4-(3'-acetyl-6-methoxy-biphenyl-3-ylamino)-phenyl]-urea (P-268): In an 8 mL vial equipped with a stir bar was placed 1-[5'-(4-amino-phenylamino)-2'-methoxy-biphenyl-3-yl]-ethanone synthesized above (free base) (60.0 mg, 0.180 mmol), water (600 μL), acetic acid (300 μL) and sodium cyanate (46.8 mg, 0.720 mmol). The mixture was stirred at room temperature for 4 hours and then water (20 mL) was added followed by an P-traction with (2×30 mL). The organic portions were combined, washed with brine (30 mL), dried (MgSO$_4$) and concentrated. The crude material was purified by column utilizing 75% acetone/DCM as the eluent to produce 32 mg of [4-(3'-acetyl-6-methoxy-biphenyl-3-ylamino)-phenyl]-urea (P-268) as a light brown solid in 47% yield. MS (APCI+): 376.1 (M+1); LC-MS: 94%.

Scheme 9.

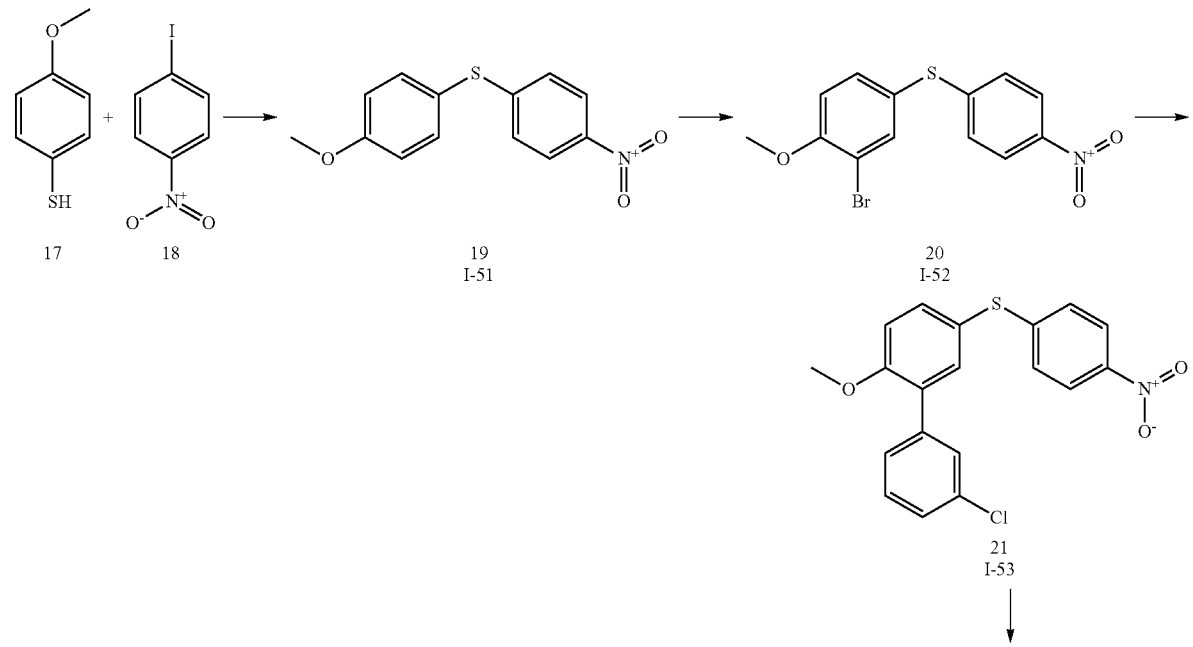

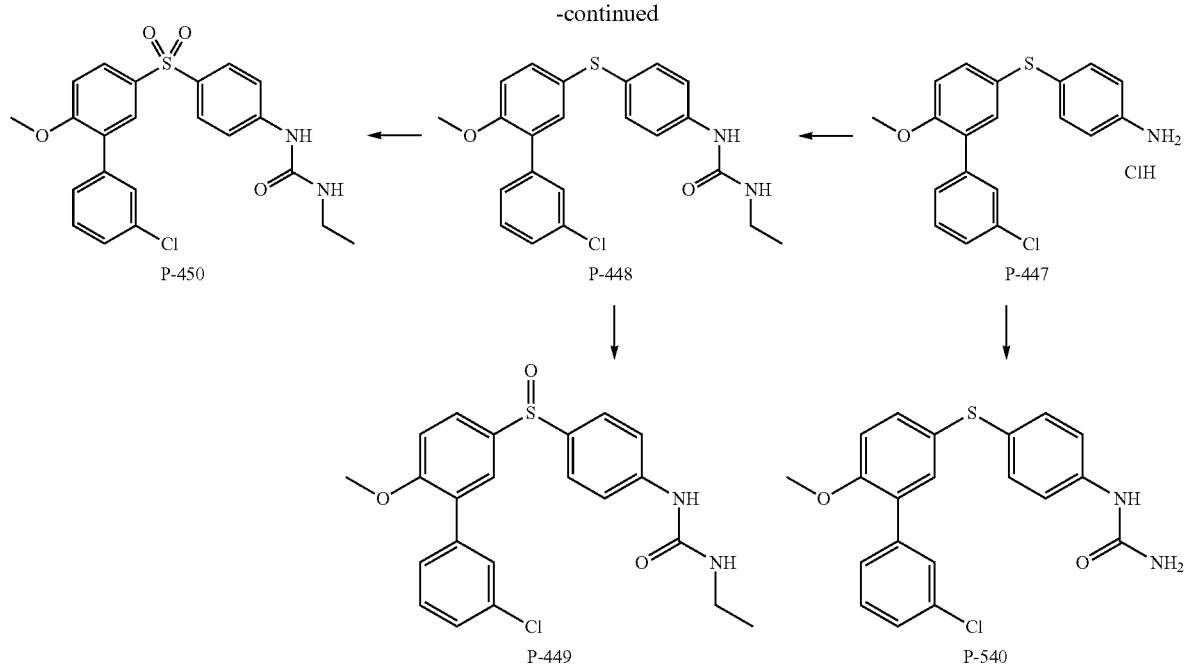

Example 15

Preparation of P-447

1-Methoxy-4-phenmylsulfanyl-(4'-nitrobenzene) (I-51). A solution of 4-methoxybenzenethiol (500 mg, 3.57 mmol) and 4-iodonitrobenzene (1.07 g, 4.28 mmol) in dimethylformamide (10 mL) was stirred at room temperature. To the orange solution was added solid cesium carbonate (3.48 g, 10.7 mmol). The resulting purple solution was stirred at room temperature overnight. The solution was diluted with ethyl acetate (50 mL) and washed with water (50 mL). The aqueous wash was extracted with ethyl acetate (50 mL). The organic washes were combined, washed with saturated aqueous sodium bicarbonate (100 mL), water (100 mL), and brine (100 mL), dried over sodium sulfate, decanted, and the solvent removed under vacuum. The resultant solid was purified by flash silica gel column chromatography using 10% ethyl acetate in hexanes as eluant to give product I-51 (933 mg, 99% yield).

2-Bromo-methoxy-4-(4'-nitro-phenyl-sulfanyl)-benzene (I-52). A 10% v/v solution of bromine (1 mL) in glacial acetic (9 mL) acid was prepared. A solution of I-51 (780 mg, 2.99 mmol) in glacial acetic acid (7.8 mL) was stirred at room temperature. To this solution was added the 10% bromine in acetic acid solution (3.53 mL total solution, 6.87 mmol of bromine). The reaction was allowed to stir at room temperature for 2 h. The reaction was combined with a previous pilot run of this reaction (100 mg 0.383 mmol). The previous run had been reacted under the same conditions and TLC showed similar results. The combined reactions were diluted with ethyl acetate (100 mL), and washed with water (100 mL). The organic extract was then washed with saturated aqueous sodium bicarbonate (2×100 mL), water (100 mL), and brine (100 mL), dried over sodium sulfate, decanted, and removed under vacuum. The resulting yellow residue was purified by flash silica gel column chromatography (10% ethyl acetate in hexanes as the eluant) to give I-52 (550 mg, 48% overall yield) and a second less pure crop (420 mg).

3'-Chloro-2-methxoy-5-(4-nitro-phenyl-sulfonyl)-biphenyl (I-53). A solution of the above compound I-52 (550 mg, 1.62 mmol) and 3-chlorobenzeneboronic acid (278 mg, 1.78 mmol) in toluene (6 mL) was degassed with a nitrogen stream for 15 min. To the reaction was added ethanol (800 uL) and 2 M aqueous sodium carbonate solution (1.6 mL) and the reaction was degassed under the nitrogen stream. To the reaction was added tetrakis(triphenylphosphine)palladium(0) (93.4 mg, 8.08×10-2 mmol) and the reaction was heated to 100° C. under nitrogen for 5 h. The reaction was cooled to room temperature and diluted with ethyl acetate (50 mL). The organic suspension was washed with water (50 mL). The aqueous wash was extracted into ethyl acetate (50 mL), the organic extractions combined, washed with water (2×30 mL) and brine (30 mL), dried over sodium sulfate, filtered, and the solvent removed under vacuum. The resulting crude red oil was purified by flash silica gel column chromatography (10% ethyl acetate in hexanes) to give I-53 (329.9 mg, 55% yield) as a yellow powder.

4-(3'-Chloro-6-methoxy-biphenyl-3-ylsulfanyl)-phenylaammonium chloride (P-447). A suspension of compound I-53 (315 mg, 0.847 mmol), iron powder (166 mg, 2.97 mmol) and solid ammonium chloride (231 mg, 4.32 mmol) in ethanol (5 mL) and water (1.5 mL) was heated to 80° C. for 21 h. The solvent was removed under vacuum and the dark residue was dissolved in ethyl acetate (30 mL) and water (30 mL). The layers were separated, and the aqueous layer was extracted with ethyl acetate (30 mL). The organic extracts were combined, washed with water (50 mL) and brine (50 mL), dried over sodium sulfate, filtered, and the solvent removed under vacuum. The residue was dried under high vacuum overnight. The orange oil was dissolved in dioxane (2 mL), stirred, and 4 N hydrogen chloride in dioxane (1 mL) was added. The reaction was stirred for 3 h at room temperature, and the solvent was removed under vacuum to give product (P-447) (257.8 mg, 81% yield) as a brown powder. $^1$H NMR (400 MHz, DMSO-$d_6$) 7.95-7.49 (m, 1H), 7.46-7.37 (m, 3H), 7.34 (dd, J=8.6, 2.2 Hz, 1H), 7.26-7.23 (m, 3H), 7.16 (d, J=8.8 Hz, 1H), 6.96-6.95 (m, 2H), 3.78 (s, 3H) ppm.

LCMS=97.5% purity. MS (APCI+)=342.0 (M+1).

Example 16

Preparation of P-448

1-[4-(3'-Chloro-6-methoxy-biphenyl-3-ylsulfanyl)-phenyl]-3-ethyl urea (P-448). A solution of the above compound (P-447) (195 mg, 0.520 mmol) in pyridine (3 mL) was stirred at room temperature. To the reaction was added ethyl isocyanate (110 mg, 1.56 mmol). The solution was stirred at room temperature for 22.5 h. The reaction was diluted in ethyl acetate (50 mL), and washed with water (50 mL). The aqueous wash was extracted into ethyl acetate (50 mL), and the organic extracts combined. The ethyl acetate solution was washed with 1 N aqueous hydrochloric acid (50 mL), water (2×50 mL), and brine (50 mL), dried over sodium sulfate, and the solvent removed under vacuum. The resultant solid was triturated with diethyl ether (5 mL), filtered, washed with diethyl ether (2×3 mL), and dried to give product (P-448) (109.2 mg, 51% yield). $^1$H NMR (400 MHz, DMSO-$d_6$) 7.49-7.48 (m, 1H), 7.39-7.29 (m, 5H), 7.26-7.19 (m, 4H), 6.94 (d, J=8.8 Hz, 1H), 6.19 (s, 1H), 4.60 (m, 1H), 3.82 (s, 3H), 3.32-3.25 (m, 2H), 1.15 (t, J=7.4 Hz, 3H) ppm. LCMS=97.3% purity. MS (APCI+)=413.0 (M+1).

Example 17

Preparation of P-449

1-[4-(3'-Chloro-6-methoxy-biphenyl-3-sulfinyl)-phenyl]-3-ethyl urea (P-449). A solution of 10% v/v 30% aqueous hydrogen peroxide (w/w) (1 mL) in glacial acetic acid (9 mL) was made. To a slurry of the above compound (P-448) (41.3 mg, 0.100 mmol) in acetic acid (300 uL) was added the hydrogen peroxide solution (96.7 uL, 0.100 mmol hydrogen peroxide). The solution was stirred for 1 hour at room temperature. The solvent was removed under vacuum, and the residue purified by silica gel thin layer chromatography (eluting with 10% acetone in dichloromethane), triturated with diethyl ether (5 mL), filtered, and dried to give the product (P-449) (29.3 mg, 68% yield) as a brown gum. $^1$H NMR (400 MHz, DMSO-$d_6$) 7.55-7.44 (m, 5H), 7.36-7.32 (m, 5H), 7.20 (s, 1H), 7.04 (d, J=8.4 Hz, 1H), 5.27 (m, 1H), 3.84 (s, 3H), 3.29-3.22 (m, 2H), 1.12 (t, J=7.4 Hz, 1H) ppm. LCMS=97.6% purity. MS (APCI+)=429.1 (M+1).

Example 18

Preparation of P-450

1-[4-(3'-Chloro-6-methoxy-biphenyl-3-sulfonyl)-phenyl]-3-ethyl-urea (P-450). A solution of 1-[4-(3'-Chloro-6-methoxy-biphenyl-3-ylsulfanyl)-phenyl]-3-ethyl urea (P-448) (41.3 mg, 0.100 mmol) in glacial acetic acid (300 uL) was stirred at room temperature. To the solution was added 290 uL of 10% v/v (30% w/w hydrogen peroxide in water) in acetic acid. The resulting solution was stirred for 1.5 h at room temperature. The solvent was removed under vacuum, and the residue was purified by silica gel thin layer chromatography (eluting with 25% acetone in dichloromethane) and dried to give the product (P-450) (20.2 mg, 45% yield) as a yellow grease. $^1$H NMR (400 MHz, DMSO-$d_6$) 7.55-7.44 (m, 5H), 7.35-7.31 (m, 4H), 7.28 (s, 1H), 7.04 (d, J=8.4 Hz, 1H), 5.32 (t, J=5.6 Hz, 1H), 3.84 (s, 3H), 3.28-3.21 (m, 2H), 1.11 (t, J=7.4 Hz, 1H) ppm. LCMS=97.9% purity. MS (APCI+) =473.1 (M+28), 443.0 (M+1).

Example 19

Preparation of P-540

P-540 Synthesis of [4-(3'-Chloro-6-methoxy-biphenyl-3-ylsulfanyl)-phenyl]-urea. A solution of PR195 (200 mg, 0.585 mmol) and sodium cyanate (76 mg, 1.17 mmol) in water (10 mL) and glacial acetic acid (5 mL) was stirred at room temperature overnight. Water (20 mL) was added to the gummy suspension, and the reaction was extracted into ethyl acetate (2×20 mL). The organic extracts were combined, washed with 1 N aqueous hydrochloric acid (2×20 mL), saturated aqueous sodium bicarbonate (2×20 mL), water (20 mL), and brine (20 mL), dried over sodium sulfate, and the solvent removed under vacuum to give crude PR199 as a yellow gum. The crude material was purified by preparatory thin layer chromatography (silica) eluting with dichloromethane and developed twice to give PR199 (53.1 mg, 22.5% yield) as a white powder. $^1$H NMR (400 MHz, CDCl$_3$) 7.49-7.48 (m, 1H), 7.41-7.28 (m, 5H), 7.23 (s, 4H), 6.95 (d, J=8.0 Hz, 1H), 6.31 (s, 1H), 4.57 (s, 2H), 3.83 (s, 3H) ppm. LCMS=95.3% purity. MS=385.1 (M+1).

The following compounds were prepared analogous to the Examples shown above.

| P-260 | P-294 | P-193 | P-283 |
| P-267 | P-288 | P-230 | P-254 |
| P-280 | P-293 | P-240 | |

General Scheme 10.

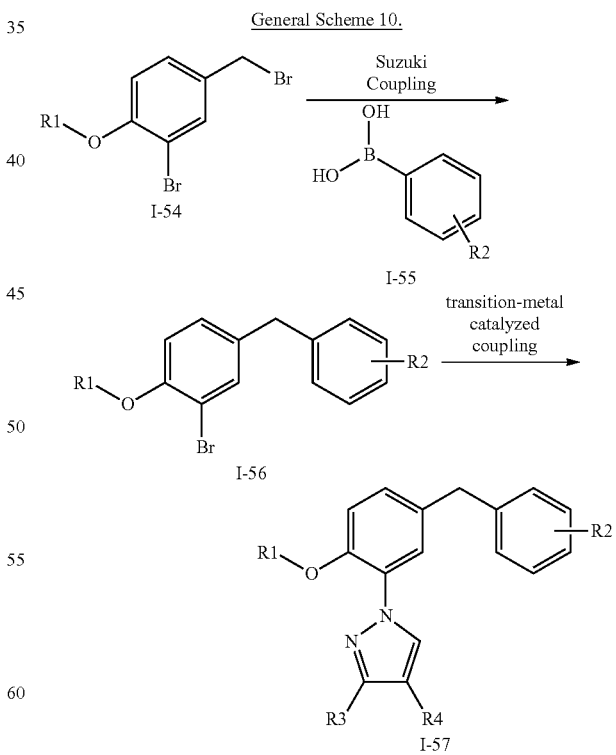

R1 = H, CH3
R2 = F
R3 = H, CF3
R4 = Cl, 4-pyridyl

Example 20

Preparation of P-380

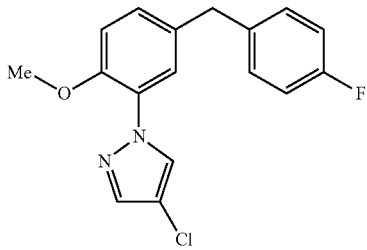

2-Bromo-4-(4-fluoro-benzyl)-1-methoxy-benzene: In a 250 mL round-bottomed flask equipped with a stir bar was placed 3-bromo-4-methoxybenzyl bromide (5.0 g, 17.9 mmol), 4-fluorophenylboronic acid (2.76 g, 19.7 mmol), potassium phosphate (tribasic) (7.60 g, 35.8 mmol), dimethoxyethane (30 mL) and 50% aqueous ethanol (30 mL). The mixture was degassed with nitrogen for 30 minutes and then added tetrakis(triphenylphosphine)palladium(0) (5.17 g, 4.48 mmol). The mixture was heated to 60° C. for 4 hours and then the palladium catalyst was filtered off. To the filtrate were added water (100 mL) and a saturated ammonium chloride solution (150 mL). After extracting with ethyl acetate (3×100 mL), the organic portions were combined, washed with brine (150 mL), dried ($MgSO_4$) and concentrated. The crude material was purified by column utilizing 5% EtOAc/hexanes as the eluent to produce 2.12 g of 2-bromo-4-(4-fluoro-benzyl)-1-methoxy-benzene as a colorless oil in 40% yield.

4-Chloro-1-[5-(4-fluoro-benzyl)-2-methoxy-phenyl]-1H-pyrazole (P-380): In a 2-5 mL microwave vial equipped with a stir bar was placed the above product (250 mg, 0.847 mmol), 4-chloro-1H-pyrazole (172 mg, 1.69 mmol), potassium carbonate (234 mg, 1.69 mmol), CuI (48.4 mg, 0.254 mmol) and N-methyl-2-pyrrolidone (2.8 mL). The mixture was heated to 190° C. in a Biotage Initiator microwave reactor for 1 hour. The mixture was quenched with water (30 mL) and a saturated ammonium chloride solution (30 mL) followed by an P-traction with ethyl acetate (2×30 mL). The organic portions of the product (P-380) as a viscous, yellow oil in 35% yield. $^1$H NMR (400 MHz, $CDCl_3$) δ 3.87 (s, 3H), 3.93 (s, 2H), 6.94-6.98 (m, 3H), 7.08 (dd, J=8, 2 Hz, 1H), 7.12-7.16 (m, 2H), 7.55 (d, J=2 Hz, 1H), 7.60 (s, 1H), 8.04 (s, 1H) ppm. MS (APCI+): 317.0 (M+1); LC-MS: 97%

Example 21

Preparation of P-389

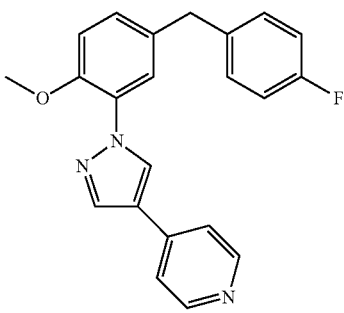

Synthesis of 4-{1-[5-(4-Fluoro-benzyl)-2-methoxy-phenyl]-1H-pyrazol-4-yl}-pyridine (P-389). In a 2-5 mL microwave vial equipped with a stir bar was placed I-185 (250 mg, 0.847 mmol), 4-(1H-pyrazol-4-yl)-pyridine (245 mg, 1.69 mmol), potassium carbonate (234 mg, 1.69 mmol) and N-methyl-2-pyrrolidone (2.8 mL). The mixture was degassed with nitrogen for 10 minutes and then CuI (48.4 mg, 0.254 mmol) was added. The mixture was heated to 190° C. in a Biotage Initiator microwave reactor for 1 hour. The mixture was quenched with water (50 mL) and a saturated ammonium chloride solution (50 mL) followed by an extraction with ethyl acetate (2×100 mL). The organic portions were combined, dried ($MgSO_4$) and concentrated. The residue was purified via column chromatography utilizing 15% acetone/dichloromethane as the eluent. After a failed recrystallization attempt with dichlormethane/hexanes, 41 mg of P-389 as a viscous, yellow oil in 13% yield. $^1$H NMR (400 MHz, $CDCl_3$) δ 3.91 (s, 3H), 3.96 (s, 2H), 6.95-7.02 (m, 3H), 7.10-7.18 (m, 3H), 7.42-7.45 (m, 2H), 7.62 (d, J=2 Hz, 1H), 8.04 (s, 1H), 8.41 (s, 1H), 8.57-8.59 (m, 2H) ppm. MS (APCI+): 360.1 (M+1); LC-MS: 90%.

Example 22

Preparation of P-396

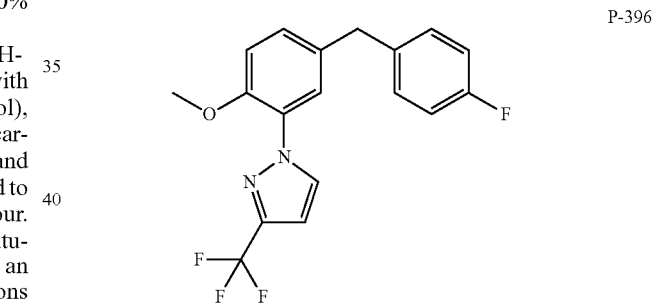

Synthesis of 1-[5-(4-Fluoro-benzyl)-2-methoxy-phenyl]-3-trifluoromethyl-1H-pyrazole (P-396). In a 2-5 mL microwave vial equipped with a stir bar was placed I-185 (250 mg, 0.847 mmol), 3-trifluoromethyl-1H-pyrazole (230 mg, 1.69 mmol), potassium carbonate (234 mg, 1.69 mmol) and N-methyl-2-pyrrolidone (2.8 mL). The mixture was degassed with nitrogen for 10 minutes and then CuI (48.4 mg, 0.254 mmol) was added. The mixture was heated to 190° C. in a Biotage Initiator microwave reactor for 1 hour. The mixture was quenched with water (30 mL) and a saturated ammonium chloride solution (30 mL) followed by an extraction with ethyl acetate (2×60 mL). The organic portions were combined, dried ($MgSO_4$) and concentrated. The residue was purified via column chromatography utilizing 20% ethyl acetate/hexanes as the eluent to produce 20 mg of P-396 as a viscous, yellow oil in 7% yield. $^1$H NMR (400 MHz, $CDCl_3$) δ 3.86 (s, 3H), 3.94 (s, 2H), 6.65 (d, J=2 Hz, 1H), 6.95-6.99 (m, 3H), 7.10-7.16 (m, 3H), 7.57 (d, J=2 Hz, 1H), 8.03 (m, 1H) ppm. MS (APCI+): 351.0 (M+1); LC-MS: 92%.

General Scheme 11.

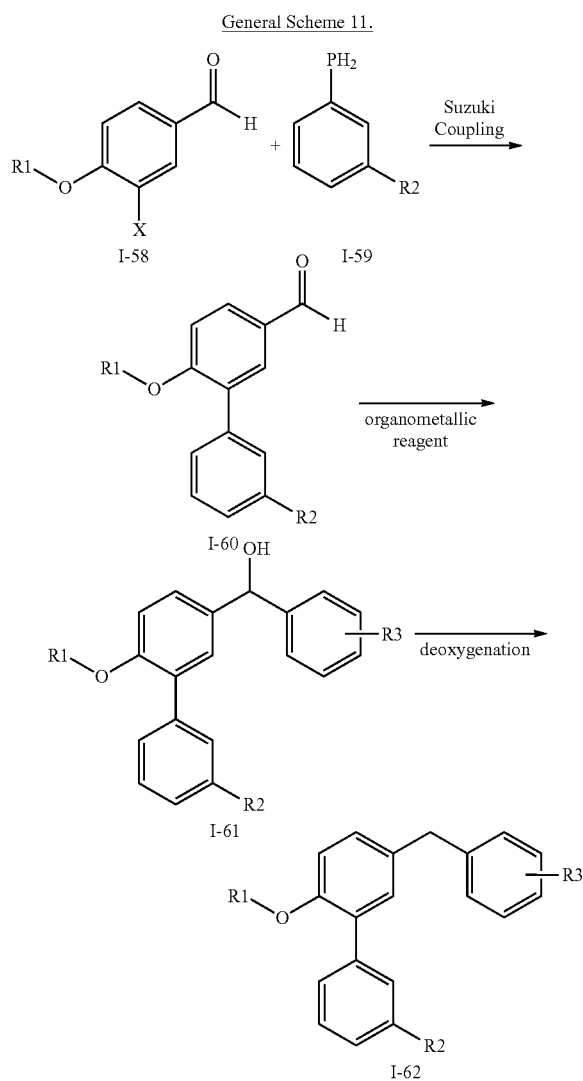

X, P = halogen, boronate
R1 = H, Me, CHF2, CF3
R2 = Cl, CH3CO, CN, NO2, Br, fused heterocycle
R3 = substituted groups

Example 23

Preparation of P-117

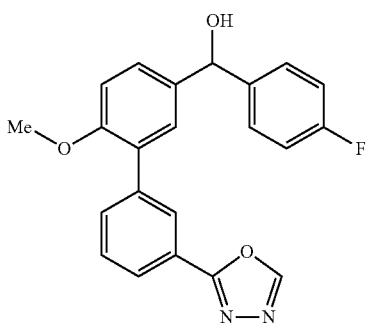

2-(3-Iodo-phenyl)-[1,3,4]oxadiazole: A mixture containing 3-iodo benzoylhydrazide (4.5 g, 17.17 mmol) and 85.6 ml of triethylorthoformate (30 equivalents) was refluxed for 16 hours. The reaction mixture was concentrated to a solid residue and triturated with 15 ml mixture of diethyl ether/heptane=1:1. After filtration and drying, 3.9 g white solid was obtained. The mother liquor was concentrated and recrystallized from a mixture of methanol/water=1:3 to give another 200 mg of the product, a total of 4.1 g.

6-Methoxy-3'-[1,3,4]oxadiazol-2-yl-biphenyl3-carbaldehyde. A mixture of 5-formyl-2-methoxyphenyl boronic acid (414 mg, 2.29 mmol), the above product, 2-(3-iodo-phenyl)-[1,3,4]oxadiazole, (626 mg, 2.29 mmol), aqueous 2N $K_2CO_3$ (3.4 mL, 3 equivalents), $Pd(PPh_3)_2Cl_2$ (50 mg, 0.068 mmol) in DME (15 mL) was stirred at room 80° C. for 7 hours. Reaction mixture was cooled to r.t., then it was diluted with ethyl acetate (45 mL) and washed with water, brine and dried over $Na_2SO_4$. After removal of solvent, 700 mg of crude was obtained. Purification by column chromatography gave 350 mg of the product (Yield: 55%).

(4-Fluoro-phenyl)-(6-methoxy-3'-[1,3,4]oxadiazol-2-yl-biphenyl-3-yl)-methanol (P-117). To a solution of the above aldehyde, 6-Methoxy-3'-[1,3,4]oxadiazol-2-yl-biphenyl3-carbaldehyde (86 mg, 0.307 mmol) in anhydrous THF (1 mL) was added dropwise a solution of 4-fluorophenyl magnesium bromide in THF (0.46 ml, 1M) at −78° C. After the addition was complete, the resulting mixture was allowed to warm to room temperature and stirred for 40 minutes. Then saturated $NH_4Cl$ aq. was added. The mixture was extracted with EtOAc (2×10 ml). The combined organic layers were washed with water and dried over $Na_2SO_4$. Removal of solvent gave a residue, which was purified by chromatography on silica gel to give 112 mg of the product (P-117). $^1H$ NMR (400 MHz, $CDCl_3$) δ ppm 3.82 (s, 3H), 5.85 (s, 1H), 6.97 (d, J=8.4 Hz, 1H), 6.98-7.05 (m, 2H), 7.31-7.39 (m, 4H), 7.54 (t, 1H), 7.67-7.7 (m, 1H), 8.01-8.04 (m, 1H), 8.23 (s, 1H), 8.46 (s, 1H) ppm; LCMS (ESI+): 377 (M+1).

The following compounds were prepared analogous to the example shown above.

Example 24

Preparation of P-118

2-[5'-(4-Fluoro-benzyl)-2'-methoxy-biphenyl-3-yl]-[1,3,4]oxadiazole (P-118). $^1H$ NMR (400 MHz, $CDCl_3$) δ 3.80 (s, 3H), 3.95 (s, 2H), 6.93 (d, J=8.4 Hz, 1H), 6.97-6.99 (m, 2H), 7.13-7.17 (m, 4H), 7.54 (t, 1H), 7.68-7.7 (m, 1H), 8.01-8.03 (m, 1H), 8.23 (s, 1H), 8.46 (s, 1H) ppm; MS (APCI+): 361 (M+1), LCMS: 96.7%.

Example 25

Preparation of P-093

(4-Fluoro-6-methoxy-3'-nitro-biphenyl-3-yl)-(4-fluoro-phenyl)-methanol (P-093). $^1H$ NMR (400 MHz, $CDCl_3$): δ 8.35 (t, J=2.0 Hz, 1H), 8.15-8.19 (m, 1H), 7.75-7.79 (m, 1H), 7.55 (t, J=8.0 Hz, 1H), 7.44 (d, J=8.4 Hz, 1H), 7.38-7.41 (m, 2H), 7.01-7.06 (m, 2H), 6.72 (d, J=12 Hz, 1H), 6.13 (br s, 1H), 3.82 (s, 3H) ppm. Calc. 373.36; $APCI^-$ (M−2): 371.0; >85%.

Example 26

Preparation of P-094

4-Fluoro-5-(4-fluoro-benzyl)-2-methoxy-3'-nitro-biphenyl (P-094). $^1H$ NMR (400 MHz, $CDCl_3$): δ=8.33 (br s, 1H), 8.15-8.17 (m, 1H), 7.75 (d, J=8.4 Hz, 1H), 7.53 (t, J=8.0 Hz, 1H), 7.12-7.18 (m, 2H), 7.10 (d, J=8.4 Hz, 1H), 6.97 (t, J=8.4

Hz, 2H), 6.74 (d, J=11.6 Hz, 1H), 3.95 (s, 2H), 3.81 (s, 3H) ppm. Calc. 357.36; APCI⁻ (M−1): 356.1, ⁻ (M−2): 355.2, 93%.

Example 27

Preparation of P-079

(4-Fluoro-phenyl)-(3'-nitro-6-trifluoromethoxy-biphenyl-3-yl)-methanol (P-079). ¹H NMR (400 MHz, CDCl₃) δ 2.29 (1H, d, J=3.2 Hz), 5.91 (1H, d, J=3.2 Hz), 7.06 (2H, m), 7.37 (3H, m), 7.44 (1H, dd, J=8.4, 2.4 Hz), 7.49 (1H, d, J=2 Hz), 7.61 (1H, dd, J=8 and 8 Hz), 7.78 (1H, m), 8.25 (1H, m), 8.32 (1H, m) ppm.

Example 28

Preparation of P-080

5-(4-Fluoro-benzyl)-3'-nitro-2-trifluoromethoxy-biphenyl (P-080).
¹H NMR (400 MHz, CDCl₃) δ 4.02 (2H, s), 7.01 (2H, m), 7.16 (2H, m), 7.24 (2H, m), 7.31 (1H, m), 7.60 (1H, dd, J=8, 8 Hz), 7.77 (1H, m), 8.24 (1H, m), 8.30 (1H, m) ppm.

General Scheme 12.

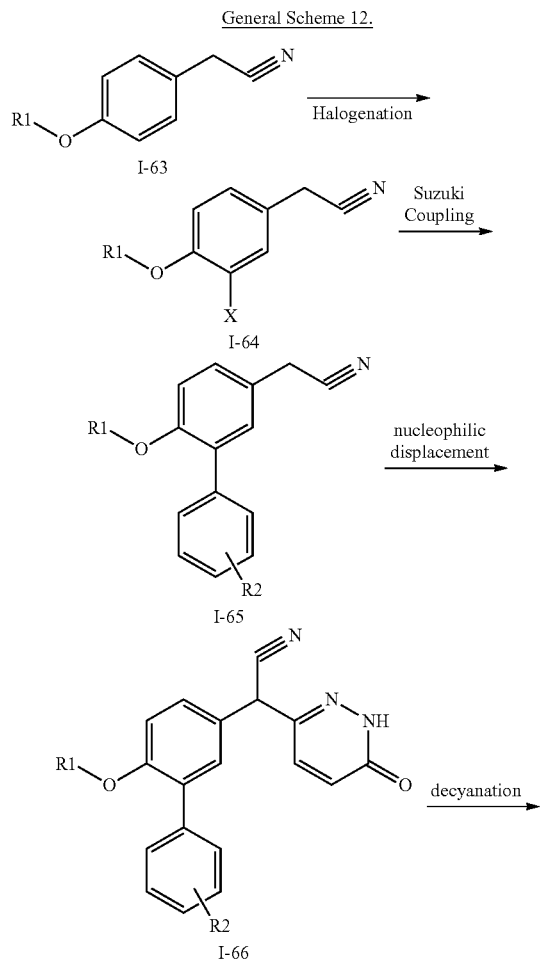

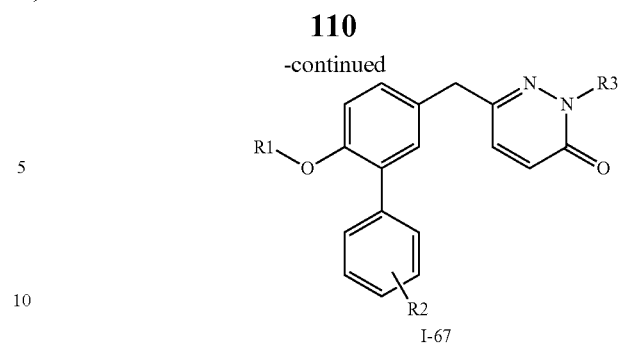

I-67
X = halogen, boronate
R1 = H, Me, CH2CH2OCH3, CONH2
R2 = Cl, CH3CO, CN, NO2, Br, fused heterocycle
R3 = substituted groups

Example 29

Preparation of P-009

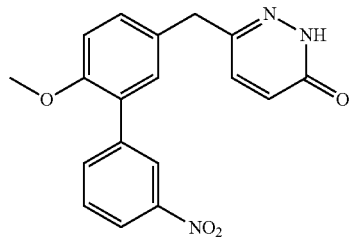

P-009

(3-Bromo-4-methoxy-phenyl)-acetonitrile; To a mixture of compound 4-methoxyphenyl acetonitrile (5.88 g, 40 mmol), KBr (9.52 g, 80 mmol), tetrabutylammonium chloride (332 mg, 1.2 mmol) in dichloroethane (80 mL), was added 21% w/w nitric acid (48 g, 160 mmol). The reaction mixture was stirred at rt for 20 h, diluted with dichloromethane (80 mL) and washed with sat. NaHCO₃ aq. (2×50 mL), water (2×50 mL), brine and dried over Na₂SO₄. After removal of solvent under vacuum, the residue was triturated with Et₂O (10 ml)/hexanes (40 ml) to give 6.32 g of product; Yield: 70%.

(6-Methoxy-3'-nitro-biphenyl-3-yl)-acetonitrile; A reaction mixture of the above product (2.26 g, 10 mmol), 3-nitrophenyl boronic acid (1.67 g, 10 mmol), triphenylphosphine (262 mg, 1 mmol), K₂CO₃ (4.14 g, 30 mmol), Pd(OAc)₂ (112 mg, 0.5 mmol) in 1,2-dimethoxyethane (80 mL), ethanol (10 mL) and water (10 mL) was stirred at 80° C. for 20 hrs under Ar. After removal of solvent under vacuum, reaction mixture was diluted with ethyl acetate (80 mL) and washed with water (2×40 mL), brine and dried over Na₂SO₄. After removal of solvent, the residue was triturated with Et₂O (20 mL) to give 2.18 g of product; Yield: 81%.

(6-Chloro-pyridazin-3-yl)-(6-methoxy-3'-nitro-biphenyl-3-yl)-acetonitrile; To a mixture of the above product (1072 mg, 4 mmol) 3,6-dichloropyridazine (1311 mg, 8.8 mmol) in DMF (15 mL), was added portion wise NaH (400 mg, 60% in oil, 10 mmol) at 0° C. under Ar. The reaction mixture was stirred at 0° C. for 1 hr and allowed to slowly warm to rt and then stirred at rt for 16 hrs. Reaction mixture was cooled to 0° C. and added sat. NH₄Cl aq. (50 mL)/water (150 mL) and stirred at rt for 10 min. The resulting solid was filtered, dissolved in ethyl acetate (80 mL) and then washed with water (2×40 mL), brine, and dried over Na₂SO₄. After removal of solvent, the residue was purified by silica gel column chromatography with ethyl acetate/hexane as eluent to give 1.4 g of product; Yield: 92%.

6-(6-Methoxy-3'-nitro-biphenyl-3-ylmethyl)-2H-pyridazin-3-one (P-009). A reaction mixture of the above product (600 mg, 1.58 mmol) in acetic acid (10 mL), concentrated HCl (20 mL) and water (10 mL) was refluxed for 18 hrs. After cooling to r.t., water (200 mL) was added to reaction mixture and stirred at rt. for 20 min. The resulted solid was filtered and dried at r.t. over night. The solid was dissolved in dichloromethane (50 ml) and filtered off solid. After removal of dichloromethane, the solid was washed with diethyl ether (20 mL) to give 310 mg of product (P-009); Yield: 58%; $^1$H NMR (400 MHz, CDCl$_3$) δ 3.83 (3H, s), 3.92 (2H, s), 6.88 (1H, d, J=9.6 Hz), 6.98 (1H, d, J=8.4 Hz), 7.13 (1H, d, J=9.6 Hz), 7.18 (1H, m), 7.22 (1H, dd, J=8.4.2 Hz), 7.56 (1H, dd, J=8, 8 Hz), 7.82 (1H, m), 8.18 (1H, m) ppm; MS (ESI+): 338.6 (M+1); LC-MS: 96%.

The following compounds were prepared analogous to the example shown above.

Example 30

Preparation of P-012

6-(3-Benzo[1,2,5]oxadiazol-5-yl-4-methoxy-benzyl)-2H-pyridazin-3-one (P-012). $^1$H NMR (400 MHz, CDCl$_3$) 6, 3.85 (3H, s), 3.92 (2H, s), 6.89 (1H, d, J=9.6 Hz), 6.99 (1H, d, J=8.4 Hz), 7.14 (1H, d, J=9.6 Hz), 7.23 (1H, d, J=2 Hz), 7.27 (1H, m), 7.60 (1H, m), 7.81 (1H, m), 7.85 (1H, m), 10.42 (1H, br s).

Example 30

Preparation of P-018

6-[6-(2-Methoxy-ethoxy)-3'-nitro-biphenyl-3-ylmethyl]-2-(2-methoxy-ethyl)-2H-pyridazin-3-one (P-018). $^1$H NMR (400 MHz, CDCl$_3$) δ 3.34 (3H, s), 3.36 (3H, s), 3.68 (2H, m), 3.80 (2H, t, J=5.5 Hz), 3.92 (2H, s), 4.14 (2H, m), 4.36 (2H, t, J=5.5 Hz), 6.84 (1H, d, J=9.5 Hz), 6.98 (1H, d, J=8 Hz), 7.05 (1H, d, J=9.5 Hz), 7.19-7.22 (2H, m), 7.55 (1H, dd, J=8 and 8 Hz), 7.87 (1H, m), 8.17 (1H, m), 8.49 (1H, m).

Example 31

Preparation of P-020

Carbamic acid 3'-nitro-5-(6-oxo-1,6-dihydro-pyridazin-3-ylmethyl)-biphenyl-2-yl ester (P-020). $^1$H NMR (400 MHz, DMSO-d6) δ, 3.92 (2H, s), 6.82 (1H, dd, J=9.6 and 2.4 Hz), 6.82 (1H, br s), 7.15 (1H, br s), 7.18 (1H, J=8.4 Hz), 7.32 (1H, dd, J=8 and 2 Hz), 7.41 (1H, d, J=10 Hz), 7.44 (1H, d, J=2 Hz), 7.75 (1H, dd, J=8 and 8 Hz), 7.88 (1H, m).

General Scheme 13

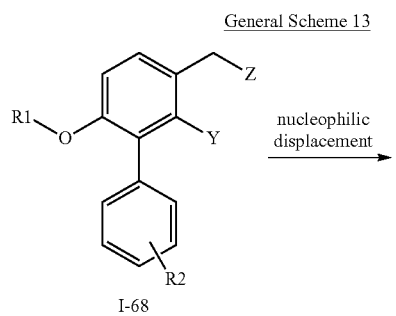

nucleophilic displacement →

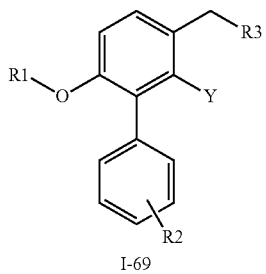

Y = H, F, OH, NH2, CN, OCH3, OEt
Z = Br, Cl, OCO$_2$CH$_3$
R1 = H, Me, CHF2, CF3
R2 = Cl, CH3CO, CN, NO2, Br, fused heterocycle
R3 = substituted aryl groups

Example 32

Preparation of P-224

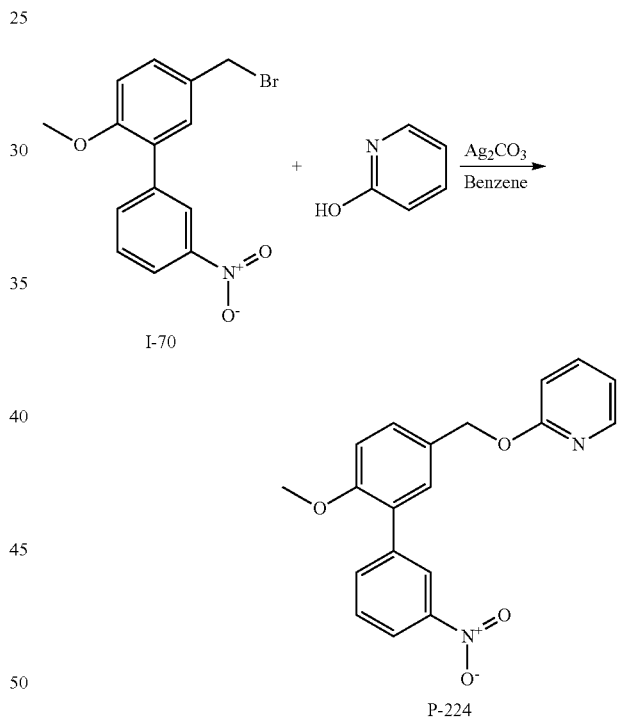

Synthesis of 2-(6-Methoxy-3'-nitro-biphenyl-3-ylmethoxy)-pyridine (P-224). Into a 20 mL vial with stir bar was added I-70 (230 mg, 0.71 mg), 2-hydroxypyridine (91 mg, 0.59 mmol), Ag$_2$CO$_3$ (236 mg, 0.89 mmol), and 4 mL of benzene. The reaction was stirred for 18 hours at 80° C. protected from light. An additional 204 mg of 2-hydroxypyridine and 515 mg of Ag$_2$CO$_3$ was added and the reaction stirred for 3 more days at 80° C. The reaction was filtered and the filtrate was concentrated. The residue was purified by flash column chromatography eluting with 20% ethyl acetate/hexanes to give 63 mg (32%) of P-224 as a light yellow oil. $^1$H NMR (400 MHz, CDCl$_3$) 8.42 (s, 1H), 8.22-8.13 (m, 2H), 7.87 (d, J=7.8 Hz, 1H), 7.63-7.53 (m, 2H), 7.52-7.44 (m, 2H), 7.02 (d, J=8.3 Hz, 1H), 6.89 (dd, J=5.4, 6.2 Hz, 1H), 6.80 (d, J=8.3 Hz, 1H), 5.37 (s, 2H), 3.85 (s, 3H) ppm. LC/MS=90.0%, 337.1 (APCI+).

Example 33

Preparation of P-479

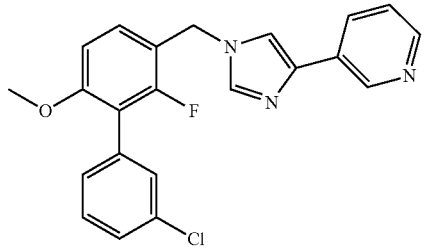

P-479

3-[1-(3'-Chloro-2-fluoro-6-methoxy-biphenyl-3-ylmethyl)-1H-imidazol-4-yl]-pyridine (P-479). A flask was charged with 3-(1H-Imidazol-4-yl)-pyridine (165 mg, 0.75 mmol) and THF (5 mL). Then NaH (60% dispersion in mineral oil, 60 mg, 1.5 mmol) was added slowly (gas evolution). After 2 min. of stirring at room temperature 3-Bromomethyl-3'-chloro-2-fluoro-6-methoxy-biphenyl (165 mg, 0.5 mmol) was added. The reaction mixture was stirred at rt. After overnight stirring the reaction mixture was quenched with water (20 mL). The mixture was extracted with EtOAc (3×10 mL). The combined organic layers were washed with brine (50 mL), dried over Na$_2$SO$_4$ and concentrated in-vacuo. The crude was purified by silica gel column chromatography, eluted with dichloromethane/MeOH (200:5) to produce 77.1 mg (39% yield) of the product (P-479) as a pale yellow solid. $^1$H NMR (400 MHz, DMSO-d) δ 3.75 (s, 3H), 5.26 (s, 2H), 7.02 (d, J=, 8.59 Hz, 1H), 7.28-7.50 (m, 6H), 7.78-7.88 (m, 2H), 8.04-8.11 (m, 1H), 8.38 (dd, J=4.7, 1.2 Hz, 1H), 8.96 (d, J=1.5 Hz, 1H) ppm.

Scheme 14.

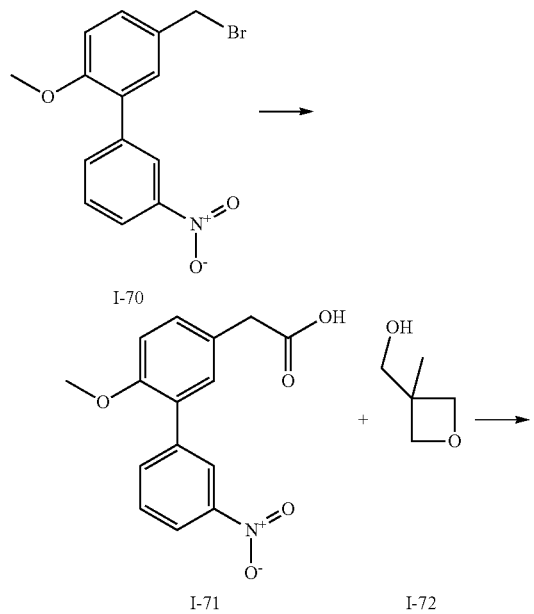

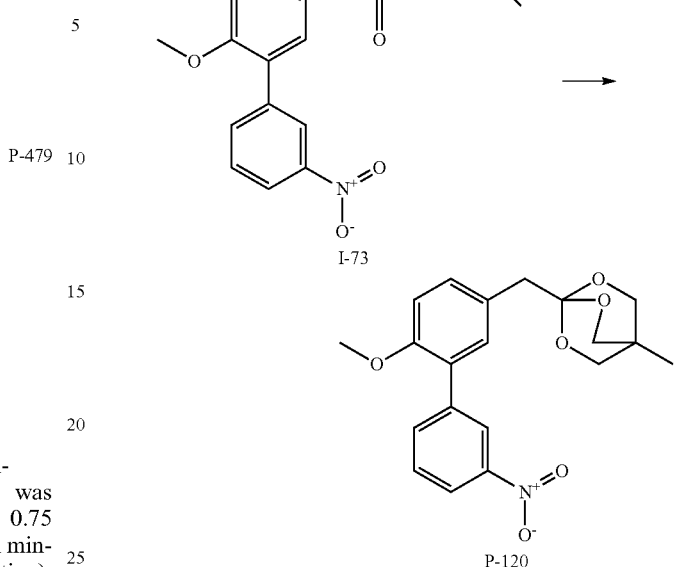

Example 34

Preparation of P-120

(6-Methoxy-3'-nitro-biphenyl-3-yl)-acetic acid (I-71) Into a 100 mL round bottom flask with stir bar was added 5-bromomethyl-2-methoxy-3'-nitro-biphenyl (I-70) (0.60 g, 1.86 mmol), NaCN (0.18 g, 3.72 mmol), and dry DMF (20 mL). The reaction was stirred at room temperature for 20 hours after which 20 mL of water and 20 mL of dichloromethane were added. The layers were separated and the aqueous was extracted with 20 mL of dichloromethane. The combined organic were washed with water (3×20 mL) and concentrated to afford the corresponding nitrile which was used as is in the next reaction. Into a 100 mL round bottom flask with a stir bar was added the crude nitrile, 10 mL of ethanol, and 5 mL of 2 N KOH. The suspension dissolved upon heating and the solution was stirred at reflux for 18 hours. The reaction was cooled to room temperature and the ethanol was removed under reduced pressure. The remaining aqueous portion was washed with 2×10 mL of dichloromethane then acidified to pH=1 using 6 N HCl. The precipitate that formed was filtered and washed with water (2×10 mL). After drying in a 40° C. vacuum oven for 4 hours, 0.32 g (60%) of I-71 was obtained as a yellow solid.

(6-Methoxy-3'-nitro-biphenyl-3-yl)-acetic acid 3-methyl-oxetan-3-ylmethyl ester (I-73). Into a 20 mL vial with stir bar were added the above acid (I-71) (0.12 g, 1.15 mmol), 2 mL dichloromethane, 3-Hydroxymethyl-3-methyl-oxetane (0.30 g, 1.04 mmol), DMAP (38 mg, 0.31 mmol), DCC (0.24 g, 1.15 mmol), and 2 mL of dichloromethane. After the reaction was stirred at room temperature for 30 minutes, 10 mL of hexanes were added and the reaction was stirred an additional 10 minutes. The suspension was filtered through celite and the celite pad was washed with 5:1 hexane:dichloromethane (3×10 mL). The filtrate was concentrated and the residue purified by flash column chromatography using 30% ethyl acetate/hexanes to give 0.33 g (85%) of I-73 as a colorless semi-solid.

1-(6-Methoxy-3'-nitro-biphenyl-3-ylmethyl)-4-methyl-2,6,7-trioxa-bicyclo[2.2.2]octane (P-120); Into a 100 mL round bottom flask with stir bar was added I-73 (0.32 g, 0.86 mmol) and 10 mL of dry dichloromethane. The solution was cooled to −15° C. and BF$_3$—OEt$_2$ (270 uL, 2.2 mmol) was added.

The reaction was allowed to slowly attain room temperature over 4 hours then cooled again to 0° C. Triethylamine (0.48 mL, 3.45 mmol) was added and the reaction was concentrated. The product was purified by flash column chromatography using 2% ethyl acetate in 50% ethyl acetate/hexanes to afford 9.8 mg (3%) of the product (P-120) as a colorless oil. $^1$H NMR (400 MHz, CDCl$_3$) 2.99 (s, 3H), 3.81 (s, 3H), 3.90 (s, 6H), 6.93 (d, J=8.3 Hz, 1H), 7.27-7.35 (m, 2H), 7.54 (t, J=8.0 Hz, 1H), 7.87 (d, J=7.8 Hz, 2H), 8.15 (dd, J=8.3, 1.3 Hz, 2H), 8.43 (t, J=1.8 Hz, 1H) ppm. MS (APCI+) 372.1.

General Scheme 15.

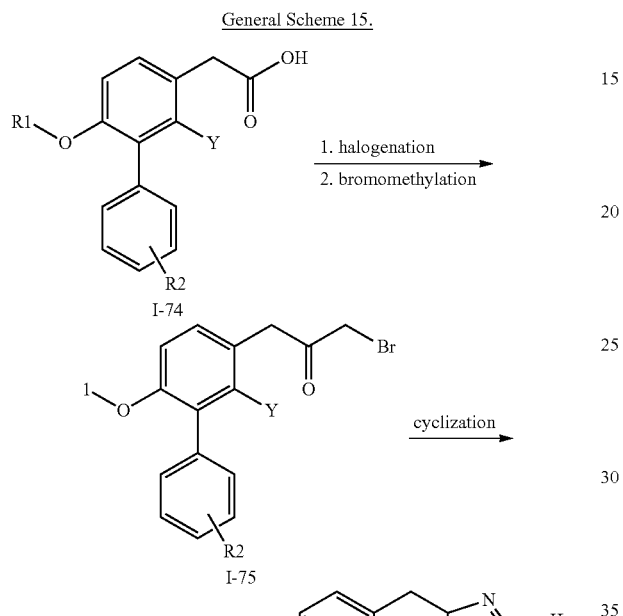

R = H, CONHCH2CH3
Y = H, F, OH, NH2, CN, OCH3, OEt
Z = Br, Cl, OCO$_2$CH$_3$
R1 = H, Me, CHF2, CF3
R2 = Cl, CH3CO, CN, NO2, Br, fused heterocycle Example 35

Preparation of P-341

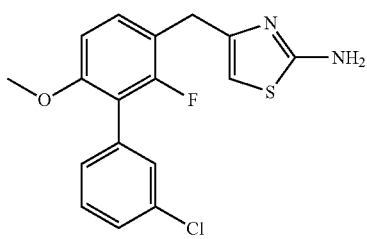

1-Bromo-3-(3'-chloro-2-fluoro-6-methoxy-biphenyl-3-yl)-propan-2-one; Into a 20 mL vial with stir bar was added (3'-Chloro-2-fluoro-6-methoxy-biphenyl-3-yl)-acetic acid (I-74, R1=Me, Y=F) (306 mg, 1.04 mmol), dichloroethane (4 mL), thionyl chloride (151 uL, 2.08 mmol) and the solution was stirred at 80° C. for 1 hour. The solution was cooled to 0° C., 4 mL of dichloromethane were added, and a solution of (trimethylsilyl)diazomethane (1.56 mL, 3.11 mmol, 2.0 M in ether) was added and the reaction stirred at room temperature for 16 hours. The reaction was cooled to 0° C. and 0.5 mL HBr (48% in H$_2$O) was added. After 30 minutes at 0° C., Na$_2$CO$_3$ was added until bubbling ceased and the reaction was dried by the addition of Na$_2$SO$_4$. The suspension was filtered and concentrated to yield product (390 mg, 99%) as a brown oil, which was used as is.

4-(3'-Chloro-2-fluoro-6-methoxy-biphenyl-3-ylmethyl)-thiazol-2-ylamine (P-341). Into a 20 mL vial were added the above compound (390 mg, 1.05 mmol), ethanol (4 mL), and thiourea (160 mg, 2.10 mmol). The reaction was stirred for 2 hours at 75° C., then cooled to room temperature. Water (10 mL) and 10 mL of brine were added and the product was extracted with ethyl acetate. The organics were dried with Na$_2$SO$_4$, filtered, and concentrated. The residue was purified by flash column chromatography eluting with 3% methanol/dichloromethane to afford crude product as a yellow solid. The solid was triturated with 1:5 ether:hexane to give pure product (135 mg, 37%) as a tan solid. The solid was dissolved in ether:THF and a solution of 2.0 M HCl/ether were added. The suspension was concentrated to give the title compound (P-341). $^1$H NMR (400 MHz, DMSO-d$_6$) δ 8.89 (br s, 1H), 7.52-7.42 (m, 2H), 7.38 (s, 1H), 7.37-7.27 (m, 2H), 6.98 (d, J=8.6 Hz, 1H), 6.42 (s, 1H), 4.00-3.55 (br s, 2H), 3.87 (s, 2H), 3.75 (s, 3H). MS: 349.0 (APCI+).

Example 36

Preparation of P-346

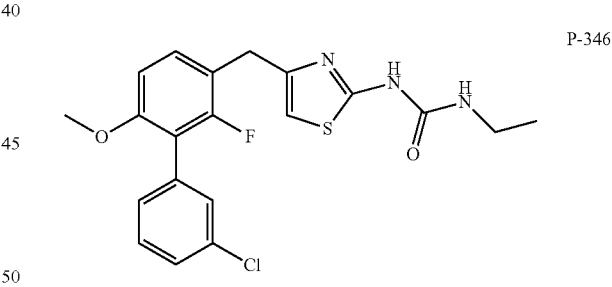

1-[4-(3'-Chloro-2-fluoro-6-methoxy-biphenyl-3-ylmethyl)-thiazol-2-yl]-3-ethyl-urea (P-346). Into an 8 mL vial was added P-341 (40 mg, 0.11 mmol), pyridine (2 mL), and ethylisocyanate (24 mg, 0.34 mmol). The solution was stirred at 50° C. for 3 days, then an additional 40 mg ethyl isocyanate was added and the reaction was stirred at 80° C. for 2 hours. After cooling to room temperature, water was added and the product was extracted with ethyl acetate. The organics were concentrated and the residue was purified by flash column chromatography eluting with 15-20% acetone/hexane to give the product (P-346) (31 mg, 64%) as an off-white solid. $^1$H NMR (400 MHz, CDCl$_3$) δ 10.42 (br s, 1H), 7.45-7.42 (m, 2H), 7.37 (s, 1H), 7.30-7.25 (m, 2H), 6.93 (d, J=8.4 Hz, 1H), 6.57 (s, 2H), 3.86 (s, 2H), 3.73 (s, 3H), 3.14-3.11 (m, 2H), 1.04 (t, J=7.2 Hz, 3H). LC/MS=95.4%, 420.0 (APCI+).

Scheme 16.

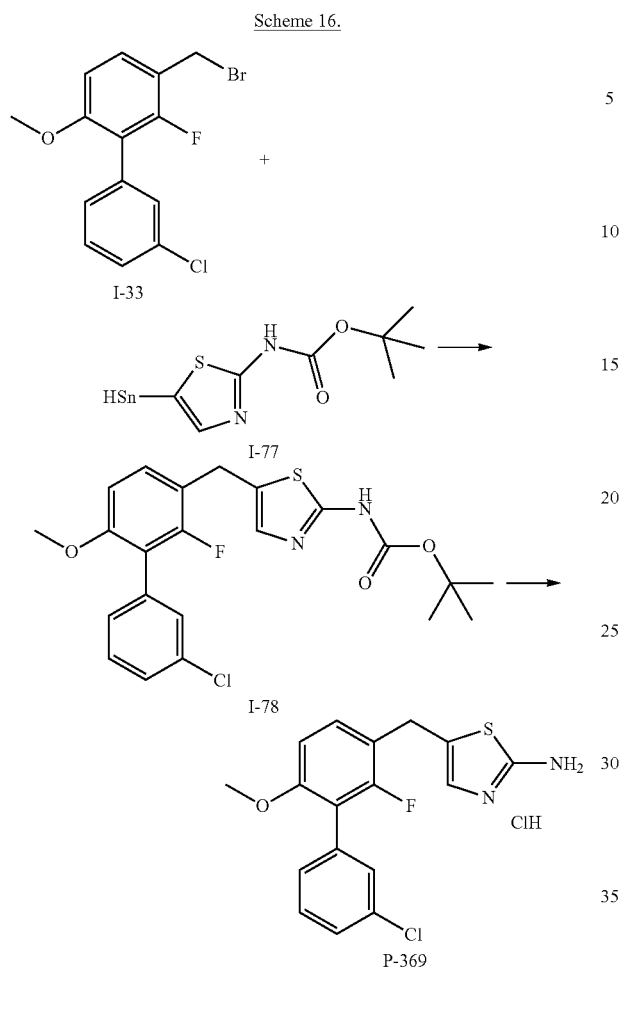

I-33

I-77

I-78

P-369

Example 37

Preparation of P-369

[5-(3'-Chloro-2-fluoro-6-methoxy-biphenyl-3-ylmethyl)-thiazol-2-yl]-carbamic acid tert-butyl ester (I-78). Into an 8 mL vial was added I-33 (70 mg, 0.21 mmol), (5-tributylstannanyl-thiazol-2-yl)-carbamic acid tert-butyl ester (I-77, 104 mg, 0.21 mmol), 4 A molecular sieves (100 mg), and THF (2 mL). The mixture was degassed for 10 minutes with $N_2$ and then $Pd(PPh_3)_4$ (25 mg, 0.021 mmol) was added. After stirring for 18 hours at 80° C., the suspension was filtered and the filter cake was washed with EtOAc. The filtrate was washed with water and then concentrated. Purification by flash column chromatography (15% acetone/hexanes) provided I-78 (11 mg, 12%) as a white semi-solid.

5-(3'-Chloro-2-fluoro-6-methoxy-biphenyl-3-ylmethyl)-thiazol-2-ylamine (P-369). Into a 4 mL vial was added I-78 (10 mg, 0.022 mmol) and 1 mL of 4N HCl/dioxane. After stirring for 8.5 hours the reaction was concentrated to obtain P-369 (6.8 mg, 77%) $^1$H NMR (400 MHz, DMSO-$d_6$) 9.69 (br s, 2H), 7.52-7.45 (m, 2H), 7.43-7.36 (m, 2H), 7.32 (d, J=4.6 Hz, 1H), 7.29 (d, J=6.3 Hz, 1H), 7.08-7.01 (m, 2H), 5.29 (s, 2H), 3.77 (s, 3H) ppm. LC/MS=94.4%, 349.0 (APCI+).

General Scheme 17.

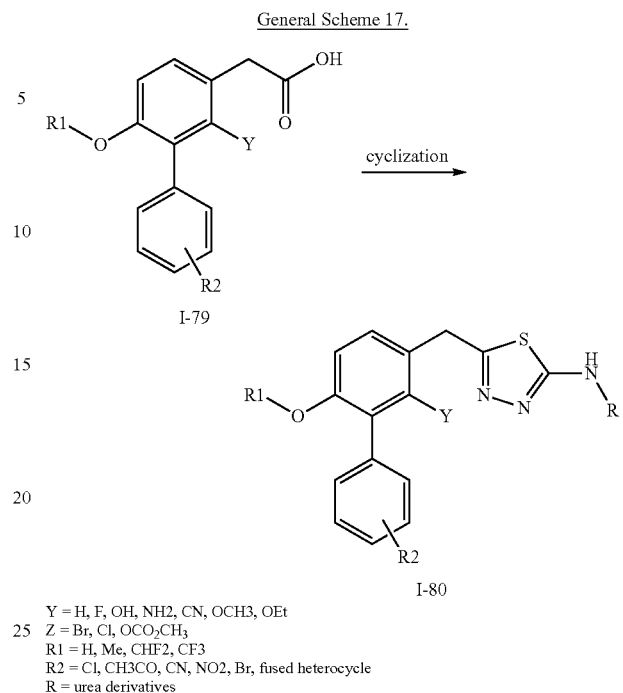

I-79

I-80

Y = H, F, OH, NH2, CN, OCH3, OEt
Z = Br, Cl, OCO$_2$CH$_3$
R1 = H, Me, CHF2, CF3
R2 = Cl, CH3CO, CN, NO2, Br, fused heterocycle
R = urea derivatives Example 38

Preparation of P-333

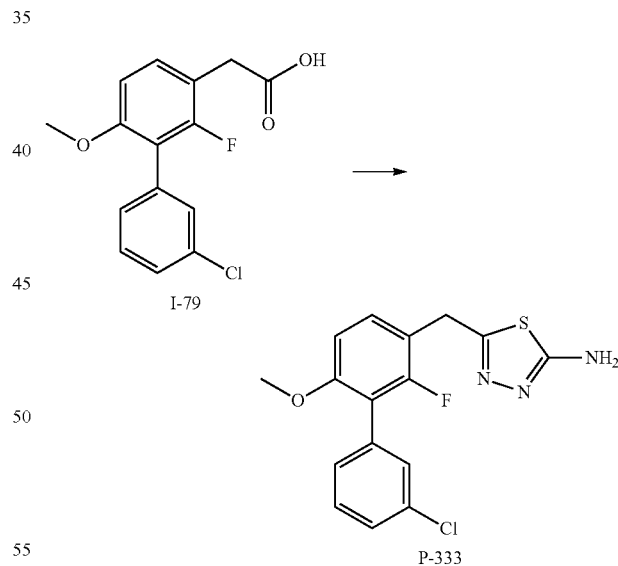

I-79

P-333

5-(3'-Chloro-2-fluoro-6-methoxy-biphenyl-3-ylmethyl)-[1,3,4]thiadiazol-2-ylamine (P-333). A mixture of (3'-Chloro-2-fluoro-6-methoxy-biphenyl-3-yl)-acetic acid (I-79) (0.998 mmol, 1.0 eq.) and thiosemicarbazide (2.99 mmol; 3 eq.) in excess phosphorous oxychloride was heated to 120° C. for 45 minutes, and allowed to cool to room temperature. The resultant mixture was added to water, and extracted with 2 portions of ethyl acetate. The organics were washed with brine, and dried over magnesium sulfate. The residue was purified via flash chromatography on silica gel using 5% (1N $NH_3$ in MeOH) in dichloromethane as eluent to afford the desired product (P-333) in 39% yield.

$^1$HNMR (DMSO-$d_6$, 400 MHz): 3.75 (s, 3H), 4.17 (s, 2H), 6.98 (d, J=8.0 Hz, 1H), 7.29 (d, J=6.4 Hz, 1H), 7.37-7.41 (m, 2H), 7.43-7.49 (m, 2H), 7.58-7.76 (br s, 2H)

Example 39

Preparation of P-342

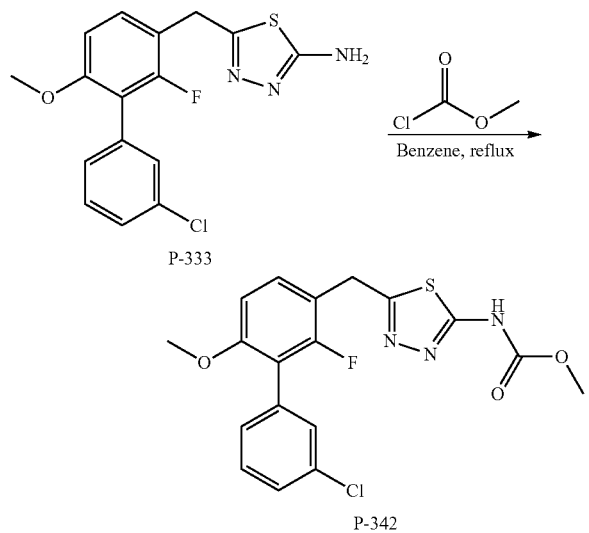

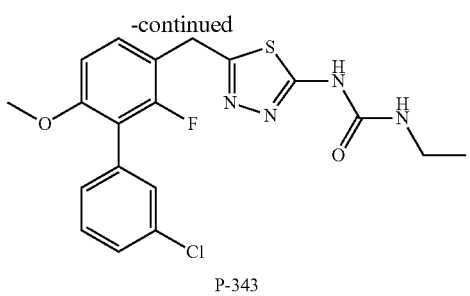

Synthesis of 1-[5-(3'-Chloro-2-fluoro-6-methoxy-biphenyl-3-ylmethyl)-[1,3,4]thiadiazol-2-yl]-3-ethyl-urea (P-343). To a solution of P-333 (0.214 mmol; 1.0 eq.) in pyridine was added ethyl isocyanate (0.643 mmol; 3 eq.), and the resultant solution stirred at room temperature for 4 days. The reaction was diluted with water, and stirred for 1 h. The solids were filtered, washed with water, and dried under high vacuum to afford the title compound, P-343, in 47% yield. $^1$H NMR (400 MHz, DMSO-$d_6$): 1.04 (t, J=7.2 Hz, 3H), 3.12 (q, J=5.6 Hz, 2H), 3.75 (s, 3H), 4.26 (s, 2H), 6.53 (br s, 1H), 6.99 (d, J=8.8 Hz, 1H), 7.29 (dd, J=6.4, 1.2 Hz, 1H), 7.38 (s, 1H), 7.40-7.48 (M, 3H), 10.71 (s, 1H) ppm. LC/MS=94.8% purity $APCI^+$ found: 421.0; calc'd: 420.9 m/z Synthesis of Methyl[5-(3'-Chloro-2-fluoro-6-methoxy-biphenyl-3-ylmethyl)-[1,3,4]thiadiazol-2-yl]-carbamate (P-342). To P-333 (0.286 mmol; 1.0 eq.) was added a solution of methyl chloroformate (0.388 mmol; 1.4 eq.) in benzene. The mixture was heated to reflux for 10 h, and allowed to cool to room temperature. The resultant mixture was diluted with ethyl ether, filtered, and washed with ethyl ether. The solids were dried at 30-35° C. under vacuum for 4 h to afford the title compound, P-342, in 41% yield.

$^1$H NMR (400 MHz, DMSO-$d_6$): 3.73 (s, 3H), 3.75 (s, 3H), 4.32 (s, 2H), 4.74 (br s, 1H), 6.99 (d, J=8.8 Hz, 1H), 7.29 (d, J=6.4 Hz, 1H), 7.38 (s, 1H) 7.42-7.47 (m, 3H) ppm. LC/MS (94.0%) $APCI^+$ found: 408.0; calc'd: 407.9 m/z Example 40

Preparation of P-343

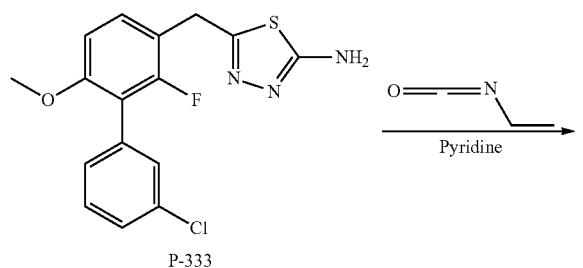

Example 41

Preparation of P-352

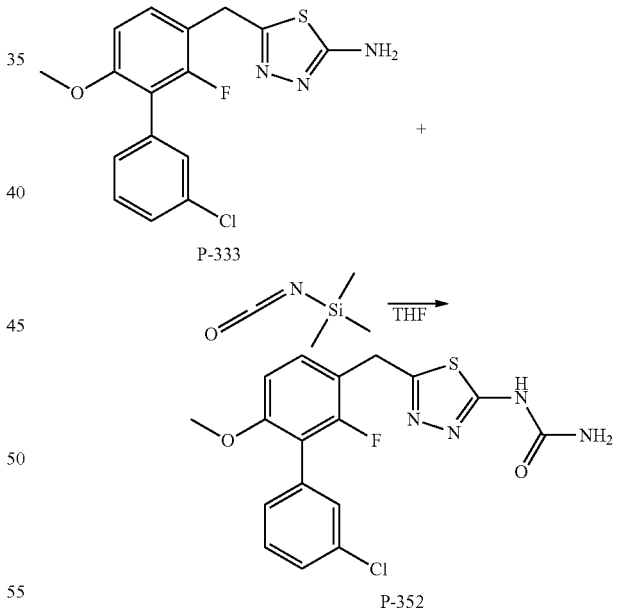

Synthesis of [5-(3'-Chloro-2-fluoro-6-methoxy-biphenyl-3-ylmethyl)-[1,3,4]thiadiazol-2-yl]-urea (P-352). To a solution of P-333 (0.177 mmol; 1 eq) in THF at room temperature was added trimethylsilyl isocyanate (0.886 mmol; 5 eq), and the resultant solution was stirred overnight. The reaction was then heated to 60° C. for 5 h, additional trimethylsilyl isocyanate (0.460 mmol; 2.6 eq) was added, and the reaction allowed to proceed overnight at 60° C. The reaction was cooled, and poured into excess aqueous 5% sodium bicarbonate. The resultant suspension was stirred at room temperature for 1 h, filtered, and washed with water. The solid was dried in vacuo to obtain the title compound, P-352, as a white solid in 46% yield. $^1$H NMR (400 MHz, DMSO-$d_6$): 3.75 (s, 3H), 4.26 (s, 2H), 6.30 (br s, 1H), 6.99 (d, J=8.4 Hz, 1H), 7.29 (d, J=6.4 Hz, 1H), 7.38 (s, 1H), 7.40-7.48 (m, 4H), 10.72 (s, 2H) ppm. LC/MS=91.1% purity. APCI$^+$ found: 393.0; calc'd: 392.8 m/z.

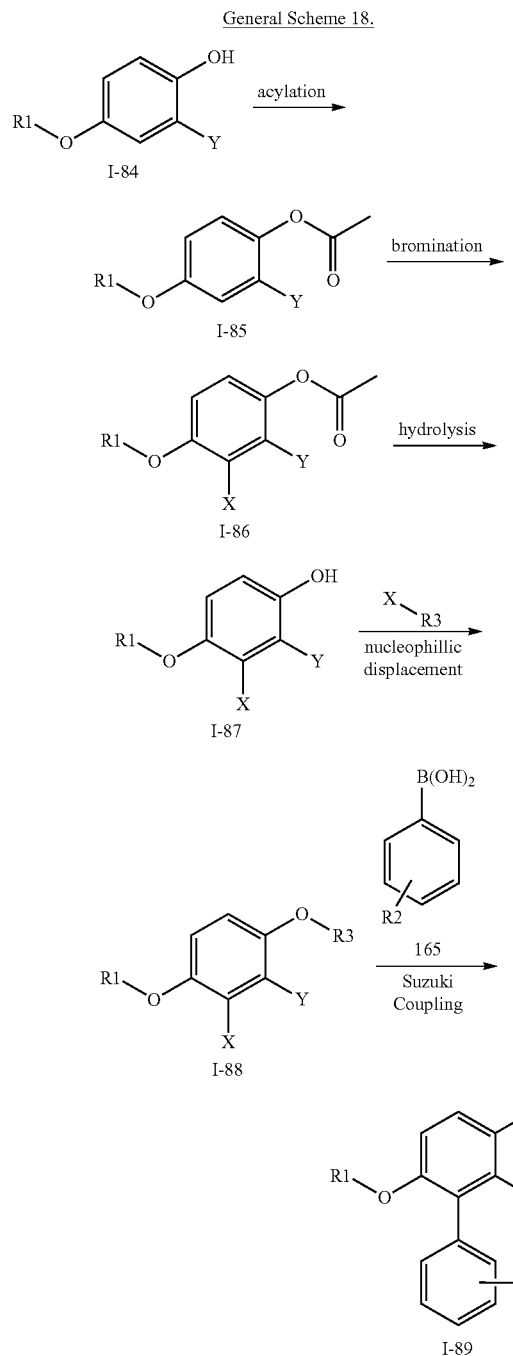

Y = H, F
X = Br, I, Cl
R1 = H, Me, CHF2, CF3
R2 = Cl, CH3CO, CN, NO2, Br, fused heterocycle
R3 = substituted aryl groups

Example 42

Preparation of P-015

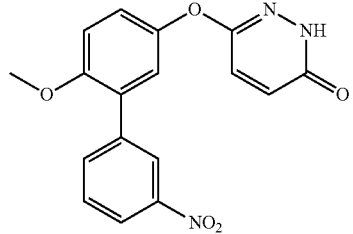

Acetic acid 4-methoxy-phenyl ester (I-85, R1=Me, Y=H); A mixture of 4-methoxyphenol (6.2 g, 50 mmol), $K_2CO_3$ (10 g, 72 mmol) and acetic anhydride (6.12 g, 60 mmol) in acetone (150 ml) was stirred at RT. over night. The solid was filtered off and washed with acetone (50 ml). After removal of acetone, 8.6 g of product was obtained. Yield: 100%.

Acetic acid 3-bromo-4-methoxy-phenyl ester (I-86, R1=Me, Y=Br); To a mixture of the above product (4.15 g, 25 mmol) in acetonitrile (100 ml), was added NBS (5.34 g, 30 mmol) at rt. The reaction mixture was stirred at rt. over night and more NBS (5.34 g, 30 mmol) was added and the reaction mixture was stirred at 75° C. over night. After removal of solvent, the crude product directly went to next step.

3-Bromo-4-methoxy-phenol (I-87, R1=Me, Y=Br): A mixture of crude the above product (25 mmol) in MeOH (100 mL) and 2N NaOH aq. (30 mL) was stirred at r.t. for 40 min. The pH of reaction mixture was adjusted to acidic by adding 2N HCl aq. and extracted with dichloromethane (4×60 mL). The dichloromethane layer was dried over $Na_2SO_4$. After removal of solvent, the residue was purified by silica gel column chromatography with dichloromethane as eluent to give 2.9 g of product Yield: 57% (for two steps)

3-(3-Bromo-4-methoxy-phenoxy)-6-chloro-pyridazine; To a mixture of the above product (1420 mg, 7 mmol) 3,6-dichloropyridazine (1252 mg, 8.4 mmol) in DMSO (15 ml), was added $K_2CO_3$ (1159 mg, 8.4 mmol) at rt. The reaction mixture was stirred at 110° C. for 3 hr under Ar. After cooling to rt, water (50 mL) was added to reaction mixture and extracted with ethyl acetate (3×50 mL). The combined ethyl acetate layer was washed with water (3×50 mL), brine and dried over $Na_2SO_4$. After removal of solvent, the solid was washed with diether (20 mL) to give 1650 mg of the product Yield: 75%

6-(3-Bromo-4-methoxy-phenoxy)-2H-pyridazin-3-one; A reaction mixture of the above product (455 mg, 1.4 mmol) in acetic acid (10 mL), was stirred at 110° C. for 7 hrs. After removal of solvent, the solid was washed with ethyl acetate (10 mL) to give 340 mg of product. Yield: 82%; MS (ESI+): 297.3 (M+1); LC-MS: 94%.

6-(6-Methoxy-3'-nitro-biphenyl-3-yloxy)-2H-pyridazin-3-one (P-015); A reaction mixture of the above product (85 mg, 0.29 mmol), 3-nitrophenyl-boronic acid (72 mg, 0.43 mmol), triphenylphosphine (16 mg, 0.06 mmol), $K_2CO_3$ (124 mg, 0.9 mmol), Pd(OAc)$_2$ (7 mg, 0.03 mmol) in 1,2-dimethoxyethane (6 ml), ethanol (0.5 ml) and water (0.5 ml) was stirred at 80° C. for 20 hrs under Ar. Reaction mixture was diluted with water (40 ml) and extracted with ethyl acetate (2×40 mL). The combined organic phase was washed with water (2×30 mL), brine and dried over $Na_2SO_4$. After removal of solvent, the residue was purified by silica gel column chromatography with ethyl acetate/hexane as eluent to give 39 mg g of the product (P-015) Yield: 40%. ¹H NMR (400 MHz, CDCl₃) δ=3.85 (3H, s), 7.03 (1H, d, J=10 Hz), 7.04 (1H, d, J=8.8 Hz), 7.16-7.20 (2H, m), 7.22 (1H, d, J=10 Hz), 7.57 (1H, dd, J=8, 8 Hz), 7.86 (1H, m), 8.19 (1H, m), 8.41 (1H, m), 9.62 (1H, br s). MS (ESI+): 340.6 (M+1); LC-MS: 92%.

General Scheme 19.

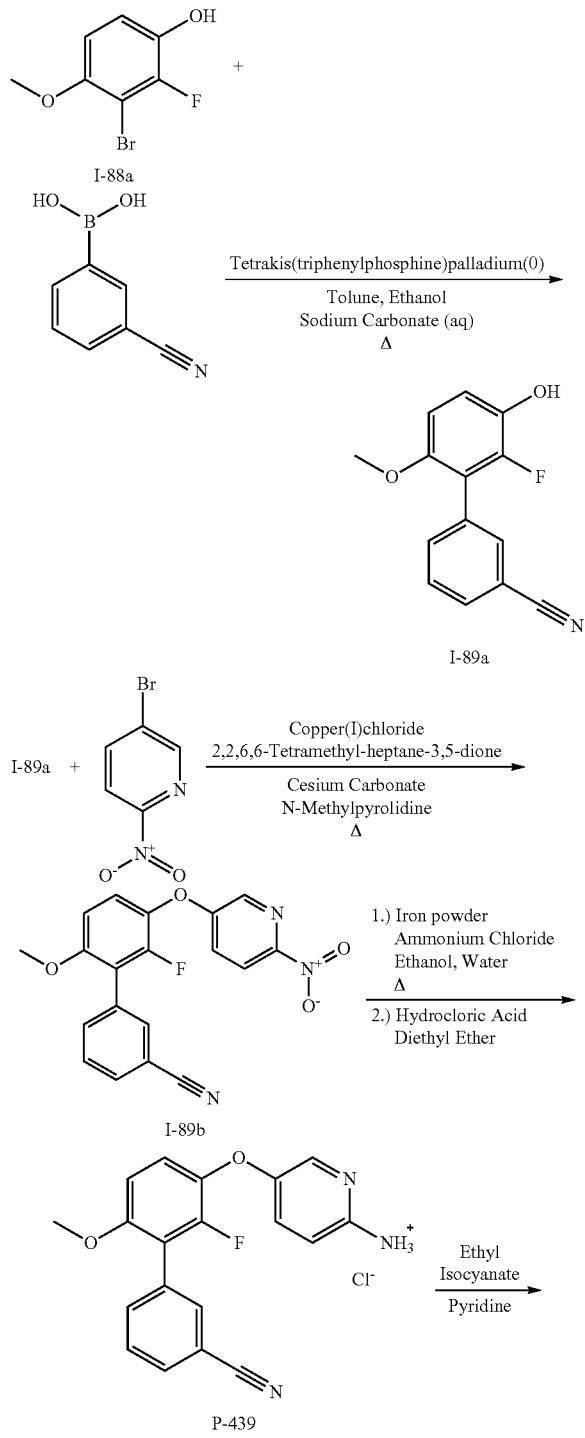

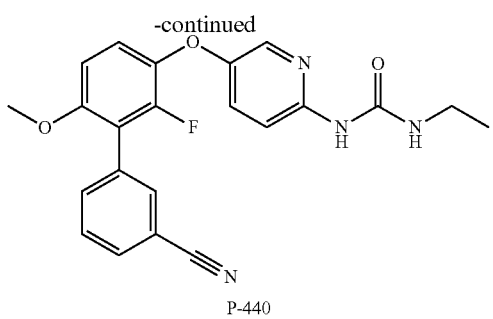

P-440

Example 43

Preparation of P-439 and P-440

Synthesis of 2'-Fluoro-3'-hydroxy-6'-methoxy-biphenyl-3-carbonitrile (I-89, R1=Me, R2=3-CN, R3=H). A solution of I-88a (2.00 g, 8.22 mmol) and 3-cyanophenylboronic acid (1.45 g, 9.87 mmol) in toluene (30 mL) was purged with a nitrogen stream for 15 min To the solution was added ethanol (5 mL) and 2 M aqueous sodium carbonate (8.2 mL), a suspension formed and palladium(0)tetrakis(triphenylphosphine) (475 mg, 0.411 mmol) was added. The reaction was heated to 108° C. and stirred at this temperature overnight. The reaction was diluted with ethyl acetate (200 mL) and water (200 mL). The layers were separated and the aqueous layer extracted with ethyl acetate (200 mL). The organic extracts were combined, washed with water (400 mL) and brine (300 mL), dried over sodium sulfate, filtered, and the solvent removed under vacuum to give crude product. The crude material was purified by flash silica gel column chromatography (0-5% methanol in dichloromethane) to give I-89a (1.53 g, 77% yield) as a beige powder.
1H NMR (400 MHz CDCl₃) d: 7.74-7.73 (m, 1H), 7.67-7.64 (m, 2H), 7.53 (t, J=7.8 Hz, 1H), 7.01 (t, J=9.4 Hz, 1H), 6.691 (dd, J=9.2, 2.0 Hz, 1H), 4.91 (br m, 1H), 3.77 (s, 3H) ppm. LCMS=100% purity. MS (APCI−)=224.0 (M−19).

Synthesis of 2'-Fluoro-6'-methoxy-3'-(6-nitro-pyridin-3-yloxy)-biphenyl-3-carbonitrile (I-89b). A solution of I-89a (500 mg, 2.06 mmol) and 5-bromo-2-nitropyridine (379 mg, 1.87 mmol) in n-methylpyrrolidine (10 mL) was purged with a nitrogen stream. To the solution was added cesium carbonate (1.22 g, 3.74 mmol), copper(I)chloride (92.4 mg, 0.934 mmol), and 2,2,6,6-tetramethyl-3,5-heptanedione (43.1 mg, 0.234 mmol) under nitrogen. The reaction was heated to 60° C. overnight. The reaction was diluted with ethyl acetate (75 mL) and water (75 mL), and the layers separated. The aqueous wash was extracted with ethyl acetate (75 mL), and the organic extracts combined. The organic extracts were washed with 1 N aqueous sodium hydroxide (100 mL), water (100 mL), and brine (100 mL), dried over sodium sulfate, decanted, and the solvent removed under reduced pressure to give crude product. The material was purified by flash silica gel column chromatography (0-50% ethyl acetate in hexanes) to give I-89b (541.8 mg, 79% yield) as a yellow powder. ¹H NMR (400 MHz, CDCl₃) 8.34 (d, J=2.8 Hz, 1H), 8.26 (d, J=8.8 Hz, 1H), 7.74 (m, 1H), 7.69-7.64 (m, 2H), 7.55 (t, J=7.8 Hz, 1H), 7.42 (dd, J=8.8, 2.4 Hz, 1H), 7.26 (t, J=9.0 Hz, 1H), 6.86 (dd, J=9.2, 1.6 Hz, 1H), 3.85 (s, 3H) ppm. LCMS=74.2% purity. MS (APCI+)=(M−29).

Synthesis of 5-(3'-Cyano-2-fluoro-6-methoxy-biphenyl-3-yloxy)-pyridin-2-yl-ammonium chloride (P-439). A suspension of I-89b (R1=Me, R2=3-CN, R3=2-NO₂-3-pyridyl) (250 mg, 0.684 mmol) and tin(II) chloride (567 mg, 2.51 mmol) in isopropyl alcohol (2.5 mL) and concentrated hydrochloric acid (1.25 mL) was stirred at reflux for 3 h. To the reaction was added ethyl acetate (50 mL) and aqueous saturated sodium bicarbonate (50 mL). The layers were separated and the aqueous layer extracted with ethyl acetate (50 mL). The combined organic extracts were washed with water (50 mL) and brine (50 mL), dried over sodium sulfate, filtered, and the solvent removed under vacuum. The residue was purified by flash silica gel column chromatography (eluting with 50% ethyl acetate in toluene) to give the free base as an orange gum. The gum was dissolved in dioxane (1 mL) and 4 N hydrochloric acid in dioxane was added (2 mL). The suspension was stirred for 2 h at room temperature and subsequently the solvent was removed under reduced pressure. The residue was triturated with diethyl ether (5 mL), filtered, and washed with diethyl ether (2×1 mL) to give P-439 (55.1 mg, 22% yield) as a pale yellow solid.

1H NMR (400 MHz d6-DMSO) d: 7.89-7.84 (m, 4H), 7.75 (d, J=7.6 Hz, 1H), 7.68 (t, J=8.2 Hz, 1H), 7.32 (t, J=9.4 Hz, 1H), 7.02-6.99 (m, 2H), 3.77 (s, 3H). LCMS=96.2% purity. MS (APCI+)=336.1 (M+1).

Synthesis of 1-[5-(3'-Cyano-2-fluoro-6-methoxy-biphenyl-3-yloxy)-pyridin-2-yl]-3-ethyl-urea (P-440). A solution of P-439 (85.0 mg, 0.230 mmol) and ethyl isocyanate (49.0 mg, 0.690 mmol) in pyridine (1.5 mL) was stirred at room temperature over night. The reaction was neutralized with water (50 mL) and extracted with ethyl acetate (2×50 mL). The combined extracts were washed with water (50 mL) and brine (50 mL), dried over sodium sulfate, filtered, and the solvent removed under vacuum. The residue was purified by preparatory silica gel thin layer chromatography (5% acetone in dichloromethane), triturated with diethyl ether (3 mL), filtered, and washed with diethyl ether (2 mL) to give P-440 (32.0 mg, 34% yield) as a white powder.

$^1$H NMR (400 MHz, DMSO-d$_6$) 9.10 (s, 1H), 7.99 (t, J=1.8 Hz, 1H), 7.90 (s, 1H), 7.87 (dt, J=7.5 Hz, 1.50 Hz, 1H), 7.76 (d, J=8.0 Hz, 1H), 7.69-7.65 (m, 2H), 7.46 (d, J=2.00 Hz, 1H), 7.25 (t, J=9.2 Hz, 1H), 6.99 (dd, J=9.2 Hz, 1.60 Hz, 1H), 3.76 (s, 2H), 3.31 (s, 3H), 3.15 (2H), 1.07 (t, J=7.4 Hz, 3H).

LCMS=97.9% purity. MS (APCI+)=407.1 (M+1).

General Scheme 20.

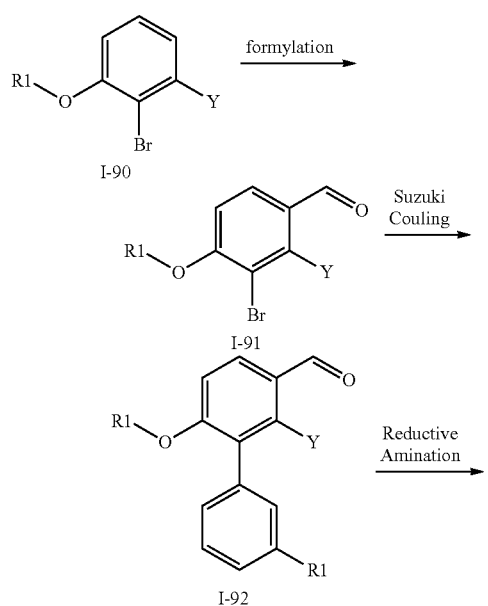

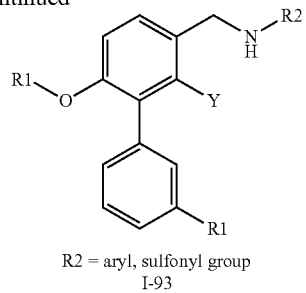

R2 = aryl, sulfonyl group
I-93

Example 44

Preparation of P-203

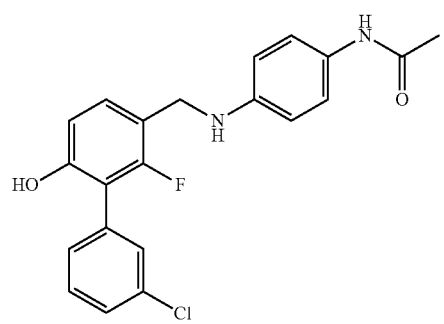

P-203

3-Bromo-2-fluoro-4-methoxy-benzaldehyde and N-{4-[(3'-Chloro-2-fluoro-6-methoxy-biphenyl-3-ylmethyl)-amino]-phenyl}-acetamide To a hot (80° C.) solution of hexamethylenetetramine (13.7 g, 97.5 mmol) in TFA (50 ml) was added a solution of 3-bromo-2-fluoro-4-methoxy-benzene (10 g, 48.8 mmol) in TFA (40 ml) over 1 hour. The resultant solution was continued to stir at 80° C. for 1 h. After it was cooled to room temperature, the reaction mixture was poured to water, and stirred for 30 min. The products were collected on a filter and dried in vacuo to yield desired aldehyde (I-91) and a dimeric amine impurity (total weight: 11 g), as an inseperable mixture. 1H-NMR indicated the molar ratio of these two products is about 1:1.

3'-Chloro-2-fluoro-6-methoxy-biphenyl-3-carbaldehyde (I-92), A mixture of the above products (1.0 g, 4.3 mmol), 3-chlorophenylboronic acid (1.34 g, 8.6 mmol), K$_2$CO$_3$ (1.36 g, 12.9 mmol) and (Ph$_3$P)$_4$Pd (1.49 g, 1.29 mmol) in dioxane/H$_2$O (5:1, 40 ml) was heated to 85 C for 20 h under nitrogen. After it was cooled to room temperature, the mixture was diluted with water, extracted with ethyl acetate, washed with water and brine, and dried over Na$_2$SO$_4$. After it was concentrated in vacuo, the residue was purified by a column chromatography on silica gel to yield the title compound (I-92) (0.4 g).

3-Hydroxymethyl-6-methoxy-3'-nitro-biphenyl-2-ol To a solution of above product (I-92) (0.4 g, 1.5 mmol) in methanol (8 ml) was added 4'-aminoacetanilide (0.34 g, 2.3 mmol) and p-toluenesulfonic acid mono-hydrate (0.013 g, 0.08 mmol). The resulting mixture was stirred at room temperature for 20 h. After the solvent was removed, the residue was dissolved in acetic acid (4 ml), and sodium cyanoborohydride (0.28 g, 4.5 mmol) at 0 C. The resultant stirred at room temperature for 2 h. The mixture was poured into ice-water, extracted with ethyl acetate, washed with water and brine, and dried over $Na_2SO_4$. After it was concentrated in vacuo, the residue was purified by a column chromatography on silica gel to yield the product (I-93, R1=Me, Y=F) (0.4 g, 67%).

N-{4-[(3'-Chloro-2-fluoro-6-hydroxy-biphenyl-3-ylmethyl)-amino]-phenyl}-acetamide (P-203). To a solution of the above product (0.17 g, 0.43 mmol) in methylene chloride (20 mL) was added $BBr_3$ (0.32 g, 1.28 mmol) at −78° C. After it was stirred at −78° C., the resultant was allowed to warm to room temperature, and continued to stir for 3 h. The reaction was quenched with ice-water and basified with $Na_2CO_3$. The resulting mixture was extracted with ethyl acetate, washed with brine, and dried over $Na_2SO_4$. The solvent was removed in vacuo to yield the product P-203 (150 mg, 95%). $^1$H NMR (400 MHz, DMSO-$d_6$) 10.06 (br s, 1H), 7.46-7.61 (m, 4H), 7.40-7.47 (m, 2H), 7.30 (s, 1H), 7.25 (d, J=6.3 Hz, 1H), 7.07-7.16 (m, 2H), 7.01 (d, J=8.7 Hz, 1H), 4.40 (s, 2H), 2.03 (s, 3H) ppm.

The following compound was prepared by procedure similar to the one described above.

Example 45

Preparation of P-251

N-{4-[(3'-Chloro-2-fluoro-6-methoxy-biphenyl-3-ylmethyl)-sulfamoyl]-phenyl}-acetamide (P-251) $^1$H NMR (400 MHz, $CDCl_3$) 7.71 (d, J=8.7 Hz, 2H), 7.58 (d, J=8.7 Hz, 2H), 7.45 (br s, 1H), 7.26-7.37 (m, 2H), 7.17-7.25 (m, 2H), 7.12-7.19 (m, 1H), 6.68 (d, J,=, 8.6 Hz, 1H) 4.83 (t, J=6.2 Hz, 1H) 4.19 (d, J,=, 6.3 Hz, 2H) 3.75 (s, 3H) 2.21 (s, 3H) ppm.

General Scheme 21.

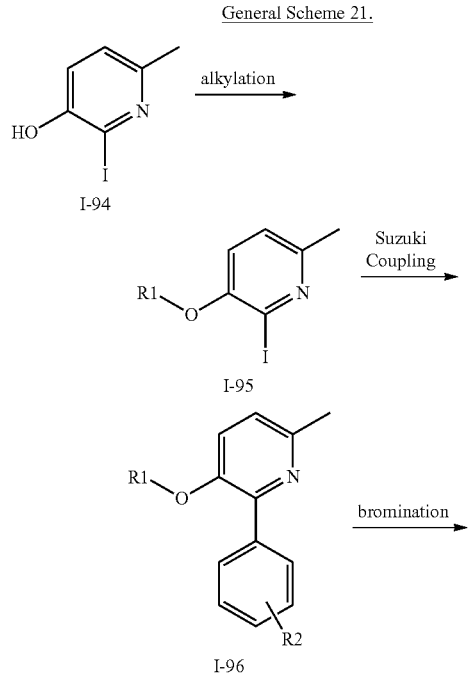

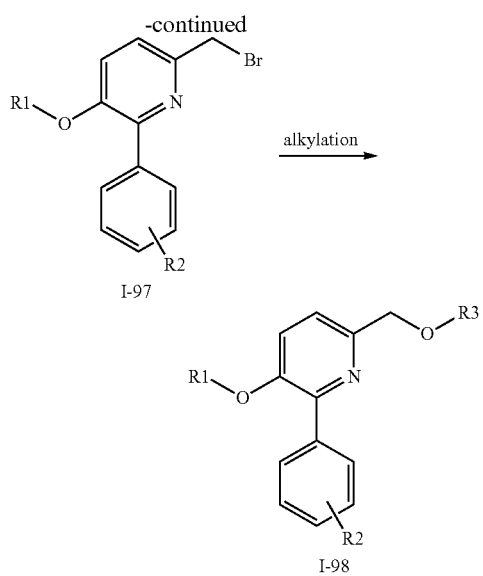

R1 = H, Me, CHF2, CF3
R2 = Cl, CH3CO, CN, NO2, Br, fused heterocycle
R3 = alkyl group Example 46

Preparation of P-025

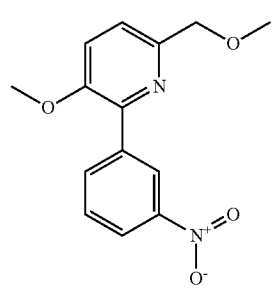

2-iodo-3-methoxy-6-methyl-pyridine (I-95): To 2-iodo-6-methyl-pyridin-3-ol (I-94) (1.0 g, 4.25 mmol) and $K_2CO_3$ (1.18 g, 8.51 mmol) in acetone (20 mL) was added MeI (0.91 g, 6.38 mmol). The reaction was stirred at 45° C. under $N_2$ for 20 h. The reaction was cooled to room temperature and concentrated. The residue was purified by silica gel column chromatography using dichloromethane to afford 1.04 g (98%) of the product (I-95, R1=Me) as light yellow solid.

3-methoxy-6-methyl-2-(3-nitro-phenyl)-pyridine (I-96): To the above product (I-95, R1=Me) (0.5 g, 2.0 mmol), 3-nitrophenylboronic acid (2) (0.5 g, 3.06 mmol), $PPh_3$ (0.11 g, 0.4 mmol), $K_2CO_3$ (0.83 g, 6.0 mmol) and $Pd(OAc)_2$ (0.045 g, 0.2 mmol) was added DME (16 mL), and EtOH—$H_2O$ (1:1, 4 mL). Ar gas was bubbled through the stirred reaction for 5 min. The reaction was stirred at 60° C. under Ar for 18 h. The reaction was cooled to room temperature, concentrated, and $H_2O$ and dichloromethane (40 mL each) were added. The organic layer was separated and the aqueous layer was extracted with dichloromethane (2×25 mL). The combined organic extracts were dried with $Na_2SO_4$, filtered, and concentrated. The residue was purified by silica gel column chromatography using 1:1 dichloromethane-hexanes then dichloromethane to afford 0.22 g (44%) of the product (I-96, R1=Me) as a light yellow solid.

6-bromomethyl-3-methoxy-2-(3-nitro-phenyl)-pyridine (I-97): To the above product (I-96, R1=Me) (0.21 g, 0.86 mmol) and NBS (0.17 g, 0.95 mmol) in CCl$_4$ (10 mL) was added benzoylperoxide (0.02 g, 0.08 mmol). The reaction was stirred at 60° C. under N$_2$ for 18 h. The reaction was cooled to room temperature and concentrated. The residue was dissolved in mixture of dichloromethane and hexanes (1:1, 8 mL) and purified by silica gel column chromatography using 1:1 dichloromethane/hexanes then dichloromethane to afford 0.15 g (55%) of the product as a light brown solid.

3-methoxy-6-methoxymethyl-2-(3-nitro-phenyl)-pyridine (P-025): To the above product (0.08 g, 0.25 mmol), methanol (0.11 g, 2.5 mmol), and CsCO$_3$ (0.24 g, 0.74 mmol) was added DMF (2 mL). The vial was capped and stirred at room temperature for 20 h. The reaction was diluted with 1:1 ethyl acetate-H$_2$O (60 mL). The organic layer was separated and the aqueous was extracted with ethyl acetate (2×20 mL). The combined organic extracts were dried with Na$_2$SO4, filtered, and concentrated to afford 0.066 g (97%) of the product (P-025) as off white solid. $^1$H NMR (CDCl$_3$, 400 MHz): 8.88 (dd, J=2.0, 1.6 Hz, 1H), 8.3-8.35 (m, 1H), 8.2-8.24 (m, 1H), 7.59 (t, J=8.0 Hz, 1H), 7.44 (d, J=8.8 Hz, 1H), 7.37 (d, J=8.4 Hz, 1H), 3.61 (s, 2H), 3.92 (s, 3H), 3.50 (s, 3H); MS (APCI+): 275.1 (M+1), LC-MS: 96.1%.

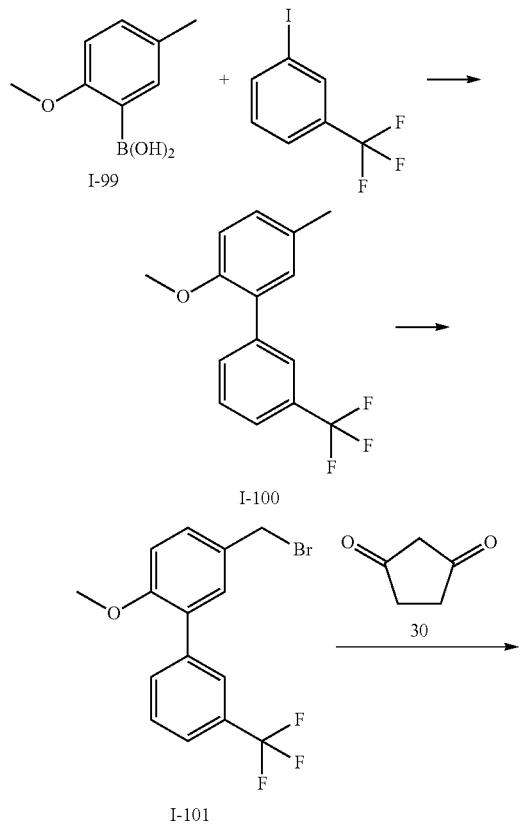

Scheme 22.

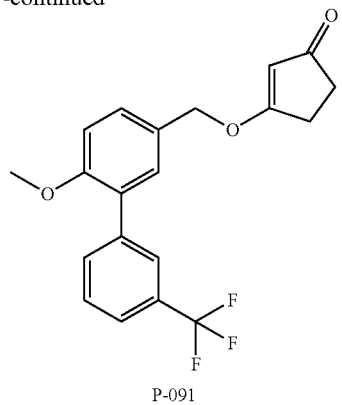

P-091

Example 47

Preparation of P-091

2-methoxy-5-methyl-3'-trifluoromethyl-biphenyl (I-100) A reaction mixture of 2-methoxy-5-methylphenyl boronic acid (I-99) (5 g, 30.3 mmol), 3-iodobenzenetrifluoride (8.24 g, 30.3 mmol), K$_2$CO$_3$ (8.3 g, 60.6 mmol), palladium acetate (350 mg, 1.5 mmol) in methanol (200 ml) and water (40 ml) was stirred at room temperature over night. Reaction mixture was concentrated to a 1/3, and then it was diluted with ethyl acetate (300 ml) and washed with 0.6 N sodium hydrogen sulfate solution (300 ml), water (2×150 ml), brine and dried over Na$_2$SO$_4$. After removal of solvent, 7.75 g of product (I-100) was obtained as oil. Yield: 100%.

5-Bromomethyl-2-methoxy-3'-trifluoromethyl-biphenyl (I-101); To a 250 mL round bottom flask equipped with stirring bar was added I-100 (5 g, 18.79 mmol) and CCl$_4$ (125 mL). To this solution 1 g of NBS and 100 mg of AIBN were added. The flask was connected to a condenser and the mixture was reflux under the sun lamp for one hour. To the reaction mixture 1 g of NBS and 100 mg AIBN were added and this stirred at reflux, under N$_2$ for 2 more hours. After 2 hours another portion of NBS (1.3 g) and 108 mg of AIBN were added and mixture was refluxed for 2 more hours. The reaction mixture was cooled to RT, concentrated to half and filtered off. The solid was washed with 100 mL of CCl$_4$. After removal of solvent 6.76 g of crude product (I-101) was obtained.

3-(6-Methoxy-3'-trifluoromethyl-biphenyl-3-ylmethoxy)-cyclopent-2-enone (P-091). To a solution of 1,3-cyclopentanedione (110 mg, 1.11 mmol) in 1.5 ml anhydrous DMF was added at 0° C. NaH (60% dispersion in mineral oil, 45 mg, 1.11 mmol). The suspension was stirred for 30 minutes, then a solution of I-101 (350 mg, 0.76 mmol) in 1.5 ml DMF was added. The reaction mixture was stirred at RT, overnight. The reaction mixture was quenched with saturated NH$_4$Cl solution and extracted with methylene chloride. Combined organic layers were washed with brine, dried over sodium sulfate, filtered, concentrated to give 300 mg crude. Purification was done using preparative silica gel plate (1500 um) to afford 125 mg of product P-091. $^1$H NMR (CDCl$_3$, 400 MHz): 2.45 (t, 2H), 2.66 (t, 2H), 3.05 (d, 1H), 3.84 (s, 3H), 5 (s, 2H), 5.43 (s, 1H), 7.02 (d, J=8.4 Hz, 1H), 7.33 (d, J=2 Hz, 1H), 7.38 (dd, J=8.4, 2.4 Hz, 1H), 7.53 (t, 1H), 7.6 (d, J=8.4 Hz, 1H), 7.7 (d, J=8.4 Hz, 1H), 7.77 (s, 1H). LCMS (APCI+): 363 (M+1), 90%.

Example 48

Preparation of P-092

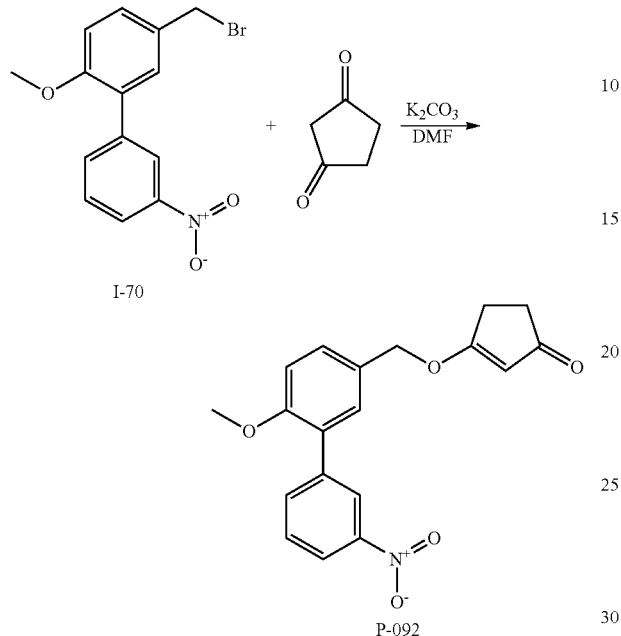

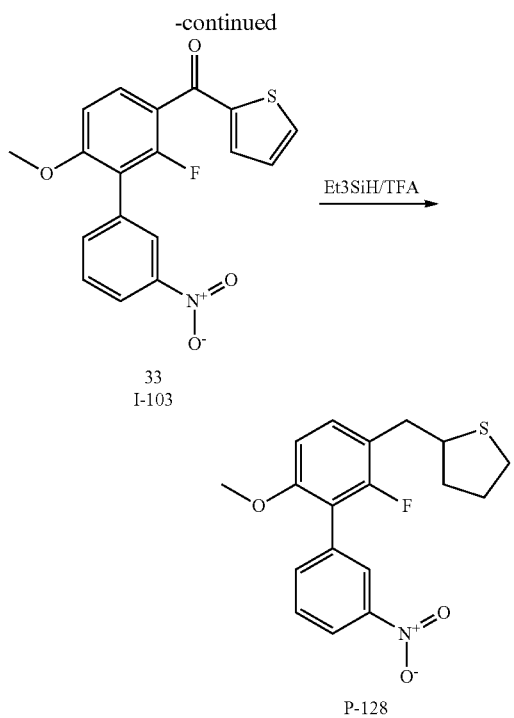

Synthesis of 3-(6-Methoxy-3'-nitro-biphenyl-3-yl-methoxy)-cyclopent-2-enone (P-092). Into a 50 mL round bottom flask with stir bar added I-70 (284 mg, 0.83 mmol), 1,3-cyclopentadione (217 mg, 2.21 mmol), $K_2CO_3$ (305 mg, 2.21 mmol), and 5 mL DMF. The reaction was stirred at room temperature for 18 hours. 5 mL of dichloromethane and 5 mL water were added. The layers were separated and the aqueous extracted with 10 mL dichloromethane. The combined organics were washed with water (4×10 mL), dried over sodium sulfate, and concentrated. The residue was purified by flash column chromatography using 0-2% methanol/dichloromethane. Obtained 112 mg (37%) P-092 as a white solid. $^1$H NMR (400 MHz, CDCl$_3$) 2.41-2.54 (m, 2H) 2.60-2.71 (m, 2H) 3.86 (s, 3H) 5.01 (s, 2H) 5.44 (s, 1H) 7.04 (d, J=8.5 Hz, 1H) 7.37 (d, J=2.2 Hz, 1H) 7.41 (dd, J=8.5, 2.2 Hz, 1H) 7.58 (t, J=8.0 Hz, 1H) 7.86 (d, J=7.8 Hz, 1H) 8.20 (dd, J=8.3, 1.3 Hz, 1H) 8.41 (t, J=1.7 Hz, 1H). LC/MS=92.0%, 340.1 (APCI+)

Scheme 23

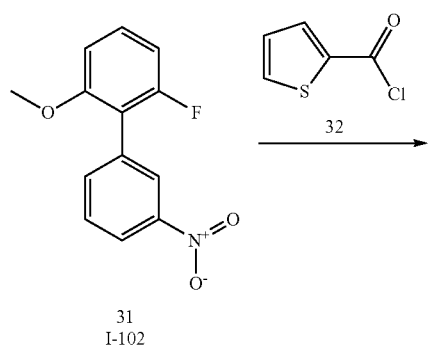

Example 49

Preparation of P-128

(2-fluoro-6-methoxy-3'-nitro-biphenyl-3-yl)-thiophen-2-yl-methanone (I-103) To a 25 mL vial which contained a solution of thiophene-2-carbonyl chloride (90 mg, 0.6 mmol) in nitrobenzene (0.5 mL) was added AlCl$_3$ (75 mg, 0.75 mmol) at −10° C. After stirring at 0° C. for 2 h, 6-Fluoro-2-methoxy-3'-nitro-biphenyl (31) (125 mg, 0.5 mmol) in nitrobenzene (0.5 mL) was added at rt. The reaction mixture was allowed to stir at rt for 24 hours. The reaction mixture was cooled to −10° C. and quenched with ice-water (10 mL, extracted with ethyl acetate (10 mL), washed with water (2×10 mL), NaHCO$_3$ (sat., 10 mL), brine (30 mL) and dried over Na$_2$SO$_4$. After removal of solvent, the crude was purified by crystallization from ether-hexane to give 100 mg of I-103 in 60% yield. LCMS: Calc. 357.4; APCI$^-$ (M):356.9, 342 (M−16-1) 97.4%

2-(2-fluoro-6-methoxy-3'-nitro-biphenyl-3-ylmethyl)-tetrahydro-thiophene (P-128). To a 25 mL vial which contained compound I-103 (90 mg, 0.25 mmol) in triethylsilane (1 mL) was added TFA (1 mL) at −10° C. The reaction mixture was allowed to warm to rt and stir at rt for 72 h. The reaction mixture was poured onto 30 mL ice-water, extracted with ethyl acetate (3×30 mL), washed with NaHCO$_3$ (sat. 30 mL), water (20 mL), brine (30 mL) and dried over Na$_2$SO$_4$. After removal of solvent, the residue was purified by silica gel column chromatography with ethyl acetate/hexane as eluent to give 30 mg of product (P-128) in 30% yield. 1H NMR (CDCl$_3$,400 MHz): 8.33 (br s, 1H), 8.22-8.26 (m, 1H), 7.59-7.76 (m, 5H), 7.15 (t, J=4.0 Hz, 1H), 6.91 (d, J=9.2 Hz, 1H), 3.89 (s, 3H)

LCMS: Calc. 347.4; APCI$^-$ (M) 347.0: 99%.

Example 50

Preparation of P-481

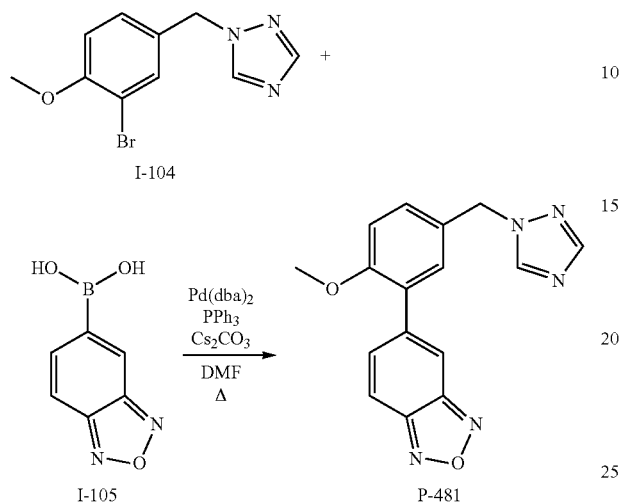

Synthesis of 5-(2-Methoxy-5-[1,2,4]triazol-1-ylmethyl-phenyl)-benzo[1,2,5]oxadiazole (P-481). A suspension of 1-(3-Bromo-4-methoxy-benzyl)-1H-[1,2,4]triazole (I-104, 402 mg, 1.50 mmol), benzo[1,2,5]oxadiazole-5-boronic acid (I-105, 246 mg, 1.50 mmol), palladium(0) bis(dibenzylideneacetone) (43 mg, 0.075 mmol), and triphenyl phosphine (39.3 mg, 0.15 mmol) in dimethylformamide (15 mL) and 1 M aqueous cesium carbonate (4.5 mL, 4.5 mmol) was heated to 85° C. with stirring overnight. The solvent was removed under vacuum and the residue suspended in ethyl acetate (15 mL). The organic suspension was washed with water (3×15 mL) and brine, dried over sodium sulfate, decolorized over activated carbon, filtered, and the solvent removed under vacuum to give crude material. The residue was purified by recyrstalization from dichloromethane (2 mL) and hexanes (10 mL) to give P-481 (180 mg, 39% yield). 1H NMR (400 MHz, CDCl$_3$) δ ppm 3.88 (s, 4H) 5.51 (s, 2H) 7.06 (d, J=7.8 Hz, 1H) 7.41-7.54 (m, 3H) 7.59 (d, J=9.3 Hz, 1H) 7.71-8.03 (m, 3H) 8.25 (s, 1H) 9.34 (br. s., 1H), LCMS=95.7% purity.

Example 51

Preparation of P-482

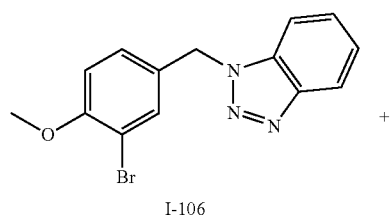

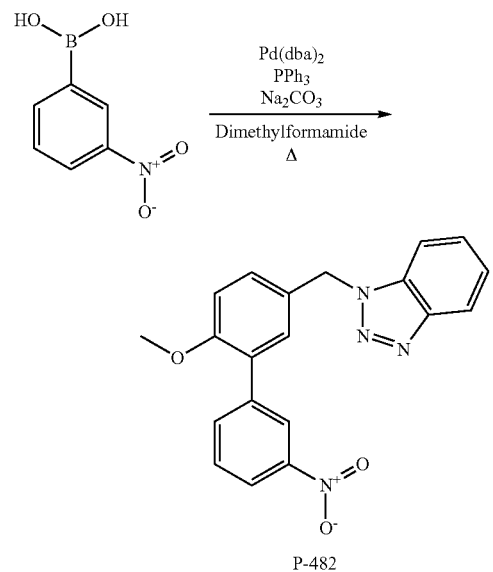

Synthesis of 1-(6-Methoxy-3'-nitro-biphenyl-3-ylmethyl)-1H-benzotriazole (P-482). A suspension of 1-(3-Bromo-4-methoxy-benzyl)-1H-benzotriazole (I-106) (477 mg, 1.50 mmol), 3-nitrophenylboronic acid (250 mg, 1.50 mmol), palladium(0) bis(dibenzylideneacetone) (43 mg, 0.075 mmol), and triphenyl phosphine (39 mg, 0.15 mmol) in dimethylformamide (10 mL) and 1 M aqueous sodium carbonate (4.5 mL, 4.5 mmol) was heated to 85° C. with stirring overnight. The solvent was removed under vacuum and the residue suspended in ethyl acetate (20 mL). The organic suspension was washed with water (3×20 mL) and brine, dried over sodium sulfate, decolorized over activated carbon, and the solvent removed under vacuum to give crude material. The residue was purified dissolving in ethyl acetate (5 mL) and adding hexanes (25 mL) until a solid formed. This was repeated 3 times to give P-482 (210 mg, 39% yield). $^1$H NMR (400 MHz, CDCl$_3$) $^1$H NMR (400 MHz, CDCl$_3$): 3.82 (s, 3H), 5.86 (s, 2H), 6.98 (d, J=8.2 Hz, 1H), 7.30-7.37 (m, 2H), 7.37-7.52 (m, 3H), 7.52-7.59 (m, 1H), 7.75 (d, J=7.8 Hz, 1H), 8.12 (d, J=8.3 Hz, 1H), 8.18 (dd, J=8.2, 1.2 Hz, 1H), 8.35 (d, J=1.6 Hz, 1H) ppm. LCMS=93.9% purity.

Scheme 24.

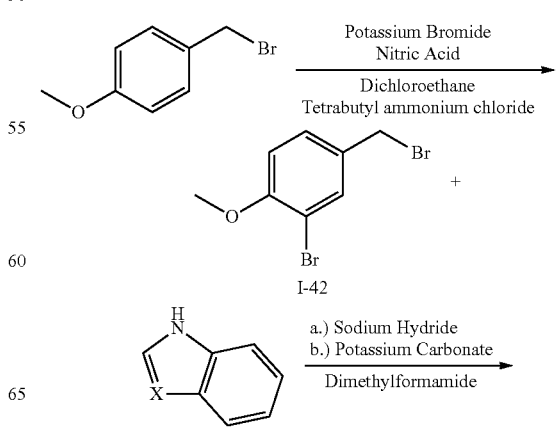

-continued

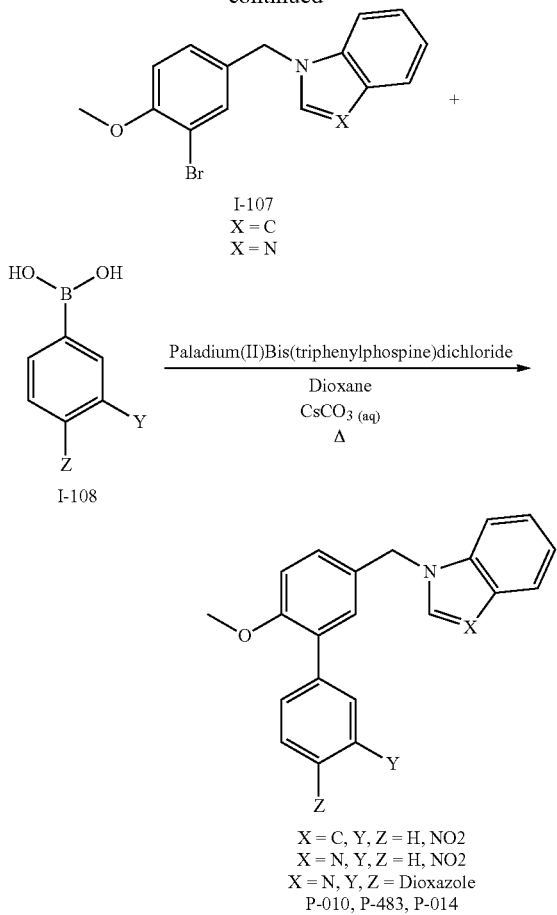

I-107
X = C
X = N

I-108

X = C, Y, Z = H, NO2
X = N, Y, Z = H, NO2
X = N, Y, Z = Dioxazole
P-010, P-483, P-014

Example 52

Preparation of P-010, P-483, P-014

Synthesis of 2-Bromo-4-bromomethyl-1-methoxy-benzene (I-42). To solution of potassium bromide (29.6 g, 248 mmol) in nitric acid (21% by volume, 149 g, 497 mmol), was added dichloroethane (188 mL) and tetrabutylammonium chloride (1.04 g, 3.73 mmol) followed by 4-(bromomethyl) anisol (25.0 g, 124 mmol) in dichloroethane (62 mL), and the reaction was stirred at room temperature for 5 h. The organic layer was separated, washed with water (2×100 mL, 2×150 mL), 2% aqueous potassium carbonate (150 mL), dried over sodium sulfate, and the solvent removed under vacuum. The residue was purified by being run through a flash silica gel plug (10% ethyl acetate in hexanes) to give the title compound (I-42) (9.22 g, 26% yield). $^1$H NMR (400 MHz, CDCl$_3$) δ: 7.59 (d, 1H), 7.30 (dd, J=8.2, 2.2 Hz, 1H), 6.85 (d, J=8.4 Hz, 1H), 4.44 (s, 2H), 4.44 (s, 3H).

Synthesis of 1-(3-Bromo-4-methoxy-benzyl)-1H-indole (I-107, X═CH). A solution of indole (250 mg, 2.14 mmol) in DMF (15 mL) was cooled in an ice bath. To this solution was added sodium hydride (64.3 mg, 2.68 mmol), followed by 2-Bromo-4-bromomethyl-1-methoxy-benzene (500 mg, 1.79 mmol). The reaction was warmed to room temperature and stirred overnight. To the reaction was added saturated aqueous ammonium chloride (75 mL) and the layers separated. The organic extract was washed with saturated aqueous ammonium chloride (2×75 mL), water (3×75 mL) and brine (50 mL). The extract was dried over sodium sulfate, and the solvent removed under reduced pressure. To residue was purified by flash silica gel column chromatography eluting with 1:3 hexanes: dichloromethane to give the title compound (I-107, X═CH) (490 mg, 87% yield) which was taken into further reactions.

1H NMR (400 MHz CDCl$_3$) d: 7.659-7.635 (m, 1H), 7.391 (dd, J=1.60 Hz, 0.80 Hz, 1H), 7.215-7.092 (m, 4H), 6.996-6.969 (m, 1H), 6.794 (d, J=8.40 Hz, 1H), 6.549 (dd, J=3.00 Hz, 1.00 Hz, 1H), 5.234 (s, 2H), 3.850 (s, 3H).

Synthesis of 1-(6-Methoxy-3'-nitro-biphenyl-3-ylmethyl)-1H-indole (P-010). A suspension of 1-(3-Bromo-4-methoxy-benzyl)-1H-indole (150 mg, 0.474 mmol), palladium bis(triphenylphosphine)dichloride (13.3 mg, 0.0190 mmol), and 3-nitrophenylboronic acid (94.9 mg, 0.569 mmol) in dioxane (10 mL) and 1 M aqueous sodium carbonate (1.1 mL) was stirred at 85° C. for 22 h. To the reaction was added ethyl acetate (30 mL). The organic suspension was washed with water (4×30 mL), brine (2×30 mL), dried over sodium sulfate, and the solvent removed under vacuum. The residue was purified by flash silica gel column chromatography (10% ethyl acetate in hexanes as the elutant) to yield 1-(6-Methoxy-3'-nitro-biphenyl-3-ylmethyl)-1H-indole P-010 (23.6 mg, 17% yield).

1H NMR (400 MHz, CDCl$_3$) d: 8.36 (t, J=1.60, 1H), 8.16 (dt, J=6.40, 0.90, 1H), 7.76 (dd, J=6.40, 0.80, 1H), 7.65 (d, J=6.40, 1H), 7.53 (t, J=6.20, 1H), 7.326 (d, J=6.40, 1H), 7.26-7.10 (m, 5H), 6.92 (d, J=7.20, 1H), 6.55 (d, J=2.40, 1H), 5.32 (s, 2H), 3.797 (s, 3H). LCMS=87.7% purity. MS (APCI+)=359.1 (M+1).

Synthesis of 1-(3-Bromo-4-methoxy-benzyl)-1H-benzoimidazole (I-107, X═N).

A suspension of 1H-benzoimidazole (317 mg, 2.68 mmol) and potassium carbonate (495 mg, 3.58 mmol) in DMF (10 mL) was stirred at 45° C. for 1 h. To the heated suspension was added 2-Bromo-4-bromomethyl-1-methoxy-benzene (500 mg, 1.79 mmol) and the reaction was stirred at 45° C. for 4 h, cooled to room temperature and stirred at room temperature overnight. About half of the solvent was removed under vacuum, and ethyl acetate (30 mL) was added. The organic solution was washed with saturated aqueous ammonium chloride (3×30 mL), water (2×15 mL), and brine (15 mL). The organic extract was dried over anhydrous sodium sulfate and the solvent removed under vacuum to give crude product as an orange oil. The product was purified by flash silica gel column chromatography eluting with 5% methanol in dichloromethane to give the title compound (282.5 mg; 48% yield) and a second crop of 50% pure 2-Bromo-4-bromomethyl-1-methoxy-benzene (207.1 mg).

1H NMR (400 MHz CDCl$_3$) 7.93 (s, 1H0 7.84-7.82 (m, 1H), 7.45 (d, J=2.40 Hz, 1H), 7.30-7.26 (m, 3H) 7.07 (dd, J=8.60 Hz, 2.20 Hz, 1H), 6.84 (d, J=8.40 Hz, 1H), 5.28 (s, 2H), 3.87 (s, 3H).

Synthesis of 1-(6-Methoxy-3'-nitro-biphenyl-3-ylmethyl)-1H-benzoimidazole (P-483). A suspension of 1-(3-Bromo-4-methoxy-benzyl)-1H-benzoimidazole (I-107, X═N) (250 mg, 0.788 mmol), 3-nitrophenylboronic acid (132 mg, 0.788 mg), triphenylphosphine (20.6 mg, 0.0788 mmol), solid potassium carbonate (326 mg, 2.37 mmol) in 1,2-dimethoxyethane (6 mL), water (1 mL), and ethanol (1 mL) was flushed with argon gas and the palladium acetate (8.9 mg, 0.0394 mmol) was added. The reaction was heated to 80° C. over night. Additional palladium acetate (8.9 mg, 0.039 mmol) and triphenylphosphine (20.6 mg, 0.0788 mmol) was added and the mixture was stirred an additional night at 80° C. The solvent was removed under vacuum and taken up in ethyl acetate (50 mL). The organic solution was washed with saturated aqueous ammonium chloride (2×75 mL), water (3×75 mL) water, and the combined aqueous layers were extracted with ethyl acetate (50 mL). The combined organic extracts were washed with brine (75 mL), decolorized using activated carbon, dried over sodium sulfate, and the solvent removed under vacuum. The residue was taken up in dichloromethane (5 mL), hexanes (20 mL) were added and the yellow powder was filtered to give crude P-483. This was purified by flash silica gel column chromatography eluting with 10-20% acetone in dichloromethane, and the excess boronic acid removed by taking up the residue in dichloromethane (3 mL), and washing with 1 N aqueous sodium hydroxide solution. This wash was extracted into dichloromethane (5 mL), the combined extracts dried over sodium sulfate, and the solvent removed under vacuum to give P-483 (23.9 mg, 8.4% yield) as an orange tacky powder.

1H NMR (400 MHz, DMSO-d$_6$) d: 8.44 (s, 1H), 8.27 (t, J=2.00 Hz, 1H), 8.21-8.178 (m, 1H), 7.924-7.898 (m, 1H), 7.711 (t, J=8.00 Hz, 1H), 7.646-7.597 (m, 2H), 7.523 (d, J=2.40 Hz, 1H), 7.398 (dd, J=8.40 Hz, 2.00 Hz, 1H), 7.219-7.127 (m, 3H), 5.485 (s, 2H), 3.764 (s, 3H). LCMS=93.1% purity. MS (ESI+)=360.9 (M+1).

Synthesis 5-(5-Benzoimidazol-1-ylmethyl-2-methoxy-phenyl)-benzo[1,2,5]oxadiazole (P-014). A suspension of 1-(3-Bromo-4-methoxy-benzyl)-1H-benzoimidazole (I-107, X=N) (250 mg, 0.778 mmol), 1 N aqueous cesium carbonate (2.4 mL), and triphenylphosphine (20.7 mg, 0.0788 mmol) in DMF (5 mL) was stirred. To the suspension was added benzo[1,3]dioxol-5-yl-boronic acid (155 mg, 0.946 mmol), the reaction purged with nitrogen, and bis(dibenzylideneacetone)palladium(0) (22.7 mg, 0.0394 mmol) was added under nitrogen. The reaction was stirred at 100° C. overnight. After cooling to room temperature, ethyl acetate (50 mL) was added. The organic suspension was washed with saturated aqueous ammonium chloride (2×50 mL), 1 N aqueous sodium hydroxide (3×50 mL), water (50 mL), and brine (50 mL), decolorized over activated carbon, dried over sodium sulfate, and removed under vacuum to give crude product. The product was purified by flash silica gel column chromatography eluting with 1% methanol in dichloromethane to give P-014 (102.1 mg, 36% yield) as an off white powder. $^1$H NMR (400 MHz, d6-DMSO) d: 8.446 (s, 1H), 8.054-8.020 (m, 2H), 7.715 (dd, J=9.60 Hz, 1.60 Hz, 1H), 7.651-7.649 (m, 2H), 7.605 (d, J=2.40 Hz, 1H), 7.440 (dd, J=8.60 Hz, 2.20 Hz, 1H), 7.244-7.147 (m, 3H), 5.485 (s, 2H), 3.787 (s, 3H). LCMS=99.5% purity. MS (ESI+)=357.8 (M+1).

Example 53

Preparation of P-005

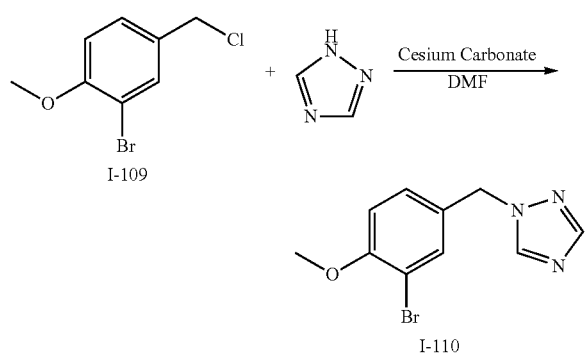

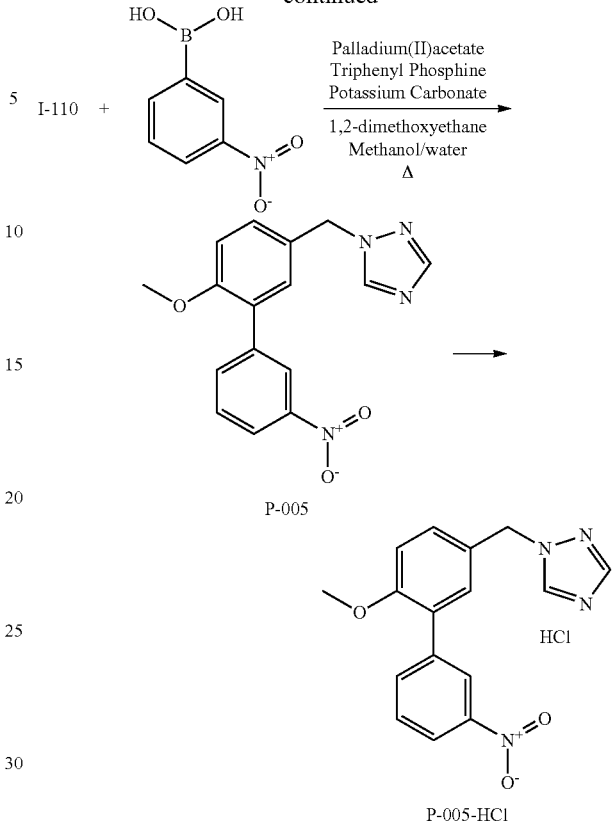

Synthesis of 2-Bromo-4-chloromethyl-1-methoxy-benzene (I-109). I-109 was synthesized from 4-chloromethylanisole (25.0 g, 159.6 mmol) using the same conditions as I-42, and was purified by dissolution in diethyl ether (50 mL) and hexanes (50 mL) and crystallization by removing the diethyl ether under vacuum to give I-109 (19.1 g, 51% yield) as a yellow powder.

1H NMR (400 MHz CDCl$_3$) d: 7.584 (d, J=2.40 Hz, 1H), 7.296 (dd, J=8.40 Hz, 2.00 Hz, 1H), 6.871 (d, J=8.40 Hz, 1H), 4.520 (s, 2H), 3.901 (s, 3H).

Synthesis of 1-(3-Bromo-4-methoxy-benzyl)-1H-[1,2,4]triazole (I-110). A suspension of 1,2,4-triazole (5.72 g, 82.8 mmol), 3-bromo-4-methoxybenzylchloride (I-109) (13.0 g, 55.2 mmol), and solid cesium carbonate (27.0 g, 82.8 mmol) in DMF (225 mL) was stirred at room temperature overnight. The reaction was diluted with ethyl acetate (400 mL) Dilute with 400 ml EA, and washed with water (300 mL). The aqueous wash was extracted with ethyl acetate (2×150 mL), and all the ethyl acetate extracts combined, washed with saturated aqueous ammonium chloride (3×300 mL), water (2×300 mL), and brine (300 mL), dried over sodium sulfate and the solvent removed under vacuum to give I-110 as a yellow oil (11.39 g; 77% yield) which solidified to a greasy yellow solid.

$^1$H NMR (400 MHz CDCl$_3$) d: 8.060 (s, 1H), 7.969 (s, 1H), 7.492 (d, J=2.00 Hz, 1H), 7.212 (dd, J=8.60 Hz, 2.20 Hz, 1H), 6.890 (d, J=8.40 Hz, 1H).

Synthesis of 1-(6-Methoxy-3'-nitro-biphenyl-3-ylmethyl)-1H-1,2,4]triazole (P-005). A solution of I-110 (12.8 g, 47.6 mmol) and 3-nitrophenylboronic acid (9.53 g, 57.1 mmol) in DMF (250 mL) was purged with nitrogen for 10 min at room temperature and 1 N aqueous sodium carbonate (143 mL), triphenylphosphine (2.49 g, 9.51 mmol), and bis(dibenzylideneacetone)palladium(0) (2.73 g, 4.75 mmol under nitrogen. The reaction was heated to 80° C. and stirred overnight. The reaction did not go to completion, so it was heated to 100° C. with vigorous stirring for 2 h. The diluted with ethyl acetate (1 L) and washed with water (3×1 L) and brine (500 mL), dried over sodium sulfate and the solvent removed under vacuum to give a brown oil. The oil was purified by silica gel column chromatography eluting with 0-5% acetone in dichloromethane, and the residue dissolved in ethyl acetate (300 mL), washed with water (2×300 mL), and brine (300 mL) to give a 30% mixture of I-110 and P-005. This mixture was added to a solution of 3-nitrophenylboronic acid (8.00 g, 47.9 mmol) and triphenylphosphine (2.24 g, 8.58 mmol) in 1,2-dimethoxyethane (150 mL). Argon was bubbled through for 10 min, and methanol (15 mL), water (15 mL), solid potassium carbonate (17.8 g, 129 mmol), and palladium acetate (960 mg, 4.29 mmol) were added under argon gas, and the argon stream was continued for 10 min. The reaction stirred at 80° C. under nitrogen overnight. The solvent was removed under vacuum, and the residue dissolved in ethyl acetate (300 mL) and washed with water (300 mL). The water was extracted with ethyl acetate (2×300 mL), and the extracts combined. The organic extracts were washed with water (2×500 mL), saturated aqueous sodium bicarbonate (2×500 mL), and brine (500 mL), dried over sodium sulfate, and removed under vacuum to give crude product as a brown oil. The product was purified by flash silica gel column chromatography eluting with 0-25% acetone in dichloromethane to give slightly impure P-005. The material was triturated with dichloromethane (30 mL) in hexanes (300 mL), then in dichloromethane (15 mL) and hexanes (10 mL) and washed with hexanes (20 mL) to give pure P-005 (5.26 g, 36% yield) as a white powder. $^1$H NMR (400 MHz, CDCl$_3$): 3.84 (s, 3H), 5.34 (s, 2H), 7.02 (d, J=8.5 Hz, 1H), 7.28 (d, 1H), 7.32 (dd, J=8.5, 2.2 Hz, 1H), 7.57 (t, J=8.0 Hz, 1H), 7.80 (d, J=7.8 Hz, 1H), 7.97 (s, 1H), 8.09 (s, 1H), 8.19 (dd, J=8.3, 1.3 Hz, 1H), 8.38 (t, J=1.7 Hz, 1H) ppm. LCMS=100.0% purity. MS (APCI+)=311.1 (M+1).

HPLC (220 nm); 99.95%. [Mobile Phase A and Mobile Phase B=Water and Acetonitrile, Symmetry C18, (250×4.6 mm, 5 um), Flow=1.0 mL/min, Inj. Wash=ACN, Inj. Vol.=10 uL. Retention time=22.16 min]

Elemental Analysis (Calc): C, 61.93; H, 4.55; N, 18.05. (Found), C, 61.92; H, 4.62; N, 17.88.

Synthesis of 1-(6-Methoxy-3'-nitro-biphenyl-3-ylmethyl)-1H-1,2,4]triazole hydrochloride salt (P-005). A solution of I-111 (200 mg, 0.645 mmol) in tetrahydrofuran (6 mL) was stirred at room temperature. To this was added 2 M hydrogen chloride in diethyl ether at room temperature. The reaction turned cloudy after 10 sec. The reaction was allowed to stir at room temperature for 45 min, and the reaction filtered and washed with diethyl ether to give P-005 (189.0 mg, 85% yield) as a white solid.

1H NMR. (400 MHz d6-DMSO) d: 8.736 (s, 1H), 8.282 (t, J=2.00 Hz, 1H), 8.219-8.192 (m, 1H), 8.026 (s, 1H), 7.941-7.922 (m, 1H), 7.724 (t, J=8.00 Hz, 1H), 7.434 (d, J=2.40 Hz, 1H), 7.389 (dd, J=8.40 Hz, 2.40 Hz, 1H), 7.175 (d, J=8.80 Hz, 1H), 5.417 (s, 2H), 3.797 (s, 3H).

LCMS=100.0% purity. MS (APCI+)=311.1 (M+1).

Elemental Analysis (Calc): C, 55.42; H, 4.36; N, 16.16; Cl, 10.22, (Found): C, 55.23; H, 4.39; N, 16.00; Cl, 11.06.

Example 54

Preparation of P-486

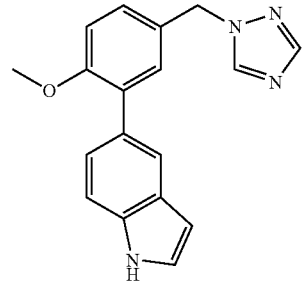

P-486

Synthesis of 5-(2-Methoxy-5-[1,2,4]triazol-1-ylmethyl-phenyl)-1H-indole (P-486). P-486 was synthesized from 1H-indole-3-boronic acid (240 mg, 1.49 mmol) and I-110 (200 mg, 0.746 mmol) using conditions similar to those that were used for I-111. The reaction was worked up by diluting the reaction with ethyl acetate (50 mL), washing with 1 N aqueous sodium hydroxide (3×30 mL), water (2×30 mL), and brine (30 mL). The organic portion was concentrated and the residue was purified by flash silica gel column chromatography eluting with 2% methanol in dichloromethane, followed by flash silica gel column chromatography eluting with 0-20% ethyl acetate in hexanes, and then separation on a silica gel preparatory plate eluting with 50% ethyl acetate in hexanes to give P-486 (51.6 mg, 23% yield).

1H NMR (400 MHz, CDCl$_3$) δ ppm 3.82 (s, 3H) 5.33 (s, 2H) 6.58 (br. s., 1H) 6.98 (d, J=8.33 Hz, 1H) 7.18-7.25 (m, 2H) 7.29-7.35 (m, 2H) 7.38-7.44 (m, 1H) 7.73 (s, 1H) 7.96 (s, 1H) 8.06 (s, 1H) 8.17 (br. s., 1H)

LCMS=100.0% purity. MS (APCI+)=305.1 (M+1).

Example 55

Preparation of P-488

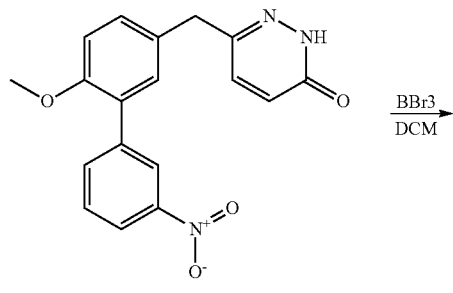

P-009

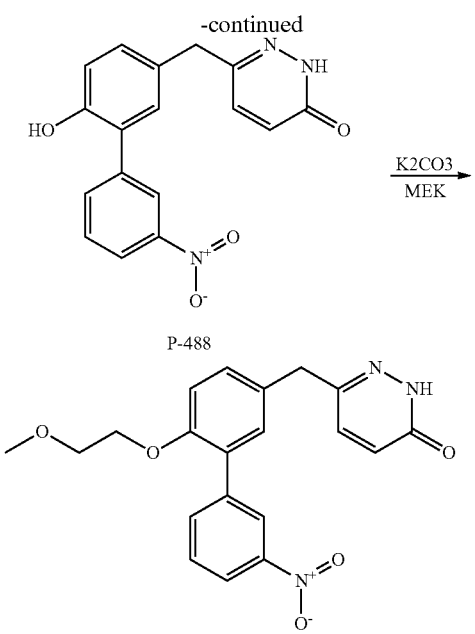

Synthesis of 6-(6-Hydroxy-3'-nitro-biphenyl-3-yl methyl)-2H-pyridazin-3-one (P-488). To a mixture of compound P-009 (260 mg, 0.77 mmol) in dichloroethane (15 ml), boron tribromide (1 M in dichloromethane, 2.3 ml, 2.3 mmol) was added at −70° C. The reaction mixture was allowed to slowly warm up to rt and then stirred at rt for 2 hrs. Water (100 ml) and sat. NaHCO3 aq. (20 ml) were added to the reaction mixture and it was stirred at rt for 1 hr. The resulting solid was filtered and washed with water (50 ml) to give 236 mg (95%) of P-488.

$^1$H-NMR (400 MHz, DMSO-$d_6$) 3.83 (2H, s), 6.79 (1H, dd, J=9.6 and 2 Hz), 6.94 (1H, d, J=8.4 Hz), 7.10 (1H, dd, J=8.4 and 2 Hz), 7.29 (1H, d, J=2.4 Hz), 7.33 (1H, d, J=9.6 Hz), 7.70 (1H, dd, J=8 and 8 Hz), 8.00 (1H, m), 8.16 (1H, m), 8.40 (1H, m), 9.83 (1H, s), 12.80 (1H, br). MS (ESI−): 322.5 (M−1) LC-MS: 97%.

Example 56

Preparation of P-487 and P-018

Synthesis of 6-[6-(2-Methoxy-ethoxy)-3'-nitro-biphenyl-3-ylmethyl]-2H-pyridazin-3-one P-018 and 6-[6-(2-Methoxy-ethoxy)-3'-nitro-biphenyl-3-ylmethyl]-2-(2-methoxy-ethyl)-2H-pyridazin-3-one P-487. A reaction mixture of compound P-488 (97 mg, 0.3 mmol), Bromoethyl methyl ether (63 mg, 0.45 mg) and K$_2$CO$_3$ (124 mg, 0.9 mmol) in 2-butanone (15 ml) was stirred at 80° C. under argon for 18 hrs. After cooling to rt, water (10 ml) was added to the reaction mixture and the pH was adjusted to acidic by addition of 2 N HCl aq. and then extracted with ethyl acetate (40 ml). The organic layer was washed with water (20 ml), brine, and dried over Na$_2$SO$_4$. After removal of solvent, the residue was purified by silica gel column chromatography with ethyl acetate/Hexane as eluent to give 30 mg of product P-487 (3a) and 20 mg of product P-018 (3b).

P-487: $^1$H-NMR (400 MHz, DMSO-$d_6$) 3.24 (3H, s), 3.61 (2H, m), 3.89 (2H, s), 4.15 (2H, m), 6.81 (1H, d, J=9.6 Hz), 7.13 (1H, d, J=8.8 Hz), 7.26 (1H, dd, J=8.8 and 2 Hz), 7.35 (2H, m), 7.71 (1H, dd, J=8 and 8 Hz), 8.00 (1H, m), 8.18 (1H, m), 8.43 (1H, m) ppm. MS (ESI−): 380.6 (M−1) LC-MS: 98%.

P-018: $^1$H-NMR (400 MHz, CDCl$_3$) 3.34 (3H, s), 3.36 (3H, s), 3.68 (2H, m), 3.80 (2H, t, J=5.5 Hz), 3.92 (2H, s), 4.14 (2H, m), 4.36 (2H, t, J=5.5 Hz), 6.84 (1H, d, J=9.5 Hz), 6.98 (1H, d, J=8 Hz), 7.05 (1H, d, J=9.5 Hz), 7.19-7.22 (2H, m), 7.55 (1H, dd, J=8 and 8 Hz), 7.87 (1H, m), 8.17 (1H, m), 8.49 (1H, m) ppm. MS (APCI+): 440.1 (M+1)

Scheme 25.

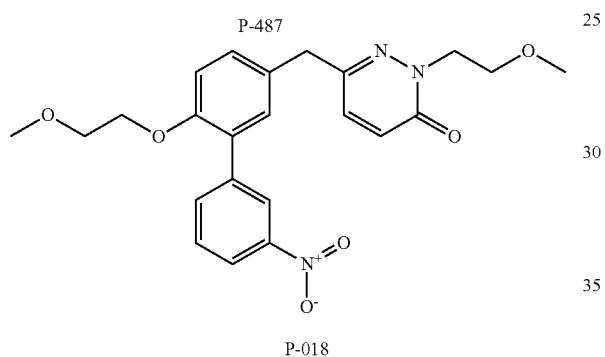

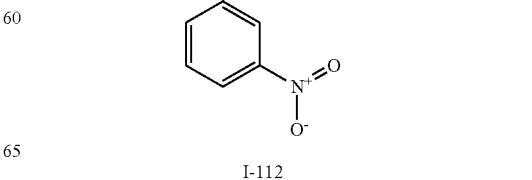

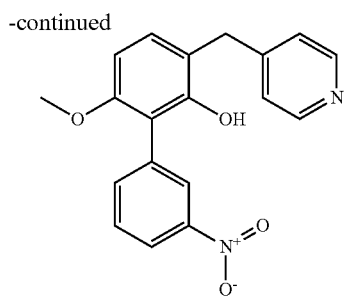

P-017

Example 57

Preparation of P-017

Synthesis of 2,6-dimethoxy-3'-nitro-biphenyl (I-81). To 1-bromo-3-nitrobenzene (2.02 g, 10.0 mmol), 2,6-dimethoxyphenylboronic acid (2.70 g, 15.0 mmol), triphenylphosphine (0.52 g, 2.0 mmol), $K_2CO_3$ (4.14 g, 30.0 mmol) and palladium(II) acetate (0.009 g, 0.04 mmol) was added DME (80 mL) and EtOH/$H_2O$ (1:1, 20 mL). Argon gas was bubbled through the stirred reaction for 5 min. The reaction was stirred at 80° C. under argon for 20 h. The reaction was cooled to room temperature, concentrated, and $H_2O$ (60 mL) and dichloromethane (80 mL) were added. The layers were separated and the aqueous was extracted with dichloromethane (2×40 mL). The combined organic extracts were dried with $Na_2SO_4$, filtered, and concentrated. The residue was purified by silica gel column chromatography using 10% ethyl acetate/hexanes as eluent to afford 1.69 g (65%) of I-81 as a white solid.

Synthesis of (2-hydroxy-6-methoxy-3'-nitro-biphenyl-3-yl)-pyridin-4-yl-methanone (I-112). I-81 (0.26 g, 1.0 mmol), 4-nicotinyl chloride (0.18 g, 1.0 mmol), and dichloromethane (2 mL) were stirred for 5 min at room temperature. $AlCl_3$ (0.33 g, 2.47 mmol) was added in portions over 30 min under argon, then argon gas was bubbled through the reaction mixture for an additional 2 min. The vial was capped and stirred at room temperature for 30 min, then at 50° C. for 4 h. The reaction was cooled to room temperature and poured onto cooled concentrated HCl (3 mL). The resulting aqueous mixture was extracted with dichloromethane (2×30 mL), the aqueous layer was separated, made basic through the addition of 50% aqueous NaOH, and extracted with ethyl acetate (2×30 mL). The combined organics were dried with $Na_2SO_4$, filtered, and concentrated. The residue was purified by silica gel column chromatography using 2% MeOH/dichloromethane as eluent to afford 0.02 g (6%) of I-112 as an off-white solid. 1H NMR ($CDCl_3$, 400 MHz): 12.53 (s, 1H), 8.84 (dd, J=4.4, 1.6 Hz, 2H), 8.3-8.32 (m, 1H), 8.21-8.25 (m, 1H), 7.74-7.78 (m, 1H), 7.48-7.63 (m, 4H), 6.61 (d, J=8.8 Hz, 1H), 3.87 (s, 3H); MS (ESI−): 349.3 (M−1), LC-MS: 94.3%.

Synthesis of 6-methoxy-3'-nitro-3-pyridin-4-ylmethyl-biphenyl-2-ol (P-017). To a cooled (0° C.) and stirred solution of TFA (2.5 ml) under $N_2$ was added $NaBH_4$ (0.12 g, 3.09 mmol) in portions over 20 min. The reaction mixture was warmed to 15° C., and a solution of I-112 (0.055 g, 0.15 mmol) in dichloromethane (2.5 mL), was added over 30 min. The reaction was stirred at room temperature for 20 h, poured onto ice-water (10 mL), made basic (pH 8-10) through the addition of 50% aqueous NaOH, and extracted with ethyl acetate (3×40 mL). The combined organic extracts were washed with brine (60 mL), dried with $Na_2SO_4$, filtered, and concentrated. The residue was purified by silica gel column chromatography using 2% MeOH/dichloromethane as eluent to afford 0.039 g (74%) of P-017 as a foamy solid. 1H NMR ($CDCl_3$, 400 MHz): 8.41 (d, J=4.4 Hz, 1H), 8.2-8.26 (m, 2H), 7.6-7.74 (m, 2H), 7.1-7.18 (m, 3H), 6.57 (d, J=8.0 Hz, 1H), 5.3 9s, 1H), 3.96 (s, 2H), 3.73 (s, 3H); MS (ESI−): 335.1 (M−1), LC-MS: 92.5%.

Example 58

Preparation of P-019

Scheme 26.

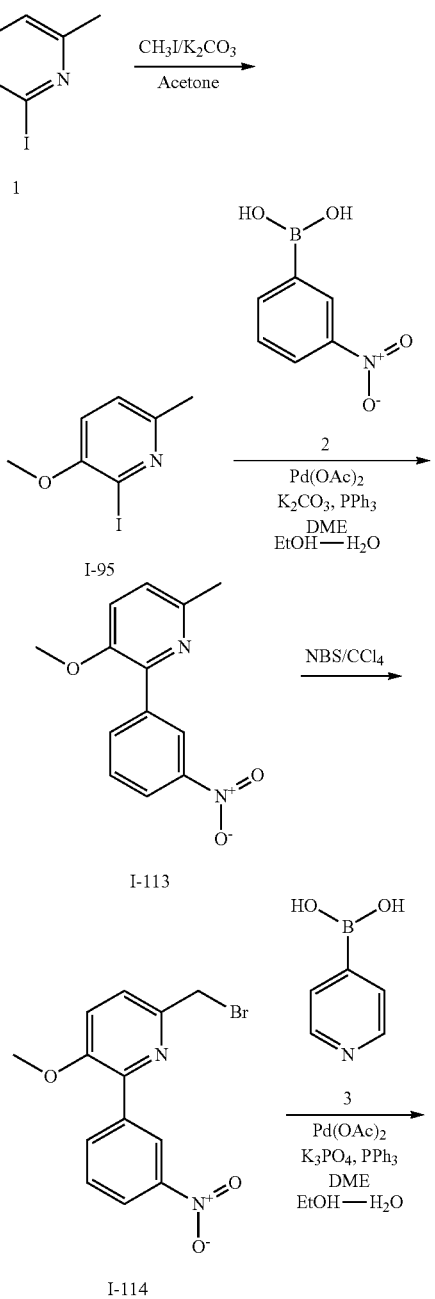

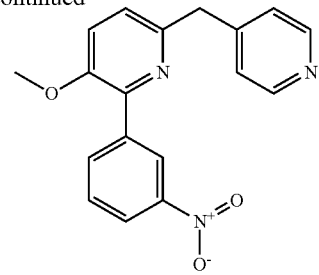

P-019

Synthesis of 2-iodo-3-methoxy-6-methyl-pyridine (I-95). To 2-iodo-6-methyl-pyridin-3-ol (1.0 g, 4.25 mmol) and K$_2$CO$_3$ (1.18 g, 8.51 mmol) in acetone (20 mL) was added MeI (0.91 g, 6.38 mmol). The reaction was stirred at 45° C. under N$_2$ for 20 h. The reaction was cooled to room temperature and concentrated. The residue was purified by silica gel column chromatography using dichloromethane to afford 1.04 g (98%) of I-95 as light yellow solid.

Synthesis of 3-methoxy-6-methyl-2-(3-nitro-phenyl)-pyridine (I-113). To I-95 (0.5 g, 2.0 mmol), 3-nitrophenylboronic acid (0.5 g, 3.06 mmol), triphenylphosphine (0.11 g, 0.4 mmol), K$_2$CO$_3$ (0.83 g, 6.0 mmol) and palladium(II) acetate (0.045 g, 0.2 mmol) was added DME (16 mL), and EtOH—H$_2$O (1:1, 4 mL). Argon gas was bubbled through the stirred reaction for 5 min. The reaction was stirred at 60° C. under argon for 18 h. The reaction was cooled to room temperature, concentrated, and H$_2$O and dichloromethane (40 mL each) were added. The organic layer was separated and the aqueous layer was extracted with dichloromethane (2×25 mL). The combined organic extracts were dried with Na$_2$SO$_4$, filtered, and concentrated. The residue was purified by silica gel column chromatography using 1:1 dichloromethane-hexanes then dichloromethane to afford 0.22 g (44%) of I-113 as a light yellow solid.

Synthesis of 6-bromomethyl-3-methoxy-2-(3-nitro-phenyl)-pyridine (I-114). To I-113 (0.21 g, 0.86 mmol) and NBS (0.17 g, 0.95 mmol) in CCl$_4$ (10 mL) was added benzoylperoxide (0.02 g, 0.08 mmol). The reaction was stirred at 60° C. under N$_2$ for 18 h. The reaction was cooled to room temperature and concentrated. The residue was dissolved in a mixture of dichloromethane and hexanes (1:1, 8 mL) and purified by silica gel column chromatography using 1:1 dichloromethane:hexanes then dichloromethane to afford 0.15 g (55%) of I-114 as a light brown solid.

Synthesis of 3-methoxy-2-(3-nitro-phenyl)-6-pyridin-4-ylmethyl-pyridine (P-019). To I-114 (0.1 g, 0.31 mmol), 4-pyridylboronic acid (0.057 g, 0.46 mmol), Triphenylphosphine (0.008 g, 0.031 mmol), K$_3$PO$_4$ (0.13 g, 0.62 mmol) and palladium(II)acetate (0.004 g, 0.015 mmol) was added DME (4 mL), and EtOH—H$_2$O (1:1, 1 mL). Argon gas was bubbled through the stirred reaction for 5 min. The reaction was stirred at 80° C. under argon for 18 h. The reaction was cooled to room temperature, concentrated, and diluted with H$_2$O and dichloromethane (40 mL each). The organic layer was separated and the aqueous was extracted with dichloromethane (2×25 mL). The combined organic extracts were dried with Na$_2$SO$_4$, filtered, and concentrated. The residue was purified by preparative TLC using 3% MeOH in dichloromethane to afford 0.051 g (51%) of P-019 as a light brown viscous liquid. 1H NMR (CDCl$_3$, 400 MHz): 8.89 (dd, J=2.0, 1.6 Hz, 1H), 8.52-8.55 (m, 1H), 8.31-8.34 (m, 1H), 8.2-8.24 (m, 1H), 7.64-7.7 (m, 1H), 7.58 (t, J=8.0 Hz, 1H), 7.44-7.49 (m, 1H), 7.2-7.3 (m, 2H), 7.12 (d, J=8.4 Hz, 1H), 4.16 (s, 2H), 3.9 (s, 3H); MS (APCI+): 322.1 (M+1), LC-MS: 95.6%.

Example 59

Preparation of P-020

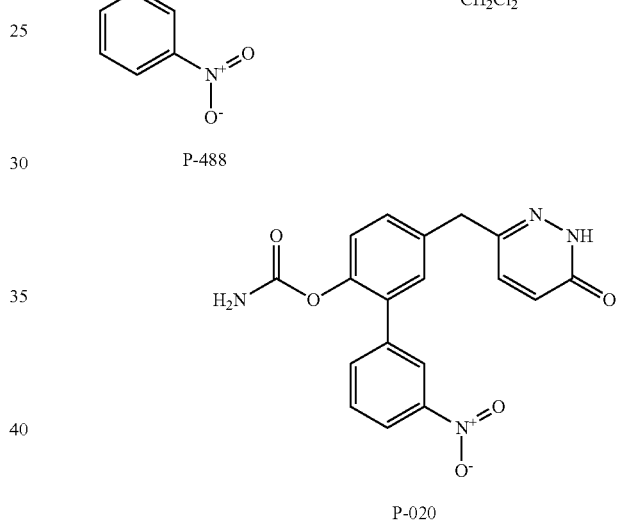

Synthesis of Carbamic acid 3'-nitro-5-(6-oxo-1,6-dihydropyridazin-3-ylmethyl)-biphenyl-2-yl ester (P-020). A reaction mixture of compound P-488 (97 mg, 0.3 mmol) and chlorosulfonyl isocyanate (64 mg, 0.45 mg) in dichloromethane (15 ml) was stirred at rt under argon for 3 days. The reaction mixture was diluted with water (40 ml) and washed with dichloromethane (40 mL) and ethyl acetate (40 mL). Water was removal under vacuum, the residue was stirred with acetone (40 mL), and the resulting solid was filtered and washed with water (30 mL) to give 20 mg of product P-020. The acetone mother liquid was concentrated to 5 ml and the resulting solid was filtered to give another 40 mg of product P-020.

Yield: 55% $^1$H-NMR (400 MHz, DMSO-d$_6$) 3.92 (2H, s), 6.82 (1H, dd, J=9.6 and 2.4 Hz), 6.82 (1H, br), 7.15 (1H, br), 7.18 (1H, J=8.4 Hz), 7.32 (1H, dd, J=8 and 2 Hz), 7.41 (1H, d, J=10 Hz), 7.44 (1H, d, J=2 Hz), 7.75 (1H, dd, J=8 and 8 Hz), 7.88 (1H, m). MS (ESI+): 367.5 (M+1) LC-MS: 92%.

Example 60

Preparation of P-021

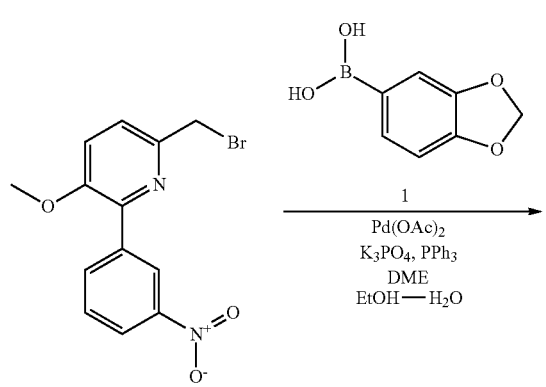

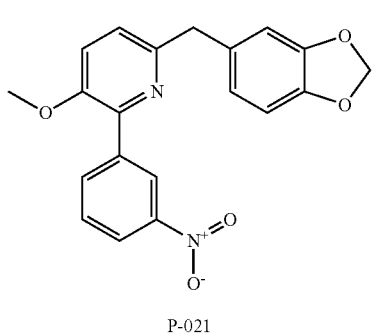

Synthesis of 6-benzo[1,3]dioxol-5-ylmethyl-3-methoxy-2-(3-nitro-phenyl)-pyridine (P-021). To I-114 (0.1 g, 0.31 mmol), 3,4-methylenedioxyphenylboronic acid (0.077 g, 0.46 mmol), Triphenylphosphine (0.008 g, 0.031 mmol), $K_3PO_4$ (0.13 g, 0.62 mmol) and palladium(II)acetate (0.004 g, 0.015 mmol) was added DME (4 mL), and EtOH—$H_2O$ (1:1, 1 mL). Argon gas was bubbled through the stirred reaction for 5 min. The reaction was stirred at 80° C. under argon for 18 h. The reaction was cooled to room temperature, concentrated, and diluted with $H_2O$ and dichloromethane (40 mL each). The organic layer was separated and the aqueous was extracted with dichloromethane (2×25 mL). The combined organic extracts were dried with $Na_2SO_4$, filtered, and concentrated. The residue was purified by silica gel column chromatography using 1:1 dichloromethane-hexanes then dichloromethane to afford 0.08 g (71%) of P-021 as a light brown viscous liquid. 1H NMR (CDCl$_3$, 400 MHz): 8.89 (dd, J=2.0, 1.6 Hz, 1H), 8.34-8.37 (m, 1H), 8.2-8.24 (m, 1H), 7.59 (t, J=8.0 Hz, 1H), 7.22-7.28 (m, 2H), 7.09 (d, J=8.4 Hz, 1H), 6.78-6.8 (m, 2H), 5.93 (s, 2H), 4.09 (s, 2H), 3.88 (s, 3H) ppm. MS (APCI+): 365.1 (M+1), LC-MS: 94.3%.

Example 61

Preparation of P-491

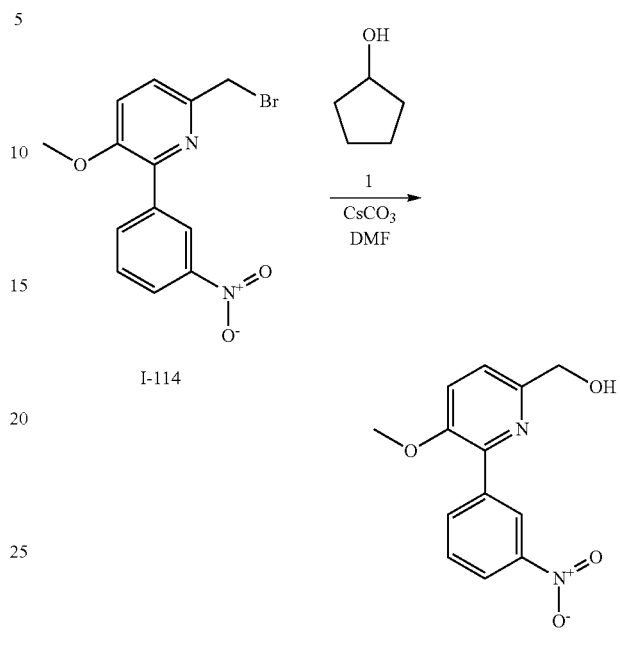

Synthesis of [5-methoxy-6-(3-nitro-phenyl)-pyridin-2-yl]-methanol (P-491). To I-114 (0.06 g, 0.19 mmol), cyclopentanol (0.032 g, 0.37 mmol), and $CsCO_3$ (0.18 g, 0.56 mmol) was added DMF (2.5 mL). The vial was capped and stirred at room temperature for 20 h. The reaction was diluted with 1:1 ethyl acetate-$H_2O$ (60 mL). The organic layer was separated and the aqueous was extracted with ethyl acetate (2×20 mL). The combined organic extracts were dried with $Na_2SO_4$, filtered, and concentrated. The residue was purified by preparative TLC using 2% MeOH in dichloromethane to afford 0.015 g (31%) of P-491 as a viscous liquid. 1H NMR (CDCl$_3$, 400 MHz): 8.88 (dd, J=2.0, 1.6 Hz, 1H), 8.32-8.36 (m, 1H), 8.22-8.26 (m, 1H), 7.62 (t, J=8.0 Hz, 1H), 7.39 (d, J=8.4 Hz, 1H), 7.29 (d, J=8.4 Hz, 1H), 4.78 (d, J=4.8 Hz, 2H), 3.94 (s, 3H), 3.37 (t, J=9.2 Hz, 1H); MS (APCI+): 261.1 (M+1), LC-MS: 100%.

Example 62

Preparation of P-023

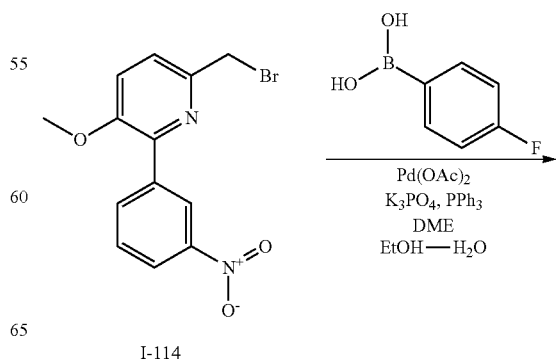

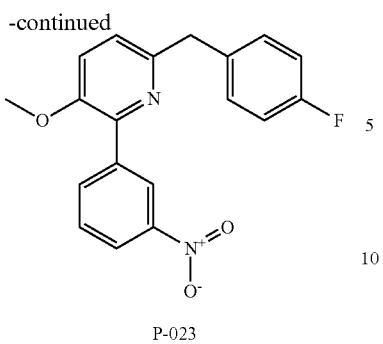

P-023

Synthesis of 6-(4-fluoro-benzyl)-3-methoxy-2-(3-nitro-phenyl)-pyridine (P-023). To I-114 (0.05 g, 0.15 mmol), 4-fluorophenylboronic acid (1) (0.032 g, 0.23 mmol), triphenylphosphine (0.004 g, 0.015 mmol), $K_3PO_4$ (0.066 g, 0.31 mmol), and palladium(II)acetate (0.002 g, 0.008 mmol) was added DME (1.8 mL), and EtOH—$H_2O$ (1:1, 0.6 mL). The reaction was stirred at 160° C. for 5 min using Biotage-60 Microwave Synthsizer. The reaction was cooled to room temperature and concentrated. The residue was purified by silica gel column chromatography using 1:1 dichloromethane-hexanes then dichloromethane to afford 0.024 g (46%) of P-023 as a light brown viscous liquid. 1H NMR (CDCl$_3$, 400 MHz): 8.89 (dd, J=2.0, 1.6 Hz, 1H), 8.32-8.36 (m, 1H), 8.2-8.24 (m, 1H), 7.59 (t, J=8.4 Hz, 1H), 7.22-7.3 (m, 3H), 7.07 (d, J=8.4 Hz, 1H), 6.96-7.04 (m, 2H), 4.14 (s, 2H), 3.88 (s, 3H); MS (APCI+): 339.1 (M+1), LC-MS: 100%.

Example 63

Preparation of P-024

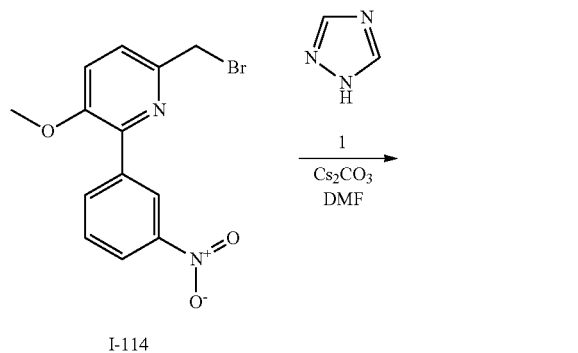

Synthesis of 3-methoxy-2-(3-nitro-phenyl)-6-[1,2,4]triazol-1-ylmethyl-pyridine (P-024). To I-114 (0.055 g, 0.17 mmol), 1H-[1,2,4]triazole (0.018 g, 0.26 mmol), and $CsCO_3$ (0.17 g, 0.51 mmol) was added DMF (2 mL). The vial was capped and stirred at room temperature for 20 h. The reaction was diluted with 1:1 ethyl acetate-$H_2O$ (60 mL). The organic layer was separated and the aqueous was extracted with ethyl acetate (2×20 mL). The combined organic extracts were dried with $Na_2SO_4$, filtered, and concentrated. The residue was purified by preparative TLC using 3% MeOH in dichloromethane to afford 0.043 g (81%) of P-024 as an off white solid. 1H NMR (CDCl$_3$, 400 MHz): 8.87 (dd, J=2.0, 1.6 Hz, 1H), 8.22-8.3 (m, 3H), 7.99 (s, 1H), 7.6 (t, J=8.0 Hz, 1H), 7.34 (d, J=8.4 Hz, 1H), 7.25 (d, J=8.4 Hz, 1H), 5.5 (s, 2H), 3.92 (s, 3H); MS (APCI+): 312.1 (M+1), LC-MS: 100%.

Example 64

Preparation of P-026

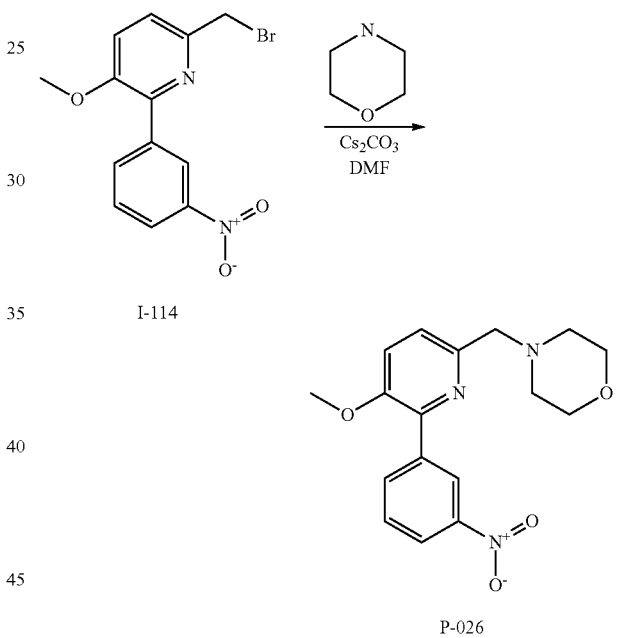

Synthesis of 4-[5-methoxy-6-(3-nitro-phenyl)-pyridin-2-ylmethyl]-morpholine (P-026). To I-114 (0.06 g, 0.19 mmol), morpholine (0.032 g, 0.37 mmol), and $Cs_2CO_3$ (0.18 g, 0.56 mmol) was added DMF (2.5 mL). The vial was capped and stirred at room temperature for 20 h. The reaction was diluted with 1:1 ethyl acetate-$H_2O$ (60 mL). The organic layer was separated and the aqueous was extracted with ethyl acetate (2×20 mL). The combined organic extracts were dried with $Na_2SO_4$, filtered, and concentrated. The residue was purified by silica gel column chromatography using 5% methanol in dichloromethane to afford 0.051 g (80%) of P-026 as a viscous liquid. 1H NMR (CDCl$_3$, 400 MHz): 8.86 (dd, J=2.4, 1.6 Hz, 1H), 8.3-8.34 (m, 1H), 8.2-8.24 (m, 1H), 7.59 (t, J=8.4 Hz, 1H), 7.45 (d, J=8.4 Hz, 1H), 7.34 (d, J=8.4 Hz, 1H), 3.91 (s, 3H), 3.75 (t, J=4.4 Hz, 4H), 3.71 (s, 2H), 2.56 (t, J=4.4 Hz, 4H); MS (APCI+): 330.9 (M+1), LC-MS: 97%.

Example 65

Preparation of P-030

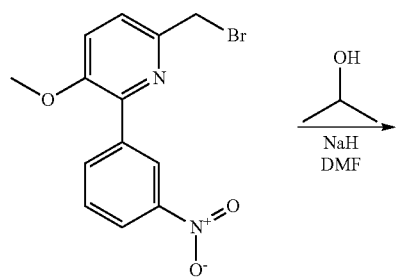

I-114

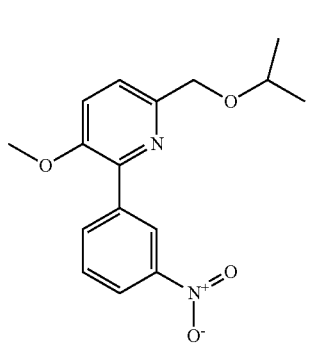

P-030

Synthesis of 6-isopropoxymethyl-3-methoxy-2-(3-nitrophenyl)-pyridine (P-030). To a cooled (0° C.) and stirred suspension of NaH (0.016 g, 0.39 mmol) in DMF (2.0 mL) was added a solution of isopropanol (0.033 g, 0.56 mmol) in DMF (0.5 ml). The reaction mixture was slowly warmed to room temperature and stirred for 2 h. After cooling to (0° C.), a solution of I-114 (0.06 g, 0.19 mmol) in DMF (1.0 mL) was added over 5 min. The reaction mixture was slowly warmed to room temperature and stirred for 20 h. The reaction was poured on to crushed ice-water and extracted with ethyl acetate (2×40 mL). The combined organic extracts were dried with Na₂SO4, filtered, and concentrated. The residue was purified by silica gel column chromatography using dichloromethane to afford 0.027 g (47%) of P-030 as a viscous liquid. 1H NMR (CDCl$_3$, 400 MHz): 8.86 (dd, J=2.0, 1.6 Hz, 1H), 8.33 (dt, J=8.0, 1.2 Hz, 1H), 8.2-8.25 (m, 1H), 7.59 (t, J=8.0 Hz, 1H), 7.49 (d, J=8.4 Hz, 1H), 7.36 (d, J=8.8 Hz, 1H), 4.66 (s, 2H), 3.91 (s, 3H), 3.72-3.81 (m, 1H), 1.27 (d, J=6.0 Hz, 6H); MS (APCI+): 303.1 (M+1), LC-MS: 100%.

Example 66

Preparation of P-031

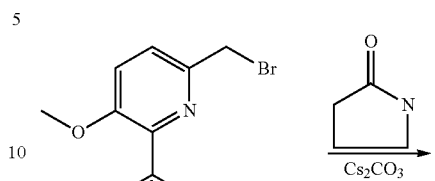

I-114

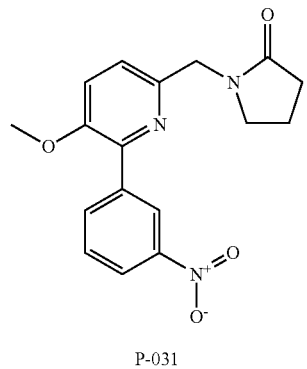

P-031

Synthesis of 1-[5-methoxy-6-(3-nitro-phenyl)-pyridin-2-ylmethyl]-pyrrolidin-2-one (P-031). To I-114 (0.08 g, 0.25 mmol), pyrrolidone (0.042 g, 0.5 mmol), and Cs₂CO₃ (0.24 g, 0.74 mmol) was added DMF (3 mL). The vial was capped and stirred at room temperature for 20 h. The reaction was diluted with 1:1 ethyl acetate-H₂O (60 mL). The organic layer was separated and the aqueous was extracted with ethyl acetate (2×20 mL). The combined organic extracts were dried with Na₂SO4, filtered, and concentrated. The residue was purified by prep TLC using 5% methanol in dichloromethane to afford 0.054 g (78%) of P-031 as a viscous liquid. 1H NMR (CDCl$_3$, 400 MHz): 8.88-8.9 (m, 1H), 8.36 (dt, J=8.0, 1.2 Hz, 1H), 8.2-8.25 (m, 1H), 7.6 (t, J=8.0 Hz, 1H), 7.26-7.34 (m, 2H), 4.61 (s, 2H), 3.92 (s, 3H), 3.49 (t, J=7.2 Hz, 2H), 2.47 (t, J=8.02 Hz, 2H), 2.0-2.2 (m, 2H); MS (APCI+): 328.8 (M+1), LC-MS: 94.0%.

Example 67

Preparation of P-033

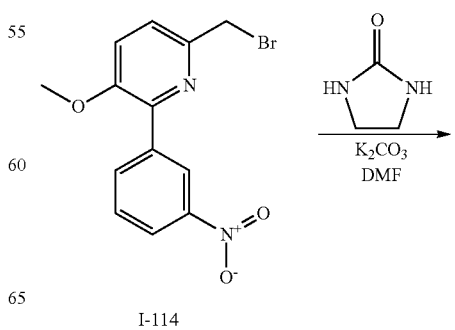

I-114

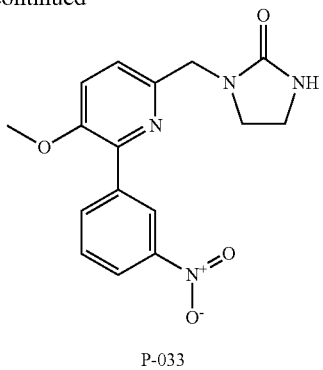

P-033

Synthesis of 1-[5-methoxy-6-(3-nitro-phenyl)-pyridin-2-ylmethyl]-imidazolidin-2-one (P-033). To I-114 (0.08 g, 0.25 mmol), imidazol-2-one (0.053 g, 0.62 mmol), and K₂CO₃ (0.086 g, 0.62 mmol) was added DMF (3 mL). The vial was capped and heated at 80° C. for 20 h. The reaction was diluted with 1:1 ethyl acetate-H₂O (60 mL). The organic layer was separated and the aqueous was extracted with ethyl acetate (2×20 mL). The combined organic extracts were dried with Na₂SO4, filtered, and concentrated. The residue was purified by prep TLC using 5% methanol in dichloromethane to afford 0.015 g (18%) of P-033 as an off white foamy solid. 1H NMR (CDCl₃, 400 MHz): 8.88-8.95 (m, 1H), 8.36 (dt, J=7.6, 1.6 Hz, 1H), 8.2-8.24 (m, 1H), 7.6 (t, J=8.4 Hz, 1H), 7.35 (s, 2H), 4.55 (s, 1H), 4.53 (s, 2H), 3.92 (s, 3H), 3.44-3.58 (m, 4H); MS (APCI+): 329.0 (M+1), LC-MS: 90.7%.

Example 68

Preparation of P-038

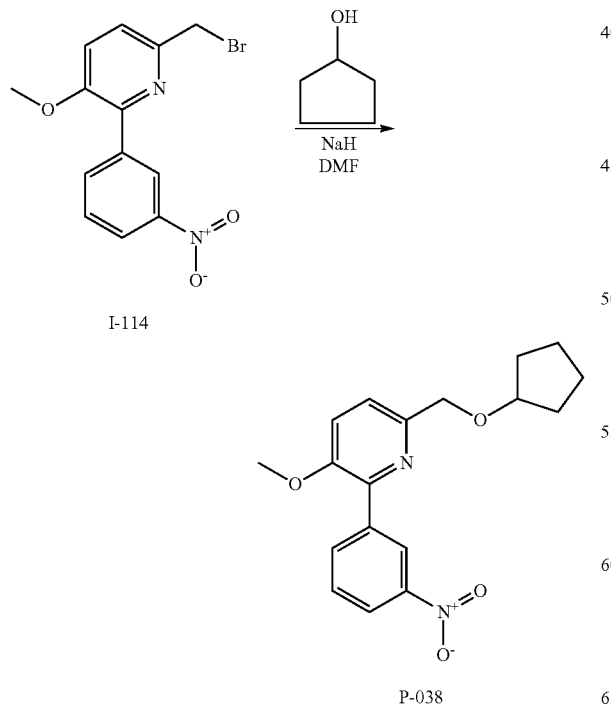

I-114

P-038

Synthesis of 6-cyclopentyloxymethyl-3-methoxy-2-(3-nitro-phenyl)-pyridine (P-038). To a cooled (0° C.) and stirred suspension of NaH (0.016 g, 0.39 mmol) in DMF (2.0 mL) was added a solution of cyclopentanol (0.048 g, 0.56 mmol) in DMF (0.5 ml). The reaction mixture was slowly warmed to room temperature and stirred for 2 h. After cooling to 0° C., a solution of I-114 (0.06 g, 0.19 mmol) in DMF (1.0 mL) was added over 5 min. The reaction mixture was slowly warmed to room temperature and stirred for 20 h. The reaction was poured on to crushed ice-water and extracted with ethyl acetate (2×40 mL). The combined organic extracts were dried with Na₂SO4, filtered, and concentrated. The residue was purified by silica gel column chromatography using dichloromethane to afford 0.047 g (77%) of P-038 as a viscous liquid. 1H NMR (CDCl₃, 400 MHz): 8.86 (dd, J=2.4, 1.6 Hz, 1H), 8.3-8.34 (m, 1H), 8.2-8.24 (m, 1H), 7.59 (t, J=8.0 Hz, 1H), 7.47 (d, J=8.4 Hz, 1H), 7.36 (d, J=8.4 Hz, 1H), 4.63 (s, 2H), 4.07-4.12 (m, 1H), 3.91 (s, 3H), 1.7-1.84 (m, 8H); MS (APCI+): 329.7 (M+1), LC-MS: 96.1%.

Example 69

Preparation of P-064

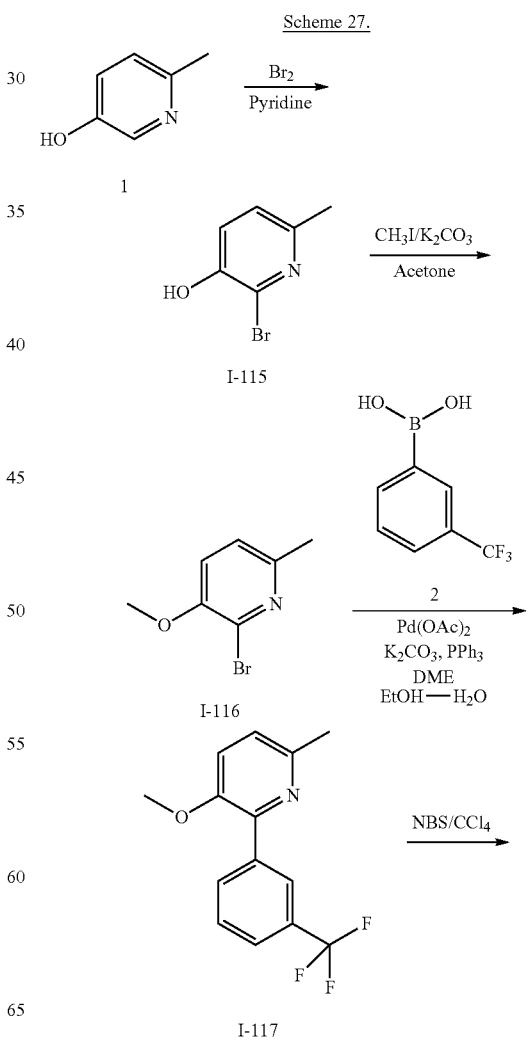

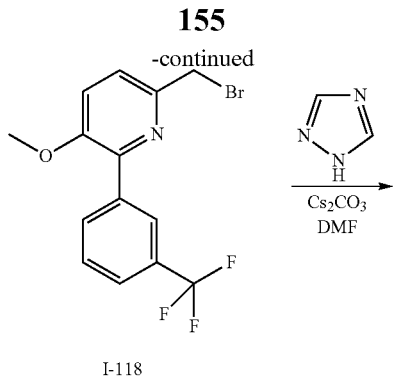

I-118

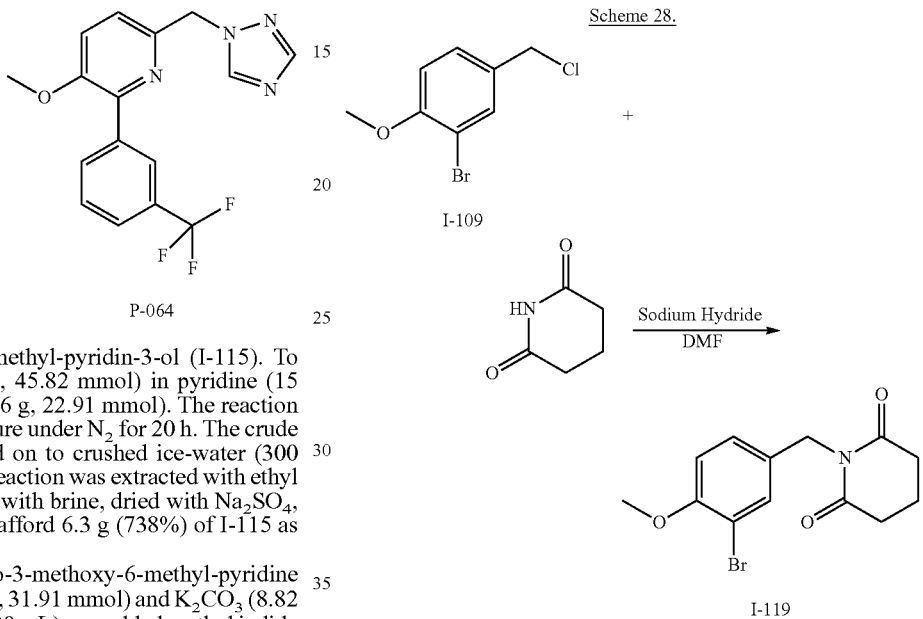

Synthesis of 3-methoxy-6-[1,2,4]triazol-1-ylmethyl-2-(3-trifluoromethyl-phenyl)-pyridine (P-064). To I-118 (0.2 g, 0.58 mmol), 1H-[1,2,4]triazole (0.048 g, 0.26 mmol), and $Cs_2CO_3$ (0.56 g, 1.73 mmol) was added DMF (4 mL). The vial was capped and stirred at room temperature for 20 h. The reaction was diluted with crushed ice-$H_2O$ (60 mL), stirred for 5 h, filtered, and dried to afford 0.14 g (73%) of P-064 as an off white solid. 1H NMR ($CDCl_3$, 400 MHz): 8.28 (s, 1H), 8.21 9s, 1H), 8.09 (d, J=7.6 Hz, 1H), 7.99 (s, 1H), 7.65 (d, J=8.0 Hz, 1H), 7.52-7.59 (m, 1H), 7.31 (d, J=8.4 Hz, 1H), 7.22 (d, J=8.4 Hz, 1H), 5.49 (s, 2H), 3.89 (s, 3H) ppm. MS (APCI+): 335.1 (M+1), LC-MS: 91.4%.

Scheme 28.

Synthesis of 2-bromo-6-methyl-pyridin-3-ol (I-115). To 6-methyl-pyridin-3-ol (5.0 g, 45.82 mmol) in pyridine (15 mL) was added bromine (3.66 g, 22.91 mmol). The reaction was stirred at room temperature under $N_2$ for 20 h. The crude reaction mixture was poured on to crushed ice-water (300 mL) and stirred for 3 h. The reaction was extracted with ethyl acetate (5×100 mL), washed with brine, dried with $Na_2SO_4$, filtered, and concentrated to afford 6.3 g (738%) of I-115 as light yellow solid.

Synthesis of 2-bromo-3-methoxy-6-methyl-pyridine (I-116). To crude I-115 (6.0 g, 31.91 mmol) and $K_2CO_3$ (8.82 g, 63.82 mmol) in acetone (100 mL) was added methyl iodide (6.79 g, 479.87 mmol). The reaction was stirred at 45° C. under $N_2$ for 20 h. The reaction was cooled to room temperature, filtered and concentrated. The residue was purified by silica gel column chromatography using 1:1 dichloromethane-hexanes to afford 2.34 g (36%) of I-116 as an off-white solid.

Synthesis of 3-methoxy-6-methyl-2-(3-trifluoromethyl-phenyl)-pyridine (I-117). To I-116 (1.2 g, 5.94 mmol), 3-trifluoromethylphenylboronic acid (1.69 g, 8.91 mmol), Triphenylphosphine (0.31 g, 1.19 mmol), $K_2CO_3$ (2.46 g, 17.82 mmol) and palladium(II)acetate (0.13 g, 0.59 mmol) was added DME (15 mL) and EtOH—$H_2O$ (1:1, 6 mL). Argon gas was bubbled through the stirred reaction for 5 min. The reaction was stirred at 80° C. under argon for 20 h. The reaction was cooled to room temperature, concentrated, and $H_2O$ and dichloromethane (40 mL each) were added. The organic layer was separated and the aqueous layer was extracted with dichloromethane (2×25 mL). The combined organic extracts were dried with $Na_2SO_4$, filtered, and concentrated. The residue was purified by silica gel column chromatography using 1:1 dichloromethane-hexanes then dichloromethane to afford 1.36 g (86%) of I-117 as a light yellow solid.

Synthesis of 6-bromomethyl-3-methoxy-2-(3-trifluoromethyl-phenyl)-pyridine (I-118). To I-117 (1.3 g, 4.86 mmol) and NBS (1.04 g, 5.83 mmol) in $CCl_4$ (25 mL) was added benzoyl peroxide (0.12 g, 0.49 mmol). The reaction was stirred at 80° C. under $N_2$ for 20 h. The reaction was cooled to room temperature and concentrated. The residue was dissolved in a mixture of dichloromethane and hexanes (1:1, 8 mL) and purified by silica gel column chromatography using 1:1 dichloromethane-hexanes to afford 0.74 g (44%) of I-118 as an off-white solid.

Example 70

Preparation of P-492

Synthesis of 1-(3-Bromo-4-methoxy-benzyl)-piperidine-2,6-dione (I-119). A suspension of sodium hydride (56.0 mg, 2.34 mmol) in anhydrous DMF (12 mL) was stirred under nitrogen for 5 min. To the suspension was added piperidine-2,6-dione (264 mg, 2.34 mmol) and the reaction was stirred under nitrogen for 5 additional minutes. After gas evolution ceased, I-109 (500 mg, 2.12 mmol) was added and the reaction stirred for 24 h under nitrogen at ambient temperature. The reaction was diluted with saturated aqueous ammonium chloride (100 mL) and the suspension was extracted with ethyl acetate (100 mL). The purple organic extract was washed with water (3×50 mL) water, saturated aqueous ammonium chloride (3×50 mL), brine (50 mL) dried over anhydrous sodium sulfate, and the solvent removed under vacuum to afford 476.1 mg of I-119 as a purple powder in 72% yield. $^1$H NMR (400 MHz, CDCl$_3$) 7.59 (d, J=2.40 Hz, 1H), 7.33 (dd, J=8.4 Hz, 2.0 Hz, 1H), 6.80 (d, J=8.40 Hz, 1H), 4.85 (s, 2H), 3.86 (s, 3H), 2.67 (t, J=6.6 Hz, 4H), 1.95-1.92 (m, 2H).

Synthesis of 1-(3-Benzo[1,3]dioxol-5-yl-4-methoxy-benzyl)-piperidine-2,6-dione (P-492). A solution of I-119 (200 mg, 0641 mmol) and benzo[1,3]dioxol-5-yl-boronic acid (117 mg, 0.705 mmol) in 1,4-dioxane were degassed with a nitrogen stream for 10 min. Subsequently, triphenylphosphine (33.5 mg, 0.128 mmol), solid potassium carbonate (265 mg, 1.92 mmol) and a mixture of ethanol and water (1:1, 1 mL) was added, and the reaction was stirred under nitrogen for 10 min. To the reaction was added palladium(II)acetate, and the reaction heated to 80° C. with stirring overnight. The solvent was removed under vacuum and the residue was suspended in saturated aqueous ammonium chloride (50 mL), and the aqueous slurry was extracted with ethyl acetate (2×50 mL). The combined extracts were washed with water (3×50 mL) and brine (30 mL), dried over sodium sulfate, decolorized using activated charcoal, and the solvent removed under vacuum. The residue was purified by chromatography on flash silica gel eluting with 0-10% acetone in dichloromethane followed by trituration with diethyl ether (10 mL) to afford 50.9 mg of P-492 as an off white solid in 22% yield). $^1$H NMR (CDCl$_3$ 400 MHz). 7.29 (m, 2H), 7.03 (d, J=1.6 Hz, 1H), 6.95 (dd, J=8.1 Hz, J=1.7 Hz, 1H), 6.86 (t, J=8.2 Hz, 2H), 5.98 (s, 2H), 4.92 (s, 2H), 3.78 (s, 3H), 2.66 (t, J=6.6 Hz, 4H), 1.93 (m, 2H). LCMS=100.0% purity. MS (APCI−) 350.0 (M−H).

Example 71

Preparation of P-070

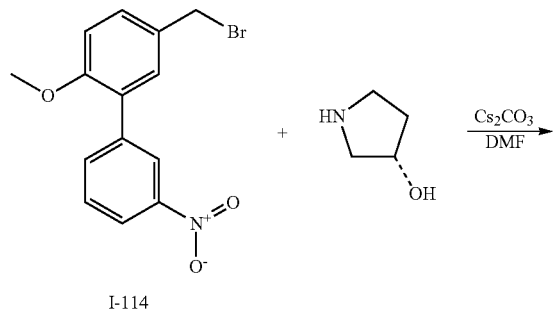

I-114

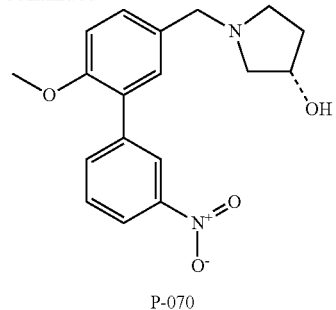

P-070

Synthesis of (S)-1-(6-Methoxy-3'-nitro-biphenyl-3-ylmethyl)-pyrrolidin-3-ol (P-070). Into a 20 mL vial with stir bar was added I-114 (0.30 g, 0.93 mmol), (S)-pyrrolidin-3-ol (54 mg, 0.62 mmol), Cs$_2$CO$_3$ (0.20 g, 0.62 mmol), and DMF (2 mL). The reaction was stirred for 4 days at room temperature and then 10 mL water was added. The product was extracted with ethyl acetate (3×10 mL) and the organics were combined and concentrated. The residue was purified by flash column chromatography using 0-5% methanol/dichloromethane to afford 27.7 mg (14%) of P-070 as a yellow oil. $^1$H NMR (400 MHz, CDCl$_3$) δ 1.75 (m, 1H) 2.14-2.27 (m, 1H) 2.29-2.41 (m, 1H) 2.56 (dd, J=10.1, 5.1 Hz, 1H) 2.68 (d, J=9.8 Hz, 1H) 2.88 (td, J=8.6, 5.3 Hz, 1H) 3.63 (s, 2H) 3.83 (s, 3H) 4.29-4.43 (m, 1H) 6.96 (d, J=8.3 Hz, 1H) 7.28-7.38 (m, 2H) 7.56 (t, J=8.0 Hz, 1H) 7.86 (d, J=7.7 Hz, 1H) 8.17 (dd, J=8.2, 1.9 Hz, 1H) 8.42 (s, 1H) ppm. LC/MS=98.5%, 329.1 (APCI+)

Example 72

Preparation of P-071

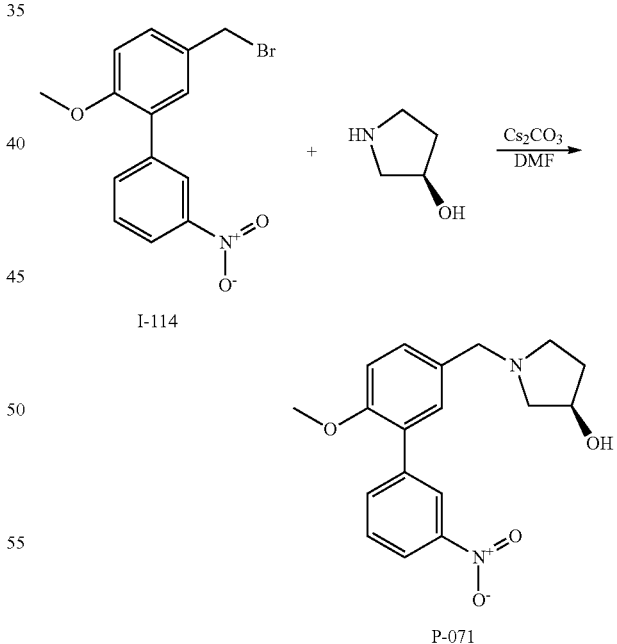

P-071

Synthesis of (R)-1-(6-Methoxy-3'-nitro-biphenyl-3-ylmethyl)-pyrrolidin-3-01 (P-071). The same procedure was used as described for P-070 except using (R)-Pyrrolidin-3-ol. P-071 was obtained 44.2 mg (22%) as a yellow oil. $^1$H NMR (400 MHz, CDCl$_3$) 1.75 (m, 1H) 2.13-2.28 (m, 1H) 2.29-2.41 (m, 1H) 2.56 (dd, J=10.0, 5.0 Hz, 1H) 2.69 (d, J=9.8 Hz, 1H) 2.88 (td, J=8.6, 5.2 Hz, 1H) 3.63 (s, 2H) 3.83 (s, 3H) 4.29-4.41 (m, 1H) 6.96 (d, J=8.3 Hz, 1H) 7.28-7.38 (m, 2H) 7.56 (t, J=8.0 Hz, 1H) 7.86 (d, J=7.8 Hz, 1H) 8.17 (dd, J=8.2, 1.3 Hz, 1H) 8.42 (t, J=1.7 Hz, 1H) ppm. LC/MS=99.0%, 329.1 (APCI+)

Example 73

Preparation of P-493

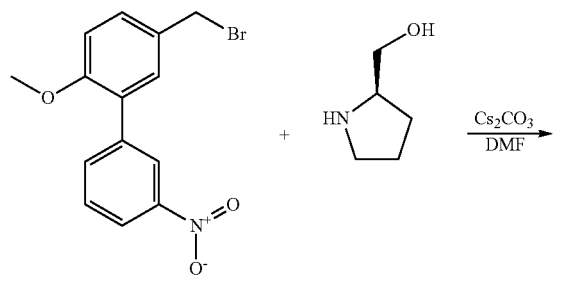

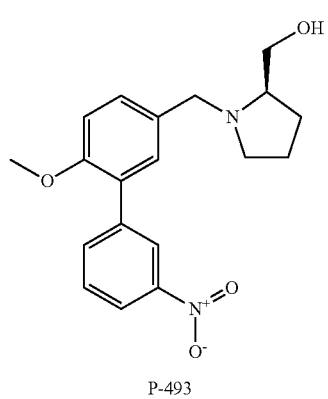

Synthesis of [(R)-1-(6-Methoxy-3'-nitro-biphenyl-3-ylmethyl)-pyrrolidin-2-yl]-methanol (P-493). The same procedure was used as described for P-070 except using (R)-1-Pyrrolidin-2-yl-methanol to obtain P-493 (110 mg, 52%). $^1$H NMR (400 MHz, CDCl$_3$) 1.63-1.77 (m, 2H) 1.78-1.89 (m, 1H) 1.89-2.03 (m, 1H) 2.28-2.37 (m, 1H) 2.74 (m, 1H) 3.01 (ddd, J=9.1, 6.0, 3.4 Hz, 1H) 3.37 (d, J=13.0 Hz, 1H) 3.44 (dd, J=10.7, 2.0 Hz, 1H) 3.66 (dd, J=10.7, 3.5 Hz, 1H) 3.83 (s, 3H) 3.95 (d, J=13.0 Hz, 1H) 6.97 (d, J=8.3 Hz, 1H) 7.25 (d, J=2.0 Hz, 1H) 7.32 (dd, J=8.3, 2.0 Hz, 1H) 7.56 (t, J=8.0 Hz, 1H) 7.85 (d, J=7.8 Hz, 1H) 8.18 (dd, J=8.3, 1.3 Hz, 1H) 8.41 (t, J=1.8 Hz, 1H) ppm. LC/MS=98.9%, 343.1 (APCI+)

Example 74

Preparation of P-072

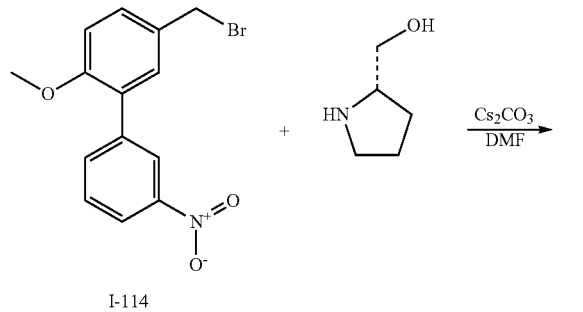

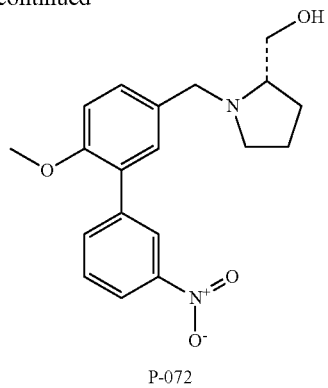

Synthesis of [(S)-1-(6-Methoxy-3'-nitro-biphenyl-3-ylmethyl)-pyrrolidin-2-yl]-methanol (P-072). The same procedure was used as described for P-070 except using (R)-1-Pyrrolidin-2-yl-methanol to obtain P-072 (68 mg, 32%). $^1$H NMR (400 MHz, CDCl$_3$) 1.63-1.78 (m, 2H) 1.84 (td, J=13.2, 5.6 Hz, 1H) 1.89-2.02 (m, 1H) 2.33 (q, J=9.0 Hz, 1H) 2.69-2.82 (m, 1H) 2.95-3.07 (m, 1H) 3.38 (d, J=12.9 Hz, 1H) 3.44 (d, J=10.6 Hz, 1H) 3.66 (dd, J=10.7, 3.4 Hz, 1H) 3.83 (s, 3H) 3.96 (d, J=13.0 Hz, 1H) 6.97 (d, J=8.3 Hz, 1H) 7.24-7.26 (m, 1H) 7.29-7.36 (m, 1H) 7.56 (t, J=8.0 Hz, 1H) 7.85 (d, J=7.8 Hz, 1H) 8.18 (dd, J=8.2, 1.3 Hz, 1H) 8.41 (t, J=1.7 Hz, 1H) ppm. LC/MS=98.8%, 343.1 (APCI+)

Example 75

Preparation of P-076

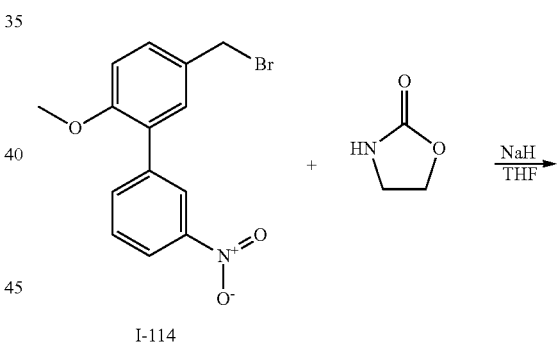

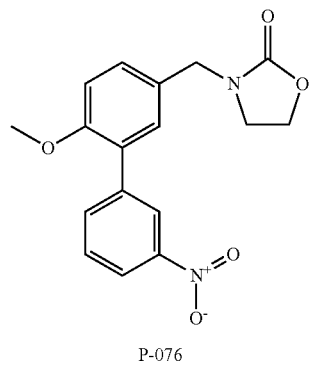

Synthesis of 3-(6-Methoxy-3'-nitro-biphenyl-3-ylmethyl)-oxazolidin-2-one (P-076). Into a dry 100 mL round bottom flask with stir bar was added oxazolidinone (0.15 g, 1.74 mmol) and dry THF (8 mL). The solution was cooled to 0° C. and NaH (83 mg, 2.09 mmol) was added. The suspension was stirred for 10 minutes at 0° C. and 20 minutes at room temperature, and then cooled to 0° C. I-114 (0.56 g, 1.74 mmol) in 2 mL dry THF was added to the above mixture and the reaction was stirred for 16 hours at room temperature. 10 mL of aqueous saturated NH$_4$Cl was added and the THF was removed under reduced pressure. An additional 10 mL of water was added and the product was extracted with ethyl acetate (3×10 mL). The combined organics were dried over sodium sulfate, concentrated, and purified by flash column chromatography using 35%-75% ethyl acetate/hexanes to obtain 94 mg (16%) of P-076 as an oil. $^1$H NMR (400 MHz, CDCl$_3$) 3.47 (t, J=8.1 Hz, 2H) 3.84 (s, 3H) 4.32 (t, J=7.8 Hz, 2H) 4.44 (s, 2H) 7.00 (d, J=8.4 Hz, 1H) 7.26 (s, 1H) 7.33 (dd, J=8.5, 2.2 Hz, 1H) 7.57 (t, J=8.0 Hz, 1H) 7.83 (d, J=7.7 Hz, 1H) 8.19 (dd, J=8.2, 1.3 Hz, 1H) 8.40 (t, J=1.8 Hz, 1H) ppm. LC/MS=98.0%, 328.1 (APCI-)

Example 76

Preparation of P-001

Scheme 29.

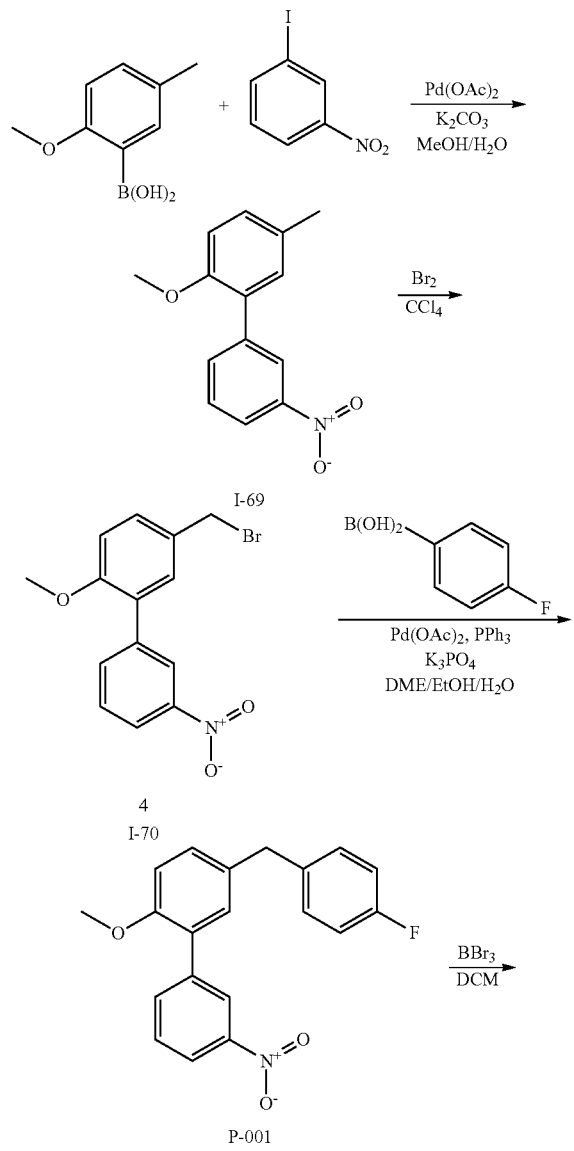

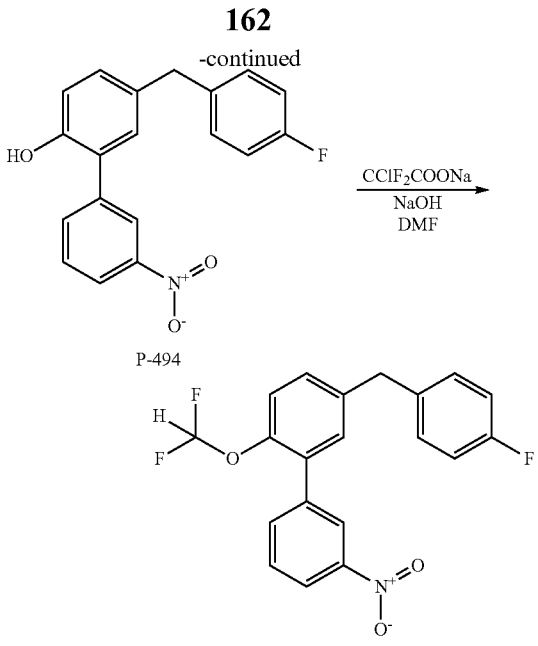

Synthesis of 2-Methoxy-5-methyl-3'-nitro-biphenyl (I-69): A reaction mixture of 2-methoxy-5-methylphenyl boronic acid (1.65 g, 10 mmol), 3-nitro-iodobenzen (2.49 g, 10 mmol), K$_2$CO$_3$ (2.76 g, 20 mmol), palladium(II)acetate (112 mg, 0.5 mmol) in methanol (75 ml) and water (15 ml) was stirred at rt overnight. The reaction mixture was diluted with ethyl acetate (300 ml) washed with diluted Na$_2$S$_2$O$_7$ aq., water, brine, and dried over Na$_2$SO$_4$. After removal of solvent, 2.5 g (100%) of I-69 was obtained.

Synthesis of 5-Bromomethyl-2-methoxy-3'-nitro-biphenyl (I-70): To a mixture of compound I-69 (2.43 g, 10 mmol) in carbon tetrachloride (150 mL), was added bromine (1.76 g, 11 mmol) at rt. The reaction mixture was stirred at 80° C. under a sun lamp for 1 hr. After removal of solvent, the residue was washed with diethylether (15 mL)/Hexane (15 mL) to give 2.1 g (65%) of compound I-70.

Synthesis of 5-(4-Fluoro-benzyl)-2-methoxy-3'-nitro-biphenyl (P-001): A reaction mixture of I-70 (300 mg, 0.93 mmol), 4-fluorophenyl-boronic acid (196 mg, 1.4 mmol), triphenylphosphine (52 mg, 0.2 mmol), K$_3$PO$_4$ (394 mg, 1.86 mmol), palladium(II)acetate (22 mg, 0.1 mmol) in DME (5 ml), ethanol (0.5 ml) and water (0.5 ml) was stirred at 80° C. overnight under argon. The reaction mixture was diluted with diethylether (40 ml), washed with water, brine, and dried over Na$_2$SO$_4$. After removal of solvent, the residue was purified by silica gel column chromatography with ethyl acetate/Hexane as eluent to give 200 mg (60%) of P-001 $^1$H NMR (400 MHz, DMSO-d$_6$): 3.77 (s, 3H), 3.94 (s, 2H), 7.05-7.14 (m, 3H), 7.22-7.34 (m, 4H), 7.65-7.78 (m, 1H), 7.92 (d, J=7.8 Hz, 1H), 8.18 (dd, J=8.2, 1.34 Hz, 1H), 8.28 (t, J=1.8 Hz, 1H) ppm. LCMS=97.4% purity TSI (+)=308.6 (M−29).

Example 77

Preparation of P-494

Synthesis of 5-(4-Fluoro-benzyl)-3'-nitro-biphenyl-2-ol (P-494): To a mixture of compound P-001 (200 mg, 0.59 mmol) in dichloromethane (15 ml) was added BBr$_3$ (1M in dichloromethane, 1.78 ml, 1.78 mmol) at −78° C. under N$_2$. The reaction mixture was stirred at −78° C. to rt overnight.

The reaction mixture was diluted with water and extracted with dichloromethane (2×20 ml). The dichloromethane layer was washed with water (2×40 ml), brine, and dried over Na$_2$SO$_4$. After removal of solvent, the residue was purified by silica gel column chromatography with ethyl acetate/Hexane as eluent to give 180 mg (94%) of P-494. $^1$H-NMR (400 MHz, CDCl$_3$) 3.94 (2H, s), 4.83 (1H, s), 6.87 (1H, d, J=8 Hz), 6.99 (2H, m), 7.07-7.17 (4H, m), 7.60 (1H, dd, J=8 and 8 Hz), 7.85 (1H, m), 8.21 (1H, m), 8.40 (1H, m). MS (APCI−): 322.1 (M−1) LC-MS: 97%.

Example 78

Preparation of P-067

Synthesis of (7) 2-Difluoromethoxy-5-(4-fluoro-benzyl)-3'-nitro-biphenyl (P-067): To a mixture of compound P-494 (100 mg, 0.3 mmol) and NaOH (40 mg, 1 mmol) in DMF (6 ml), was added sodium chlorodifluoroacetate (228 mg, 1.5 mmol). The reaction mixture was stirred at 50° C. overnight. After removal of solvent, the residue was diluted with water (40 mL) and extracted with dichloromethane (2×30 mL). The combined organic extracts were washed with water (4×30 ml), brine, and dried over Na$_2$SO$_4$. After removal of solvent, the residue was purified by silica gel column chromatography with dichloromethane/Hexane as eluent to give 45 mg (40%) of P-067. $^1$H-NMR (400 MHz, CDCl$_3$) 4.00 (2H, s), 6.37 (1H, t, J=7.3 Hz), 7.00 (2H, m), 7.15 (2H, m), 7.22 (1H, m), 7.59 (1H, dd, J=8 and 8 Hz), 7.80 (1H, m), 8.22 (1H, m), 8.32 (1H, m) ppm. MS (APCI−): 373.1 (M−1) LC-MS: 98%.

Example 79

Preparation of P-022

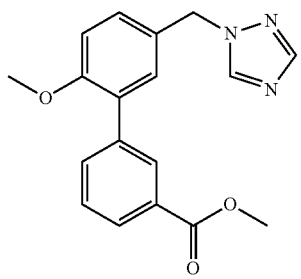

P-022

Synthesis of 2'-Methoxy-5'-[1,2,4]triazol-1-ylmethyl-biphenyl-3-carboxylic acid methyl ester (P-022). A nitrogen stream was bubbled through a solution of I-110 (810 mg, 3.02 mmol) and 3-methoxycarbonylphenylboronic acid (816 mg, 4.53 mmol) in 1,4-dioxane (50 mL) for 45 min. To this solution was added bis(triphenylphosphine)palladium(II) dichloride (106 mg, 0.151 mmol) and 1 M aqueous sodium carbonate (9 mL) under nitrogen. The reaction was heated to 85° C. overnight. The reaction was cooled to room temperature and diluted with ethyl acetate (150 mL). The organic solution was washed with water (5×100 mL), brine (100 mL), dried over sodium sulfate, and the solvent removed under vacuum. The residue was purified by flash silica gel column chromatography eluting with 0-2% methanol in dichloromethane followed by flash silica gel column chromatography with 50% ethyl acetate in hexanes, and the residue wash dissolved in ethyl acetate (10 mL). The organic solution was washed with water (2×10 mL) and the wash extracted with ethyl acetate (2×10 mL). The combined ethyl acetate extracts were washed with water (3×10 mL), dried over sodium sulfate, and the solvent removed under vacuum. The product was recrystallized by dissolving in hot diethyl ether (2 mL), adding hexanes (3 mL), and removing the diethyl ether under a nitrogen stream. The product was filtered and washed with hexanes (3×3 mL) to give P-022 (233.6 mg, 23.9% yield) as a white solid.

$^1$H NMR (400 MHz, CDCl$_3$) d: 8.15 (t, J=1.60 Hz, 1H), 8.066 (s, 1H), 8.019-7.999 (m, 1H), 7.97 (s, 1H), 7.69-7.67 (m, 1H), 7.47 (t, J=7.60 Hz, 1H), 7.29-7.26 (m, 2H), 6.989 (d, J=9.20, 1H), 5.33 (s, 2H), 3.93 (s, 3H), 3.82 (s, 3H) ppm.

LCMS=99.0% purity. MS (APCI+)=324.1 (M+1).

Example 80

Preparation of P-044

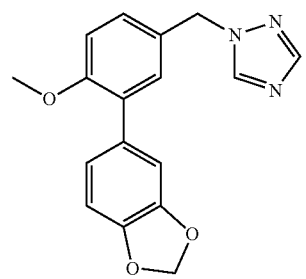

P-044

Synthesis of 1-(3-Benzo[1,3]dioxol-5-yl-4-methoxy-benzyl)-1H-[1,2,4]triazole (P-044). A nitrogen stream was bubbled through a solution of I-110 (500 mg, 1.87 mmol) and benzo[1,3]dioxol-5-yl-boronic acid (345 mg, 2.08 mmol) in DMF (40 mL) for 10 min. To the solution was added bis(dibenzylideneacetone)palladium(0) (120 mg, 0.208 mmol), triphenylphosphine (109 mg, 0.416 mmol), and 1 M aqueous sodium carbonate (6.25 mL) under nitrogen. The reaction was heated to 80° C. under a nitrogen atmosphere and stirred for 16 h. Approximately three quarters of the solvent was removed under vacuum and the remaining suspension was diluted with ethyl acetate (50 mL). The organic solution was washed with water (3×50 mL), saturated aqueous sodium bicarbonate (50 mL), brine (50 mL), dried over sodium sulfate, and the solvent removed under reduced pressure. The product was twice purified by flash silica gel column chromatography eluting with 0-1% methanol in dichloromethane, followed by 0-25% acetone in dichloromethane to give P-044 (296.1 mg, 51% yield) as a yellow oil. 1H NMR (400 MHz, CDCl$_3$) 8.05 (s, 1H), 7.96 (s, 1H), 7.24-7.21 (m, 2H), 7.01 (d, J=2.0 Hz, 1H), 6.98-6.89 (2H), 6.85 (d, J=8.0 Hz, 1H), 5.99 (s, 2H), 5.31 (s, 2H), 3.82 (s, 3H) ppm. LCMS=100.0% purity. MS (APCI+)=310.1 (M+1). HPLC (220 nm); 97.7%. [Water and acetonitrile with 0.05% trifluoroacetic acid, Column: Symmetry C18 (250×4.6 mm, 5 um), Gradient, Flow=1.0 ml/min, Wash=CAN, Inj vol.=10 ul, Retention time=21.2 min]

Example 81

Preparation of P-058

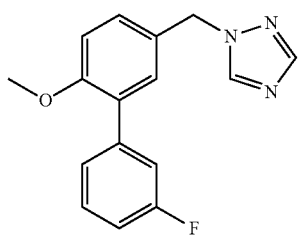

P-058

Synthesis of 1-(3'-Fluoro-6-methoxy-biphenyl-3-ylmethyl)-1H-[1,2,4]triazole (P-058). A nitrogen stream was bubbled through a solution of I-110 (300 mg, 1.12 mmol) and 3-fluorophenylboronic acid (172 mg, 1.23 mmol) in 1,2-dimethoxyethane (5 mL) for 10 min. To this solution was added triphenylphosphine (58.8 mg, 0.112 mmol), solid potassium carbonate (463 mg, 3.36 mmol), ethanol (1 mL), water (1 mL), and palladium(II)acetate (25.1 mg, 0.112 mmol) under nitrogen. The reaction was stirred at 100° C. for 18 h. The solvent was removed under vacuum and the residue taken up in ethyl acetate (50 mL). The organic solution was washed with saturated aqueous ammonium chloride (50 mL), the residual palladium was filtered, and the organic extract was washed with water (2×50 mL), brine (50 mL), dried over sodium sulfate, and removed under vacuum. The crude product was purified by flash silica gel column chromatography eluting with 5% methanol in dichloromethane, followed by a second flash silica gel column eluting with 5% acetone in dichloromethane. The solid thus obtained was recrystallized in diethyl ether (5 mL) and hexanes (10 mL), filtered, and washed with hexanes (5 mL) to give P-058 (65 mg; 21% yield) as a white powder. $^1$H NMR (400 MHz CDCl$_3$): δ 8.07 (s, 1H), 7.97 (s, 1H), 7.36 (dt, J=8.0 Hz, J=6.0 Hz, 1H), 7.25 (m, 2H), 7.03 (m, 1H), 6.98 (d, J=8.4 Hz, 1H), 5.32 (s, 2H), 3.83 (s, 3H) ppm. LCMS=100.0% purity. MS: (APCI+) =284.1 (M+1).

Example 82

Preparation of P-081

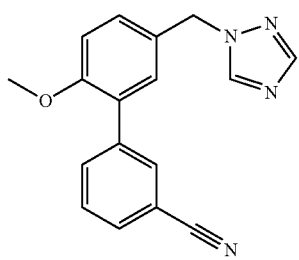

P-081

Synthesis of 2'-Methoxy-5'-[1,2,4]triazol-1-ylmethyl-biphenyl-3-carbonitrile (P-081). A nitrogen stream was bubbled through a solution of I-110 (200 mg, 0.746 mmol) and 3-cyanophenylboronic acid (121 mg, 0.821 mmol) in 1,2-dimethoxyethane (5 mL) for 15 min. To the solution was added ethanol (0.5 mL) and water (0.5 mL) and degassing was continued for 5 min. To the solution was added solid potassium carbonate (309 mg, 2.24 mmol), triphenylphosphine (39.1 mg, 0.149 mmol), and palladium(II)acetate (16.7 mg, 0.0746 mmol) simultaneously under nitrogen. The reaction was heated to 80° C. and stirred with heating overnight. The reaction was cooled to room temperature and the solvent removed under vacuum. The residue was diluted with ethyl acetate (30 mL), washed with water (2×30 mL), the spent catalyst was filtered off, and the combined aqueous layers extracted with ethyl acetate (30 mL). The combined organic extracts were washed with saturated aqueous ammonium chloride (50 mL), water (2×50 mL), brine (50 mL), dried over sodium sulfate, and the solvent removed under vacuum. The residue was purified by flash silica gel column chromatography eluting with 3-15% acetone in dichloromethane to give a white solid, which was triturated with diethyl ether (10 mL), filtered and washed with diethyl ether (2×5 mL) to give P-081 (112.8 mg, 52% yield) as a white solid.

1H NMR (400 MHz CDCl$_3$) 8.08 (s, 1H), 7.97 (s, 1H), 7.81 (t, J=1.8 Hz, 1H), 7.69 (dt, J=8.0 Hz, 1.5, 1H), 7.61 (dt, J=8.0 Hz, 1.3, 1H), 7.50 (t, J=7.8 Hz, 1H), 7.31 (dd, J=8.6, 2.2 Hz, 1H), 7.22 (d, J=2.0 Hz, 1H), 7.00 (d, J=8.4 Hz, 1H), 5.33 (s, 2H), 3.83 (s, 3H) ppm. MS (ESI+)=291.4 (M+1).

Example 83

Preparation of P-082

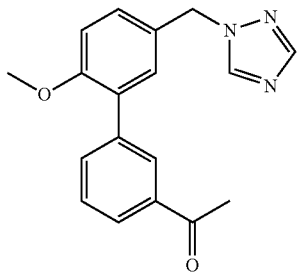

P-082

Synthesis of 1-(2'-Methoxy-5'-[1,2,4]triazol-1-ylmethyl-biphenyl-3-yl)-ethanone (P-082). A nitrogen stream was bubbled through a solution of I-110 (200 mg, 0.746 mmol) and 3-acetylphenlyboronic acid (135 mg, 0.821 mmol) in 1,2-dimethoxyethane (5 mL) for 20 min. To the solution was added ethanol (0.5 mL) and water (0.5 mL) and degassing was continued for 5 min. To the solution was added solid potassium carbonate (309 mg, 2.24 mmol), triphenylphosphine (39.1 mg, 0.149 mmol) and palladium(II)acetate (16.7 mg, 0.0746 mmol) simultaneously under nitrogen. The reaction was heated to 80° C. and stirred with heating overnight. The reaction was cooled to room temperature and the solvent removed under vacuum. The residue was diluted with ethyl acetate (50 mL). The organic solution was washed with water (3×50 mL), saturated aqueous ammonium chloride (50 mL), brine (50 mL), dried over sodium sulfate, decolorized in activated carbon, and the solvent removed under vacuum. The residue was purified by flash silica gel column chromatography eluting with 3-15% acetone in dichloromethane followed by silica gel preparatory plate eluting with 10% acetone in dichloromethane to give P-082 (109.1 mg, 48% yield) as a tacky gum. 1H NMR (400 MHz, CDCl$_3$) 8.08-8.07 (m, 2H), 7.97 (s, 1H), 7.94-7.92 (m, 1H), 7.70-7.68 (m, 1H), 7.50 (t, J=7.8 Hz, 1H), 7.30-7.26 (m, 2H), 67.00 (d, J=8.0 Hz, 1H), 5.33 (s, 2H), 3.83 (s, 3H), 2.63 (s, 3H) ppm. LCMS=99.5% purity. MS (APCI+)=308.1 (M+1).

Example 84

Preparation of P-084

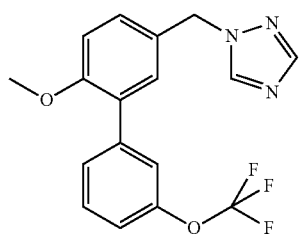

Synthesis of 1-(6-Methoxy-3'-trifluoromethoxy-biphenyl-3-ylmethyl)-1H-[1,2,4]triazole (P-084). P-084 was synthesized from I-110 (200 mg, 0.746 mmol) and 3-trifluoromethoxyphenylboronic acid (169 mg, 0.821 mmol) by the same reaction conditions that were used for P-081. After removal of the solvent under vacuum, the residue was diluted with ethyl acetate (30 mL) and washed with water (30 mL). The aqueous wash was extracted with ethyl acetate (30 mL), and the combined organic extracts were washed with water (2×50 mL), saturated aqueous ammonium chloride (50 mL), brine (50 mL), dried over sodium sulfate, decolorized over activated charcoal, and the solvent removed under vacuum. The residue was purified by flash silica gel column chromatography eluting with 5% acetone in dichloromethane to give P-084 as a yellow oil (187.3 mg, 54% yield). 1H NMR (400 MHz, DMSO-d$_6$) 8.45 (s, 1H), 7.87 (s, 1H), 7.57-7.53 (m, 2H), 7.48-7.48 (brm, 1H), 7.43-7.39 (m, 2H), 7.31-7.29 (m, 1H), 7.14 (d, J=8.4 Hz, 1H), 5.45 (s, 2H), 3.84 (s, 3H) ppm. LCMS=100.0% purity. MS (APCI+)=350.1 (M+1).

Example 85

Preparation P-085

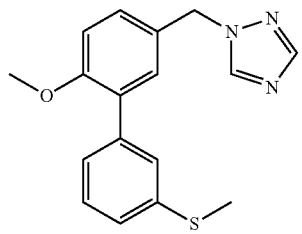

Synthesis of 1-(6-Methoxy-3'-methylsulfanyl-biphenyl-3-ylmethyl)-1H-[1,2,4]triazole (P-085). P-085 was synthesized from I-110 (200 mg, 0.746 mmol) and 3-methylsulfanylphenylboronic acid (138 mg, 0.821 mmol) using the same conditions as P-081. The reaction was worked up by diluting with ethyl acetate (30 mL) and washing with water (30 mL). The aqueous wash was extracted with ethyl acetate (30 mL), and the organic extractions combined, washed with water (2×50 mL), saturated aqueous ammonium chloride (50 mL), brine (50 mL), decolorized with activated carbon, dried over sodium sulfate, and the solvent removed under vacuum. The residue was purified by flash silica gel column chromatography eluting with 5% acetone in dichloromethane to give P-085 (117.1 mg, 50% yield) as a yellow gum. 1H NMR (400 MHz, CDCl$_3$) 8.06 (s, 1H), 7.97 (s, 1H), 7.37 (t, J=1.4 Hz, 1H), 7.32 (t, J=7.6 Hz, 1H), 7.26-7.23 (m, 4H), 6.97 (d, J=8.4 Hz, 1H), 5.32 (s, 2H), 3.81 (s, 3H), 2.50 (s, 3H) ppm. LCMS=100.0% purity. MS (APCI+)=312.1 (M+1).

Example 86

Preparation of P-086

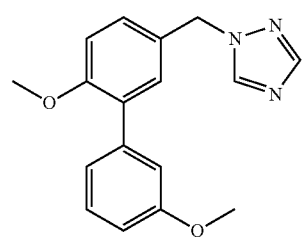

Synthesis of 1-(6,3'-Dimethoxy-biphenyl-3-ylmethyl)-1H-[1,2,4]triazole (P-086). P-086 was synthesized from I-110 (200 mg, 0.746 mmol) and 3-methoxyphenylbronic acid (125 mg, 0.821 mmol) using the same conditions as P-081. The reaction was cooled to room temperature and the solvent removed under vacuum. The residue was suspended in ethyl acetate (30 mL), washed with water (30 mL), the aqueous wash extracted with ethyl acetate (30 mL), and the organic extracts combined. The organic extracts were washed with water (3×30 mL), saturated aqueous ammonium chloride (30 mL), brine (30 mL), decolorized with activated carbon, dried over sodium sulfate, and the solvent removed under vacuum. The product was purified by flash silica gel column chromatography eluting with 5% acetone in dichloromethane to obtain P-086 (148.9 mg, 68% yield) as a yellow oil. $^1$H NMR (400 MHz, acetone-d$_6$) 8.45 (s, 1H), 7.86 (s, 1H), 7.36-7.28 (m, 3H), 7.10-7.03 (m, 3H), 6.91-6.88 (m, 1H), 5.43 (s, 2H), 3.82 (s, 6H) ppm. LCMS=100% purity MS (APCI+)=296.1 (M+1).

Example 87

Preparation of P-102

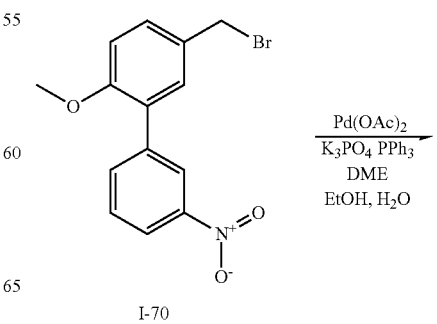

-continued

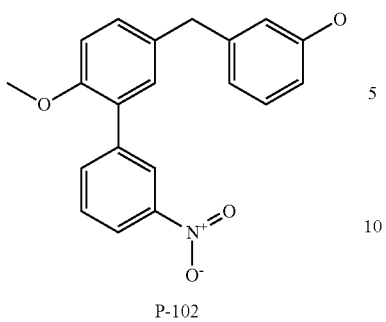

P-102

-continued

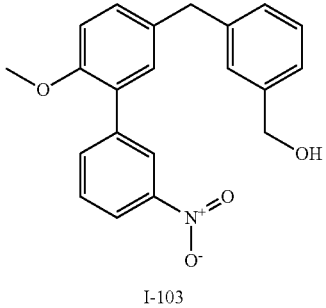

I-103

Synthesis of 3-(6-Methoxy-3'-nitro-biphenyl-3-ylmethyl)-phenol (P-102). Into a 20 mL vial with stir bar was added I-70 (0.30 g, 0.93 mmol), 3-hydroxyphenylboronic acid (0.19 g, 1.40 mmol), triphenylphosphine (49 mg, 0.19 mmol), $K_3PO_4$ (0.40 g, 1.86 mmol), DME (5 mL), water (0.5 mL), and ethanol (0.5 mL). $N_2$ gas was bubbled through the stirred reaction for 10 minutes. Palladium(II) acetate (21 mg, 0.09 mmol) was added and $N_2$ was bubbled through for an additional 5 minutes. The reaction was stirred at 80° C. under $N_2$ for 18 hours. The reaction was cooled to room temperature and 20 mL of water and 20 mL of ethyl acetate were added. The layers were separated and the aqueous was extracted with ethyl acetate (3×15 mL). The organics were combined, dried with sodium sulfate, and concentrated. The residue was purified by flash column chromatography using 15% ethyl acetate/Hexanes to obtain 177 mg (57%) of P-102 as a light-yellow oil. $^1$H NMR (400 MHz, $CDCl_3$) 3.81 (s, 3H) 3.93 (s, 2H) 4.72 (s, 1H) 6.62-6.72 (m, 2H) 6.79 (d, J=7.7 Hz, 1H) 6.94 (d, J=8.3 Hz, 1H) 7.11-7.23 (m, 3H) 7.54 (t, J=8.0 Hz, 1H) 7.82 (d, J=7.8 Hz, 1H) 8.16 (dd, J=8.2, 1.34 Hz, 1H) 8.39 (t, J=1.8 Hz, 1H) ppm. MS: (APCI−) 335.1

Example 88

Preparation of P-103

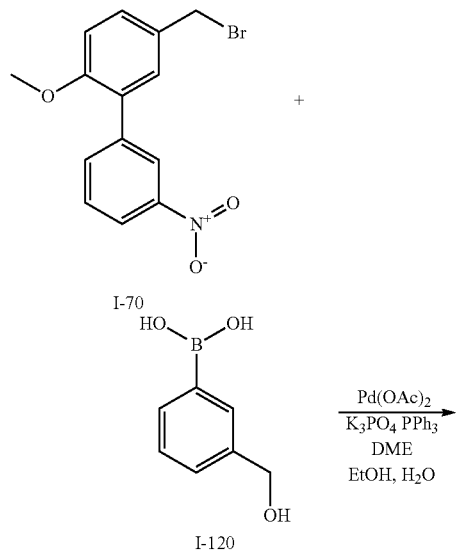

Synthesis of [3-(6-Methoxy-3'-nitro-biphenyl-3-ylmethyl)-phenyl]-methanol (P-103). The same procedure that was used for P-102 was used, except using 3-hydroxybenzylboronic acid. The title compound P-103 was obtained (209 mg, 64%) as a yellow oil. $^1$H NMR (400 MHz, $CDCl_3$) 1.62 (t, J=5.8 Hz, 1H) 3.81 (s, 3H) 3.99 (s, 2H) 4.67 (d, J=5.6 Hz, 2H) 6.94 (d, J=8.3 Hz, 1H) 7.10-7.24 (m, 5H) 7.27-7.34 (m, 1H) 7.54 (t, J=8.0 Hz, 1H) 7.83 (d, J=7.7 Hz, 1H) 8.16 (dd, J=8.3, 1.0 Hz, 1H) 8.38 (s, 1H) ppm. LC/MS=96.8%, (APCI−) 349.1

Example 89

Preparation of P-104

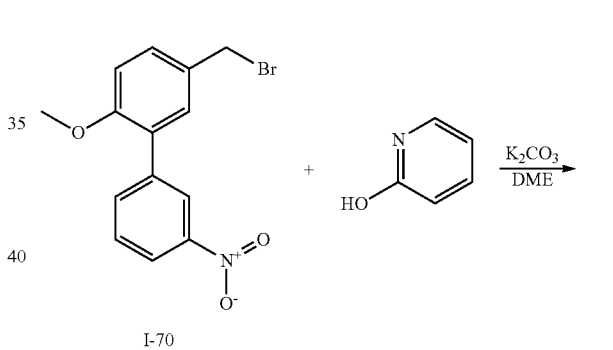

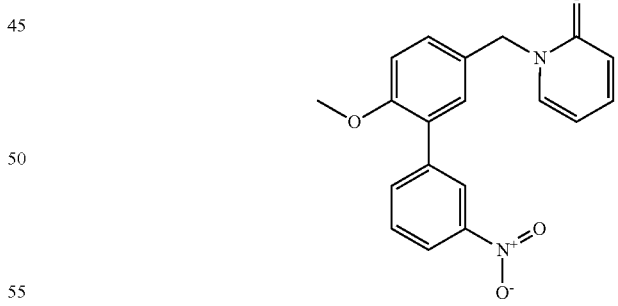

P-104

Synthesis of 1-(6-Methoxy-3'-nitro-biphenyl-3-ylmethyl)-1H-pyridin-2-one (P-104). Into a 20 mL vial with stir bar was added 2-hydroxypyridine (74 mg, 0.78 mmol), $K_2CO_3$ (0.24 g, 1.71 mmol), I-70 (0.30 g, 0.94 mmol), and 3 mL of DME. The mixture was stirred at 80° C. for 18 hours, and then cooled to room temperature, filtered to remove the solids, and concentrated. The residue was purified by flash column chromatography using 30%-75% ethyl acetate/hexanes to obtain 124 mg (40%) of P-104 as a tan-colored solid.

$^1$H NMR (500 MHz, CDCl$_3$) 8.38 (t, J=1.9 Hz, 1H), 8.17 (dd, J=1.3, 8.2 Hz, 1H), 7.81 (d, J=7.8 Hz, 1H), 7.56 (t, J=7.9 Hz, 1H), 7.40-7.27 (m, 5H), 6.99 (d, J=8.6 Hz, 1H), 6.60 (d, J=8.9 Hz, 1H), 6.17 (td, J=1.2, 6.7 Hz, 1H), 5.14 (s, 2H), 3.82 (s, 3H) ppm. $^{13}$C NMR (125 MHz, CDCl$_3$) δ 162.8, 156.4, 148.3, 139.8, 139.6, 137.3, 135.8, 130.9, 130.1, 129.3, 129.1, 128.7, 124.7, 122.2, 121.6, 111.9, 106.5, 55.9, 51.7 ppm. LC/MS=96.7%, 337.1 (APCI+).

Example 90

Preparation of P-105

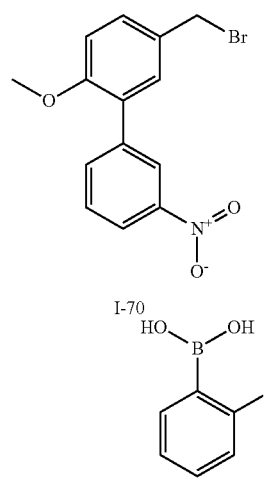

+

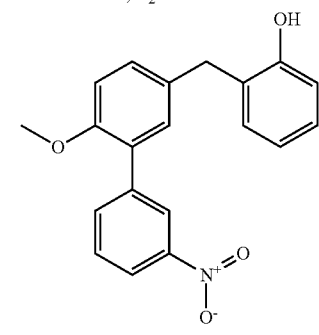

P-105

Synthesis of 2-(6-Methoxy-3'-nitro-biphenyl-3-ylmethyl)-phenol (P-105), Into a 20 mL vial with stir bar was added I-70 (0.30 g, 0.93 mmol), 2-hydroxyphenylboronic acid (GS39) (0.19 g, 1.40 mmol), triphenylphosphine (49 mg, 0.19 mmol), K$_3$PO$_4$ (0.40 g, 1.86 mmol), DME (5 mL), water (0.5 mL), and ethanol (0.5 mL). N$_2$ gas was bubbled through the stirred reaction for 10 minutes. palladium(II) acetate (21 mg, 0.09 mmol) was added and N$_2$ was bubbled through for an additional 5 minutes. The vial was capped and the reaction was stirred at 80° C. for 18 hours. The reaction was cooled to room temperature and 5 mL of water and 5 mL of ethyl acetate were added. The layers were separated and the aqueous was extracted with ethyl acetate (3×10 mL). The organics were combined, dried with sodium sulfate, and concentrated. The residue was purified by flash column chromatography using 15% ethyl acetate/hexanes to afford 120 mg (38%) of P-105 as a yellow oil. $^1$H NMR (400 MHz, CDCl$_3$) 3.80 (s, 3H) 3.99 (s, 2H) 4.74 (s, 1H) 6.78 (d, J=7.8 Hz, 1H) 6.90 (t, J=7.5 Hz, 1H) 6.94 (d, J=8.2 Hz, 1H) 7.09-7.17 (m, 2H) 7.19-7.25 (m, 2H) 7.53 (t, J=8.0 Hz, 1H) 7.82 (d, J=7.8 Hz, 1H) 8.15 (dd, J=8.2, 1.2 Hz, 1H) 8.38 (t, J=1.8 Hz, 1H) ppm. MS: 334.1 (APCI−)

Example 91

Preparation of P-119

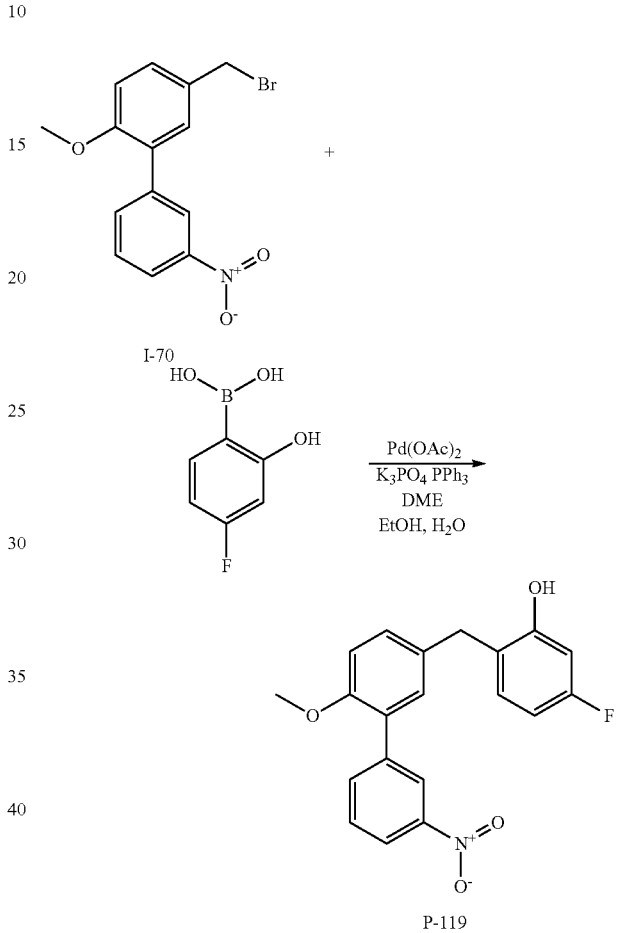

Synthesis of 5-Fluoro-2-(6-methoxy-3'-nitro-biphenyl-3-ylmethyl)-phenol (P-119). Into a 20 mL vial with stir bar was added I-70 (0.30 g, 0.93 mmol), 4-fluoro-2-hydroxyphenyl-boronic acid (0.22 g, 1.40 mmol), triphenylphosphine (49 mg, 0.19 mmol), K$_3$PO$_4$ (0.40 g, 1.86 mmol), DME (5 mL), water (0.5 mL), and ethanol (0.5 mL). N$_2$ gas was bubbled through the stirred reaction for 10 minutes. palladium(II) acetate (21 mg, 0.09 mmol) was added and N$_2$ was bubbled through for an additional 5 minutes. The vial was capped and the reaction was stirred at 80° C. for 18 hours. The reaction was cooled to room temperature and 5 mL of water and 5 mL of ethyl acetate were added. The layers were separated and the aqueous was extracted with ethyl acetate (3×10 mL). The organics were combined, dried with sodium sulfate, and concentrated. The residue was purified by flash column chromatography using 15% ethyl acetate/hexanes followed by preparative TLC using 1:1 dichloromethane/Hexanes to obtain 24.3 mg (7%) of P-119 as a light-yellow oil. $^1$H NMR (400 MHz, CDCl$_3$) 3.81 (s, 3H) 3.94 (s, 2H) 5.07 (br s, 1H) 6.55 (dd, J=9.8, 2.6 Hz, 1H) 6.61 (td, J=8.4, 2.55 Hz, 1H) 6.94 (d, J=8.3 Hz, 1H) 7.07 (dd, J=8.3, 6.7 Hz, 1H) 7.17-7.24 (m, 2H) 7.54 (t, J=8.0

Hz, 1H) 7.81 (d, J=7.7 Hz, 1H) 8.16 (dd, J=8.3, 1.3 Hz, 1H) 8.38 (t, J=1.8 Hz, 1H) ppm. LC/MS=97.2%, 352.1 (APCI−)

Example 92

Preparation of P-134

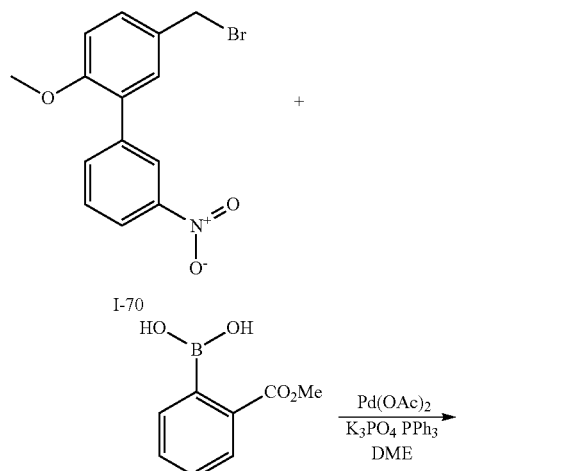

I-70

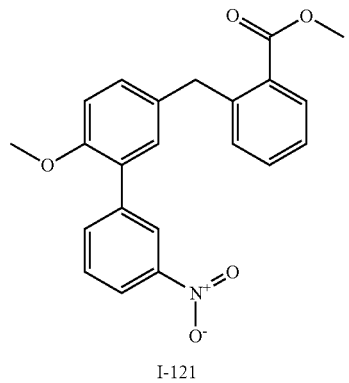

I-121

Synthesis of 2-(6-Methoxy-3'-nitro-biphenyl-3-ylmethyl)-benzoic acid methyl ester (I-121). Into a 20 mL vial with stir bar was added I-70 (0.30 g, 0.93 mmol), 2-methoxycarbonylphenylboronic acid (0.18 g, 1.02 mmol), triphenylphosphine (49 mg, 0.19 mmol), $K_3PO_4$ (0.40 g, 1.86 mmol), DME (5 mL), water (0.5 mL), and ethanol (0.5 mL). $N_2$ gas was bubbled through the stirred reaction for 10 minutes. Palladium(II) acetate (21 mg, 0.09 mmol) was added and $N_2$ was bubbled through for an additional 5 minutes. The vial was capped and the reaction was stirred at 80° C. for 18 hours. The reaction was cooled to room temperature and 5 mL of water and 5 mL of ethyl acetate were added. The layers were separated and the aqueous was extracted with ethyl acetate (3×10 mL). The organics were combined, dried with sodium sulfate, and concentrated. The residue was purified by flash column chromatography using 10% acetone/hexanes to afford 241.0 mg (69%) of I-121 as a colorless oil.

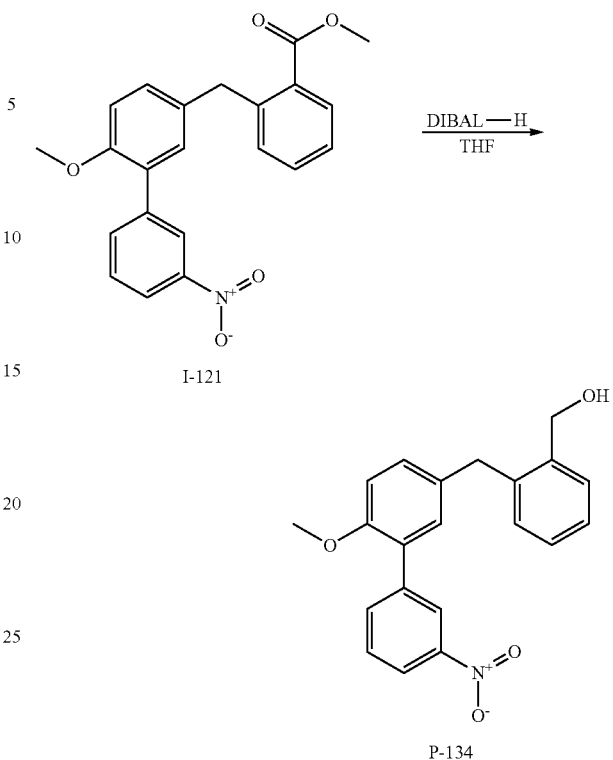

[2-(6-Methoxy-3'-nitro-biphenyl-3-ylmethyl)-phenyl]-methanol (P-134). Into a 20 mL vial with stir bar was added I-121 (126.5 mg, 0.34 mmol) and 4 mL dry THF. The solution was cooled to 0° C. and DIBAL-H (0.84 mL, 0.84 mmol, 1.0 M in hexane) was added. The reaction was stirred at 0° C. for 30 minutes. Aqueous 1 N HCl (1 mL) was added followed by 5 mL of water. The aqueous solution was extracted with ethyl acetate (3×10 mL). The organic were combined, dried over sodium sulfate, and concentrated. The product was purified by flash column chromatography using 12% acetone/hexane to afford 71 mg (66%) of P-134 as a colorless oil. $^1$H NMR (400 MHz, CDCl$_3$) 1.44 (t, J=5.9 Hz, 1H), 3.80 (s, 3H), 4.10 (s, 2H), 4.70 (d, J=5.8 Hz, 2H), 6.92 (d, J=8.9 Hz, 1H), 7.10-7.16 (m, 2H), 7.16-7.22 (m, 1H), 7.27-7.30 (m, 2H), 7.39-7.45 (m, 1H), 7.53 (t, J=8.0 Hz, 1H), 7.80 (d, J=7.7 Hz, 1H), 8.15 (dd, J=8.2, 1.3 Hz, 1H), 8.38 (t, J=1.7 Hz, 1H). LC/MS=99.9%, 349.1 (APCI−).

Example 93

Preparation of P-108

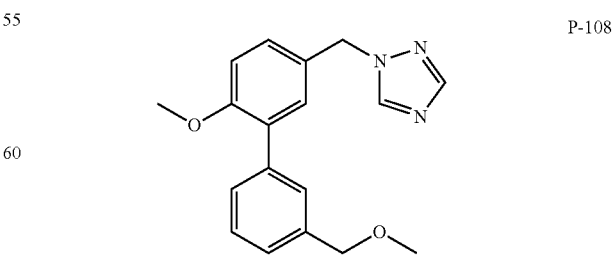

Synthesis of 1-(6-Methoxy-3'-methoxymethyl-biphenyl-3-ylmethyl)-1H-[1,2,4]triazole (P-108). P-108 was synthesized from I-110 (200 mg, 0.746 mmol) and 3-methoxymethylphenylboronic acid (136 mg, 0.821 mmol) using the same conditions as P-081. The reaction was cooled to room temperature and the solvent removed under vacuum. The residue was suspended in ethyl acetate (30 mL), washed with water (30 mL), the aqueous wash extracted with ethyl acetate (30 mL), and the organic extracts combined. The organic extracts were washed with water (3×30 mL), saturated aqueous ammonium chloride (2×30 mL), brine (30 mL), decolorized with activated carbon, dried over sodium sulfate, and the solvent removed under vacuum. The product was purified by flash silica gel column chromatography eluting with 0-25% acetone in dichloromethane, and was run on a silica gel preparatory plate eluting with 1% acetone in dichloromethane for three developments to obtain P-108 (49.0 mg, 19% yield) as a yellow oil.

$^1$H NMR (CDCl$_3$) d: 8.444 (s, 1H), 7.849 (s, 1H), 7.44-7.354 (m, 4H), 7.295-7.280 (m, 2H), 7.104-7.086 (m 1H), 5.435 (s, 2H), 4.472 (s, 2H), 3.805 (s, 3H), 3.350 (s, 3H).

LCMS=100.0% purity. MS (APCI+)=310.1 (M+1).

Example 94

Preparation of P-495

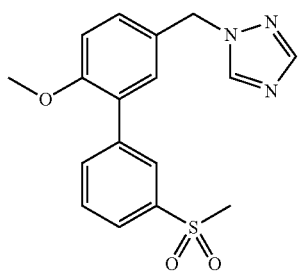

P-495

Synthesis of 1-(3'-Methanesulfonyl-6-methoxy-biphenyl-3-ylmethyl)-1H-[1,2,4]triazole (P-495). P-495 was synthesized from I-110 (200 mg, 0.746 mmol) and 3-methanesulfonylphenylboronic acid (136 mg, 0.821 mmol) by a similar procedure to P-081. Upon completion, the residue was suspended in ethyl acetate (20 mL), washed with (20 mL), and the aqueous wash was extracted with ethyl acetate (2×30 mL). The organic extracts were combined and washed with water (3×50 mL), saturated aqueous ammonium chloride (2×50 mL), and brine (50 mL), dried over sodium sulfate, and the solvent removed under vacuum. The impure product was purified by flash silica gel column chromatography eluting with 5-15% acetone in dichloromethane, and by separation on a silica gel preparatory plate eluting with 5% acetone in dichloromethane to give P-495 (145.0 mg, 57% yield). $^1$H NMR (400 MHz, CDCl$_3$) d: 8.09-8.08 (m, 2H), 7.97 (s, 1H), 7.97-7.90 (m, 1H), 7.79-7.77 (m, 1H), 7.60 (t, J=6.4 Hz, 1H), 7.32-7.26 (m, 2H), 7.01 (d, J=6.8 Hz, 1H), 5.34 (s, 2H), 3.83 (s, 3H), 3.09 (s, 3H).

LCMS=100.0% purity. MS (APCI+)=344.0 (M+1).

Example 95

Preparation of P-163

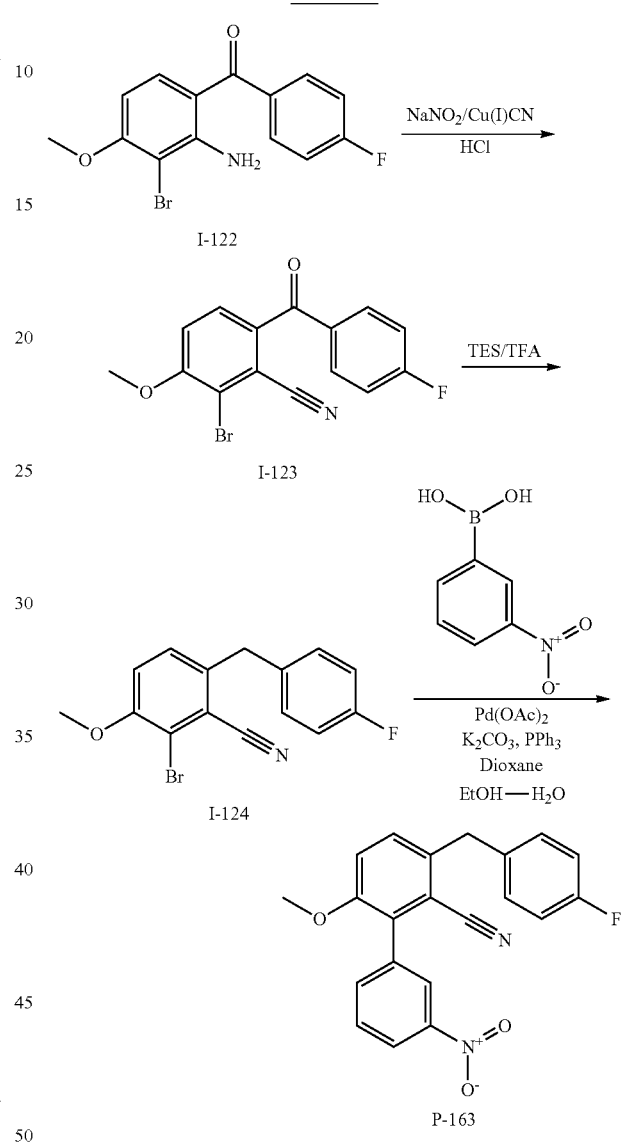

Synthesis of 2-bromo-6-(4-fluoro-benzoyl)-3-methoxy-benzonitrile (I-123). To a cooled (0° C.) solution of (2-amino-3-bromo-4-methoxy-phenyl)-(4-fluoro-phenyl)-methanone (I-122, 0.32 g, 1.0 mmol) in con. HCl (1.5 mL) was added a solution of NaNO$_2$ (0.065 g, 0.95 mmol). The reaction mixture was stirred for 10 min at 0° C., then added to a suspension of Cu(I)CN (0.031 g, 1.2 mmol) in water (0.5 mL) and toluene (1 mL) over 5 min at 0° C. The reaction mixture was slowly warmed to room temperature, stirred at room temperature for 2 h, then at 50° C. for 30 min. The reaction was extracted with dichloromethane (3×5 mL), and the combined organic extracts were washed with brine, dried with Na$_2$SO4, filtered, and concentrated under vacuum. The residue was purified by silica gel column chromatography using 1:1 dichloromethane-hexanes then dichloromethane to afford I-123 (0.201 g, 61% yield) as white solid.

Synthesis of 2-bromo-6-(4-fluoro-benzyl)-3-methoxy-benzonitrile (I-124): To a solution of I-123 (0.15 g, 0.45 mmol) in trifluoroacetic acid (1.0 mL) was added triethylsilane (0.55 g, 4.5 mmol). The reaction mixture was stirred at room temperature for 20 h, then concentrated under vacuum to afford I-124 (0.14 g, 94% yield) as white solid.

Synthesis of 3-(4-fluoro-benzyl)-6-methoxy-3'-nitro-biphenyl-2-carbonitrile (P-163): To I-124 (0.14 g, 0.42 mmol), 3-nitrophenylboronic acid (0.07 g, 0.44 mmol), PPh$_3$ (0.05 g, 0.21 mmol), K$_2$CO$_3$ (0.02 g, 0.16 mmol) and Pd(OAc)$_2$ (0.01 g, 0.06 mmol) was added dioxane (10 mL) and EtOH—H$_2$O (1:1, 5 mL). The reaction was degassed with an Argon stream for 5 min. The reaction was then stirred at 85° C. under Ar for 18 h. The reaction was cooled to room temperature, concentrated under vacuum, and H$_2$O (40 mL) and dichloromethane (40 mL) were added. The organic layer was separated and the aqueous layer was extracted with dichloromethane (2×25 mL). The combined organic extracts were dried with Na$_2$SO$_4$, filtered, and concentrated under vacuum. The residue was purified by silica gel column chromatography using dichloromethane to afford P-163 (0.07 g, 46% yield) as an off-white solid. 1H NMR (CDCl$_3$, 400 MHz): 8.12-8.26 (m, 2H), 7.54-7.62 (m, 2H), 7.1-7.2 (m, 3H), 6.9-7.04 (m, 2H), 6.86 (d, J=8.4 Hz, 1H), 4.07 (s, 2H), 3.71 (s, 3H); MS (APCI+): 383.1 (M+1).

Example 96

Preparation of P-169

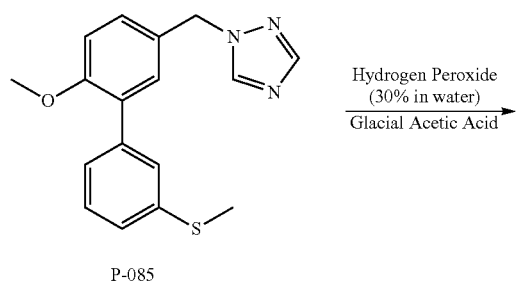

P-085

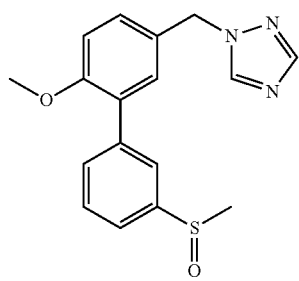

P-169

Synthesis of 1-(3'-Methanesulfinyl-6-methoxy-biphenyl-3-ylmethyl)-1H-[1,2,4]triazole (P-169). A 30% hydrogen peroxide by weight in water solution (1 mL) was diluted with glacial acetic acid (9 mL). A solution of P-085 (38.1 mg, 0.111 mmol) in glacial acetic acid (300 uL) was stirred at room temperature, and the hydrogen peroxide solution was added (107 uL total solution, 3.78 mg hydrogen peroxide, 0.111 mmol) dropwise. The reaction was stirred for 1 h at room temperature. Following completion, solid sodium carbonate was added (~100 mg) to the mixture. The reaction was diluted with water (500 uL), and extracted with ethyl acetate (3×1 mL). The organic extracts were combined, dried over sodium sulfate, and the solvent removed under vacuum. The residue was dried under high vacuum overnight to give P-169 (25.6 mg, 70% yield).

1H NMR (400 MHz, CDCl$_3$) 8.08 (s, 1H), 7.97 (s, 1H), 7.79-7.78 (m, 1H), 7.64-7.54 (m, 3H), 7.31-7.28 (m, 2H), 7.00 (d, J=8.40 Hz, 1H), 5.33 (s, 2H), 3.83 (s, 3H), 2.76 (s, 3H) ppm. LCMS=96.4% purity. MS (APCI+)=328.1 (M+1).

Example 97

Preparation of P-530

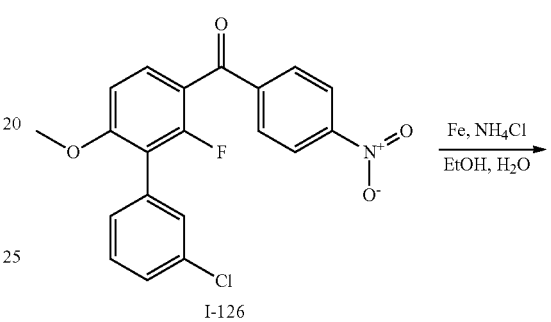

I-126

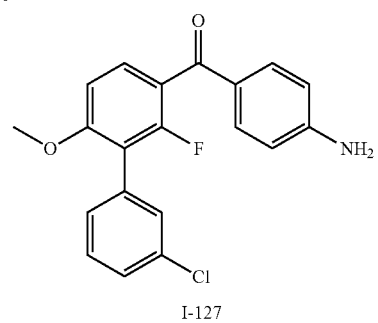

I-127

Synthesis of (4-Amino-phenyl)-(3'-chloro-2-fluoro-6-methoxy-biphenyl-3-yl)-methanone (I-127). A suspension of I-126 (108 mg, 0.28 mmol), Fe powder (55 mg, 0.98 mmol), NH$_4$Cl (75 mg, 1.40 mmol), in ethanol (3 mL), and water (1 mL) was stirred for 2 hours at 80° C. Upon completion the reaction was filtered through Celite, washed with ethyl acetate, and concentrated under vacuum. The residue was taken up in ethyl acetate and washed with saturated aqueous NaHCO$_3$. The combined extracts were concentrated under vacuum to afford compound I-127 (90 mg, 90% yield) as a yellow gum.

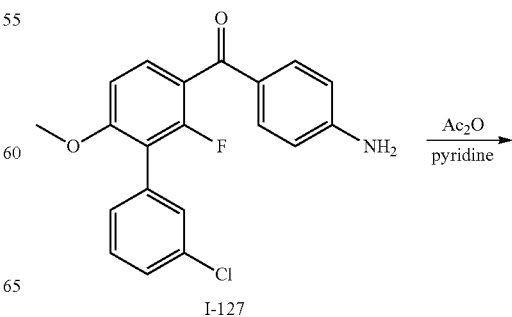

I-127

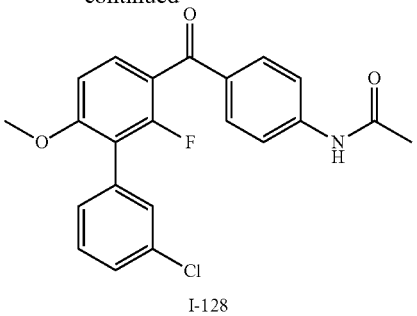

I-128

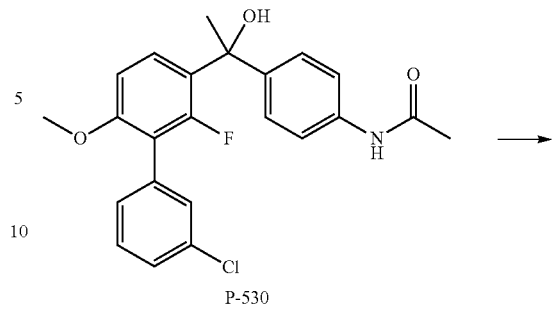

P-530

Synthesis of N-[4-(3'-Chloro-2-fluoro-6-methoxy-biphenyl-3-carbonyl)-phenyl]acetamide (I-128). A solution of I-127 (88 mg, 0.25 mmol) in pyridine (2 mL), and acetic anhydride (35 uL, 0.37 mmol) was stirred at room temperature for 2 hours. The reaction was diluted with ethyl acetate, and was washed with 1N aqueous HCl. The combined extracts were dried over Na$_2$SO$_4$ and concentrated to a solid which was triturated with diethyl ether to give I-128 (21 mg, 21% yield) as a white solid.

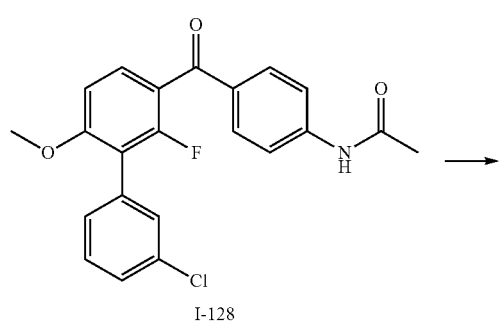

I-128

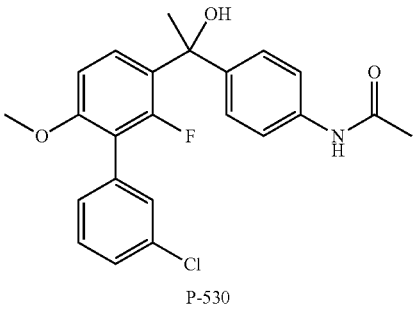

P-530

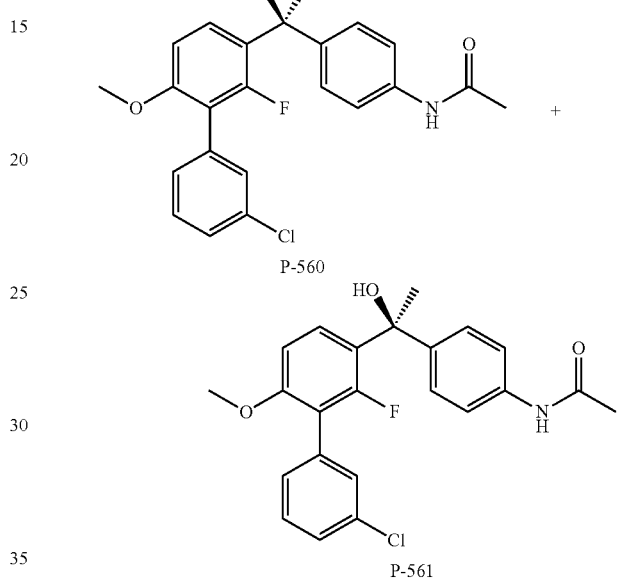

P-560

P-561

Synthesis of N-{4-[1-(3'-Chloro-2-fluoro-6-methoxy-biphenyl-3-yl)-1-hydroxy-ethyl]-phenyl}-acetamide (P-530). A mixture of I-128 (18.4 mg, 0.046 mmol) and methylmagnesium bromide (46 uL, 0.14 mmol, 3.0M in ether) in THF (1 mL) was stirred at room temperature for 10 min, The reaction was quenched by the addition of saturated aqueous NH$_4$Cl. The reaction was extracted with ethyl acetate, and the combined extracts washed with brine, dried over Na$_2$SO$_4$, and concentrated under vacuum. The residue was filtered through SiO$_2$ to remove any remaining inorganic impurities to give P-530 (4.6 mg, 24% yield) as a white solid. $^1$H NMR (400 MHz, DMSO-d$_6$) 9.85 (s, 1H), 7.70 (t, J=9.1 Hz, 1H), 7.50-7.34 (m, 4H), 7.29-7.21 (m, 3H), 7.21-7.12 (m, 1H), 6.97 (d, J=8.9 Hz, 1H), 3.74 (s, 3H), 2.00 (s, 3H), 1.82 (s, 3H)

Purification of P-560 and P-561.

The enantiomers of P-530 were separated by semi-preparative chiral HPLC. The sample for injections was dissolved in warm EtOH. The column used was a Chiralpack AD (250×20 mm, 10 um). The mobile phase was 15% EtOH, 85% hexane (with 0.2% DEA), isocratic at 9.9 mL/min. The injection volume was 385 uL and the fractions were collected by manually changing fractions. The run time was 60 minutes and the UV detection was set at 254 nm. The retention time of the first enantiomer collected was 33.2 min which is P-560, and the second enantiomer was 41.5 min which is P-561.

The chiral purity of each fraction was then determined by analytical scale chiral HPLC using a Chiralpack AD column (250×4.6 mm, 5um). The mobile phase was 15% EtOH, 85% hexane (with 0.2% DEA), isocratic at 1.0 mL/min. The injection volume was 10 uL, the run time was 30 min, and the UV detection was set at 254 nm. A sample of the original racemic mixture was injected and the retention times were 12.3 and 14.9 minutes, respectively. The retention time of P-560 was 12.3 minutes and the enantiomeric excess was determined to be 100.0%. The retention time of P-561 was 15.0 minutes and the enantiomeric excess was determined to be 99.2%.

The absolute stereochemistry of P-560 and P-561 is not known. The stereochemistry of the structures was drawn arbitrarily.

N-{4-[(R)-1-(3'-Chloro-2-fluoro-6-methoxy-biphenyl-3-yl)-1-hydroxy-ethyl]-phenyl}-acetamide (P-560).

$^1$H NMR (400 MHz, DMSO-d$_6$) 9.85 (s, 1H), 7.70 (t, J=9.1 Hz, 1H), 7.44 (d, J=8.7 Hz, 2H), 7.41-7.37 (m, 2H), 7.29-7.22 (m, 3H), 7.19-7.14 (m, 1H), 6.97 (d, J=8.9 Hz, 1H), 5.67 (br. s., 1H), 3.74 (s, 3H), 2.00 (s, 3H), 1.82 (s, 3H)

N-{4-[(S)-1-(3'-Chloro-2-fluoro-6-methoxy-biphenyl-3-yl)-1-hydroxy-ethyl]-phenyl}-acetamide (P-561).

$^1$H NMR (400 MHz, DMSO-d$_6$) 9.85 (s, 1H), 7.70 (t, J=9.1 Hz, 1H), 7.44 (d, J=8.6 Hz, 2H), 7.41-7.36 (m, 2H), 7.29-7.21 (m, 3H), 7.20-7.15 (m, 1H), 6.97 (d, J=8.9 Hz, 1H), 5.67 (br s, 1H), 3.74 (s, 3H), 2.00 (s, 3H), 1.82 (s, 3H)

Example 98

Preparation of P-547

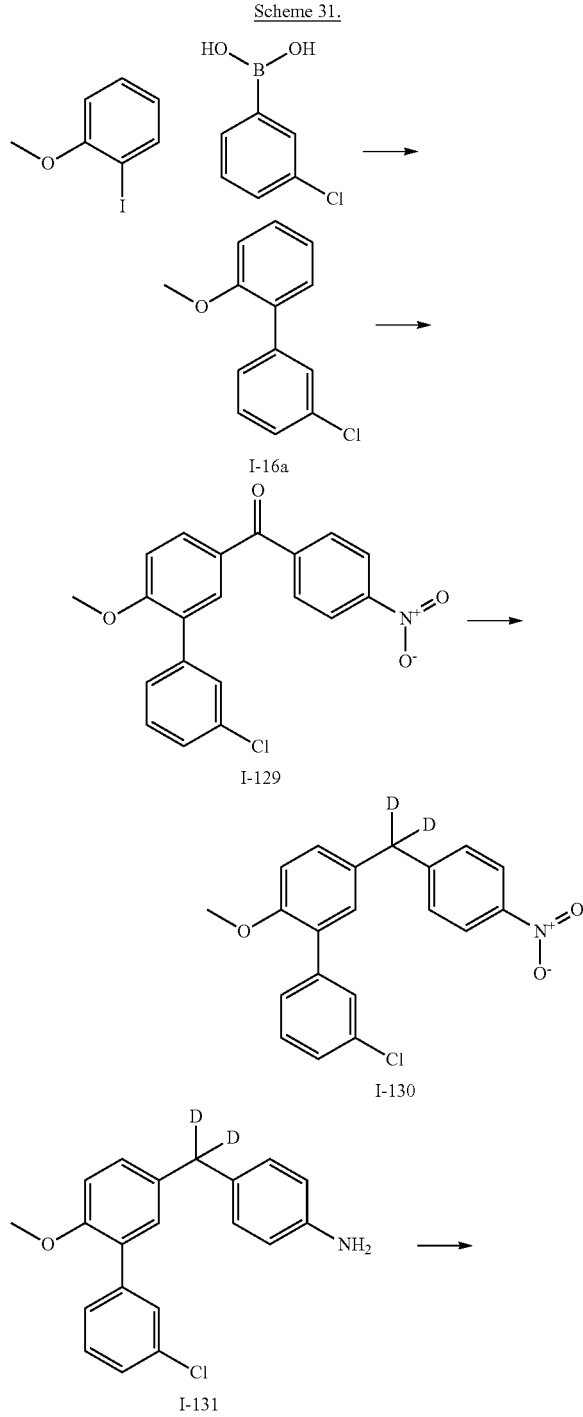

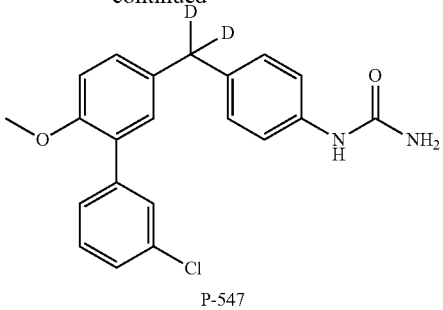

Synthesis of 3'-Chloro-2-methoxy-biphenyl (I-16). A suspension of 2-iodoanisol (3.00 g, 12.8 mmol), 3-chlorophenylboronic acid (2.41 g, 15.4 mmol), and potassium carbonate (3.54 g, 25.6 mmol) in water (10 mL) and methanol (50 mL) was purged with a nitrogen stream for 20 min. To the suspension was added palladium(II) acetate (57.6 mg, 0.2564 mmol) and the solution was stirred at room temperature overnight (18 h). To the reaction was added ethyl acetate (100 mL) and water (100 mL). The layers were separated, the aqueous layer extracted with ethyl acetate (100 mL), and the organic extracts were combined. The organic solution was washed with water (2×150 mL) and brine (150 mL), decolorized with activated charcoal, dried over sodium sulfate, and the solvent removed under reduced pressure. The resulting residue was purified by flash silica gel column chromatography eluting with 10-30% ethyl acetate in hexanes to give I-16 (2.50 g, 89% yield) as colorless oil. 1H NMR (400 MHz CDCl$_3$) 7.53 (t, J=1.8 Hz, 1H), 7.40 (dt, J=7.2 Hz, 1.6 Hz, 1H), 7.38-7.28 (m, 4H), 7.05-6.97 (m, 2H), 3.82 (s, 3H).

Synthesis of (3'-Chloro-6-methoxy-biphenyl-3-yl)-(4-nitro-phenyl)-methanone (I-129). A solution of I-16a (1.50 g, 6.86 mmol) in nitrobenzene (6 mL) was cooled to 0° C. in an ice water bath. Aluminum trichloride (1.10 g, 8.23 mmol) was added portionwise, and the solution stirred at 0° C. for 1 h. To the solution was added, 4-nitro-benzoylchloride (1.53 g, 8.23 mmol) and the reaction was stirred for 20 h allowing warming to room temperature. The solution was poured into 100 mL of an ice-water mixture and stirred for 2 h. The yellow oil was extracted into ethyl acetate (2×100 mL), and the organic extracts combined. The extracts were washed with saturated aqueous sodium bicarbonate (100 mL), water (2×150 mL), and brine (150 mL), dried over sodium sulfate, and the solvent removed under vacuum to give crude I-129 The resultant oil was purified by flash silica gel column chromatography (10-33% ethyl acetate in hexanes) to give I-129 (1.66 g, 66% yield).

1H NMR (400 MHz CDCl$_3$) d: 8.35-8.34 (m, 2H), 7.92-7.91 (m, 2H), 7.84-7.81 (m, 2H), 7.51-7.51 (m, 1H), 7.37-7.34 (m, 3H), 7.08 (d, J=6.8 Hz, 1H), 3.94 (s, 3H). MS (APCI+)=304.1 (M−63.0)

Synthesis of 3'-Chloro-2-methoxy-5-[bisdeutero-(4-nitro-phenyl)-methyl]-biphenyl (I-130). A solution of I-129 (500 mg, 1.36 mmol) in dichloromethane (10 mL) was purged with nitrogen. To the solution was added duetro-trifluoroacetic acid (3.91 g, 34.0 mmol) and the resultant orange solution was cooled to 0° C. in a ice water bath. To the solution was slowly added sodium borodeuteride (569 mg, 13.6 mmol) portion wise over 45 min. The reaction was stirred overnight allowing the mixture to warm to room temperature. The reaction was basified to pH 9 with saturated aqueous sodium bicarbonate, and extracted into ethyl acetate (75 mL). The extract was washed with water (2×50 mL) and brine (50 mL), dried over sodium sulfate, and the solvent removed under vacuum. The crude material was purified by flash silica gel column chromatography (10% ethyl acetate in hexanes) to give I-130 (500 mg, quantitative yield.)

1H NMR (400 MHz CDCl$_3$) 8.16-8.14 (m, 2H), 7.489-7.48 (m, 1H), 7.37-7.26 (m, 5H), 7.13 (dd, J=8.4 Hz, 2.4 Hz, 1H), 7.10 (d, J=2.4 Hz, 1H), 6.93 (d, J=8.4 Hz, 1H), 3.80 (s, 3H).

Synthesis of 4-[Bisdeutero-(3'-chloro-6-methoxy-biphenyl-3-yl)-methyl]-phenylamine (I-131). A suspension of I-130 (440 mg, 1.24 mmol), iron powder (241 mg, 4.33 mmol), and ammonium chloride (337 mg, 6.31 mmol) in ethanol (5 mL) and water (1.6 mL) was stirred at room temperature for 1 h and at 100° C. for 30 min. The ethanol was removed under reduced pressure, the reaction diluted with water (50 mL), and extracted with ethyl acetate (2×50 mL). The combined extracts were washed with water (2×50 mL) and brine (50 mL), dried over sodium sulfate, and the solvent removed under vacuum to give I-131 (279 mg, 70% yield) as an orange oil.

1H NMR (400 MHz CDCl$_3$) d: 7.43 (m, 1H), 7.31-7.19 (m, 3H), 7.07-7.04 (m, 2H), 6.93-6.910 (m, 2H), 6.82 (d, J=8.4 Hz, 1H), 6.57-6.55 (m, 2H), 3.72 (s, 2H), 3.50 (s, 2H).

Synthesis of {4-[Bisduetero-(3'-chloro-6-methoxy-biphenyl-3-yl)-methyl]-phenyl}-urea (P-547). A suspension of I-131 (270 mg, 0.829 mmol) and sodium cyanate (107.7 mg, 1.66 mmol) in water (15 mL) and glacial acetic acid (7.5 mL) was stirred at room temperature over night. To the solution was added aqueous saturated sodium bicarbonate (10 mL), and the reaction was extracted with ethyl acetate (50 mL, 25 mL). The extracts were combined, washed with water (50 mL) and brine (50 mL), dried over sodium sulfate, and the solvent removed under vacuum to give P-547 as an orange gum. The material was purified by flash silica gel column chromatography (eluting with 10-25% ethyl acetate in dichloromethane) and recrystallized by in water (10 mL) and isopropanol (8 mL) to give P-547 (111 mg, 36% yield) as a white powder.

1H NMR (400 MHz, d6-DMSO): 8.40 (s, 1H), 7.48-7.36 (m, 4H), 7.29-7.27 (m, 2H), 7.20-7.10 (m, 2H0, 7.09-7.08 (m, 2H), 7.03 (d, J=8.8 Hz, 1H), 5.75 (s, 2H), 3.74 (s, 3H).

LCMS=96.9% purity. MS (APCI+)=369.1 (M+1), 326.1 (M−42.0).

HPLC (254 nm); 96.6%. [Mobile Phase A and Mobile Phase B=Water and Acetonitrile, Symmetry C18, (250×4.6 mm, 5 um), Flow=1.0 mL/min, Inj. Wash=ACN, Inj. Vol.=10 uL. Retention time=28.37 min]

Example 99

Preparation of P-537, P-538, and P-539

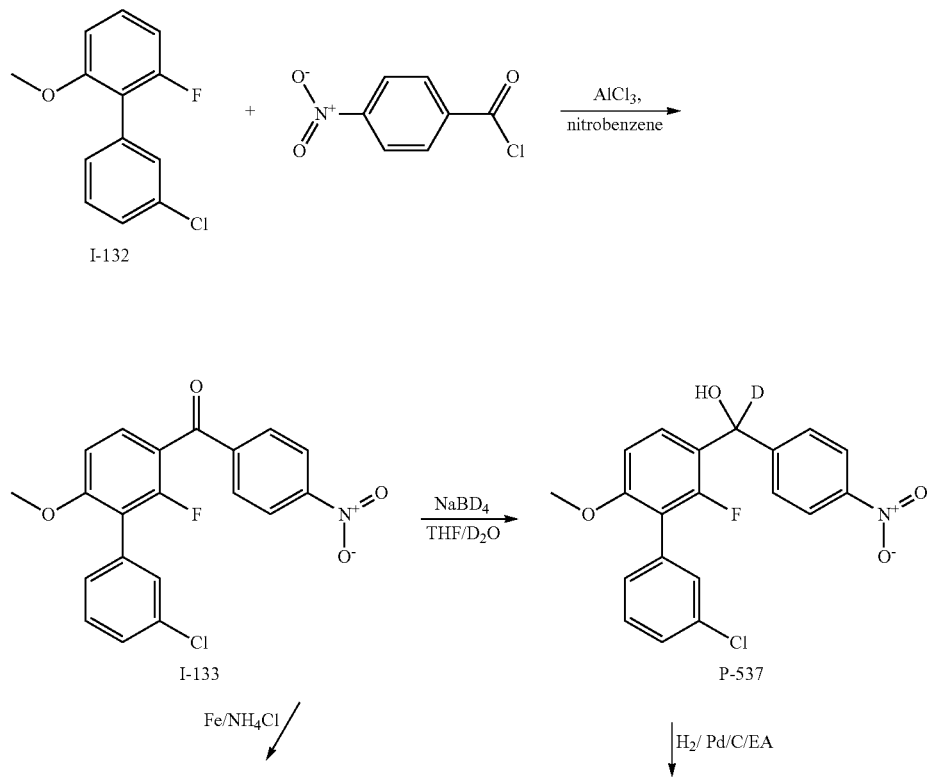

Scheme 32

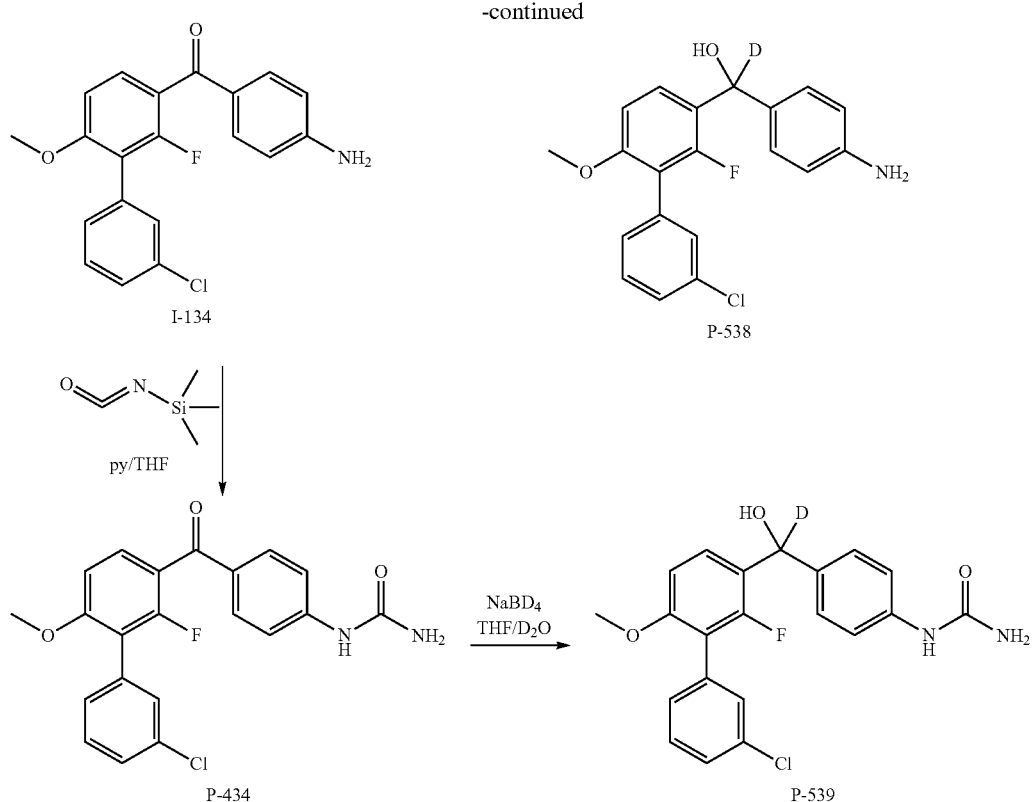

Synthesis of (3'-chloro-2-fluoro-6-methoxy-biphenyl-3-yl)-(4-nitro-phenyl)-methanone (I-133). To a solution of 4-nitro-benzoyl chloride (1900 mg, 10.2 mmol) in nitrobenzene (6 mL) was added aluminum trichloride (1360 mg, 10.2 mmol) at 0° C. The mixture was allowed to warm to room temperature and stirred at room temperature for 1 h, cooled to 0° C., and 3'-chloro-6-fluoro-2-methoxy-biphenyl (2.01 g, 8.5 mmol) in nitrobenzene (1 mL) was added at 0° C. The reaction mixture was allowed to warm to room temperature and stirred 24 h. The reaction mixture was cooled to −10° C. and quenched with ice-water (50 mL), extracted with ethyl acetate (2×25 mL), washed with water (2×10 mL), saturated aqueuos sodium bicarbonate (10 mL), brine (30 mL), and dried over $Na_2SO_4$. After filtration and removal of solvent, the crude was purified by crystallization from ether-hexane to give I-133 (3.00 g, 91% yield).

Synthesis of deutero-(3'-chloro-2-fluoro-6-methoxy-biphenyl-3-yl)-(4-nitro-phenyl)-methanol (P-537). To a mixture of I-133 (500 mg, 1.25 mmol) in THF-$D_2O$ (1:1, 20 mL) was added $NaBD_4$ (190 mg, 3.1 mmol) at 0° C. The reaction mixture was allowed to warm to room temperature and stirred for 24 h. The mixture was poured into ice-water (100 mL), neutralized with aqueous saturated $NH_4Cl$ (5 mL), extracted with ethyl acetate (3×30 mL), washed with water (20 mL), brine (30 mL) and dried over $Na_2SO_4$. After filtration and removal of solvent, the residue was purified by silica gel column chromatography with ethyl acetate-hexane as eluent to give P-537 (350 mg, 70% yield).

1H NMR ($CDCl_3$, 400 MHz) 8.21 (d, J=8.8 Hz, 2H), 7.62 (d, J=8.8 Hz, 2H), 7.23-7.37 (m, 5H), 6.78 (dd, J=8.8, 1.2 Hz, 1H), 3.77 (s, 3H), 2.39 (s, 1H). Calc. 388.8; $APCI^+$ (M−OH): 371.1, 100%.

Synthesis of deutero-(4-amino-phenyl)-(3'-chloro-2-fluoro-6-methoxy-biphenyl-3-yl)-methanol (P-538). To a mixture of P-537 (300 mg, 0.7 mmol) in ethyl acetate (10 mL) was added Pd/C (10%, 450 mg, 4 mmol) at room temperature. The reaction vessle was sealed and the mixture was shacken under a Hydrogen atmosphere (30 psi) for 60 min. The solid was filtered, and the filtrate was concentrated to give crude product. The crude was purified by silica gel column chromatography with ethyl acetate-hexane as eluent and then was further purified by a preparation TLC to yield P-538 (45 mg, 16% yield).

1H NMR ($CDCl_3$, 400 MHz) 7.46 (t, J=8.4 Hz, 1H), 7.23-7.37 (m, 4H), 7.18 (d, J=8.4 Hz, 2H), 6.77 (dd, J=8.8, 1.2 Hz, 1H), 6.55 (d, J=8.4 Hz, 2H), 3.77 (s, 3H), 2.10 (s, 1H). Calc. 358.8; $APCI^+$ (M−OH): 341.1, 91%.

Synthesis of (4-amino-phenyl)-(3'-chloro-2-fluoro-6-methoxy-biphenyl-3-yl)-methanone (I-134). To a solution of I-133 (500 mg, 1.2 mmol) in EtOH—$H_2O$ (1:1, 15 mL) was added solid $NH_4Cl$ (200 mg, 4 mmol) and iron powder (150 mg, 3 mmol), and the reaction was stirred at room temperature for 72 h. The mixture was poured into water (50 mL), extracted with ethyl acetate (3×30 mL), washed with water (20 mL) and brine (30 mL), and dried over $Na_2SO_4$, and filtered. The solvent was removed under vacuum to yield I-134 (380 mg, 82% yield).

Synthesis of [4-(3'-chloro-2-fluoro-6-methoxy-biphenyl-3-carbonyl)-phenyl]-urea (P-434). To a solution of I-134 (220 mg, 0.7 mmol) in pyridine (1 mL) and THF (4 mL) was added trimethylsilylisocyanate (1 mL, excess) and the reaction stirred at room temperature for 36 h. The mixture was poured into 25 mL ice-water solution. To the suspension was added saturated aqueous sodium bicarbonate (5 mL), and the resultant mixture was stirred at room temperature for 2 h. The mixture was extracted with ethyl acetate (3×30 mL), washed with water (20 mL), and brine (30 mL), dried over $Na_2SO_4$, and filtered. The solvent was removed under vacuum, and the crude product was purified by silica gel column chromatography with ethyl acetate-hexane as eluent to yield P-434 (50 mg, 20% yield).

Synthesis of {4-[(3'-chloro-2-fluoro-6-methoxy-biphenyl-3-yl)-hydroxy-deutero-methyl]-phenyl}-urea (P-539). To a mixture of P-434 (50 mg, 0.13 mmol) in THF (5 mL) and D₂O (2 mL) was added NaBD₄ (50 mg, 0.25 mmol) at 0° C. The reaction mixture was allowed to warm to room temperature and stirred for 24 h. The reaction mixture was poured into 20 mL ice-water, neutralized with NH₄Cl (sat. 2 mL), extracted with ethyl acetate (3×10 mL), and washed with water (10 mL) and brine (10 mL). The organic layer was dried over Na₂SO₄, filtered, and the solvent removed under vacuum. After removal of solvent, the residue was purified by a preparation TLC to give P-539 (12 mg, 26% yield). 1H NMR (DMSO-d6, 400 MHz) d: 8.45 (s, 1H), 7.49 (t, J=8.8 Hz, 1H), 7.41-7.44 (m, 2H), 7.24-7.34 (m, 4H), 7.17 (d, J=8.8 Hz, 1H), 6.97 (d, J=9.2 Hz, 1H) 5.79 (s, 1H), 3.73 (s, 3H) ppm. Calc. 401.85; APCI⁺ (M−OH): 384.1, 98.6%.

Example 100

Preparation of P-541

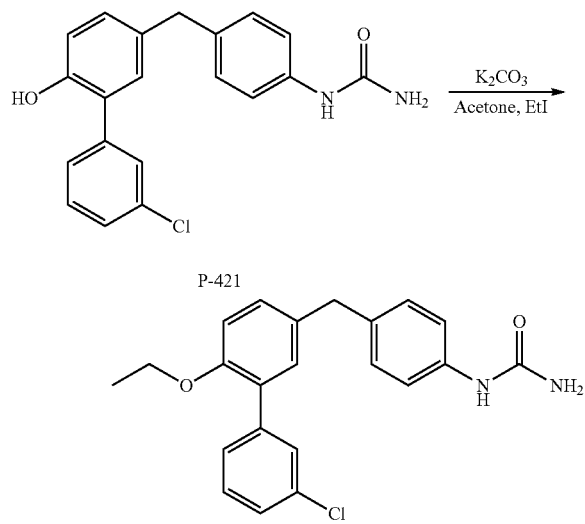

P-541

[4-(3'-Chloro-6-ethoxy-biphenyl-3-ylmethyl)-phenyl]-urea (P-541). A suspension of P-421 (66 mg, 0.19 mmol), K₂CO₃ (39 mg, 0.28 mmol), and EtI (23 uL, 0.28 mmol) in acetone (2 mL) was stirred for 16 hours at 50° C. An additional 50 uL of EtI and 80 mg of K₂CO₃ were added and the reaction was stirred for 4 h at 50° C. To the reaction was added 80 mg of Cs₂CO₃ and 50 uL of EtI, the reaction stirred 2 h at 60° C., and the reaction was concentrated. The crude product was purificated by flash column chromatography eluting with 20%-30% Acetone/DCM afforded the title compound P-541 (37 mg, 51%) as a white solid. ¹H NMR (400 MHz, DMSO-d₆) δ=8.40 (s, 1H), 7.53 (s, 1H), 7.45-7.39 (m, 2H), 7.39-7.34 (m, 1H), 7.28 (d, J=8.3 Hz, 2H), 7.19-7.13 (m, 2H), 7.09 (d, J=8.5 Hz, 2H), 7.01 (d, J=8.1 Hz, 1H), 5.75 (s, 2H), 4.01 (q, J=7.0 Hz, 2H), 3.82 (s, 2H), 1.31-1.18 (m, 3H). LC/MS=96.5%, 381.1 (APCI+).

Example 101

Preparation of P-542

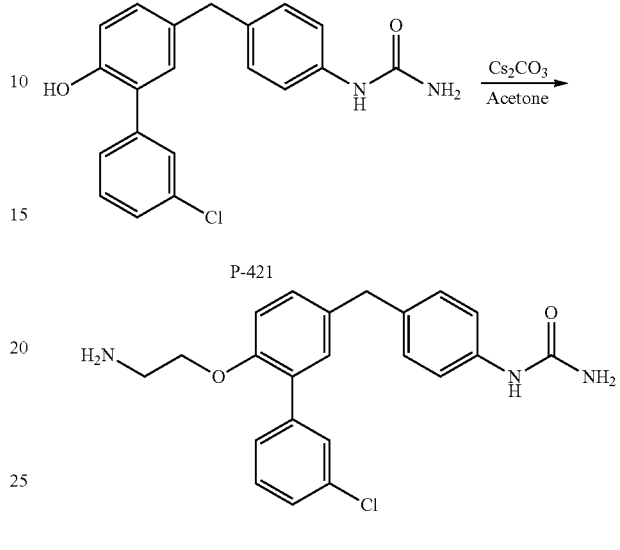

P-542

{4-[6-(2-Amino-ethoxy)-3'-chloro-biphenyl-3-ylmethyl]-phenyl}-urea (P-542). A suspension of P-421 (100 mg, 0.28 mmol), 2-bromoethylamine hydrobromide (204 mg, 8.8 mmol), Cs₂CO₃ (600 mg, 18.4 mmol), and sodium iodide (20 mg) in acetone (10 mL) was stirred at reflux for 20 h. The reaction mixture was then portioned between dichloromethane and water, and the organic layer was extracted with 1N NaOH followed by 1 N HCl. The acidic extract was adjusted to pH 10 by addition of NaOH followed by extraction with dichloromethane. The solvent was removed in vacuo and the residue was chromatographed with dichloromethane:methanol (9:1) to yield P-542 (9 mg, 8.1% yield) as a solid.

¹H NMR (CDCl₃) 7.50-7.52 (m, 1H), 7.28-7.32 (m, 2H), 7.17-7.23 (m, 3H), 7.11-7.13 (m, 2H), 7.09-7.11 (m, 1H), 6.89-6.92 (m, 2H), 3.96 (t, J=5 Hz, 2H), 3.93 (s, 2H), 2.99 (t, J=5 Hz, 2H), APCI (M+1; 396.1) LCMS 95%.

Example 102

Preparation of P-543

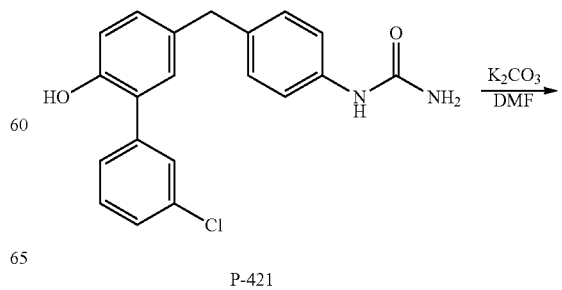

P-421

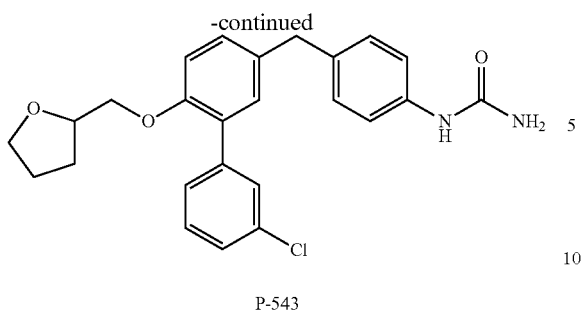

P-543

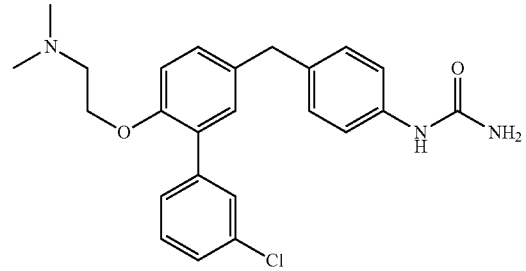

P-548

{4-[3'-Chloro-6-(tetrahydro-furan-2-ylmethoxy)-biphenyl-3-ylmethyl]-phenyl}-urea (P-543). A mixture of phenol P-421 (100 mg, 0.28 mmol), tetrahydrofurfuryl bromide (50 mg, 0.28 mmol), and $K_2CO_3$ (78 mg, 0.56 mmol) in DMF (2 mL) was heated at 80° C. for 24 h. To this mixture, $K_2CO_3$ (78 mg), NaI (10 mg), and tetrahydrofurfuryl bromide (50 mg) were added and the reaction was run at 100° C. for 6 h. The mixture was cooled to room temperature and patitioned between dichloromethane and water, the dichloromethane layer was washed with brine, dried over $Na_2SO_4$, filtered, and concentrated. The residue was purified by preparative plate with dichloromethane:methanol (95:5) to yield P-543 (55 mg, 45% yield).

$^1$H NMR (400 MHz, DMSO-d6) 8.39 (s, 1H), 7.58 (s, 1H), 7.37-7.43 (m, 3H), 7.28 (d, J=7.2 Hz, 1H), 7.14-7.17 (m, 2H), 7.08 (d, J=7.2 Hz, 2H), 7.02 (d, J=7.2 Hz, 1H), 4.07 (m, 1H), 3.94 (t, J=5 Hz, 2H), 3.82 (s, 2H), 3.6-3.69 (m, 2H), 1.88-1.93 (m, 1H), 1.73-1.77 (m, 2H), 1.62-1.69 (m, 1H).

APCI (M+1; 437) LCMS 93.5%;

Example 103

Preparation of P-548 and P-557

Synthesis of {4-[3'-Chloro-6-(2-dimethylamino-ethoxy)-biphenyl-3-ylmethyl]-phenyl}-urea (P-548). A suspension of P-421 (100 mg, 0.283 mmol), dimethylaminoethylbromide hydrobromide (198 mg, 0.850 mmol), and cesium carbonate (600 mg, 1.84 mmol) in acetone (10 mL) was stirred at reflux for 17 h. The suspension was diluted with dichloromethane (50 mL), washed with 0.5 N aqueous hydrochloric acid (100 mL), and the solvent removed under vacuum. The crude orange oil was purified by preparatory thin layer chromatography (silica gel) eluting with 10% acetone in dichloromethane followed by eluting with 10% methanol in dichloromethane to give P-548 (13.4 mg, 11% yield) as a colorless gum.

1H NMR (400 MHz $CDCl_3$) d: 7.54 (m, 1H), 7.39-7.36 (m, 1H), 7.31-7.08 (m, 8H), 6.90-6.89 (m, 1H), 6.23 (s, 1H), 4.57 (s, 2H), 4.05 (t, J=5.8 Hz, 2H), 3.92 (s, 2H), 2.68 (t, J=5.60 Hz, 2H), 2.27 (s, 6H).

LCMS=97.3% purity. MS (APCI+)=424.2 (M+1)

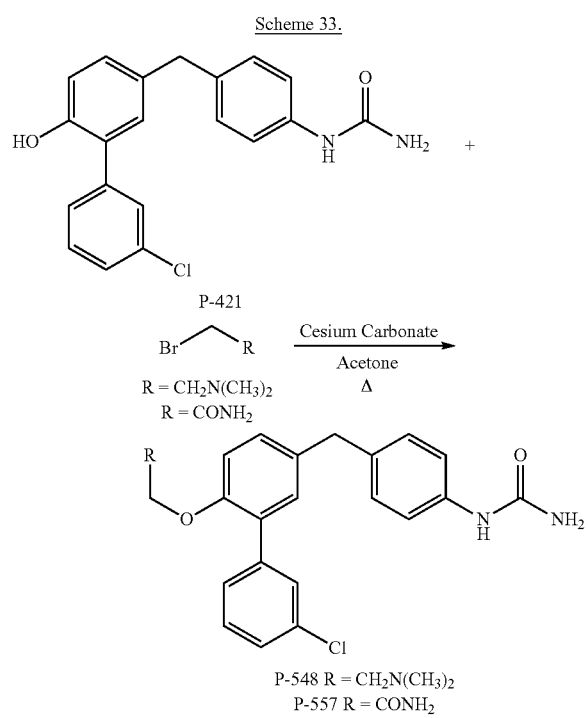

Scheme 33.

P-421

R = $CH_2N(CH_3)_2$
R = $CONH_2$

Cesium Carbonate / Acetone / Δ

P-548 R = $CH_2N(CH_3)_2$
P-557 R = $CONH_2$

P-557

Synthesis of 2-[3'-Chloro-5-(4-ureido-benzyl)-biphenyl-2-yloxy]-acetamide (P-557). A suspension of P-421 (150 mg, 0.425 mmol), 2-bromoacetamide (175 mg, 1.28 mmol), and cesium carbonate (900 mg, 2.76 mmol) in acetone (15 mL) was stirred at reflux overnight. The solvent was removed under a nitrogen stream, and the dry residue was suspended in ethyl acetate (50 mL). The organic solution was washed with water (50 mL) and brine (15 mL), dried over sodium sulfate, decanted, and the solvent removed under vacuum to give crude product. The solid was triturated in a mixture of dichloromethane (5 mL), methanol (5 mL), and acetone (2 mL) to give P-557 (58.9 mg, 34% yield) as a white powder.

1H NMR (400 MHz, DMSO-$d_6$) 8.40 (s, 1H), 7.65 (t, J=2.0 Hz, 1H), 7.52-7.50 (m, 1H), 7.41 (t, J=7.2 Hz, 1H), 7.43-7.37 (m, 2H), 7.28 (d, J=8.4 Hz, 1H), 7.20-7.15 (m, 3H), 7.09 (d, J=8.4 Hz, 1H), 6.90 (d, J=8.0 Hz, 1H), 5.75 (s, 2H), 4.42 (s, 2H), 3.83 (s, 2H). LCMS=93.63% purity. MS (APCI+)=410.1 (M+1).

Example 104

Preparation of P-554

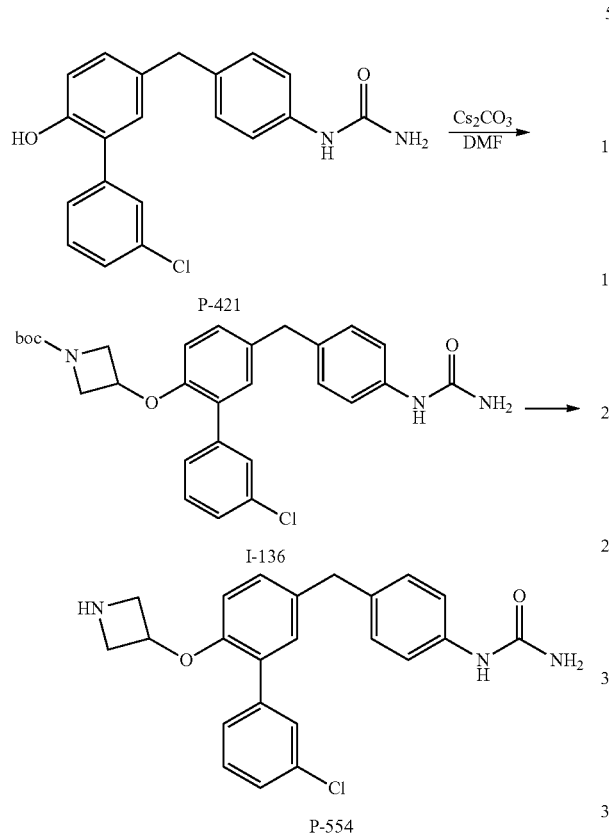

3-[3'-Chloro-5-(4-ureido-benzyl)-biphenyl-2-yloxy]-azetidine-1-carboxylic acid tert-butyl ester (I-136). A mixture of phenol P-421 (150 mg, 0.42 mmol), 3-methanesulfonyloxy-azetidine-1-carboxylic acid t-butyl ester (200 mg, 0.79 mmol), and $Cs_2CO_3$ (277 mg, 0.85 mmol) in DMF (2 mL) was heated at 100° C. for 18 h. The mixture was cooled to room temperature and partitioned between dichloromethane and water. The water layer was extracted twice with dichloromethane. The combined organic layers were washed with brine, dried over $Na_2SO_4$, filtered, and concentrated. The residue was purified by preparative plate with dichloromethane:methanol (95:5) to yield I-136 (200 mg, quantitative yield) as an oil.

{4-[6-(Azetidin-3-yloxy)-3'-chloro-biphenyl-3-ylmethyl]-phenyl}-urea (P-554). To a solution of I-136 (200 mg, 0.393 mmol) dichloromethane (2 mL), at 0° C. was added trifluoroacetic acid (0.5 mL). The reaction mixture was stirred at room temperature overnight. The reaction mixture was concentrated under vacuum, diluted with water, saturated aqueous Na2HCO3 (0.5 mL) was added and the mixture was extracted with dichloromethane (3×5 mL). The combined organic layers were dried over $Na_2SO_4$, filtered, and concentrated under vacuum The residue was purified by preparative plate thin layer chromatography eluting with dichloromethane:methanol (95:5) to yield P-554 (20 mg, 12% yield) as a solid.

$^1$H NMR (400 MHz, $CDCl_3$) 7.51 (t, 1H), 7.38-7.41 (m, 1H), 7.27-7.33 (m, 2H), 7.12-7.22 (m, 5H), 7.06 (dd, J=8.4, 2.4 Hz, 1H), 6.58 (d, J=8.4 Hz, 1H), 6.22 (br s, 1H), 4.97 (m, 1H), 4.56 (br s, 1H), 3.91 (s, 2H), 3.85-3.89 (t, 2H), 3.73-3.75 (m, 2H), 3.48-3.52 (m, 1H) ppm.

APCI (M+1; 408) LCMS 97%;

Example 105

Preparation of P-553

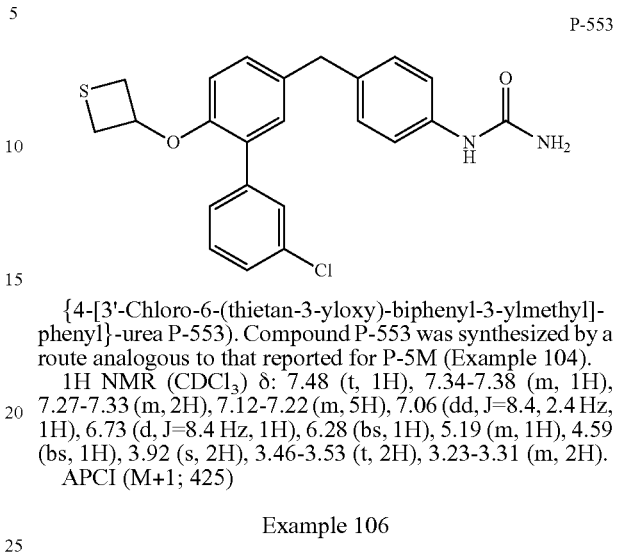

{4-[3'-Chloro-6-(thietan-3-yloxy)-biphenyl-3-ylmethyl]-phenyl}-urea P-553). Compound P-553 was synthesized by a route analogous to that reported for P-5M (Example 104).

1H NMR ($CDCl_3$) δ: 7.48 (t, 1H), 7.34-7.38 (m, 1H), 7.27-7.33 (m, 2H), 7.12-7.22 (m, 5H), 7.06 (dd, J=8.4, 2.4 Hz, 1H), 6.73 (d, J=8.4 Hz, 1H), 6.28 (bs, 1H), 5.19 (m, 1H), 4.59 (bs, 1H), 3.92 (s, 2H), 3.46-3.53 (t, 2H), 3.23-3.31 (m, 2H). APCI (M+1; 425)

Example 106

Preparation of P-555

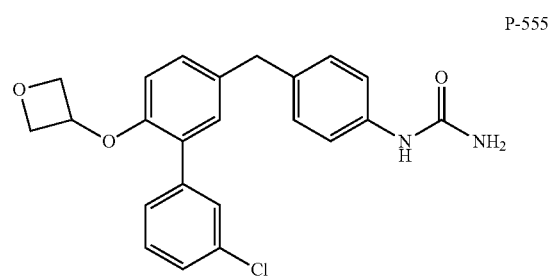 [SMILES: NC(=O)Nc1ccc(Cc2ccc(OC3COC3)c(-c3cccc(Cl)c3)c2)cc1]

{4-[3'-Chloro-6-(oxetan-3-yloxy)-biphenyl-3-ylmethyl]-phenyl}-urea (P-555). Compound P-555 was synthesized by a route analogous to that reported for P-554. 1H NMR (DMSO-$d_6$) δ 8.39 (s, 1H), 7.57 (t, 1H), 7.38-7.48 (m, 3H), 7.28 (d, J=8.4 Hz, 2H), 7.22 (d, J=2.4 Hz, 1H), 7.09-7.14 (m, 1H), 7.08 (d, J=8.4 Hz, 2H), 6.62 (d, J=8.4 Hz, 1H), 5.75 (s, 2H), 5.25 (m, 1H), 4.87 (t, J=5 Hz, 2H), 4.46 (m, 2H), 3.82 (s, 2H). APCI (M+1; 409) LCMS 97%.

Example 107

Preparation of P-556

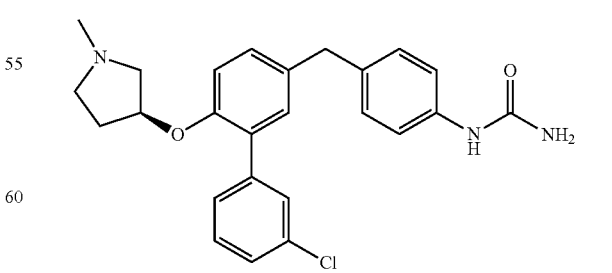

4-[3'-Chloro-6-((S)-1-methyl-pyrrolidin-3-yloxy)-biphenyl-3-ylmethyl]-phenyl}-urea (P-556). Compound P-556 was synthesized by a route analogous to that reported for P-554 (Example 104).

1H NMR (400 MHz, CDCl₃) 7.51 (t, 1H), 7.37-7.39 (m, 1H), 7.27-7.33 (m, 2H), 7.12-7.22 (m, 5H), 7.06 (dd, J=8.4, 2.4 Hz, 1H), 6.8 (d, J=8.4 Hz, 1H), 6.29 (br s, 1H), 4.76 (m, 1H), 4.59 (br s, 1H), 3.91 (s, 2H), 3.02 (m, 1H), 2.6 (t, 2H), 2.35 (s, 3H), 2.17-2.24 (m, 2H). APCI (M+1; 436)

Example 108

Preparation of P-562

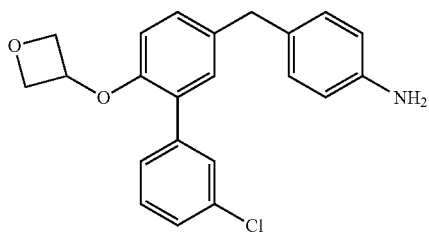

P-562

4-[3'-Chloro-6-(oxetan-3-yloxy)-biphenyl-3-ylmethyl]-phenylamine (P-562). Compound P-562 was synthesized by a route analogous to that reported for P-554 (Example 104).

1H NMR (400 MHz, DMSO-d₆) 7.56 (t, 1H), 7.57 (t, 1H), 7.37-7.48 (m, 3H), 7.18 (d, J=2 Hz, 1H), 7.01 (dd, J=8.4, 2 Hz, 1H), 6.88 (d, J=8.4 Hz, 2H), 6.61 (d, J=8.4 Hz, 1H), 6.47 (d, J=8.4 Hz, 1H), 5.75 (s, 2H), 5.25 (m, 1H), 4.93 (br s, 2H), 4.87 (t, J=5 Hz, 2H), 4.46 (m, 2H), 3.72 (s, 2H) ppm. APCI (M+1; 366) LCMS 97%;

Example 109

Preparation of P-563

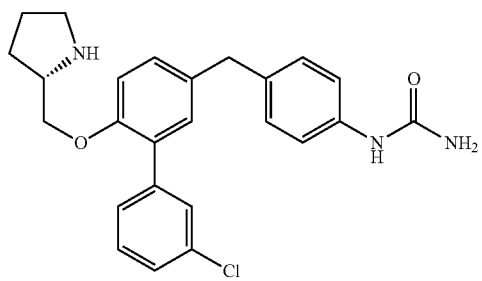

P-563

{4-[3'-Chloro-6-((S)-1-pyrrolidin-2-ylmethoxy)-biphenyl-3-ylmethyl]-phenyl}-urea (P-563). Compound P-562 was synthesized by a route analogous to that reported for P-554 (Example 104).

1H NMR (400 MHz, DMSO-d₆) 9.25 (br s, 1H), 8.77 (br s, 1H), 8.49 (s, 1H), 7.57 (s, 1H), 7.37-7.46 (m, 3H), 7.28 (d, J=8.4 Hz, 1H), 7.19 (overlap, 2H), 7.08 (d, overlap, J=8.4 Hz, 3H), 4.09-4.22 (m, 2H), 3.84 (overlap, 1H), 3.13 (m, 1H), 2.97 (m, 1H), 2.05 (m, 1H), 1.71-1.83 (m, 3H) ppm.

Example 110

Preparation of P-565

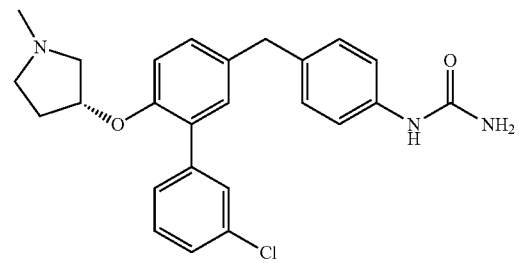

P-565

{4-[3'-Chloro-6-((R)-1-methyl-pyrrolidin-3-yloxy)-biphenyl-3-ylmethyl]-phenyl}-urea (P-565). Compound P-562 was synthesized by a route analogous to that reported for P-554 (Example 104).

1H NMR (400 MHz, CDCl₃) 7.51 (t, 1H), 7.35-7.38 (m, 1H), 7.23-7.31 (m, 4H), 7.13 (d, J=8.4 Hz), 7.11 (s, 1H), 7.06 (dd, J=8.4, 2.4 Hz, 1H), 6.95 (br s, 1H), 6.78 (d, J=8.4 Hz, 1H), 4.8 (br s, 2H), 4.75 (m, 1H), 3.89 (s, 2H), 3.06 (t, 2H), 2.62 (m, 2H), 2.36 (s, 3H), 2.17-2.24 (m, 1H), 1.93-1.98 (m, 1H) ppm. APCI (M+1; 436) LCMS 98%.

Example 111

Preparation of P-550

Scheme 34.

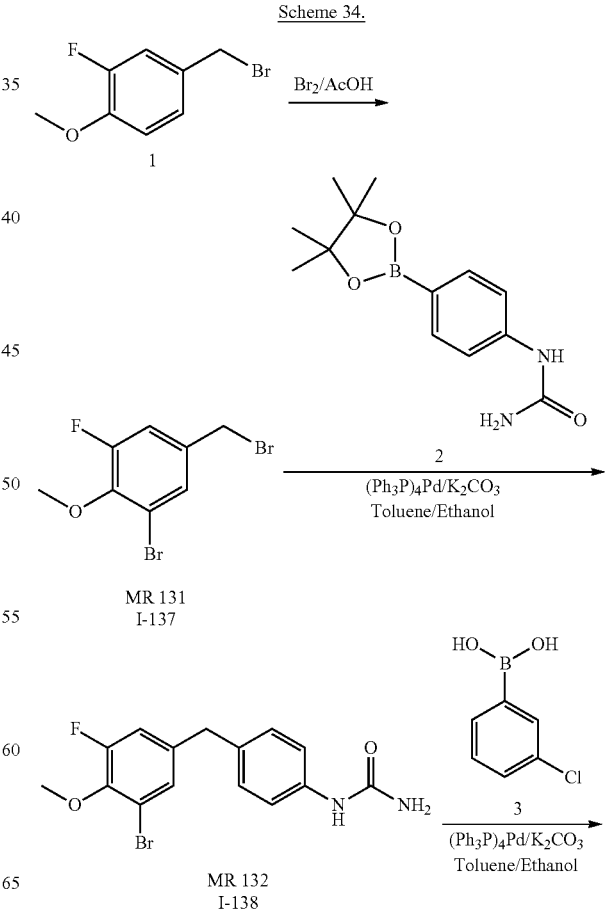

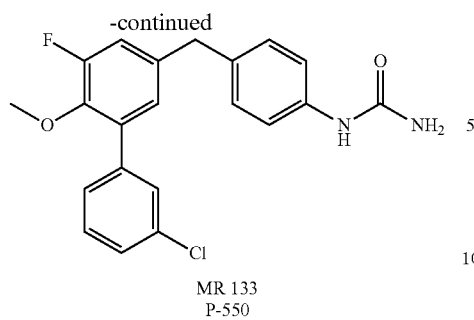

MR 133
P-550

Synthesis of 1-bromo-5-bromomethyl-3-fluoro-2-methoxy-benzene (I-137). To a heated (80° C.) and stirred solution of 4-bromomethyl-2-fluoro-1-methoxy-benzene (1.0 g, 4.57 mmol) in acetic acid (4 mL) was added a solution of bromine (1.09 g, 6.85 mmol) in acetic acid (2 mL) over 30 min. The reaction mixture was stirred at 80° C. for 18 h, cooled to room temperature, and poured on to crushed ice-water (50 mL). Ammonium hydroxide solution (28%) was added to pH 8, extracted with dichloromethane (2×40 mL), washed with water, dried over $Na_2SO_4$, filtered, and concentrated under vacuum. The residue was purified by silica gel column chromatography using 5% ethyl acetate in hexanes to afford I-137 (0.43 g, 31% yield) as a viscous liquid.

Synthesis of 4-(3-bromo-5-fluoro-4-methoxy-benzyl)-phenyl]urea (I-138): To I-137 (0.2 g, 0.67 mmol), [4-(4,4,5,5-tetramethyl-[1,3,2]dioxaborolan-2-yl)-phenyl]-urea (0.19 g, 0.74 mmol), and $Pd(Ph_3P)_4$ (0.04 g, 0.04 mmol), was added toluene (8 mL), EtOH (2 mL) and 2 M aqueous $Na_2CO_3$ solution (0.7 mL, 1.4 mmol). The suspension was degassed by bubbling argon gas for 15 min. The reaction was stirred at 60° C. under an argon atmosphere for 24 h. The reaction was cooled to room temperature, and $H_2O$ (20 mL) and ethyl acetate (30 mL) were added. The layers were separated and the aqueous wash extracted with ethyl acetate (2×20 mL). The combined organic extracts were dried over $Na_2SO_4$, filtered, and concentrated under vacuum. The residue was triturated with dichloromethane to afford I-138 (0.18 g, 77% yield) as yellow solid.

Synthesis of [4-(3'-chloro-5-fluoro-6-methoxy-biphenyl-3-ylmethyl)-phenyl]-urea (P-550): To a suspension of I-138 (0.11 g, 0.31 mmol), 3-chlorophenylboronic acid (0.05 g, 0.34 mmol) and $Pd(Ph_3P)_4$ (0.02 g, 0.02 mmol) was added toluene (6 mL), EtOH (1.5 mL) and 2 M aqueous $NaCO_3$ solution (0.31 mL, 0.62 mmol). The reaction was degassed with an argon stream for 15 min. The reaction was stirred at 80° C. under an argon atmosphere for 18 h. The reaction was cooled to room temperature, and $H_2O$ (20 mL) and ethyl acetate (20 mL) were added. The layers were separated and the aqueous wash was extracted with ethyl acetate (2×10 mL). The combined organic extracts were dried with $Na_2SO_4$, filtered, and concentrated under vacuum. The residue was purified by preparative thin layer chromatography using 8% methanol in dichloromethane to afford P-550 (0.064 g, 53% yield) as an off-white solid. 1H NMR (DMSO-$d_6$, 400 MHz): 8.42 (s, 1H), 7.41-7.54 (m, 4H), 7.30 (d, J=8.4 Hz, 2H), 7.1-7.17 (m, 3H), 7.08 (s, 1H), 5.77 (s, 2H), 3.85 (s, 2H), 3.64 (s, 3H); MS (APCI+): 485.1 (M+1), LC-MS: 99.1%; HPLC 96.8% pure.

Example 112

Preparation of P-558

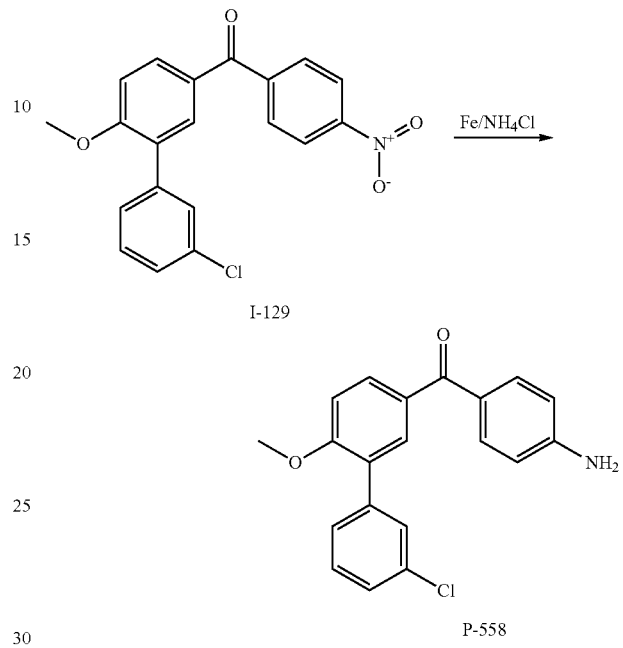

Synthesis of (4-amino-phenyl)-(3'-chloro-6-methoxy-biphenyl-3-yl)-methanone (P-558). To a solution of I-129 (500 mg, 1.3 mmol) in EtOH—$H_2O$ (1:1, 15 mL) was added $NH_4Cl$ (200 mg, 4 mmol) and iron powder (150 mg, 3 mmol). The reaction mixture was stirred at room temperature for 72 h. The mixture was poured into water (50 mL), extracted with ethyl acetate (3×30 mL), washed with water (20 mL) and brine (30 mL), dried over $Na_2SO_4$, and filtered. The solvent was removed under vacuum to yield P-558 (420 mg, 85% yield). $^1$H NMR (DMSO-$d_6$, 400 MHz) 7.70 (dd, J=8.4, 2.4 Hz, 1H), 7.40-7.57 (m, 7H), 7.25 (d, J=8.8 Hz, 1H), 6.61 (d, J=8.8 Hz, 2H), 6.09 (s, 2H), 3.88 (s, 3H) ppm. Calc. 337.8; APCI$^+$ (M+1): 338, 98%.

Example 113

P-566

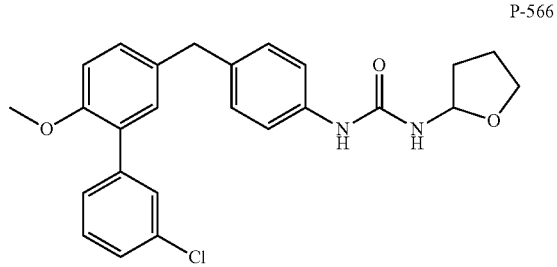 [SMILES: COc1ccc(Cc2ccc(NC(=O)NC3CCCO3)cc2)cc1-c1cccc(Cl)c1]

1-[4-(3'-Chloro-6-methoxy-biphenyl-3-ylmethyl)-phenyl]-3-(tetrahydro-furan-2-yl)-urea (P-566). 1H NMR (DMSO-$d_6$,400 MHz): 8.27 (s, 1H), 7.47-7.50 (m, 1H), 7.34-7.45 (m, 3H), 7.27-7.32 (m, 2H), 7.09-7.21 (m, 4H), 7.03 (d, J=8.4 Hz, 1H), 6.71 (d, J=9.3 Hz, 1H), 5.52-5.48 (m, 1H), 3.84 (s, 2H), 3.73 (s, 3H), 3.70-3.79 (m, 1H), 3.62-3.69 (m, 1H), 1.99-2.11 (m, 1H), 1.79-1.91 (m, 2H), 1.57-1.69 (m, 1H) ppm.

Example 114

Preparation of P-523 and P-533

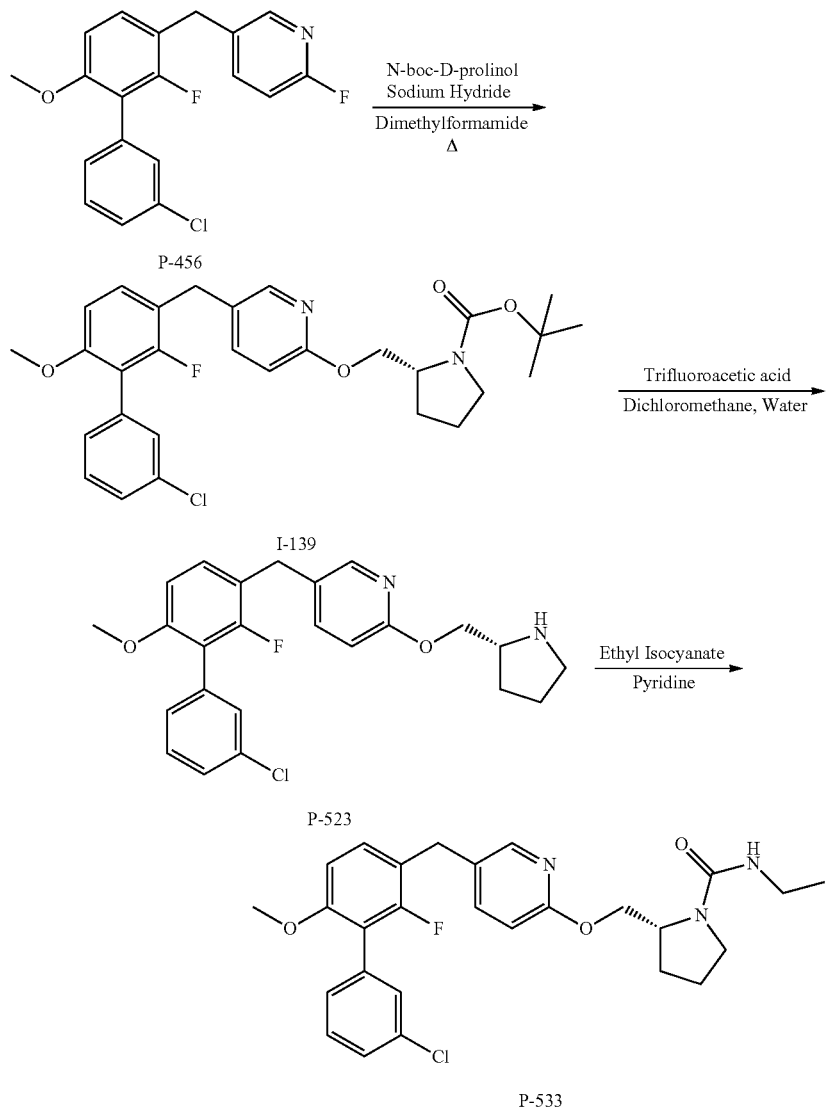

Synthesis of (R)-2-[5-(3'-Chloro-2-fluoro-6-methoxy-biphenyl-3-ylmethyl)-pyridin-2-yloxymethyl]-pyrrolidine-1-carboxylic acid tert-butyl ester (I-139). A mixture of N-boc-D-prolinol (225 mg, 1.12 mmol) and sodium hydride (60% weight dispersion, 66 mg, 1.68 mmol) in dimethylformamide (2 mL) was stirred until gas evolution ceased. After 2 min of stirring P-456 (194 mg, 0.56 mmol) was added, and the reaction heated at 120° C. overnight. The reaction was cooled to room temperature, diluted ethyl acetate (10 mL), washed with water (10 mL), and the aqueous wash extracted with ethyl acetate (25 mL). The combined extracts were dried over sodium sulfate, filtered, and the solvent removed under vacuum. The residue was purified by silica gel column chromatography (9:1 hexanes/ethyl acetate) to give I-139 (60.4 mg, 25% yield) as a thick colorless oil.

Synthesis of 5-(3'-Chloro-2-fluoro-6-methoxy-biphenyl-3-ylmethyl)-2-((R)-1-pyrrolidin-2-ylmethoxy)-pyridine (P-523). A biphasic solution of I-139 (60 mg, 0.11 mmol) and trifluoroacetic acid (851 mg, 0.75 mmol) in dichloromethane (2 mL) and water (0.5 mL) was heated to 80° C. for 4 h. The mixture was concentrated under vacuum, and the residue purified by silica gel column chromatography (9:1 dichloromethane/methanol) to give P-523 (32.4 mg, 69% yield). LCMS=100% purity.

Synthesis of (R)-2-[5-(3'-Chloro-2-fluoro-6-methoxy-biphenyl-3-ylmethyl)-pyridin-2-yloxymethyl]-pyrrolidine-1-carboxylic acid ethylamide (P-533). A solution of P-523 (235 mg, 0.55 mmol) and ethyl isocyanate (0.2 mL, 2.8 mmol) in pyridine (1 mL) was stirred at room temperature overnight. The reaction was diluted with water (5 mL), extracted with ethyl acetate (2×3 mL), and the extracts combined. The organic solution was dried over sodium sulfate, filtered, and the solvent removed under vacuum. The residue was purified by silica gel column chromatography (19:1 dichloromethane/methanol) to give P-533 (92.1 mg, 34% yield). A portion of P-533 (19.0 mg) was further purified by a sodium bicarbonate wash, and silica gel preparatory thin layer chromatography (9:1 dichloromethane/methanol) to give (14.1 mg). $^1$H NMR (400 MHz, DMSO-$d_6$) 1.03 (t, J=7.2 Hz, 3H), 1.80-1.95 (m, 4H), 3.07 (m, 2H), 3.18 (m, 1H), 3.30 (m, 1H), 3.72 (s, 3H), 3.87 (s, 2H), 3.97 (m, 1H), 4.05 (m, 1H), 4.28 (m, 1H), 6.22 (t, J=5.2 Hz, 1H), 6.76 (d, J=8.4 Hz, 1H), 6.93 (d, J=8.8 Hz, 1H), 7.26-7.32 (m, 2H), 7.36 (s, 1H), 7.39-7.50 (m, 2H), 7.55 (dd, J=8.4, 2.2 Hz, 1H), 8.03 (d, J=2.01 Hz, 1H) ppm. MS (APCI+): 498.2 (M+1), LC-MS: 92.2%.

Example 115

Preparation of P-568

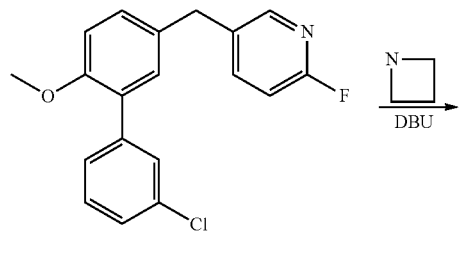

I-140

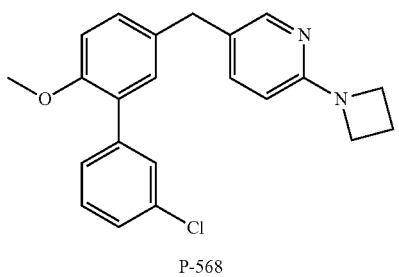

P-568

Synthesis of 2-azetidin-1-yl-5-(3'-chloro-6-methoxy-biphenyl-3-ylmethyl)-pyridine (P-568): To a mixture of I-140 (0.15 g, 0.46 mmol) and azetidine (0.09 g, 0.92 mmol) was added 1,8-diazabicyclo[5.4.0]undec-7-ene (0.35 g, 2.29 mmol). The reaction mixture was stirred and at 85° C. for 15 min. The reaction was then cooled to room temperature, diluted with dichloromethane (6 mL), washed with 0.5 N aqueous HCl (2×4 mL), dried over Na$_2$SO$_4$, filtered, and concentrated. The residue was purified by silica gel column chromatography using 3% methanol in dichloromethane followed by preparative thin layer chromatography using 5% methanol in dichloromethane to afford P-568 (0.05 g, 30% yield) as a viscous liquid. 1H NMR (DMSO-$d_6$, 400 MHz): 7.99 (d, J=1.6 Hz, 1H), 7.34-7.49 (m, 5H), 7.14-7.2 (m, 2H), 7.04 (d, J=8.8 Hz, 1H), 6.28 (dd, J=8.4, 0.8 Hz, 1H), 3.86 (t, J=7.2 Hz, 4H), 3.77 (s, 2H), 3.74 (s, 3H), 2.22-2.32 (m, 2H); MS (APCI+): 365.1 (M+1), LC-MS: 100%.

Example 116

Preparation of P-571

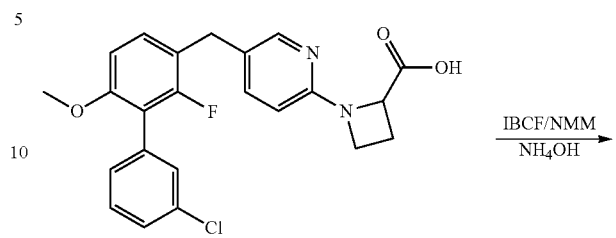

MR 128
I-141

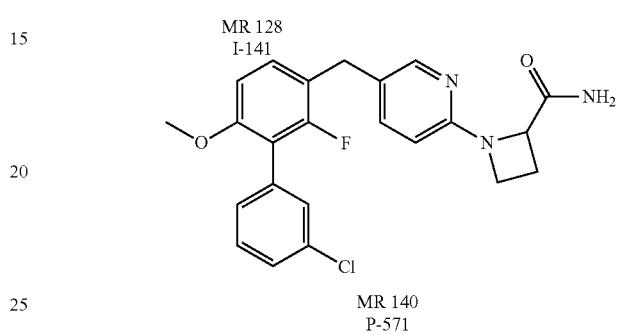

MR 140
P-571

Synthesis of 1-[5-(3'-chloro-2-fluoro-6-methoxy-biphenyl-3-ylmethyl)-pyridin-2-yl]-azetidine-2-carboxylic acid amide (P-571): To a cooled (0° C.) solution of I-141 (0.23 g, 0.54 mmol) in THF (10 mL) was added N-methylmorpholine (0.05 g, 0.54 mmol). The reaction mixture was stirred for 5 min, and isobutylchloroformate (0.07 g, 0.54 mmol) was added. The reaction was stirred at 0° C. for 45 min, and ammonium hydroxide (28%, 4.0 mL) was added. The reaction was warmed to room temperature, stirred for 1.5 h, and diluted with water (5 mL). The organic layer was separated, the aqueous layer extracted with ethyl acetate (2×20 mL). The combined organic layers were dried over Na$_2$SO$_4$, filtered, and concentrated. The residue was purified by silica gel column chromatography using 5% methanol in dichloromethane, and preparative thin layer chromatography using 5% methanol in dichloromethane to afford P-571 (0.03 g, 13% yield) as off-white solid. 1H NMR (DMSO-$d_6$, 400 MHz): 7.99 (d, J=2.0 Hz, 1H), 7.51 (br s, 1H), 7.4-7.48 (m, 3H), 7.36 (s, 1H), 7.24-7.3 (m, 2H), 7.14 (br s, 1H), 6.92 (d, J=8.8 Hz, 1H), 6.34 (d, J=8.4 Hz, 1H), 4.39 (dd, J=9.2, 6.4 Hz, 1H), 3.7-3.9 (m, 2H), 3.8 (s, 2H), 3.72 (s, 3H), 2.26-2.46 (m, 2H); MS (APCI+): 426.1 (M+1), LC-MS: 94.3%.

Example 117

Preparation of P-572

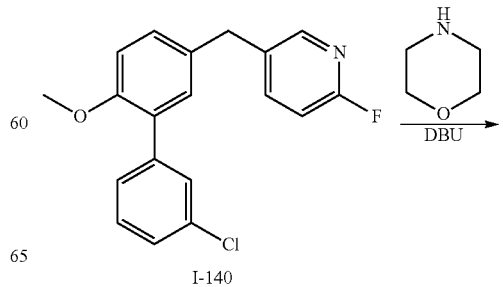

I-140

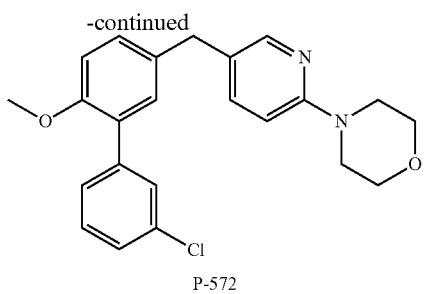

P-572

Synthesis of 4-[5-(3'-chloro-6-methoxy-biphenyl-3-ylmethyl)-pyridin-2-yl]-morpholine (P-572). To I-140 (0.15 g, 0.46 mmol) and morpholine (0.08 g, 0.92 mmol) was added 1,8-diazabicyclo[5.4.0]undec-7-ene (0.35 g, 2.29 mmol). The reaction mixture was stirred at 160° C. for 6 h. The reaction was cooled to room temperature, diluted with dichloromethane (6 mL), washed with 0.5 N aqueous HCl (2×4 mL), dried over Na$_2$SO$_4$, filtered, and concentrated under vacuum. The residue was purified by silica gel column chromatography using 3% methanol in dichloromethane to afford P-572 (0.042 g, 23% yield) as a viscous liquid. 1H NMR (DMSO-d$_6$, 400 MHz): 8.07 (d, J=2.8 Hz, 1H), 7.38-7.45 (m, 5H), 7.16-7.24 (m, 2H), 7.04 (d, J=8.4 Hz, 1H), 6.76 (d, J=8.8 Hz, 1H), 3.8 (s, 2H), 3.74 (s, 3H), 3.67 (t, J=4.8 Hz, 4H), 3.36 (t, J=4.8 Hz, 4H); MS (APCI+): 395.1 (M+1), LC-MS: 95.1%.

Example 118

Preparation of P-581

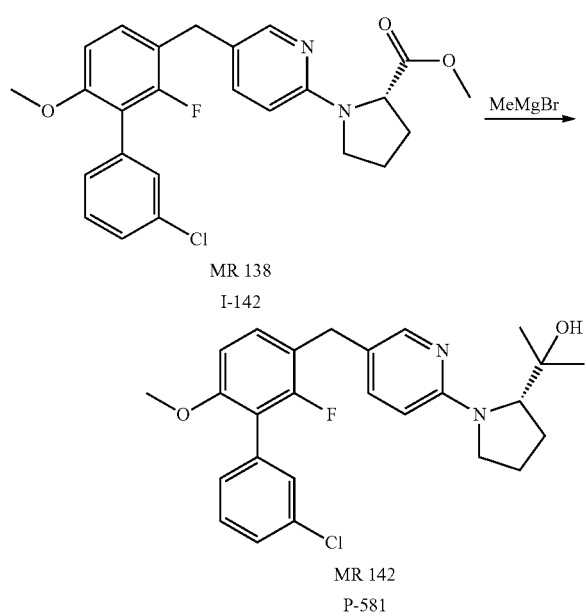

Synthesis of 2-{(S)-1-[5-(3'-chloro-2-fluoro-6-methoxy-biphenyl-3-ylmethyl)-pyridin-2-yl]-pyrrolidin-2-yl}-propan-2-ol (P-581). To a cooled (0° C.) and solution of I-142 (0.05 g, 0.11 mmol) in THF (8.0 mL) was added methylmagnesium bromide (3M sol, 0.26 mL, 0.88 mmol). The reaction mixture was slowly warmed to room temperature, and stirred for 3 h. The reaction was then cooled to 0° C., and saturated aqueous ammonium chloride solution (5 mL), was added. The aqueous suspensions was extracted with diethyl ether (2×30 mL), washed with brine (10 mL), dried over Na$_2$SO$_4$, filtered, and concentrated under vacuum to afford P-581 (0.046 g, 88% yield) as an off-white solid. 1H NMR (DMSO-d$_6$, 400 MHz): 7.90 (d, J=2.4 Hz, 1H), 7.75 (br s, 1H), 7.36-7.48 (m, 4H), 7.26-7.32 (m, 2H), 6.92 (d, J=8.8 Hz, 1H), 6.61 (d, J=8.8 Hz, 1H), 6.33 (br s, 1H), 4.0-4.08 (m, 1H), 3.79 (s, 2H), 3.72 (s, 3H), 3.3-3.45 (m, 2H), 1.7-2.0 (m, 4H), 1.11 (s, 3H), 0.98 (s, 3H); MS (APCI+): 455.1 (M+1), LC-MS: 97.5%.

Example 119

Preparation of P-601

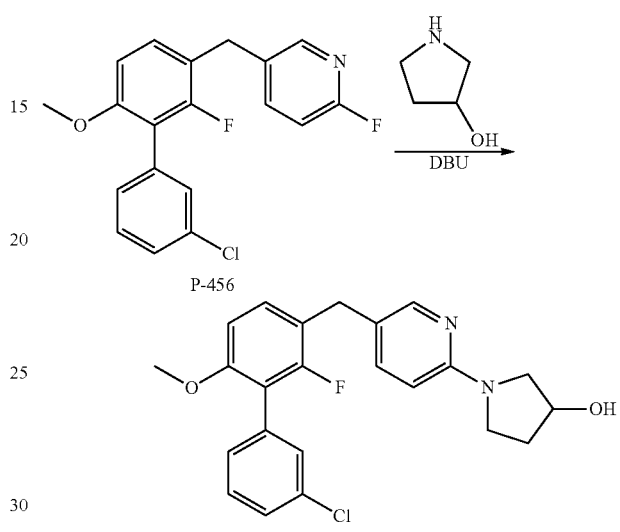

Synthesis of 1-[5-(3'-chloro-2-fluoro-6-methoxy-biphenyl-3-ylmethyl)-pyridin-2-yl]-pyrrolidin-3-ol (P-601). To 5-(3'-chloro-2-fluoro-6-methoxy-biphenyl-3-ylmethyl)-2-fluoro-pyridine (P-456, 0.3 g, 0.87 mmol) and 3-pyrrolidinol (2) (0.15 g, 1.74 mmol) was added 1,8-diazabicyclo[5.4.0]undec-7-ene (DBU) (0.66 g, 4.34 mmol). The reaction mixture was stirred and heated at 100° C. for 2.5 h, cooled to room temperature, diluted with dichloromethane (8 mL), washed with 0.5 N HCl (2×4 mL), dried with Na$_2$SO$_4$, filtered, and concentrated. The residue was purified by silica gel column chromatography using 5% methanol in dichloromethane to afford 0.27 g (75%) of P-601 as white solid. 1H NMR (DMSO-d$_6$, 400 MHz): 7.95 (s, 1H), 7.2-7.46 (m, 6H), 6.91 (d, J=8.4 Hz, 1H), 6.35 (d, J=8.4 Hz, 1H), 4.9 (d, J=3.6 Hz, 1H), 4.32-4.4 (m, 1H), 3.76 (s, 2H), 3.71 (s, 3H), 3.12-3.45 (m, 4H), 1.8-2.05 (m, 2H) ppm; MS (APCI+): 413.1 (M+1), LC-MS: 91.6%.

Example 120

Preparation of P-602

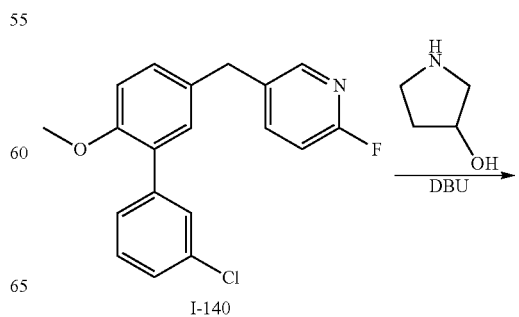

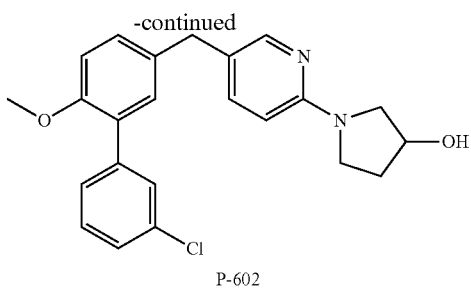

P-602

Synthesis of 1-[5-(3'-chloro-6-methoxy-biphenyl-3-ylmethyl)-pyridin-2-yl]-pyrrolidin-3-ol (P-602): To 5-(3'-chloro-6-methoxy-biphenyl-3-ylmethyl)-2-fluoro-pyridine (I-140, 0.22 g, 0.67 mmol) and 3-pyrrolidinol (2) (0.12 g, 1.34 mmol) was added 1,8-diazabicyclo[5.4.0]undec-7-ene (DBU) (0.51 g, 3.36 mmol). The reaction mixture was stirred and heated at 100° C. for 1.5 h, cooled to room temperature, diluted with dichloromethane (8 mL), washed with 0.5 N HCl (2×4 mL), dried with $Na_2SO_4$, filtered, and concentrated. The residue was purified by silica gel column chromatography using 5% methanol in dichloromethane to afford 0.13 g (49%) of P-602 as white solid. 1H NMR (DMSO-$d_6$, 400 MHz): 7.9 (d, J=2.4 Hz, 1H), 7.3-7.49 (m, 5H), 7.12-7.2 (m, 2H), 7.03 (d, J=8.4 Hz, 1H), 6.34 (d, J=8.8 Hz, 1H), 4.89 (d, J=3.6 Hz, 1H), 4.35 (br s, 1H), 3.76 (s, 2H), 3.73 (s, 3H), 3.2-3.45 (m, 4H), 1.8-2.05 (m, 2H) ppm; MS (APCI+): 395.1 (M+1), LC-MS: 99.1%.

Example 121

Preparation of P-612

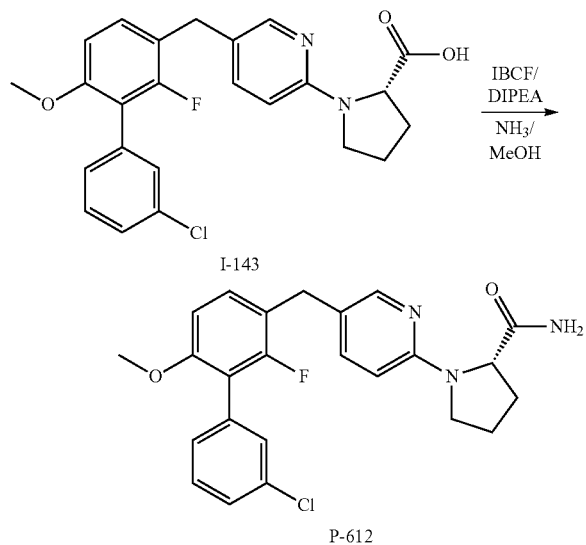

P-612

Synthesis of (S)-1-[5-(3'-chloro-2-fluoro-6-methoxy-biphenyl-3-ylmethyl)-pyridin-2-yl]-pyrrolidine-2-carboxylic acid amide (P-612): To a cooled (0-5° C.) and stirred solution of (S)-1-[5-(3'-chloro-2-fluoro-6-methoxy-biphenyl-3-ylmethyl)-pyridin-2-yl]-pyrrolidine-2-carboxylic acid (I-143, 0.15 g, 0.34 mmol) in THF (2 mL) was added diisopropylethylamine (0.05 g, 0.37 mmol). The reaction mixture was stirred for 5 min, isobutylchloroformate (0.05 g, 0.37 mmol) was added, stirred at 0-5° C. for 45 min. Ammonium hydroxide (28%, 4.0 mL) was added, the reaction warmed to ambient temperature, stirred for 1.5 h. The reaction mixture was diluted with water (5 mL). The organic layer was separated, the aqueous layer was extracted with ethyl acetate (2×20 mL). The combined organic layers were dried with $Na_2SO_4$, filtered, and concentrated. The residue was purified by silica gel column chromatography using 5% methanol in dichloromethane followed by preparative thin layer chromatography using 5% methanol in dichloromethane to afford 0.074 g (49%) of P-612 as an off-white solid. 1H NMR (DMSO-$d_6$, 400 MHz): 8.27 (d, J=2.4 Hz, 1H), 7.34-7.46 (m, 4H), 8.2 (d, J=8.8 Hz, 1H), 7.65 (dd, J=8.8, 2.4 Hz, 1H), 7.4-7.46 (m, 2H), 7.37 (br s, 1H), 7.26-7.38 (m, 2H), 6.94 (d, J=8.0 Hz, 1H), 3.92-3.98 (m 3H), 3.93 (s, 2H), 3.73 (s, 3H), 2.55 (t, J=8.4 Hz, 2H), 1.98-2.06 (m, 2H) ppm; MS (APCI+): 441.1 (M+1), LC-MS: 97.0%; HPLC 97.1% pure.

Example 122

Preparation of P-615

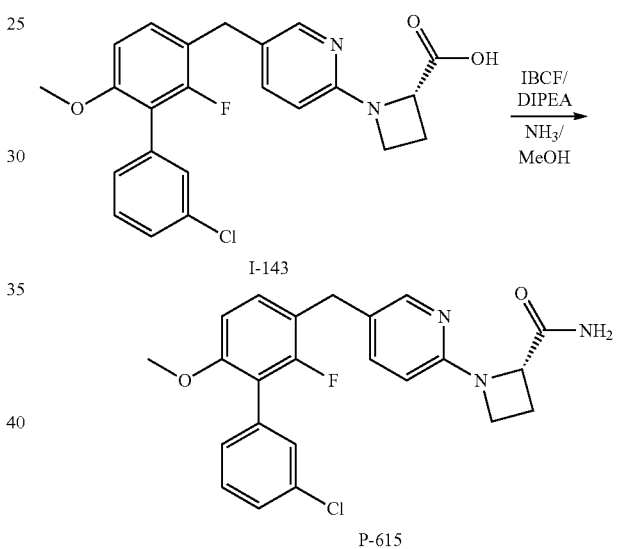

P-615

Synthesis of (S)-1-[5-(3'-chloro-2-fluoro-6methoxy-biphenyl-3-ylmethyl)-pyridin-2-yl]-azetidine-2-carboxylic acid amide (P-615). To a cooled (0-5° C.) and stirred solution of (S)-1-[5-(3'-chloro-2-fluoro-6methoxy-biphenyl-3-ylmethyl)-pyridin-2-yl]-azetidine-2-carboxylic acid (I-143, 0.22 g, 0.54 mmol) in THF (2.5 mL) was added N,N-diisopropylethylamine (0.07 g, 0.57 mmol). The reaction mixture was stirred for 5 min, isobutylchloroformate (0.08 g, 0.57 mmol) was added, stirred at 0-5° C. for 45 min. Ammonia in methanol (7M sol, 1.0 mL, 7.0 mmol) was added, the reaction warmed to room temperature, and stirred for 0.5 h. The reaction mixture was diluted with water (5 mL). The organic layer was separated, the aqueous layer was extracted with ethyl acetate (2×20 mL). The combined organic layers were dried with $Na_2SO_4$, filtered, and concentrated. The residue was purified by silica gel column chromatography using 5% methanol in dichloromethane, followed by preparative thin layer chromatography using 5% methanol in dichloromethane to afford 0.06 g (27%) of P-615 as an off-white solid. 1H NMR (DMSO-$d_6$, 400 MHz): 7.99 (d, J=2.8 Hz, 1H), 7.51 (br s, 1H), 7.34-7.46 (m, 4H), 7.24-7.3 (m, 2H), 7.14 (br s, 1H), 6.92 (d, J=8.4 Hz, 1H), 6.35 (d, J=8.4 Hz, 1H), 4.39 (dd, J=9.6, 6.8 Hz, 1H), 3.7-3.9 (m, 2H), 3.8 (s, 2H), 3.72 (s, 3H), 2.26-2.48 (m, 2H) ppm;

MS (APCI+): 426.6 (M+1), LC-MS: 98.0%.

Example 123

Preparation of P-617

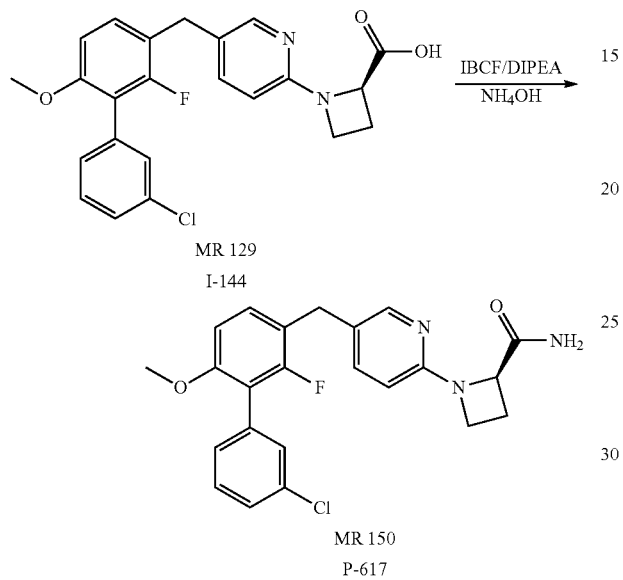

Synthesis of (R)-1-[5-(3'-chloro-2-fluoro-6methoxy-biphenyl-3-ylmethyl)-pyridin-2-yl]-azetidine-2-carboxylic acid amide (P-617). To a cooled 0-5° C. and stirred solution of (R)-1-[5-(3'-chloro-2-fluoro-6methoxy-biphenyl-3-ylmethyl)-pyridin-2-yl]-azetidine-2-carboxylic acid (I-144, 0.14 g, 0.33 mmol) in THF (2.5 mL) was added N,N-diisopropylethylamine (0.09 g, 0.69 mmol). The reaction mixture was stirred for 5 min, isobutylchloroformate (0.05 g, 0.36 mmol) was added, and the reaction stirred at 0-5° C. for 30 min. Ammonium hydroxide solution (28%, 1.0 mL, 8.0 mmol) was added, the reaction warmed to room temperature, and stirred for 0.5 h. The reaction mixture was diluted with water (5 mL). The organic layer was separated, the aqueous layer was extracted with ethyl acetate (2×20 mL). The combined organic layers were dried with Na$_2$SO$_4$, filtered, and concentrated. The residue was purified by silica gel column chromatography using 5% methanol in dichloromethane, followed by preparative thin layer chromatography using 5% methanol in dichloromethane to afford 0.07 g (47%) of P-617 as an off-white solid. 1H NMR (DMSO-d$_6$, 400 MHz): 7.99 (d, J=2.8 Hz, 1H), 7.51 (br s, 1H), 7.38-7.46 (m, 3H), 7.4 (br s, 1H), 7.24-7.3 (m, 2H), 7.14 (br s, 1H), 6.92 (d, J=8.4 Hz, 1H), 6.34 (d, J=8.0 Hz, 1H), 4.39 (dd, J=9.6, 6.8 Hz, 1H), 3.7-3.9 (m, 2H), 3.84 (s, 2H), 3.72 (s, 3H), 2.26-2.48 (m, 2H) ppm; MS (APCI+): 426.9 (M+1), LC-MS: 100%.

Example 124

Preparation of P-615-HCl

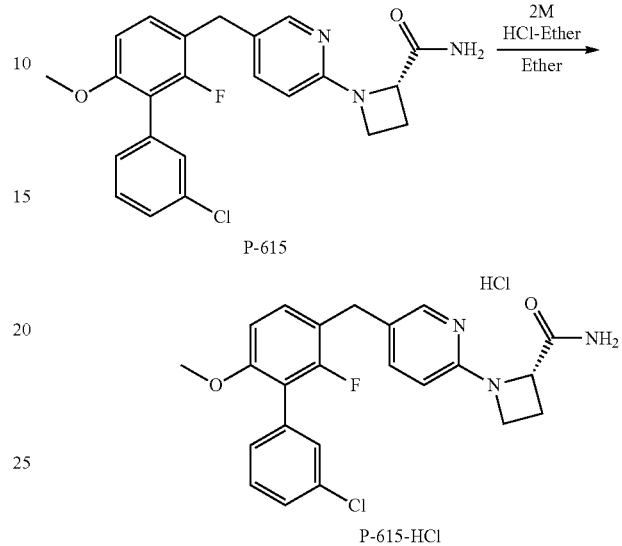

Synthesis of (S)-1-[5-(3'-chloro-2-fluoro-6methoxy-biphenyl-3-ylmethyl)-pyridin-2-yl]-azetidine-2-carboxylic acid amide hydrochloride (P-615-HCl). To a cooled (0-5° C.) and stirred solution of (S)-1-[5-(3'-chloro-2-fluoro-6methoxy-biphenyl-3-ylmethyl)-pyridin-2-yl]-azetidine-2-carboxylic acid amide (P-615, 0.04 g, 0.1 mmol) in ether (2 mL) was added 2M HCl in ether (0.5 ml, 1.0 mmol), and the reaction, stirred for 1 h. The ether layer was removed, again triturated with ether (2.0 mL), concentrated to afford 0.045 g (98%) of P-615-HCl as a white solid. 1H NMR (DMSO-d$_6$, 400 MHz): 7.92 (d, J=2.0 Hz, 1H), 7.78 (d, J=7.6 Hz, 1H), 7.69 (br s, 1H), 7.26-7.48 (m, 6H), 6.95 (d, J=8.8 Hz, 1H), 6.72 (d, J=9.2 Hz, 1H), 4.8-4.9 (m, 1H), 4.0-4.18 (m, 2H), 3.89 (s, 2H), 3.73 (s, 3H), 2.64-2.74 (m 1H), 2.26-2.34 (m, 1H) ppm; MS (APCI+): 426.16 (M+1), LC-MS: 98.8%; HPLC 98.3% pure.

Example 125

Preparation of P-617-HCl

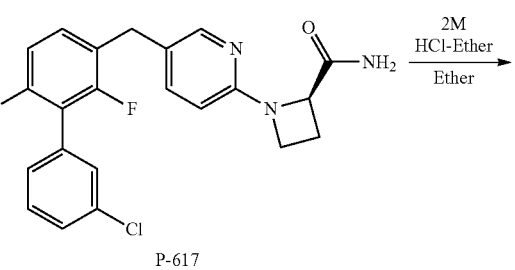

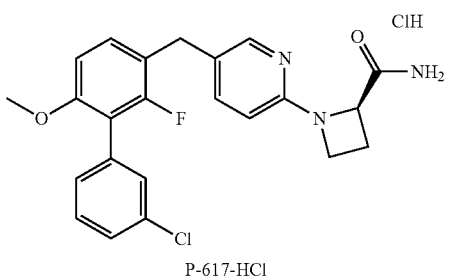

P-617-HCl

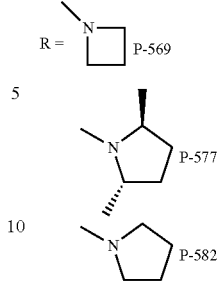

R =

P-569

P-577

P-582

Synthesis of (R)-1-[5-(3'-chloro-2-fluoro-6-methoxy-biphenyl-3-ylmethyl)-pyridin-2-yl]-azetidine-2-carboxylic acid amide hydrochloride (P-617-HCl): To a cooled (0-5° C.) and stirred solution of (R)-1-[5-(3'-chloro-2-fluoro-6methoxy-biphenyl-3-ylmethyl)-pyridin-2-yl]-azetidine-2-carboxylic acid (P-617, 0.057 g, 0.13 mmol) in ether (2 mL) was added 2M HCl in ether (0.65 ml, 1.3 mmol) and the reaction stirred for 1 h. The ether layer was removed, again triturated with ether (2.0 mL), concentrated to afford 0.059 g (98%) of P-617-HCl as a white solid. 1H NMR (DMSO-$d_6$, 400 MHz): 7.92 (d, J=2.0 Hz, 1H), 7.78 (d, J=7.6 Hz, 1H), 7.69 (br s, 1H), 7.26-7.48 (m, 6H), 6.95 (d, J=8.8 Hz, 1H), 6.72 (d, J=7.62 Hz, 1H), 4.8-4.9 (m, 1H), 4.0-4.16 (m, 2H), 3.89 (s, 2H), 3.73 (s, 3H), 2.64-2.74 (m 1H), 2.26-2.36 (m, 1H) ppm; MS (APCI+): 426.16 (M+1), LC-MS: 95.8%; HPLC 97.3% pure.

Scheme 36.

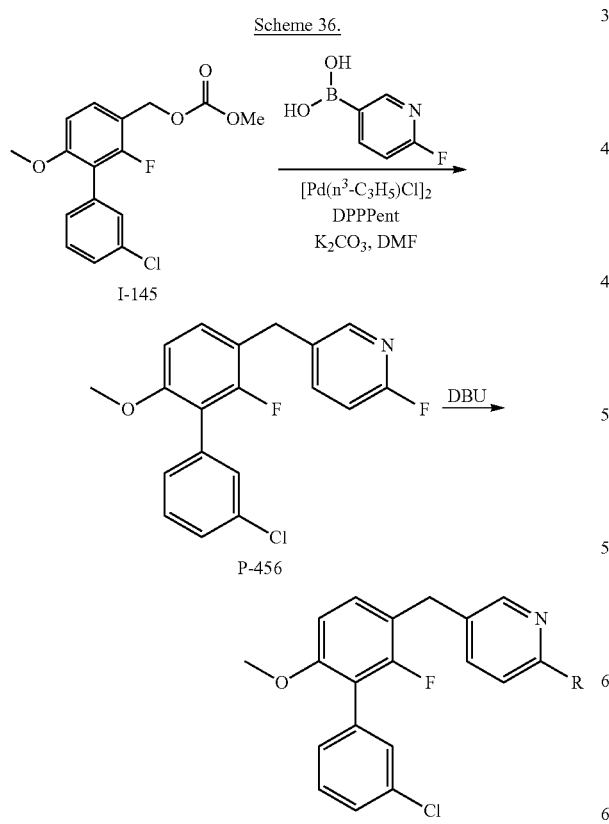

Example 126

Preparation of P-569

Synthesis of 5-(3'Chloro-2-fluoro-6-methoxy-biphenyl-3-ylmethyl)-2-fluoro-pyridine (P-456). In a 250 mL round bottomed flask equipped with a condenser, nitrogen lines and a stir bar was placed carbonic acid 3'-chloro-2-fluoro-6-methoxy-biphenyl-3-ylmethyl methylcarbonate (I-145, 3.61 g, 11.1 mmol), 2-fluoropyridineboronic acid (1.72 g, 12.2 mmol), potassium carbonate (4.60 g, 33.3 mmol), 1,5-bis(diphenylphosphino)pentane (1.47 g, 3.33 mmol) and DMF (56 mL). The reaction mixture was degassed for 15 minutes by bubbling nitrogen and then allylpalladium(II) chloride dimer (609 mg, 1.67 mmol) was added. The reaction mixture was heated to 85° C. for 18 hours. To the reaction mixture was added water (80 mL), and saturated ammonium chloride (150 mL). The aqueous portion was extracted with ethyl acetate (3×125 mL). The organic portions were combined, washed with brine (150 mL), dried (MgSO$_4$) and concentrated. The crude material was purified by column chromatography utilizing 10% hexanes/dichloromethane as the eluent to produce 2.45 g of P-456 as a pale yellow solid in 64% yield.

Synthesis of 2-Azetidin-1-yl-5-(3'-chloro-2-fluoro-6-methoxy-biphenyl-3-ylmethyl)-pyridine (P-569). In an 8 mL vial equipped with a stir bar was placed 5-(3'-chloro-2-fluoro-6-methoxy-biphenyl-3-ylmethyl)-2-fluoro-pyridine (P-456, 150 mg, 0.434 mmol), azetidine (88.0 uL, 1.30 mmol) and 1,8-diazabicyclo[5.4.0]undec-7-ene (306 uL, 2.17 mmol). The mixture was heated to 160° C. for 1 hour and then cooled to room temperature. The reaction mixture was treated with water (4 mL) and 1M HCl (6 mL). The aqueous portion was extracted with dichloromethane (2×30 mL), the organic portions were combined, washed with brine (15 mL), dried (MgSO$_4$) and concentrated to produce 156 mg of P-569 as a white solid in 94% yield.

$^1$H NMR (400 MHz, DMSO-$d_6$) δ 2.37-2.44 (m, 2H), 3.73 (s, 3H), 3.87 (s, 2H), 4.19 (t, J=8 Hz, 4H), 6.76 (bd, J=9 Hz, 1H), 6.95 (d, J=9 Hz, 1H), 7.28 (bd, J=7 Hz, 1H), 7.33 (d, J=8 Hz, 1H), 7.36 (bs, 1H), 7.42-7.48 (m, 2H), 7.76 (bd, J=9 Hz, 1H), 7.86 (s, 1H) ppm. MS (APCI+): 383.1 (M+1) LC-MS: 96%

Example 127

Preparation of P-577

Synthesis of 5-(3'-Chloro-2-fluoro-6-methoxy-biphenyl-3-ylmethyl)-2-((2S,5S)-2,5-dimethyl-pyrrolidin-1-yl)-pyridine (P-577): In an 8 mL vial equipped with a stir bar was placed 5-(3'Chloro-2-fluoro-6-methoxy-biphenyl-3-ylmethyl)-2-fluoro-pyridine (P-456, 100 mg, 0.289 mmol), (2S, 5S)-2,5-dimethyl-pyrrolidine (176 mg, 1.30 mmol) and 1,8-diazabicyclo[5.4.0]undec-7-ene (367 uL, 2.60 mmol). The mixture was heated to 160° C. for 3 hours and then cooled to room temperature. The reaction mixture was treated with water (4 mL) and 1M HCl (6 mL). The aqueous portion was extracted with dichloromethane (2×30 mL), the organic portions were combined, washed with brine (15 mL), dried (MgSO$_4$) and concentrated. The crude material was purified by silica gel column chromatography utilizing 5% acetone/dichloromethane as the eluent to produce 10 mg of P-577 as a pale viscous oil. $^1$H NMR (400 MHz, DMSO-d$_6$) δ 1.05 (d, J=6 Hz, 6H), 1.56-1.61 (m, 4H), 3.72 (s, 3H), 3.75 (s, 2H), 4.07-4.12 (m, 2H), 6.38 (d, J=9 Hz, 1H), 6.92 (d, J=8 Hz, 1H), 7.27-7.32 (m, 3H), 7.37 (s, 1H), 7.41-7.47 (m, 2H), 7.95 (d, J=2 Hz, 1H) ppm. MS (APCI+): 425.1 (M+1) LC-MS: 92%

Example 128

Preparation of P-582

Synthesis of 5-(3'-Chloro-2-fluoro-6-methoxy-biphenyl-3-ylmethyl)-2-pyrrolidin-1-yl-pyridine (P-582). In an 8 mL vial equipped with a stir bar was placed 5-(3'-chloro-2-fluoro-6-methoxy-biphenyl-3-ylmethyl)-2-fluoro-pyridine (P-456, 100 mg, 0.289 mmol), pyrrolidine (60.3 uL, 0.723 mmol) and 1,8-diazabicyclo[5.4.0]undec-7-ene (204 uL, 1.45 mmol). The mixture was heated to 160° C. for 30 minutes and then cooled to room temperature. The reaction mixture was diluted with dichloromethane (25 mL) and washed with 0.5M HCl (3×10 mL). The combined aqueous portions were extracted with dichloromethane (15 mL), the organic portions were combined, washed with brine (15 mL), dried (MgSO$_4$) and concentrated. The crude material was purified by silica gel column chromatography utilizing 10% acetone/dichloromethane as the eluent to produce 79 mg of P-582 as a pale orange semisolid in 69% yield. $^1$H NMR (400 MHz, DMSO-d$_6$) δ 1.89-1.93 (m, 4H), 3.31-3.34 (m, 4H), 3.71 (s, 3H), 3.77 (s, 2H), 6.37 (d, J=9 Hz, 1H), 6.91 (d, J=9 Hz, 1H), 7.23-7.28 (m, 2H), 7.32 (dd, J=9, 2 Hz, 1H), 7.36 (s, 1H), 7.41-7.47 (m, 2H), 7.95 (d, J=2 Hz, 1H) ppm. MS (APCI+): 397.1 (M+1) LC-MS: 98%

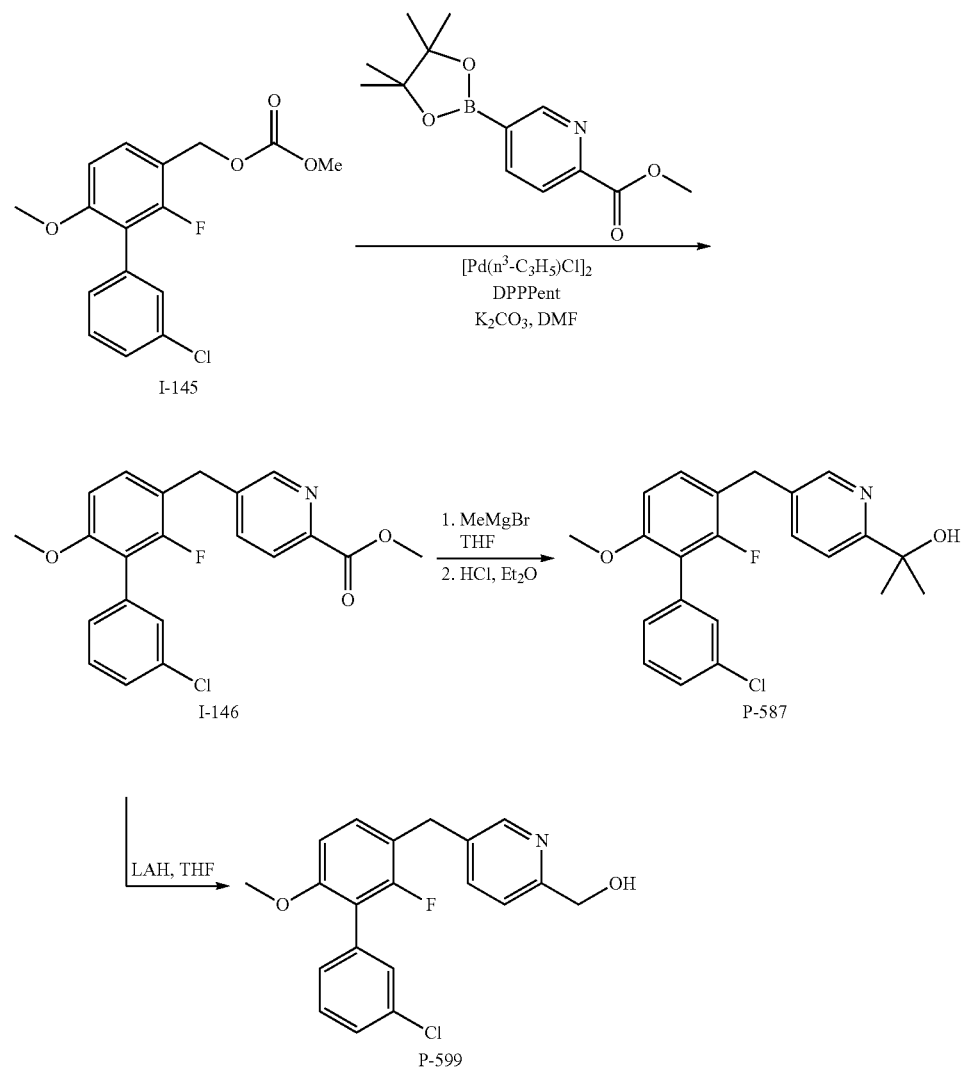

Scheme 37.

Example 129

Preparation of P-587

Synthesis of 5-(3'-chloro-2-fluoro-6-methoxy-biphenyl-3-ylmethyl)-pyridine-2-carboxylic acid methyl ester (I-146). In a 250 mL round bottomed flask equipped with a condenser, nitrogen lines and a stir bar was placed carbonic acid 3'-chloro-2-fluoro-6-methoxy-biphenyl-3-ylmethyl methyl-carbonate (I-145, 3.60 g, 11.1 mmol), 5-(4,4,5,5-Tetramethyl-[1,3,2]dioxaborolan-2-yl)-pyridine-2-carboxylic acid methyl ester (3.21 g, 12.2 mmol), potassium carbonate (4.60 g, 33.3 mmol), 1,5-bis(diphenylphosphino)pentane (1.47 g, 3.33 mmol) and DMF (56 mL). The reaction mixture was degassed for 15 minutes by bubbling nitrogen and then allylpalladium(II) chloride dimer (609 mg, 1.67 mmol) was added. The reaction mixture was heated to 85° C. for 8 hours. After the addition of water (50 mL) and dichlormethane (100 mL), the mixture was filtered through Celite. The layers were separated and the aqueous portion was extracted with dichlormethane (75 mL). The organic portions were combined, washed with brine (150 mL), dried (MgSO$_4$) and concentrated. The crude material was purified by column chromatography utilizing a gradient elution of 1%, 5%, 10% acetone/dichloromethane as the eluent to produce 3.13 g of I-146 as an orange-yellow viscous oil with solids forming in 73% yield.

Synthesis of 2-[5-(3'-Chloro-2-fluoro-6-methoxy-biphenyl-3-ylmethyl)-pyridin-2-yl]-propan-2-ol hydrochloride (P-587). In a 100 mL round bottomed flask was placed 5-(3'-chloro-2-fluoro-6-methoxy-biphenyl-3-ylmethyl)-pyridine-2-carboxylic acid methyl ester (I-146, 2.0 g, 5.18 mmol) and tetrahydrofuran (26 ml). The solution was cooled to 0° C. and then a solution of methylmagnesium bromide (3M in diethyl ether) (8.6 mL, 25.9 mmol) was added over a 10 minute period. The mixture was stirred at 0° C. for 5 minutes and then at room temperature for 3 hours. The reaction mixture was concentrated by a stream of nitrogen, cooled to 0° C. and then quenched slowly with saturated ammonium chloride (20 mL). The aqueous portion was extracted with ethyl acetate (3×40 mL), the organic portions were combined, washed with brine (25 mL), (MgSO$_4$) and concentrated. The crude material was purified by column chromatography utilizing 7% acetone/DCM as the eluent to produce a colorless viscous oil. This product was combined with material isolated from a 1.04 g run of the exact same reaction conditions and purification (442 mg as a white semi-solid isolated from the 1.04 gram run). The combined lots were purified by silica gel column chromatography utilizing a gradient elution of 50%, then 60% ethyl acetate/hexanes as the eluent to produce 1.33 g of P-587 as a colorless, viscous oil in 44% yield. In an 18 mL vial equipped with a stir bar was placed P-587 (325 mg, 0.842 mmol), diethyl ether (3.5 mL) followed by 2M HCl in diethyl ether (1.5 mL, 3.00 mmol). The mixture was stirred for 45 minutes, concentrated by stream of nitrogen and then dried in a high vacuum oven set at 40° C. for 18 hours to produce 355 mg of P-587HCl salt as an off-white solid. $^1$H NMR (400 MHz, DMSO-d$_6$) δ 1.53 (s, 6H), 3.74 (s, 3H), 4.13 (s, 2H), 6.98 (d, J=8 Hz, 1H), 7.29 (bd, J=7 Hz, 1H), 7.38 (s, 1H), 7.40-7.48 (m, 3H), 7.95 (bd, J=8 Hz, 1H), 8.18 (bs, 1H), 8.56 (s, 1H) ppm. MS (APCI+): 386.1 (M+1). HPLC purity: 98.8%.

Example 130

Preparation of P-599

Synthesis of [5-(3'-Chloro-2-fluoro-6-methoxy-biphenyl-3-ylmethyl)-pyridin-2-yl]-methanol (P-599). In an 8 mL vial equipped with a stir bar was placed 5-(3'-chloro-2-fluoro-6-methoxy-biphenyl-3-ylmethyl)-pyridine-2-carboxylic acid methyl ester (I-146, 100 mg, 0.259 mmol) and tetrahydrofuran (1.3 mL). The solution was cooled to 0° C. and then lithium aluminum hydride (39.3 mg, 1.04 mmol) was added resulting in strong gas evolution. Then mixture was stirred at 0° C. for 1 hour and then concentrated with a stream of nitrogen. The solid was diluted with dichloromethane (2 mL) and then slowly quenched with water (7 mL). The aqueous portion was extracted with DCM (3×6 mL), the organic portions were combined, filtered through Celite, dried (MgSO$_4$) and concentrated. The crude material was purified by silica gel column chromatography utilizing 30% acetone/dichloromethane to produce 22 mg of P-599 as a pale orange viscous oil in 24% yield.

$^1$H NMR (400 MHz, DMSO-d$_6$) δ 3.72 (s, 3H), 3.95 (s, 2H), 4.51 (s, 2H), 5.33 (bs, 1H), 6.94 (d, J=9 Hz, 1H), 7.27-7.46 (m, 6H), 7.61 (bd, J=8 Hz, 1H), 8.38 (s, 1H) ppm. MS (APCI+): 358.1 (M+1) LC-MS: 96%.

Example 131

Preparation of P-588

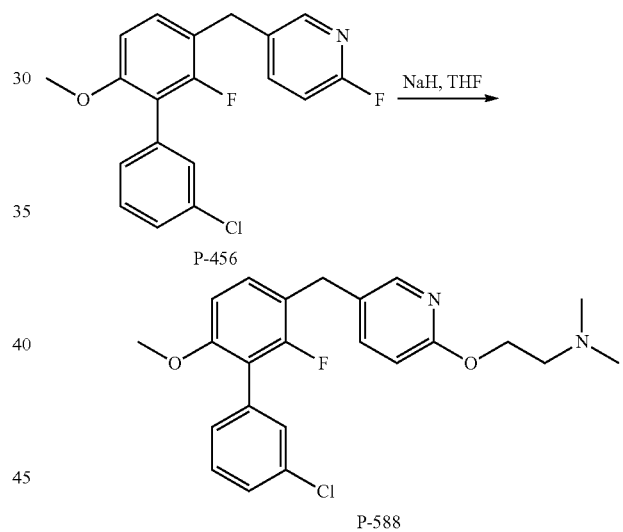

Synthesis of {2-[5-(3'-Chloro-2-fluoro-6-methoxy-biphenyl-3-ylmethyl)-pyridin-2-yloxy]-ethyl}-dimethyl-amine (P-588). In an 8 mL vial equipped with a stir bar was sodium hydride (34.7 mg, 0.867 mmol), THF (1.1 mL) and 2-diemethylamino-ethanol (87.2 uL, 0.867 mmol. The mixture was stirred for 5 minutes and then a solution of 5-(3'Chloro-2-fluoro-6-methoxy-biphenyl-3-ylmethyl)-2-fluoro-pyridine (P-456, 100 mg, 0.289 mmol) and THF (1.1 mL) was added. After stirring at 60° C. for 2 hours, the reaction was combined with a previous run (30 mg scale) and the quenched with water (20 mL). After extractions with ethyl acetate (2×30 mL),), the organic portions were combined, dried (MgSO$_4$), concentrated and dried in a high vacuum oven at 60° C. for 18 hours to produce 136 mg of P-588 as a cloudy, pale yellow viscous oil in 87% yield.

$^1$H NMR (400 MHz, DMSO-d$_6$) δ 2.18 (s, 6H), 2.57 (t, J=6 Hz, 2H), 3.72 (s, 3H), 3.87 (s, 2H), 4.28 (t, J=6 Hz, 2H), 6.73 (d, J=8 Hz, 1H), 6.93 (d, J=8 Hz, 1H), 7.27-7.29 (m, 1H), 7.32

(d, J=9 Hz, 1H), 7.37 (s, 1H), 7.41-7.47 (m, 2H), 7.53 (dd, J=8, 2 Hz, 1H), 8.03 (br s, 1H). MS (APCI+): 415.1 (M+1) LC-MS: >99%.

Example 132

Preparation of P-595

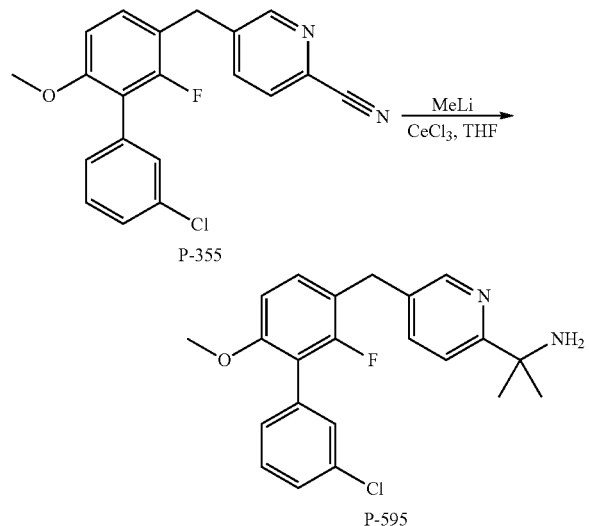

Synthesis of 1-[5-(3'-Chloro-2-fluoro-6-methoxy-biphenyl-3-ylmethyl)-pyridin-2-yl]-1-methyl-ethylamine (P-595). In an 18 mL vial equipped with a stir bar was placed cerium (III) chloride (315 mg, 1.28 mmol) which was placed under and vacuum and heated with heat gun to remove residual moisture. Then, THF (2 mL) was added and the mixture was cooled to 0° C. and stirred for 1 hour and then at room temperature for 25 minutes. After cooling to −78° C. for 15 minutes, methyl lithium (1.6M in diethyl ether) (800 uL, 1.28 mmol) was added and the mixture was stirred at −78° C. for 15 additional minutes. After this time period, a solution of 5-(3'-Chloro2-fluoro-6-difluoromethoxy-biphenyl-3-ylmethyl)-pyridine-2-carbonitrile (P-355, 150 mg, 0.425 mmol) and THF (800 uL) was added and the mixture was stirred at −78° C. for 1 hour and then reacted at room temperature for 2 hours. Additional methyl lithium (1.6M in diethyl ether) (530 uL, 0.850 mmol) was introduced after cooling to 0° C. and the mixture was allowed to react at room temperature for 1 hour. The reaction was then cooled to 0° C. and quenched with isopropanol (2 mL). After filtration through Celite, the filtrate was concentrated and then combined with material from a previous run (30 mg scale). The combined material was purified by silica gel column chromatography utilizing gradient elution of 10% 1M NH₃ in MeOH/dichloromethane and then 20% to produce 17 mg of P-595 as a dark orange oil in 8% yield. $^1$H NMR (400 MHz, DMSO-$d_6$) δ 1.35 (s, 6H), 3.72 (s, 3H), 3.93 (s, 2H), 6.95 (d, J=8 Hz, 1H), 7.27-7.47 (m, 6H), 7.55 (s, 1H), 8.40 (s, 1H) ppm.

MS (APCI+): 385.1 (M+1).

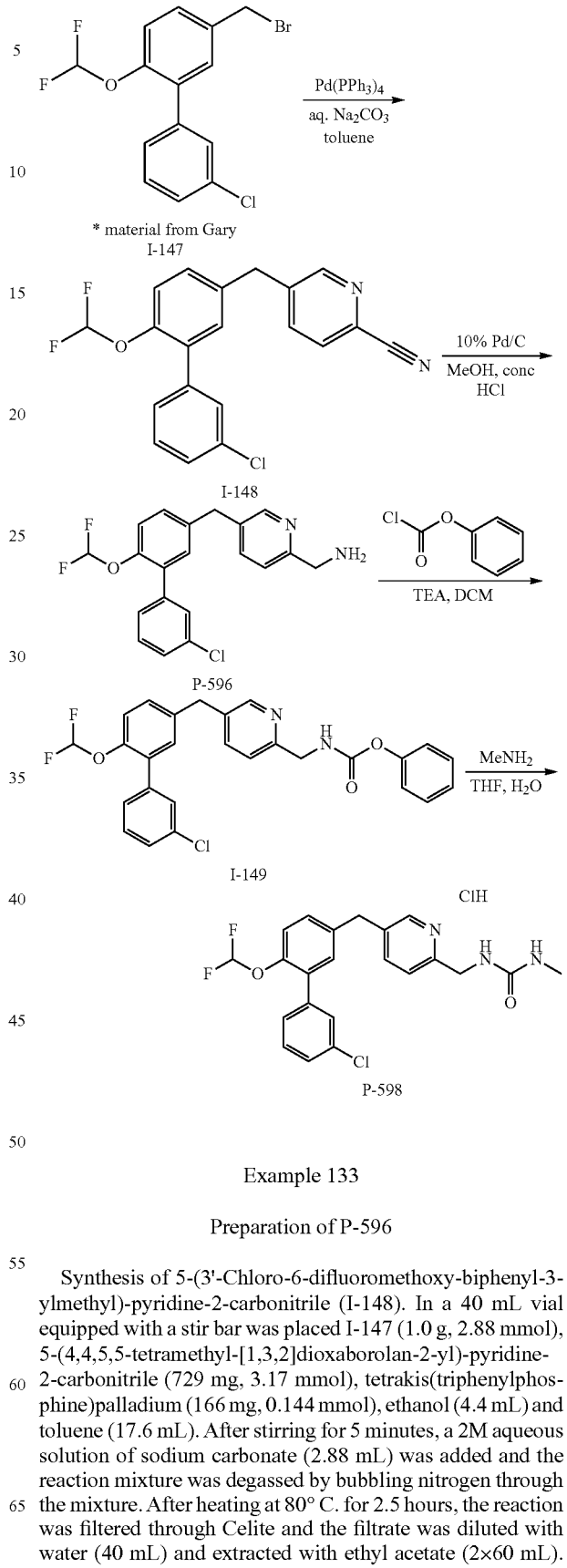

Example 133

Preparation of P-596

Synthesis of 5-(3'-Chloro-6-difluoromethoxy-biphenyl-3-ylmethyl)-pyridine-2-carbonitrile (I-148). In a 40 mL vial equipped with a stir bar was placed I-147 (1.0 g, 2.88 mmol), 5-(4,4,5,5-tetramethyl-[1,3,2]dioxaborolan-2-yl)-pyridine-2-carbonitrile (729 mg, 3.17 mmol), tetrakis(triphenylphosphine)palladium (166 mg, 0.144 mmol), ethanol (4.4 mL) and toluene (17.6 mL). After stirring for 5 minutes, a 2M aqueous solution of sodium carbonate (2.88 mL) was added and the reaction mixture was degassed by bubbling nitrogen through the mixture. After heating at 80° C. for 2.5 hours, the reaction was filtered through Celite and the filtrate was diluted with water (40 mL) and extracted with ethyl acetate (2×60 mL).

The organic portions were combined, dried (MgSO$_4$), concentrated and purified by silica gel column chromatography utilizing 40% ethyl acetate/hexanes as the eluent to produce 859 mg of I-148 as a yellow viscous oil in 80% yield.

Synthesis of C-[5-(3'-Chloro-6-difluoromethoxy-biphenyl-3-ylmethyl)-pyridin-2-yl]-methylamine (P-596). In a 40 mL vial equipped with a stir bar was placed 5-(3'-Chloro-6-difluoromethoxy-biphenyl-3-ylmethyl)-pyridine-2-carbonitrile (I-148, 860 mg, 2.32 mmol), methanol (20 mL) concentrated HCl (967 uL, 11.6 mmol) and 10% Pd/C. The reaction is allowed to stir at ambient temperature for 6 hours under a hydrogen atmosphere. After filtering the mixture through Celite, the filtrate is concentrated, diluted with 0.5M HCl (20 mL) and water (20 mL) followed by extractions with ethyl acetate (2×50 mL). The organic portions were combined, dried (MgSO$_4$), concentrated and purified by silica gel column chromatography utilizing 10% 1M NH$_3$ in MeOH/dichloromethane as the eluent to produce 121 mg of P-596 as a pale yellow solid in 14% yield.

$^1$H NMR (400 MHz, DMSO-d$_6$) δ 2.12 (bs, 2H), 3.74 (s, 2H), 3.99 (s, 2H), 7.11 (t, J=74 Hz, 1H), 7.23 (d, J=8 Hz, 1H), 7.32-7.35 (m, 2H), 7.40-7.51 (m, 5H), 7.64 (dd, J=10, 2 Hz, 1H), 8.45 (s, 1H) ppm. MS (APCI+): 375.1 (M+1), LC-MS: 99%.

Example 134

Preparation of P-598

Synthesis of [5-(3'-Chloro-6-difluoromethoxy-biphenyl-3-ylmethyl)-pyridin-2-ylmethyl]-carbamic acid phenyl ester (I-149). In an 8 mL vial equipped with a stir bar was placed C-[5-(3'-chloro-6-difluoromethoxy-biphenyl-3-ylmethyl)-pyridin-2-yl]-methylamine (P-596, 115 mg, 0.307 mmol), dichloromethane (1.5 mL) and triethylamine (85.6 uL, 0.614 mmol). The solution was cooled to 0° C. and then phenyl chloroformate (57.8 uL, 0.461 mmol) was added and the mixture was stirred at 0° C. for 15 minutes. The reaction was quenched with water (3 mL) and then the organic portion was removed. The aqueous portion was extracted with dichloromethane (2 mL), the organic portions were combined, washed with brine (3 mL), dried (MgSO$_4$), concentrated and purified by silica gel column chromatography utilizing 70% ethyl acetate/hexanes as the eluent to produce 78 mg of I-149 as a yellow viscous oil in 51% yield.

$^1$H NMR (400 MHz, DMSO-d$_6$) δ 4.01 (s, 2H), 4.32 (d, J=6 Hz, 2H), 6.92-7.39 (m, 9H), 7.41-7.48 (m, 4H), 7.51 (s, 1H), 7.71 (dd, J=8, 2 Hz, 1H), 8.292 (t, J=6 Hz, 1H), 8.51 (d, J=2 Hz, 1H). MS (APCI+): 495.1 (M+1). LC-MS: >99%.

Synthesis of 1-[5-(3'-Chloro-6-difluoromethoxy-biphenyl-3-ylmethyl)-pyridin-2-ylmethyl]-3-methyl-urea hydrochloride (P-598). In an 8 mL vial equipped with a stir bar was placed 5-(3'-chloro-6-difluoromethoxy-biphenyl-3-ylmethyl)-pyridin-2-ylmethyl]carbamic acid phenyl ester (I-149, 74 mg, 0.150 mmol), tetrahydrofuran (300 uL) and methylamine (40 wt. % in water) (116 uL, 1.50 mmol). The solution was stirred at room temperature for 2 hours and then concentrated by a stream of nitrogen. The solid was triturated with diethyl ether (2 mL), collected and washed with diethyl ether (2 mL) to produce 48 mg of P-598 as a white solid. To P-598 (41 mg, 0.0949) was added diethyl ether (2 mL) and 2M HCl in diethyl ether (700 uL). The mixture was stirred at ambient temperature for 2 hours, the solids collected, washed with diethyl ether (1 mL) and dried in a high vacuum oven to produce 35 mg of P-598HCl salt as a white solid in 50% yield.

$^1$H NMR (400 MHz, DMSO-d$_6$) δ 2.55 (s, 3H), 4.18 (s, 2H), 4.46 (s, 2H), 6.29 (bs, 1H), 6.78 (bs, 1H), 7.13 (t, J=74 Hz, 1H), 7.27 (d, J=8 Hz, 1H), 7.42-7.49 (m, 5H), 7.52 (s, 1H), 7.76 (d, J=8 Hz, 1H), 8.39 (d, J=8 Hz, 1H), 8.79 (s, 1H). MS (APCI+): 432.1 (M+1-HCl). LC-MS: >99%.

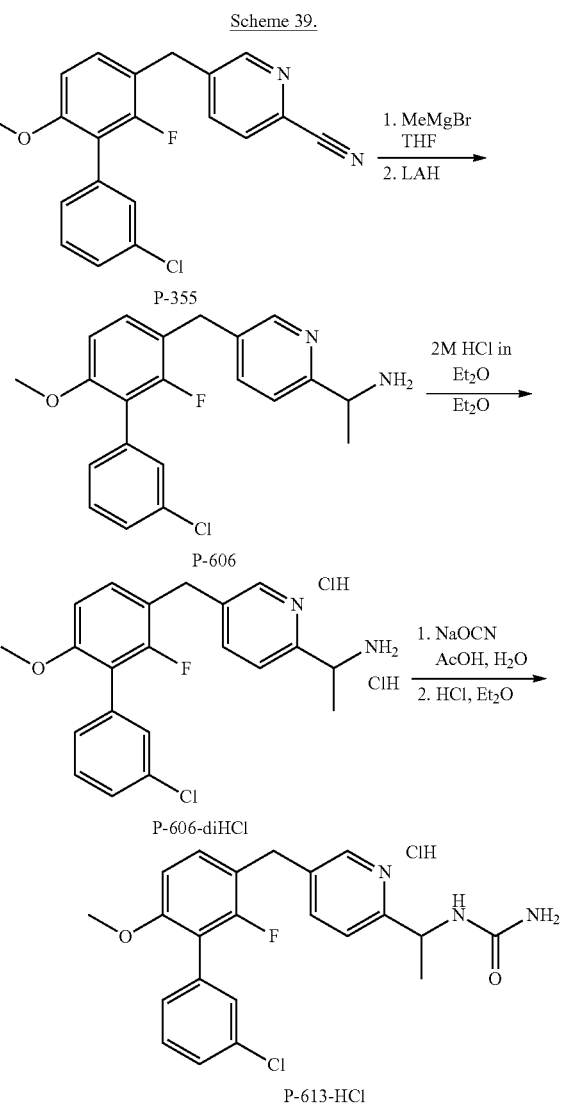

Scheme 39.

Example 135

Preparation of P-606

Synthesis of 1-[5-(3'-Chloro-2-fluoro-6-methoxy-biphenyl-3-ylmethyl)-pyridin-2-yl]-ethylamine (P-606). In a 40 mL vial equipped with a stir bar was placed methylmagnesium bromide (3M in diethyl ether) (1.32 mL, 3.96 mmol), nitrogen in/out lines attached and the solution was cooled to 0-5° C. After the addition of a solution of 5-(3'-Chloro2-fluoro-6-difluoromethoxy-biphenyl-3-ylmethyl)-pyridine-2-carbonitrile (P-355, 700 mg, 1.98 mmol) in tetrahydrofuran (10 mL), the reaction was warmed to ambient temperature and stirred for 40 minutes. Additional methylmagnesium bromide (3M in diethyl ether) (660 uL, 1.98 mmol) was introduced and the reaction was heated to 60° C. for 3 hours. The reaction was cooled to 0-5° C. and a slurry of lithium aluminum hydride (150 mg, 3.96 mmol) in tetrahydrofuran (1 mL)

was added. The reaction was heated to 60° C. for 1 hour and then partially concentrated, cooled to 0-5° C. and quenched with water (5 mL) and 1M NaOH (3 mL). After the addition of ethyl acetate (10 mL), the reaction was filtered through Celite and the filtrate layers were separated. The aqueous portion was extracted with ethyl acetate (30 mL), the organic portions were combined, dried (MgSO$_4$), concentrated and purified by a 50 gram silica gel SNAP cartridge (Biotage SP4 Flash Chromatography instrument) utilizing gradient elution of 5-40% MeOH/dichloromethane to produce 124 mg of P-606 as a yellow viscous oil in 17% yield. $^1$H NMR (400 MHz, DMSO-d$_6$) δ 1.26 (d, J=7 Hz, 3H), 3.72 (s, 3H), 3.94 (s, 2H), 3.99 (q, J=6 Hz, 1H), 6.94 (d, J=8 Hz, 1H), 7.27-7.29 (m, 1H), 7.32-7.38 (m, 3H), 7.41-7.47 (m, 2H), 7.57 (dd, J=8, 2 Hz, 1H), 8.39 (s, 1H). MS (APCI+): 372.3 (M+2). LC-MS: 95%

Example 136

Preparation of P-606-diHCl

Synthesis of 1-[5-(3'-Chloro-2-fluoro-6-methoxy-biphenyl-3-ylmethyl)-pyridin-2-yl]-ethylamine dihydrochloride (P-606-diHCl): In an 8 mL vial equipped with a stir bar was placed 1-[5-(3'-Chloro-2-fluoro-6-methoxy-biphenyl-3-ylmethyl)-pyridin-2-yl]-ethylamine (P-606, 115 mg, 0.311 mmol), diethyl ether (3 mL), 1,4-dioxane (300 uL) and 2M HCl in diethyl ether (600 uL). The mixture was stirred at ambient temperature for 15 minutes, the solid was collected, washed with diethyl ether (3 mL) and dried to produce 98 mg of P-606-diHCl as a light tan solid in 71% yield.

$^1$H NMR (400 MHz, DMSO-d$_6$) δ 1.47 (d, J=7 Hz, 3H), 3.73 (s, 3H), 4.01 (s, 2H), 4.46-4.51 (m, 1H), 6.96 (d, J=8 Hz, 1H), 7.27 (d, J=6 Hz, 1H), 7.36 (s, 1H), 7.38-7.48 (m, 4H), 7.72 (dd, J=8, 2 Hz, 1H), 8.33 (bs, 3H), 8.55 (d, J=2 Hz, 1H).
MS (APCI+): 371.5 (M+1-2HCl)
LC-MS: 92%

Example 137

Preparation of P-613

Synthesis of {1-[5-(3'-Chloro-2-fluoro-6-methoxy-biphenyl-3-ylmethyl)-pyridin-2-yl]-ethyl}-urea hydrochloride (P-613): In an 8 mL vial equipped with a stir bar was placed 1-[5-(3'-Chloro-2-fluoro-6-methoxy-biphenyl-3-ylmethyl)-pyridin-2-yl]-ethylamine dihydrochloride (P-606, 55 mg, 0.124 mmol), water (800 uL), glacial acetic acid (400 uL) followed by sodium cyanate (32.2 mg, 0.496 mmol). The mixture was stirred at room temperature for 18 hours and then slowly quenched with a saturated solution of sodium bicarbonate (3 mL) and extracted with dichloromethane (3×4 mL). The organic portions were combined, dried (MgSO$_4$), concentrated and purified by a 10 gram silica gel SNAP cartridge (Biotage SP4 Flash Chromatography instrument) utilizing gradient elution of 2-20% MeOH/dichloromethane to produce 13 mg of P-613 (free base) as an off-white solid in 25% yield. To P-613 (free base) (13 mg, 0.0314 mmol) was added diethyl ether (1 mL) and 2M HCl in diethyl ether (300 uL). The mixture was allowed to stir at room temperature for 10 minutes, concentrated and dried to produce 14 mg of P-613HCl salt as an off-white solid in quantitative yield. $^1$H NMR (400 MHz, DMSO-d$_6$) δ 1.36 (d, J=7 Hz, 3H), 3.73 (s, 3H), 4.06 (s, 2H), 4.82 (m, 1H), 5.53 (br s, 2H), 6.69 (br s, 1H), 6.97 (d, J=9 Hz, 1H), 7.29 (br d, J=6 Hz, 1H), 7.38-7.47 (m, 4H), 7.60 (br d, J=8 Hz, 1H), 8.02 (br d, J=8 Hz, 1H), 8.58 (s, 1H) ppm.

Scheme 40:

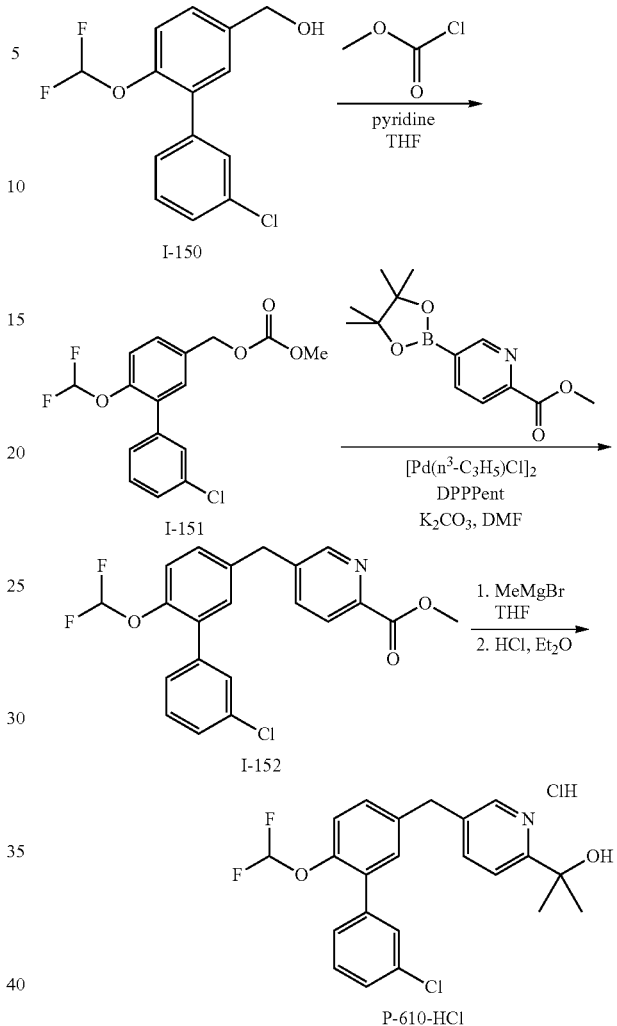

Example 138

Preparation of P-610

Synthesis of carbonic acid 3'-chloro-6-difluoromethoxy-biphenyl-3-ylmethyl ester methyl ester (I-151). Compound I-151 was synthesized following the same procedure as that for the generation of I-223.

Synthesis of 5-(3'-Chloro-6-difluoromethoxy-biphenyl-3-ylmethyl)-pyridine-2-carboxylic acid methyl ester (I-152). In a 40 mL vial equipped with a stir bar was placed carbonic acid 3'-chloro-6-difluoromethoxy-biphenyl-3-ylmethyl ester methyl ester (I-151, 700 mg, 2.04 mmol), 5-(4,4,5,5-tetramethyl-[1,3,2]dioxaborolan-2-yl)-pyridine-2-carboxylicacid methyl ester (590 mg, 2.24 mmol), potassium carbonate (846 mg, 6.12 mmol), 1,5-bis(diphenylphosphino)pentane (270 mg, 0.612 mmol) and DMF (10 mL). The reaction mixture was degassed for 15 minutes by bubbling nitrogen and then allylpalladium(II) chloride dimer (112 mg, 0.306 mmol) was added. The reaction mixture was heated to 85° C. for 4 hours. To the reaction mixture was added water (40 mL) and ethyl acetate (40 mL) and the mixture was filtered through Celite. The layers of the filtrate were separated and the aqueous portion was extracted with ethyl acetate (40 mL). The organic portions were combined, washed with brine (40 mL), dried (MgSO$_4$) and concentrated. The crude material was purified by a 50 gram silica gel SNAP cartridge (Biotage SP4 Flash Chromatography instrument) utilizing gradient elution of 12-100% ethyl acetate/hexanes to produce 458 mg of I-152 as a viscous yellow solid in 56% yield.

$^1$H NMR (400 MHz, DMSO-d$_6$) δ 3.86 (s, 3H), 4.12 (s, 2H), 7.13 (t, J=74 Hz, 1H), 7.25 (d, J=8 Hz, 1H), 7.37 (dd, J=8, 2 Hz, 1H), 7.57 (dt, J=7, 2 Hz, 1H), 7.44-7.52 (m, 4H), 7.88 (dd, J=8, 2 Hz, 1H), 7.99 (d, J=8 Hz, 1H), 8.71 (s, 1H) ppm. MS (APCI+): 404.5 (M+1). LC/MS: 98%.

Synthesis of 2-[5-(3'-Chloro-6-difluoromethoxy-biphenyl-3-ylmethyl)-pyridin-2-yl]-propan-2-ol hydrochloride (P-610). In a 40 mL vial equipped with a stir bar was placed 5-(3'-Chloro-6-difluoromethoxy-biphenyl-3-ylmethyl)-pyridine-2-carboxylic acid methyl ester (I-152, 385 mg, 0.953 mmol) and tetrahydrofuran (8 mL). The solution was cooled to 0° C. and then methylmagnesium bromide (3M in diethyl ether) (3.2 mL, 9.53 mmol) was added and the reaction was warmed to ambient temperature and allowed to stir for 2 hours. The reaction was concentrated, placed in an ice bath and slowly quenched with a saturated solution of ammonium chloride (5 mL). After adding dichloromethane (15 mL), the mixture was filtered through Celite, the layers of the filtrate were separated and the aqueous portion was extracted with dichloromethane (15 mL). The organic portions were combined, washed with brine (40 mL), dried (MgSO$_4$) and concentrated. The crude material was purified by a 10 gram silica gel SNAP cartridge (Biotage SP4 Flash Chromatography instrument) utilizing gradient elution of 2-20% acetone/dichloromethane to produce 183 mg P-610 as a colorless oil in 48% yield. To P-610 (175 mg, 0.433 mmol) was added diethyl ether (1 mL) and 2M HCl in diethyl ether (700 uL). The mixture was allowed to stir at room temperature for 20 minutes, concentrated and dried to produce 139 mg of P-610-HCl as an off-white solid in 73% yield. $^1$H NMR (400 MHz, DMSO-d$_6$) δ 1.53 (s, 6H), 3.82 (bs, 1H), 4.17 (s, 2H), 7.14 (t, J=74 Hz, 1H), 7.27 (d, J=9 Hz, 1H), 7.43-7.54 (m, 6H), 7.97 (bs, 1H), 8.32 (bs, 1H), 8.67 (s, 1H) ppm. MS (ESI+): 405.6 (M+1-HCl. LC/MS: 92%.

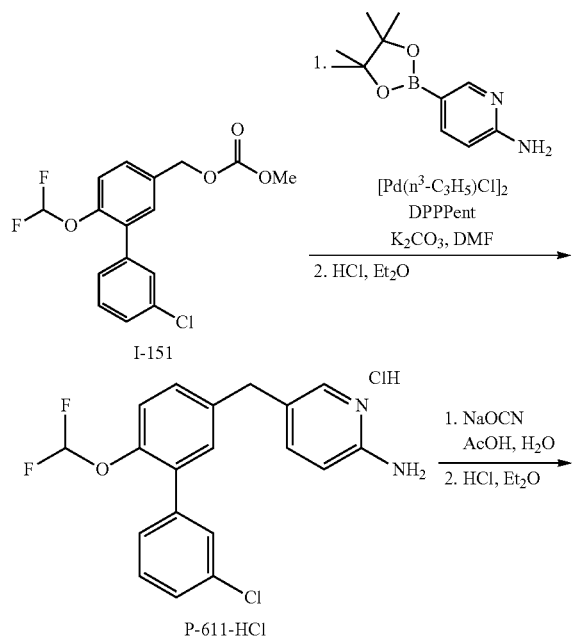

Scheme 41.

I-151

P-611-HCl

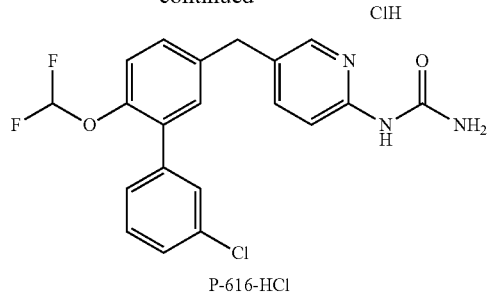

P-616-HCl

Example 139

Preparation of P-611

Synthesis of 5-(3'-Chloro-6-difluoromethoxy-biphenyl-3-ylmethyl)-pyridin-2-ylamine hydrochloride (P-611). In a 40 mL vial equipped with a stir bar was placed compound I-151 (1.0 g, 2.92 mmol), 5-(4,4,5,5-tetramethyl-[1,3,2]dioxaborolan-2-yl)-pyridin-2-ylamine (707 mg, 3.21 mmol), potassium carbonate (1.21 g, 8.76 mmol), 1,5-bis(diphenylphosphino)pentane (386 mg, 0.876 mmol) and DMF (15 mL). The reaction mixture was degassed for 15 minutes by bubbling nitrogen and then allylpalladium(II) chloride dimer (160 mg, 0.438 mmol) was added. The reaction mixture was heated to 85° C. for 4 hours. To the reaction mixture was added water (40 mL) and ethyl acetate (40 mL) and the mixture was filtered through Celite. The layers of the filtrate were separated and the aqueous portion was extracted with ethyl acetate (40 mL). The organic portions were combined, washed with brine (40 mL), dried (MgSO$_4$) and concentrated. The crude material was purified by a 50 gram silica gel SNAP cartridge (Biotage SP4 Flash Chromatography instrument) utilizing gradient elution of 1-10% methanol/dichloromethane to produce 841 mg of P-611 as a viscous dark yellow oil in 80% yield. To P-611 (840 mg, 2.33 mmol) was added 1,4-dioxane (8 mL) and 4M HCl in 1,4-dioxane (2 mL). The mixture was allowed to stir at room temperature for 20 minutes, concentrated and dried to produce 643 mg of P-611-HCl as a yellow-orange solid in 70% yield. $^1$H NMR (400 MHz, DMSO-d$_6$) δ 3.39 (bs, 2H), 3.89 (s, 2H), 6.932 (s, 1H), 7.14 (t, J=74 Hz, 1H), 7.26 (d, J=8 Hz, 1H), 7.36 (dd, J=9, 2 Hz, 1H), 7.42-7.52 (m, 4H), 7.85 (dd, J=9, 2 Hz, 1H), 7.91 (br s, 1H), 7.94 (br s, 1H), 13.71 (br s, 1H) ppm. LC/MS: 94%.

Example 140

Preparation of P-616

Synthesis of [5-(3'-Chloro-6-difluoromethoxy-biphenyl-3-ylmethyl)-pyridin-2-yl]-urea (P-616). In an 18 mL vial equipped with a stir bar was placed P-611 (80 mg, 0.222 mmol), glacial acetic acid (1.5 mL), water (750 uL) and sodium cyanate (57.7 mg, 0.888 mmol). The mixture was heated to 80° C. for 3 hours, cooled to room temperature, diluted with dichloromethane (4 mL) and slowly quenched with a saturated solution of sodium bicarbonate (20 mL) to pH 8. The layers were separated and the aqueous portion was extracted with dichloromethane (2×15 mL). The organic portions were combined, washed with brine (15 mL), dried (MgSO$_4$) and concentrated. The crude material was purified by silica gel column chromatography utilizing 5% methanol/dichloromethane as the eluent to produce a brown oil. To this material was added diethyl ether (1 mL) and 2M HCl in diethyl ether (500 uL). After stirring at room temperature for 30 minutes, the mixture was concentrated and dried to produce 39 mg of P-616-HCl as a yellow solid in 40% yield ¹H NMR (400 MHz, DMSO-$d_6$) δ 3.89 (s, 2H), 6.93 (d, J=9.0 Hz, 1H), 7.13 (t, J=74 Hz, 1H), 7.35 (dd, J=8, 2 Hz, 1H), 7.41-7.52 (m, 4H), 7.84 (d, J=2 Hz, 1H), 7.86-7.90 (m, 2H), 13.55 (s, 1H) ppm. MS (ESI+): 404.5 (M+1-HCl).

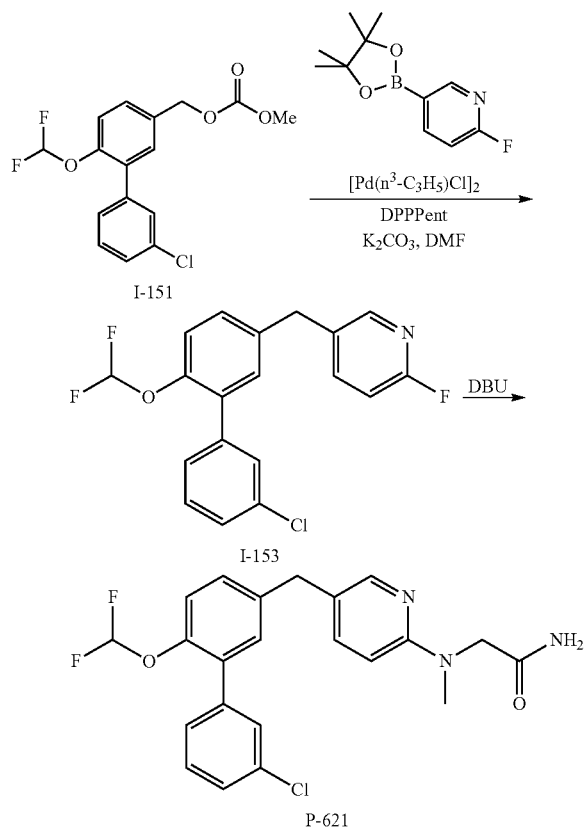

Example 141

Preparation of P-621

Synthesis of 5-(3'-Chloro-6-difluoromethoxy-biphenyl-3-ylmethyl)-2-fluoro-pyridine (I-153). Compound I-153 was prepared in a manner analogous to P-611 (Example 138) in 70% yield. MS (ESI+): 364.4 (M+1). LC/MS: 96%.

Synthesis of 2-{[5-(3'-Chloro-6-difluoromethoxy-biphenyl-3-ylmethyl)-pyridin-2-yl]-methyl-amino}-acetamide (P-621). In an 8 mL vial equipped with a stir bar was placed 5-(3'-Chloro-6-difluoromethoxy-biphenyl-3-ylmethyl)-2-fluoro-pyridine (I-153, 210 mg, 0.577 mmol), 2-methylamino-acetamide hydrochloride (216 mg, 1.73 mmol) and 1,8-diazabicyclo[5.4.0]undec-7-ene (488 uL, 3.46 mmol). The mixture was heated to 160° C. for 3 hours and then diluted with dichloromethane (5 mL). The organic portion was washed with 0.5M HCl (3 mL) and the aqueous washes were combined and extracted with dichloromethane (2×3 mL). The organic portions were combined, washed with brine (4 mL), dried (MgSO$_4$) and concentrated. The crude material was purified by Teledyne CombiFlash system utilizing a 12 g RediSepRf silica gel cartridge and a gradient elution of 0-30% methanol/dichloromethane, followed by preparative TLC (20×20 cm, 1000 microns) using 5% methanol/dichloromethane as the eluent to produce 8 mg of P-621?? as a dark brown semi-solid in 3% yield. ¹H NMR (400 MHz, DMSO-$d_6$) δ 2.98 (s, 3H), 3.83 (s, 2H), 4.03 (s, 2H), 6.53 (d, J=9 Hz, 1H), 7.10 (t, J=74 Hz, 1H), 7.21 (d, J=8 Hz, 1H), 7.30 (dd, J=8, 2 Hz, 1H), 7.36 (d, J=2 Hz, 1H), 7.40-7.50 (m, 5H), 8.01 (d, J=2 Hz, 1H) ppm. MS (APCI+): 432.1 (M+1). LC/MS: 86%.

Example 142

Preparation of P-618

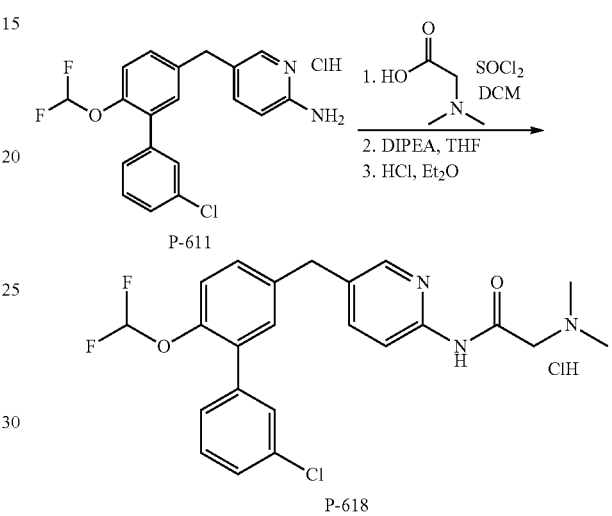

Synthesis of N-[5-(3'-Chloro-6-difluoromethoxy-biphenyl-3-ylmethyl)-pyridin-2-yl]-2-dimethylamino-acetamide hydrochloride (P-618). In an 18 mL vial equipped with a stir bar was placed dimethylglycine (58.5 mg, 0.567 mmol), dichloromethane (2.8 mL) and thionyl chloride (82.5 uL, 1.13 mmol). The solution was stirred at room temperature for 4 hours and then concentrated. To the reaction mixture was added a solution of P-611 (150 mg, 0.378 mmol), tetrahydrofuran (2.8 mL) and diisopropylethylamine (263 uL, 1.51 mmol). The mixture was stirred at ambient temperature for 2 hours and then heated to 45° C. for 60 hours. The reaction was concentrated, diluted with ethyl acetate (3 mL) and washed with water (5 mL). The layers were separated and the aqueous portion was extracted with ethyl acetate (3×3 mL). The organic portions were combined, washed with brine (5 mL), dried (MgSO$_4$) and concentrated. The crude material was purified by silica gel column chromatography utilizing 5% methanol/dichloromethane (with 1% AcOH) as the eluent, followed by preparative TLC (20×20 cm, 1500 microns) using 10% methanol/dichloromethane as the eluent to produce 27 mg of P-618 as an orange semi-solid in 16% yield. To P-618 (45 mg, 0.0561 mmol) was added diethyl ether (1 mL) and 2M HCl in diethyl ether (500 uL). The mixture was allowed to stir at room temperature for 20 minutes, concentrated and dried to produce 8 mg of P-618-HCl as a pale orange solid in 30% yield. ¹H NMR (400 MHz, DMSO-$d_6$) δ 2.86 (d, J=4 Hz, 6H), 4.00 (s, 2H), 4.16 (m, 2H), 7.17 (t, J=74 Hz, 1H), 7.25 (d, J=8 Hz, 1H), 7.34 (dd, J=8, 2 Hz, 1H), 7.41-7.51 (m, 5H), 7.77 (dd, J=8, 2 Hz, 1H), 7.97-7.99 (m, 1H), 8.34 (d, J=2 Hz, 1H), 9.82 (bs, 1H), 11.14 (s, 1H) ppm. MS (APCI+): 446.1 (M+1).

LC/MS: 96%

Example 143

Preparation of P-622

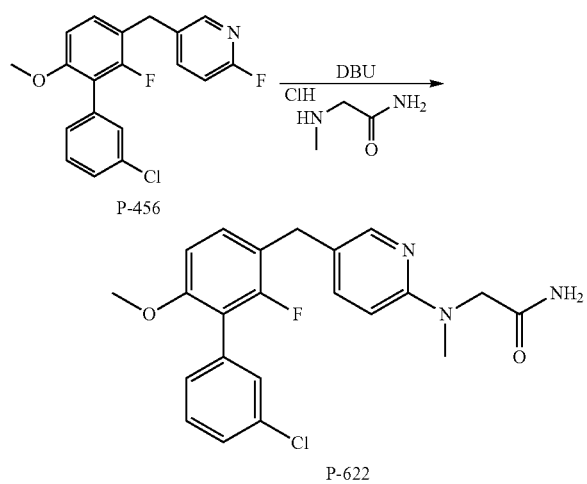

Synthesis of 2-{[5-(3'-Chloro-2-fluoro-6-methoxy-biphenyl-3-ylmethyl)-pyridin-2-yl]-methyl-amino}-acetamide (P-622). In an 8 mL vial equipped with a stir bar was placed P-456 (210 mg, 0.607 mmol), 2-methylamino-acetamide hydrochloride (227 mg, 1.82 mmol) and 1,8-diazabicyclo[5.4.0]undec-7-ene (513 uL, 3.64 mmol). The mixture was heated to 160° C. for 2.5 hours and then diluted with dichloromethane (5 mL). The organic portion was washed with 0.5M HCl (3×3 mL) and the aqueous washes were combined and extracted with dichloromethane (3×3 mL). The organic portions were combined, washed with brine (4 mL), dried (MgSO4) and concentrated. The crude material was purified by Teledyne CombiFlash system utilizing a RediSepRf 12 g silica gel cartridge and a gradient elution of 0-30% isopropanol/dichloromethane to produce material that still contained impurities. The impure material was purified by preparative TLC (20×20 cm, 1000 microns) using 10% isopropanol/dichloromethane as the eluent to produce 89 mg of P-622 as a yellow solid in 35% yield. $^1$H NMR (400 MHz, DMSO-$d_6$) δ 2.99 (s, 3H), 3.71 (s, 3H), 3.78 (s, 2H), 4.03 (s, 2H), 6.53 (d, J=9 Hz, 1H), 6.90-6.92 (m, 2H), 7.23-7.25 (m, 1H), 7.28 (d, J=8 Hz, 2H), 7.34-7.37 (m, 2H), 7.40-7.47 (m, 2H), 7.95 (d, J=2 Hz, 1H) ppm. MS (APCI+): 414.1 (M+1).

Example 144

Preparation of P-573

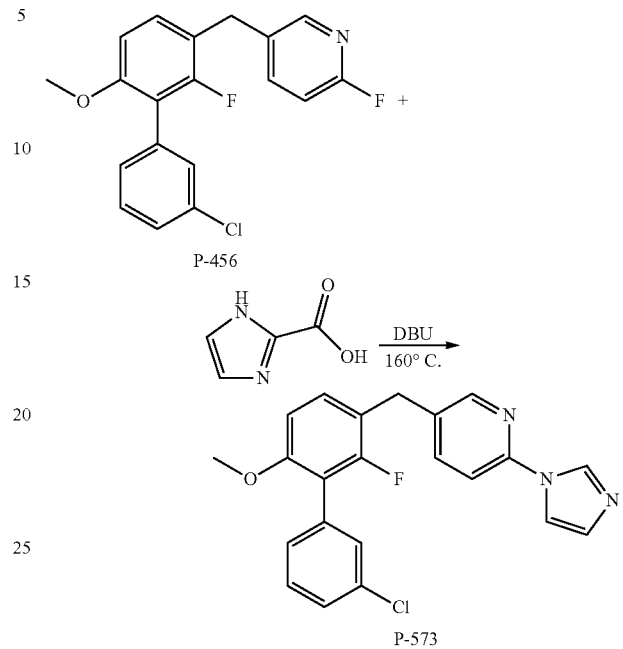

Synthesis of 5-(3'-chloro-2-fluoro-6-methoxy-biphenyl-3-ylmethyl)-2-imidazol-1-yl-pyridine (P-573). To a 20 mL vial which contained P-456 (200 mg, 0.55 mmol) and 1H-imidazole-2-carboxylic acid (202 mg, 1.8 mmol) was added DBU (0.5 mL, excess), at rt. The vial was sealed and the mixture was allowed to heat to 160° C. and stir at 160° C. for 2.5 h. The mixture was cooled to rt and then poured onto 20 mL ice-water solution, acidified with 2N HCl to pH=1-2, extracted with ethyl acetate (3×15 mL), washed with water (3×15 mL), brine (20 mL) and dried over Na2SO4. After removal of solvent, the residue was separated by a chromatography on silica gel with dichloromathane/iPA as eluent to yield P-573 (60 mg) in 26% yield.

1H NMR (DMSO-$d_6$, 400 MHz): 8.48 (s, 1H), 8.40 (d, J=2.4 Hz, 1H), 7.91 (br s, 1H), 7.85 (dd, J=8.2, 2.4 Hz, 1H), 7.74 (d, J=9.2 Hz, 1H), 7.27-7.47 (m, 5H), 7.11 (s, 1H), 6.86 (d, J=7.6 Hz, 1H), 4.01 (s, 2H), 3.73 (s, 3H) ppm.

LC/MS: 393.84 Calc. 393.8; APCI+ (M+1): 394.1, 99%

Scheme 43.

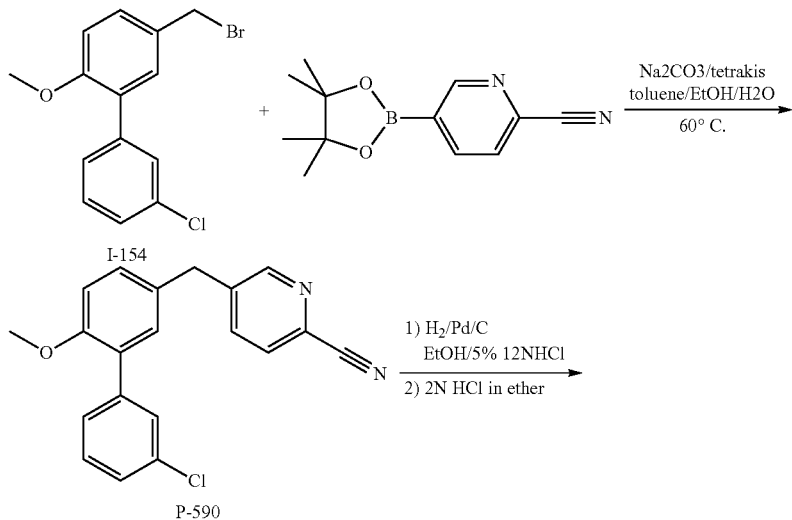

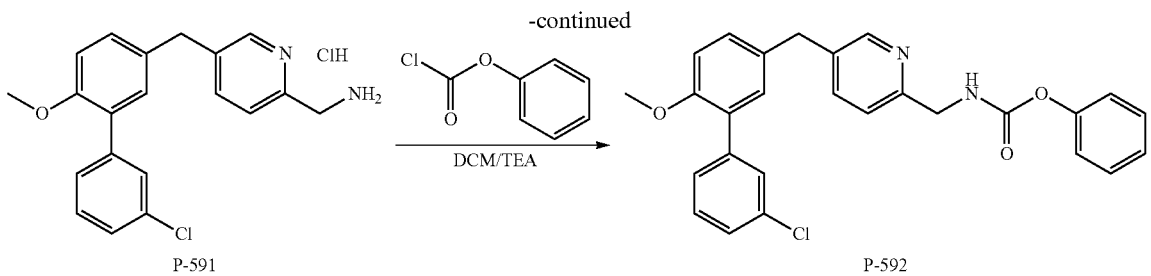

P-591 → P-592

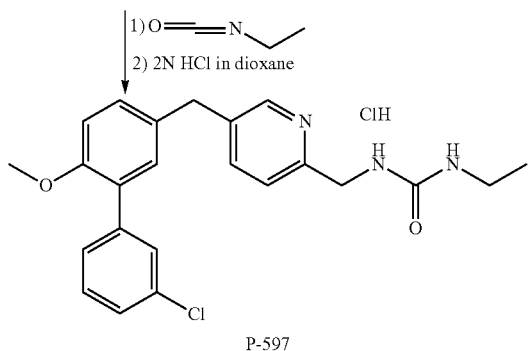

P-597

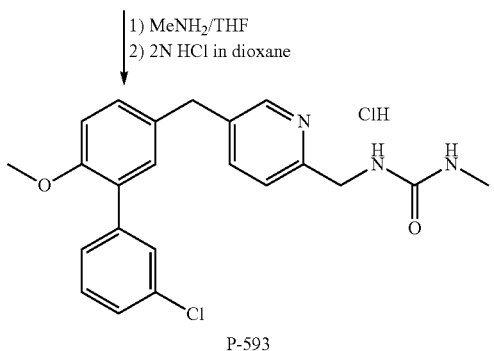

P-593

Example 145

Preparation of P-590

Synthesis of 5-(3'-chloro-6-methoxy-biphenyl-3-ylmethyl)-pyridine-2-carbonitrile (P-590). To a 100 mL flask which contained the mixture of I-154 (1324 mg, 4 mmol) and 5-(4,4,5,5-tetramethyl-[1,3,2]dioxaborolan-2-yl)-pyridine-2-carbonitrile (1.1 g, 4.4 mmol) in toluene/EtOH/H$_2$O (4/1/1, 25 mL) was added potassium phosphate (1.7 g, 8 mmol) and tetrakis(triphenylphosphine)palladium (0) (400 mg, 0.3 mmol) under nitrogen. The reaction mixture was stirred at 60° C. for 4 h. The reaction mixture was cooled to ambient temperature, poured onto ice-water solution (100 mL), and extracted with ethyl acetate (3×30 mL). The combined organic layers was washed with water (30 mL), brine (25 mL), dried over Na$_2$SO$_4$, and concentrated in vacuo. The residue was separated by a chromatography on silica gel with ethyl acetate-hexane as eluent to afford P-590 (380 mg, 27%). $^1$H NMR (CDCl$_3$, 400 MHz): 8.61 (s, 1H), 7.61 (d, J=1.2 Hz, 2H), 7.46-7.48 (m, 1H), 7.29-7.37 (m, 3H), 7.11 (dd, J=8.4, 2.4 Hz, 1H), 7.08 (d, J=2.4 Hz, 1H), 6.94 (d, J=8.4 Hz, 1H), 4.03 (s, 2H), 3.81 (s, 3H) ppm.

Example 146

Preparation of P-591

Synthesis of C-[5-(3'-chloro-6-methoxy-biphenyl-3-ylmethyl)-pyridin-2-yl]-methylamine hydrochloride (P-591). To a 50 mL flask which contained P-590 (220 mg, 0.66 mmol) in EtOH (14 mL) was added 12 N HCl (1 mL) and then Pd/C (10%, 200 mg) at rt. The system was allowed to stir at ambient temperature under a hydrogen atmosphere (15 psi) for 3 h. The solids were removed by filtration and the filtrate was concentrated. The residue was purified via chromatography on silica gel with ethyl acetate as eluent to yield P-591 (160 mg) in 70% yield. P-591 (25 mg) was treated with 2N HCl in diethyl ether (2 mL) to afford P-591HCl salt (16 mg) in 60% yield. $^1$H NMR (DMSO-d$_6$, 400 MHz): 8.54 (s, 1H), 8.26 (br. s, 2H), 7.76 (d, J=8.4 Hz, 1H), 7.39-7.47 (m, 4H), 7.22-7.27 (m, 2H), 7.06 (d, J=8.4 Hz, 1H), 4.14 (br s, 2H), 3.99 (s, 2H), 3.74 (s, 3H) ppm.

Calc. 338.84; APCI$^+$ (M+1): 339.1, 100%.

Example 147

Preparation of P-592

Synthesis of [5-(3'-Chloro-6-methoxy-biphenyl-3-ylmethyl)-pyridin-2-ylmethyl]-carbamic acid phenyl ester (P-592). To a 20 mL vial which contained P-591 (140 mg, 0.4 mmol) and triethylamine (85 mg, 0.8 mmol) in dichloromethane (3 mL) was added phenyl chloroformate (95 mg, 0.6 mmol) at 0-5° C. The reaction mixture was allowed to warm to ambient temperature and stir for 1 h. The mixture was poured onto 30 mL ice-water solution, extracted with dichloromethane (3×15 mL). The combined organic layers were washed with water (20 mL), brine (15 mL), dried over Na$_2$SO$_4$, and concentrated in vacuo. The residue was purified via chromatography on silica gel with ethyl acetate-hexane as eluent to yield 150 mg (79%) of P-592. 1H NMR (CDCl$_3$, 400 MHz): 8.46 (s, 1H), 7.48-7.52 (m, 2H), 7.11-7.37 (m, 10H), 6.92 (d, J=8.4 Hz, 1H), 6.13 (br.s, 1H), 4.55 (d, J=4.8 Hz, 2H), 3.97 (s, 2H), 3.80 (s, 3H) ppm.

Calc. 458.9; APCI$^+$ (M+1): 459.1, 100%.

Example 148

Preparation of P-597

Synthesis of 1-[5-(3'-chloro-6-methoxy-biphenyl-3-ylmethyl)-pyridin-2-ylmethyl]-3-ethyl-urea hydrochloride (P-597). To a 20 mL vial which contained P-591 (66 mg, 0.2 mmol) in pyridine (2 mL) was added isocyanato-ethane (0.2 mL, excess) at ambient temperature, and the resultant mixture stirred for 48 h. The mixture was poured onto 20 mL ice-water solution and the solid was filtered, washed with water (2×20 mL) and air dried to afford 55 mg of P-597. The free base was treated with 4N HCl in dioxane at ambient temperature to afford 55 mf of P-597HCl salt in 63% yield. 1H NMR (DMSO-d$_6$, 400 MHz). 8.72 (s, 1H), 8.29 (d, J=7.6 Hz, 1H), 7.68 (d, J=8.8 Hz, 1H), 7.50 (br s, 1H), 7.37-7.41 (m, 3H), 7.29-7.31 (m, 2H), 7.08 (d, J=8.8 Hz, 1H), 6.67 (s, 1H), 6.36 (s, 1H), 4.44 (s, 2H), 4.09 (s, 2H), 3.75 (s, 3H), 3.00 (d, J=7.2 Hz, 2H), 0.98 (t, J=7.2 Hz, 3H) ppm.

Example 149

Preparation of P-593

Synthesis of 1-[5-(3'-chloro-6-methoxy-biphenyl-3-ylmethyl)-pyridin-2-ylmethyl]-3-methyl-urea hydrochloride (P-593). To a 20 mL vial which contained P-592 (92 mg, 0.2 mmol) in THF (3 mL) was added excess methylamine (40% in H$_2$O, 1 mL), and the resultant mixture allowed to stir at ambient temperature for 4 h. The solvent was removed and diethyl ether (10 mL) was added. The solids were filtered, washed with diethyl ether (2×5 mL) and air dried to afford 50 mg of P-593. The free base was treated with 4 N HCl in dioxane (0.5 mL) to afford 45 mg of P-593HCl salt in 52% yield. $^1$H NMR (DMSO-d$_6$,400 MHz): 8.77 (s, 1H), 8.41 (d, J=8.4 Hz, 1H), 7.78 (d, J=8.4 Hz, 1H), 7.51 (s, 1H), 7.31-7.44 (m, 5H), 7.08 (d, J=8.4 Hz, 1H), 6.90 (s, 1H), 4.49 (s, 1H), 4.12 (s, 3H), 3.75 (s, 3H), 2.54 (s, 2H) ppm. Calc. 395.88; APCI$^+$ (M+1): 396.1, 100%.

Example 150

Preparation of P-600

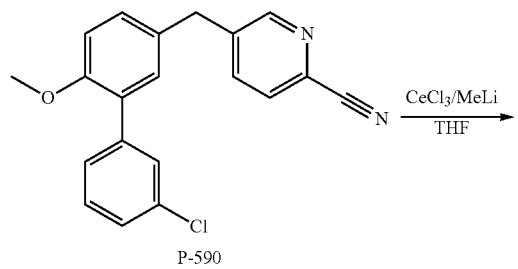

P-590

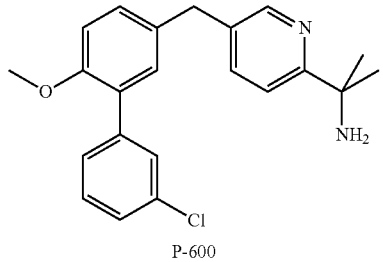

P-600

Synthesis of 1-[5-(3'-chloro-6-methoxy-biphenyl-3-ylmethyl)-pyridin-2-yl]-methylamine hydrochloride (P-600). A 50 mL flask which contained CeCl$_3$ (370 mg, 1. mmol) was dried with a heat gun for 0.5 h. After cooling to ambient temperature, THF (5 mL) was added and the mixture was allowed to stir for 2 h, and cooled to −78° C. Methyl lithium (1 M in ether, 1 mL) was added at −78° C. and stirred at −78° C. for 1 h and then P-590 (170 mg, 0.5 mmol) in THF (0.5 mL) was added. The mixture was allowed to stir at −78° C. for 0.5 h, allowed to warm to ambient temperature, and stirred for 16 h. The reaction was quenched with the addition of isopropanol (1 mL). The solids were removed by filtration, and the filtrate concentrated. The residue was purified via chromatography on silica gel with ethyl acetate-EtOH as eluent to yield 30 mg of P-600 which was treated with 2N HCl in diethyl ether (2 mL) to afford 15 mg of P-600HCl salt in 8% yield.

$^1$H NMR (DMSO-d$_6$,400 MHz): 8.59 (d, J=2.0 Hz, 1H), 8.39 (br s, 2H), 7.80 (dd, J=8.0, 2.0 Hz, 1H), 7.54 (d, J=8.4 Hz, 1H), 7.48 (br s, 1H), 7.36-7.45 (m, 3H), 7.25-7.28 (m, 2H), 7.06 (d, J=9.2 Hz, 1H), 3.99 (s, 2H), 3.74 (s, 3H), 1.57 ppm (s, 6H) ppm. LC/MS: Calc. 409.9; APCI+ (M+1): 410.1, 100%

Scheme 44.

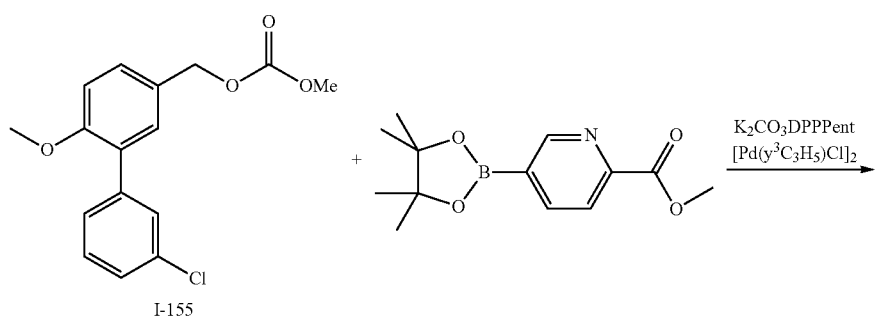

I-155

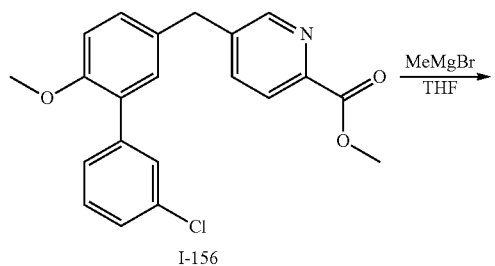

I-156

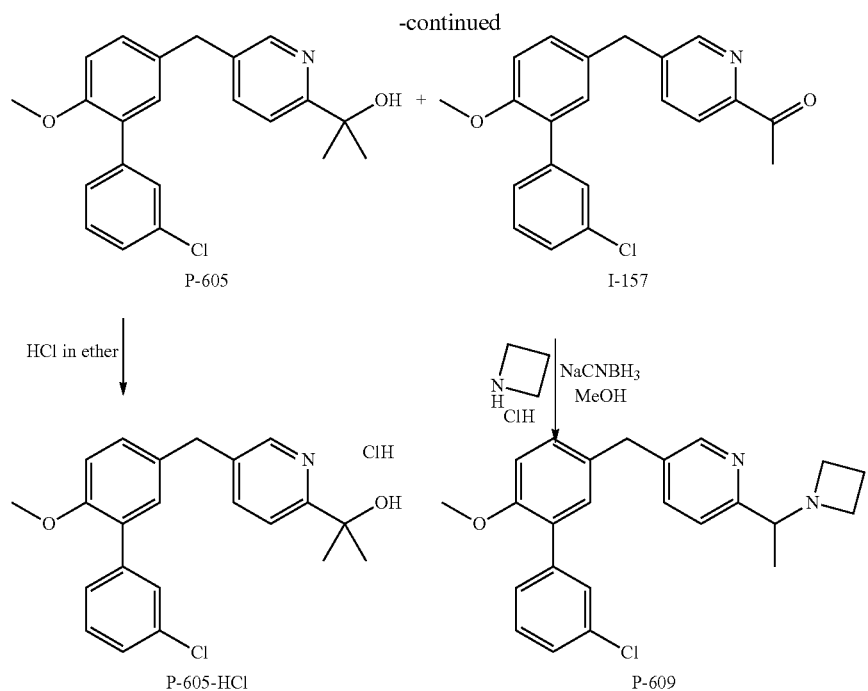

P-605                I-157

P-605-HCl           P-609

Example 151

Preparation of P-605

Synthesis of 5-(3'-chloro-6-methoxy-biphenyl-3-ylmethyl)-pyridine-2-carboxylic methyl ester (I-156). To a 250 mL flask which contained the mixture of I-155 (2.0 g, 6.6 mmol) and 5-(4,4,5,5-tetramethyl-[1,3,2]dioxaborolan-2-yl)-pyridine-2-carboxylic acid methyl ester (1.6 g, 6 mmol) in DME (30 mL) was added $K_2CO_3$ (2.5 g, 18 mmol), [Pd$(y^3C_3H_5Cl)]_2$ (300 mg, 0.8 mmol) and DPPPent (800 mg, 1.9 mmol) at rt under nitrogen. The reaction mixture was heated to 85° C. and stirred at 85° C. for 16 h. The reaction mixture was cooled to rt, poured onto ice-water (200 mL), The semi-solid which formed was separated from the aq. layer to provide the crude which was purified by a chromatography on silica gel with dichloromethane-acetone as eluent to yield I-156 (1200 mg, 50%). 1H NMR (CDCl$_3$, 400 MHz): 8.64 (s, 1H), 8.05 (d, J=8.0 Hz, 1H), 7.62 (d, J=8.0 Hz, 1H), 7.47 (s, 1H), 7.29-7.36 (m, 2H), 7.11 (d, J=8.0 Hz, 1H), 7.09 (d, J=2.0 Hz, 1H), 6.93 (d, J=8.4 Hz, 1H), 4.04 (s, 2H), 3.99 (s, 3H), 3.80 (s, 3H) ppm. LC/MS: Calc. 367.84; APCI+ (M+1): 368.1, 99%.

Synthesis of 2-[5-(3'-chloro-6-methoxy-biphenyl-3-ylmethyl)-pyridin-2-yl]-propan-2-ol HCl salt (P-605) and 1-[5-(3'-chloro-6-methoxy-biphenyl-3-ylmethyl)-pyridin-2-yl]-ethanone (I-157). To a 50 mL dried flask containing I-156 (350 mg, 1 mmol) in THF (5 mL) and cooled to 0° C. was added methylmagnesium bromide (3M in ether, 3 mL, 9 mmol). The reaction mixture was allowed to warm to ambient temperature and stirred for 16 h, and then poured onto 50 mL ice-water. The mixture was neutralized with NH$_4$Cl (sat. 10 mL), extracted with ethyl acetate (3×20 mL), and the organics washed with water (20 mL), brine (20 mL) and dried over Na$_2$SO$_4$. After removal of solvent, the residue was purified by silica gel column chromatography with dichloromethane-acetone as eluent to give 100 mg of the P-605 in 28% yield and 60 mg of I-157 in 15% yield. 50 mg of P-605 was treated with 2N HCl in diethyl ether (1 mL) to afford 55 mg of P-605HCl salt in 99% yield. $^1$H NMR (DMSO-d$_6$, 400 MHz): 8.60 (br s, 1H), 7.85-8.24 (m, 2H), 7.30-7.52 (m, 6H), 7.08 (d, J=6.8 Hz, 1H), 4.08 (s, 2H), 3.75 (s, 3H), 1.51 ppm (s, 6H) ppm.
LC/MS: Calc. 367.88; APCI+ (M+1): 368.1, 96%.

Example 152

Preparation of P-609

Synthesis of 2-(1-azetidin-1-yl-ethyl)-5-(3'-chloro-6-methoxy-biphenyl-3-ylmethyl)-pyridine (P-609). To a 25 mL vial which contained I-157 (52 mg, 0.15 mmol) and azetidine HCl salt (30 mg, 0.3 mmol) in MeOH (2 mL) was added sodium cyanoborohydride (16 mg, 22 mmol) at 0° C. The reaction mixture was allowed to warm to ambient temperature and stir for 72 h. The mixture was poured onto 5 mL 0.5 N aqueous sodium hydroxide solution and extracted with ethyl acetate (3×10 mL). The combined organics were washed with water (10 mL), brine (10 mL) and dried over Na$_2$SO$_4$. After removal of the solvent, the residue was purified by a chromatography on silica gel with dichloromethane-acetone as eluent to afford 30 mg of P-609 in 54% yield.

$^1$H NMR (CDCl$_3$, 400 MHz): 8.41 (d, J=2.0 Hz, 1H), 7.27-7.48 (m, 6H), 7.10-7.15 (m, 2H), 6.91 (d, J=8.0 Hz, 1H), 3.92 (s, 2H), 3.79 (s, 3H), 3.41-3.46 (m, 1H), 3.10-3.25 (m, 4H), 2.00-2.07 (m, 2H), 1.21 (d, J=6.4 Hz, 3H) ppm.

Example 153

Preparation of P-567

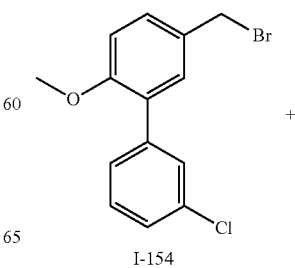

I-154

231

-continued

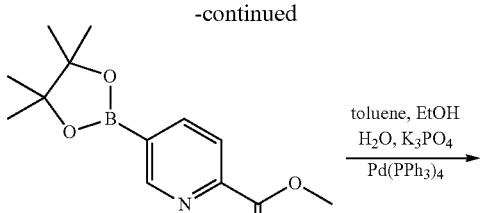

toluene, EtOH
H₂O, K₃PO₄
Pd(PPh₃)₄
→

I-158

Synthesis of 5-(3'-Chloro-6-methoxy-biphenyl-3-ylmethyl)-pyridine-2-carboxylic acid methyl ester (I-158). Into a 250 mL round-bottomed flask was added I-154 (4.89 g, 15.69 mmol), 5-(4,4,5,5-Tetramethyl-[1,3,2]dioxaborolan-2-yl)-pyridine-2-carboxylic acid methyl ester (4.52 g, 17.26 mmol), toluene (120 mL), EtOH (20 mL), water (20 mL), and K₃PO₄ (6.66 g, 31.38 mmol). The suspension was degassed with N₂ for 15 minutes and then Pd(PPh₃)₄ (1.81 g, 1.57 mmol) was added and the reaction was stirred at 80° C. for 1 hour. The layers were separated and the aqueous was extracted with 50 mL EtOAc. The organics were combined and washed with 50 mL of brine, dried over Na₂SO₄, filtered and concentrated. The residue was purified by flash column chromatography eluting with 10% acetone/hexanes to afford 890 mg of I-158 as a light-yellow oil in 15% yield.

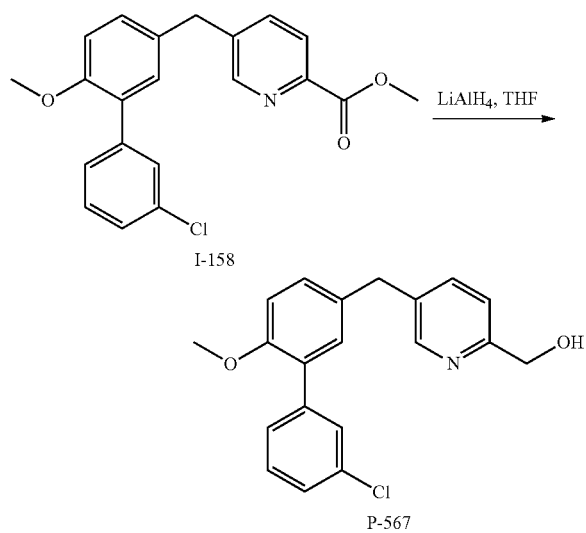

I-158

LiAlH₄, THF
→

P-567

[5-(3'-Chloro-6-methoxy-biphenyl-3-ylmethyl)-pyridin-2-yl]-methanol (P-567). Into a 100 mL round-bottomed flask was added I-158 (0.71 g, 1.93 mmol), THF (20 mL), and the solution was cooled to 0° C. LiAlH₄ (0.29 g, 7.72 mmol) was added and the reaction was stirred at 0° C. for 1 hour. 20 mL of water was slowly added and the product was extracted with EtOAc (3×20 mL). The organics were combined and filtered through Celite and then concentrated. The residue was puri-

232 fied by flash column chromatography eluting with 20% acetone/hexanes to provide 352 mg of P-567 as a light-yellow oil in 54% yield. ¹H NMR (400 MHz, DMSO-d₆) 8.42 (d, J=1.6 Hz, 1H), 7.64 (dd, J=2.0, 7.9 Hz, 1H), 7.49 (s, 1H), 7.45-7.34 (m, 4H), 7.25-7.20 (m, 2H), 7.05 (d, J=8.6 Hz, 1H), 5.31 (t, J=5.8 Hz, 1H), 4.50 (d, J=5.9 Hz, 2H), 3.93 (s, 2H), 3.74 (s, 3H) ppm. LC/MS=92.1%, 340.1 (APCI+).

Example 154

Preparation of P-570

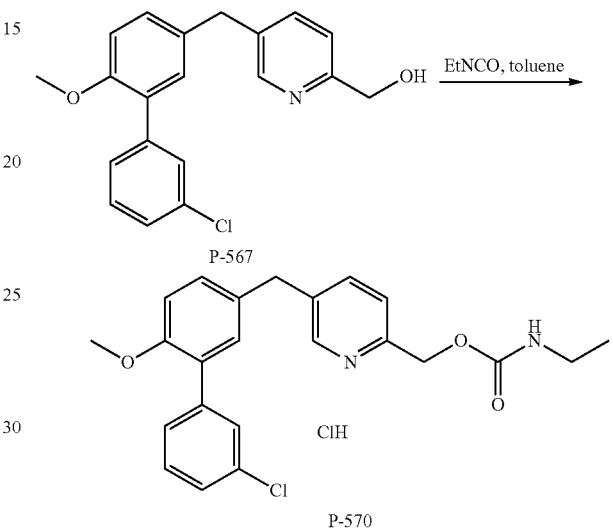

Ethyl-carbamic acid 5-(3'-chloro-6-methoxy-biphenyl-3-ylmethyl)-pyridin-2-ylmethyl ester hydrochloride (P-570). Into an 18 mL vial was added P-567 (98 mg, 0.29 mmol), toluene (2 mL), and ethyl isocyanate (57 uL, 0.72 mmol). The reaction was stirred at 60° C. for 6 hours and then concentrated. The solid was triturated with ether to obtain 79 mg of P-570 as a white solid. Of this material, 68 mg was dissolved in 4N HCl/Dioxane and then concentrated. This solid was triturated with ether, filtered, and washed with ether to afford 50 mg of P-570HCl salt as a tan solid in 45% yield. ¹H NMR (400 MHz, DMSO-d₆) 8.48 (d, J=1.5 Hz, 1H), 7.71-7.64 (m, 1H), 7.49 (s, 1H), 7.45-7.34 (m, 3H), 7.32-7.19 (m, 3H), 7.05 (d, J=9.1 Hz, 1H), 5.01 (s, 2H), 3.94 (s, 2H), 3.74 (s, 3H), 3.07-2.95 (m, 2H), 1.01 (t, J=7.2 Hz, 3H) ppm. LC/MS=100.0%, 411.0 (APCI+).

Example 155

Preparation of P-534

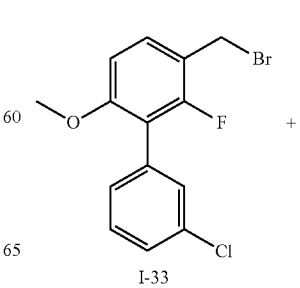

I-33

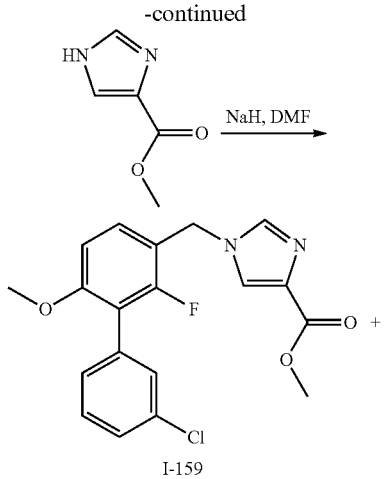

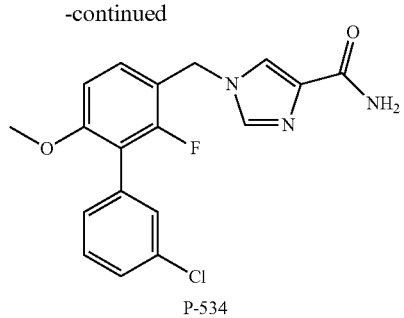

1-(3'-Chloro-2-fluoro-6-methoxy-biphenyl-3-ylmethyl)-1H-imidazole-4-carboxylic acid amide (P-534). Into an 8 mL vial was added I-159 (30 mg, 0.08 mmol) and 2 mL of 7N NH₃/MeOH. The reaction was stirred at 60° C. for 6 days after which it was concentrated. Ether was added to form a solid which was filtered and washed with ether to afford 8 mg of P-534 as a tan solid in 28% yield. ¹H NMR (400 MHz, DMSO-d₆) 7.77 (s, 1H), 7.63 (s, 1H), 7.48-7.36 (m, 4H), 7.29 (d, J=6.4 Hz, 1H), 7.26 (br s, 1H), 7.05 (br s, 1H), 7.02 (d, J=8.7 Hz, 1H), 5.25 (s, 2H), 3.75 (s, 3H) ppm.

Example 156

Preparation of P-535

1-(3'-Chloro-2-fluoro-6-methoxy-biphenyl-3-ylmethyl)-1H-imidazole-4-carboxylic acid methyl ester (I-159) and 3-(3'-Chloro-2-fluoro-6-methoxy-biphenyl-3-ylmethyl)-3H-imidazole-4-carboxylic acid methyl ester (I-160). Into an 18 mL vial was added methyl 4-imidazole carboxylate (113 mg, 0.90 mmol), DMF (3 mL), and NaH (43 mg, 1.08 mmol). After 20 minutes at room temperature I-33 (295 mg, 0.90 mmol) was added. The reaction was stirred for 2 hours at room temperature and then water was added. The product was extracted with EtOAc and the organics were concentrated. The residue was purified by flash column chromatography eluting with 6%-10% acetone/dichloromethane to separate the regioisomers. The 4-substituted ester I-159 (67 mg, 20%) and the 2-substituted ester I-160 (79 mg, 23%) were obtained as colorless oils.

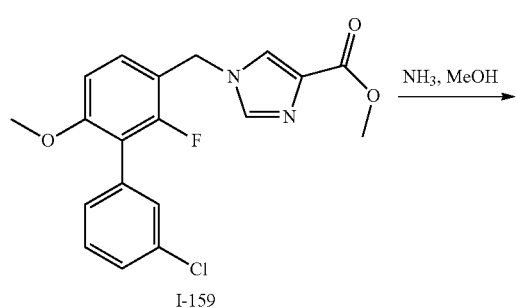

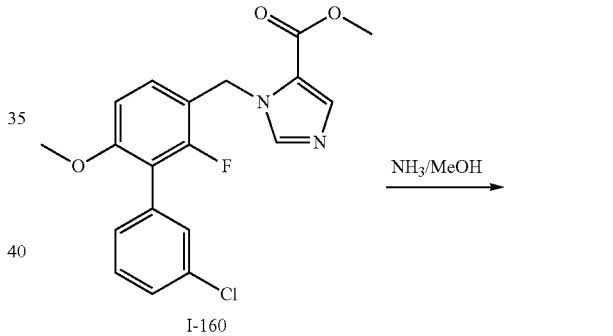

3-(3'-Chloro-2-fluoro-6-methoxy-biphenyl-3-ylmethyl)-3H-imidazole-4-carboxylic acid amide (P-535). Into an 8 mL vial was added I-160 (36 mg, 0.096 mmol) and 2 mL of 7N NH₃/MeOH. The reaction was stirred at 60° C. for 6 days after which it was concentrated. The solid was triturated with ethe, filtered, and washed with ether to afford 7 mg of P-535 as a white solid in 20% yield. ¹H NMR (400 MHz, DMSO-d₆) 7.83 (s, 1H), 7.75 (br s, 1H), 7.63 (s, 1H), 7.51-7.41 (m, 2H), 7.38 (s, 1H), 7.29 (d, J=6.6 Hz, 1H), 7.19 (br s, 1H), 7.10-7.00 (m, 1H), 6.94 (d, J=8.7 Hz, 1H), 5.59 (s, 2H), 3.72 (s, 3H) ppm. LC/MS=92.2%, 359.1 (APCI–).

Example 157

Preparation of P-536

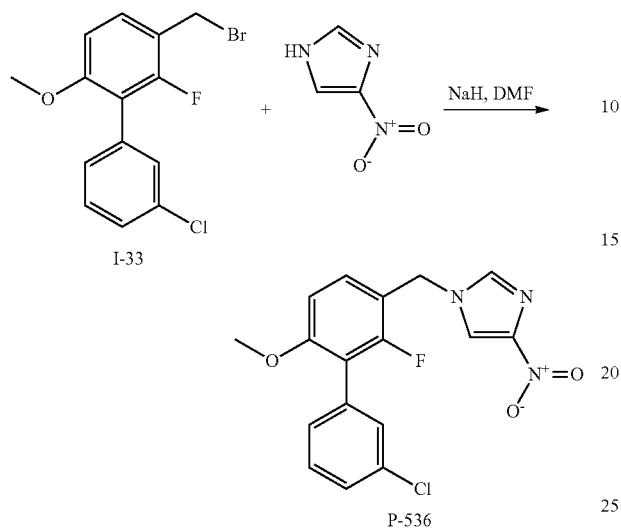

1-(3'-Chloro-2-fluoro-6-methoxy-biphenyl-3-ylmethyl)-4-nitro-1H-imidazole (P-536). Into a 100 mL round bottom flask was added I-33 (1.0 g, 3.03 mmol), DMF (25 mL), and the solution was cooled to 0° C. Sodium hydride (145 mg, 3.64 mmol) was added followed by 4-nitro-1H-imidazole (377 mg, 3.34 mmol). The reaction was stirred at 0° C. for 2 hours and then 10 mL of water was added. The product was extracted with 3×15 mL EtOAc and the combined organics were concentrated. The product was purified by flash column chromatography eluting with 20% acetone/hexanes to afford 625 mg of P-536 as an amber oil in 57% yield. $^1$H NMR (400 MHz, DMSO-$d_6$) 8.41 (d, J=0.9 Hz, 1H), 7.94 (s, 1H), 7.56-7.37 (m, 4H), 7.30 (d, J=6.4 Hz, 1H), 7.03 (d, J=8.6 Hz, 1H), 5.34 (s, 2H), 3.76 (s, 3H) ppm

Example 158

Preparation of P-531

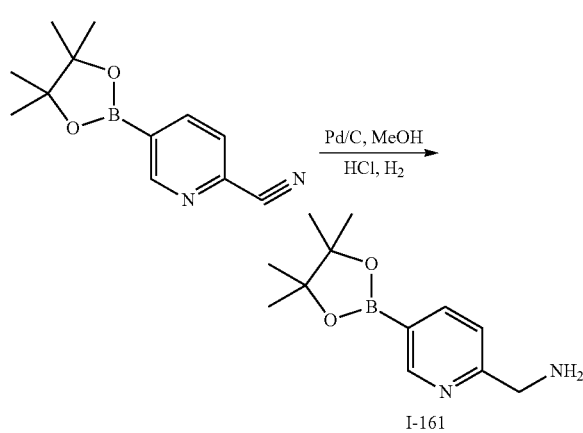

C-[5-(4,4,5,5-Tetramethyl-[1,3,2]dioxaborolan-2-yl)-pyridin-2-yl]-methylamine (I-161), Into a 100 ml round bottom flask was added 5-(4,4,5,5-Tetramethyl-[1,3,2]dioxaborolan-2-yl)-pyridine-2-carbonitrile (1.0 g, 0.43 mmol), 20 mL of MeOH, conc. HCl (1.8 mL, 2.17 mmol), and 10% Pd/C (0.2 g). The reaction was stirred under a hydrogen atmosphere for 18 hours. The reaction was filtered through Celite, washed with MeOH, and then concentrated to a yellow solid. The material was used as is.

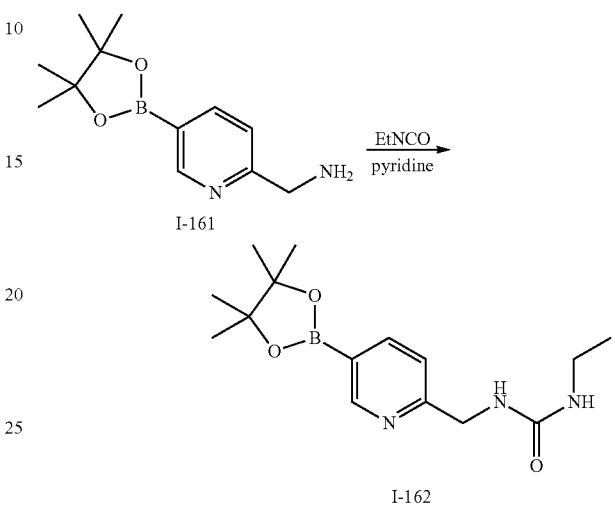

1-Ethyl-3-[5-(4,4,5,5-tetramethyl-[1,3,2]dioxaborolan-2-yl)-pyridin-2-ylmethyl]-urea (I-162). Into a 50 mL round bottom flask was added C-[5-(4,4,5,5-Tetramethyl-[1,3,2]dioxaborolan-2-yl)-pyridin-2-yl]-methylamine (I-161, 1 g, crude), pyridine (10 mL), and ethyl isocyanate (0.5 mL, 6.5 mmol). The reaction was stirred at room temperature for 30 minutes and then NaHCO$_3$ (sat) was added. The product was extracted with 3×10 mL EtOAc and the combined organics were dried over Na$_2$SO$_4$, and concentrated. The residue was purified by flash column chromatography eluting with 50% acetone/dichloromethane—100% MeOH to afford 289 mg of I-162 as a brown oil in 22% yield.

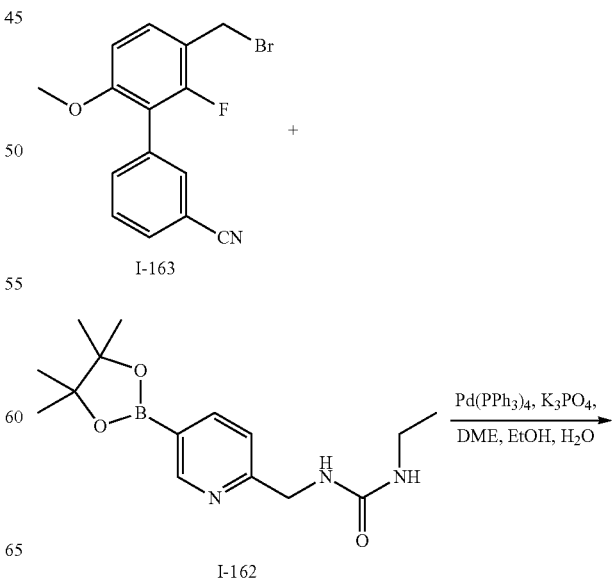

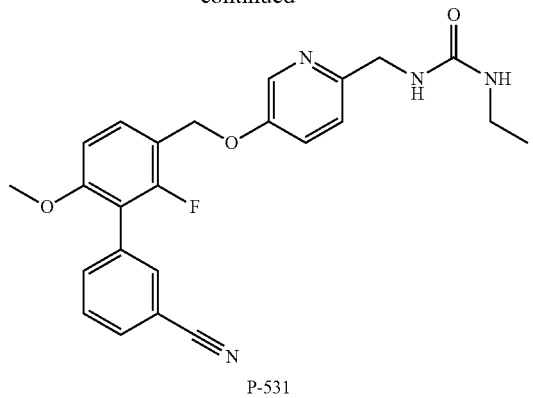

P-531

1-[4-(3'-Cyano-2-fluoro-6-methoxy-biphenyl-3-yl-methoxy)-pyridin-2-ylmethyl]-3-ethyl-urea (P-531). Into an 8 mL vial was added I-163 (125 mg, 0.39 mmol), 1-ethyl-3-[5-(4,4,5,5-tetramethyl-[1,3,2]dioxaborolan-2-yl)-pyridin-2-ylmethyl]-urea (I-162, 119 mg, 0.39 mmol), $K_3PO_4$ (248 mg, 1.17 mmol), DME (2.5 mL), EtOH (0.5 mL), and water (0.5 mL). The suspension was degassed with $N_2$ and then $Pd(PPh_3)_4$ was added. The reaction was stirred for 1 hour at 80° C. Water (2 mL) was added and the product was extracted with EtOAc (3×2 mL). The organic extracts were combined and concentrated. The residue was purified by flash column chromatography eluting with 25%-50% acetone/dichloromethane to give a tan-gray solid which was then triturated with ether. The resulting solid was recrystallized from EtOH to provide 7 mg of P-531 as a white solid in 4% yield. $^1$H NMR (400 MHz, DMSO-$d_6$) 8.26 (d, J=2.8 Hz, 1H), 7.89-7.82 (m, 2H), 7.75-7.53 (m, 3H), 7.47 (dd, J=3.0, 8.6 Hz, 1H), 7.22 (d, J=8.6 Hz, 1H), 7.04 (d, J=8.6 Hz, 1H), 6.33 (t, J=5.8 Hz, 1H), 6.01 (t, J=5.4 Hz, 1H), 5.16 (s, 2H), 4.22 (d, J=5.9 Hz, 2H), 3.78 (s, 3H), 3.09-2.95 (m, 2H), 0.99 (t, J=7.1 Hz, 3H) ppm. LC/MS=90.7%, 435.2 (APCI+).

Example 159

Preparation of P-244

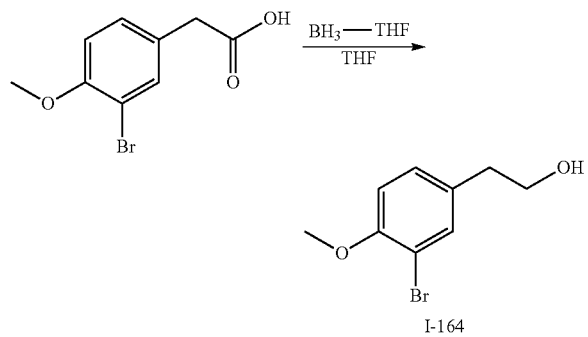

2-(3-Bromo-4-methoxy-phenyl)-ethanol (I-164). Into a 100 mL round bottom flask was added (3-bromo-4-methoxy-phenyl)-acetic acid (0.58 g, 2.37 mmol), THF (10 mL), and the mixture was cooled to 0° C. $BH_3$-THF (10.6 mL, 10.6 mmol, 1.0M in THF) was added and the reaction was stirred at room temperature for 20 hours. 20 mL of MeOH was added and the solvent was removed on a rotary evaporator. This was repeated an additional 5 times. The residue was purified by flash column chromatography eluting with 10-20% acetone/hexanes to afford 457 mg of I-164 as a light yellow oil in 83% yield.

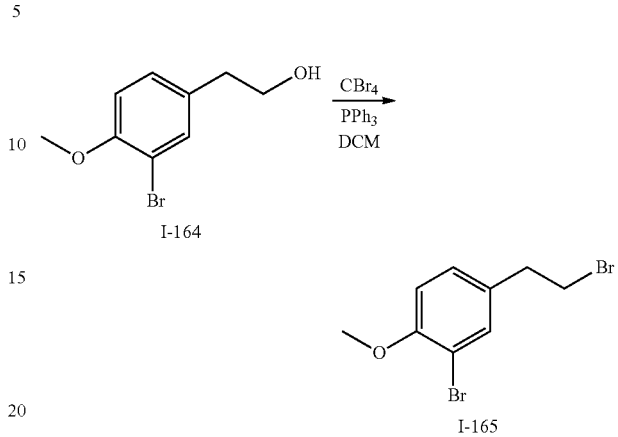

2-Bromo-4-(2-bromo-ethyl)-1-methoxy-benzene (I-165). Into a 100 mL round bottom flask was added 2-(3-bromo-4-methoxy-phenyl)-ethanol (I-164, 418 mg, 1.81 mmol), dichloromethane (15 mL), carbon tetrabromide (1.50 g, 4.52 mmol), and triphenylphosphine (1.19 g, 4.52 mmol). After stirring for 1 hour at room temperature the reaction was concentrated. The residue was purified by flash column chromatography eluting with hexanes to afford 1.91 g of I-165 as a colorless oil, which was used without further purification.

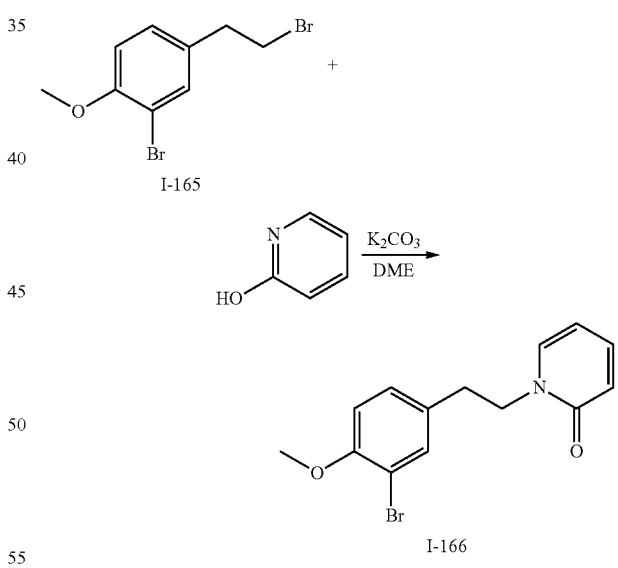

1-[2-(3-Bromo-4-methoxy-phenyl)-ethyl]-1H-pyridin-2-one (I-166). Into a 100 mL round bottom flask was added 2-bromo-4-(2-bromo-ethyl)-1-methoxy-benzene (I-165, 1.82 g, crude), 2-hydroxypyridine (258 mg, 2.72 mmol), $K_2CO_3$ (625 mg, 4.53 mmol), and DME (20 mL). After stirring for 18 hours at 80° C. the suspension was filtered and the filtrate was concentrated. The residue was purified by flash column chromatography eluting with 25-50% acetone/hexanes to afford 221 mg of I-166 as a brown oil in 40% yield (2 steps).

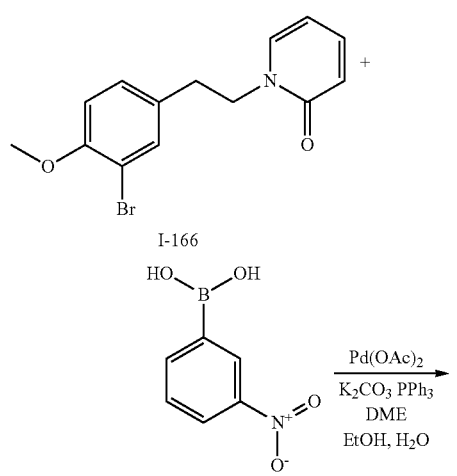

I-166

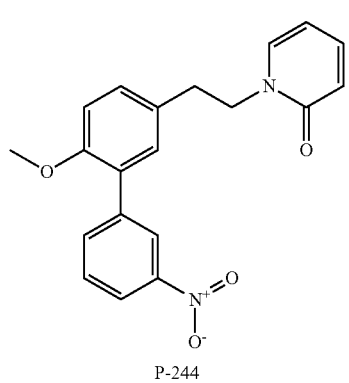

P-244

1-[2-(6-Methoxy-3'-nitro-biphenyl-3-yl)-ethyl]-1H-pyridin-2-one (P-244). Into a 40 mL vial were added 1-[2-(3-bromo-4-methoxy-phenyl)-ethyl]-1H-pyridin-2-one (I-166, 210 mg, 0.68 mmol), 3-nitrophenylboronic acid (125 mg, 0.75 mmol), PPh$_3$ (36 mg, 0.014 mmol), potassium carbonate (283 mg, 2.04 mmol), dimethoxyethane (10 mL), ethanol (1 mL), and water (1 mL). The suspension was degassed with N$_2$ for 5 minutes and then palladium(II) acetate (15 mg, 0.068 mmol). After degassing for an additional 2 minutes the reaction was stirred at 80° C. for 18 hours. To the reaction was added 5 mL of water and 10 mL of ethyl acetate. The layers were separated and the aqueous was extracted with ethyl acetate (3×10 mL). The organics were combined and concentrated. The residue was purified by flash column chromatography eluting with 10-20% acetone/dichloromethane. The yellow oil which was obtained (136 mg) was dissolved in 1 mL of ether and allowed to stand at room temperature for 3 days. The tan solid which formed was filtered, washed with ether, and dried to afford 74 mg of P-244 in 31% yield. $^1$H NMR (400 MHz, CDCl$_3$) δ 8.30-8.29 (m, 1H), 8.18-8.15 (m, 1H), 7.81-7.79 (m, 1H), 7.54 (t, J=8.0 Hz), 7.37-7.33 (m, 1H), 7.19 (dd, J=8.2, 2.2 Hz, 1H), 7.05 (d, J=2.4 Hz, 1H), 6.95-6.93 (m, 2H), 6.61 (d, J=9.2 Hz, 1H), 6.06 (td, J=6.6, 1.2 Hz, 1H), 4.15 (t, J=7.0 Hz, 2H), 3.82 (s, 3H), 3.07 (t, J=7.0 Hz, 2H) ppm. LC/MS=99.4%, 351.6 (ESI+).

Example 160

Preparation of P-003

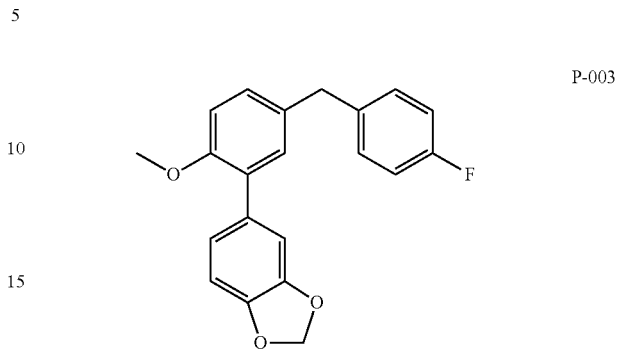

P-003

5-[5-(4-Fluoro-benzyl)-2-methoxy-phenyl]-benzo[1,3]dioxole (P-003). P-003 was prepared by according to the method described for P-001. $^1$H NMR (400 MHz, CDCl$_3$) 3.80 (s, 3H) 3.93 (s, 2H) 5.98 (s, 2H) 6.83-6.92 (m, 2H) 6.92-7.05 (m, 4H) 7.05-7.12 (m, 2H) 7.16 (dd, J=8.4, 5.6 Hz, 2H) ppm. LCMS=94.4% purity. TSI (+)=365.4 (M+29).

Example 161

Preparation of P-004

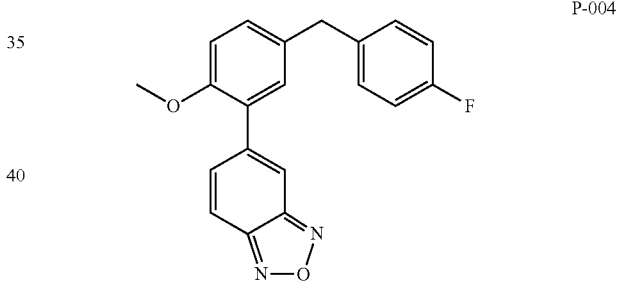

P-004

5-[5-(4-Fluoro-benzyl)-2-methoxy-phenyl]-benzo[1,2,5]oxadiazole (P-004). P-004 was prepared by according to the method described for P-001. $^1$H NMR (400 MHz, CDCl$_3$) 3.84 (s, 3H), 3.97 (s, 2H), 6.91-7.05 (m, 3H), 7.13-7.24 (m, 4H), 7.62 (dd, J=9.3, 1.3 Hz, 1H) 7.75-7.87 (m, 2H) ppm. LCMS=96.2% purity. TSI (+)=365.4 (M+31).

Example 162

Preparation of P-006

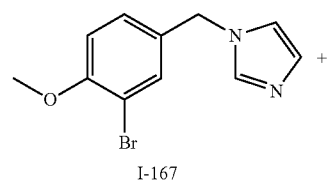

I-167

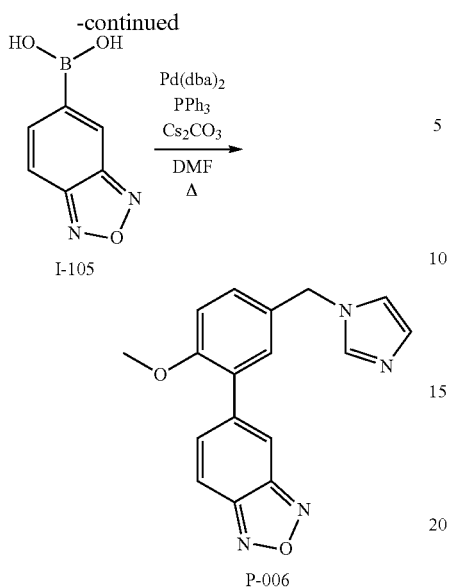

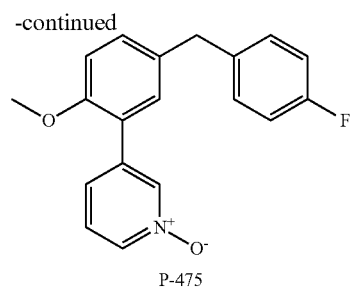

Example 163

Preparation of P-474

Synthesis of 3-[5-(4-Fluoro-benzyl)-2-methoxy-phenyl]-pyridine (P-474). A suspension of I-168 (158 mg, 0.53 mmol), 3-pyridineboronic acid (61.5 mg, 0.50 mmol), palladium(0)bis(dibenzylideneacetone) (14.4 mg, 0.025 mmol), and triphenylphosphine (13.1 mg, 0.050 mmol) in dimethylformamide (5 mL) and 1 M aqueous sodium carbonate (1.5 mL, 1.5 mmol) was heated to 85° C. with stirring overnight. The solvent was removed under vacuum and the residue suspended in ethyl acetate (15 mL). The organic suspension was washed with water (3×15 mL) and brine, dried over sodium sulfate and the solvent removed under vacuum to give crude material. The residue was purified by silica gel preparatory thin layer chromatography to afford 69.1 mg (47%) of P-474

LCMS=94.6% purity.

Synthesis of 5-(5-Imidazol-1-ylmethyl-2-methoxy-phenyl)-benzo[1,2,5]oxadiazole (P-006). A suspension of 1-(3-bromo-4-methoxy-benzyl)-1H-imidazole (I-167, 267 mg, 1.00 mmol), benzo[1,2,5]oxadiazole-5-boronic acid (I-105, 164 mg, 1.00 mmol), palladium(0)bis(dibenzylideneacetone) (28.7 mg, 0.050 mmol), and triphenylphosphine (26.2 mg, 0.10 mmol) in dimethylformamide (20 mL) and 1 M aqueous cesium carbonate (3.0 mL, 3.0 mmol) was heated to 85° C. with stirring overnight. The solvent was removed under vacuum and the residue suspended in ethyl acetate (25 mL). The organic suspension was washed with water (3×20 mL) and brine, dried over sodium sulfate, decolorized over activated carbon, filtered, and concentrated under. The residue was purified by silica gel preparatory thin layer chromatography (ethyl acetate:dichloromethane 3:1) to give 10.4 mg of P-006 in 9.1% yield. $^1$H NMR (400 MHz, CDCl$_3$) 3.86 (s, 3H) 5.13 (s, 2H) 6.93 (s, 1H) 7.01 (d, J=8.32 Hz, 1H) 7.10 (s, 1H) 7.17-7.25 (m, 2H) 7.52-7.62 (m, 2H) 7.78-7.85 (m, 2H) ppm. LCMS=100% purity. APCI (+)=307.1 (M+1).

Example 164

Preparation of P-475

Synthesis of 3-[5-(4-Fluoro-benzyl)-2-methoxy-phenyl]-pyridine 1-oxide (P-475). A vial was charged with P-474 (60 mg, 0.20 mmol), methyl ruthenium oxide (2.5 mg, 0.010 mmol), 30% aqueous hydrogen peroxide (0.5 mL), and dichloromethane (1.0 mL). The reaction was allowed to stir at room temperature for 3 days. The biphasic mixture was treated with catalytic amount of manganese dioxide (1.7 mg, 0.02 mmol) and carefully stirred until the oxygen evolution ceased (1 h). The phases were separated, the aqueous layer extracted into dichloromethane (2×1 mL), the organic layers combined, dried over sodium sulfate, and the solvent removed under vacuum to afford 20.9 mg of P-475 in 34% yield. $^1$H NMR (400 MHz, CDCl$_3$) 3.82 (s, 3H) 3.94 (s, 2H) 6.89-7.24 (m, 8H) 7.41 (d, J=8.1 Hz, 1H) 8.16 (d, J=6.3 Hz, 1H) 8.44 (s, 1H) ppm. LCMS=92.0% purity.

Example 165

Preparation of P-007

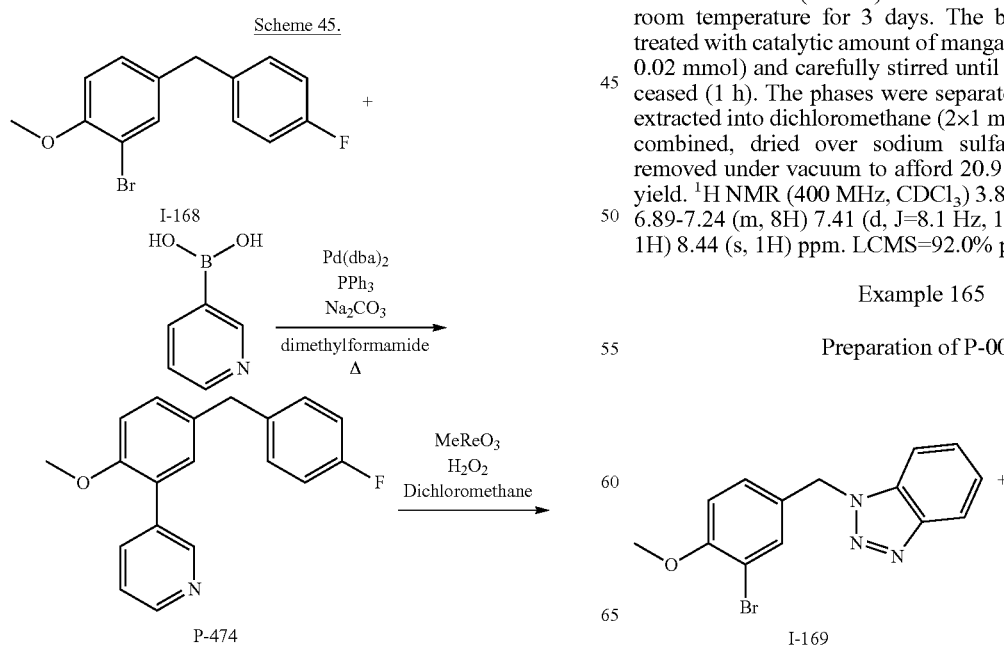

Scheme 45.

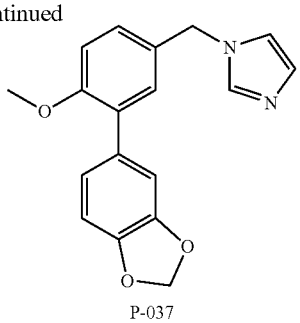

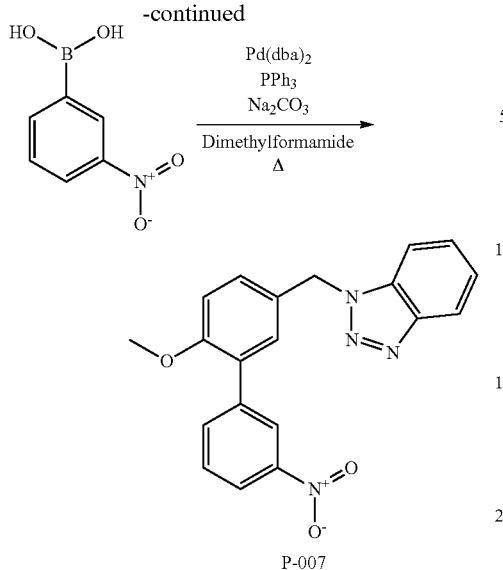

P-007

Synthesis of 1-(6-Methoxy-3'-nitro-biphenyl-3-ylmethyl)-1H-benzotriazole (P-007). A suspension of I-169 (477 mg, 1.50 mmol), 3-nitrophenylboronic acid (250 mg, 1.50 mmol), palladium(0) bis(dibenzylideneacetone) (43 mg, 0.075 mmol), and triphenyl phosphine (39 mg, 0.15 mmol) in dimethylformamide (10 mL) and 1 M aqueous sodium carbonate (4.5 mL, 4.5 mmol) was heated to 85° C. with stirring overnight. The solvent was removed under vacuum and the residue suspended in ethyl acetate (20 mL). The organic suspension was washed with water (3×20 mL) and brine, dried over sodium sulfate, decolorized over activated carbon, filtered and the solvent removed under vacuum to give a residue. The residue was purified dissolving in ethyl acetate (5 mL) and adding hexanes (25 mL) until a solid formed. This was repeated 3 times to afford 210 mg of P-007 in 39% yield. $^1$H NMR (400 MHz, CDCl$_3$) 3.83 (s, 3H), 5.87 (s, 2H), 6.99 (d, J=8.2 Hz, 1H), 7.31-7.52 (m, 4H), 7.56 (t, J=7.9 Hz, 1H), 7.76 (d, J=7.8 Hz, 1H), 8.13 (d, J=8.3 Hz, 1H), 8.19 (dd, J=8.2, 1.2 Hz, 1H), 8.36 (d, J=1.6 Hz, 1H) ppm. LCMS=93.9% purity. APCI (+)=361.10 (M+1).

Example 166

Preparation of P-037

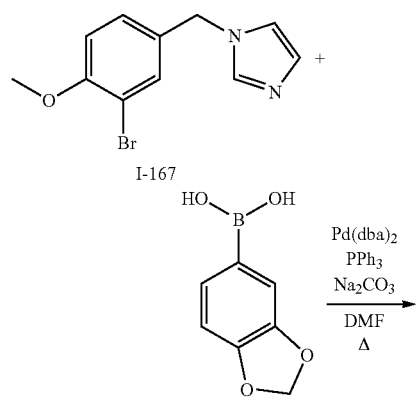

I-167

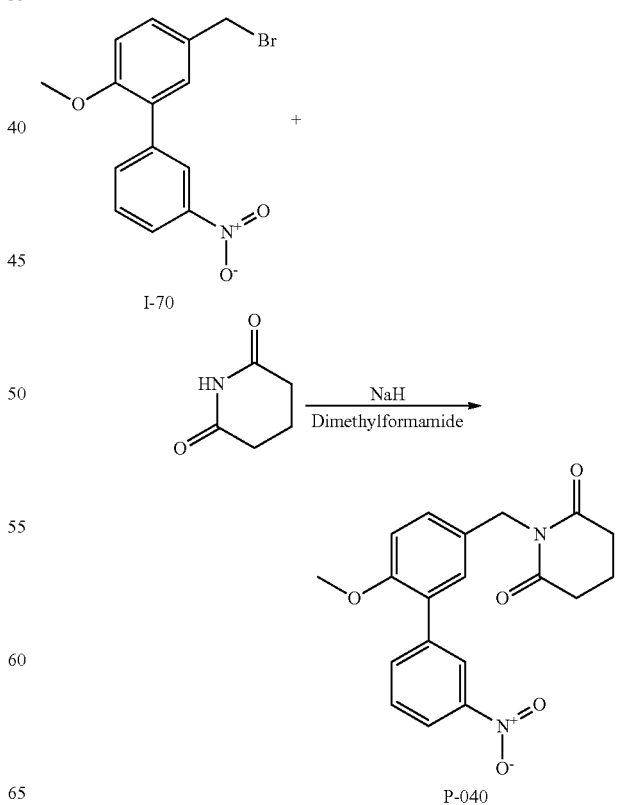

P-037

Synthesis of 1-(3-Benzo[1,3]dioxol-5-yl-4-methoxy-benzyl)-1H-imidazole (P-037). To a solution of I-167 (484 mg, 1.80 mmol) and benzo[1,3]dioxole-5-boronic acid (332 mg, 2.00 mmol) were added palladium(0) bis(dibenzylideneacetone) (57.5 mg, 0.100 mmol), and triphenylphosphine (52.4 mg, 0.200 mmol) in dimethylformamide (40 mL) and 1 M aqueous sodium carbonate (6.0 mL, 6.0 mmol) was heated to 80° C. with stirring overnight. The solvent was removed under vacuum and the residue suspended in ethyl acetate (30 mL). The organic suspension was washed with water (3×30 mL) and brine, dried over sodium sulfate, decolorized over activated carbon, filtered, and the solvent removed under vacuum to give a residue. The residue was purified by reverse phase (water:acetonitrile 3:1 to 1:1) followed by extraction with dichloromethane and removal of solvent under reduced pressure to afford 69.6 mg of P-037 as a clear viscous oil in 13% yield. $^1$H NMR (400 MHz, CDCl$_3$) 3.81 (s, 3H), 5.08 (s, 2H), 5.99 (s, 2H), 6.82-6.96 (m, 4H), 7.00 (d, J=1.5 Hz, 1H), 7.09 (d, J=10.2 Hz, 3H), 7.55 (s, 1H) ppm. LCMS=100% purity. APCI (+)=309.10 (M+1).

Example 167

Preparation of P-040

I-70

P-040

Synthesis of 1-(6-Methoxy-3'-nitro-biphenyl-3-ylm-ethyl)-piperidine-2,6-dione (P-040). To a solution of I-70 (161 mg, 0.500 mmol) and glutarimide (113 mg, 1.00 mmol) in dimethyl formamide (1.5 mL) was added sodium hydride (60% weight dispersion, 40 mg, 1.00 mmol) at −78° C. After hydrogen gas evolution ceased the reaction was stirred at 120° C. overnight. The reaction mixture was filtered, and the filtrate concentrated under reduced pressure. The residue was diluted with ethyl acetate (15 mL), washed with water, brine, dried over sodium sulfate, filtered, and the solvent removed under vacuum. The product was purified by trituration with hexanes (50 mL) and dichloromethane (2 mL) followed by silica gel column chromatography (50% ethyl acetate in hexanes) to afford 79.8 mg of P-040 in 45% yield. $^1$H NMR (400 MHz, CDCl$_3$) 1.94 (quintet, J=6.4 Hz, 2H), 2.67 (t, J=6.4 Hz, 4H), 3.81 (s, 3H), 4.94 (s, 2H), 6.92 (d, J=8.4 Hz, 1H), 7.39 (d, J=2.4 Hz, 1H), 7.44 (dd, J=8.4, 2.0 Hz, 1H), 7.55 (t, J=8.0 Hz, 1H), 7.81 (ddd, J=8.0, 1.6, 1.2 Hz, 1H), 8.16 (ddd, J=8.4, 2.4, 1.2 Hz, 1H), 8.39 (t, J=2.0 Hz, 1H) ppm. LCMS=92% purity.

Example 168

Preparation of P-041

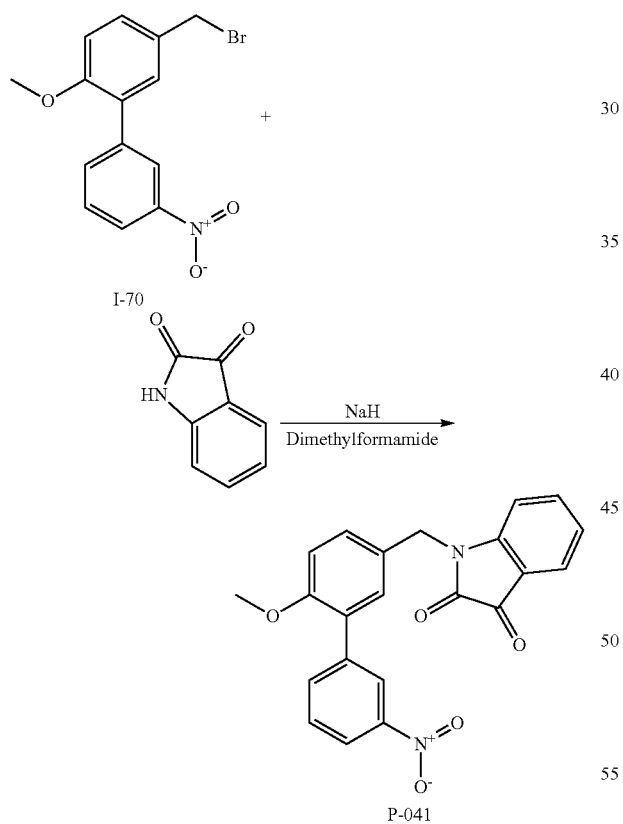

Synthesis of 1-(6-Methoxy-3'-nitro-biphenyl-3-ylm-ethyl)-1H-indole-2,3-dione (P-041). To a solution of I-70 (98 mg, 0.300 mmol) and isatin (88 mg, 0.60 mmol) in dimethyl formamide (1.0 mL) was added sodium hydride (60% weight dispersion, 24 mg, 0.6 mmol) at −78° C. After hydrogen gas evolution ceased the reaction was stirred at room temperature overnight. The reaction mixture was filtered, and the filtrate concentrated under reduced pressure. The residue was diluted with ethyl acetate (15 mL), washed with water, brine, dried over sodium sulfate, filtered, and the solvent removed under vacuum. The crude product was purified by silica gel column chromatography (4:1 ethyl acetate:hexanes) to afford 45.5 mg of P-041 in 39.1% yield. $^1$H NMR (400 MHz, CDCl$_3$) 3.82 (s, 3H), 4.93 (s, 2H), 6.85 (d, J=7.9 Hz, 1H), 6.98 (d, J=8.6 Hz, 1H), 7.07-7.14 (m, 1H), 7.29-7.40 (m, 2H), 7.49-7.65 (m, 4H), 7.79 (d, J=7.8 Hz, 1H), 8.18 (s, 1H), 8.37 (t, J=1.74 Hz, 1H) ppm. Turb. Spray (+)=389.60 (M+1)

Example 169

Preparation of P-042

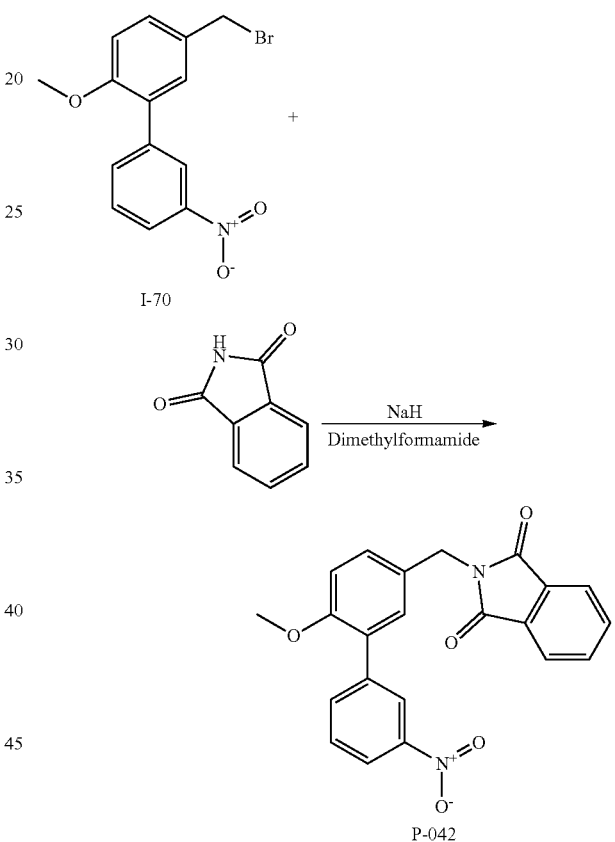

Synthesis of 2-(6-Methoxy-3'-nitro-biphenyl-3-ylm-ethyl)-isoindole-1,3-dione (P-042). To a solution of I-70 (161 mg, 0.500 mmol) and phthalimide (147 mg, 1.00 mmol) in dimethyl formamide (1.5 mL) was added sodium hydride (60% weight dispersion, 40 mg, 1.0 mmol) at −78° C. After hydrogen gas evolution ceased the reaction was stirred at 80° C. overnight. The reaction mixture was filtered, and the filtrate concentrated under reduced pressure. The residue was diluted with ethyl acetate (15 mL), washed with water, brine, dried over sodium sulfate, filtered, and the solvent removed under vacuum. The crude product was purified by trituration several times in hexanes (100 mL) and ethyl acetate (5 mL) to afford 43.8 mg of P-042 as a grey-white solid in 26% yield. $^1$H NMR (400 MHz, CDCl$_3$) 3.80 (s, 3H), 4.84 (s, 2H), 6.95 (d, J=, 8.5 Hz, 1H), 7.43 (d, J=2.2 Hz, 1H), 7.49 (dd, J=8.5, 2.2 Hz, 1H), 7.55 (t, J=8.0 Hz, 1H), 7.65-7.76 (m, 2H), 7.77-7.87

(m, 3H), 8.17 (dd, J=8.2, 1.3 Hz, 1H), 8.39 (t, J=1.8 Hz, 1H) ppm. LCMS=97.1% purity. APCI (+)=359.1 (M−29).

Example 170

Preparation of P-043

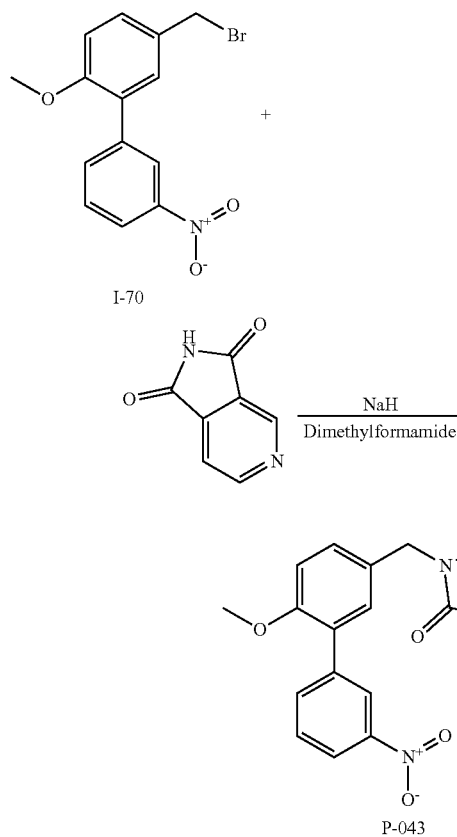

Synthesis of 2-(6-Methoxy-3'-nitro-biphenyl-3-ylmethyl)-pyrrolo[3,4-c]pyridine-1,3-dione (P-043). To a solution of I-70 (161 mg, 0.500 mmol) and pyridinecarboximide (148 mg, 1.00 mmol) in dimethyl formamide (1.5 mL) was added sodium hydride (60% weight dispersion, 40 mg, 1.0 mmol) at −78° C. After hydrogen gas evolution ceased the reaction was stirred at 80° C. overnight. The reaction was diluted with ethyl acetate (15 mL), washed with water, brine, decolorized with activated charcoal, dried over sodium sulfate, filtered, and the solvent removed under vacuum. The crude product was purified by trituration several times in hexanes (100 mL) and ethyl acetate (5 mL) to afford 20.9 mg of P-043 as a grey-white solid in 11% yield. $^1$H NMR (400 MHz, CDCl$_3$) 3.81 (s, 3H), 4.86 (s, 2H), 6.96 (d, J=8.5 Hz, 1H), 7.43 (d, J=2.2 Hz, 1H), 7.45-7.52 (m, 1H), 7.56 (t, J=8.0 Hz, 1H), 7.71-7.83 (m, 3H), 8.18 (d, J=8.3 Hz, 1H), 8.38 (s, 1H), 9.06 (d, J=4.70 Hz, 1H), 9.08-9.17 (m, 2H), 9.20 (s, 1H) ppm. LCMS=95.2% purity. APCI (−)=389.1 (M).

Example 171

Preparation of P-047

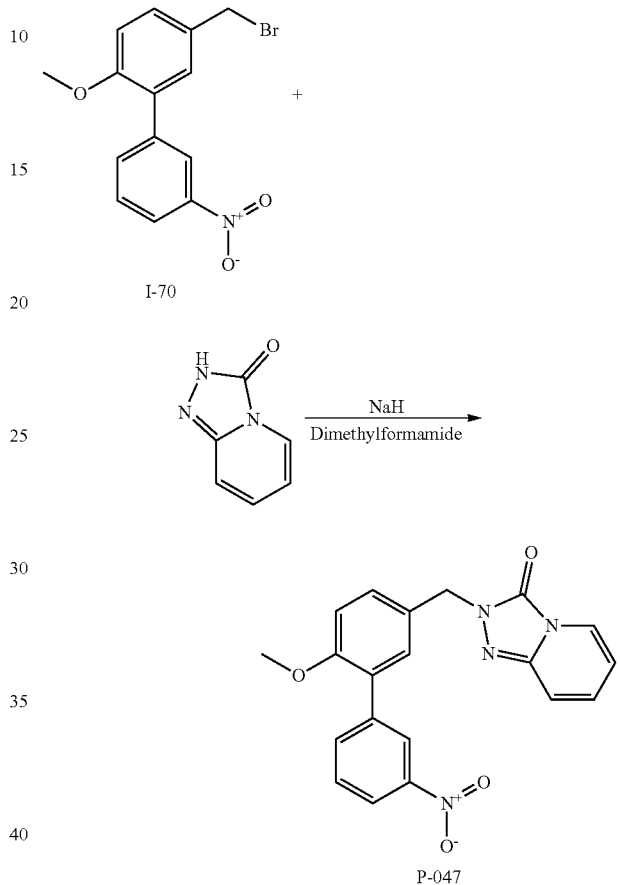

Synthesis of 2-(6-Methoxy-3'-nitro-biphenyl-3-ylmethyl)-2H-[1,2,4]triazolo[4,3-a]pyridin-3-one (P-047). To a solution of I-70 (161 mg, 0.500 mmol) and triazolepyridinone (135 mg, 1.00 mmol) in dimethyl formamide (1.5 mL) was added sodium hydride (60% weight dispersion, 40 mg, 1.0 mmol) at −78° C. After hydrogen gas evolution ceased the reaction was stirred at 75° C. for 4 h. The reaction was diluted water (15 mL). The resultant precipitate was isolated, dissolved in ethyl acetate (10 mL), decolorized with activated carbon, dried over sodium sulfate, filtered, and the solvent removed under vacuum to afford 43.2 mg of P-047 as a cream colored solid in 23% yield). $^1$H NMR (400 MHz, CDCl$_3$) 3.82 (s, 3H), 5.16 (s, 2H), 6.48 (ddd, J=7.1, 4.0, 3.2 Hz, 1H), 6.99 (d, J=8.5 Hz, 1H), 7.04-7.13 (m, 2H), 7.41 (d, J=2.2 Hz, 1H), 7.47 (dd, J=8.5, 2.2 Hz, 1H), 7.55 (t, J=8.0 Hz, 1H), 7.73-7.86 (m, 2H), 8.17 (dd, J=8.2, 1.2 Hz, 1H), 8.39 (t, J=1.8 Hz, 1H) ppm. LCMS=98.0% purity. APCI (+)=377.1 (M+1).

Example 172

Preparation of P-052

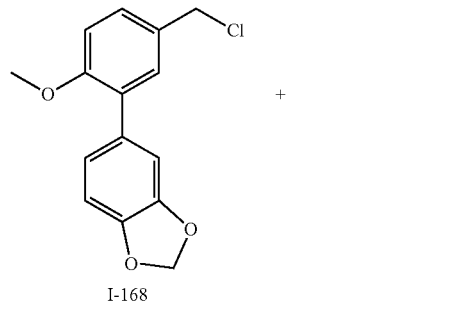

I-168

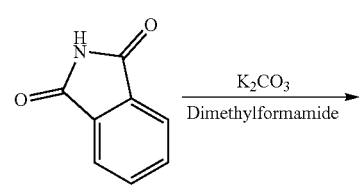

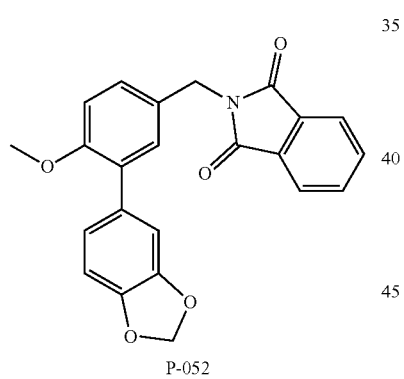

P-052

Synthesis of 2-(3-Benzo[1,3]dioxol-5-yl-4-methoxy-benzyl)-isoindole-1,3-dione (P-052). A suspension of phthalimide (147 mg, 1.00 mmol), I-168 (138 mg, 0.500 mmol), and solid potassium carbonate (138 mg, 1.00 mmol) was stirred over 72 h. Water was added, and a precipitate was formed. The suspension was stirred for 10 min, and the solid collected and dissolved in ethyl acetate (20 mL). The organic solution was dried over sodium sulfate, filtered, and the solvent removed under vacuum to afford 173 mg of P-052 in 93% yield. $^1$H NMR (400 MHz, CDCl$_3$) 3.78 (s, 3H), 4.82 (s, 2H), 5.91-6.00 (m, 2H), 6.80-6.98 (m, 3H), 7.02 (d, J=1.3 Hz, 1H), 7.35-7.43 (m, 2H), 7.70 (dd, J=5.4, 3.0 Hz, 2H), 7.80-7.88 (m, 2H) ppm. LCMS=95.6% purity.

Example 173

Preparation of P-055

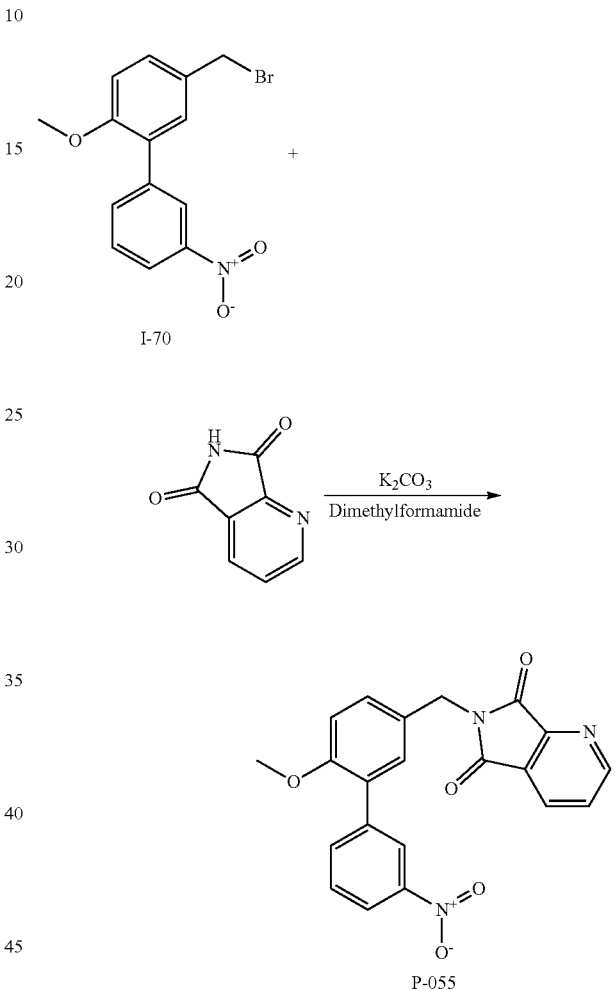

Synthesis of 6-(6-Methoxy-3'-nitro-biphenyl-3-ylmethyl)-pyrrolo[3,4-b]pyridine-5,7-dione (P-055). A suspension of I-70 (322 mg, 1.00 mmol), quinolinimide (148 mg, 1.00 mmol), and solid potassium carbonate (276 mg, 2.00 mmol) in dimethyl formamide (20 mL) was stirred at room temperature overnight. The reaction was diluted water, stirred for 10 min, and the resultant precipitate was isolated. The solid was dissolved in ethyl acetate (20 mL), dried over sodium sulfate, filtered, and the solvent removed under vacuum to afford 145 mg of P-055 as a pale yellow solid in 37% yield. $^1$H NMR (400 MHz, CDCl$_3$) 3.81 (s, 3H), 4.91 (s, 2H), 6.96 (d, J=8.5 Hz, 1H), 7.45 (d, J=2.2 Hz, 1H), 7.48-7.66 (m, 3H), 7.80 (d, J=7.8 Hz, 1H), 8.10-8.22 (m, 2H), 8.39 (t, J=1.8 Hz, 1H), 8.96 (dd, J=4.9, 1.4 Hz, 1H) ppm. LCMS=95% purity. TSI (+)=390.40 (M+1).

Example 174

Preparation of P-062

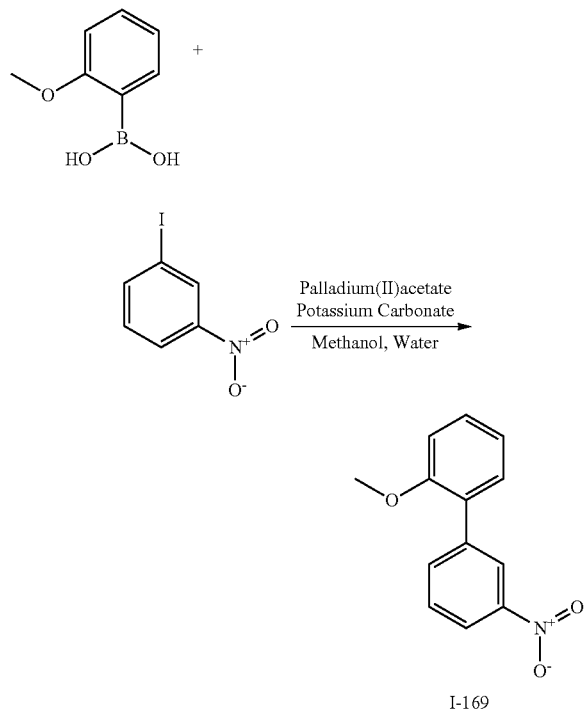

Synthesis of 2-Methoxy-3'-nitro-biphenyl (I-169). A suspension of 2-methoxyphenylboronic acid (911 mg, 6.00 mmol), 3-nitro-iodobenzne (1.24 g, 5.00 mmol), palladium (II) acetate (22 mg, 0.10 mmol), and solid potassium carbonate (1.38 g, 10. mmol), in methanol (25 mL), and water (5 mL) was stirred at room temperature overnight. The reaction was diluted with ethyl acetate (50 mL), washed with water (2×50 mL) and brine, dried over sodium sulfate, filtered, and the solvent removed under vacuum to give crude product. The product was purified by silica gel column chromatography (hexanes/ethyl acetate 9:1) to afford 940 mg of I-169 as a white solid in 82% yield. $^1$H NMR (400 MHz, CDCl$_3$) 3.84 (s, 3H), 6.96-7.14 (m, 2H), 7.30-7.44 (m, 2H), 7.56 (t, J=8.0 Hz, 1H), 7.86 (d, J=7.7 Hz, 1H), 8.17 (dd, J=8.2, 1.2 Hz, 1H), 8.42 (s, 1H) ppm.

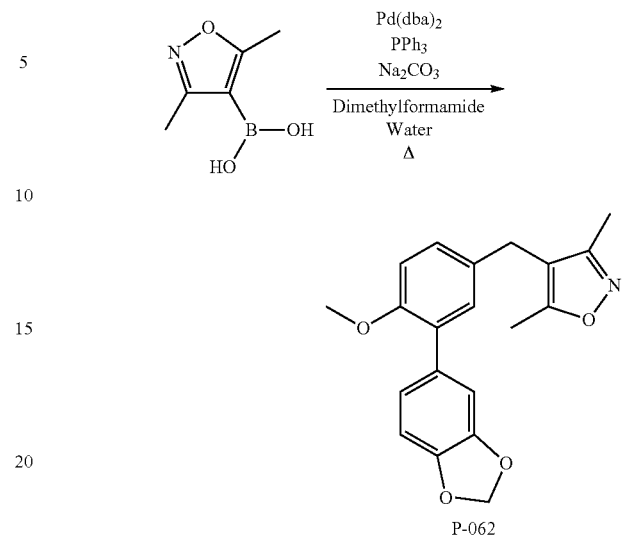

Synthesis of 4-(3-Benzo[1,3]dioxol-5-yl-4-methoxy-benzyl)-3,5-dimethyl-isoxazole (P-062). To a solution of I-168 (138 mg, 0.500 mmol) and 3,5-dimethyl-isoxazole-4-boronic acid (70 mg, 0.500 mmol) in dimethyl formamide (5 mL) were added palladium(0) bis(dibenzylideneacetone (14 mg, 0.025 mmol), triphenylphosphine (13 mg, 0.0500 mmol) and 1 M aqueous sodium carbonate (1.5 mL, 1.5 mmol). The resultant suspension was stirred at 85° C. for 72 h. The reaction was concentrated under reduced pressure, diluted with ethyl acetate (10 mL), washed with water (3×10 mL) and brine, dried over sodium sulfate, filtered, and the solvent removed under reduced pressure. The crude residue was purified by silica gel preparatory thin layer chromatography eluting with 1:1 hexanes and dichloromethane to afford 16.2 mg (10%) of P-062. $^1$H NMR (400 MHz, CDCl$_3$) 2.11 (s, 3H), 2.31 (s, 3H), 3.64 (s, 2H), 3.79 (s, 3H), 5.98 (s, 2H), 6.80-6.94 (m, 3H), 6.94-7.05 (m, 3H) ppm. LCMS=100% purity. APCI (+)=338.10 (M+1).

Example 175

Preparation of P-066

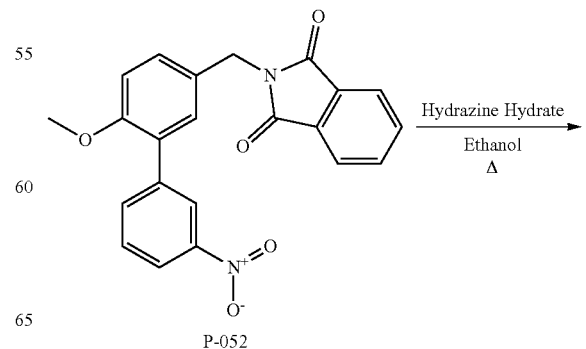

-continued

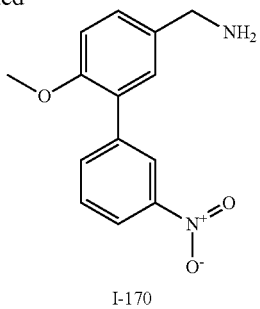

I-170

Synthesis of C-(6-Methoxy-3'-nitro-biphenyl-3-yl)-methylamine (I-170): A suspension of P-052 (700 mg, 1.80 mmol) and hydrazine hydrate (0.35 mL. 7.2 mmol) in ethanol (60 mL) was stirred at reflux for 6 h. The reaction was cooled to room temperature, filtered, and the solvent was evaporated. The residue was dissolved in ethanol (15 mL), precipitated with water (50 mL), and filtered to afford 97.9 mg as a white solid in 21% yield.

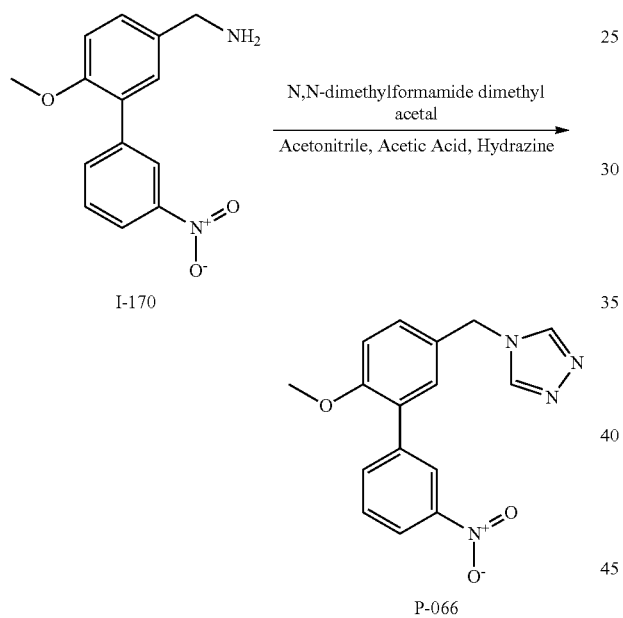

Synthesis of 4-(6-Methoxy-3'-nitro-biphenyl-3-ylmethyl)-4H-[1,2,4]triazole (P-066). A solution of formic hydrazine (25 mg, 0.41 mmol) and N,N-dimethylformamide dimethyl acetal (0.050 mL, 0.41 mmol) in acetonitrile (0.5 mL) was stirred at 50° C. for 30 min. To the solution was added I-170 (98 mg, 0.38 mmol) and acetic acid (0.5 mL). The reaction was then stirred at 160° C. for 6 h. The reaction was cooled to room temperature and the concentrated under vacuum. The reaction was diluted with water (30 mL) and extracted with dichloromethane (2×30 mL), the combined extracts were washed with brine, dried over sodium sulfate, filtered, and the solvent removed under vacuum. The crude material was purified by silica gel preparatory thin layer chromatography (9:1 dichloromethane:methanol) to afford 19.4 mg of P-066 in 17% yield. $^1$H NMR (400 MHz, CDCl$_3$): 3.86 (s, 3H), 5.19 (s, 2H), 7.03 (d, J=8.5 Hz, 1H), 7.17-7.25 (m, 2H), 7.58 (t, J=8.0 Hz, 1H), 7.79 (d, J=7.8 Hz, 1H), 8.16-8.24 (m, 3H), 8.37 (t, J=1.9 Hz, 1H) ppm. LCMS=94.0% purity. APCI (+)=311.1 (M+1).

Scheme 46.

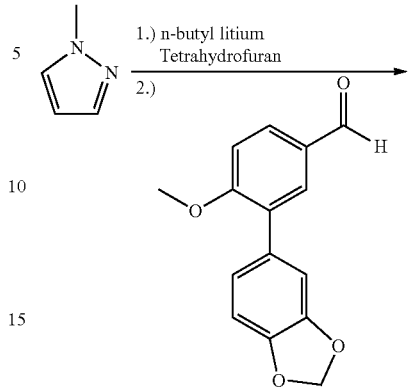

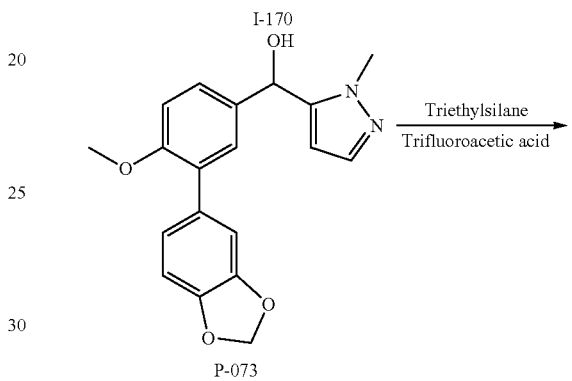

P-073

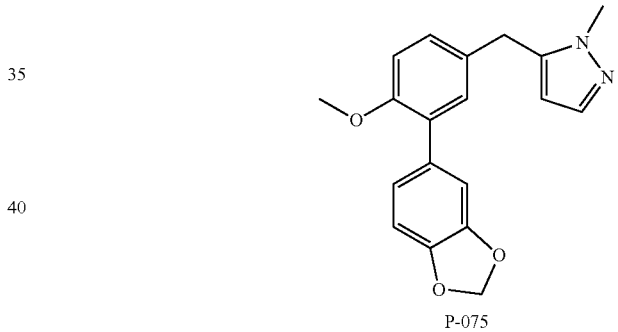

P-075

Example 176

Preparation of P-073

Synthesis of (3-Benzo[1,3]dioxol-5-yl-4-methoxy-phenyl)-(2-methyl-2H-pyrazol-3-yl)-methanol (P-073). A solution of 1-methylpyrazole (123 mg, 1.50 mmol) in tetrahydrofuran (10 mL) was cooled to 0° C. in an ice bath, and n-butyl lithium (2.5 M in hexanes, 0.80 mL, 2.0 mmol) was added. The yellow solution was stirred at 0° C. for 30 min followed by the addition of I-170 (256 mg, 1.00 mmol), and the resultant pale green solution stirred for 2 h. The reaction was diluted with water (50 mL), and extracted with ethyl acetate (2×30 mL). The combined extracts were washed with brine, dried over sodium sulfate, filtered, and concentrated under reduced pressure. The crude material was purified by silica gel column chromatography (1:1 hexanes:dichloromethane) to afford 259.1 mg of P-073 as a pale yellow solid in 77% yield. $^1$H NMR (400 MHz, CDCl$_3$): 3.81 (s, 3H), 3.83 (s, 3H), 5.90 (s, 1H), 5.98 (s, 2H), 6.12 (d, J=1.6 Hz, 1H), 6.82-6.89

(m, 1H), 6.91-6.98 (m, 2H), 7.03 (d, J=1.5 Hz, 1H), 7.29 (s, 2H), 7.40 (d, 1H) ppm. LCMS=98.9%; APCI (+)=339.1 (M+1).

Example 177

Preparation of P-075

Synthesis of 5-(3-Benzo[1,3]dioxol-5-yl-4-methoxy-benzyl)-1-methyl-1H-pyrazole (P-075). To a solution of P-073 (169 mg, 0.500 mmol) in trifluoroacetic acid (2.0 mL), was added triethylsilane (0.50 mL, 3.0 mmol). The reaction was stirred at room temperature overnight. The reaction was diluted with water (10 mL) and extracted with dichloromethane (2×10 mL). The combined organic extracts were washed with brine, dried over sodium sulfate, filtered, and the solvent removed under vacuum. The crude product was purified by silica gel column chromatography (20% methanol in dichloromethane) to afford 39.1 mg (24%) of P-075. ¹H NMR (400 MHz, CDCl₃) 7.40 (d, J=1.7 Hz, 1H), 7.07 (d, J=2.3 Hz, 1H), 7.02-7.06 (m, J=2.4 Hz, 1H), 7.02 (d, J=1.7 Hz, 1H), 6.91-6.94 (m, 1H), 6.90 (s, 1H), 6.86 (t, J=8.5 Hz, 2H), 5.98 (s, 2H), 3.95 (s, 2H), 3.80 (s, 3H), 3.74 (s, 3H) ppm.

Example 178

Preparation of P-074

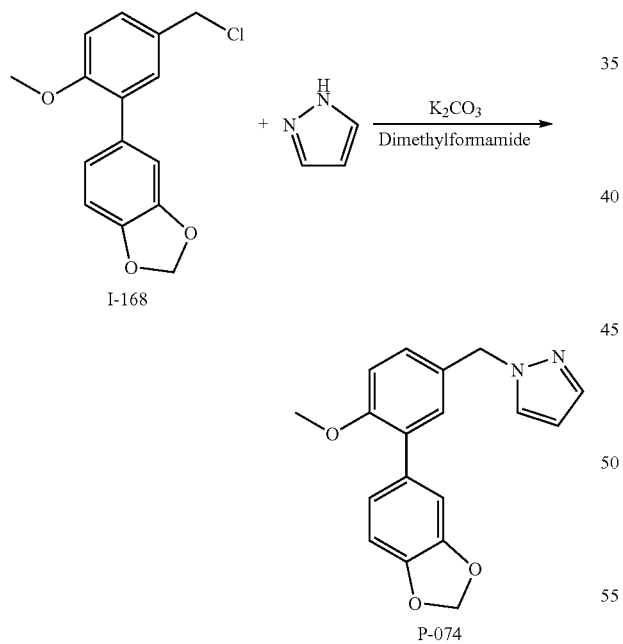

Synthesis of 1-(3-Benzo[1,3]dioxol-5-yl-4-methoxy-benzyl)-1H-pyrazole (P-074). A suspension of pyrazole (136 mg, 2.00 mmol), I-168 (108 mg, 1.00 mmol), and solid potassium carbonate (276 mg, 2.00 mmol) was stirred at room temperature overnight. Water (30 mL) was added, and the suspension extracted with ethyl acetate (2×30 mL). The combined organic layers were washed with brine, dried over sodium sulfate, filtered, and the solvent removed under vacuum. The product was purified by silica gel column chromatography (10% ethyl acetate in hexanes) to afford 44.4 mg of P-074 as a pale yellow oil in 14% yield. ¹H NMR (400 MHz, CDCl₃) 7.54 (d, J=1.8 Hz, 1H), 7.38 (d, J=2.3 Hz, 1H), 7.17 (dd, J=4.4, 2.2 Hz, 2H), 7.01 (d, J=1.7 Hz, 1H), 6.91-6.94 (m, 2H), 6.82-6.87 (m, 1H), 6.26 (t, J=2.1 Hz, 1H), 5.98 (s, 2H), 5.28 (s, 2H), 3.80 (s, 3H)

Example 179

Preparation of P-077

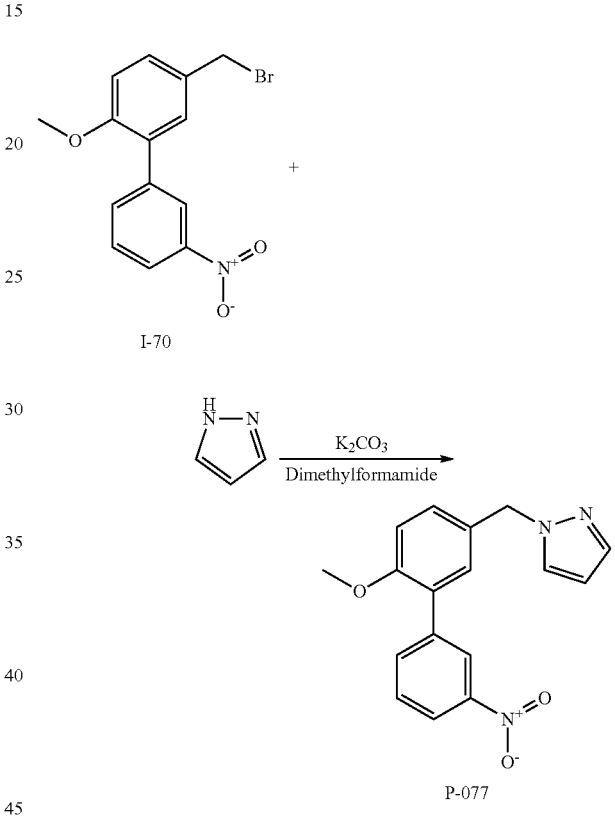

Synthesis of 1-(6-Methoxy-3'-nitro-biphenyl-3-ylmethyl)-1H-pyrazole (P-077). A suspension of I-70 (322 mg, 1.00 mmol), pyrazole (136 mg, 2.00 mmol), and solid potassium carbonate (276 mg, 2.00 mmol) in dimethyl formamide (10 mL) was stirred at room temperature overnight. The reaction was diluted water (30 mL), and extracted with ethyl acetate (2×30 mL). The combined extracts were washed with brine, dried over sodium sulfate, filtered, and the solvent removed under vacuum. The residue was purified by silica gel column chromatography (15% ethyl acetate in hexanes) to give P-077 (148 mg, 48% yield) as a white solid. ¹H NMR (400 MHz, DMSO-d₆): 8.27 (s, 1H), 8.17-8.22 (m, 1H), 7.89-7.94 (m, 1H), 7.83 (d, J=2.2 Hz, 1H), 7.72 (t, J=8.0 Hz, 1H), 7.44 (d, J=1.7 Hz, 1H), 7.35 (d, J=2.1 Hz, 1H), 7.28-7.33 (m, 1H), 7.15 (d, J=8.5 Hz, 1H), 6.19-6.30 (m, 1H), 5.32 (s, 2H), 3.79 (s, 3H) ppm.

LCMS=99.7% purity. APCI (+)=310.1 (M+1)

Example 180

Preparation of P-087

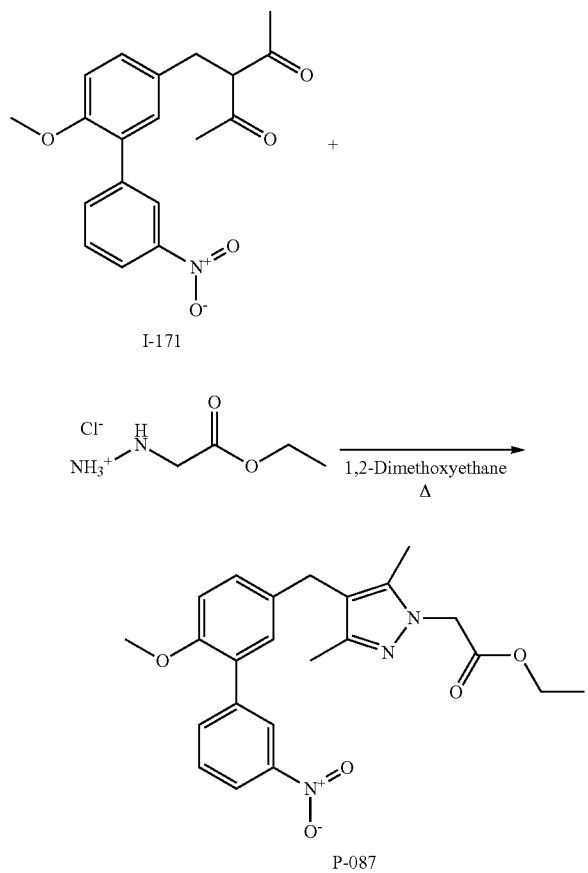

Synthesis of [4-(6-Methoxy-3'-nitro-biphenyl-3-ylmethyl)-3,5-dimethyl-pyrazol-1-yl]-acetic acid ethyl ester (P-087). To a solution of I-171 (102 mg, 0.300 mmol) in 1,2-dimethoxyethane (5 mL), were added ethyl hydrazinoacetate hydrochloride (93 mg, 0.60 mmol) and 4 Angstrom molecular sieves (200 mg), and the reaction was stirred at reflux for 3 h. The hot suspension was filtered and the solvent removed under vacuum. The residue was dissolved in dichloromethane (10 mL) and washed with water (30 mL). The aqueous wash was extracted with dichloromethane (2×30 mL), and the extracts combined. The organic solution was washed with brine, dried over sodium sulfate, filtered, and the solvent removed under vacuum. The residue was purified by silica gel column chromatography (2:1 hexanes:ethyl acetate) to give P-087 (97.1 mg, 76% yield). $^1$H NMR (400 MHz, CDCl$_3$): 8.38 (t, J=1.9 Hz, 1H), 8.15 (dd, J=8.2, 2.3 Hz, 1H), 7.79-7.82 (m, 1H), 7.53-7.56 (m, 1H), 7.07-7.10 (m, 2H), 6.90 (d, J=9.1 Hz, 1H), 4.79 (s, 2H), 4.21 (q, J=7.1 Hz, 2H), 3.80 (s, 3H), 3.74 (s, 2H), 2.13 (s, 3H), 2.13 (s, 3H), 1.26 (t, J=7.1 Hz, 3H) ppm. LCMS: 98.7% purity. APCI (+)=310.1 (M−29)

Example 181

Preparation of P-088

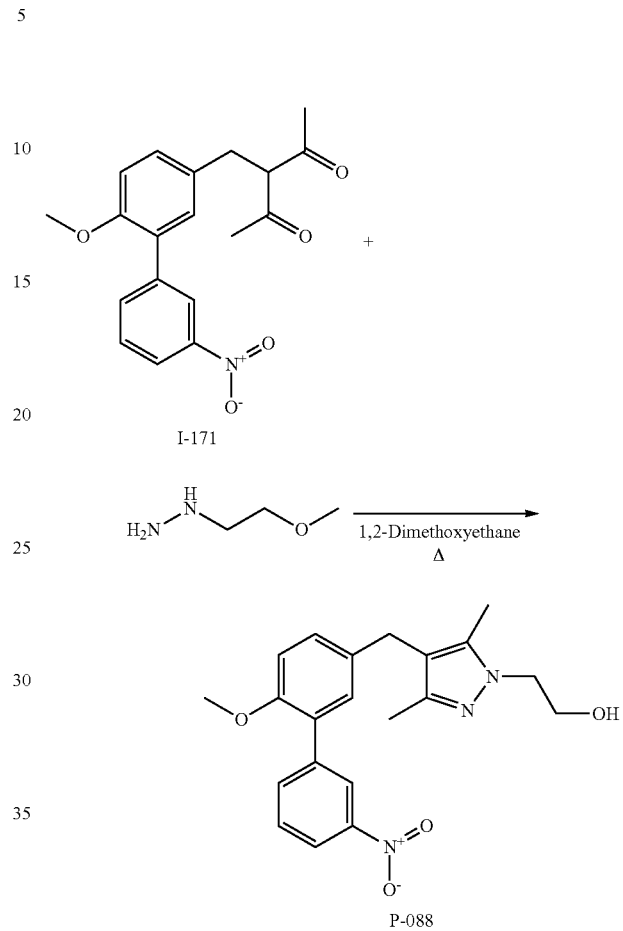

Synthesis of 2-[4-(6-Methoxy-3'-nitro-biphenyl-3-ylmethyl)-3,5-dimethyl-pyrazol-1-yl]-ethanol (P-088). To a solution of I-171 (102 mg, 0.300 mmol) in 1,2-dimethoxyethane (5 mL), were added 2-hydroxyethyl hydrazine (0.037 mL, 0.60 mmol) and 4 Angstrom molecular sieves (200 mg), and the reaction was stirred at reflux for 3 h. The hot suspension was filtered and the solvent removed under vacuum. The residue was dissolved in dichloromethane (10 mL) and washed with water (30 mL). The aqueous wash was extracted with dichloromethane (2×30 mL), and the extracts combined. The organic solution was washed with brine, dried over sodium sulfate, filtered, and the solvent removed under vacuum. The crude material was purified by silica gel column chromatography (2:1:0.3 hexanes:ethyl acetate:methanol) to give P-088 (61.0 mg, 53% yield) as a yellow solid. $^1$H NMR (400 MHz, CDCl$_3$): 8.37 (t, J=2.0 Hz, 1H), 8.16 (dt, J=8.2, 1.1 Hz, 1H), 7.81 (dt, J=7.7, 0.8 Hz, 1H), 7.54-7.57 (m, 1H), 7.06-7.10 (m, 2H), 6.91 (d, J=9.1 Hz, 1H), 4.05-4.09 (m, 2H), 3.95-4.02 (m, 2H), 3.80 (s, 3H), 3.73 (s, 2H), 2.14 (s, 3H), 2.16 (s, 3H) ppm. LCMS: 98.2% purity. APCI (+)=382.1 (M+1)

Example 182

Preparation of P-089

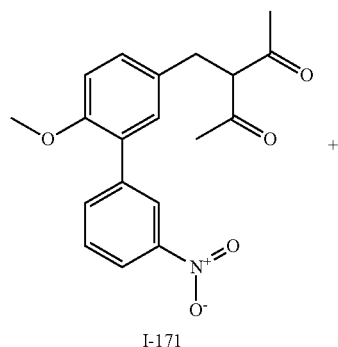

I-171

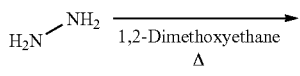

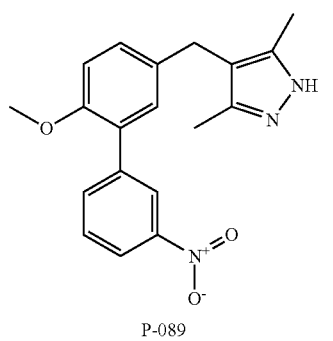

P-089

Example 183

Preparation of P-090

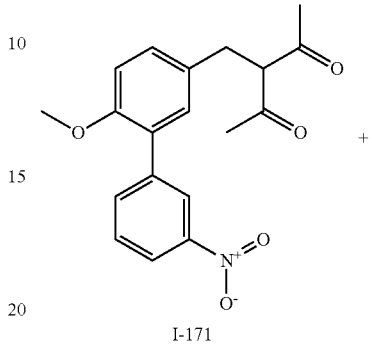

I-171

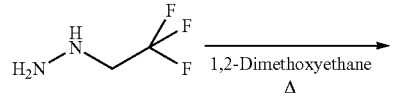

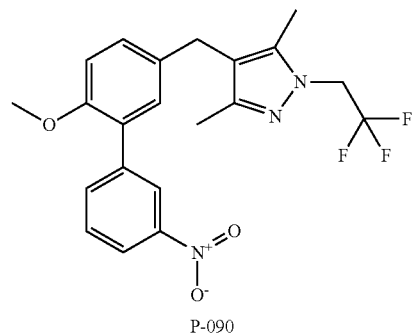

P-090

Synthesis of 4-(6-Methoxy-3'-nitro-biphenyl-3-ylmethyl)-3,5-dimethyl-1H-pyrazole (P-089). To a solution of I-171 (102 mg, 0.300 mmol) in 1,2-dimethoxyethane (5 mL), were added hydrazine (0.029 mL, 0.60 mmol) and 4 Angstrom molecular sieves (200 mg), and the reaction was stirred at reflux for 3 h. The hot suspension was filtered and the solvent removed under vacuum. The residue was dissolved in dichloromethane (10 mL) and washed with water (30 mL). The aqueous wash was extracted with dichloromethane (2×30 mL), and the extracts combined. The organic solution was washed with brine, dried over sodium sulfate, filtered, and the solvent removed under vacuum. The crude material was purified by silica gel column chromatography (1:1 hexanes:ethyl acetate) to give P-089 (67.8 mg, 67% yield) $^1$H NMR (400 MHz, CDCl$_3$): 8.38 (s, 1H), 8.13-8.20 (m, 1H), 7.75-7.83 (m, 1H), 7.50-7.58 (m, 1H), 7.05-7.13 (m, 2H), 6.91 (d, J=8.1 Hz, 1H), 3.80 (s, 3H), 3.74 (s, 2H), 2.18 (s, 6H) ppm. LCMS=97.2% purity. APCI (+)=338.1 (M+1).

Synthesis of 4-(6-Methoxy-3'-nitro-biphenyl-3-ylmethyl)-3,5-dimethyl-1-(2,2,2-trifluoro-ethyl)-1H-pyrazole (P-090). To a solution of I-171 (102 mg, 0.300 mmol) in 1,2-dimethoxyethane (5 mL), were added 2,2,2-trifluoroethyl hydrazine (0.098 mL, 0.60 mmol) and 4 Angstrom molecular sieves (200 mg), and the reaction was stirred at reflux for 3 h. The hot suspension was filtered and the solvent removed under vacuum. The residue was dissolved in dichloromethane (10 mL) and washed with water (30 mL). The aqueous wash was extracted with dichloromethane (2×30 mL), and the extracts combined. The organic solution was washed with brine, dried over sodium sulfate, filtered, and the solvent removed under vacuum. The crude material was purified by silica gel column chromatography (5:1 hexanes:ethyl acetate) to give P-090 (64.5 mg, 51% yield) as a yellow-red oil. $^1$H NMR (400 MHz, CDCl$_3$): 8.38 (t, J=2.0 Hz, 1H), 8.16 (ddd, J=8.2, 2.3, 1.1 Hz, 1H), 7.78-7.81 (m, 1H), 7.52-7.55 (m, 1H), 7.04-7.07 (m, 2H), 6.91 (d, J=9.1 Hz, 1H), 4.58 (q, J=8.4 Hz, 2H), 3.78-3.81 (m, 3H), 3.73 (s, 2H), 2.20 (s, 3H), 2.14 (s, 3H) ppm. LCMS=97.6% purity. APCI (+)=420.1 (M+1).

Example 184

Preparation of P-101

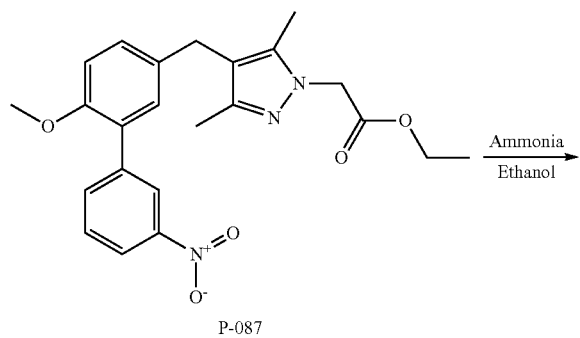

Synthesis of 2-[4-(6-Methoxy-3'-nitro-biphenyl-3-ylmethyl)-3,5-dimethyl-pyrazol-1-yl]-acetamide (P-101). To a solution of P-087 (212 mg, 0.500 mmol) in methanol (5 mL) was added ammonia (7 M in methanol, 0.5 mL, 3.5 mmol) and the solution was stirred at room temperature overnight. The resulting suspension was concentrated under vacuum, and dissolved in ethyl acetate (10 mL). The reaction was washed with water (10 mL) and brine (10 mL), dried over sodium sulfate, filtered, and the solvent removed under vacuum. The resulting solid was triturated in dichloromethane (1 mL) in hexanes (10 mL) to give P-101 (85.8 mg, 44% yield) as a white solid. $^1$H NMR (400 MHz, CDCl$_3$) 8.31-8.37 (m, 1H), 8.14-8.20 (m, 1H), 7.77-7.84 (m, 1H), 7.51-7.59 (m, 1H), 7.01-7.10 (m, 2H), 6.91 (d, J=8.1 Hz, 1H), 6.05 (br s, 1H), 5.39 (br s, 1H), 4.68 (s, 2H), 3.80 (s, 3H), 3.73 (s, 2H), 2.17 (s, 3H), 2.16 (s, 3H) ppm. LCMS=98.2% purity. APCI (+)=395.1 (M+1).

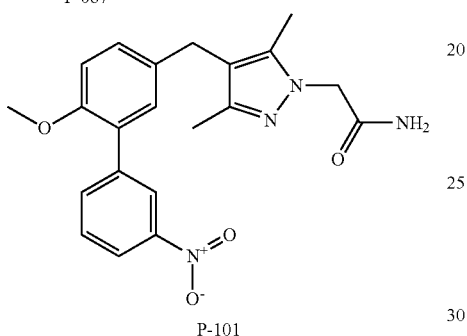

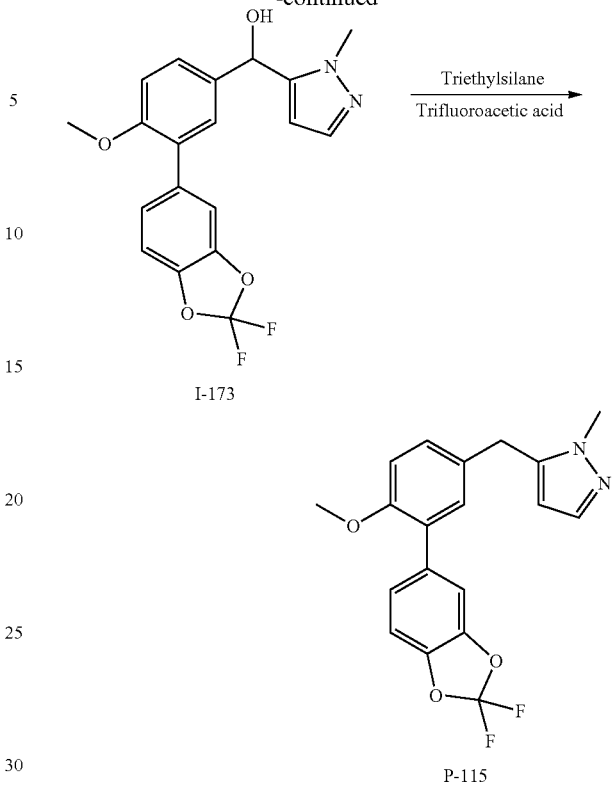

Example 185

Preparation of P-115

Synthesis of 3-(2,2-Difluoro-benzo[1,3]dioxol-5-yl)-4-methoxy-benzaldehyde (I-172). To a solution of 5-formyl-2-methoxy phenyl boronic acid (1.0 g, 5.5 mmol) in water (6 mL) and methanol (30 mL), was added 5-bromo-2,2-difluoro-1,3-benzodioxole (0.97 mL, 7.2 mmol), solid potassium carbonate (1.5 g, 11 mmol), and palladium(II) acetate (25 mg, 0.11 mmol). The reaction was stirred at room temperature for 16 h. The black mixture was diluted with water (30 mL) and extracted with ethyl acetate (2×30 mL). The combined extracts were decolorized with activated charcoal, dried over sodium sulfate, filtered, and concentrated to 20 mL under vacuum. The solution was purified by silica gel column chromatography eluting with hexanes/ethyl acetate (11:1) to give I-172 (620 mg, 39% yield) as a white solid.

Synthesis of [3-(2,2-Difluoro-benzo[1,3]dioxol-5-yl)-4-methoxy-phenyl]-(2-methyl-2H-pyrazol-3-yl)-methanol (I-173). A solution of 1-methylpyrazole (123 mg, 1.5 mmol) under a positive nitrogen atmosphere was cooled to 0° C. in an ice water bath. To the stirring solution was added n-butyl lithium (2.5 M in hexanes, 0.80 mL, 2.0 mmol) The reaction mixture was stirred at 0° C. for 30 min, and I-172 (292 mg, 1.0 mmol) was added in one portion. The reaction was stirred an additional 2 h. The reaction was diluted with water (50 mL), and extracted with ethyl acetate (2×30 mL). The combined extracts were washed with brine, dried over sodium sulfate, filtered, and the solvent removed under reduced pressure to give I-173 (220 mg, 59% yield) as a yellow solid.

Synthesis of 5-[3-(2,2-Difluoro-benzo[1,3]dioxol-5-yl)-4-methoxy-benzyl]-1-methyl-1H-pyrazole (P-115). To a solution of I-173 (187 mg, 0.500 mmol) in trifluoroacetic acid (2.0

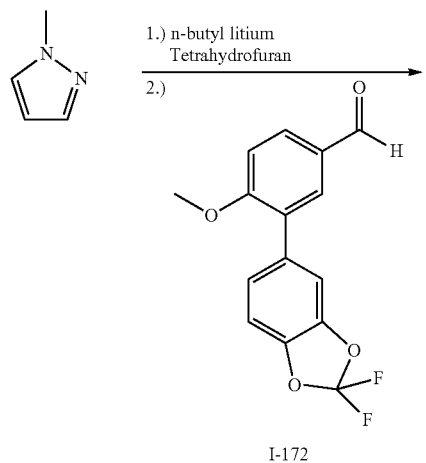

mL), was added triethyl silane (0.50 mL, 3.0 mmol). The reaction was stirred at room temperature overnight. The reaction was diluted with water (10 mL) and extracted with dichloromethane (2×10 mL). The combined extracts were washed with brine, dried over sodium sulfate, filtered, and the solvent removed under vacuum. The residue was purified by silica gel column chromatography (5:2 hexanes/ethyl acetate) and silica gel preparatory thin layer chromatography (20:1 dichloromethane/methanol) to give P-115 (29.9 mg, 17% yield). $^1$H NMR (400 MHz, CDCl$_3$): 3.74 (s, 3H), 3.81 (s, 3H), 3.96 (s, 2H), 6.02 (d, J=1.6 Hz, 1H), 6.91 (d, J=8.3 Hz, 1H), 7.00-7.17 (m, 4H), 7.24 (d, J=1.5 Hz, 1H), 7.40 (d, J=1.6 Hz, 1H) ppm. LCMS=100% purity. APCI (+)=359.1 (M+1).

Example 186

Preparation of P-201

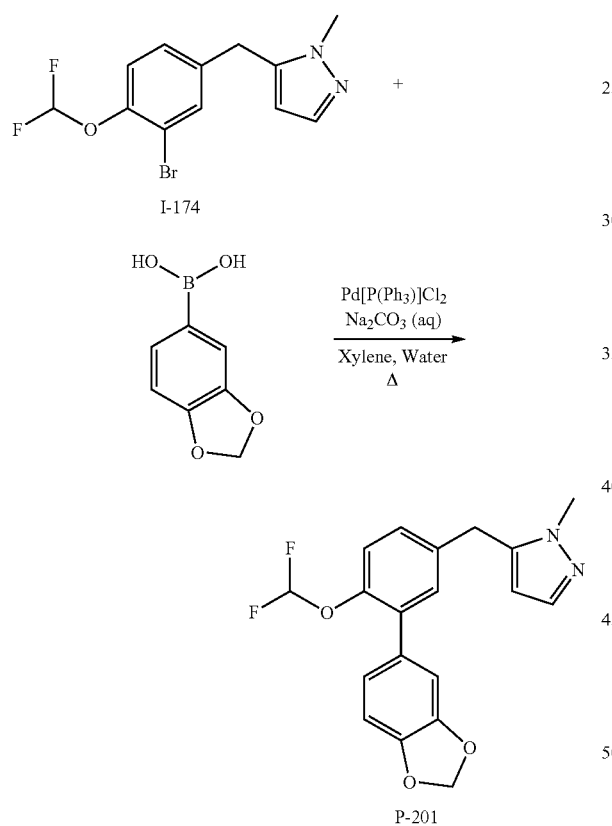

Synthesis of 5-(3-Benzo[1,3]dioxol-5-yl-4-difluoromethoxy-benzyl)-1-methyl-1H-pyrazole (P-201). A suspension of benzo[1,3]dioxole-5-boronic acid (108 mg, 0.65 mmol), I-174 (158 mg, 0.500 mmol), palladium(II) triphenylphosphindichloride (35 mg, 0.050 mmol), and 1M aqueous sodium carbontate (1.0 mL, 1.00 mmol) in xylene (3 mL) was stirred at 150° C. for 24 h. The reaction was diluted with ethyl acetate (10 mL), washed with water (3×10 mL) and brine, dried over sodium sulfate, filtered, and the solvent removed under vacuum. The residue was purified by silica gel column chromatography (4:1 hexanes/ethyl acetate), and then by silica gel preparatory thin layer chromatography (5:1 dichloromethane/acetone) to give P-201 (13.4 mg, 7% yield).

$^1$H NMR (400 MHz, CDCl$_3$): 3.64 (s, 3H), 4.05 (s, 2H), 5.82 (s, 1H), 5.95 (s, 2H), 6.63-6.94 (m, 7H), 7.59 (s, 1H) ppm. LCMS=99% purity. APCI (−)=321.1 (M−37).

Example 187

Preparation of P-306

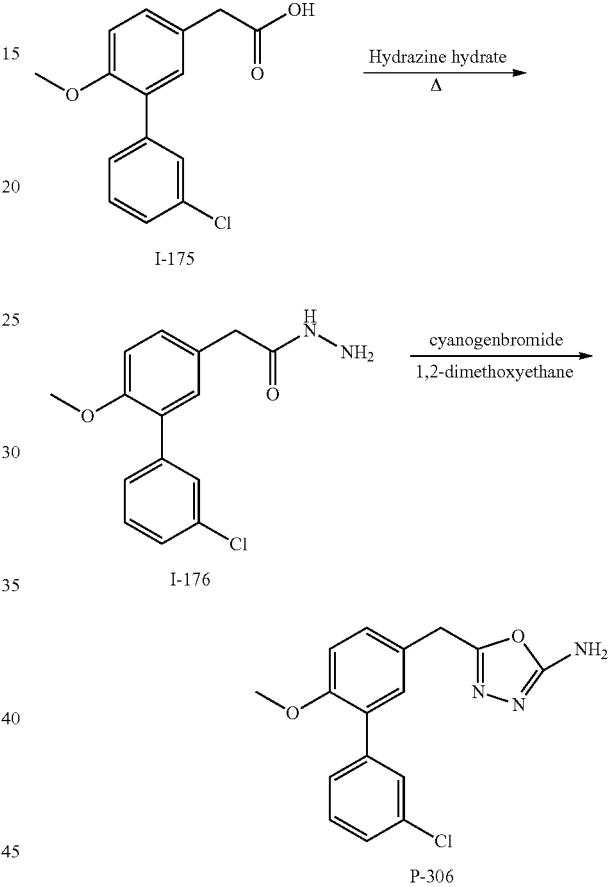

Synthesis of 5-(3'-Chloro-6-methoxy-biphenyl-3-ylmethyl)-[1,3,4]oxadiazol-2-ylamine (P-306). A solution of I-176 (277 mg, 1.00 mmol) in hydrazine hydrate (0.5 mL) was stirred at 100° C. overnight. The reaction was concentrated under vacuum to obtain a gummy white solid. The crude material was dissolved in 1,2-dimethoxyethane (0.5 mL) and cyanogen bromide (212 mg, 2.00 mmol) was added. The reaction was stirred at room temperature for 3 h. The reaction was diluted with dichloromethane (5 mL) and washed with 1 M aqueous sodium hydroxide (5 mL). The organic layer was separated, dried over sodium sulfate, filtered and concentrated under vacuum. The residue was purified by silica gel preparatory thin layer chromatography (hexanes/ethyl acetate) to give P-306 (64.2 mg, 30% yield). $^1$H NMR (400 MHz, DMSO-d$_6$): 3.77 (s, 3H), 4.01 (s, 2H), 6.87 (s, 2H), 7.10 (d, J=8.5 Hz, 1H), 7.21-7.29 (m, 2H), 7.36-7.47 (m, 3H), 7.50 (s, 1H) ppm. LCMS=97.1% purity. APCI (+)=316 (M).

Example 188

Preparation of P-393

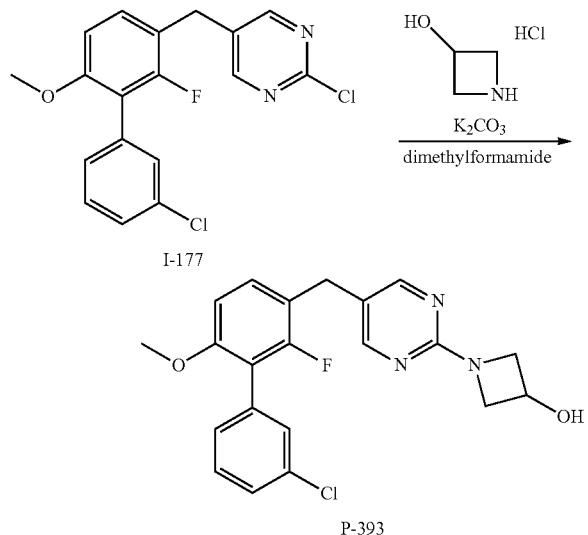

Synthesis 1-[5-(3'-Chloro-2-fluoro-6-methoxy-biphenyl-3-ylmethyl)-pyrimidin-2-yl]-azetidin-3-ol (P-393). A suspension of I-177 (72 mg, 0.20 mmol), azetidin-3-ol hydrochloride (44 mg, 0.40 mmol) and potassium carbonate (55 mg, 0.40 mmol) in dimethyl formamide (1.5 mL) was stirred at 80° C. overnight. The mixture was cooled to room temperature, diluted with water (5 mL), and extracted with diethyl ether (3×5 mL). The combined extracts were concentrated, and the crude material purified by silica gel column chromatography (2:1 hexanes/ethyl acetate) to give P-393 (73.3 mg, 92% yield) as a cream white solid. $^1$H NMR (400 MHz, CDCl$_3$): 3.75 (s, 3H), 3.77 (s, 2H), 3.98 (dd, J=10.3, 4.3 Hz, 2H), 4.34-4.43 (m, 2H), 4.77 (br s, 1H), 6.70 (d, J=8.3 Hz, 1H), 7.08 (t, J=8.6 Hz, 1H), 7.26-7.40 (m, 4H), 8.21 (s, 2H) ppm.

LCMS=100% purity. APCI (+)=400 (M).

Example 189

Preparation of P-397

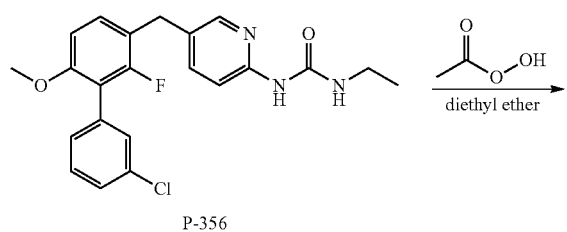

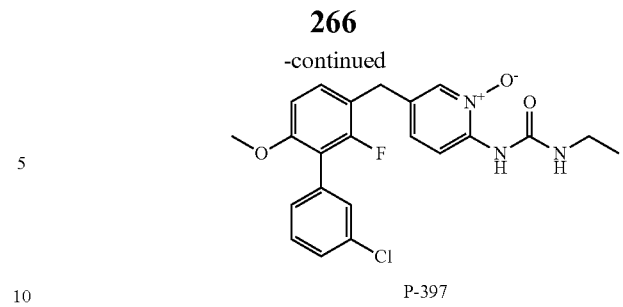

Synthesis of 1-[5-(3'-Chloro-2-fluoro-6-methoxy-biphenyl-3-ylmethyl)-1-oxy-pyridin-2-yl]-3-ethyl-urea (P-397). A solution of P-356 (82.7 mg, 0.200 mmol) in diethyl ether (5 mL) was stirred at room temperature with peracetic acid (32% wt., 0.06 mL, 0.300 mmol) for 3 h. The mixture was concentrated and the residue purified by silica gel column chromatography (19:1 dichloromethane/methanol) to give P-397 (27.6 mg, 32% yield).

$^1$H NMR (400 MHz, CDCl$_3$): 1.12 (t, 3H) 3.17-3.35 (m, 2H), 3.72-3.80 (m, 3H), 3.87 (s, 2H), 6.64-6.78 (m, 1H), 6.86 (br s, 1H), 7.02-7.17 (m, 1H), 7.22 (s, 1H), 7.29-7.43 (m, 3H), 7.93 (s, 1H), 8.36 (d, J=8.9 Hz, 1H), 9.73 (s, 1H) ppm.

LCMS=100% purity. APCI (−)=428.1 (M−2).

Example 190

Preparation of P-398

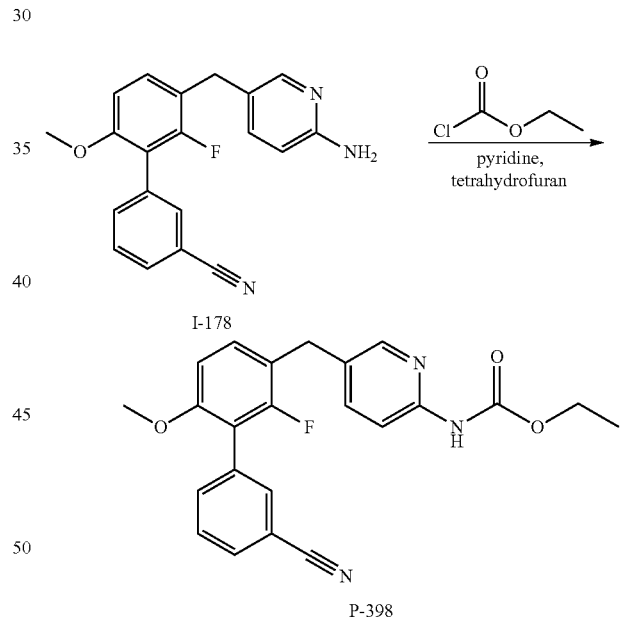

Synthesis of [5-(3'-Cyano-2-fluoro-6-methoxy-biphenyl-3-ylmethyl)-pyridin-2-yl]-carbamic acid ethyl ester (P-398). A solution of I-178 (166 mg, 0.500 mmol) in tetrahydrofuran was cooled to 0° C. To the reaction was added pyridine (0.08 mL, 1 mmol), and the reaction stirred for 10 min. To the solution was added ethyl chloroformate (0.09 mmol, 1 mmol) slowly, and the yellow suspension was stirred at room temperature overnight. The reaction was allowed to sit after the addition of water (10 mL), and the solid that settled to the bottom was collected by filtration. The solid was suspended in dimethyl sulfoxide (5 mL) and water (5 mL), and filtered to give P-398 (14.6 mg, 7.2% yield) as a white solid. $^1$H NMR (400 MHz, CDCl$_3$): 1.31 (t, J=7.1 Hz, 3H), 3.76 (s, 3H), 3.91

(s, 2H), 4.23 (q, J=7.1 Hz, 2H), 6.73 (d, J=8.6 Hz, 1H), 7.12 (t, J=8.5 Hz, 1H), 7.32-7.41 (m, 1H), 7.44-7.56 (m, 2H), 7.63 (d, J=7.8 Hz, 2H), 7.70 (s, 1H), 7.88 (d, J=8.5 Hz, 1H), 8.12 (s, 1H) ppm. LCMS=94.0% purity. APCI (+)=406.1 (M+1).

Example 191

Preparation of P-405-HCl

Example 192

Preparation of P-406

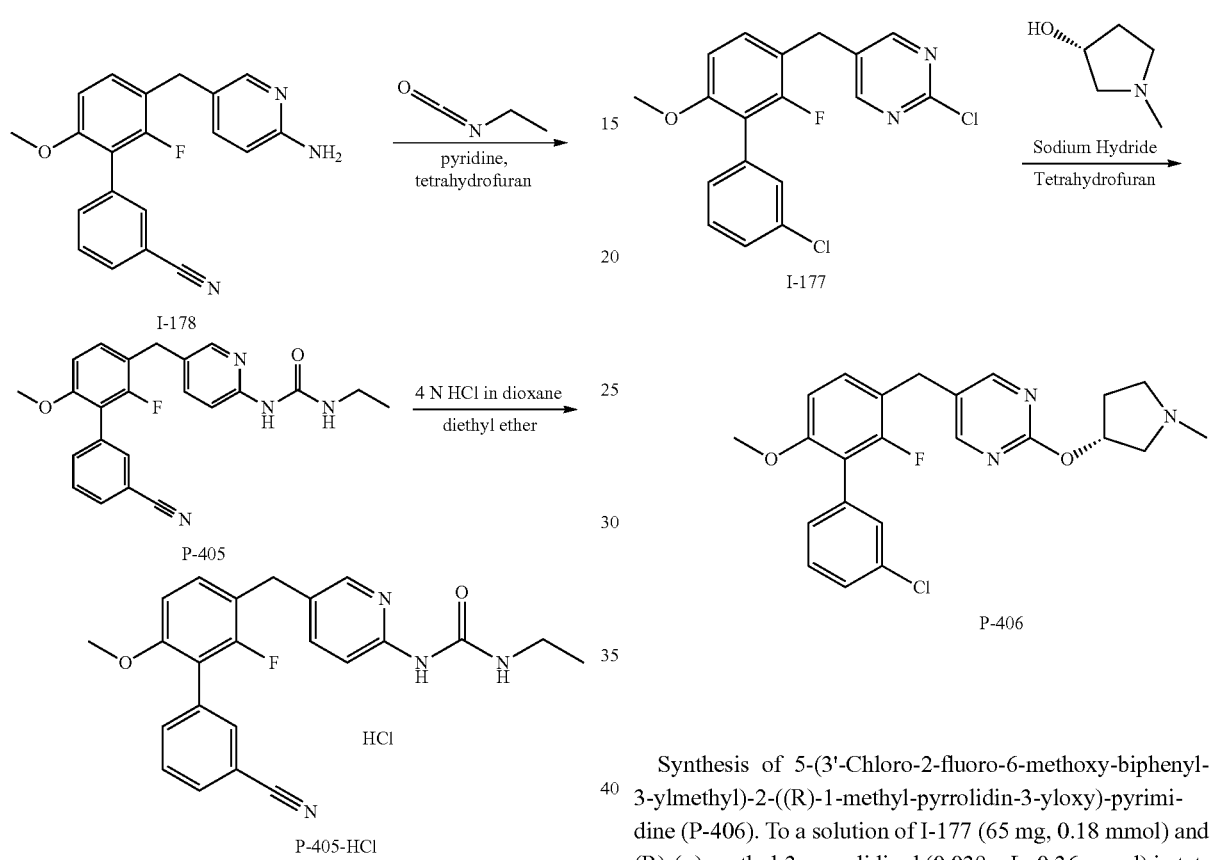

Synthesis of 1-[5-(3'-Cyano-2-fluoro-6-methoxy-biphenyl-3-ylmethyl)-pyridin-2-yl]-3-ethyl-urea hydrochloride salt (P-405-HCl). A solution of I-178 (166 mg, 0.500 mmol) and ethyl isocyanate (0.2 mL, 2.5 mmol) in pyridine (0.5 mL) was stirred at room temperature overnight. To the solution was added water (5 mL), and the reaction stirred for 1 h. The solid that formed was filtered, triturated with tetrahydrofuran and water to give a residue. This residue was purified by silica gel column chromatography (100:1 dichloromethane/methanol) to give impure P-405 (131 mg, 65% yield). The whole of the material was suspended in diethyl ether (1.5 mL) and 4 N hydrogen chloride in dioxane (0.75 mL, 3.0 mmol) was added. Additional hydrogen chloride solution was added (2.25 mL, 9 mmol). The reaction mixture was allowed to stir at room temperature overnight. The precipitate was filtered and dried to give P-405-HCl (52.5 mg, 24% yield).

$^1$H NMR (400 MHz, DMSO-d$_6$): 1.09 (t, J=7.2 Hz, 3H), 3.12-3.25 (m, 2H), 3.74 (s, 3H), 3.94 (s, 2H), 6.97 (d, J=8.7 Hz, 1H), 7.25-7.47 (m, 2H), 7.53-7.92 (m, 5H), 8.10 (s, 1H) ppm. LCMS=100% purity. APCI (+)=405.1 (M+1).

Synthesis of 5-(3'-Chloro-2-fluoro-6-methoxy-biphenyl-3-ylmethyl)-2-((R)-1-methyl-pyrrolidin-3-yloxy)-pyrimidine (P-406). To a solution of I-177 (65 mg, 0.18 mmol) and (R)-(−)-methyl-3-pyrrolidinol (0.039 mL, 0.36 mmol) in tetrahydrofuran (1 mL) was added NaH (60% weight dispersion, 29 mg, 0.72 mmol) slowly. Once gas evolution ceased, the reaction was stirred at 80° C. for 4 h. The reaction was cooled to room temperature and diluted with water (10 mL). The mixture was extracted with ethyl acetate (3×2 mL), the pH of the aqueous layer adjusted to pH 7 by addition of 1 M aqueous hydrochloric acid, and the aqueous mixture again extracted with ethyl acetate (2×2 mL). The combined extracts were dried over sodium sulfate, filtered and the solvent removed under vacuum. The residue was purified by silica gel column chromatography (9:1 dichloromethane/methanol) to give P-406 (46.8 mg, 61% yield) as a thick pale yellow oil.

$^1$H NMR (400 MHz, CDCl$_3$): 2.03-2.48 (m, 2H), 2.54 (s, 3H), 2.72-2.93 (m, 2H), 3.00 (br s, 1H), 3.47 (dd, J=11.4, 5.9 Hz, 1H), 3.77 (s, 3H), 3.87 (s, 2H), 5.45 (t, J=6.4 Hz, 1H), 6.73 (d, J=8.5 Hz, 1H), 7.12 (t, J=8.5 Hz, 1H), 7.29-7.41 (m, 3H), 8.37 (s, 2H) ppm. LCMS=100% purity. MS (ESI+) 428.1 (M+H).

Example 193

Preparation of P-417

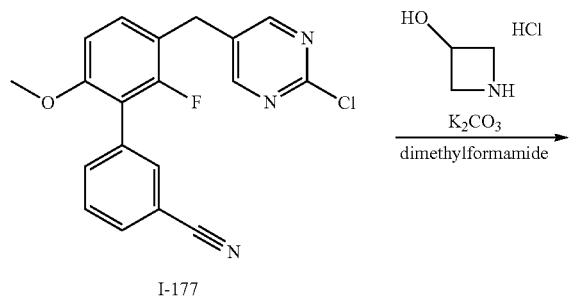

Synthesis of 2'-Fluoro-3'-[2-(3-hydroxy-azetidin-1-yl)-pyrimidin-5-ylmethyl]-6'-methoxy-biphenyl-3-carbonitrile (P-417). To a stirred solution of I-177 (61 mg, 0.17 mmol) and azetidin-3-ol hydrochloride (40 mg, 0.34 mmol) in dimethylformamide (0.5 mL) was added solid potassium carbonate (48 mg, 0.34 mmol), and the pale yellow solution was subsequently stirred at 80° C. overnight. The reaction was cooled to room temperature, diluted with water (15 mL), stirred for 30 min at room temperature, and the resulting precipitate collected by filtration. The crude was purified by trituration in dichloromethane/diethyl ether/hexanes to give P-417 (26 mg, 39% yield) as a white-cream solid. $^1$H NMR (400 MHz, DMSO-$d_6$): 3.68-3.74 (m, 5H), 3.77 (s, 2H), 4.08-4.26 (m, 2H), 4.52 (br s, 1H), 5.63 (d, J=6.4 Hz, 1H), 6.95 (d, J=8.7 Hz, 1H), 7.32 (t, J=8.7 Hz, 1H), 7.54-7.74 (m, 2H), 7.74-7.91 (m, 2H), 8.24 (s, 2H) ppm.
LCMS=100% purity. APCI (+)=391.1 (M+1).

Example 194

Preparation of P-513

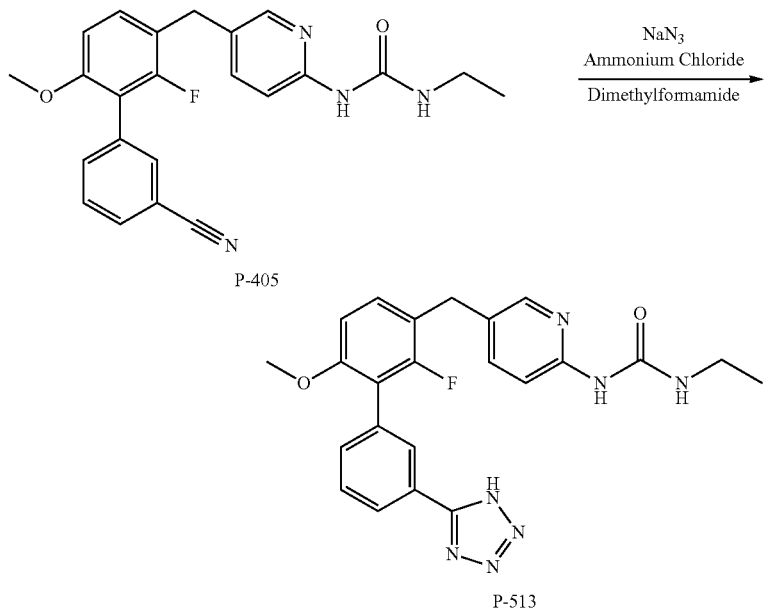

Synthesis of 1-Ethyl-3-{5-[2-fluoro-6-methoxy-3'-(1H-tetrazol-5-yl)-biphenyl-3-ylmethyl]-pyridin-2-yl}-urea (P-513). A mixture of P-405 (405 mg, 1.00 mmol), sodium azide (325 mg, 5.00 mmol), and ammonium chloride (374 mg, 7.00 mmol) in dimethylformamide (10 mL) was stirred at 80° C. overnight. The reaction was cooled to room temperature, diluted with ethyl acetate (30 mL), and washed with water (50 mL). The aqueous wash was extracted with ethyl acetate (2×30 mL), the extracts combined, dried over sodium sulfate, and the solvent removed under vacuum. The residue was purified by silica gel column chromatography (19:1 to 4:1 dichloromethane/methanol) to give P-513 (11.5 mg, 2.5% yield) as an off-white solid. $^1$H NMR (400 MHz, DMSO-$d_6$): 1.05-1.10 (m, 3H), 3.11-3.21 (m, 2H), 3.72 (s, 3H), 3.88 (s, 2H), 6.93 (d, J=8.6 Hz, 1H), 7.10-7.37 (m, 3H), 7.42 (s, 1H), 7.54 (s, 1H), 7.90 (br s, 2H), 8.07 (s, 2H), 9.09 (s, 1H) ppm. LCMS=95.9% yield. APCI (+)=448.1

Example 195

Preparation of P-456

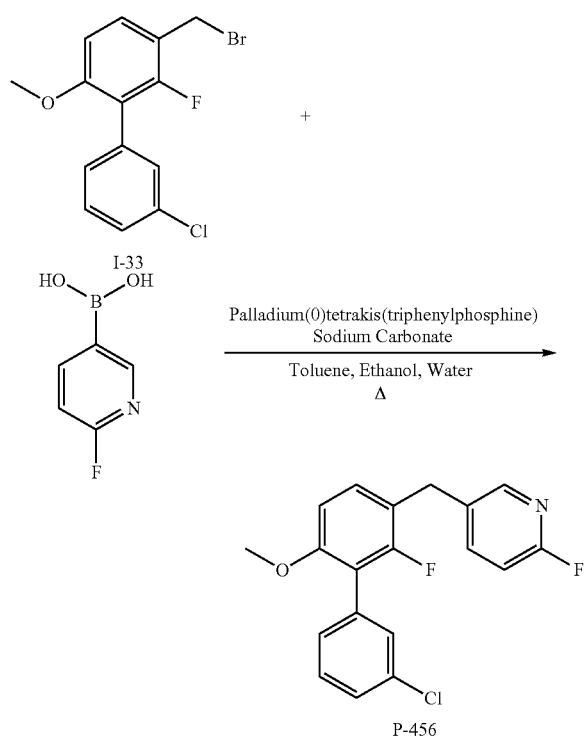

Synthesis of 5-(3'-Chloro-2-fluoro-6-methoxy-biphenyl-3-ylmethyl)-2-fluoro-pyridine (P-456). A suspension of I-33 (824 mg, 2.50 mmol), 2-fluoropyridin-5-boronic acid (352 mg, 2.50 mmol), 2 M aqueous sodium carbonate (2.5 mL, 5.00 mmol), and palladium(0)tetrakis(triphenylphosphine) (144 mg, 0.125 mmol) in toluene (10 mL) and ethanol (2.5 mL) was stirred at 80° C. overnight under a high pressure nitrogen atmosphere. The reaction was cooled to room temperature, diluted with water (10 mL), and extracted with ethyl acetate (2×20 mL). The combined extracts were dried over sodium sulfate, filtered, and concentrated under vacuum. The residue was purified by silica gel column chromatography (4:1 hexanes/ethyl acetate) to give P-456 (695 mg, 78% yield) as a white solid. $^1$H NMR (400 MHz, DMSO-d$_6$): 3.73 (s, 3H), 3.98 (s, 2H), 6.95 (d, J=8.6 Hz, 1H), 7.11 (dd, J=8.4, 2.7 Hz, 1H), 7.25-7.51 (m, 5H), 7.82 (td, J=8.2, 2.4 Hz, 1H), 8.14 (s, 1H), 8.32 (s 1H) ppm. LCMS=97.4% purity. APCI (+)=346 (M)

Example 196

Preparation of P-457

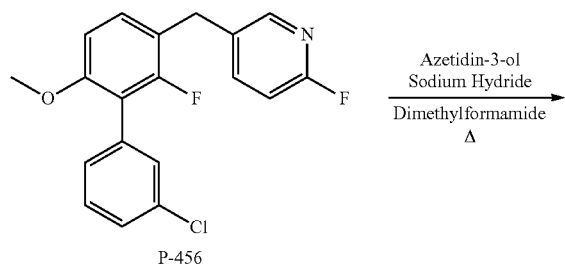

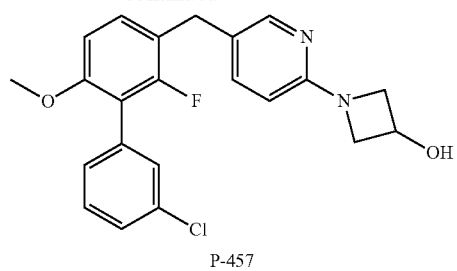

Synthesis of 1-[5-(3'-Chloro-2-fluoro-6-methoxy-biphenyl-3-ylmethyl)-pyridin-2-yl]-azetidin-3-ol (P-457). A mixture of azetidin-3-ol (56 mg, 0.56 mmol) and sodium hydride (60% weight dispersion, 33 mg, 0.84 mmol) in dimethylformamide (1 mL) was stirred under gas evolution ceased. After 2 min of stirring P-456 (97 mg, 0.28 mmol) was added, and the reaction heated at 140° C. overnight. The reaction was cooled to room temperature, diluted with water (5 mL), and extracted with ethyl acetate (2×5 mL). The combined extracts were dried over sodium sulfate, filtered, and the solvent removed under vacuum. The residue was purified by silica gel column chromatography (1:2 hexanes/ethyl acetate followed by 9:1 dichloromethane/methanol) and trituration in ethyl acetate and hexanes to give P-457 (22.2 mg, 19.9% yield) as a cream colored solid.

$^1$H NMR (400 MHz, DMSO-d$_6$): 3.61 (dd, 2H), 3.68-3.74 (m, 3H), 3.78 (s, 2H), 4.09 (t, J=7.5 Hz, 2H), 4.47-4.60 (m, 1H), 5.59 (d, J=6.6 Hz, 1H), 6.33 (d, J=8.5 Hz, 1H), 6.92 (d, J=8.6 Hz, 1H), 7.20-7.32 (m, 2H), 7.32-7.39 (m, 2H), 7.39-7.50 (m, 2H), 7.96 (d, J=1.6 Hz, 1H) ppm. LCMS=98.5% purity. APCI (+)=399 (M).

Scheme 47.

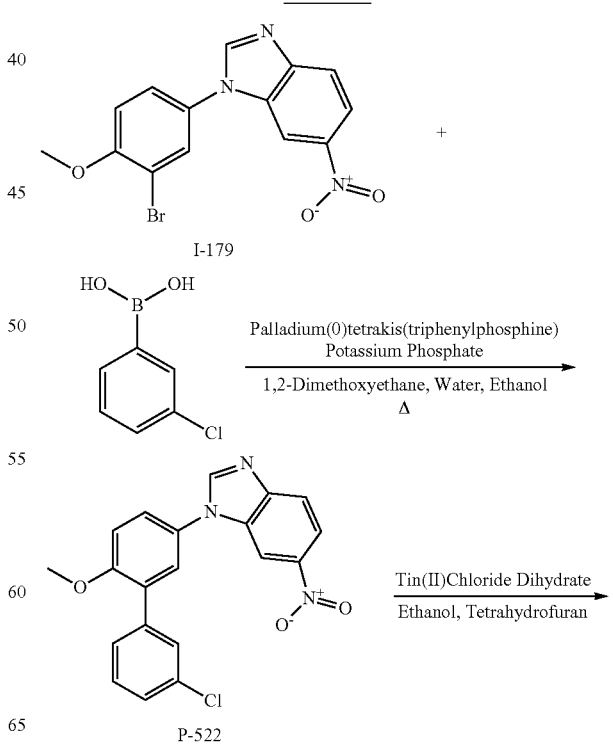

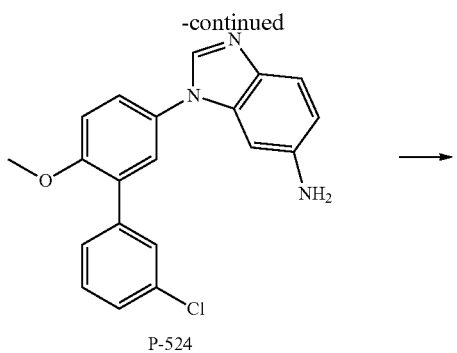

P-524

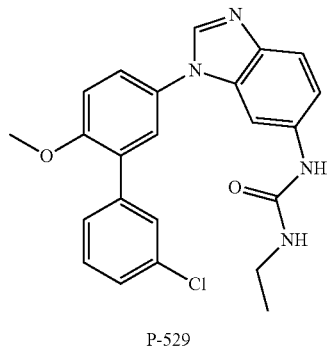

P-529

Example 197

Preparation of P-522

Synthesis of 1-(3'-Chloro-6-methoxy-biphenyl-3-yl)-6-nitro-1H-benzoimidazole (P-522). A suspension of I-179 (328 mg, 1.00 mmol), potassium phosphate (424 mg, 2.00 mmol), and 3-chlorophenylboronic acid (313 mg, 1.30 mmol) in ethanol (1 mL), water (1 mL), and 1,2-dimethoxyethane (2 mL) was degassed with nitrogen stream for 15 min. To the mixture was added palladium(0)tetrakis(triphenylphosphine), and the reaction stirred at 80° C. overnight. The reaction was cooled to room temperature, basified with 1 M aqueous sodium hydroxide (2 mL), diluted with water (15 mL), and extracted with ethyl acetate (2×15 mL). The combined organic layers were dried over sodium sulfate, filtered, and concentrated under vacuum. The crude was purified by silica gel column chromatography (4:1 to 1:1 hexanes/ethyl acetate) to give P-522 (310 mg, 82% yield) as a pale yellow solid. $^1$H NMR (400 MHz, DMSO-$d_6$) 3.90 (s, 3H), 7.36-7.51 (m, 3H), 7.60 (d, J=7.4 Hz, 1H), 7.64-7.77 (m, 3H), 7.81 (d, J=9.1 Hz, 1H), 8.23 (dd, J=9.1, 2.2 Hz, 1H), 8.67 (d, J=2.0 Hz, 1H), 8.88 (s, 1H) ppm.

LCMS=96.1% purity. APCI (+)=380 (M).

Example 198

Preparation of P-524

Synthesis of 3-(3'-Chloro-6-methoxy-biphenyl-3-yl)-3H-benzoimidazol-5-ylamine (P-524). A solution of P-522 (310 mg, 0.811 mmol) in ethanol (577 mg) and tetrahydrofuran (5 mL) was stirred at room temperature. To the solution was added tin(II) chloride hydrate (900 mg, 4.00 mmol) and the reaction stirred at 80° C. for 3 h. The reaction was then cooled to room temperature, and concentrated in vacuo. The residue was diluted with chloroform (10 mL), washed with 1 N aqueous sodium hydroxide (4 mL), water, and brine, dried over sodium sulfate, filtered, and the solvent removed under vacuum. The residue was purified by silica gel column chromatography (9:1 dichloromethane/methanol) to give P-524 (55.3 mg, 19% yield) as off-white solid.

$^1$H NMR (400 MHz, DMSO-$d_6$): 3.86 (s, 3H), 4.87 (s, 2H), 6.66 (dd, J=8.6, 1.9 Hz, 1H), 6.86 (d, J=1.9 Hz, 1H), 7.25-7.35 (m, 2H), 7.38-7.65 (m, 4H), 7.66 (s, 1H), 8.30 (s, 1H) ppm. LCMS=93.9% purity. APCI (+)=380 (M).

Example 199

Preparation of P-529

Synthesis of 1-[3-(3'-Chloro-6-methoxy-biphenyl-3-yl)-3H-benzoimidazol-5-yl]-3-ethyl-urea (P-529). A solution of P-524 (35 mg, 0.10 mmol) and ethyl isocyanate (0.04 mL, 0.5 mmol) in pyridine (0.2 mL) was stirred at room temperature overnight. The reaction was diluted with water (2 mL), extracted with ethyl acetate (2×2 mL), and the extracts combined. The extracts were dried over sodium sulfate, filtered, and the solvent removed under vacuum. The residue was purified by trituration in ethyl acetate and diethyl ether to give P-529 (19.0 mg, 45% yield) as an off-white solid. $^1$H NMR (400 MHz, DMSO-$d_6$): 1.07 (t, J=7.2 Hz, 3H), 3.02-3.20 (m, 2H), 3.88 (s, 3H), 5.96-6.09 (m, 1H), 7.23 (dd, J=8.7, 1.9 Hz, 1H), 7.35 (d, J=8.9 Hz, 1H), 7.40-7.54 (m, 3H), 7.54-7.62 (m, 2H), 7.62-7.73 (m, 2H), 7.89 (d, J=1.7 Hz, 1H), 8.42 (s, 1H), 8.46 (s, 1H) ppm.

LCMS=94.17% purity. APCI (+)=421.1 (M).

Example 200

Preparation of P-473

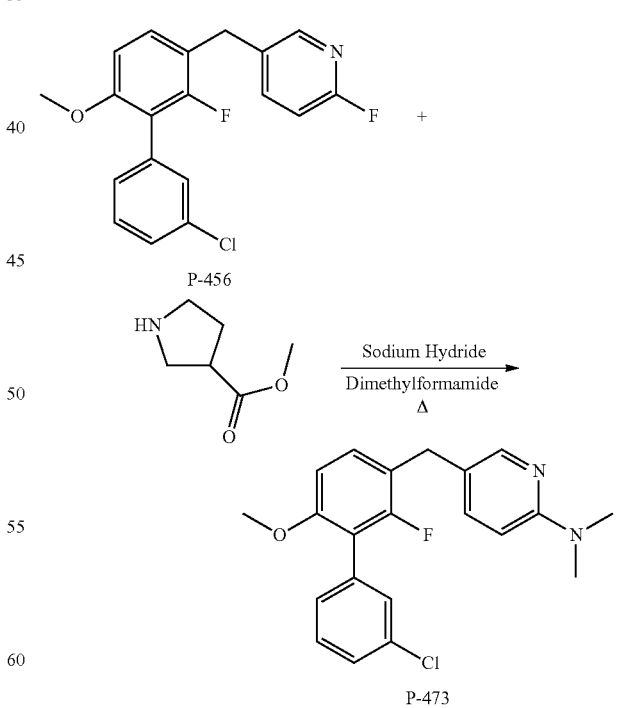

Synthesis of [5-(3'-Chloro-2-fluoro-6-methoxy-biphenyl-3-ylmethyl)-pyridin-2-yl]-dimethyl-amine (P-473). To a solution of pyrrolidine-3-carboxylic acid methyl ester (185 mg, 1.12 mmol), was added sodium hydride (60% weight dispersion, 66 mg, 1.68 mmol). After 2 min of stirring, P456 (194 mg, 0.56 mmol) was added, and the reaction stirred for 10 min in a microwave reactor at 240° C. and 15 bar. The reaction was diluted with ethyl acetate (5 mL), washed with 0.1 N aqueous hydrochloric acid (5 mL), and the aqueous layer was extracted with ethyl acetate (3×5 mL). The combined extracts were washed with brine, dried over sodium sulfate, filtered, and the solvent removed under vacuum. The crude material was purified by silica gel column chromatography (9:1 ethyl acetate/hexanes) to give P-473 (80.7 mg, 39% yield). $^1$H NMR (400 MHz, DMSO-$d_6$): 2.96 (s, 6H), 3.71 (s, 3H), 3.77 (s, 2H), 6.57 (d, J=8.6 Hz, 1H), 6.91 (d, J=8.6 Hz, 1H), 7.18-7.50 (m, 6H), 7.98 (d, J=2.0 Hz, 1H) ppm.

LCMS=96.9% purity. APCI (+)=371.1 (M).

Example 201

Preparation of P-029

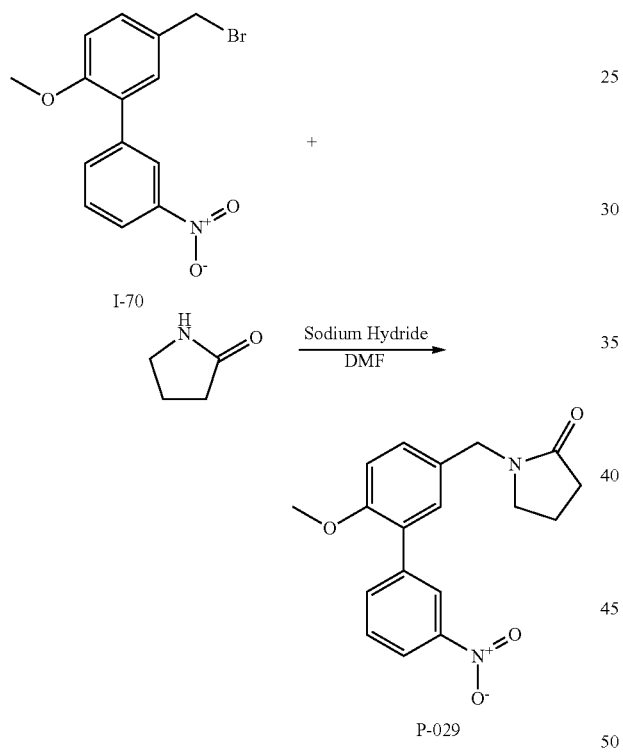

Synthesis of 1-(6-Methoxy-3'-nitro-biphenyl-3-ylmethyl)-pyrrolidin-2-one (P-029). A suspension of sodium hydride (15.6 mg, 0.652 mmol) in DMF (10 mL) was allowed to stir under nitrogen for 15 min. To the suspension was added 2-pyrrolidone (55.5 mg, 0.652 mmol) and the reaction allowed to stir at room temperature for 15 min under nitrogen. To the reaction was added I-70 (200 mg, 0.621 mmol) and the reaction stirred under nitrogen at ambient temperature for 16 h. The reaction was diluted with saturated aqueous ammonium chloride (50 mL), extracted with ethyl acetate (50 mL), and the layers separated. The organic extract was washed with saturated aqueous ammonium chloride (2×50 mL), water (3×50 mL), brine (50 mL), dried over sodium sulfate, and the solvent removed under vacuum. The product was purified by separation on a silica gel preparatory plate eluting with 10% methanol in dichloromethane to give P-029 (108 mg, 53% yield) as a yellow gum. $^1$H NMR (400 MHz, CDCl$_3$): 8.40 (t, J=2.2 Hz, 1H), 8.20-8.17 (m, 1H), 7.82 (dt, J=7.6 Hz, 1.2 Hz, 1H), 7.56 (t, J=8.0 Hz, 1H), 7.28 (dd, J=8.4 Hz, 2.4 Hz, 1H), 7.21 (d, J=2.4 Hz, 1H), 6.97 (d, J=8.8 Hz, 1H), 4.45 (s, 2H), 3.83 (s, 3H), 3.30 (t, J=7.0 Hz, 2H), 2.44 (t, J=8.2 Hz, 2H), 2.03-1.99 (m, 2H) ppm.

LCMS=93.9% purity. MS (ESI+)=327.7 (M+1).

Example 202

Preparation of P-034

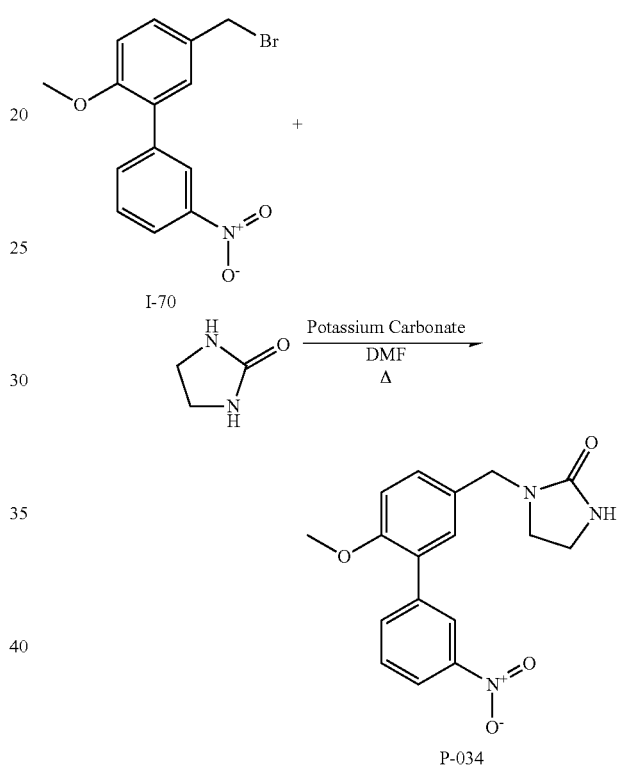

Synthesis of 1-(6-Methoxy-3'-nitro-biphenyl-3-ylmethyl)-imidazolidin-2-one (P-034). A suspension of potassium carbonate (160 mg, 1.16 mmol), 2-imidazolidone (104 mg, 1.21 mmol), and I-70 (150 mg, 0.466 mmol) in DMF (10 mL) was heated to 80° C. overnight. The reaction was cooled to room temperature, ethyl acetate (30 mL) and saturated aqueous ammonium chloride (30 mL) were added, and the layers separated. The extract was washed with saturated aqueous ammonium chloride (2×30 mL), water (2×30 mL), brine (30 mL), dried over sodium sulfate, and the solvent removed under vacuum. The crude product was purified by silica gel preparatory TLC to give P-034 (30.2 mg, 20% yield) as a white powder. $^1$H NMR (400 MHz, CDCl$_3$): 8.41 (t, J=2.0 Hz, 1H), 8.19-8.16 (m, 1H), 7.84 (dt, J=7.9 Hz, 1.5 Hz, H), 7.56 (t, J=8.0 Hz, 1H), 7.32 (dd, J=8.2 Hz, 2.2 Hz, 1H), 7.25 (d, J=2.4 Hz, 1H), 6.98 (d, J=8.4 Hz, 1H), 4.37 (s, 2H), 4.32 (brs, 1H), 3.84 (s, 3H), 3.41-3.33 (m, 4H) ppm.

LCMS=86.3% purity. MS (ESI+)=328.3 (M+1).

Example 203

Preparation of P-035

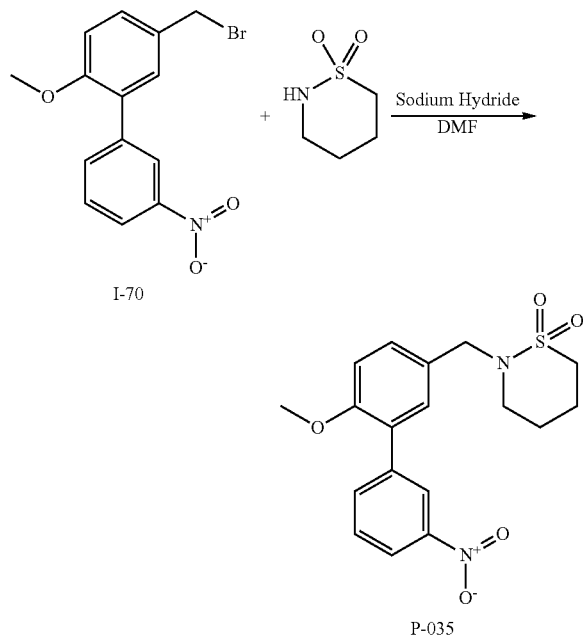

Synthesis of 2-(6-Methoxy-3'-nitro-biphenyl-3-ylmethyl)-[1,2]thiazinane 1,1-dioxide (P-035). A suspension of sodium hydride (11.7 mg, 0.489 mmol) in DMF (8 mL) was stirred under nitrogen for 5 min. To the suspension was added 1,4-butanesultam (66.1 mg, 0.489 mmol) under nitrogen, and the reaction was stirred at room temperature for 30 min. To the reaction was added I-70 (150 mg, 0.466 mmol), and the reaction stirred overnight at room temperature under nitrogen. The reaction was diluted with ethyl acetate (40 mL), washed with saturated aqueous ammonium chloride (2×50 mL), water (2×50 mL), brine (40 mL), dried over sodium sulfate, and the solvent removed under vacuum. The residue was purified by silica gel preparatory TLC eluting with dichloromethane to give P-035 (99.4 mg; 57% yield) as an off white powder. $^1$H NMR (400 MHz, CDCl$_3$): 8.41 (t, J=1.8 Hz, 1H), 8.20-8.17 (m, 1H), 7.85-7.83 (m, 1H), 7.57 (t, J=8.0 Hz, 1H), 7.37 (dd, J=8.4 Hz, 2.4 Hz, 1H), 7.30 (d, J=2.0 Hz, 1H), 7.00 (d, J=8.4 Hz, 1H), 4.30 (s, 2H), 3.84 (s, 3H), 3.27-3.24 (m, 2H), 2.11-3.08 (m, 2H), 2.24-2.21 (m, 2H), 1.66-1.570 (m, 2H) ppm. LCMS=98.9% purity. MS (APCI−)=376.1 (M).

Example 204

Preparation of P-036

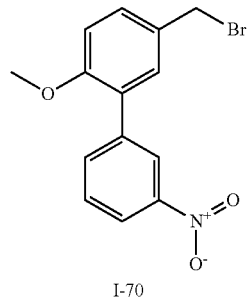

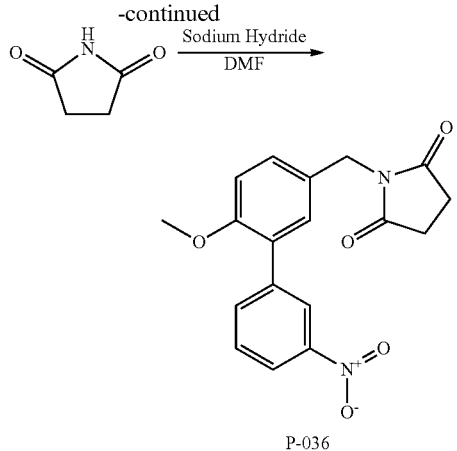

Synthesis of 1-(6-Methoxy-3'-nitro-biphenyl-3-ylmethyl)-pyrrolidine-2,5-dione (P-036). To a solution of pyrrolidine-2,5-dione (67.2 mg, 0.679 mmol) in DMF (10 mL) was added sodium hydride (16.3 mg, 0.679 mmol) and the reaction was stirred under nitrogen for 15 min until gas evolution ceased. To the reaction was added I-70 (100 mg, 0.310 mmol) and the reaction was stirred under nitrogen at room temperature for 16 h. The reaction was diluted with ethyl acetate, the organic layer washed with water (2×50 mL) and saturated aqueous ammonium chloride (2×50 mL), and the aqueous washes were combined. The aqueous washes were extracted with ethyl acetate (50 mL) and the organic extracts combined. The combined extracts were washed with brine (50 mL), dried over sodium sulfate, filtered and the solvent removed under vacuum. The resulting yellow oil was purified by silica preparatory TLC eluting with dichloromethane to give P-036 (68.6 mg; 65% yield) as a yellow oil. $^1$H NMR (400 MHz, CDCl$_3$): 8.39 (t, J=2.0 Hz, 1H), 8.18 (ddd, J=8.2, 2.2, 2.0 Hz, 1H), 7.80 (dt, J=8.0, 1.3 Hz, 1H), 7.56 (t, J=8.0 Hz, 1H) 7.45 (dd, J=7.2, 2.4 Hz, 1H), 7.39 (d, J=2.4 Hz, 1H), 6.95 (d, J=8.4 Hz, 1H), 4.66 (s, 2H), 3.82 (s, 3H), 2.71 (s, 4H) ppm. MS (ESI+)=341.4 (M+1). LCMS=97.5% purity.

Example 205

Preparation of P-045

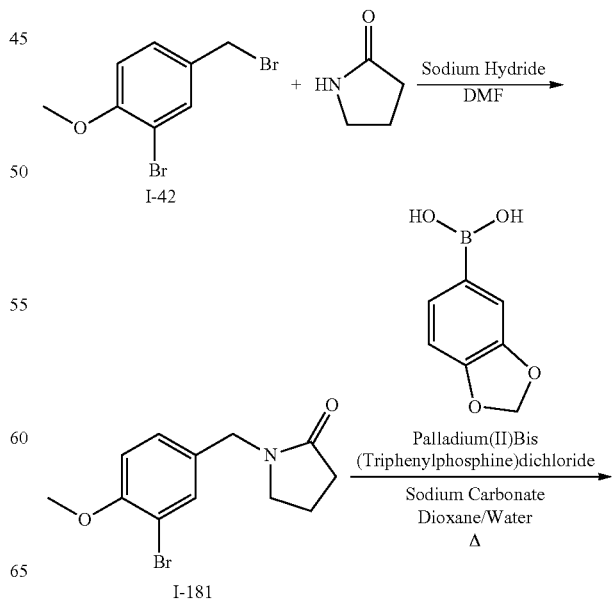

-continued

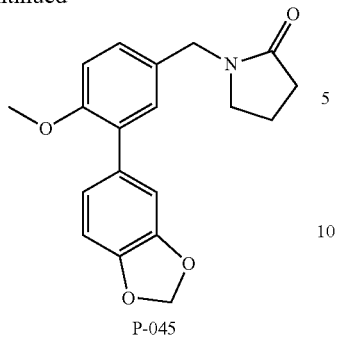

P-045

Synthesis of 1-(3-Bromo-4-methoxy-benzyl)-pyrrolidin-2-one (I-181). A suspension of sodium hydride (28.8 mg, 1.20 mmol) in anhydrous DMF (15 mL) was stirred at room temperature under nitrogen for 5 min. To the reaction was added 2-pyrollidone (102 mg, 1.20 mmol) under nitrogen and the reaction stirred for 10 min. Subsequently I-42 (320 mg, 1.14 mmol) was added and the reaction was stirred at room temperature overnight. The reaction was diluted with ethyl acetate (50 mL). The organic material was washed with saturated aqueous ammonium chloride (2×30 mL), water (2×30 mL), brine (2×30 mL), dried over sodium sulfate and the solvent removed under vacuum to give I-42 (243 mg) which was taken on without purification.

Synthesis of 1-(3-Benzo[1,3]dioxol-5-yl-4-methoxy-benzyl)-pyrrolidin-2-one (P-045). A solution of I-42 (230 mg, 0.809 mmol) and benzo[1,3]dioxol-5-yl-boronic acid (201 mg, 1.21 mmol) in 1,4-dioxane (15 mL) was degassed with a nitrogen stream for 30 min, and subsequently bis(triphenylphosphine)palladium(II) dichloride (28.4 mg, 0.0405 mmol) was added under nitrogen. Degassing was continued for 5 min, followed by the addition of 1 M aqueous sodium carbonate (2.5 mL). The reaction was heated to 80° C. with stirring overnight under nitrogen. The reaction did not go to completion, so additional benzo[1,3]dioxol-5-yl-boronic acid (201 mg, 1.21 mmol) and bis(triphenylphosphine)palladium(II) dichloride (28.4 mg, 0.0405 mmol) were added and the reaction stirred for 5 h at 80° C. The reaction was diluted with ethyl acetate (40 mL), washed with brine (2×40 mL), water (4×40 mL), and brine (40 mL). The solution was dried over sodium sulfate, filtered and the solvent removed under vacuum to give a residue. This material was purified by multiple development silica gel preparatory plate thin layer chromatography eluting with 10% methanol in dichloromethane, followed by 10% acetone in dichloromethane to give P-045 (21.3 mg, 8.1% yield) as a yellow syrup.

¹H NMR (400 MHz, CDCl₃): 7.19-7.17 (m, 2H), 7.04 (d, J=1.6 Hz, 1H), 6.96-6.85 (m, 3H), 5.99 (s, 2H), 4.42 (s, 2H), 3.81 (s, 3H), 2.43 (t, J=8.0 Hz, 1H), 2.00-1.97 (m, 2H) ppm. MS (ESI+)=326.7 (M+1).

Scheme 48.

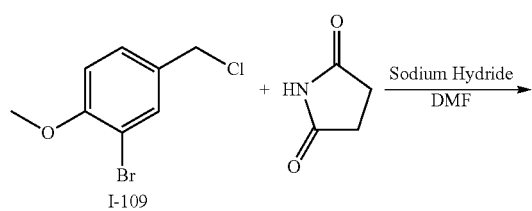

I-109

-continued

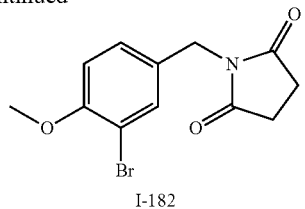

I-182

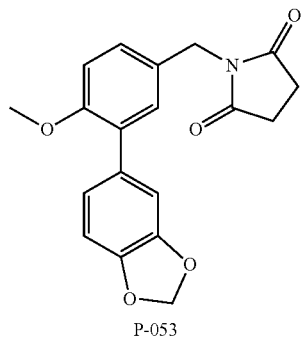

P-053

Example 206

Preparation of P-053

Synthesis of 1-(3-Bromo-4-methoxy-benzyl)-pyrrolidine-2,5-dione (I-182): A suspension of sodium hydride (56.2 mg, 2.34 mmol) in anhydrous DMF (20 mL) was stirred under nitrogen for 5 min. To the suspension was added pyrrolidine-2,5-dione (231 mg, 2.34 mmol), and the resulting slurry was stirred for 5 min. After stirring, I-109 (500 mg, 2.13 mmol) was added under nitrogen, and the reaction was allowed to stir at ambient temperature under nitrogen for 17.5 h, and diluted with ethyl acetate (50 mL). The organic solution was washed with water (4×50 mL), brine (2×50 mL), dried over anhydrous sodium sulfate, and the solvent removed under vacuum to afford 532.8 mg, I-182 as a yellow powder in 84% yield. ¹H NMR (400 MHz CDCl₃) d: 7.59 (d, J=2.4 Hz, 1H), 7.34 (dd, J=8.4 Hz, 2.0 Hz, 1H), 6.82 (d, J=8.4 Hz, 1H), 4.569 (s, 2H), 3.870 (s, 3H), 2.710 (s, 4H).

Synthesis of 1-(3-Benzo[1,3]dioxol-5-yl-4-methoxy-benzyl)-pyrrolidine-2,5-dione (P-053). A solution of I-182 (300 mg, 1.01 mmol) and benzo[1,3]dioxol-5-yl-boronic acid (183 mg, 1.10 mmol) in 1,4-dioxane (5 mL) were degassed with a nitrogen stream for 10 min. Subsequently triphenylphosphine (52.7 mg, 0.201 mmol), solid potassium carbonate (417 mg, 3.02 mmol) and an ethanol in water mixture (1:1, 1 mL) were added under nitrogen. The reaction was stirred under nitrogen for 5 min, palladium(II) acetate (22.6 mg, 0.101 mmol) was added, and the reaction was heated under nitrogen to 80° C. for 19 h. The solvent was removed under vacuum and the mixture was diluted with saturated aqueous ammonium chloride (50 mL) and ethyl acetate (50 mL), the layers separated, and the aqueous layer extracted with ethyl acetate (50 mL). The combined organic extracts were washed with water (3×30 mL), brine (30 mL), dried over sodium sulfate, and the solvent removed under. The residue was chromatographed on flash silica gel eluting with 10% acetone in dichloromethane to afford 153.7 mg of P-053 as a yellow powder in 45% yield. $^1$H NMR (CDCl$_3$, 400 MHz): δ 7.35 (m, 2H), 7.02 (d, J=1.6 Hz, 1H), 6.94 (ddd, J=8.0 Hz, J=1.6 Hz, J=0.8 Hz, 1H), 6.87 (m, 2H), 4.63 (s, 2H), 3.79 (s, 3H), 2.70 (s, 4H). LCMS=91.2%. MS (ESI+)=340.3 (M+1).

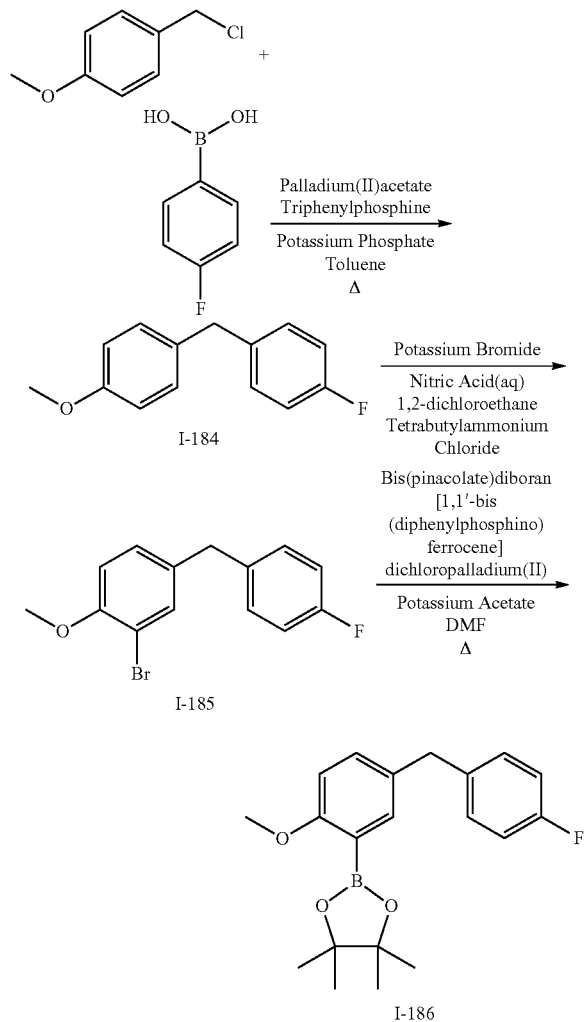

Example 207

Preparation of I-186

Synthesis of 4-Fluoro-4'-methoxydiphenylmethane (I-184). A suspension of 4-fluorophenylboronic acid (6.70 g, 47.9 mmol), ground solid potassium phosphate (13.6 g, 63.9 mmol), triphenylphosphine (168 mg, 0.639 mmol), and palladium(II)acetate (72 mg, 0.319 mmol) was stirred under nitrogen in toluene (100 mL). Nitrogen was streamed through with stirring for 15 min, and subsequently 4-(chloromethyl) anisol (5.00 g, 31.9 mmol) was added under nitrogen, and the reaction was heated to 80° C. overnight. Additional palladium (II) acetate (72 mg, 0.319 mmol) was added and the reaction stirred at 80° C. for an additional 6 h. The reaction was not complete so a third portion of palladium(II)acetate (144 mg, 0.639 mmol) and more triphenylphosphine (336 mg, 1.28 mmol) was added and the reaction stirred at 80° C. overnight. The reaction was diluted with ethyl acetate (300 mL), washed with 1 N aqueous sodium hydroxide (2×300 mL), water (3×300 mL), and brine (2×300 mL). The organic extract was dried over sodium sulfate and decolorized over activated carbon, filtered and the solvent removed under. The residue was purified by flash silica gel column chromatography (10% ethyl acetate in hexanes Rf=0.31) to afford 2.50 g of I-184 as a clear oil in 36% yield, which was taken on without further purification. $^1$H NMR (400 MHz, CDCl$_3$) 7.13-7.06 (m, 4H), 6.976-6.93 (m, 2H), 6.84-6.82 (m, 2H), 3.89 (s, 2H), 3.78 (s, 3H) ppm.

Synthesis of 2-Bromo-4-(4-fluoro-benzyl)-1-methoxybenzene (I-185). A biphasic solution potassium bromide (1.65 g, 13.9 mmol) in 21% (w/v) aqueous nitric acid (8.32 g, 27.7 mmol) and 4-fluoro-4-methoxydiphenylmethane (I-184, 1.50 g, 6.94 mmol) and tetrabutylammonium chloride (57.7 mg, 0.208 mmol) in 1,2-dichloroethane (16 mL) was stirred at room temperature overnight, and the red suspension diluted with dichloromethane (30 mL). The aqueous layer was removed and the organic layer washed with aqueous potassium carbonate (2% w/v, 3×50 mL), water (2×50 mL), and brine (50 mL). The reaction was dried over magnesium sulfate, filtered, and the solvent removed under vacuum. The crude product was purified by flash silica gel column chromatography (10% ethyl acetate in hexanes Rf=0.39) to 1.24 g of I-185 as a yellow oil in 60% yield. $^1$H NMR (400 MHz, CDCl$_3$) d: 7.34 (d, J=1.6 Hz, 1H), 7.12-7.10 (m, 2H), 7.05 (dd, J=6.6 Hz, 1.80 Hz, 1H), 6.99-6.96 (m, 2H), 6.82 (d, J=6.80 Hz, 1H), 3.867 (s, 5H) ppm.

Synthesis of 2-[5-(4-Fluoro-benzyl)-2-methoxy-phenyl]-4,4,5,5-tetramethyl-[1,3,2]dioxaborolane (I-186). A stream of nitrogen was blown through a solution of 2-bromo-4-(4-fluoro-benzyl)-1-methoxy-benzene (I-185, 500 mg, 1.69 mmol) in DMF (5 mL) for 15 min. Subsequently solid potassium acetate (499 mg, 5.08 mmol), [1,1'-bis(diphenylphosphino)ferrocene]dichloropalladium(II) (138 mg, 0.169 mmol), and bis(pinocolate)diboron (516 mg, 2.03 mmol) were added under nitrogen. The reaction was heated to 85° C. 16 h. The reaction was cooled to room temperature, diluted with ethyl acetate (50 mL) and water (50 mL). The biphasic suspension was filtered twice to removed spent catalyst and separated. The organic extract was washed with water (3×50 mL) and brine (50 mL), decolorized over activated carbon, dried over sodium sulfate, filtered, and the solvent removed under vacuum. The residue was purified by flash silica gel column chromatography (10% acetone in hexanes, Rf=0.10) to afford 419.8 mg of I-186 as a colorless oil in 72% yield. $^1$H NMR (400 MHz, CDCl$_3$) d: 7.50 (d, J=2.4 Hz, 1H), 7.14-7.09 (m, 3H), 6.97-6.92 (m, 2H), 6.78 (d, J=8.4 Hz, 1H), 3.88 (s, 2H), 3.80 (s, 3H), 1.35 (s, 12H) ppm. MS (ESI+)=341.3 (M−1), 500.7 (M+159).

Example 208

Preparation of I-187

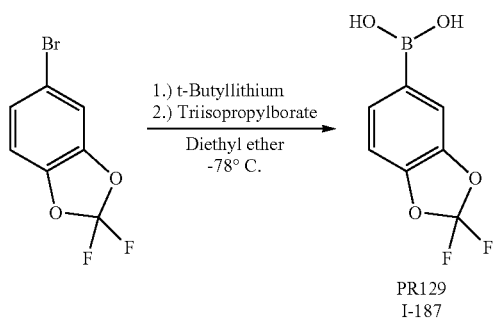 [SMILES: FC1(F)Oc2ccc(Br)cc2O1 ; OB(O)c1ccc2c(c1)OC(F)(F)O2]

Synthesis of 2,2-Difluoro-benzo[1,3]dioxol-5-yl-boranic acid (I-187): A solution of tert-butyl lithium (1.15 mL, 1.95 mmol) in anhydrous diethyl ether (5 mL) was cooled to −78° C. under nitrogen. 5-bromo-2,2-difluoro-benzo[1,3]dioxole (180 mg, 0.760 mmol) in diethyl ether (0.80 mL) was added, and the reaction was stirred for 1 h at −78° C., followed by the addition of triisopropylborate (0.37 mL, 1.60 mmol) under nitrogen. The reaction allowed to stir for 1.5 h while allowing to warm to ambient temperature. The reaction was poured into 4 N aqueous sodium hydroxide (5 mL), stirred, and adjusted to pH ~1 by the dropwise addition of concentrated aqueous hydrochloric acid, and the product extracted with ethyl acetate (10 mL). The organic extract was dried over anhydrous sodium sulfate, filtered, and the solvent removed under vacuum to afford 140.2 mg of I-187 as a brown solid, which was taken on without further purification.

$^1$H NMR (400 MHz, DMSO-$d_6$) 7.77-7.74 (m, 1H), 7.67-7.65 (m, 1H), 7.51 (s, 1H).

Scheme 50

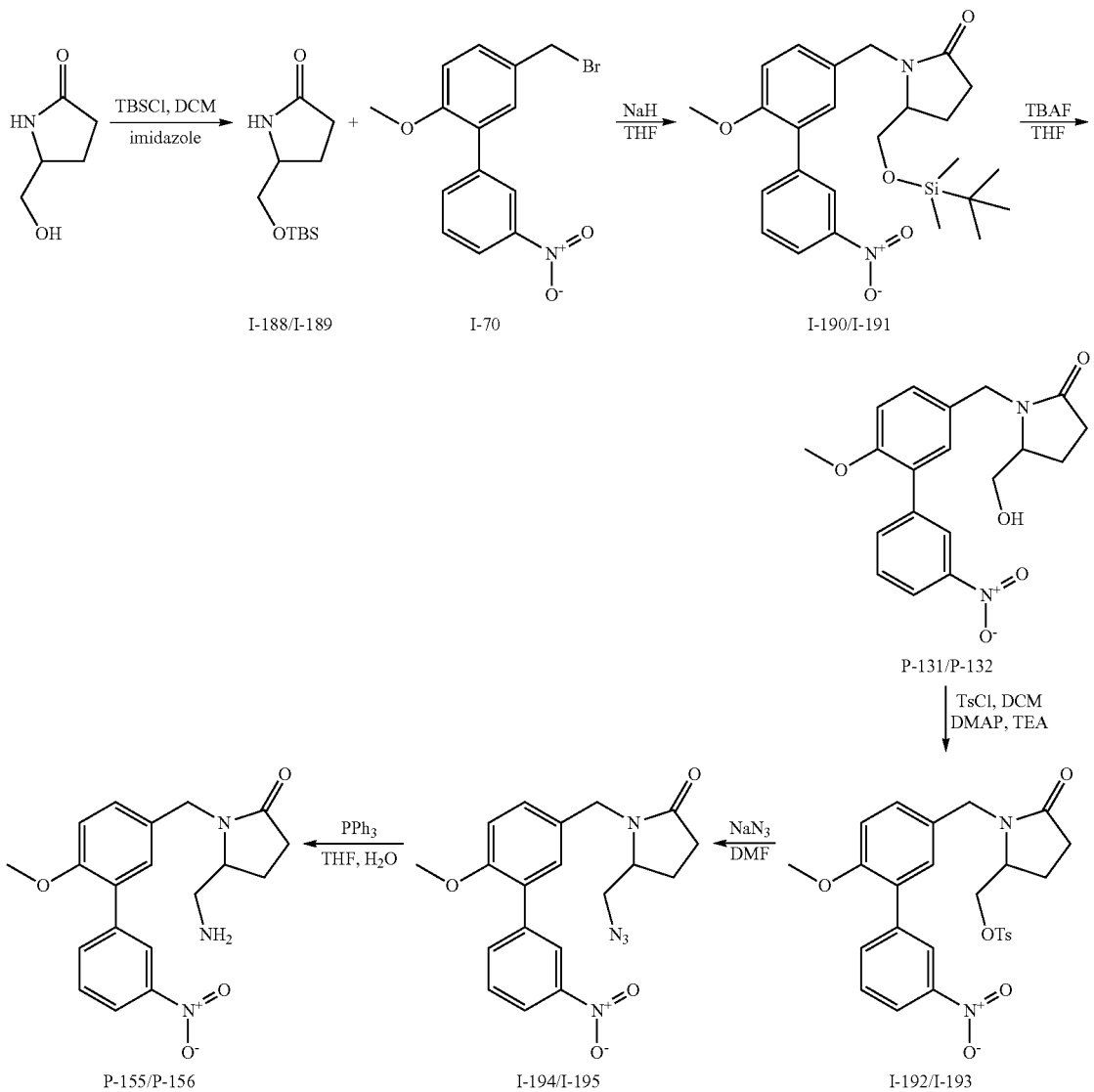

Example 209

Preparation of P-131 and P-132

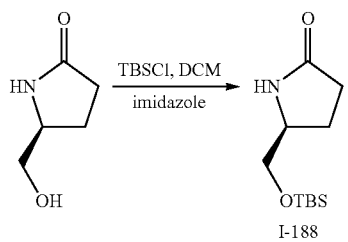 [SMILES: O=C1CC[C@@H](CO)N1 ; CC(C)(C)[Si](C)(C)OC[C@@H]1CCC(=O)N1]

Synthesis of (S)-5-(tert-Butyl-dimethyl-silanyloxymethyl)-pyrrolidin-2-one (I-188). A solution of (S)-5-hydroxymethyl-pyrrolidin-2-one (1.0 g, 8.69 mmol), DMF (10 mL), t-butyldimethylsilyl chloride (1.57 g, 10.42 mmol), and imidazole (0.89 g, 13.03 mmol) was stirred at ambient temperature for 4 hours after which time 4 mL of water were added. The layers were separated and the aqueous was extracted with dichloromethane (10 mL). The combined organics were washed with water (15 mL) and brine (15 mL), dried with sodium sulfate, filtered and concentrated to afford 1.91 g of I-188 as a colorless oil in 96% yield.

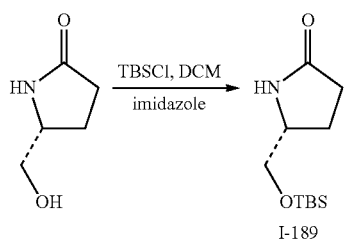 [SMILES: O=C1CC[C@H](CO)N1 ; CC(C)(C)[Si](C)(C)OC[C@H]1CCC(=O)N1]

Synthesis of (R)-5-(tert-Butyl-dimethyl-silanyloxymethyl)-pyrrolidin-2-one (I-189).

I-189 was prepared in an analogous manner as that for I-188, starting from (R)-5-Hydroxymethyl-pyrrolidin-2-one. 1.91 g of I-189 was obtained as a colorless oil in 96%.

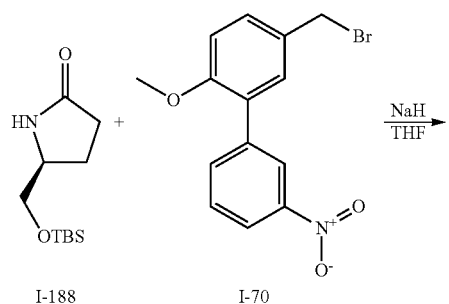

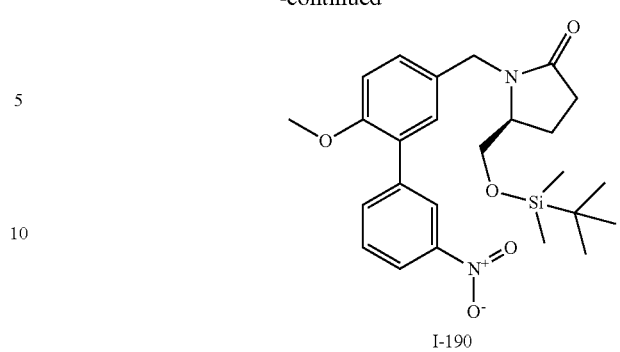

Synthesis of (S)-5-(tert-Butyl-dimethyl-silanyloxymethyl)-1-(6-methoxy-3'-nitro-biphenyl-3-ylmethyl)-pyrrolidin-2-one (I-190). Into a 20 mL vial with stir bar was added I-188 (0.28 g, 1.24 mmol), dry THF (4 mL), and the solution cooled to 0° C. sodium hydride (65 mg, 1.61 mmol) was added and the suspension stirred for 30 minutes at ambient temperature. After cooling to 0° C., I-70 (0.40 g, 1.24 mmol) was added the reaction stirred at ambient temperature for 18 hours after which 5 mL water was added. The product was extracted with ethyl acetate (4×15 mL). The organics were combined and dried with sodium sulfate, filtered, and concentrated. Flash column chromatography purification using 30% ethyl acetate/Hexanes afforded 476 mg of I-190 as a colorless oil in 83% yield.

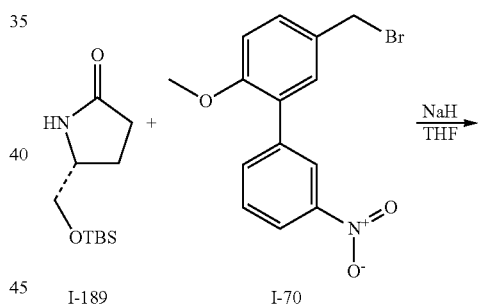

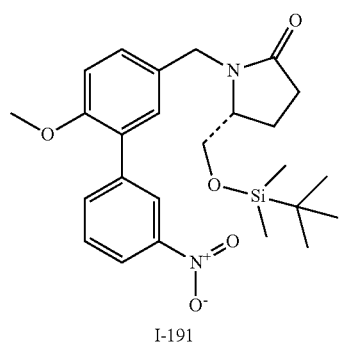

(R)-5-(tert-Butyl-dimethyl-silanyloxymethyl)-1-(6-methoxy-3'-nitro-biphenyl-3-ylmethyl)-pyrrolidin-2-one (I-191). I-191 was prepared in an analagous manner as that for I-190, starting from I-189. 462 mg of I-191 was obtained as a colorless oil in 80% yield.

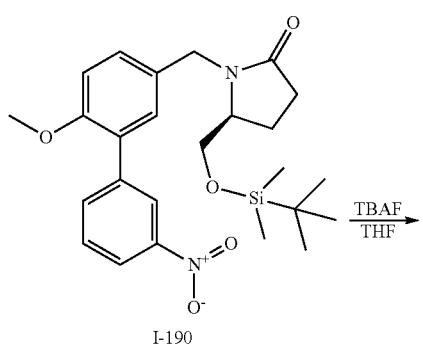

I-190

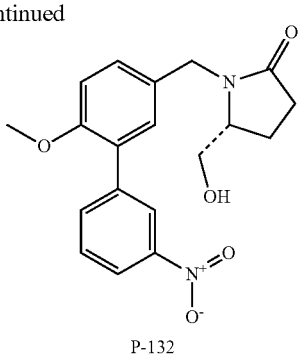

P-132

Synthesis of (R)-5-Hydroxymethyl-1-(6-methoxy-3'-nitro-biphenyl-3-ylmethyl)-pyrrolidin-2-one (P-132). P-132 was prepared in a similar manner as that for P-131, except beginning with I-191. 310 mg (91%) of P-132 was obtained as a colorless oil. $^1$H NMR (400 MHz, CDCl$_3$) 8.39 (t, J=1.7 Hz, 1H), 8.18 (dd, J=1.3, 8.3 Hz, 1H), 7.82 (d, J=7.8 Hz, 1H), 7.56 (t, J=8.0 Hz, 1H), 7.32 (dd, J=2.1, 8.5 Hz, 1H), 7.25 (d, J=2.1 Hz, 1H), 6.97 (d, J=8.5 Hz, 1H), 4.80 (d, J=14.9 Hz, 1H), 4.30 (d, J=15.0 Hz, 1H), 3.83 (s, 3H), 3.79 (dd, J=2.8, 11.4 Hz, 1H), 3.68-3.53 (m, 2H), 2.64-2.50 (m, 1H), 2.46-2.32 (m, 1H), 2.15-2.03 (m, 1H), 2.02-1.90 (m, 1H). LC/MS=100.0%, 357.1 (APCI+).

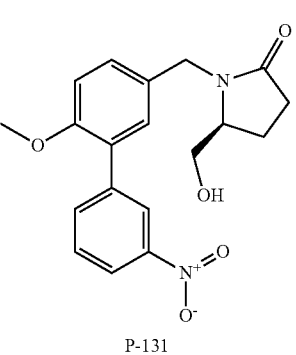

P-131

Synthesis of (S)-5-Hydroxymethyl-1-(6-methoxy-3'-nitro-biphenyl-3-ylmethyl)-pyrrolidin-2-one (P-131). Into a 50 mL round bottom flask equipped with a stir bar was added I-190 (0.45 g, 0.96 mmol), dry THF (5 mL), and the solution was cooled to 0° C. TBAF (1.4 mL, 1.43 mmol, 1.0 M in THF) was added and the reaction was stirred at 0° C. for 30 minutes. 2 mL of saturated aqueous NH$_4$Cl and 2 mL of water were added and the product was extracted with ethyl acetate (3×10 mL). The combined organics were washed with brine, dried over sodium sulfate, filtered, and concentrated. The residue was purified by flash column chromatography using 10-25% acetone/dichloromethane to afford 307 mg (90%) of P-131 as a colorless semi-solid. $^1$H NMR (400 MHz, CDCl$_3$) 8.39 (s, 1H), 8.18 (dd, J=1.3, 8.3 Hz, 1H), 7.81 (d, J=7.8 Hz, 1H), 7.56 (t, J=7.9 Hz, 1H), 7.32 (dd, J=1.9, 8.4 Hz, 1H), 7.25 (d, J=2.0 Hz, 1H), 6.97 (d, J=8.3 Hz, 1H), 4.81 (d, J=15.0 Hz, 1H), 4.29 (d, J=14.9 Hz, 1H), 3.83 (s, 3H), 3.78 (d, J=2.5 Hz, 1H), 3.68-3.50 (m, 2H), 2.65-2.48 (m, 1H), 2.46-2.31 (m, 1H), 2.16-2.03 (m, 1H), 2.02-1.91 (m, 1H). LC/MS=100.0%, 357.1 (APCI+).

Example 210

Preparation of P-155 and P-156

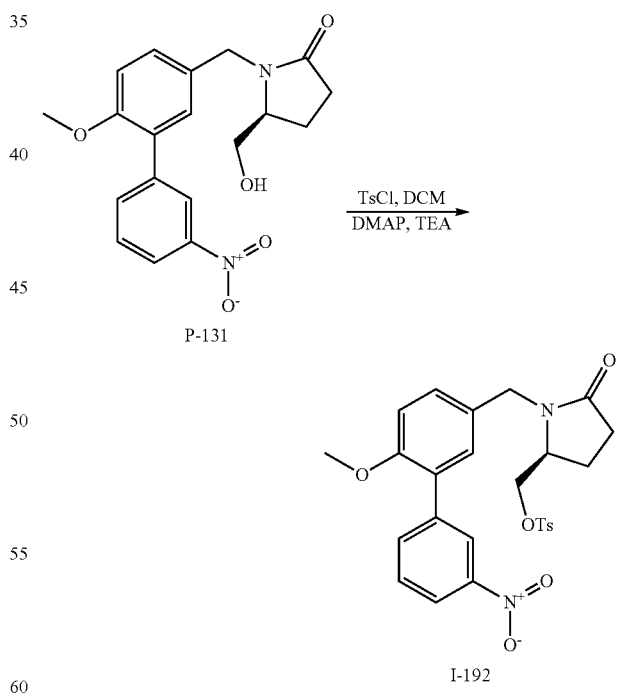

P-131

I-192

Synthesis of Toluene-4-sulfonic acid (S)-1-(6-methoxy-3'-nitro-biphenyl-3-ylmethyl)-5-oxo-pyrrolidin-2-ylmethyl ester (I-192). Into a 20 mL vial with stir bar and dichloromethane (5 mL) at 0° C. was added P-131 (0.25 g, 0.70 mmol), TsCl (0.16 g, 0.84 mmol), triethylamine (0.15 mL, 1.05 mmol), and DMAP (9 mg, 0.07 mmol). The reaction was

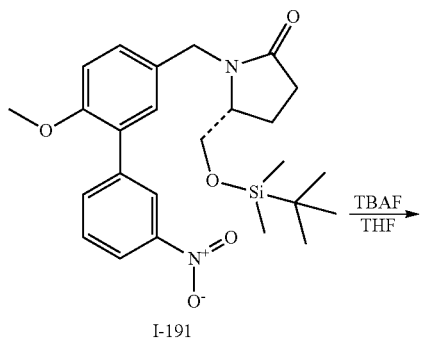

I-191 stirred at room temperature for 18 hours and then concentrated. The residue was purified by flash column chromatography using 10% acetone/dichloromethane to afford 340 mg (95%) of I-192 as a colorless oil.

stirred for 1 hour at 60° C., and then cooled to room temperature. 5 mL of water was added and the product was extracted with dichloromethane (2×5 mL). The combined organics were washed with water (4×5 mL), dried over sodium sulfate, filtered, and concentrated to obtain 0.24 g (97%) of I-194 as a colorless oil.

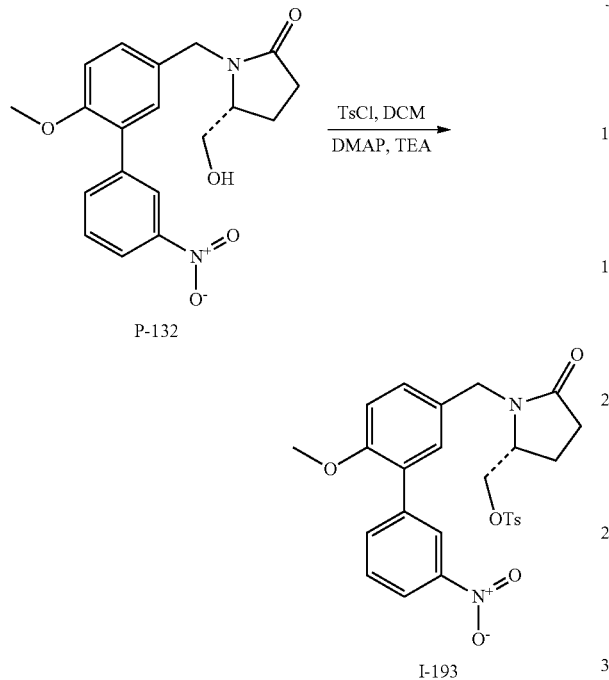

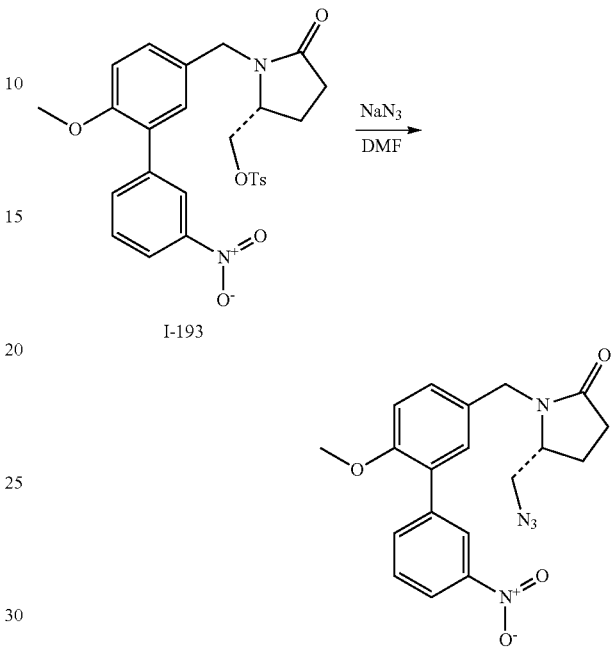

Synthesis of Toluene-4-sulfonic acid (R)-1-(6-methoxy-3'-nitro-biphenyl-3-ylmethyl)-5-oxo-pyrrolidin-2-ylmethyl ester (I-193). I-193 was prepared in a similar manner as that for I-192, except beginning with P-132. 290 mg (92%) of I-193 was obtained as a colorless oil.

Synthesis of (R)-5-Azido methyl-1-(6-methoxy-3'-nitro-biphenyl-3-ylmethyl)-pyrrolidin-2-one (I-195). I-195 was prepared in a similar manner as that for I-194 except beginning with I-193. I-195 (0.20 g, 96%) was obtained as a colorless oil.

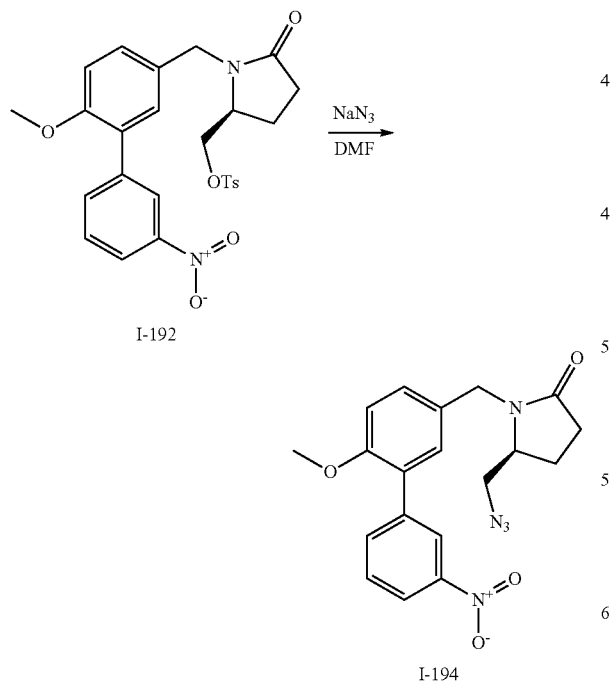

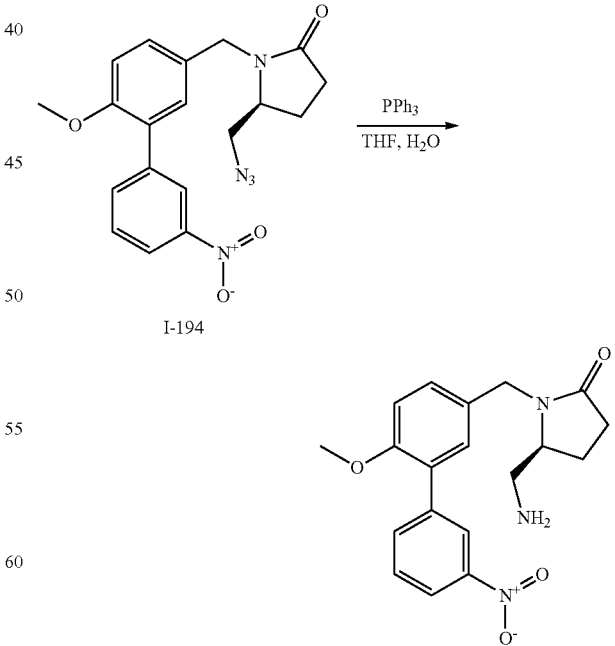

Synthesis of (S)-5-Azidomethyl-1-(6-methoxy-3'-nitro-biphenyl-3-ylmethyl)-pyrrolidin-2-one (I-194). Into a 20 mL vial with stir bar was added I-192 (0.33 g, 0.65 mmol), DMF (4 mL), and NaN₃ (63 mg, 0.97 mmol). The reaction was Synthesis of (S)-5-Aminomethyl-1-(6-methoxy-3'-nitro-biphenyl-3-ylmethyl)-pyrrolidin-2-one (P-155). Into a 50 mL round bottom flask with stir bar was added I-194 (0.24 g, 0.63 mmol), THF (4 mL), and PPh₃ (0.50 g, 1.89 mmol). The reaction was stirred at room temperature for 18 hours after which 1 mL of water was added. After stirring at room temperature for 2 more days, the THF was removed under reduced pressure. 1 N HCl was added to until the aqueous material was pH=1 and the solution was washed with dichloromethane (3×3 mL). The aqueous phase was basified with 1 N NaOH to pH=11 and the product was extracted with dichloromethane (3×3 mL) and concentrated. The residue was purified by flash column chromatography using 5% methanol/dichloromethane and afforded 164 mg (73%) of P-155 as a light-yellow oil. ¹H NMR (400 MHz, CDCl₃) 8.39 (s, 1H), 8.18 (dd, J=1.3, 8.2 Hz, 1H), 7.81 (d, J=7.8 Hz, 1H), 7.56 (t, J=7.9 Hz, 1H), 7.30 (dd, J=1.9, 8.4 Hz, 1H), 7.23 (d, J=2.0 Hz, 1H), 6.96 (d, J=8.5 Hz, 1H), 4.85 (d, J=14.9 Hz, 1H), 4.15 (d, J=14.9 Hz, 1H), 3.83 (s, 3H), 3.61-3.50 (m, 1H), 2.93-2.84 (m, J=4.8 Hz, 1H), 2.80 (br. s., 1H), 2.61-2.49 (m, 1H), 2.47-2.35 (m, 1H), 2.19-2.03 (m, 1H), 1.95-1.83 (m, 1H). LC/MS=100.0%, 356.1 (APCI+).

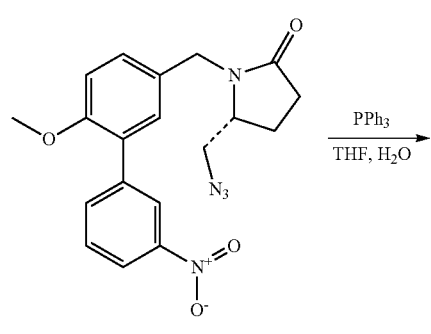

I-195

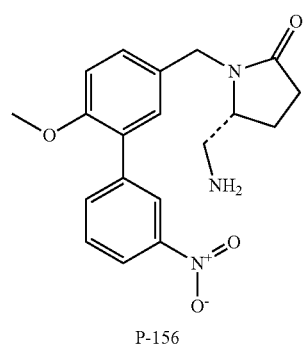

P-156

Synthesis of (R)-5-Aminomethyl-1-(6-methoxy-3'-nitro-biphenyl-3-ylmethyl)-pyrrolidin-2-one (P-156). P-156 was prepared in a similar manner as that for P-155, except beginning with I-195. P-156 (80 mg, 43%) was obtained as a light-yellow oil. ¹H NMR (400 MHz, CDCl₃) 8.39 (s, 1H), 8.18 (dd, J=1.1, 8.3 Hz, 1H), 7.81 (d, J=7.8 Hz, 1H), 7.56 (t, J=8.0 Hz, 1H), 7.30 (dd, J=1.8, 8.4 Hz, 1H), 7.23 (d, J=1.9 Hz, 1H), 6.96 (d, J=8.5 Hz, 1H), 4.85 (d, J=14.9 Hz, 1H), 4.15 (d, J=14.9 Hz, 1H), 3.83 (s, 3H), 3.61-3.49 (m, 1H), 2.93-2.84 (m, 1H), 2.83-2.74 (m, 1H), 2.61-2.49 (m, 1H), 2.46-2.35 (m, 1H), 2.15-2.03 (m, 1H), 1.95-1.83 (m, 1H). LC/MS=100.0%, 356.1 (APCI+).

Example 211

Preparation of P-135

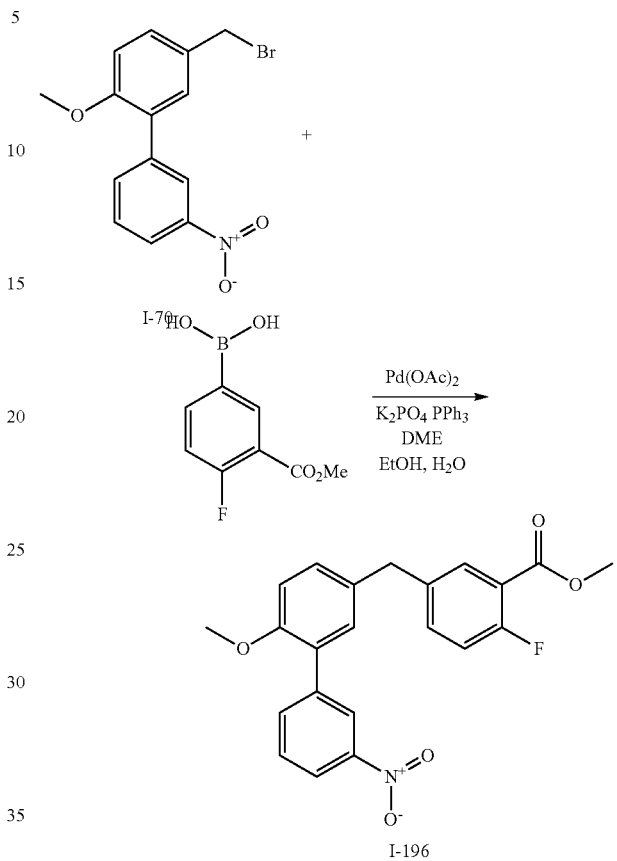

Synthesis of 2-Fluoro-5-(6-methoxy-3'-nitro-biphenyl-3-ylmethyl)-benzoic acid methyl ester (I-196). Into a 20 mL vial with stir bar was added I-70 (0.30 g, 0.93 mmol), 4-Fluoro-3-methoxycarbonylphenylboronic acid (203 mg, 1.02 mmol), triphenylphosphine (49 mg, 0.19 mmol), K₃PO₄ (0.40 g, 1.86 mmol), DME (5 mL), water (0.5 mL), and ethanol (0.5 mL). N₂ gas was bubbled through the stirred reaction for 10 minutes. Pd(OAc)₂ (21 mg, 0.09 mmol) was added and N₂ was bubbled through for an additional 5 minutes. The vial was capped and the reaction was stirred at 80° C. for 18 hours. The reaction was cooled to room temperature and 5 mL of water and 5 mL of ethyl acetate were added. The layers were separated and the aqueous was extracted with ethyl acetate (3×10 mL). The organics were combined, dried with sodium sulfate, and concentrated. The residue was purified by flash column chromatography using 10% acetone/Hexanes to obtain 207 mg (56%) of I-196 as a colorless oil.

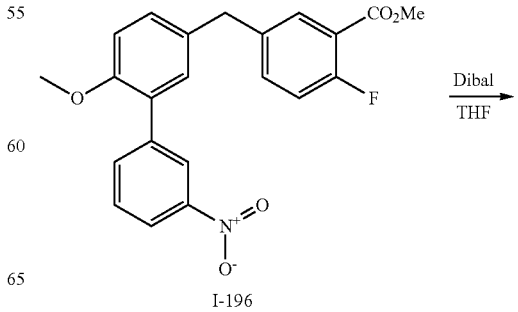

I-196

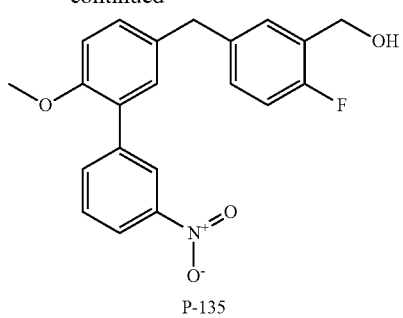

P-135

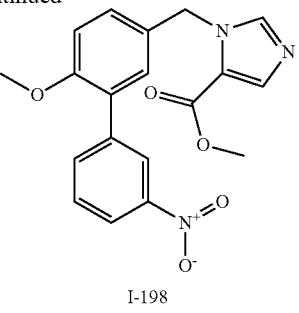

I-198

Synthesis of Fluoro-5-(6-methoxy-3'-nitro-biphenyl-3-yl-methyl)-phenyl]-methanol (P-135). Into a 20 mL vial with stir bar was added I-196 (112.3 mg, 0.28 mmol) and 4 mL of dry THF. The solution was cooled to 0° C. and DIBAL-H (0.71 mL, 0.71 mmol, 1.0 M sol. in hexane) was added. The reaction was stirred at 0° C. for 1 hour. Aqueous 1 N HCl (1 mL) was added followed by water (5 mL). The aqueous solution was extracted with ethyl acetate (3×10 mL). The organics were combined, dried over sodium sulfate, and concentrated. The product was purified by flash column chromatography using 10% acetone/hexanes to obtain 53 mg (51%) of P-135 as colorless oil $^1$H NMR (400 MHz, CDCl$_3$) 1.72 (t, J=6.2 Hz, 1H) 3.81 (s, 3H) 3.95 (s, 2H) 4.73 (d, J=6.2 Hz, 2H) 6.91-7.02 (m, 2H) 7.06-7.21 (m, 3H) 7.23-7.28 (m, 1H) 7.54 (t, J=8.0 Hz, 1H) 7.82 (d, J=7.7 Hz, 1H) 8.16 (dd, J=8.3, 1.3 Hz, 1H) 8.38 (s, 1H) ppm. LC/MS=100.0%, 367.1 (APCI−).

Synthesis of 1-(6-Methoxy-3'-nitro-biphenyl-3-ylmethyl)-1H-imidazole-4-carboxylic acid methyl ester (I-197) and 1-(6-Methoxy-3'-nitro-biphenyl-3-ylmethyl)-1H-imidazole-5-carboxylic acid methyl ester (I-198). Into a 20 mL vial with stir bar was added I-70 (0.30 g, 0.92 mmol), 1H-imidazole-4-carboxylic acid methyl ester (0.12 g, 0.93 mmol), K$_2$CO$_3$ (0.15 g, 1.12 mmol), and DMF (3 mL). The reaction was stirred at room temperature for 20 hours. To the reaction was added 10 mL of dichloromethane and 10 mL of water and the layers were separated. The aqueous was extracted with 10 mL of dichloromethane and the combined organics were washed with water (3×10 mL). The dichloromethane portion was concentrated and purified first by flash column chromatography using 0-5% methanol/dichloromethane followed by preparative TLC using 10% acetone/dichloromethane. 72.4 mg (21%) of I-197 and 91.1 mg (27%) of I-198 were obtained as light-yellow oils.

Example 212

Preparation of P-153 and P-154

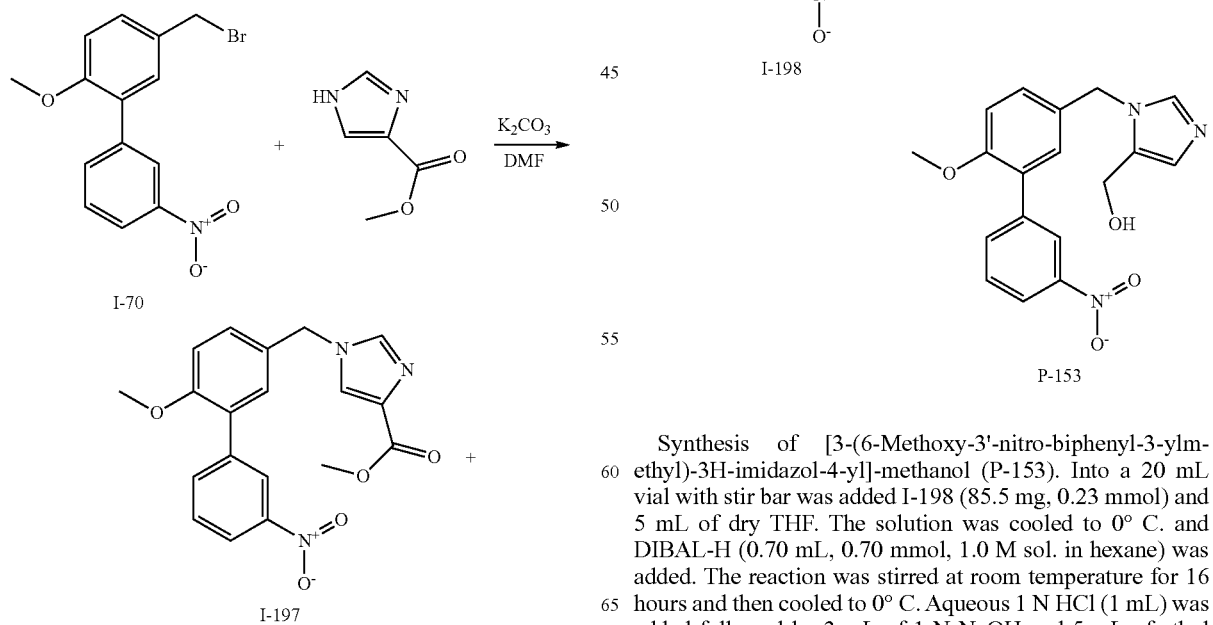

Synthesis of [3-(6-Methoxy-3'-nitro-biphenyl-3-ylmethyl)-3H-imidazol-4-yl]-methanol (P-153). Into a 20 mL vial with stir bar was added I-198 (85.5 mg, 0.23 mmol) and 5 mL of dry THF. The solution was cooled to 0° C. and DIBAL-H (0.70 mL, 0.70 mmol, 1.0 M sol. in hexane) was added. The reaction was stirred at room temperature for 16 hours and then cooled to 0° C. Aqueous 1 N HCl (1 mL) was added followed by 3 mL of 1 N NaOH and 5 mL of ethyl acetate. The layers were separated and the aqueous was extracted with ethyl acetate (3×10 mL). The organic were combined, dried over sodium sulfate, and concentrated. The residue was purified by flash column chromatography using 50% acetone/dichloromethane, followed by flash column chromatography using 5% methanol/dichloromethane to obtain 52.2 mg (66%) of P-153 as a tan solid. $^1$H NMR (400 MHz, DMSO-$d_6$) 3.79 (s, 3H) 4.38 (d, J=5.2 Hz, 2H) 5.13 (t, J=5.3 Hz, 1H) 5.21 (s, 2H) 6.80 (br. s., 1H) 7.16 (d, J=8.5 Hz, 1H) 7.27 (dd, J=0.5, 1.9 Hz, 1H) 7.34 (d, J=1.9 Hz, 1H) 7.65-7.77 (m, 2H) 7.92 (d, J=7.8 Hz, 1H) 8.20 (dd, J=8.1, 1.7 Hz, 1H) 8.28 (s, 1H) ppm. LC/MS=99.9%, 340.1 (APCI+)

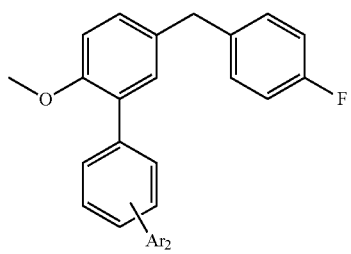

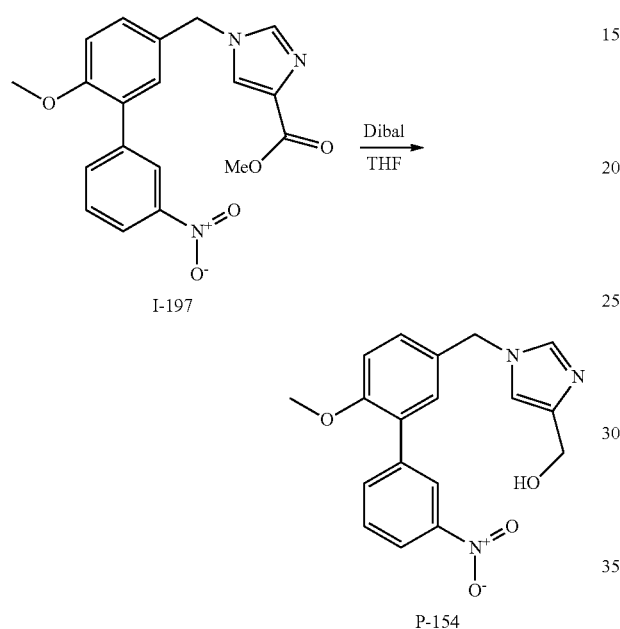

Synthesis of [1-(6-Methoxy-3'-nitro-biphenyl-3-ylmethyl)-1H-imidazol-4-yl]-methanol (P-154). P-154 was prepared in a similar manner as that for P-153 except beginning with I-197. P-154 (45.0 mg, 71%) was obtained as a tan solid. $^1$H NMR (400 MHz, DMSO-$d_6$) 3.79 (s, 3H) 4.28 (d, J=5.5 Hz, 2H) 4.75 (t, J=5.6 Hz, 1H) 5.12 (s, 2H) 7.03 (s, 1H) 7.16 (d, J=8.5 Hz, 1H) 7.38 (dd, J=8.5, 2.1 Hz, 1H) 7.44 (d, J=2.2 Hz, 1H) 7.68 (d, J=0.8 Hz, 1H) 7.72 (t, J=8.0 Hz, 1H) 7.94 (d, J=7.9 Hz, 1H) 8.20 (dd, J=8.2, 1.5 Hz, 1H) 8.29 (t, J=1.7 Hz, 1H). LC/MS=99.9%, 340.1 (APCI+).

General Scheme 51.

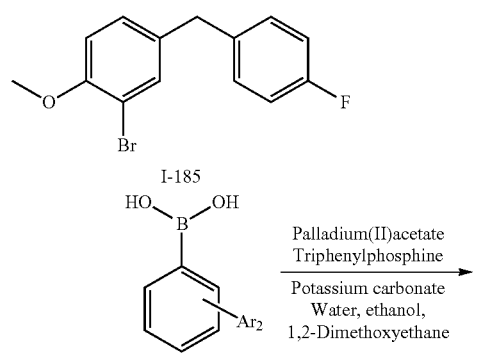

Example 213

Preparation of P-140

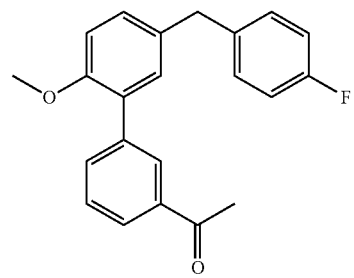

Synthesis of 1-[5'-(4-Fluoro-benzyl)-2'-methoxy-biphenyl-3-yl]-ethanone (P-140). A nitrogen stream was bubbled through a solution of I-185 (150 mg, 0.508 mmol) and 3-acetylphenylboronic acid (91.7 mg, 0.559 mmol) in 1,2-dimethoxyethane (4 mL) for 15 min, followed by the addition of ethanol:water (1:1, 1 mL). The nitrogen stream was continued for 10 min, and solid potassium carbonate (210 mg, 1.52 mmol), triphenylphosphine (26.8 mg, 0.102 mmol), and palladium(II) acetate (11.4 mg, 0.0508 mmol) were added. The reaction was heated to 80° C. and heated with stirring overnight. The reaction was diluted with ethyl acetate (50 mL) and saturated aqueous ammonium chloride (50 mL), filtered twice, and separated. The organic extract was washed with water (3×50 mL), brine (50 mL), dried over anhydrous sodium sulfate, filtered, and the solvent removed under vacuum. The reaction was purified by flash silica gel column chromatography (5% ethyl acetate in hexanes, Rf=0.10 in 10% ethyl acetate in hexanes) to give P-140 (88.0 mg, 52% yield) as a colorless oil. $^1$H NMR (400 MHz, DMSO-$d_6$) d: 7.98 (t, J=1.6 Hz, 1H), 7.91 (dt, J=7.9 Hz, 1.4 Hz, 1H), 7.70 (dt, J=8.0 Hz, 1.5 Hz, 1H), 7.56 (t, J=7.6 Hz, 1H), 7.30-7.30 (m, 2H), 7.23-7.21 (m, 2H), 7.12-7.05 (m, 3H), 3.93 (s, 2H), 3.74 (s, 3H), 2.60 (s, 3H) ppm. LCMS=98.5% purity. MS (APCI+)=335.1 (M+1).

Example 214

Preparation of P-141

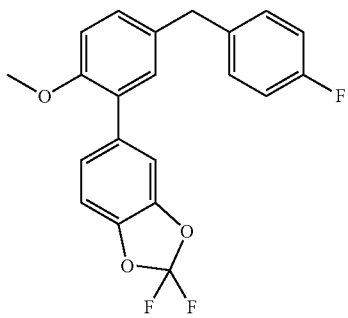

Synthesis of 2,2-Difluoro-5-[5-(4-fluoro-benzyl)-2-methoxy-phenyl]-benzo[1,3]dioxole (P-141). A nitrogen stream was bubbled through a solution of I-185 (114 mg, 0.385 mmol) and I-187 (140 mg, 0.693 mmol) in 1,2-dimethoxy ethane (3 mL) for 20 min, followed by addition of ethanol and water solution (1:1, 0.75 mL) and the nitrogen stream was continued for 5 min. To the reaction was added solid potassium carbonate (160 mg, 1.16 mmol), triphenyl phospine (20.2 mg, 0.0770 mmol), and palladium(II) acetate (8.6 mg, 0.0385 mmol) under nitrogen, the reaction was heated to 80° C., and stirred at this temperature overnight. The solvent was removed under vacuum, the residue dissolved in ethyl acetate (20 mL) and water (20 mL), the biphasic solution was filtered, and the two layers separated. The aqueous wash was extracted into ethyl acetate (20 mL), and the combined extracts were washed with water (3×50 mL), saturated aqueous ammonium chloride (50 mL), dried over sodium sulfate, decolorized with activated carbon, filtered, and the solvent removed under vacuum. The residue was purified by flash silica gel column chromatography (5% acetone in dichloromethane, Rf=0.40 in 10% acetone in dichloromethane) followed by preparatory silica TLC (2.5% acetone in dichloromethane) to give P-141 (96.8 mg, 68% yield). $^1$H NMR (400 MHz, DMSO-d$_6$) 7.48 (d, J=1.6 Hz, 1H), 7.42 (d, J=8.4 Hz, 1H), 7.30-7.179 (m, 5H), 7.11-7.03 (m, 3H), 3.90 (s, 2H), 3.74 (s, 3H) ppm. MS (ESI+) =371.8 (M−1), 353.0 (M−19).

Example 215

Preparation of P-151

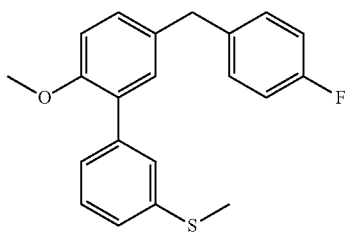

Synthesis of 5-(4-Fluoro-benzyl)-2-methoxy-3'-methylsulfanyl-biphenyl (P-151). P-151 was synthesized from I-185 (160 mg, 0.542 mmol) and 3-methylsulfanylphenylboronic acid (100 mg, 0.596 mmol) using the same condition as described for P-141. To the reaction vial was added ethyl acetate (50 mL) and water (50 mL), the biphasic solution filtered, and the layers separated. The organic extract was washed with water (3×50 mL), aqueous saturated ammonium chloride (50 mL), brine (50 mL), dried over sodium sulfate, filtered, and the solvent removed under vacuum. The product was purified by flash silica gel column chromatography (5% acetone in hexanes) followed by preparatory silica gel TLC (2.5% acetone in hexanes) to give P-151 (47.6 mg, 26% yield). $^1$H NMR (400 MHz, DMSO-d$_6$) 7.35-7.27 (m, 4H), 7.22-7.16 (m, 4H), 7.11-7.07 (m, 2H), 7.03 (d, J=8.4 Hz, 1H), 3.909 (s, 2H), 3.73 (s, 2H). LCMS=99.4% purity. MS (APCI+)=338.1 (M).

Example 216

Preparation of P-170

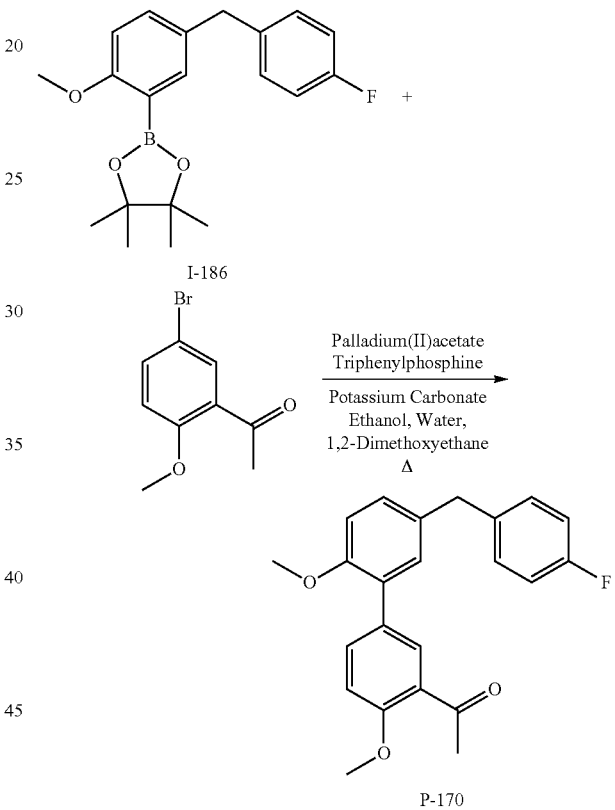

Synthesis of 1-[5'-(4-Fluoro-benzyl)-4,2'-dimethoxy-biphenyl-3-yl]-ethanone (P-170). A nitrogen steam was bubbled through a solution of I-186 (150 mg, 0.438 mmol) and 1-(5-bromo-2-methoxy-phenyl)-ethanone (110 mg, 0.482 mmol) in 1,2-dimethoxy ethane (4 mL) for 10 min, followed by the addition of an ethanol and water solution (1:1, 1 mL). Nitrogen bubbling was continued for 5 min, palladium (II) acetate (9.8 mg, 0.044 mmol), triphenylphosphine (23.0 mg, 0.0877 mmol), and solid potassium carbonate (181 mg, 1.32 mmol) were added under nitrogen, and the reaction was heated at 80° C. under nitrogen for 16 h. The solvent was removed under vacuum and ethyl acetate (50 mL) was added. The organic solution was washed with water (3×50 mL) and brine (50 mL). The organic extract was removed under vacuum. The residue was purified by two silica gel preparatory TLC plates (10% ethyl acetate in hexane with 2 developments followed by 5% acetone in hexanes with 6 developments) to give P-170 (43.0 mg, 27% yield) as an orange oil. $^1$H NMR (400 MHz, CDCl$_3$): 7.63-7.60 (m, 2H), 7.29-7.25 (m, 2H), 7.21-7.07 (m, 5H), 7.02 (d, J=8.4 Hz, 1H), 3.92 (s, 3H), 3.91 (s, 2H), 3.32 (s, 3H), 2.55 (s, 3H). LCMS=100.0% purity. MS (APCI+)=365.1 (M+1).

General Scheme 52.

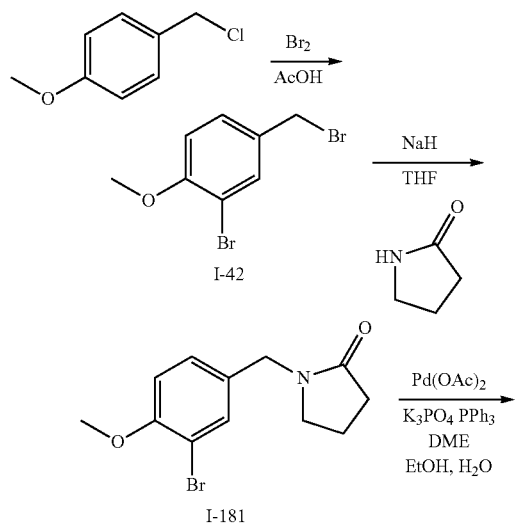

Example 217

Preparation of P-162

Synthesis of 2-Bromo-4-bromomethyl-1-methoxy-benzene (I-42). Into a 1 L round bottom flask was added 4-methoxybenzyl chloride (19.7 g, 125.8 mmol), glacial acetic acid (400 mL), and Br$_2$ (9.1 mL, 177.5 mmol, dropwise over 5 minutes). The brown solution was stirred at room temperature for 20 hours and then poured into a 10% (w/v) aqueous NaHSO$_3$ solution (2000 mL). After stirring at room temperature for 30 minutes, the white solid was filtered through a coarse glass-frit and the solids were washed with water (4×500 mL). The solid was dried in a vacuum dessicator for 16 hours. I-42 (24.5 g, 74%) was obtained as a white solid.

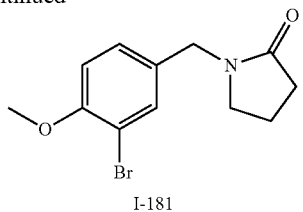

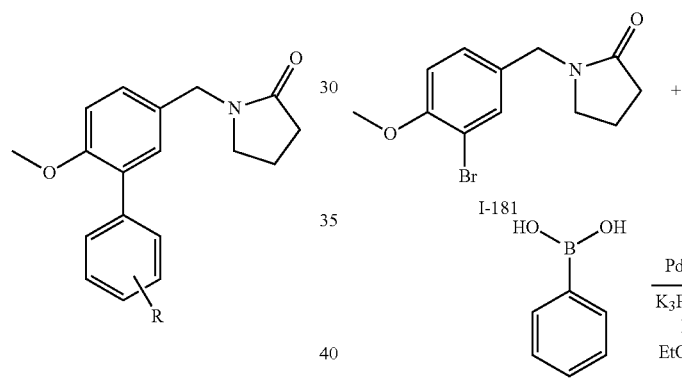

Synthesis of 1-(3-Bromo-4-methoxy-benzyl)-pyrrolidin-2-one (I-181). Into a dry 100 mL round bottom flask was added pyrrolidin-2-one (0.20 g, 2.34 mmol), dry DMF (20 mL), and the solution was cooled to 0° C. NaH (110 mg, 2.76 mmol) was added and the suspension was stirred at room temperature for 30 minutes. I-42 (0.50 g, 2.12 mmol) was added and the reaction was stirred at 80° C. for 30 minutes and then cooled to room temperature. After extraction with dichloromethane (2×20 mL), the combined organics were washed with water (4×20 mL), dried over sodium sulfate, filtered, and concentrated. The residue was purified by flash column chromatography using 10% acetone/dichloromethane to obtain 482 mg (80%) of I-181 as a light-yellow oil.

Synthesis of 1-(6-Methoxy-biphenyl-3-ylmethyl)-pyrrolidin-2-one (P-162). Into a 20 mL vial with stir bar was added I-181 (95.5 mg, 0.34 mmol), phenylboronic acid (45 mg, 0.37 mmol), triphenylphosphine (18 mg, 0.07 mmol), K$_2$CO$_3$ (139 mg, 1.01 mmol), DME (5 mL), water (0.5 mL), and ethanol (0.5 mL). N$_2$ gas was bubbled through the stirred reaction for 10 minutes. Palladium(II) acetate (8 mg, 0.03 mmol) was added and N$_2$ was bubbled through for an additional 5 minutes. The vial was capped and the reaction was stirred at 80° C. for 18 hours. The reaction was cooled to room temperature and 5 mL of water and 5 mL of ethyl acetate were added. The layers were separated and the aqueous was extracted with ethyl acetate (3×10 mL). The organics were combined, dried with sodium sulfate, concentrated, and the residue was purified by prep TLC using 10% acetone/dichloromethane to obtain 38.9 mg (41%) of P-162 as a light-yellow oil. ¹H NMR (400 MHz, CDCl₃) 1.98 (quin, J=7.6 Hz, 2H) 2.43 (t, J=8.1 Hz, 2H) 3.29 (t, J=7.1 Hz, 2H) 3.80 (s, 3H) 4.43 (s, 2H) 6.94 (d, J=8.2 Hz, 1H) 7.17-7.24 (m, 2H) 7.29-7.36 (m, 1H) 7.40 (t, J=7.5 Hz, 2H) 7.51 (d, J=7.3 Hz, 2H) ppm. LC/MS=100.0%, 282.1 (APCI+).

Example 218

Preparation of P-184

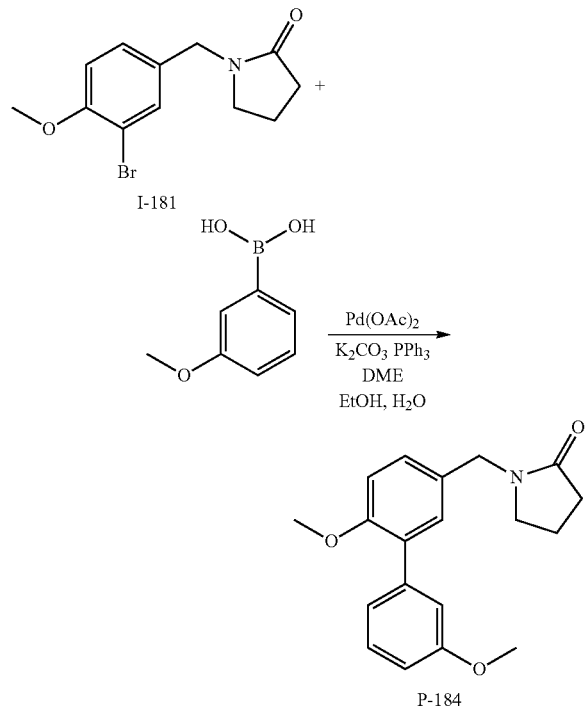

Synthesis of 1-(6,3'-Dimethoxy-biphenyl-3-ylmethyl)-pyrrolidin-2-one (P-184). Into a 20 mL vial with stir bar was added I-181 (0.21 g, 0.73 mmol), 3-methoxyphenylboronic acid (0.11 g, 0.73 mmol), triphenylphosphine (39 mg, 0.15 mmol), K₂CO₃ (0.31 g, 2.22 mmol), DME (5 mL), water (0.5 mL), and ethanol (0.5 mL). N₂ gas was bubbled through the stirred reaction for 10 minutes. Palladium(II) acetate (17 mg, 0.07 mmol) was added and N₂ was bubbled through the reaction for an additional 5 minutes. The reaction was stirred at 80° C. for 18 hours under N₂. The reaction was cooled to room temperature and 5 mL of water and 5 mL of ethyl acetate were added. The layers were separated and the aqueous was extracted with ethyl acetate (3×10 mL). The organics were combined, dried with sodium sulfate, and concentrated. The residue was purified by flash column chromatography using 10% acetone/dichloromethane to obtain 40.2 mg (17%) of P-184 as a brown oil. ¹H NMR (400 MHz, CDCl₃) 1.98 (quin, J=7.6 Hz, 2H) 2.43 (t, J=8.1 Hz, 2H) 3.28 (t, J=7.1 Hz, 2H) 3.80 (s, 3H) 3.84 (s, 3H) 4.43 (s, 2H) 6.88 (dd, J=8.3, 2.0 Hz, 1H) 6.93 (d, J=8.2 Hz, 1H) 7.04-7.11 (m, 2H) 7.17-7.23 (m, 2H) 7.32 (t, J=7.9 Hz, 1H) ppm. LC/MS=100.0%, 312.1 (APCI+).

Example 219

Preparation of P-503

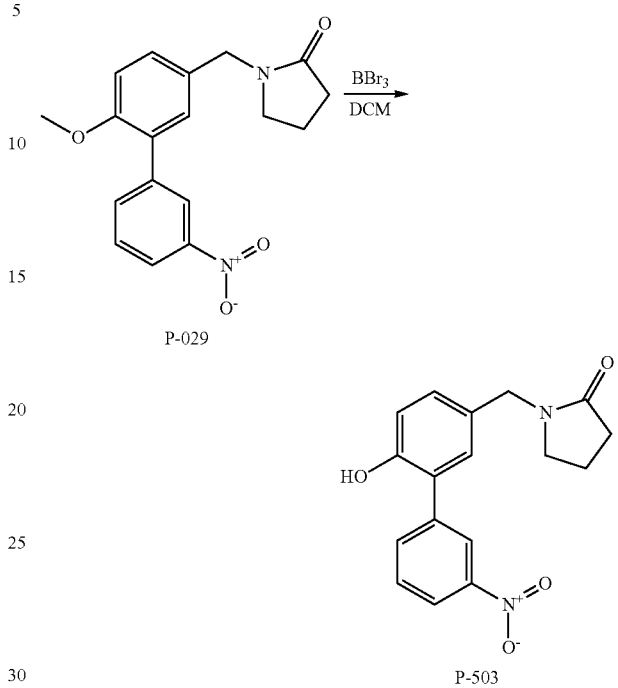

Synthesis of 1-(6-Hydroxy-3'-nitro-biphenyl-3-ylmethyl)-pyrrolidin-2-one (P-503). Into a 50 mL round bottom flask with stir bar was added P-029 (324.5 mg, 0.99 mmol) and dichloromethane (10 mL). The solution was cooled to 0° C. and BBr₃ (3.0 mL, 2.98 mmol, 1.0 M in dichloromethane) was added. The reaction was stirred at room temperature for 18 hours and then water was added. The layers were separated and the aqueous was extracted with dichloromethane (4×15 mL). The organics were combined, dried with sodium sulfate, and concentrated. The solid was triturated with ether and 284.4 mg (92%) of P-503 was obtained as a tan-colored solid. ¹H NMR (400 MHz, DMSO-d₆) 1.90 (quin, J=7.5 Hz, 2H) 2.26 (t, J=8.1 Hz, 2H) 3.24 (t, J=7.0 Hz, 2H) 4.32 (s, 2H) 6.97 (d, J=8.3 Hz, 1H) 7.11 (dd, J=8.3, 2.0 Hz, 1H) 7.25 (d, J=2.0 Hz, 1H) 7.71 (t, J=8.0 Hz, 1H) 8.00 (d, J=7.8 Hz, 1H) 8.17 (dd, J=8.2, 1.6 Hz, 1H) 8.40 (t, J=1.7 Hz, 1H) 9.91 (br. s., 1H) ppm. LC/MS=98.4%, 313.1 (APCI+).

Example 220

Preparation of P-188

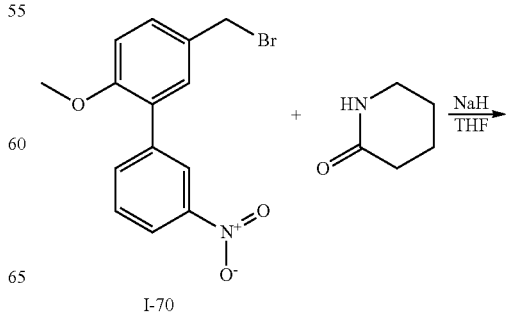

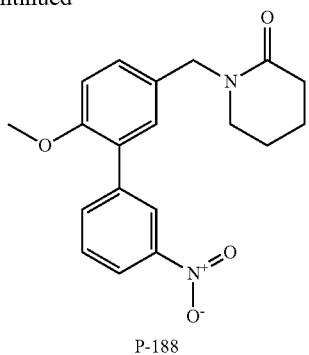

P-188

Synthesis of 1-(6-Methoxy-3'-nitro-biphenyl-3-ylmethyl)-piperidin-2-one (P-188). Into a 50 mL round bottom flask with stir bar was added 2-Piperidone (88 mg, 0.89 mmol), dry THF (5 mL), NaH (42 mg, 1.05 mmol), and the suspension was stirred for 10 minutes at room temperature. I-70 (261 mg, 0.81 mmol) was added and the reaction was stirred for 18 hours at room temperature. To the reaction was added 10 mL of H$_2$O and the THF was removed by rotary evaporation. The product was extracted with ethyl acetate (3×10 mL) and the combined organics were washed with 20 mL of brine, dried over Na$_2$SO$_4$, and concentrated. The residue was purified by flash column chromatography using 5-10% acetone/dichloromethane to obtain 201 mg (73%) of P-188 as a light-yellow semi-solid. $^1$H NMR (500 MHz, CDCl$_3$) 8.40-8.39 (m, 1H), 8.18-8.15 (m, 1H), 7.84-7.82 (m, 1H), 7.56 (t, J=8.0 Hz), 7.31 (dd, J=8.5, 2.0 Hz, 1H), 7.24-7.23 (m, 1H), 6.97 (d, J=8.0 Hz, 1H), 4.59 (s, 2H), 3.83 (s, 3H), 3.26-3.24 (m, 2H), 2.47-2.44 (m, 2H), 1.80-1.79 (m, 4H) ppm. $^{13}$C-NMR (100 MHz, CDCl$_3$) δ 170.0, 155.9, 148.2, 140.1, 135.8, 130.7, 130.3, 129.9, 129.0, 128.3, 124.7, 122.0, 111.7, 55.9, 49.6, 47.4, 32.6, 23.4, 21.5 ppm. LC/MS=100.0%, 341.1 (APCI+).

Example 221

Preparation of P-192

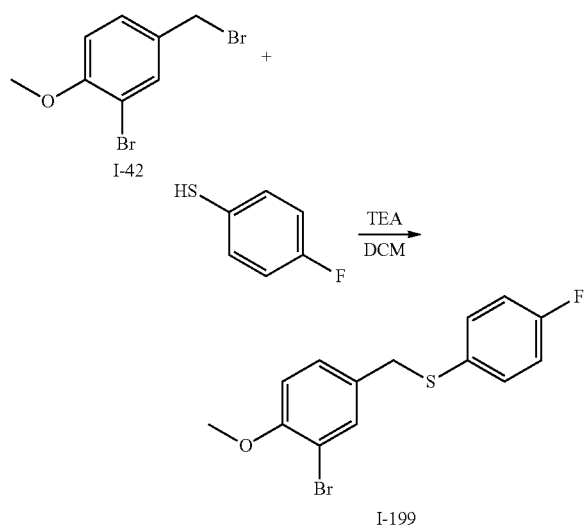

Synthesis of 2-Bromo-4-(4-fluoro-phenylsulfanylmethyl)-1-methoxy-benzene (I-199). Into a 20 mL vial with stir bar was added I-42 (0.50 g, 1.90 mmol), 4-fluorothiophenol (0.27 g, 2.09 mmol), dichloromethane (5 mL), and TEA (0.43 mL, 3.14 mmol). The solution was stirred at room temperature for 16 hours and then concentrated. The residue was purified by flash column chromatography using 15% acetone/hexane to obtain I-199 which was used without further purification in the next step.

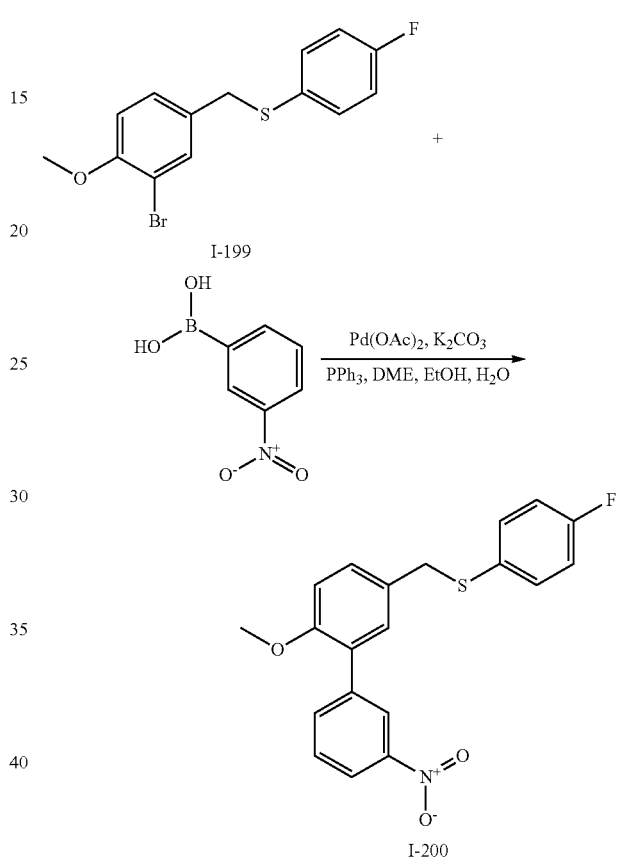

Synthesis of 5-(4-Fluoro-phenylsulfanylmethyl)-2-methoxy-3'-nitro-biphenyl (I-200). Into a 20 mL vial with stir bar was added I-199 (0.40 g, 1.22 mmol), 3-nitrophenylboronic acid (0.20 g, 1.22 mmol), K$_2$CO$_3$ (0.51 g, 3.67 mmol), triphenylphosphine (64 mg, 0.24 mmol), DME (5 mL), EtOH (0.5 mL), and H$_2$O (0.5 mL). The mixture was degassed with N$_2$ for 10 minutes and then palladium(II) acetate (27 mg, 0.12 mmol) was added. The reaction was stirred at 80° C. for 18 hours and then filtered through Celite and concentrated. The residue was purified by flash column chromatography using 10% acetone/dichloromethane, then by flash column chromatography using 12% acetone/hexane, followed by preparative layer chromatography using 15% ethyl acetate/hexane to give 102 mg (23%) of I-200 as a light-yellow oil. $^1$H NMR (400 MHz, CDCl$_3$) 8.33 (s, 1H), 8.17 (dd, J=1.3, 8.3 Hz, 1H), 7.78 (d, J=7.8 Hz, 1H), 7.55 (t, J=8.0 Hz, 1H), 7.35-7.27 (m, 2H), 7.23 (dd, J=2.1, 8.5 Hz, 1H), 7.15 (d, J=2.1 Hz, 1H), 6.98 (t, J=8.7 Hz, 2H), 6.91 (d, J=8.5 Hz, 1H), 4.04 (s, 2H), 3.82 (s, 3H) ppm. LC/MS=369.0 (APCI-).

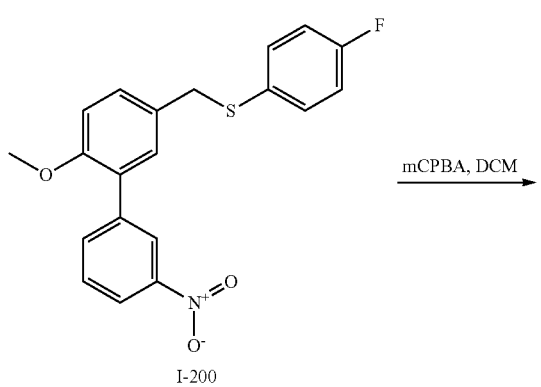

I-200

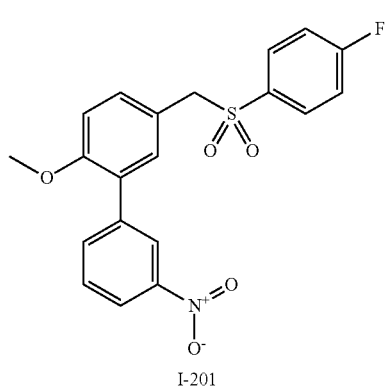

I-201

Synthesis of 5-(4-Fluoro-benzenesulfonylmethyl)-2-methoxy-3'-nitro-biphenyl (I-201). Into a 20 mL vial with stir bar was added I-200 (38.4 mg, 0.10 mmol), dichloromethane (2 mL), and mCPBA (45 mg, 0.26 mmol). The reaction was stirred at room temperature for 30 minutes and then 5 mL of saturated NaHCO₃ (aq.) was added. The product was extracted with dichloromethane (2×5 mL) and then concentrated. Purification by preparative layer chromatography using 35% acetone/hexane gave 18.3 mg (44%) of I-201 as a colorless semi-solid. $^{1}$H NMR (400 MHz, CDCl₃) 8.22 (d, J=1.6 Hz, 1H), 8.21-8.14 (m, 1H), 7.76-7.67 (m, 3H), 7.55 (t, J=8.1 Hz, 1H), 7.23-7.15 (m, 3H), 7.01 (d, J=2.3 Hz, 1H), 6.94 (d, J=8.5 Hz, 1H), 4.30 (s, 2H), 3.84 (s, 3H) ppm. LC/MS=100.0%, 401.0 (APCI−)

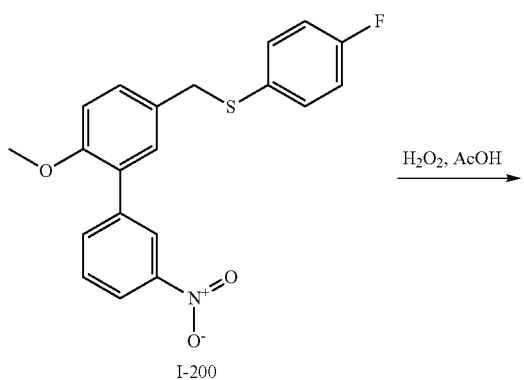

I-200

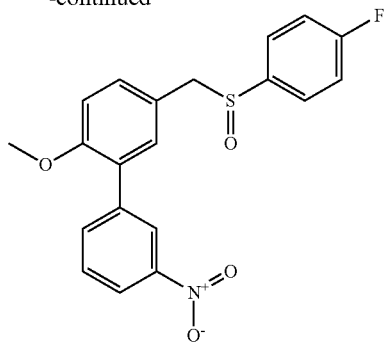

P-192

Synthesis of 5-(4-Fluoro-benzenesulfinylmethyl)-2-methoxy-3'-nitro-biphenyl (P-192). Into a 20 mL vial with stir bar was added I-200 (35.5 mg, 0.096 mmol), glacial AcOH (0.5 mL), and H₂O₂ (1.1 mL, 0.096 mmol, 0.088M solution in AcOH)). The reaction was stirred at room temperature for 1 hour and then 10 mL of saturated NaHCO₃ (aq.) and 1 mL of 1N NaOH were added until pH=10. The product was extracted with dichloromethane (3×5 mL) and then concentrated. Purification by preparative layer chromatography using 35% acetone/hexane gave 21.0 mg (57%) of P-192 as a colorless semi-solid. $^{1}$H NMR (400 MHz, CDCl₃) 8.24 (t, J=1.8 Hz, 1H), 8.17 (dd, J=1.3, 8.3 Hz, 1H), 7.71 (d, J=7.6 Hz, 1H), 7.54 (t, J=8.0 Hz, 1H), 7.45-7.36 (m, 2H), 7.17 (t, J=8.5 Hz, 2H), 7.07 (dd, J=2.1, 8.5 Hz, 1H), 6.93 (d, J=8.5 Hz, 1H), 6.85 (d, J=2.3 Hz, 1H), 4.03 (d, J=2.7 Hz, 2H), 3.83 (s, 3H) ppm. LC/MS=100.0%, 386.0 (APCI+).

Example 222

Preparation of P-195

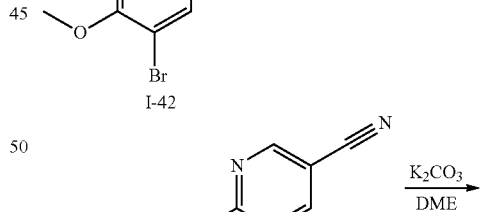

I-42

I-202

Synthesis of 1-(3-Bromo-4-methoxy-benzyl)-6-oxo-1,6-dihydro-pyridine-3-carbonitrile (I-202). Into a 100 mL round-bottomed flask with a stir bar was added I-42 (2.59 g, 9.84 mmol), 6-hydroxy-nicotinonitrile (985 mg, 8.20 mmol), K$_2$CO$_3$ (2.49 g, 18.0 mmol), and DME (30 mL). The reaction was stirred at 80° C. for 20 hours and then cooled to room temperature and filtered. The filtrate was concentrated and the resulting light-pink solid was triturated with 40 mL of ether to obtain 529 mg (20%) of I-202 as a white solid.

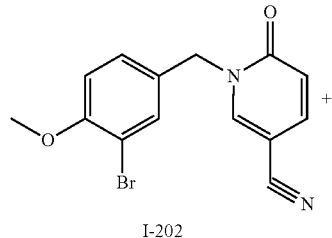

I-202

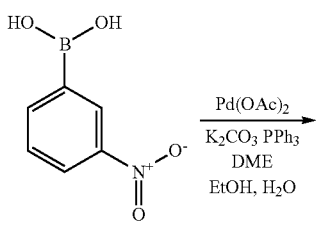

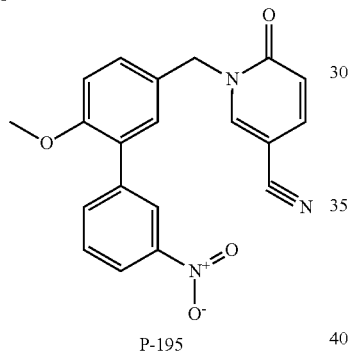

P-195

Synthesis of 1-(6-Methoxy-3'-nitro-biphenyl-3-ylm-ethyl)-6-oxo-1,6-dihydro-pyridine-3-carbonitrile (P-195). Into a 50 mL round bottom flask with a stir bar was added I-202 (510 mg, 1.60 mmol), 3-nitrophenylboronic acid (0.40 g, 2.40 mmol), triphenylphosphine (84 mg, 0.32 mmol), K$_2$CO$_3$ (0.66 g, 4.79 mmol), DME (10 mL), H$_2$O (1 mL), EtOH (1 mL), and the suspension was degassed with N$_2$ for 5 minutes. To this was added palladium(II) acetate (36 mg, 0.16 mmol) and the reaction was stirred at 80° C. for 18 hours. The reaction was cooled to rt and 50 mL of H$_2$O was added and the product was extracted with ethyl acetate (3×20 mL). The combined organics were washed with brine, dried over Na$_2$SO$_4$, filtered, and concentrated. The resulting solid was triturated with ether (2×25 mL) to afford 391 mg (68%) of P-195 as a tan solid. $^1$H NMR (400 MHz, DMSO-d$_6$) 8.84 (d, J=2.1 Hz, 1H), 8.30 (s, 1H), 8.21 (d, J=8.2 Hz, 1H), 7.94 (d, J=7.6 Hz, 1H), 7.73 (t, J=8.0 Hz, 1H), 7.67 (dd, J=2.4, 9.5 Hz, 1H), 7.52 (d, J=1.9 Hz, 1H), 7.47 (dd, J=1.9, 8.5 Hz, 1H), 7.16 (d, J=8.6 Hz, 1H), 6.51 (d, J=9.5 Hz, 1H), 5.09 (s, 2H), 3.80 (s, 3H) ppm. LC/MS=93.4%, 362.6 (ESI+).

Example 223

Preparation of P-196

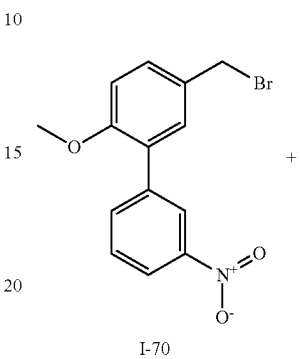

I-70

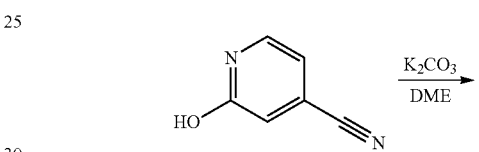

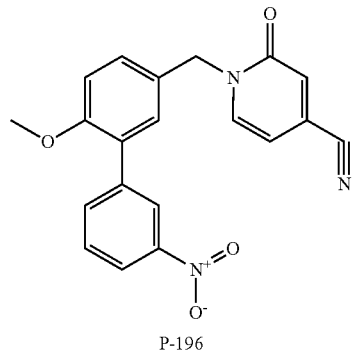

P-196

Synthesis of 1-(6-Methoxy-3'-nitro-biphenyl-3-ylm-ethyl)-2-oxo-1,2-dihydro-pyridine-4-carbonitrile (P-196). Into a 100 mL round bottom flask with a stir bar was added I-70 (2.76 g, 8.55 mmol), 2-hydroxy-isonicotinonitrile (934 mg, 7.78 mmol), K$_2$CO$_3$ (2.36 g, 17.11 mmol), and DME (30 mL). The suspension was stirred for 18 hours at 80° C. and then at rt for 2 days. The reaction was filtered, the filtrate was concentrated, and the resulting solid was triturated with ether to give 2.12 g (75%) of P-196 as a yellow solid. $^1$H NMR (400 MHz, DMSO-d$_6$) 8.29 (s, 1H), 8.20 (dd, J=1.3, 8.3 Hz, 1H), 8.12 (d, J=7.1 Hz, 1H), 7.93 (d, J=7.8 Hz, 1H), 7.73 (t, J=8.0 Hz, 1H), 7.49 (d, J=2.0 Hz, 1H), 7.43 (dd, J=1.9, 8.5 Hz, 1H), 7.16 (d, J=8.6 Hz, 1H), 7.04 (d, J=1.3 Hz, 1H), 6.56 (dd, J=1.7, 7.0 Hz, 1H), 5.12 (s, 2H), 3.79 (s, 3H) ppm. LC/MS=96.1%, 361.0 (APCI−).

Example 224

Preparation of P-207

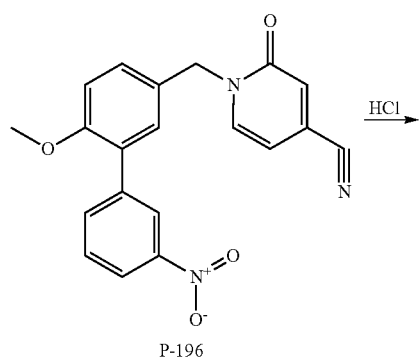

Synthesis of 1-(6-Methoxy-3'-nitro-biphenyl-3-ylmethyl)-2-oxo-1,2-dihydro-pyridine-4-carboxylic acid amide (P-207). Into a 20 mL vial with a stir bar was added P-196 (132 mg, 0.37 mmol) and concentrated HCl (2 mL). The reaction was stirred at rt for 18 hours, basified with 4N aqueous NaOH, and the product was extracted with ethyl acetate (3×5 mL). The combined organics were concentrated to half their original volume and 5 mL of hexane was added. The resulting solids were filtered, washed with hexane, and triturated with ether to afford 29.8 mg (22%) of P-207 as a tan solid. $^1$H NMR (400 MHz, DMSO-$d_6$) 8.28 (s, 1H), 8.20 (dd, J=1.4, 8.3 Hz, 1H), 8.05 (br. s., 1H), 7.93 (t, J=7.4 Hz, 2H), 7.72 (t, J=8.0 Hz, 1H), 7.61 (br s, 1H), 7.48 (d, J=2.0 Hz, 1H), 7.42 (dd, J=2.1, 8.5 Hz, 1H), 7.15 (d, J=8.5 Hz, 1H), 6.84 (d, J=1.5 Hz, 1H), 6.54 (dd, J=1.8, 7.0 Hz, 1H), 5.10 (s, 2H), 3.79 (s, 3H) ppm. MS: 380.1 (APCI+).

Example 225

Preparation of P-208

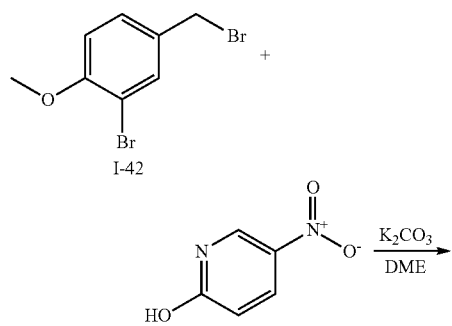

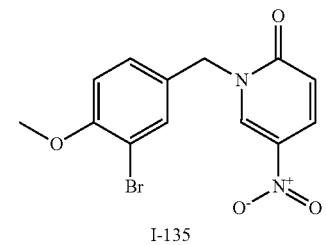

Synthesis of 1-(3-Bromo-4-methoxy-benzyl)-5-nitro-1H-pyridin-2-one (I-135). Into a 100 mL round-bottomed flask with a stir bar was added I-42 (3.0 g, 11.41 mmol), 5-nitropyridin-2-ol (1.60 g, 11.41 mmol), $K_2CO_3$ (3.47 g, 25.10 mmol), and 30 mL of DME. The reaction was stirred at 80° C. for 18 hours and then cooled to rt and filtered. The filtrate was concentrated and the resulting solid was triturated with 50 mL of ether to give 3.01 g (78%) of I-135 as a yellow solid.

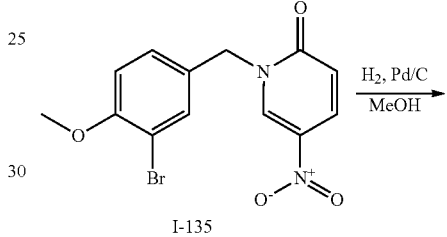

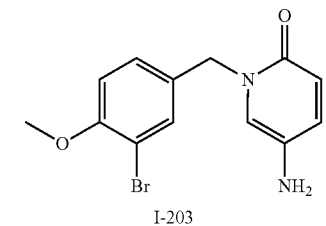

Synthesis of 5-Amino-1-(3-bromo-4-methoxy-benzyl)-1H-pyridin-2-one (I-203). Into a 250 mL round bottom flask with a stir bar was added I-135 (1.93 g, 5.69 mmol), 75 mL of MeOH, and 400 mg of 10% Pd/C. The suspension was stirred under a $H_2$ atmosphere for 1 hour, and then filtered through Celite and concentrated. To the residue was added 30 mL of 1N HCl and the reaction was washed with dichloromethane (3×20 mL). The aqueous portion was basified with 1N NaOH until pH=10, then extracted with dichloromethane (3×15 mL). The organics were dried with $Na_2SO_4$ and concentrated to give 825 mg of I-203 as a light-green solid which used without further purification.

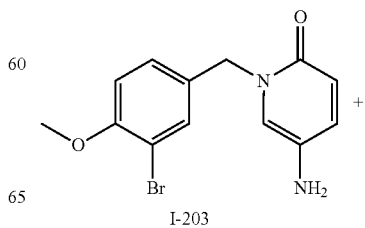

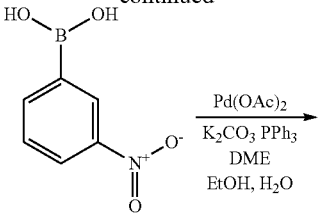

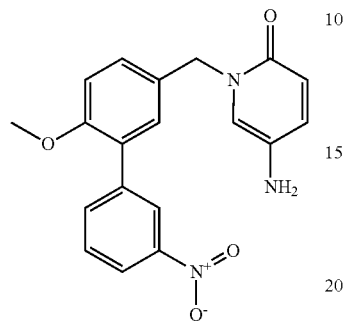

I-204

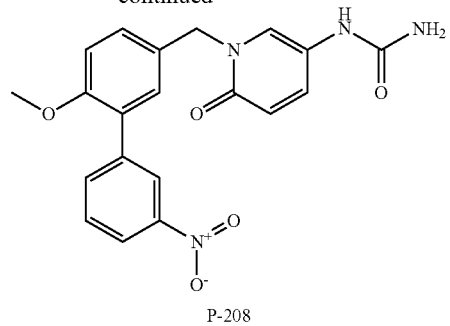

P-208

Synthesis of [1-(6-Methoxy-3'-nitro-biphenyl-3-ylmethyl)-6-oxo-1,6-dihydro-pyridin-3-yl]-urea (P-208). Into a 20 mL vial with a stir bar was added I-204 (36.5 mg, 0.10 mmol), NaOCN (13.5 mg, 0.21 mmol), H₂O (2 mL), and 1 mL glacial acetic acid. The reaction was stirred as 40° C. for 2 hours, then cooled to r.t. and 10 mL of H₂O was added. The suspension was filtered to obtain 19.8 mg (48%) of P-208 as a gray solid. $^1$H NMR (400 MHz, DMSO-d$_6$) 8.29 (s, 1H), 8.20 (d, J=8.2 Hz, 1H), 8.03 (s, 1H), 7.92 (d, J=7.6 Hz, 1H), 7.88 (d, J=2.3 Hz, 1H), 7.72 (t, J=7.9 Hz, 1H), 7.44 (s, 1H), 7.40-7.35 (m, 1H), 7.31 (dd, J=2.5, 9.5 Hz, 1H), 7.15 (d, J=8.5 Hz, 1H), 6.37 (d, J=9.7 Hz, 1H), 5.79 (s, 2H), 5.07 (s, 2H), 3.79 (s, 3H) ppm. LC/MS=90.5%, 395.1 (APCI+).

Synthesis of 5-Amino-1-(6-methoxy-3'-nitro-biphenyl-3-ylmethyl)-1H-pyridin-2-one (I-204). Into a 100 mL round bottom flask with a stir bar was added I-203 (802 mg, 2.59 mmol), 3-nitrophenylboronic acid (433 mg, 2.59 mmol), triphenylphosphine (136 mg, 0.52 mmol), K₂CO₃ (1.07 g, 7.77 mmol), DME (15 mL), H₂O (1.5 mL), EtOH (1.5 mL), and the suspension was degassed with N₂ for 10 minutes. To this was added palladium(II) acetate (58 mg, 0.26 mmol) and the reaction was stirred at 80° C. for 18 hours. After cooling to rt 5 mL of aqueous 1N NaOH was added and the product was extracted with ethyl acetate (3×15 mL). The combined organics were filtered through Celite and concentrated. The residue was purified by flash column chromatography using 5% MeOH/dichloromethane to give 185 mg (21%) of I-204 as a brown solid. $^1$H NMR (400 MHz, DMSO-d$_6$) 8.28 (s, 1H), 8.20 (dd, J=1.3, 8.2 Hz, 1H), 7.92 (d, J=7.8 Hz, 1H), 7.72 (t, J=8.0 Hz, 1H), 7.40 (d, J=1.9 Hz, 1H), 7.35 (dd, J=1.9, 8.5 Hz, 1H), 7.15 (d, J=8.6 Hz, 1H), 7.05 (dd, J=2.9, 9.5 Hz, 1H), 6.91 (d, J=2.8 Hz, 1H), 6.29 (d, J=9.5 Hz, 1H), 4.99 (s, 2H), 4.29 (br. s., 2H), 3.79 (s, 3H) ppm. LC/MS=100.0%, 352.1 (APCI+).

Example 226

Preparation of P-212

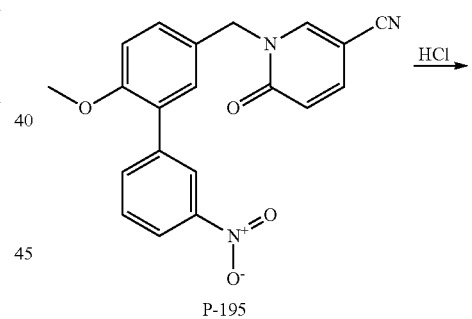

P-195

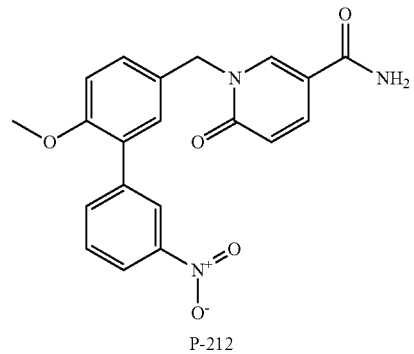

P-212

Synthesis of 1-(6-Methoxy-3'-nitro-biphenyl-3-ylmethyl)-6-oxo-1,6-dihydro-pyridine-3-carboxylic acid amide (P-212). Into an 8 mL vial with a stir bar was added P-195 (44 mg, 0.12 mmol) and concentrated HCl (2 mL). The reaction was stirred at r.t. for 24 hours. To the reaction was added 5 mL

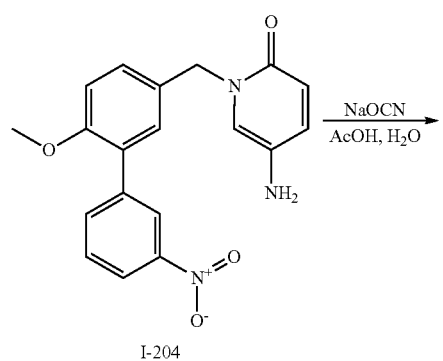

I-204 of ethyl acetate and the solution was basified with aqueous 4N NaOH. The ethyl acetate layer was removed and concentrated. The resulting solid was triturated with ether to obtain 15.6 mg (34%) of P-212 as a tan solid. $^1$H NMR (400 MHz, DMSO-$d_6$) 8.52 (d, J=2.4 Hz, 1H), 8.32-8.26 (m, 1H), 8.20 (dd, J=1.3, 8.3 Hz, 1H), 7.93 (d, J=7.8 Hz, 1H), 7.85 (dd, J=2.5, 9.5 Hz, 1H), 7.76 (br. s., 1H), 7.73 (t, J=8.1 Hz, 1H), 7.49 (d, J=2.0 Hz, 1H), 7.44 (dd, J=2.0, 8.6 Hz, 1H), 7.28 (br. s., 1H), 7.16 (d, J=8.6 Hz, 1H), 6.42 (d, J=9.5 Hz, 1H), 5.14 (s, 2H), 3.79 (s, 3H) ppm. LC/MS=96.4%, 380.1 (APCI+).

Example 227

Preparation of P-213

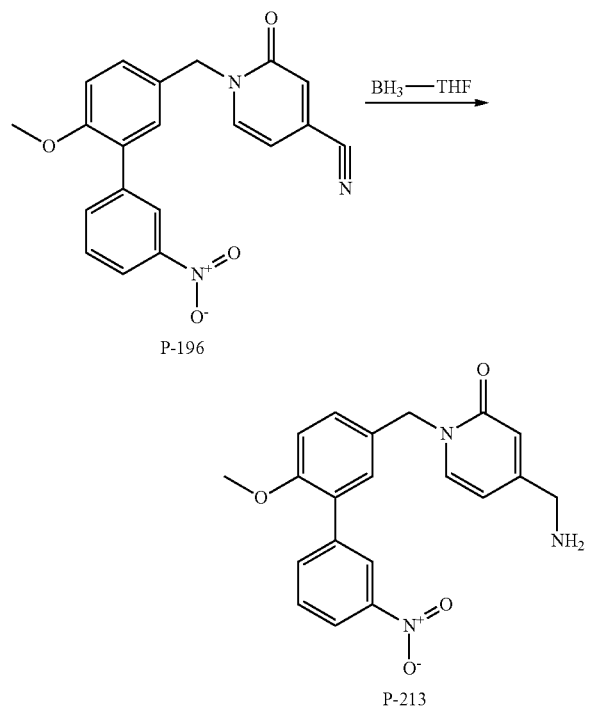

Synthesis of 4-Aminomethyl-1-(6-methoxy-3'-nitro-biphenyl-3-ylmethyl)-1H-pyridin-2-one (P-213). Into a 20 mL vial with a stir bar with P-196 (144 mg, 0.40 mmol) and 3 mL of THF was added BH$_3$-THF (2.0 mL, 2.0 mmol, 1.0M solution in THF). The solution was stirred at 60° C. for 4 hours, then cooled to 0° C. and a solution of 2.0 M HCl in ether was added slowly, followed by 5 mL of methanol. The solution was stirred at room temperature for 16 hours and then concentrated. To the residue was added aqueous 1N HCl and it was washed with dichloromethane, then basified with aqueous 4N NaOH and extracted with dichloromethane and concentrated. The residue was purified by flash column chromatography eluting with 10-17% methanol/dichloromethane and afforded 7.2 mg (5%) of P-213 as a tan solid. $^1$H NMR (400 MHz, DMSO-$d_6$) 8.27 (s, 1H), 8.23-8.17 (m, 1H), 7.92 (d, J=7.6 Hz, 1H), 7.79-7.67 (m, 2H), 7.45 (d, J=1.9 Hz, 1H), 7.39 (dd, J=1.8, 8.4 Hz, 1H), 7.14 (d, J=8.5 Hz, 1H), 6.35 (s, 1H), 6.19 (dd, J=1.5, 7.0 Hz, 1H), 5.05 (s, 2H), 3.78 (s, 2H), 3.51 (s, 2H) ppm. LC/MS=98.4%, 366.1 (APCI+).

Example 228

Preparation of P-215

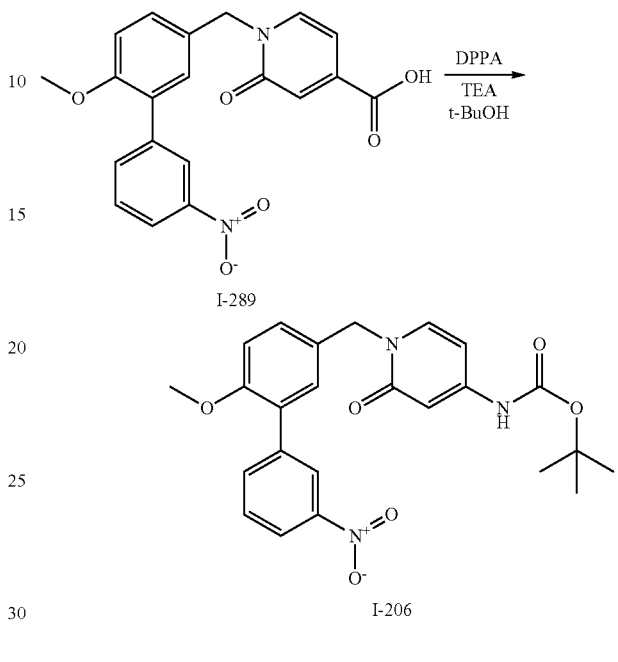

Synthesis of [1-(6-Methoxy-3'-nitro-biphenyl-3-ylmethyl)-2-oxo-1,2-dihydro-pyridin-4-yl]-carbamic acid tert-butyl ester (I-206). Into a 25 mL round bottom flask was placed I-289 (97.5 mg, 0.26 mmol), diphenylphosphoryl azide (71 mg, 0.26 mmol), triethylamine (26 mg, 0.26 mmol), and t-BuOH (5 mL). The solution was refluxed for 16 hours, then cooled to room temperature. The reaction was diluted with ethyl acetate, washed with saturated aqueous NaHCO$_3$, and brine. After concentration of the organics, the residue was purified by flash column chromatography eluting with 40% acetone/hexane to afford 61 mg (53%) of I-206 as a colorless oil. $^1$H NMR (400 MHz, DMSO-$d_6$) 9.60 (s, 1H), 8.27 (s, 1H), 8.20 (dd, J=1.6, 8.2 Hz, 1H), 7.91 (d, J=7.8 Hz, 1H), 7.78-7.65 (m, 2H), 7.40 (d, J=2.0 Hz, 1H), 7.36 (dd, J=2.0, 8.5 Hz, 1H), 7.14 (d, J=8.5 Hz, 1H), 6.53 (d, J=2.1 Hz, 1H), 6.34 (dd, J=2.3, 7.5 Hz, 1H), 4.99 (s, 2H), 3.78 (s, 3H), 1.45 (s, 9H) ppm. LC/MS=93.0%, 452.1 (APCI+).

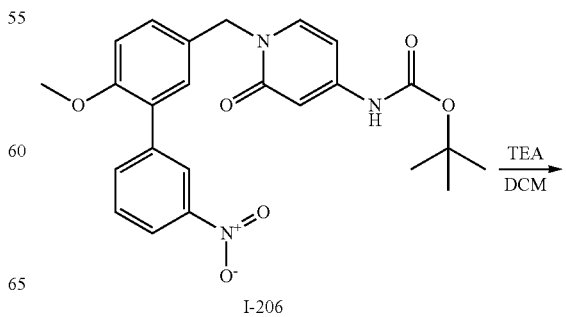

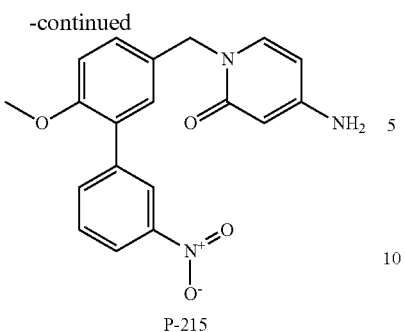

P-215

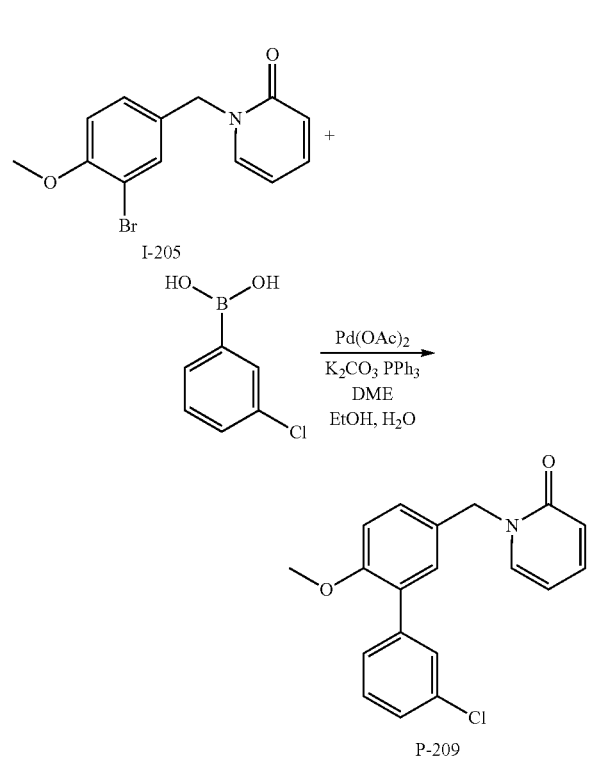

Synthesis of 4-Amino-1-(6-methoxy-3'-nitro-biphenyl-3-ylmethyl)-1H-pyridin-2-one (P-215). Into a 20 mL vial with a stir bar was added I-206 (50 mg, 0.11 mmol), dichloromethane (2 mL), and 1 mL of TFA. The reaction was stirred at room temperature for 4 hours and then concentrated. The residue was diluted with aqueous 1N HCl and washed with dichloromethane. The aqueous portion was basified with aqueous 4N NaOH, extracted with dichloromethane, and concentrated to afford 22 mg (56%) of P-215 as a tan solid. $^1$H NMR (400 MHz, DMSO-d$_6$) 8.27 (s, 1H), 8.23-8.16 (m, 1H), 7.91 (d, J=7.6 Hz, 1H), 7.72 (t, J=8.0 Hz, 1H), 7.41 (d, J=7.4 Hz, 1H), 7.38-7.30 (m, 2H), 7.13 (d, J=8.5 Hz, 1H), 5.99 (s, 2H), 5.66 (dd, J=2.3, 7.4 Hz, 1H), 5.24 (d, J=2.3 Hz, 1H), 4.90 (s, 2H), 3.78 (s, 3H) ppm. LC/MS=97.8%, 352.1 (APCI+).

Example 229

Preparation of P-209

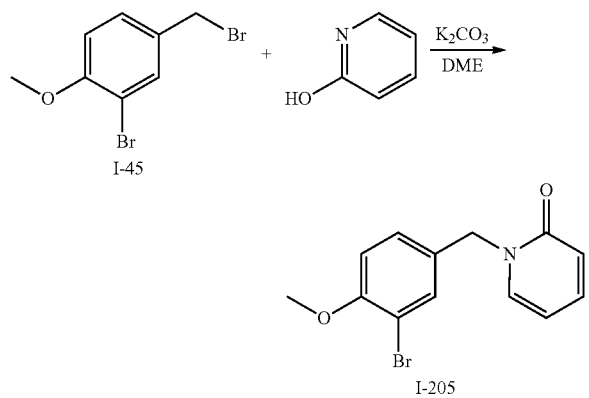

Synthesis of 1-(3-Bromo-4-methoxy-benzyl)-1H-pyridin-2-one (I-205). Into a 100 mL round bottom flask with a stir bar was added I-45 (2.56 g, 9.73 mmol), 2-hydroxypyridine (926 mg, 9.73 mmol), K$_2$CO$_3$ (2.96 g, 21.41 mmol), and 30 mL of DME. The suspension was stirred at 80° C. for 18 hours and then r.t. for 2 days after which it was filtered and concentrated. The solid was triturated with ether to afford 2.20 g (77%) of I-205 as a white solid.

Synthesis of 1-(3'-Chloro-6-methoxy-biphenyl-3-ylmethyl)-1H-pyridin-2-one (P-209). Into a 40 mL vial with a stir bar was added I-205 (250 mg, 0.81 mmol), 3-chlorophenylboronic acid (126 mg, 0.81 mmol), triphenylphosphine (42 mg, 0.16 mmol), K$_2$CO$_3$ (335 mg, 2.43 mmol), DME (10 mL), H$_2$O (1 mL), EtOH (1 mL), and the suspension was degassed with N$_2$ for 10 minutes. To this was added palladium (II) acetate (18 mg, 0.08 mmol) and the reaction was stirred at 80° C. for 18 hours. After cooling to r.t., 10 mL of H$_2$O was added and the product was extracted with ethyl acetate (3×15 mL). The combined organics were concentrated. The residue was purified by flash column chromatography using 20%-35% acetone/hexanes to give 241 mg (91%) of P-209 as a light-yellow oil. $^1$H NMR (400 MHz, DMSO-d$_6$) 7.84 (dd, J=1.3, 6.6 Hz, 1H), 7.66-7.52 (m, 1H), 7.51-7.31 (m, 6H), 7.10 (d, J=9.1 Hz, 1H), 6.39 (d, J=9.1 Hz, 1H), 6.22 (t, J=6.5 Hz, 1H), 5.06 (s, 2H), 3.76 (s, 3H) ppm. LC/MS=97.6%, 326.2 (APCI+).

Scheme 53.

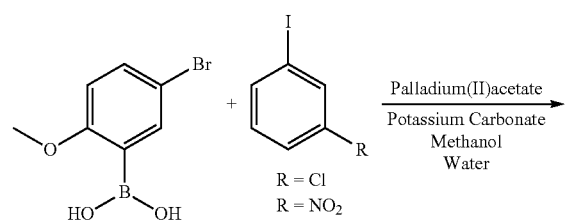

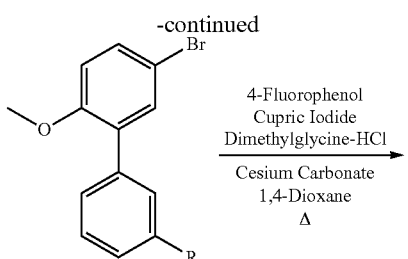

I-207 R = NO$_2$
I-208 R = Cl

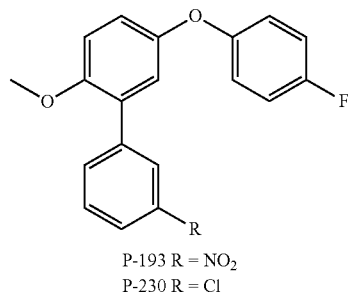

P-193 R = NO$_2$
P-230 R = Cl

Example 230

Preparation of P-193

Synthesis of 5-Bromo-2-methoxy-3'-nitro-biphenyl (I-207). A suspension of 5-bromo-2-methoxyphenylboronic acid (500 mg, 2.17 mmol), 3-iodonitrobenzene (647 mg, 2.60 mmol), and potassium carbonate (599 mg, 4.33 mmol) in methanol (10 mL) and water (2 mL) was degassed for 30 min under a nitrogen stream followed by the addition of palladium (II) acetate (9.72 mg, 0.0433 mmol). The reaction was stirred at room temperature for 4 h. The methanol was removed under reduced pressure, ethyl acetate (50 mL) and water (50 mL) were added, and the biphasic suspension was filtered. The layers were separated and the organic was washed with water (50 mL). The aqueous washes were combined and extracted with ethyl acetate (2×50 mL), and the organic extracts combined. The organic solution was washed with water (3×50 mL), saturated aqueous sodium bicarbonate (50 mL), brine, dried over sodium sulfate, filtered, and the solvent removed under vacuum to give a crude brown gum. The product was purified by flash silica gel column chromatography (5% ethyl acetate in hexanes), and crystallized by dissolving in diethyl ether (20 mL) and hexanes (50 mL), removing one half of the solvent under vacuum, filtering and washing with hexanes (2×10 mL) to give I-207 (417.8 mg, 63% yield). $^1$H NMR (400 MHz, CDCl$_3$) 8.38 (t, J=1.8 Hz, 1H), 8.21-8.19 (m, 1H), 7.81 (dt, J=7.5 Hz, 1.3 Hz, 1H), 7.58 (t, J=8.0 Hz, 1H), 7.50-7.45 (m, 2H), 6.90 (d, J=8.8 Hz, 1H), 3.82 (s, 3H) ppm.

Synthesis of 5-(4-Fluoro-phenoxy)-2-methoxy-3'-nitrobiphenyl (P-193). To a suspension of I-207 (200 mg, 0.649 mmol), 4-fluorophenol (109 mg, 0.974 mmol), cesium carbonate (423 mg, 1.30 mmol), and N,N-dimethylglycine (20.1 mg, 0.195 mmol) in 1,4-dioxane (2 mL) was added copper(I) iodide (12.4 mg, 0.0649 mmol) under argon, and the reaction was heated to 105° C. The reaction was left to stir overnight under argon at 105° C. The blue solution was diluted with ethyl acetate (50 mL), washed with water (2×50 mL), brine (50 mL), dried over sodium sulfate, filtered, and the solvent removed under vacuum. The residue was purified by flash silica gel column chromatography (10% ethyl acetate in hexanes), and was crystallized from diethyl ether (5 mL) to give P-193 (61.4 mg, 28% yield) as a white powder. 1H NMR (400 MHz, CDCl$_3$) 8.40 (t, J=2.0 Hz, 1H), 8.19-8.16 (m, 1H), 7.82 (dt, J=7.6 Hz, 1.2 Hz, 1H), 7.56 (t, J=8.0 Hz, 1H), 7.04-6.95 (m, 7H), 3.83 (s, 3H) ppm. LCMS=98.3% purity. MS (APCI−)=339.2 (M).

Example 231

Preparation of P-230

Synthesis of 5-Bromo-3'-chloro-2-methoxy-biphenyl (I-208). I-208 was synthesized from 5-bromo-2-methoxyphenylboronic acid (2.00 g, 8.66 mmol) and 3-chloroiodobenzene (2.48 g, 10.4 mmol) using the same conditions as for I-207. The reaction time was extended to 16 h. The methanol was removed under vacuum, and the residue dissolved in ethyl acetate (100 mL), washed with water (100 mL), and the aqueous wash extracted with ethyl acetate (100 mL). The combined organic extracts were washed with saturated aqueous sodium bicarbonate (2×200 mL), water (2×200 mL) and brine (150 mL), dried over sodium sulfate, filtered and the solvent removed under vacuum to give I-208 (2.56 g, 99% yield). 1H NMR (400 MHz, CDCl$_3$) 7.49-7.48 (m, 1H), 7.44-7.40 (m, 2H), 7.36-7.31 (m, 3H), 6.85 (d, J=8.4 Hz, 1H), 3.80 (s, 3H) ppm.

Synthesis of 3'-Chloro-2-fluoro-3-(4-fluoro-phenoxy)-6-methoxy-biphenyl (P-230). To a suspension of I-208 (200 mg, 0.672 mmol), 4-fluorophenol (113 mg, 1.01 mmol), cesium carbonate (438 mg, 1.34 mmol), and N,N-dimethylglycine hydrochloride salt (28.2 mg, 0.202 mmol) in 1,4-dioxane (2 mL) was added copper(I) iodide (12.8 mg, 0.0672 mmol) under argon. The reaction was heated to 105° C. under argon, and stirred at 105° C. overnight. The reaction was diluted with ethyl acetate (20 mL), washed with water (20 mL), and the aqueous wash extracted into ethyl acetate (20 mL). The combined organic extracts were washed with 1 N aqueous sodium hydroxide (20 mL), 1 N aqueous hydrochloric acid (20 mL), water (2×20 mL), brine (20 mL), dried over sodium sulfate, filtered, and the solvent removed under vacuum. The product was purified by preparatory TLC eluting with 5% acetone in hexanes with 3 developments to give P-230 (140.6 mg, 64% yield) as a yellow gummy solid. 1H NMR (400 MHz, CDCl$_3$) 7.51-7.51 (m, 1H), 7.38-7.30 (m, 3H), 7.023-6.93 (m, 7H), 3.81 (s, 3H) ppm. MS (ESI+)=389.6 (M+61), 328.2 (M), 279.5 (M−49).

Example 232

Preparation of P-236

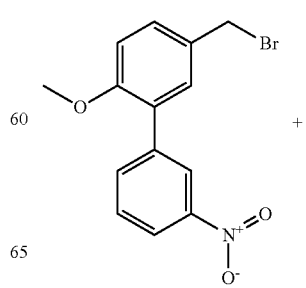

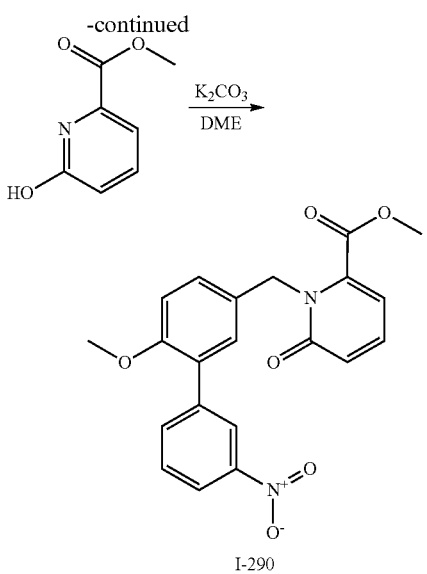

Synthesis of 1-(6-Methoxy-3'-nitro-biphenyl-3-ylmethyl)-6-oxo-1,6-dihydro-pyridine-2-carboxylic acid methyl ester (I-290). Into a 20 mL vial with stir bar was added I-70 (268 mg, 0.83 mmol), 6-hydroxy-pyridine-2-carboxylic acid methyl ester (98 mg, 0.64 mmol), K$_2$CO$_3$ (195 mg, 1.41 mmol), and DME (4 mL). The reaction was stirred at 80° C. for 4 hours and then cooled to room temperature and filtered. The filtrate was concentrated and purified by flash column chromatography using 15-50% acetone/hexanes to afford 98 mg (39%) of I-290 as a tan solid.

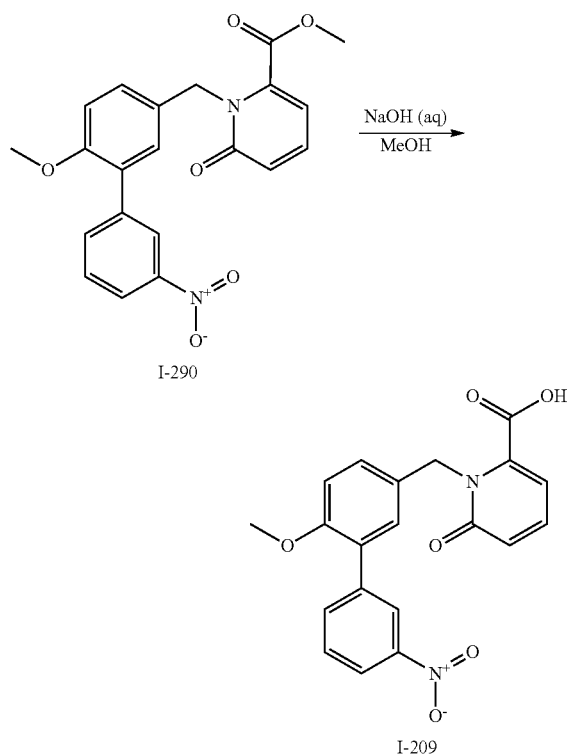

Synthesis of 1-(6-Methoxy-3'-nitro-biphenyl-3-ylmethyl)-6-oxo-1,6-dihydro-pyridine-2-carboxylic acid (I-209). Into a 20 mL vial with a stir bar was added I-290 (92 mg, 0.23 mmol), 1N aqueous NaOH (2 mL), and methanol (2 mL). The reaction was stirred at 60° C. for 18 hours and then cooled to room temperature and washed with dichloromethane. The aqueous portion was acidified with 6N aqueous HCl and extracted with ethyl acetate. The organics were dried over Na$_2$SO$_4$ and concentrated to give I-209 (61 mg, 69%) as a tan solid. $^1$H NMR (400 MHz, DMSO-d$_6$) 8.25 (s, 1H), 8.19 (dd, J=1.4, 8.3 Hz, 1H), 7.88 (d, J=7.8 Hz, 1H), 7.72 (t, J=7.9 Hz, 1H), 7.48 (dd, J=6.8, 9.1 Hz, 1H), 7.24 (d, J=1.7 Hz, 1H), 7.21-7.15 (m, 1H), 7.14-7.08 (m, 1H), 6.71 (d, J=6.6 Hz, 1H), 6.63 (d, J=9.0 Hz, 1H), 5.50 (s, 2H), 3.77 (s, 3H) ppm. LC/MS=99.9%, 381.0 (APCI+)

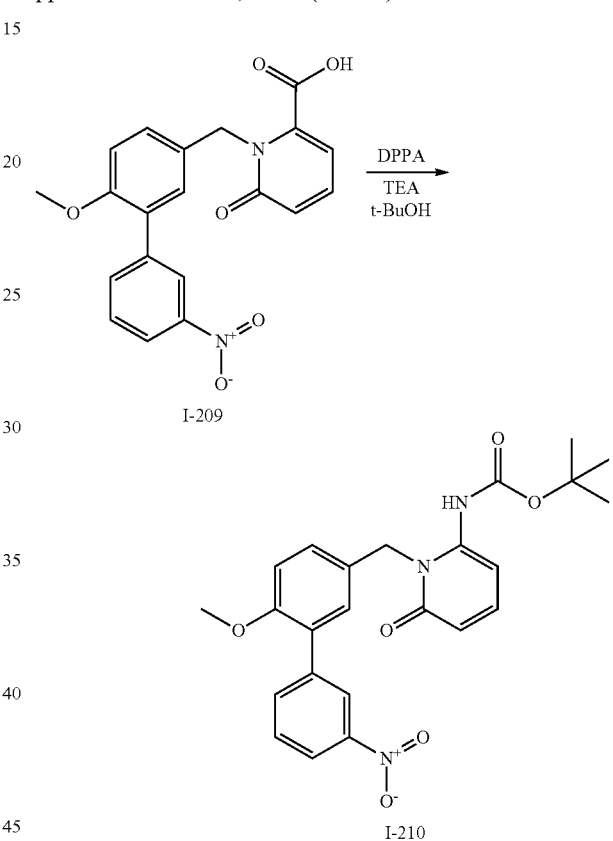

Synthesis of [1-(6-Methoxy-3'-nitro-biphenyl-3-ylmethyl)-6-oxo-1,6-dihydro-pyridin-2-yl]-carbamic acid tert-butyl ester (I-210). Into a 20 mL vial was placed I-209 (48 mg, 0.13 mmol), diphenylphosphoryl azide (35 mg, 0.13 mmol), triethylamine (13 mg, 0.13 mmol), and t-BuOH (4 mL). The solution was stirred at 80° C. for 24 hours and then cooled to room temperature. The solvent was evaporated, the residue diluted with saturated aqueous NaHCO$_3$ and extracted with ethyl acetate. The organics were concentrated and purified by flash column chromatography eluting with 15% acetone/ dichloromethane to give I-210 (43 mg, 75%) as a white solid. $^1$H NMR (400 MHz, DMSO-d$_6$) 9.42 (br s, 1H), 8.27 (s, 1H), 8.20 (d, J=8.2 Hz, 1H), 7.90 (d, J=7.6 Hz, 1H), 7.72 (t, J=7.9 Hz, 1H), 7.40 (dd, J=7.4, 9.0 Hz, 1H), 7.27-7.18 (m, 2H), 7.12 (d, J=8.3 Hz, 1H), 6.31 (d, J=9.0 Hz, 1H), 6.14 (d, J=7.0 Hz, 1H), 5.28 (br s, 2H), 3.76 (s, 3H), 1.27 (s, 9H) ppm. LC/MS=94.2%, 452.1 (APCI+).

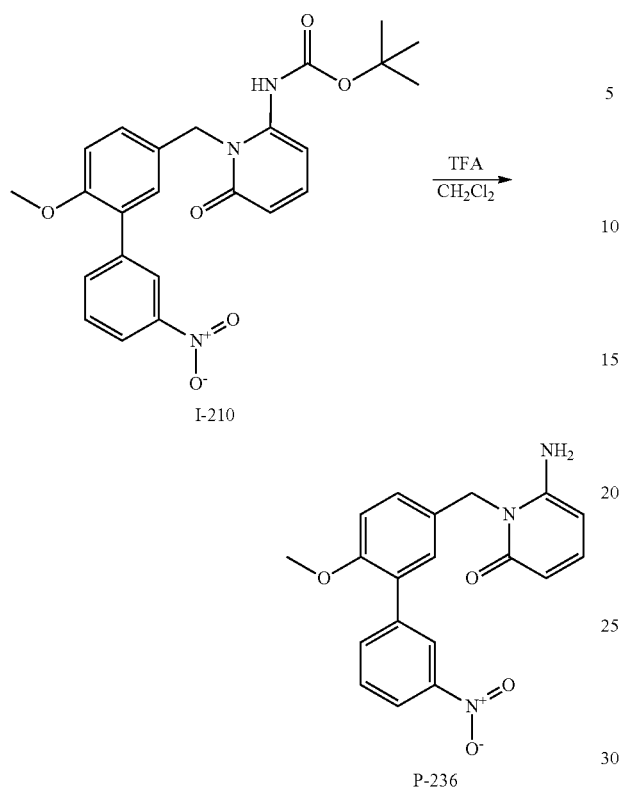

Synthesis of 6-Amino-1-(6-methoxy-3'-nitro-biphenyl-3-ylmethyl)-1H-pyridin-2-one (P-236). Into a 20 mL vial with a stir bar was added I-210 (22 mg, 0.049 mmol), dichloromethane (2 mL), and TFA (2 mL). After 6 hours at room temperature the solution was concentrated. The residue was purified by flash column chromatography using 2-5% methanol/dichloromethane to give 12.5 mg (74%) of P-236 as a brown solid. $^1$H NMR (400 MHz, DMSO-$d_6$) 8.27 (s, 1H), 8.20 (d, J=8.2 Hz, 1H), 7.91 (d, J=7.6 Hz, 1H), 7.76-7.69 (m, 1H), 7.39 (d, J=1.7 Hz, 1H), 7.25 (dd, J=1.7, 8.5 Hz, 1H), 7.15-7.08 (m, 2H), 6.44 (s, 1H), 5.76 (s, 2H), 5.53 (d, J=8.7 Hz, 1H), 5.40 (d, J=7.6 Hz, 1H), 5.19 (br s, 1H), 3.77 (s, 3H) ppm. LC/MS=100.0%, 352.1 (APCI+).

Scheme 54.

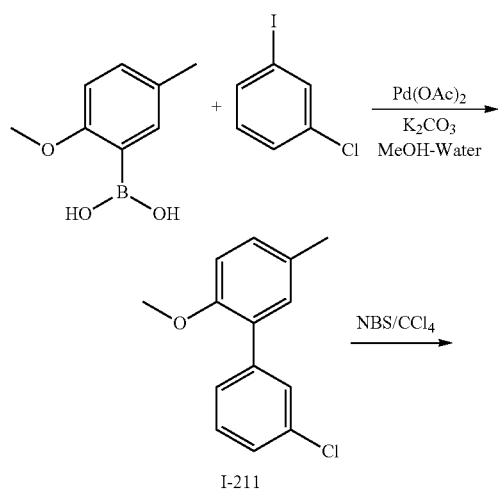

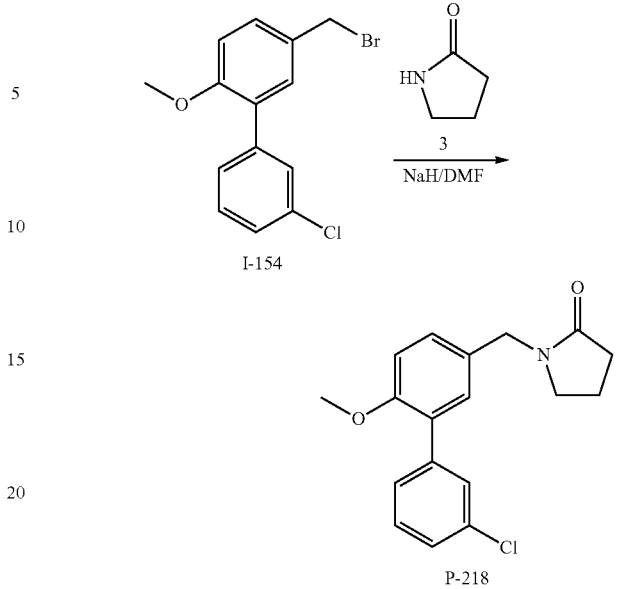

Example 233

Preparation of P-218

Synthesis of 3'-chloro-2-methoxy-5-methyl-biphenyl (I-211). To 2-methoxy-5-methylboronic acid (4.0 g, 24.1 mmol), 1-chloro-3-iodo-benzene (6.32 g, 26.51 mmol), $K_2CO_3$ (8.33 g, 60.25 mmol), and palladium(II) acetate (0.27 g, 1.2 mmol) was added methanol (150 mL), and $H_2O$ (30 mL). Argon gas was bubbled through the stirred reaction for 5 min. The reaction was stirred at room temperature under argon for 20 h. The reaction mixture was concentrated, and $H_2O$ and dichloromethane (60 mL each) were added. The organic layer was separated and the aqueous layer was extracted with dichloromethane (2×60 mL). The combined organic extracts were dried with $Na_2SO_4$, filtered, and concentrated. The residue was purified by silica gel column chromatography using 1:1 dichloromethane-hexanes then dichloromethane to afford 5.6 g (98%) of I-211 as a viscous liquid.

Synthesis of 5-bromomethyl-3'-chloro-2-methoxy-biphenyl (I-154). To I-211 (2.0 g, 8.59 mmol) and NBS (1.68 g, 9.45 mmol) in $CCl_4$ (30 mL) was added benzoylperoxide (0.1 g, 0.43 mmol). The reaction was stirred at 85° C. under $N_2$ for 5 h. The reaction was cooled to room temperature and concentrated. The residue was dissolved in mixture of 5% ethyl acetate in hexanes (20 mL) and purified by silica gel column chromatography using 5% ethyl acetate in hexanes to afford 2.81 g (98%) of I-154 as light yellow viscous liquid.

Synthesis of 1-(3'-chloro-6-methoxy-biphenyl-3-ylmethyl)-pyrrolidin-2-one (P-218). To a solution of 2-pyrrolidone (0.2 g, 2.41 mmol) in DMF (1 mL) was added to a cooled (0° C.) slurry of NaH (0.1 g, 2.41 mmol) in DMF (3 mL) under Ar. The reaction mixture was slowly warmed to room temperature, stirred for 45 min, then cooled to 0° C. To this I-154 (0.5 g, 1.6 mmol) in DMF (2 mL) was added over 5 min. The reaction mixture was slowly warmed to room temperature, stirred for 20 h, poured on to crushed-ice water, and extracted with ethyl acetate (2×60 mL). The combined organic extracts were dried with $Na_2SO_4$, filtered, and concentrated. The residue was dissolved in dichloromethane (20 mL) and purified by silica gel column chromatography using 5% ethyl acetate in hexanes to afford 0.22 g (43%) of P-218 as a viscous liquid. 1H NMR ($CDCl_3$, 400 MHz): 7.49-7.51 (m, 1H), 7.27-7.4 (m, 4H), 7.23 (dd, J=8.4, 2.4 Hz, 1H), 7.16

(d, J=2.4 Hz, 1H), 6.93 (d, J=8.4 Hz, 2H), 4.43 (s, 2H), 3.81 (s, 3H), 3.28 (t, J=7.2 Hz, 2H), 2.44 (t, J=8.0 Hz, 2H), 1.95-2.05 (m, 2H) ppm; MS (APCI+): 316.1 (M+1), LC-MS: 100%.

Example 234

Preparation of P-211

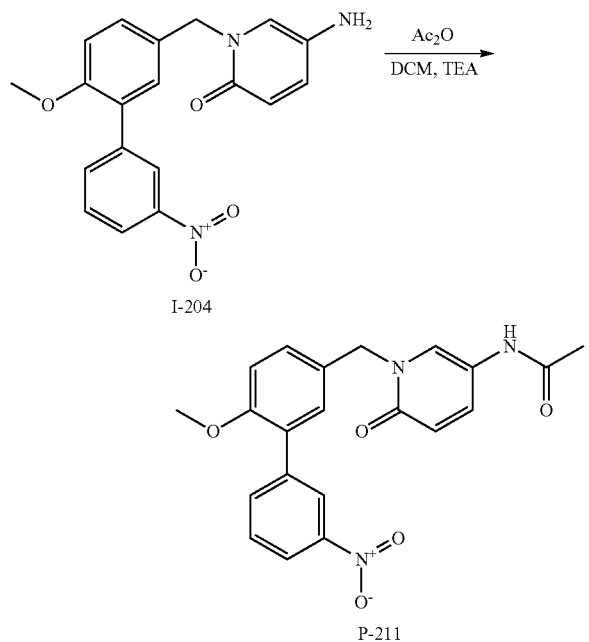

Synthesis of N-[1-(6-Methoxy-3'-nitro-biphenyl-3-ylmethyl)-6-oxo-1,6-dihydro-pyridin-3-yl]-acetamide (P-211). Into a 20 mL vial with a stir bar was added I-204 (113 mg, 0.32 mmol), dichloromethane (2 mL), Ac₂O (46 uL, 0.48 mmol), and TEA (90 uL, 0.64 mmol). The reaction was stirred at room temperature for 4 hours, 1N aqueous HCl was added, the product was extracted with dichloromethane, and the organics were concentrated. The residue was purified by flash column chromatography using 25%-35% acetone/dichloromethane to afford 12.5 mg (10%) of P-211 as a tan solid. ¹H NMR (400 MHz, DMSO-d₆) 9.66 (s, 1H), 8.28 (s, 1H), 8.23-8.12 (m, 2H), 7.92 (d, J=7.8 Hz, 1H), 7.72 (t, J=8.0 Hz, 1H), 7.43 (d, J=1.9 Hz, 1H), 7.41-7.32 (m, 2H), 7.16 (d, J=8.5 Hz, 1H), 6.42 (d, J=9.5 Hz, 1H), 5.09 (s, 2H), 3.79 (s, 3H), 1.95 (s, 3H) ppm. LC/MS=95.5%.

Example 235

Preparation of P-223

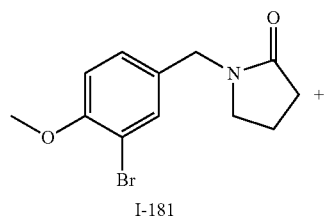

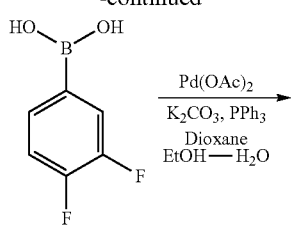

Synthesis of 1-(3',4'-difluoro-6-methoxy-biphenyl-3-ylmethyl)-pyrrolidin-2-one (P-223). To I-181 (0.15 g, 0.53 mmol), 3,4-difluorophenylboronic acid (0.13 g, 0.79 mmol), triphenylphosphine (0.07 g, 0.26 mmol), K₂CO₃ (0.03 g, 0.21 mmol) and palladium(II) acetate (0.014 g, 0.06 mmol) were added dioxane (6 mL) and EtOH—H₂O (1:1, 3 mL). Argon gas was bubbled through the stirred reaction for 5 min. The reaction was stirred at 85° C. under argon for 20 h. The reaction was cooled to room temperature and concentrated. The residue was purified by silica gel column chromatography using 30-50% ethyl acetate in hexanes to afford 0.15 g (89%) of P-223 as a light brown viscous liquid. 1H NMR (CDCl₃, 400 MHz): 7.33-7.38 (m 1H), 7.14-7.24 (m, 4H), 6.93 (d, J=8.4 Hz, 1H), 4.43 (s, 2H), 3.81 (s, 3H), 3.29 (t, J=7.2 Hz, 2H), 2.44 (t, J=8.4 Hz, 2H), 1.95-2.05 (m, 2H) ppm; MS (APCI+): 318.1 (M+1), LC-MS: 100%.

Example 236

Preparation of P-240

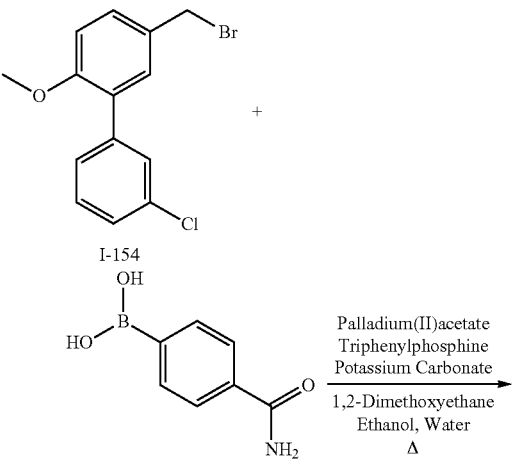

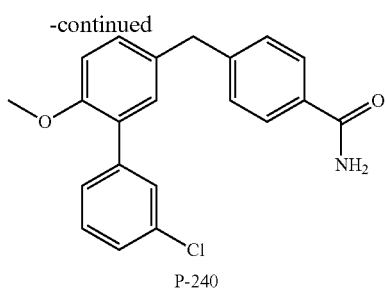

P-240

Synthesis of 4-(3'-Chloro-6-methoxy-biphenyl-3-ylmethyl)-benzamide (P-240). A suspension of I-154 (300 mg, 0.963 mmol), 4-aminocarboxyphenylboronic acid (238 mg, 1.44 mmol), triphenylphosphine (50.4 mg, 0.193 mmol), and water (1 mL) was degassed with a nitrogen stream for 30 minutes. To the reaction was added palladium(II) acetate (22 mg, 0.0963 mmol) under nitrogen and the reaction was heated to 90° C. under nitrogen with stirring overnight. The solvent was removed under vacuum and the product crystallized in hexanes (50 mL). The product was purified by flash silica gel column chromatography (5% methanol in dichloromethane) to give P-240 (112 mg, 33% yield) as a grey solid. 1H NMR (400 MHz, CDCl$_3$) 7.75-7.73 (m, 2H), 7.49 (t, J=1.6 Hz, 1H), 7.38-7.27 (m, 5H), 7.14-7.10 (m, 2H), 6.91 (d, J=8.0 Hz, 1H), 6.0 (br s, 1H), 5.75 (br s, 1H), 4.01 (s, 2H), 3.79 (s, 3H) ppm. LCMS=92.3% purity. MS (APCI+)=352.1 (M+1).

Example 237

Preparation of P-245

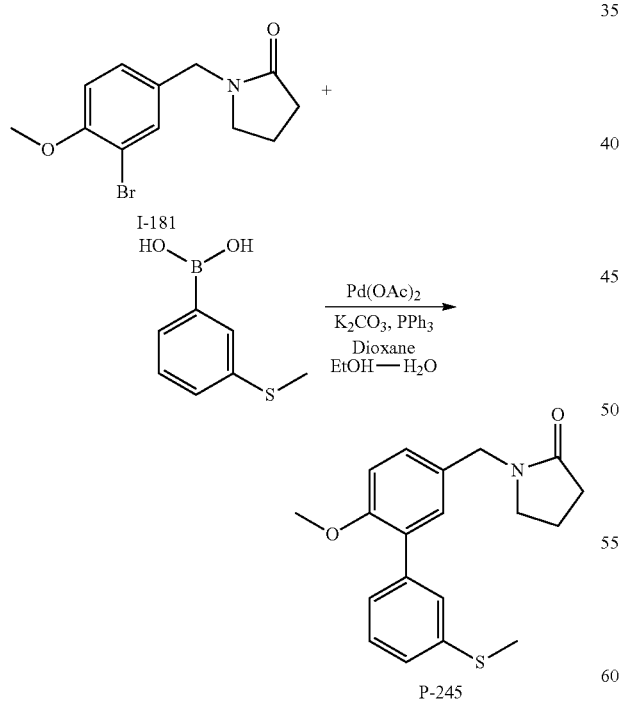

Synthesis of 1-(6-methoxy-3'-methylsulfanyl-biphenyl-3-ylmethyl)-pyrrolidin-2-one (P-245). To I-181 (0.15 g, 0.53 mmol), 3-methylsulfanyl-benzeneboronic acid (0.11 g, 0.639 mmol), triphenylphosphine (0.07 g, 0.26 mmol), K$_2$CO$_3$ (0.03 g, 0.21 mmol) and palladium(II) acetate (0.014 g, 0.06 mmol) were added dioxane (6 mL) and EtOH—H$_2$O (1:1, 3 mL). Argon gas was bubbled through the stirred reaction for 5 min. The reaction was stirred at 85° C. under argon for 20 h. The reaction was cooled to room temperature and concentrated. The residue was purified by silica gel column chromatography using 15% acetone in dichloromethane then reverse phase (C$_{18}$) prep TLC using 40% acetonitrile in water then by silica gel column chromatography using 5% methanol in dichloromethane to afford 0.013 g (8%) of P-245 as a viscous liquid. 1H NMR (CDCl$_3$, 400 MHz): 7.39-7.45 (m 1H), 7.2-7.34 (m, 4H), 7.17 (d, J=6.4 Hz, 1H), 6.93 (d, J=8.4 Hz, 1H), 4.43 (s, 2H), 3.8 (s, 3H), 3.28 (t, J=7.2 Hz, 2H), 2.43 (t, J=8.0 Hz, 2H), 1.95-2.05 (m, 2H) ppm; MS (APCI+): 328.1 (M+1), LC-MS: 93.2%.

Example 238

Preparation of P-248

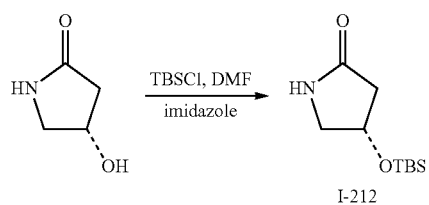 [SMILES: O=C1C[C@H](O)CN1 ; CC(C)(C)[Si](C)(C)O[C@@H]1CNC(=O)C1]

Synthesis of (S)-4-(tert-Butyl-dimethyl-silanyloxy)-pyrrolidin-2-one (I-212). Into a 100 mL round-bottomed flask with a stir bar was added (S)-4-hydroxy-pyrrolidin-2-one (3.04 g, 30.07 mmol), TBSCl (4.99 g, 33.07 mmol), imidazole (3.07 g, 45.10 mmol), and DMF (30 mL). After stirring at room temperature for 18 hours, the reaction was added to 100 mL of water and stirred for 30 minutes. The solids were filtered and washed with water. After drying the solids in a vacuum dessicator for 3 days, 5.97 g (92%) of I-212 was obtained.

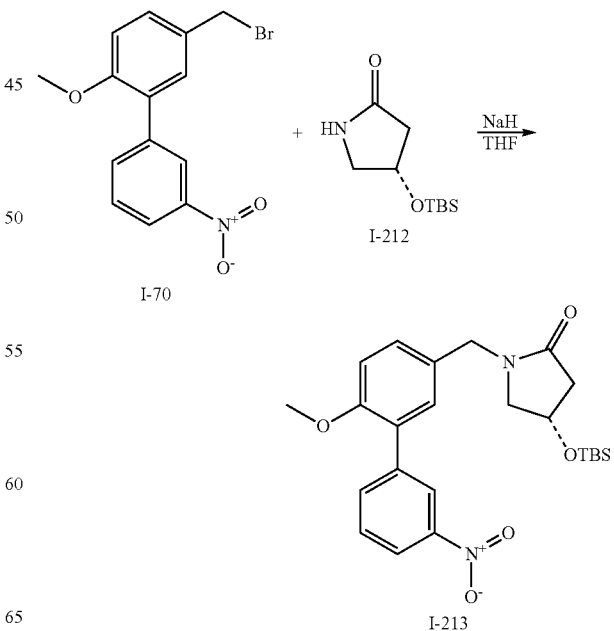

Synthesis of ((S)-4-(tert-Butyl-dimethyl-silanyloxy)-1-(6-methoxy-3'-nitro-biphenyl-3-ylmethyl)-pyrrolidin-2-one (I-213). Into a 250 mL round-bottomed flask with a stir bar was added I-212 (2.57 g, 11.95 mmol), THF (150 mL), and the solution was cooled to 0° C. NaH (0.56 g, 14.12 mmol) was added and the suspension was stirred at room temperature for 30 minutes. To this, I-70 (3.50 g, 10.86 mmol) was added and the reaction was stirred for 20 hours at room temperature after which time 50 mL of water was added and the product was extracted with ethyl acetate. The organics were concentrated to yield 8.9 g of I-213, which was used as is in the next reaction.

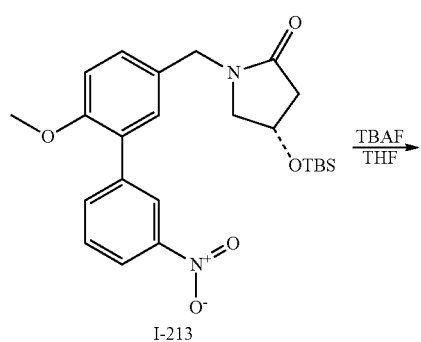

I-213

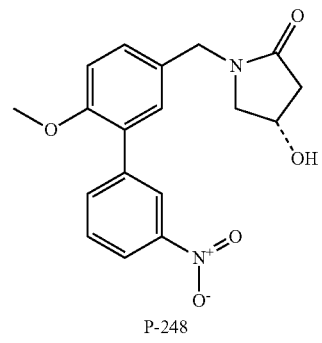

P-248

Synthesis of (S)-4-Hydroxy-1-(6-methoxy-3'-nitro-biphenyl-3-ylmethyl)-pyrrolidin-2-one (P-248). Compound I-213 (8.9 g, 19.5 mmol) from the step described above was added to a 100 mL round-bottomed flask, followed by 10 mL of THF and TBAF (29 mL, 29 mmol, 1.0M in THF). The solution was stirred at room temperature for 30 minutes after which time NH$_4$Cl and brine were added. The product was extracted with ethyl acetate, dried over Na$_2$SO$_4$, filtered and concentrated. Flash column chromatography purification eluting with 25-50% acetone/dichloromethane followed by flash column chromatography eluting with 5% methanol/dichloromethane gave 143 mg (4%, 2 steps) of P-248. $^1$H NMR (400 MHz, CDCl$_3$) 8.40 (d, J=1.6 Hz, 1H), 8.21-8.14 (m, 1H), 7.84 (d, J=7.8 Hz, 1H), 7.56 (t, J=8.0 Hz, 1H), 7.31-7.20 (m, 2H), 6.98 (d, J=8.5 Hz, 1H), 4.63-4.48 (m, 2H), 4.46-4.34 (m, 1H), 3.83 (s, 3H), 3.56 (dd, J=5.6, 10.8 Hz, 1H), 3.24 (dd, J=1.6, 10.9 Hz, 1H), 2.76 (dd, J=6.5, 17.4 Hz, 1H), 2.45 (dd, J=2.1, 17.3 Hz, 1H), 1.83 (d, J=4.0 Hz, 1H) ppm. LC/MS=97.4%, 343.1 (APCI+).

Example 239

Preparation of P-253

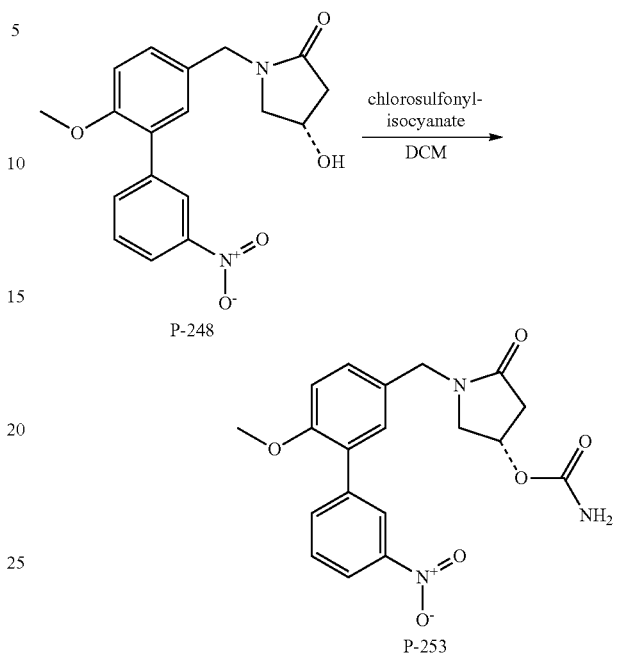

Synthesis of Carbamic acid (S)-1-(6-methoxy-3'-nitro-biphenyl-3-ylmethyl)-5-oxo-pyrrolidin-3-yl ester (P-253). Into a 20 mL vial with a stir bar was added chlorosulfonyl isocyanate (42 mg, 0.30 mmol), 1 mL dichloromethane, then P-248 (51.3 mg, 0.15 mmol) in 2 mL of dichloromethane. The reaction was stirred at room temperature for 18 hours after which 2 mL of water was added and the mixture was stirred at room temperature for 30 minutes. The layers were separated and the aqueous was extracted with dichloromethane. The combined organics were concentrated and then purified by preparative layer TLC using 50% acetone/dichloromethane to obtain P-253 (12.4 mg, 21%) as an off-white semi-solid. $^1$H NMR (400 MHz, DMSO-d$_6$) 8.30 (s, 1H), 8.20 (dd, J=2.1, 8.6 Hz, 1H), 7.94 (d, J=7.8 Hz, 1H), 7.72 (t, J=8.0 Hz, 1H), 7.33-7.26 (m, 2H), 7.16 (d, J=9.0 Hz, 1H), 6.59 (br. s., 2H), 5.04 (t, J=5.8 Hz, 1H), 4.49-4.30 (m, 2H), 3.80 (s, 3H), 3.46-3.38 (m, 1H), 3.21 (d, J=11.4 Hz, 1H), 2.78 (dd, J=6.9, 17.5 Hz, 1H), 2.23 (d, J=18.1 Hz, 1H) ppm. LC/MS=100.0%, 386.1 (APCI+).

Example 240

Preparation of P-506

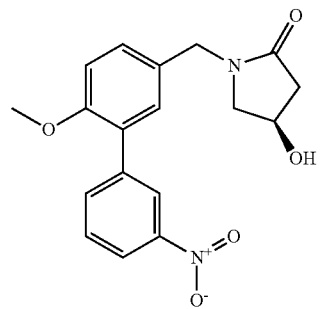

P-506

Synthesis of (R)-4-Hydroxy-1-(6-methoxy-3'-nitro-biphenyl-3-ylmethyl)-pyrrolidin-2-one (P-506). P-506 was prepared in a similar manner as that described above for P-248 except starting with (R)-4-Hydroxy-pyrrolidin-2-one. $^{1}$H NMR (400 MHz, CDCl$_3$) 8.40 (t, J=1.9 Hz, 1H), 8.17 (dd, J=1.7, 8.2 Hz, 1H), 7.84 (d, J=7.8 Hz, 1H), 7.55 (t, J=8.0 Hz, 1H), 7.30-7.27 (m, 1H), 7.22 (d, J=2.1 Hz, 1H), 6.97 (d, J=8.5 Hz, 1H), 4.61-4.48 (m, 2H), 4.41 (d, J=14.8 Hz, 1H), 3.85-3.81 (m, 3H), 3.56 (dd, J=5.6, 10.9 Hz, 1H), 3.24 (dd, J=1.8, 10.8 Hz, 1H), 2.75 (dd, J=6.5, 17.3 Hz, 1H), 2.44 (dd, J=2.1, 17.4 Hz, 1H), 2.12 (br s, 1H) ppm. LC/MS=95.6%, 343.1 (APCI+).

Example 241

Preparation of P-266

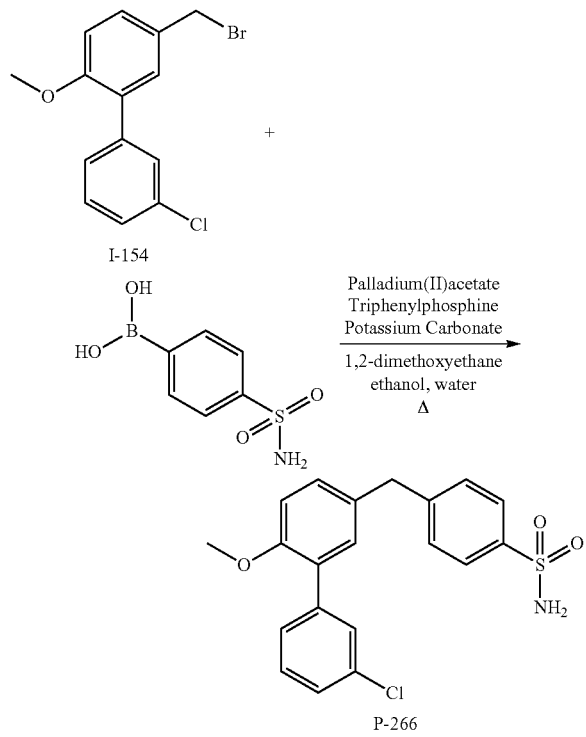

Synthesis of 4-(3'-Chloro-6-methoxy-biphenyl-3-ylmethyl)-benzenesulfonamide (P-266). P-266 was synthesized from I-154 (300 mg, 0.963 mmol) and 4-aminosulfonylphenylboronic acid pinocolate ester (409 mg, 1.44 mmol) using the same conditions as for the synthesis of P-240. The solvent was removed under vacuum and the residue suspended in ethyl acetate (20 mL) and water (20 mL). The layers were separated and the organic solution was washed with water (40 mL), saturated aqueous sodium bicarbonate (40 mL), water (2×40 mL), and brine (40 mL), dried over sodium sulfate, filtered, and the solvent removed under vacuum. The residue was purified by flash silica gel column chromatography (2.5% acetone in dichloromethane) to give a material which was then purified by preparatory silica gel TLC (eluting with 2.5% acetone in dichloromethane with 3 developments) to give P-266 (52.2 mg, 14% yield) as a clear gum. 1H NMR (400 MHz, CDCl$_3$) 7.86-7.83 (m, 2H), 7.49-7.48 (m, 1H), 7.38-7.29 (m, 5H), 7.14-7.09 (m, 2H), 6.92 (d, J=8.4 Hz, H), 4.71 (s, 2H), 4.03 (s, 2H), 3.80 (s, 3H) ppm. LCMS=100.0% purity. MS (APCI−)=386.0 (M−1), 217.0 (M−171).

Example 242

Preparation of I-216

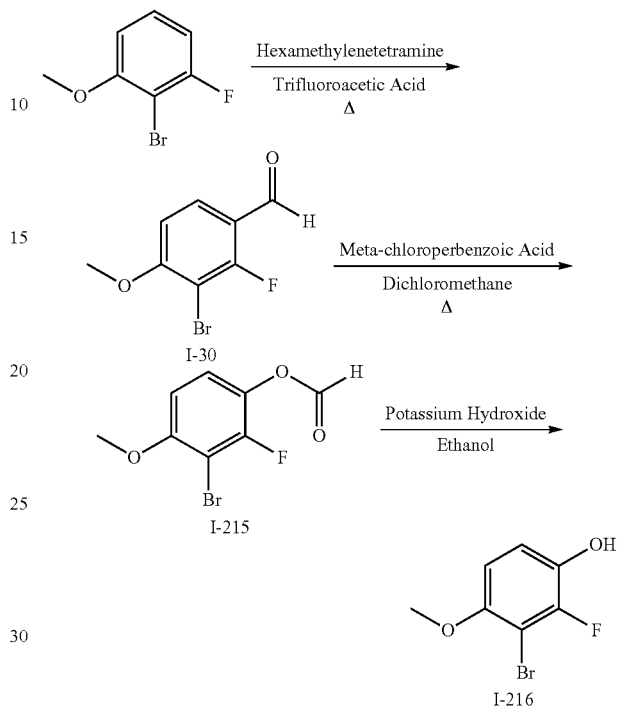

Synthesis of 3-Bromo-2-fluoro-4-methoxy-benzaldehyde (I-30). A solution of 2-bromo-3-fluoroanisol (5.00 g, 24.4 mmol) in trifluoroacetic acid (25 mL) was heated to 80° C. and then a solution of hexamethylenetetramine (6.83 g, 48.8 mmol) in trifluoroacetic acid (25 mL) was added dropwise over 1.5 h. Upon completion of the addition, the reaction was stirred at 80° C. for 1 h under nitrogen. The excess trifluoroacetic acid was removed under vacuum, and the pH was adjusted to 7.5-8.0 by addition of saturated aqueous potassium carbonate (~100 mL). The white solid that formed was filtered to give I-30 which was used without additional purification.

Synthesis of Formic acid 3-bromo-2-fluoro-4-methoxyphenyl ester (I-215). To a solution of I-30 (4.84 g) in dichloromethane (60 mL) was added meta-chloroperbenzoic acid (16.09 g) and the reaction was stirred at room temperature overnight. The reaction was diluted with dichloromethane (200 mL), washed with saturated aqueous sodium thiosulfate (300 mL), and extracted into dichloromethane (2×100 mL). The combined organic extracts were washed with saturated aqueous sodium bicarbonate (3×400 mL), water (2×400 mL), and brine (400 mL), dried over sodium sulfate, decanted, and the solvent removed under vacuum to give I-215 (12:5, 4.05 g) which was used as is without additional purification. $^{1}$H NMR (400 MHz, CDCl$_3$) d: 8.27 (t, J=0.8 Hz, 1H), 7.10-7.06 (m, 1H), 6.70 (dd, J=8.2 Hz, 1.0 Hz, 1H), 3.92 (s, 3H) ppm.

Synthesis of 3-Bromo-2-fluoro-4-methoxy-phenol (I-216). To a solution of I-215 (4.05 g) in ethyl alcohol (75 mL) was added solid potassium hydroxide pellets (1.71 g) and the brown solution was stirred at room temperature overnight. The reaction was acidified to pH 2 using concentrated hydrochloric acid and the ethanol was removed under vacuum. The material was diluted with water (300 mL) and extracted with dichloromethane (300 mL, 2×100 mL). The combined extracts were washed with brine (500 mL), dried over sodium sulfate, decanted, and the solvent removed under vacuum. The residue was then dissolved in diethyl ether (500 mL) and extracted with 1 M aqueous sodium hydroxide (300 mL, 2×250 mL). The combined aqueous layers were acidified to pH 2 with concentrated hydrochloric acid and extracted into diethyl ether (2×300 mL). The combined diethyl ether extracts were washed with water (500 mL) and brine (300 mL), dried over sodium sulfate, decanted, and the solvent removed under vacuum to give an orange solid. The solid was purified by flash silica gel column chromatography eluting with dichloromethane to give I-216 (1.45 g) as a yellow powder. 1H NMR (400 MHz, CDCl$_3$) 6.96-6.91 (m, 1H), 6.62 (dd, J=9.2 Hz, 2.0 Hz, 1H), 4.78 (d, J=3.6 Hz, 1H), 3.86 (s, 3H) ppm.

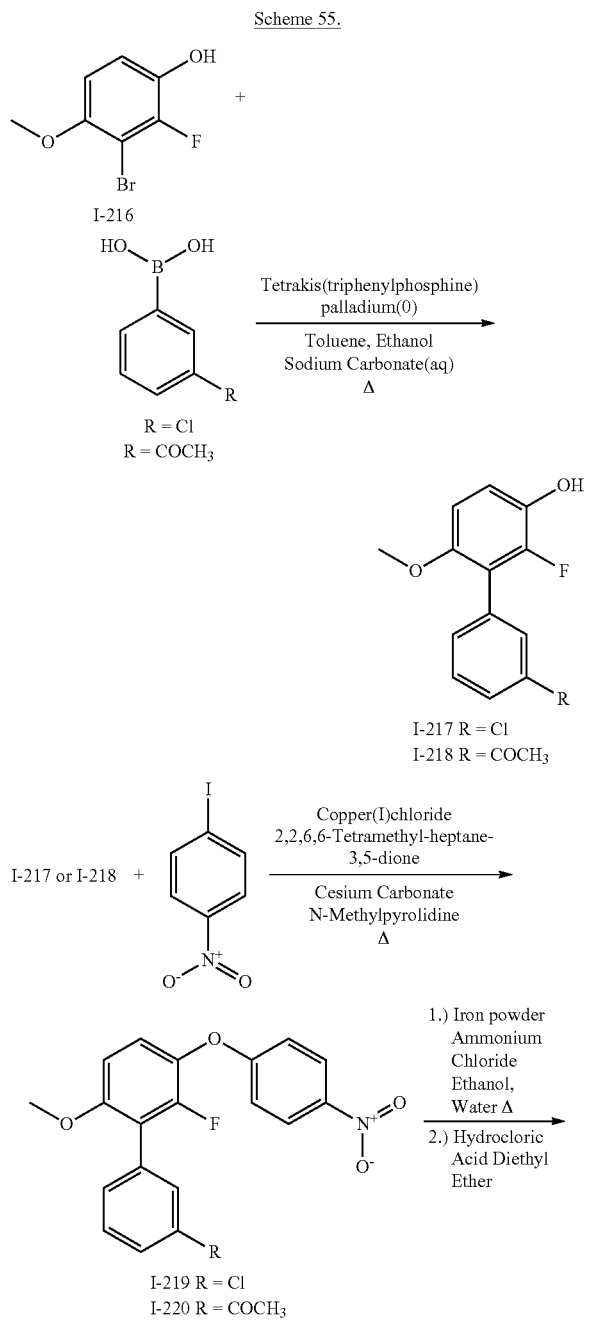

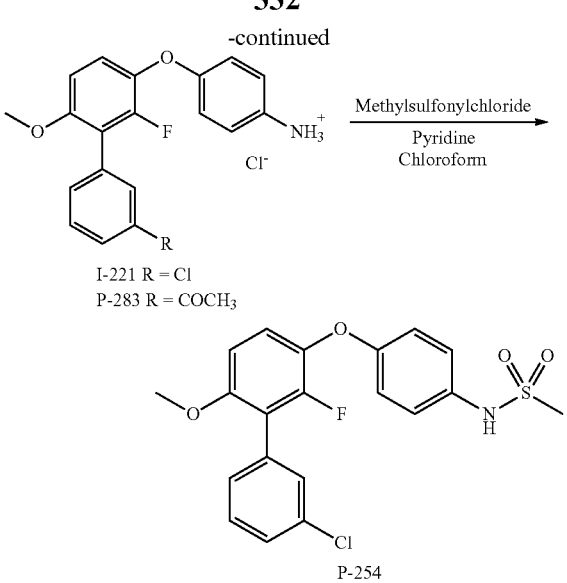

Example 243

Preparation of P-254

Synthesis of 3'-Chloro-2-fluoro-6-methoxy-biphenyl-3-ol (I-217). A solution of I-216 (390 mg, 1.76 mmol) in toluene (6 mL) was degassed with a nitrogen stream for 10 min. To this solution was added ethanol (1 mL), 3-chlorophenylboronic acid (331 mg, 2.12 mmol), 2 M aqueous sodium carbonate (1.76 mL, 3.53 mmol), and the nitrogen stream was continued for 15 min. To this suspension was added tetrakis(triphenylphosphine) palladium(0) (102 mg, 0.0882 mmol) under nitrogen and the reaction was heated to 90° C. overnight. Additional tetrakis(triphenylphosphine)palladium(0) (102 mg, 0.0882 mmol) was added under nitrogen and the reaction reacted at 90° C. for 24 h, and a third portion of tetrakis(triphenylphosphine)palladium(0) (102 mg, 0.0882 mmol) was added and the reaction heated to 90° C. for 24 hours. Approximately one half of the solvent was removed under vacuum and the residual material was diluted with ethyl acetate (100 mL) and saturated aqueous ammonium chloride (100 mL). The layers were filtered, separated, and the organic solution was washed with saturated aqueous sodium bicarbonate (2×100 mL), water (100 mL), and brine (50 mL). The solvent was dried over sodium sulfate, filtered, and the solvent removed under reduced pressure. The product was purified by flash silica gel column chromatography (eluting with 2.5% acetone in dichloromethane) to give I-217 (398 mg, 89% yield). 1H NMR (400 MHz, CDCl$_3$) 7.41 (s, 1H), 7.39-7.28 (m, 3H), 6.97 (t, J=9.4 Hz, 1H), 6.67 (dd, J=9.2 Hz, 2.0 Hz, 1H), 4.79 (s, 1H), 3.72 (s, 3H) ppm.

Synthesis of 3'-Chloro-2-fluoro-6-methoxy-3-(4-nitrophenoxy)-biphenyl (I-219). A suspension of I-217 (200 mg, 0.792 mmol), 4-iodonitrobenzene (179 mg, 0.720 mmol), cesium carbonate (469 mg, 1.44 mmol), and 2,2,6,6-tetramethylheptane-3,5-dione (37 uL, 0.180 mmol) in N-methylpyrrolidone (4 mL) was stirred under nitrogen. To this reaction was added copper(I) chloride (35.6 mg, 0.360 mmol) and the reaction was heated to 100° C. under nitrogen overnight. The reaction was diluted with ethyl acetate (20 mL) and washed with water (20 mL). The aqueous wash was extracted with ethyl acetate (20 mL) and the organic extracts were combined. The organic extracts were washed with water (2×20 mL), 1 N aqueous sodium hydroxide (2×20 mL), 1 N aqueous hydrochloric acid (2×20 mL), brine (20 mL), dried over sodium sulfate, filtered, and the solvent removed under vacuum to give crude I-219 (181.0 mg, 61% yield) which was used as is in the next reaction.

Synthesis of 4-(3'-Chloro-2-fluoro-6-methoxy-biphenyl-3-yloxy)-phenyl-amine hydrochloride salt (I-221). To a suspension of I-219 (180 mg, 0.645 mmol) and iron powder (126 mg, 2.26 mmol) in ethanol (2.6 mL) and water (0.8 mL) was added solid ammonium chloride (193 mg, 3.60 mmol). The reaction was purged with nitrogen, and heated to 85° C. with stirring for 3 h. The solvent was removed under vacuum and the material was diluted in ethyl acetate (50 mL) and water (50 mL). The layers were separated and the aqueous layer was extracted with ethyl acetate (50 mL). The combined organic extracts were washed with water (2×50 mL) and brine (50 mL), dried over sodium sulfate, filtered, and the solvent removed under reduced pressure. The product was purified by flash silica gel column chromatography (5% acetone in dichloromethane) to give the free base of I-221 (136 mg). The free base was dissolved in diethyl ether (2.5 mL) and 2 N hydrogen chloride in diethyl ether (0.8 mL) was added drop wise. The salt began to precipitate out after 15 min and the suspension was allowed to stir for an additional 1.5 h. The solid was filtered and washed with diethyl ether (3 mL) and hexanes (4×5 mL) to give I-221 (104 mg, 47% yield) as a beige powder. 1H NMR (400 MHz, DMSO-$d_6$) 9.6 (br s, 2H), 7.51-7.45 (m, 3H), 7.36-7.25 (m, 4H), 7.08-7.01 (m, 3H), 3.77 (s, 3H) ppm. MS (ESI+)=345.5 (M+1).

Synthesis of N-[4-(3'-Chloro-2-fluoro-6-methoxy-biphenyl-3-yloxy)-phenyl]-methanesulfonamide (P-254). A suspension of I-221 (50.0 mg, 0.138 mmol) and pyridine (21.8 mg, 0.276 mmol) in chloroform (1 mL) was stirred for 10 min. To the suspension was added methanesulfonylchloride (15.8 mg, 0.138 mmol) and the reaction was stirred at room temperature overnight. The solvent was removed under vacuum and the residue was purified by preparatory silica gel TLC (5% acetone in dichloromethane, 2 developments, 0.5% acetone in dichloromethane, 5 developments, and 5% acetone in dichloromethane) to give P-254 (26.1 mg, 47% yield) as a orange gum. 1H NMR (400 MHz, CDCl$_3$) 7.42-7.42 (m, 1H), 7.35-7.29 (m, 3H), 7.25-7.18 (m, 2H), 7.18 (t, J=2.8 Hz, 1H), 7.00-6.95 (m, 2H), 6.75 (dd, J=7.4 Hz, 0.2 Hz, 1H), 6.20 (s, 1H), 3.80 (s, 3H), 2.98 (s 3H) ppm. MS (ESI+)=421.6 (M), 343.0 (M−79.0).

Example 244

Preparation of P-283

Synthesis of 1-(2'-Fluoro-3'-hydroxy-6'-methoxy-biphenyl-3-yl)-ethanone (I-218). A solution of I-216 (500 mg, 2.26 mmol) and 3-acetylphenylboronic acid (446 mg, 2.72 mmol) in toluene (8 mL) was degassed with a nitrogen stream. To this solution was added ethanol (1.5 mL) and 2 M aqueous sodium carbonate (2.25 mL, 4.52 mmol), followed by the addition of tetrakis(triphenylphosphine)palladium(0) (130 mg, 0.113 mmol). The reaction was heated to 100° C. for 24 h. An additional portion of tetrakis(triphenylphosphine)palladium (0) (130 mg, 0.113 mmol) was added under nitrogen and the reaction was heated to 100° C. overnight. An additional portion of 3-acetylphenyl boronic acid (223 mg, 1.36 mmol) was added and the reaction heated to 100° C. an additional 24 hours. The reaction was diluted with ethyl acetate (50 mL) and water (50 mL), filtered, and the layers separated. The aqueous layer was extracted with ethyl acetate (50 mL) and the organic extracts combined. The organic solution was washed with water (2×100 mL), saturated aqueous sodium bicarbonate (100 mL), brine (50 mL), dried over sodium sulfate, filtered and the solvent removed under vacuum. The product was purified by flash silica gel column chromatography (0-5% acetone in dichloromethane) to give I-218 (280 mg, 48% yield) as a brown solid.

1H NMR (400 MHz, CDCl$_3$) 8.01 (m, 1H), 7.97 (dt, J=7.9 Hz, 1.5 Hz, 1H), 7.62 (dd, J=7.6 Hz, 1.2 Hz, 1H), 7.54 (t, J=7.0 Hz, 1H), 6.99 (t, J=9.2 Hz, 1H), 6.69 (dd, J=9.2 Hz, 2.0 Hz, 1H), 4.81 (d, J=4.4 Hz, 1H), 3.73 (s, 3H), 2.63 (s, 3H) ppm.

Synthesis of 1-[2'-Fluoro-6'-methoxy-3'-(4-nitro-phenoxy)-biphenyl-3-yl]-ethanone (I-220). A solution of I-218 (275 mg, 1.06 mmol) and 4-iodonitrobenzene (264 mg, 1.06 mmol) in N-methylpyrrolidone (5.5 mL) was degassed with a nitrogen stream for 1 min. To the solution was added cesium carbonate (689 mg, 2.11 mmol), copper(I) chloride (52.3 mg, 0.528 mmol), 2,2,6,6-tetramethylheptane-3,5-dione (48.6 mg, 0.264 mmol), and the reaction was heated to 90° C. for 18 h. The reaction was cooled to room temperature and the solvent was removed under vacuum. The residue was taken up in ethyl acetate (20 mL), washed with water (20 mL), the aqueous wash extracted with ethyl acetate (20 mL), and the organic extracts combined. The organic extracts were washed with water (2×40 mL), 1 N aqueous sodium hydroxide (40 mL), 1 N aqueous hydrochloric acid (2×40 mL), and brine (50 mL). The solvent was dried over sodium sulfate, filtered, and removed under vacuum to give a brown solid. The residue was purified by flash silica gel column chromatography (1-5% acetone in dichloromethane) followed by flash silica gel column chromatography (30% ethyl acetate in hexanes) to give I-220 (78.4 mg, 19% yield). 1H NMR (400 MHz, CDCl$_3$) 8.23-8.20 (m, 2H), 8.02 (m, 1H), 7.98-7.96 (m, 1H), 7.62-7.60 (m, 1H), 7.55 (t, J=7.8 Hz, 1H), 7.20 (t, J=9.0 Hz, 1H), 7.05-7.02 (m, 2H), 6.84 (dd, J=9.2 Hz, 1.6 Hz, 1H), 3.83 (s, 3H), 2.63 (s, 3H) ppm.

Synthesis of 4-(3'-Acetyl-2-fluoro-6-methoxy-biphenyl-3-yloxy)-phenyl-amine hydrochloride salt (P-283). A suspension of I-220 (75.0 mg, 0.197 mmol), ammonium chloride (53.5 mg, 1.00 mmol), and iron powder (38.5 mg, 0.690 mmol) in ethanol (0.8 mL) and water (0.25 mL) was purged with nitrogen and stirred under nitrogen for 4 h at 85° C. The solvent was removed under vacuum and the residual material was suspended in ethyl acetate (50 mL). The organic suspension was washed with water (50 mL), the aqueous layer was extracted with ethyl acetate (50 mL), and the organic solutions combined. The combined extracts were washed with water (2×50 mL) and brine (50 mL), dried over sodium sulfate, filtered, and the solvent removed under vacuum. The residue was dissolved in diethyl ether (2 mL), and 2 N hydrogen chloride in diethyl ether (400 uL) was added. The reaction was stirred for 1 h and filtered to give P-283 (57.0 mg, 75% yield) as a white powder.

1H NMR (400 MHz, DMSO-$d_6$) d: 7.98 (dt, J=7.3 Hz, 1.5 Hz, 1H), 7.93 (s, 1H), 7.66-7.59 (m, 2H), 7.34-7.29 (m, 3H), 7.09-7.03 (m, 3H), 3.77 (s, 3H), 2.60 (s, 3H) ppm. MS (ESI+) =352.9 (M+1)

Scheme 56.

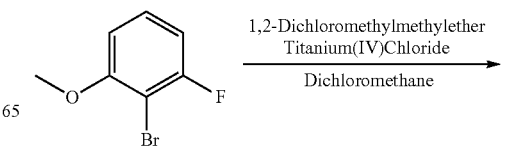

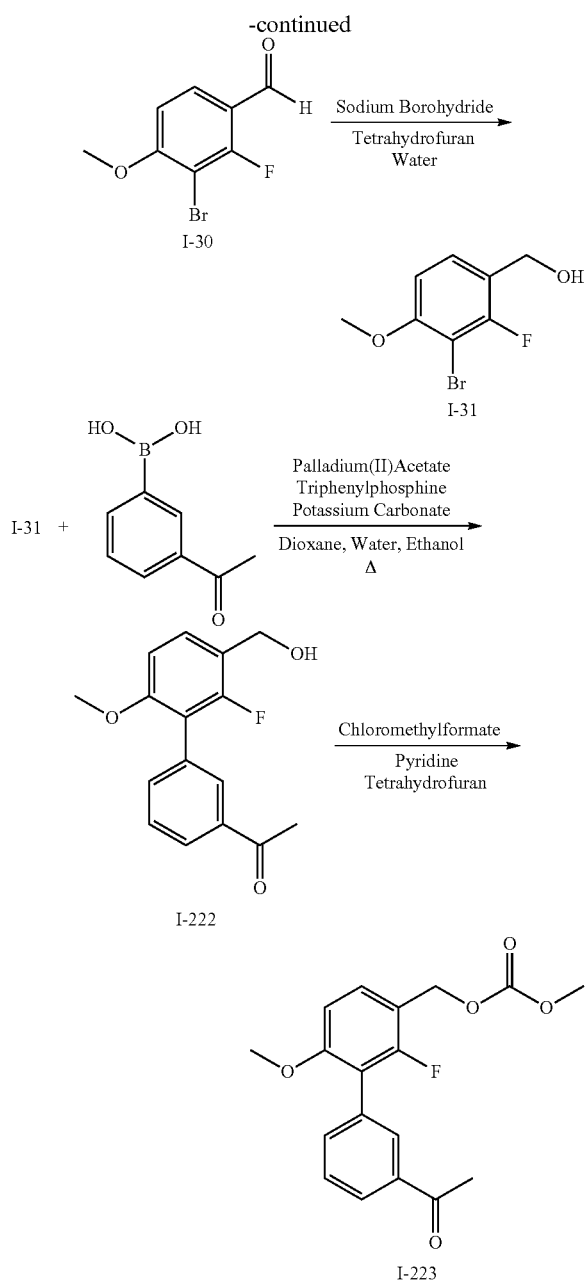

Example 245

Preparation of I-223

Synthesis of 3-Bromo-2-fluoro-4-methoxy-benzaldehyde using titanium(IV)chloride (I-30). A solution of 2-bromo-3-fluoroanisol (5.00 g, 24.3 mmol) in dichloromethane (120 mL) was cooled to 0° C. in a salt-ice bath and purged with nitrogen. The reaction was allowed to stir 15 min under nitrogen. To the reaction was added titanium(IV) chloride (23.1 g, 122 mmol), followed by α,α-dichloromethyl-methyl ether (4.21 g, 36.6 mmol) at 0° C. under nitrogen. The reaction was allowed to warm to room temperature and stirred for 22 h. The red solution was poured into ice water (600 mL), and extracted into dichloromethane (3×200 mL). The organic extracts were combined, washed with saturated aqueous sodium bicarbonate (2×400 mL), water (2×400 mL), and brine (400 mL), dried over sodium sulfate, filtered, and the solvent was removed under vacuum. The product was dried in a vacuum oven at 80° C. overnight to give I-30 (5.75 g, quantitative yield). 1H NMR (400 MHz, CDCl$_3$) 10.22 (s, 1H), 7.86 (dd, J=8.8 Hz, 7.6 Hz, 1H), 6.82 (d, J=8.4 Hz, 1H), 4.01 (s, 3H) ppm.

Synthesis of (3-Bromo-2-fluoro-4-methoxy-phenyl)-methanol (I-31). A suspension of I-30 (5.20 g, 22.3 mmol) in tetrahydrofuran (40 mL) and water (40 mL) was cooled to 0° C. and sodium borohydride (2.53 g, 66.9 mmol) was added portionwise. The reaction was stirred for 3.5 h allowing the reaction to warm to room temperature. The tetrahydrofuran was removed under vacuum, water was added (100 mL) and the resultant solid was extracted into ethyl acetate (2×200 mL). The combined extracts were washed with water (2×200 mL), brine (200 mL), dried over sodium sulfate, filtered, and the solvent removed under vacuum to give I-31 (4.82 g, 92% yield) as a white powder. 1H NMR (400 MHz, CDCl$_3$) 7.32 (t, J=8.4 Hz, 1H), 6.71 (dd, J=8.4 Hz, 1.6 Hz, 1H), 4.72 (d, J=6.0 Hz, 2H), 3.92 (s, 3H), 1.70 (t, J=6.0 Hz, 1H) ppm.

Synthesis of 1-(2'-Fluoro-3'-hydroxymethyl-6'-methoxy-biphenyl-3-yl)-ethanone (I-222). A solution of I-31 (4.00 g, 17.0 mmol), 3-acetylphenylboronic acid (3.07 g, 18.7 mmol) in ethanol (17.5 mL), water (17.5 mL) and 1,4-dioxane (35 mL) was degassed with a nitrogen stream for 30 min. To the solution was added potassium carbonate (7.06 g, 51.1 mmol), triphenylphosphine (1.34 g, 5.11 mmol), and palladium(II) acetate (382 mg, 1.70 mmol), and the reaction was stirred under nitrogen for 10 min. The reaction was heated to 85° C. for 4 h under nitrogen, and additional palladium(II) acetate (191 mg, 0.851 mmol) and triphenylphosphine (700 mg, 2.55 mmol) were added. Heating with stirring was continued for 4 h, the reaction was cooled to room temperature, and ethyl acetate (300 mL) was added. The reaction was washed with water (300 mL), sodium chloride was added (~1 g) and the aqueous wash was extracted with ethyl acetate (300 mL). The organic extracts were combined, washed with water (500 mL) and brine (500 mL), dried over sodium sulfate, decolorized with activated charcoal, filtered, and the solvent was removed under reduced pressure. The crude product was purified by flash silica gel column chromatography (50% ethyl acetate in hexanes) to give pure I-222 (700 mg, 15% yield). 1H NMR (400 MHz, CDCl$_3$) 8.00-8.00 (m, 1H), 7.97 (dt, J=7.9 Hz, 1.6 Hz, 1H), 7.61 (dd, J=6.2 Hz, 1.4 Hz, 1H), 7.53 (t, J=7.6 Hz, 1H), 7.38 (t, J=8.6 Hz, 1H), 6.80 (dd, J=8.8 Hz, 1.2 Hz, 1H), 4.74 (d, J=6.0 Hz, 2H), 3.79 (s, 3H), 2.63 (s, 3H), 1.74 (t, J=6.0 Hz, 1H) ppm. H)

Synthesis of Carbonic acid 3'-acetyl-2-fluoro-6-methoxy-biphenyl-3-ylmethyl ester methyl ester (I-223). A solution of I-222 (700 mg, 2.55 mmol) and pyridine (429 uL, 6.64 mmol) in tetrahydrofuran (10 mL) was cooled to 0° C. in an ice water bath. To the solution was added methylchloroformate (542 uL, 5.61 mmol) under nitrogen. The white suspension that formed was stirred at room temperature overnight. The pH was adjusted to 1 by the addition of concentrated aqueous hydrochloric acid, and the solution was extracted with dichloromethane (2×30 mL). The combined organic extracts were washed with brine (30 mL), dried over magnesium sulfate, filtered, and the solvent was removed under vacuum to give I-223 (661.3 mg, 78% yield) as an orange syrup. $^1$H NMR. (400 MHz, CDCl$_3$) 7.98-7.95 (m, 2H), 7.61-7.58 (m, 1H), 7.53 (t, J=7.6 Hz, 1H), 7.41 (t, J=8.4 Hz, 1H), 6.79 (dd, J=8.6 Hz, 1.0 Hz, 1H), 5.22 (s, 2H), 3.81 (s, 3H), 3.79 (s, 3H) ppm.

Example 246

Preparation of P-304

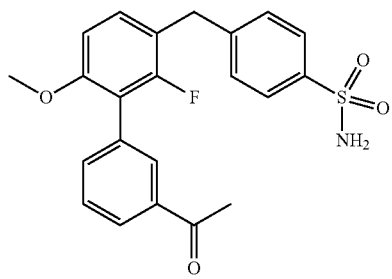

P-304

Synthesis of 4-(3'-Acetyl-2-fluoro-6-methoxy-biphenyl-3-ylmethyl)-benzenesulfinic acid amide (P-304). A suspension of I-223 (300 mg, 0.928 mmol), 4-amino sulfonylbenzylboronic pinocolate ester (289 mg, 1.02 mmol), and potassium carbonate (385 mg, 2.78 mmol) in dimethylformamide (2 mL) was purged with nitrogen and allylpalladium chloride dimer (50.9 mg, 0.139 mmol) and bis(diphenylphosphino)pentane (123 mg, 0.278 mmol) were added. The reaction was heated to 65° C. overnight. To this reaction was added ethyl acetate (25 mL) and water (25 mL) and the layers separated. The aqueous layer was extracted with ethyl acetate (2×25 mL), and the organic extracts were combined and washed with brine (50 mL). The organic solution was dried over magnesium sulfate, filtered, and the solvent removed under vacuum. The product was purified by flash silica gel column chromatography (5% acetone in dichloromethane) followed by trituration with diethyl ether (25 mL) to give P-304 (117 mg, 30% yield) as a faint yellow powder. $^1$H NMR (400 MHz, CDCl$_3$) 7.99-7.98 (m, 1H), 7.95 (dt, J=7.6 Hz, 1.4 Hz, 1H), 7.86-7.84 (m, 2H), 7.60-7.58 (m, 2H), 7.52 (t, J=7.6 Hz, 1H), 7.38 (d, J=8.4 Hz, 2H), 7.13 (t, J=8.6 Hz, 1H), 6.75 (d, J=8.8 Hz, 1H), 4.74 (s, 2H), 4.04 (s, 2H), 3.77 (s, 3H), 2.62 (s, 3H) ppm. LCMS=100.0% purity. MS (APCI+)=414.0 (M+1).

Example 247

Preparation of P-305

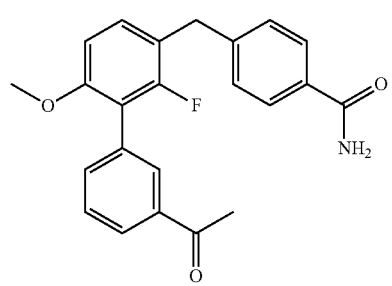

P-305

Synthesis of 4-(3'-Acetyl-2-fluoro-6-methoxy-biphenyl-3-ylmethyl)-benzamide (P-305). A suspension of I-223 (300 mg, 0.928 mmol), 4-aminocarbonylbenzylboronic acid (190 mg, 1.02 mmol), and potassium carbonate (385 mg, 2.78 mmol) in dimethylformamide (2 mL) was purged with nitrogen and allylpalladium chloride dimer (50.9 mg, 0.139 mmol) and bis(diphenylphosphino)pentane (123 mg, 0.278 mmol) were added. The reaction was heated to 65° C. overnight. To this reaction was added ethyl acetate (25 mL) and water (25 mL) and the layers separated. The aqueous layer was extracted with ethyl acetate (2×25 mL), and the organic extracts combined and washed with brine (50 mL). The organic solution was dried over magnesium sulfate, filtered, and the solvent removed under vacuum to give crude product. The product was purified by flash silica gel column chromatography (5-10% acetone in dichloromethane) followed by trituration with diethyl ether (25 mL) to give P-305 (160 mg, 46% yield) as a white powder. $^1$H NMR (400 MHz, CDCl$_3$) 7.99 (m, 1H), 7.95 (dt, J=7.7 Hz, 1.3 Hz, 1H), 7.75-7.73 (m, 2H), 7.61-7.58 (m, 1H), 7.52 (t, J=7.6 Hz, 1H), 7.32 (d, J=8.4 Hz, 2H), 7.11 (t, J=8.6 Hz, 1H), 6.73 (d, J=8.8 Hz, 1H), 5.97 (br s, 1H), 5.54 (br s, 1H), 4.03 (s, 2H), 3.76 (s, 3H), 2.62 (s, 3H) ppm. LCMS=96.5% purity. MS (APCI+)=378.1 (M+1).

Example 248

Preparation of P-276

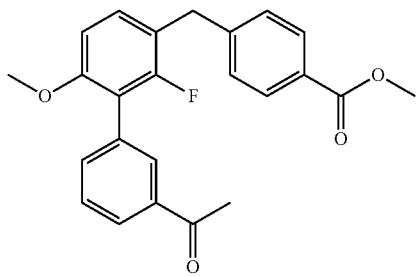

P-276

Synthesis of 4-(3'-Acetyl-2-fluoro-6-methoxy-biphenyl-3-ylmethyl)-benzoic acid methyl ester (P-276). A suspension of I-223 (300 mg, 0.928 mmol), 4-methoxycarbonyl-benzylboronic acid (184 mg, 1.02 mmol), and potassium carbonate (385 mg, 2.78 mmol) in dimethylformamide (2 mL) was purged with nitrogen and allylpalladium chloride dimer (50.9 mg, 0.139 mmol) and bis(diphenylphosphino)pentane (123 mg, 0.278 mmol) were added. The reaction was heated to 65° C. overnight. To this reaction was added ethyl acetate (5 mL) and water (5 mL), the layers were filtered through celite, the celite washed with ethyl acetate (15 mL) and water (15 mL), and the layers separated. The aqueous layer was extracted with ethyl acetate (2×50 mL), and the organic extracts combined and washed with brine (100 mL). The organic solution was dried over magnesium sulfate, filtered, and the solvent removed under vacuum to give crude product. The product was purified by flash silica gel column chromatography (25% ethyl acetate in hexanes), followed by a preparatory silica gel TLC plate (eluting with 25% ethyl acetate in hexanes), and trituration with diethyl ether (5 mL) to give P-276 (72.4 mg, 20% yield) as a white powder. $^1$H NMR (400 MHz, CDCl$_3$) 7.99-7.94 (m, 4H), 7.59-7.58 (m, 1H), 7.52 (t, J=7.8 Hz, 1H), 7.30 (d, J=8.80\ Hz, 2H), 7.11 (t, J=8.6 Hz, 1H), 6.74-6.72 (m, 1H), 4.03 (s, 2H), 3.90 (s, 3H), 3.76 (s, 3H), 2.62 (s, 3H) ppm. LCMS=96.6% purity. MS (APCI+)=394.1 (M+2).

Example 249

Preparation of I-226

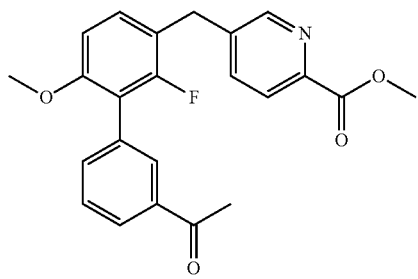

I-226

Synthesis of 5-(3'-Acetyl-2-fluoro-6-methoxy-biphenyl-3-ylmethyl)-pyridine-2-carboxylic acid methyl ester (I-226). A suspension of I-223 (500 mg, 1.50 mmol), 2-methylcarboxypyridine-5-boronic acid pinocol ester (435 mg, 1.65 mmol), and potassium carbonate (624 mg, 4.51 mmol) in dimethylformamide (3.5 mL) was degassed under a nitrogen stream for 15 min. To this solution was added bis(diphenylphosphino)pentate (199 mg, 0.451 mmol) and allylpalladium chloride dimer (82.7 mg, 0.226 mmol). The reaction was heated to 65° C. for 50 h. The reaction was diluted with ethyl acetate (50 mL) and filtered through celite. To the filtrate was added water (50 mL), and the layers were separated. The aqueous wash was extracted with ethyl acetate (2×50 mL), and all three organic extracts were combined and washed with brine (100 mL). The organic solution was dried over magnesium sulfate, filtered, and the solvent removed under vacuum. The residue was purified by flash silica gel column chromatography (5% acetone in dichloromethane) followed by trituration with diethyl ether (15 mL), filtered, and washed with diethyl ether (5 mL) to give I-226 (190.6 mg, 32% yield) as a white powder. $^1$H NMR (400 MHz, CDCl$_3$) 8.66 (d, J=2.0 Hz, 1H), 8.06 (d, J=8.0 Hz, 1H), 7.97-7.94 (m, 2H), 7.67 (dd, J=8.2 Hz, 2.2 Hz, 1H), 7.57 (dd, J=7.6 Hz, 1.6 Hz, H), 7.52 (t, J=7.6 Hz, 1H), 7.13 (t, J=8.6 Hz, 1H), 6.75 (d, J=8.8 Hz, 1H), 4.05 (s, 2H), 4.00 (s, 3H), 3.77 (s, 3H), 2.62 (s, 3H) ppm. LCMS=100.0% purity. MS (APCI+)=394.1 (M+1).

Example 250

Preparation of I-224

I-224

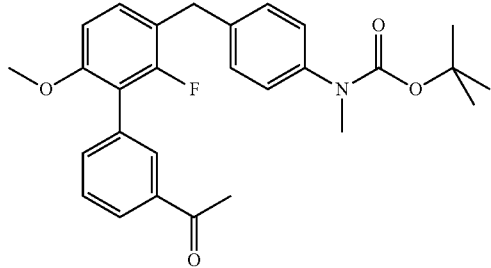

Synthesis of [4-(3'-Acetyl-2-fluoro-6-methoxy-biphenyl-3-ylmethyl)-phenyl]-methyl-carbamic acid tert-butyl ester (I-224). To a suspension of I-223 (500 mg, 1.50 mmol) and 4-(tert-butoxycarbonyl-N-methylamino)phenyl boronic acid (415 mg, 1.65 mmol), and potassium carbonate (624 mg, 4.51 mmol) in dimethylformamide (3.5 mL) was added bis(diphenylphosphino)pentate (199 mg, 0.451 mmol) and allylpalladium chloride dimer (82.7 mg, 0.226 mmol) under nitrogen. The reaction was heated to 85° C. for 29 h. The reaction was diluted with ethyl acetate (30 mL) and water (30 mL) and filtered through a Celite plug. The Celite was washed with ethyl acetate (2×20 mL) and water (20 mL), and the layers separated. The aqueous wash was extracted with ethyl acetate (2×50 mL), and all three organic extracts were combined and washed with water (2×100 mL) and brine (100 mL). The organic solution was dried over sodium sulfate, filtered, and the solvent removed under vacuum. The residue was purified by flash silica gel column chromatography (dichloromethane) to give I-224 (624.3 mg, 90% yield) as a yellow oil which was used as is without further purification. $^1$H NMR (400 MHz, CDCl$_3$) 8.00 (d, J=1.0 Hz, 1H), 7.95 (dt, J=7.7 Hz, 1.3 Hz, 1H), 7.60 (dd, J=7.6 Hz, 1.2 Hz, 1H), 7.52 (t, J=7.6 Hz, 1H), 7.19-7.09 (m, 5H), 6.72 (d, J=8.4 Hz, 1H), 3.95 (s, 2H), 3.75 (s, 3H), 2.62 (s, 3H), 1.45 (s, 9H) ppm. LCMS=94.1% purity. MS (APCI+)=364.1 (M−100).

Example 251

Preparation of P-328

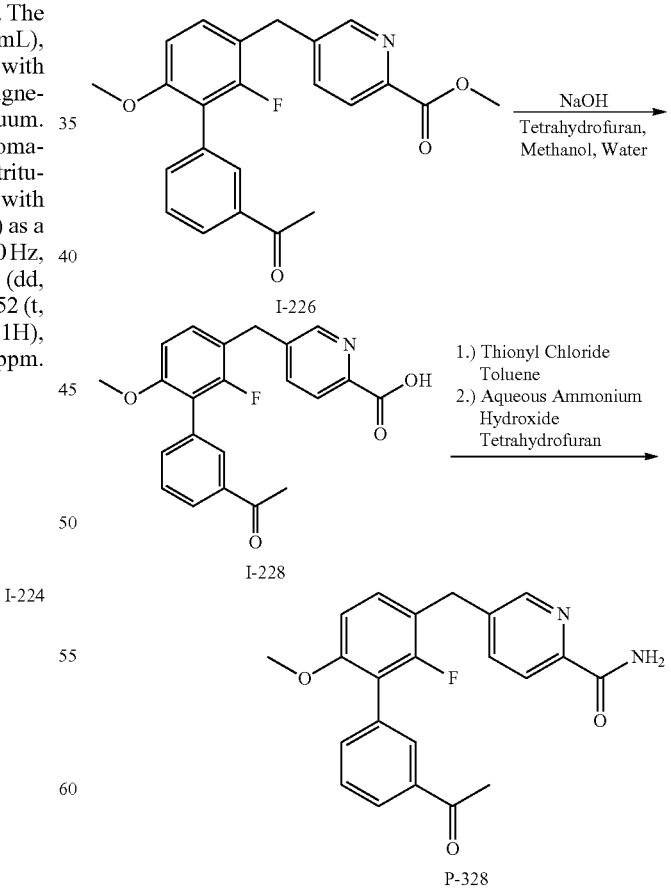

Synthesis of 5-(3'-Acetyl-2-fluoro-6-methoxy-biphenyl-3-ylmethyl)-pyridine-2-carboxylic acid (I-228). A solution of I-226 (150 mg, 0.381 mmol) in tetrahydrofuran (1 mL), methanol (1 mL), water (1 mL) and 1 N aqueous sodium hydroxide (0.763 mL) was stirred at room temperature for 18 h. Approximately one half of the solvent was removed under vacuum. The remaining solution was adjusted to pH 3 by addition of glacial acetic acid. The suspension was extracted with dichloromethane (10 mL), water (5 mL) was added to the wash, and the aqueous wash was extracted with additional dichloromethane (2×10 mL). All three organic extracts were combined, dried over magnesium sulfate, filtered, and the solvent was removed under vacuum, and the residue was dried under high vacuum for 24 h. The resultant beige syrup crystallized in diethyl ether (5 mL), stirred for 30 min, filtered, and washed with hexanes (2×2 mL) to give I-226 (90.6 mg, 63% yield) as a white powder. $^1$H NMR (400 MHz, DMSO-d$_6$) 8.62 (d, J=2.0 Hz, 1H), 7.99-7.94 (m, 2H), 7.87 (s, 1H), 7.78 (dd, J=7.8 Hz, 2.2 Hz, 1H), 7.58 (d, J=5.2 Hz, 2H), 7.39 (t, J=8.8 Hz, 1H), 6.98 (d, J=8.4 Hz, 1H), 4.08 (s, 2H), 3.73 (s, 3H), 2.588 (s, 3H) ppm. LCMS=100.0% purity (APCI+). MS (APCI+)=424.1 (M+45), 380.0 (M+1).

Synthesis of 5-(3'-Acetyl-2-fluoro-6-methoxy-biphenyl-3-ylmethyl)-pyridine-2-carboxylic acid amide (P-328). A solution of I-228 (50.0 mg, 0.184 mmol) in toluene (2 mL) was stirred under nitrogen. To this reaction was added thionyl chloride (65.7 mg, 0.552 mmol) and the reaction was heated to 100° C. for 2 h over which time it turned from colorless to a deep red. The solvent and excess thionyl chloride was removed under reduced pressure and the residue was dissolved in tetrahydrofuran (2 mL). To the solution was then added aqueous ammonium hydroxide (40 uL). The reaction was stirred at room temperature for 1 h. The reaction was diluted with ethyl acetate (30 mL) and washed with saturated aqueous sodium bicarbonate (30 mL). The aqueous wash was extracted with ethyl acetate (30 mL) and the organic extracts were combined. The combined extracts were washed with saturated aqueous sodium bicarbonate (25 mL), dried over sodium sulfate, filtered, and the solvent removed under vacuum. The residue was purified by preparatory silica gel TLC (eluting with 12.5% acetone in dichlormethane, 3 developments) to give P-328 (12.6 mg, 18% yield) as a white powder. $^1$H NMR. (400 MHz, CDCl$_3$) 8.47 (d, J=2.0 Hz, 1H), 8.13 (d, J=8.0 Hz, 1H), 7.98-7.94 (m, 2H), 7.78 (s, 1H), 7.69 (dd, J=8.0 Hz, 2.0 Hz, 1H), 7.96-7.58 (m, 1H), 7.52 (t, J=7.6 Hz, 1H), 7.14 (t, J=8.6 Hz, 1H), 6.76 (d, J=8.4 Hz, 1H), 5.48 (s, 1H), 4.05 (s, 3H), 3.77 (s, 3H), 2.62 (s, 3H) ppm. LCMS=95.9% purity.
MS (APCI+)=379.1 (M+1).

Example 252

Preparation of P-324

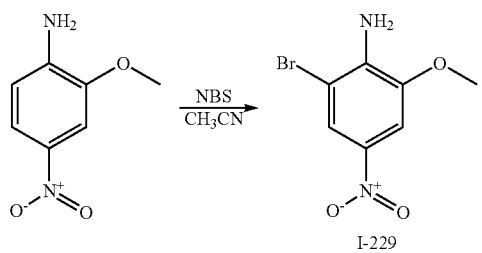

Synthesis of 2-Bromo-6-methoxy-4-nitro-phenylamine (I-229). Into a 2 L round bottom flask with a stir bar was added 2-methoxy-4-nitro-phenylamine (50.0 g, 297.4 mmol), CH$_3$CN (1 L), and NBS (53.5 g, 297.4 mmol). The reaction was stirred at room temperature for 2 hours while protected from light. The reaction was concentrated and then 500 mL water was added. The product was extracted with ethyl acetate and concentrated. The solid which precipitated from the aqueous washes was combined with the solid which resulted from the organic concentration to give I-229 (59.6 g) which was used without further purification.

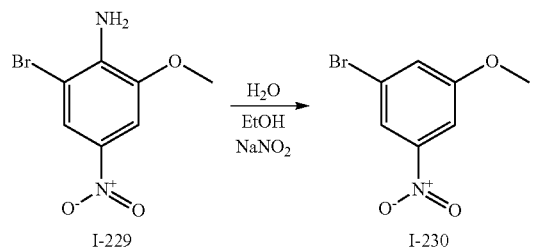

Synthesis of 1-Bromo-3-methoxy-5-nitro-benzene (I-230). Into a 2 L round-bottomed flask equipped with a mechanical stirrer was added I-229 (59.8, 249.2 mmol), ethanol (167 mL), water (83 mL), and the mixture was cooled to 0° C. H$_2$SO$_4$ (750 mL) was added followed by NaNO$_2$ (25.8 g, 373.8 mmol) in 75 mL water. The reaction was stirred at 0° C. for 15 minutes, room temperature for 30 minutes, and 60° C. for 15 minutes, after which it was cooled to room temperature and filtered. The solids were washed with water, dried in a 40° C. vacuum oven for 1 hour, then a vacuum dessicator for 5 days. After drying for an additional 6 hours in a 60° C. vacuum oven, 47.3 g (84%) of I-230 was obtained as a rust-colored solid.

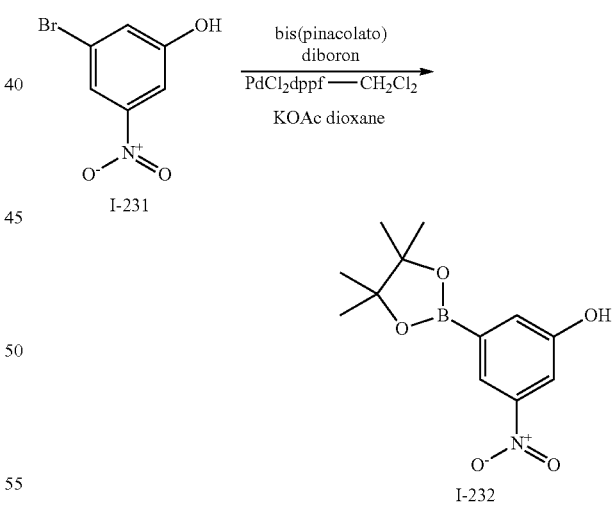

Synthesis of 3-Nitro-5-(4,4,5,5-tetramethyl-[1,3,2]dioxaborolan-2-yl)-phenol (I-232). Into a 250 mL round bottom flask was placed I-231 (2.03 g, 9.31 mmol), bis(piniacolato) diboron (2.60 g, 10.24 mmol), KOAc (2.74 g, 27.93 mmol), and 50 mL dioxane. After degassing with N$_2$ for 10 minutes, PdCl$_2$dppf-CH$_2$Cl$_2$ (0.38 g, 0.47 mmol) was added and the reaction was stirred at 90° C. for 20 hours. Most of the solvent was removed by rotary evaporation and brine was added. The product was extracted with ethyl acetate and the organics were filtered through Celite and concentrated. The residue was purified by flash column chromatography eluting with 20% ethyl acetate/hexanes to afford 1.44 g (58%) of I-232.

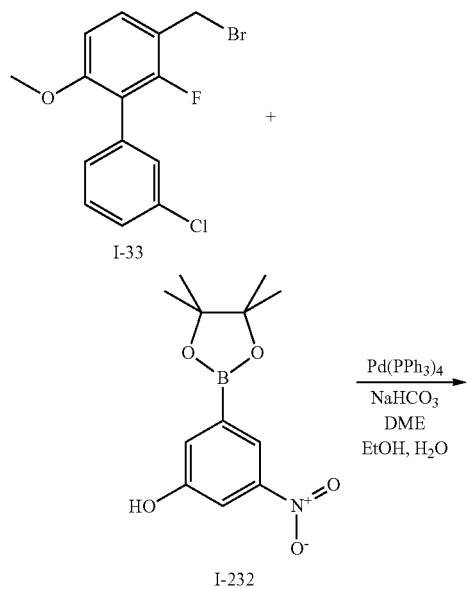

Synthesis of 3-(3'-Chloro-2-fluoro-6-methoxy-biphenyl-3-ylmethyl)-5-nitro-phenol (I-233). Into a 40 mL vial with a stir bar was added I-33 (597 mg, 1.81 mmol), I-232 (480 mg, 1.81 mmol), NaHCO₃ (456 mg, 5.43 mmol), DME (10 mL), ethanol (1 mL), and water (1 mL). After degassing for 10 minutes, tetrakis(triphenylphosphine)palladium(0) (208 mg, 0.18 mmol) was added and the reaction was stirred at 65° C. for 18 hours. The reaction was cooled to room temperature and diluted with 10 mL water. The product was extracted with ethyl acetate, dried over Na₂SO₄, and concentrated. Flash column chromatography purification of the residue with 15-20% ethyl acetate/hexanes afforded 175 mg (25%) of I-233 as a yellow oil.

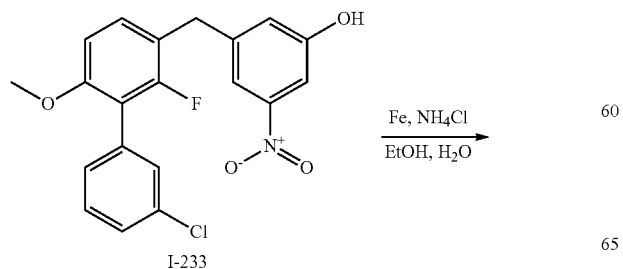

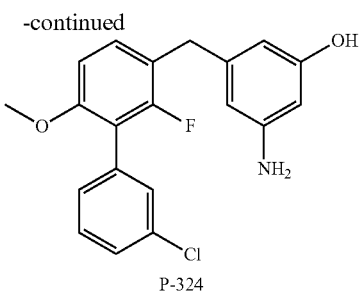

Synthesis of 3-Amino-5-(3'-chloro-2-fluoro-6-methoxy-biphenyl-3-ylmethyl)-phenol (P-324). Into a 40 mL vial was added I-233 (175 mg, 0.39 mmol), Fe powder (89 mg, 1.35 mmol), NH₄Cl (120 mg, 1.93 mmol), water (1 mL), and ethanol (3 mL). The suspension was stirred at 80° C. for 2 hours, then filtered through Celite. The filtrate was diluted with ethyl acetate and washed with water and brine. After concentrating the organics, the residue was purified by flash column chromatography eluting with 20-50% ethyl acetate/hexanes to give 104 mg (65%) of P-324 as a colorless oil. ¹H NMR (400 MHz, CDCl₃) 7.40 (s, 1H), 7.38-7.27 (m, 3H), 7.11 (t, J=8.6 Hz, 1H), 6.74-6.61 (m, 2H), 6.12 (d, J=17.4 Hz, 2H), 6.04 (t, J=1.9 Hz, 1H), 3.80 (s, 2H), 3.75 (s, 3H), 3.63 (br s, 2H) ppm. LC/MS=97.7%, 358.2 (APCI+).

Example 253

Preparation of P-331 and P-338

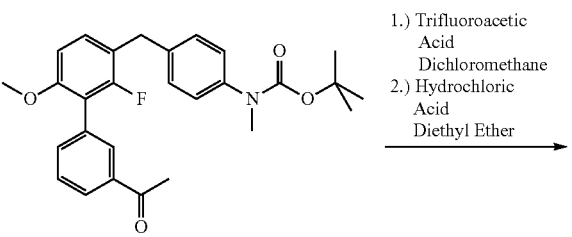

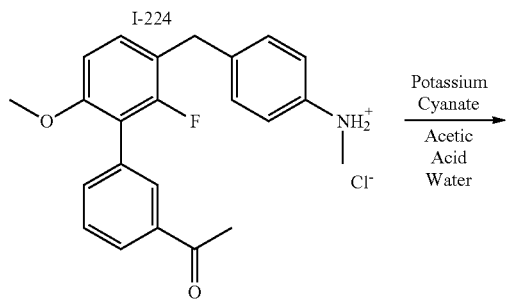

Synthesis of [4-(3'-Acetyl-2-fluoro-6-methoxy-biphenyl-3-ylmethyl)-phenyl]-methyl-amine hydrochloride (P-331).

345

To a solution of I-224 (485 mg, 1.05 mmol) in dichloromethane (2 mL) was added trifluoroacetic acid (1 mL) dropwise and the reaction was allowed to stir at room temperature for 4 h. The solvent was removed under vacuum, and the residue was dissolved in ethyl acetate (20 mL) and water (10 mL). The pH of the aqueous layer was adjusted to 8 using solid sodium bicarbonate. The layers were separated and the organic solution was washed with brine. The organic extract was dried over sodium sulfate and the solvent was removed under vacuum. The residue was dried under high vacuum overnight to give the free base. A portion of the free base (44.5 mg) was dissolved in diethyl ether (2 mL). To the solution was added 2 N hydrogen chloride in diethyl ether (184 uL, 0.367 mmol) dropwise, and the reaction was stirred at room temperature for 3 h. The resultant solid was filtered and dried under vacuum in an abderhaulden apparatus under acetone at reflux to give P-331 (28.8 mg). $^1$H NMR (400 MHz, DMSO-d$_6$) 7.94 (m, 1H), 7.86 (s, 1H), 7.58 (d, J=5.2 Hz, 1H), 7.26 (t, J=8.8 Hz, 1H), 7.09 (d, J=8.4 Hz, 2H), 6.93 (d, J=9.2 Hz, 1H), 6.77 (br m, 2H), 3.84 (s, 2H), 3.71 (s, 3H), 2.72 (s, 3H), 2.59 (s, 3H) ppm.

LCMS=94.4% purity. MS (APCI+)=364.1 (M+1).

Synthesis of 1-[4-(3'-Acetyl-2-fluoro-6-methoxy-biphenyl-3-ylmethyl)-phenyl]-1-methyl-urea (P-338). A suspension of P-331 free base (180 mg, 0.495 mmol) in glacial acetic acid (1 mL) and water (1 mL) was stirred until a solution formed. To the solution was added a solution of potassium cyanate (120 mg, 1.49 mmol) in water (250 uL), and the solution became cloudy. The reaction was stirred at room temperature for 2.5 h. The reaction was diluted with diethyl ether (10 mL) and water (5 mL) and the layers separated. The organic extract was washed with saturated aqueous sodium bicarbonate (10 mL), dried over sodium sulfate, filtered, and the solvent removed under vacuum. The residue was dissolved in diethyl ether (30 mL), washed with saturated aqueous sodium bicarbonate (30 mL) and brine (30 mL), dried over sodium sulfate, filtered, and the solvent was removed under vacuum. The residue was purified by preparatory silica TLC (10% acetone in dichloromethane, 2 developments), and dried overnight in a vacuum oven at 40° C. to give P-338 (96.1 mg, 48% yield) as a white powder. 1H NMR (400 MHz CDCl$_3$) d: 8.00 (d, J=1.2 Hz, 1H), 7.95 (dt, J=7.7 Hz, 1.4 Hz, 1H). 7.61 (dd, J=7.6 Hz, 1.6 Hz, 1H), 7.52 (t, J=7.6 Hz, 1H), 7.28 (d, J=8.4 Hz, 2H), 7.22-7.14 (m, 3H), 6.75 (d, J=8.4 Hz, 1H), 4.34 (brs, 2H), 3.98 (s, 2H), 3.76 (s, 3H), 3.24 (s, 3H), 2.62 (s, 3H). LCMS=96.1% purity. MS (APCI+)=407.1 (M+1).

Scheme 57.

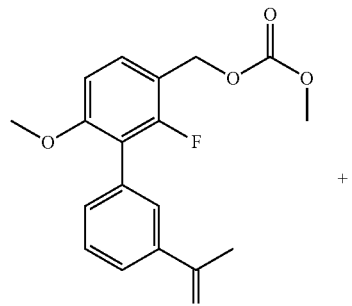

I-223

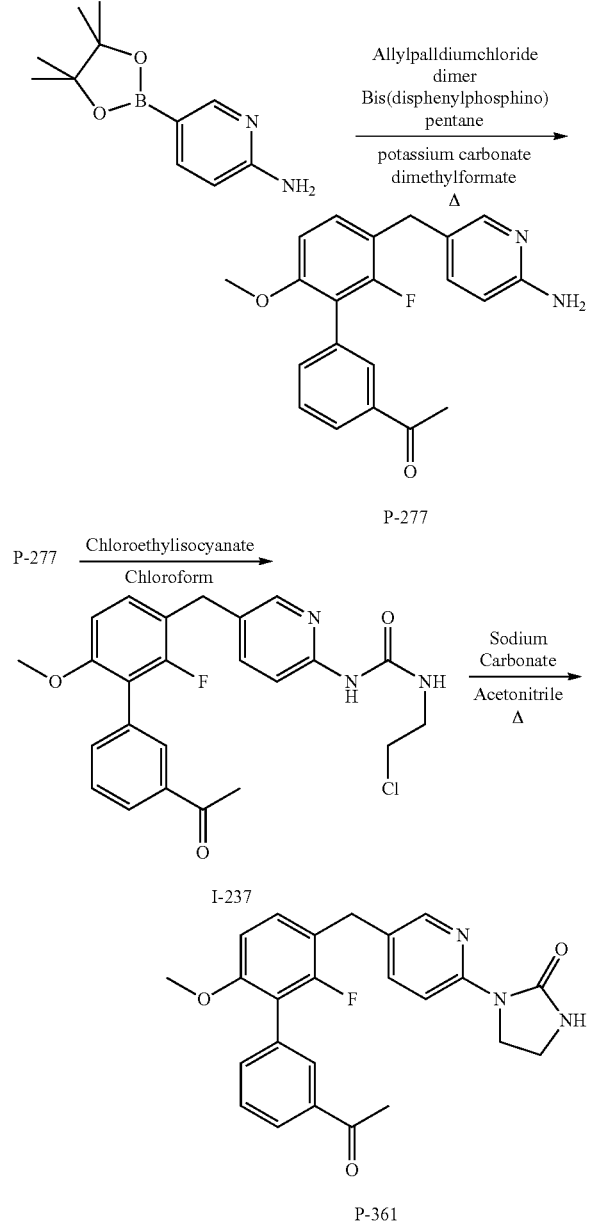

Example 254

Preparation of P-277

Synthesis of 1-[3'-(6-Amino-pyridin-3-ylmethyl)-2'-fluoro-6'-methoxy-biphenyl-3-yl]-ethanone (P-277). A solution of I-223 (1.00 g, 3.01 mmol) and 2-aminopyridine-5-boronic acid pinacol ester (728 mg, 3.31 mmol) in N,N-dimethylformamide (8 mL) was degassed using a nitrogen stream for 10 min. To the solution was added potassium carbonate (1.25 g, 9.03 mmol), allylpalladium(II) chloride dimer (165 mg, 0.451 mmol), and bis(diphenylphosphino) pentane (398 mg, 0.903 mmol) under nitrogen and the suspension was stirred at 65° C. under nitrogen for 15 h. To the reaction was added ethyl acetate (50 mL) and water (50 mL) and the biphasic suspension was filtered through celite (~15 g). The celite was washed with ethyl acetate (2×20 mL), and water (2×20 mL) and the filtrate was separated. The aqueous layer was extracted with ethyl acetate (100 mL) and the organic extracts were combined. The organic solution was washed with water (200 mL) and brine (200 mL), dried over sodium sulfate, filtered, and the solvent removed under vacuum. The residue was purified by flash silica gel column chromatography (impurities eluted with 50% ethyl acetate in hexanes, product eluted with 12.5% acetone in dichloromethane) to give P-277 (653 mg, 62% yield) as an orange oil. $^1$H NMR (400 MHz, CDCl$_3$) 7.99 (m, 1H), 7.95 (dt, J=7.73 Hz, 1.6 Hz, 1H), 7.61-7.59 (m, 1H), 7.52 (t, J=7.6 Hz, 1H), 7.30 (dd, J=8.2 Hz, 2.2 Hz, 1H), 7.09 (t, J=8.6 Hz, 1H), 6.71 (dd, J=8.4 Hz, 0.8 Hz, 1H), 6.46 (d, J=8.8 Hz, 1H), 4.33 (s, 2H), 3.83 (s, 2H), 3.75 (s, 3H), 2.62 (s, 3H). LCMS=100.0% purity. MS (APCI+)=351.1 (M+1).

Example 255

Preparation of P-361

Synthesis of 1-[5-(3'-Acetyl-2-fluoro-6-methoxy-biphenyl-3-ylmethyl)-pyridin-2-yl]-3-(2-chloro-ethyl)-urea (I-237). A solution of P-277 (300 mg, 0.856 mmol) in chloroform (7.4 mL) was purged with nitrogen for 5 min at room temperature. To this solution was added 2-chloroethylisocyanate (90.3 mg, 0.856 mmol), and the reaction was stirred at reflux for 24 h. Additional 2-chloroethylisocyanate (220 uL, 2.57 mmol) was added and the reaction was heated at reflux for an additional 16 h. The solvent was removed under vacuum and the resultant red syrup was purified by flash silica gel column chromatography (0-25% acetone in dichoromethane) followed by preparatory thin layer chromatography to give I-237 (41.7 mg, 11% yield) as a yellow oil.

Synthesis of 1-[5-(3'-Acetyl-2-fluoro-6-methoxy-biphenyl-3-ylmethyl)-pyridin-2-yl]-imidazolidin-2-one (P-361). A suspension of I-237 (40.0 mg, 0.0877 mmol) and sodium carbonate (27.9 mg, 0.263 mmol) in acetonitrile (1 mL) was stirred at reflux overnight. The reaction was cooled to room temperature and filtered. The solvent was removed under vacuum and the resultant yellow oil was crystallized in diethyl ether (2 mL), filtered, washed with hexanes (2×1 mL) and dried in a vacuum oven overnight at 40° C. to give P-361 (17.1 mg, 46% yield) as an off white powder. $^1$H NMR (400 MHz, CDCl$_3$) 8.10 (d, J=1.6 Hz, 1H), 7.99 (s, 1H), 7.95 (d, J=7.8 Hz, 1H), 7.63-7.48 (m, 3H), 7.46-7.39 (m, 1H), 7.14-7.05 (m, 1H), 6.97 (d, J=8.3 Hz, 1H), 6.72 (d, J=8.5 Hz, 1H), 4.42 (t, J=7.9 Hz, 2H), 3.89 (s, 2H), 3.82 (t, J=7.9 Hz, 2H), 3.75 (s, 3H), 2.62 (s, 3H) ppm. LCMS=91.4% purity. MS (APCI+)=420.1 (M+1).

Example 256

Preparation of P-355

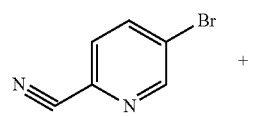

+

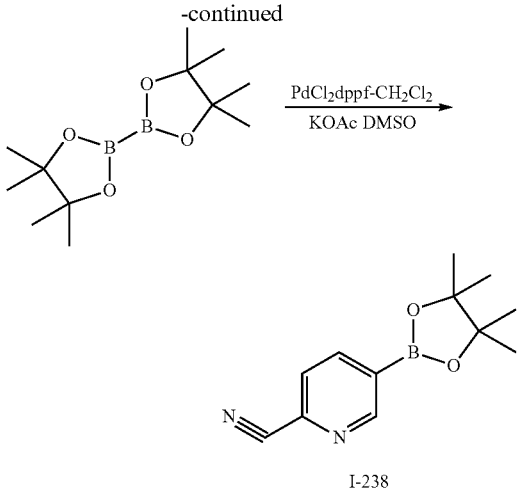

Synthesis of 5-(4,4,5,5-Tetramethyl-[1,3,2]dioxaborolan-2-yl)-pyridine-2-carbonitrile (I-238). Into a 250 mL round-bottomed flask was added 3.0 g of 5-bromo-pyridine-2-carbonitrile (3.0 g, 16.39 mmol), bis(piniacolato)diboron (4.58 g, 18.03 mmol), KOAc (5.47 g, 55.74 mmol), and DMSO (100 mL). After degassing for 20 minutes, PdCl$_2$dppf-CH$_2$Cl$_2$ (1.39 g, 1.64 mmol) was added and the solution was stirred for 24 hours at 80° C., and then at room temperature for 3 days. 50 mL water was added and the product was extracted with ethyl acetate. The combined organics were washed with brine, dried over Na$_2$SO$_4$ and concentrated. The dark-colored residue was purified by flash column chromatography eluting with 20% acetone/hexanes to give a red solid. The solid was triturated with hexane to give 1.72 g (46%) of I-238 as a light-pink solid.

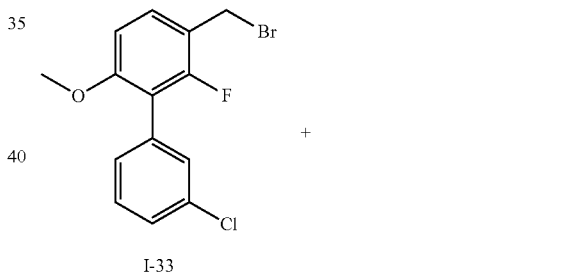

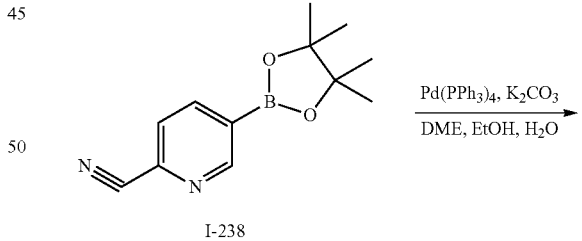

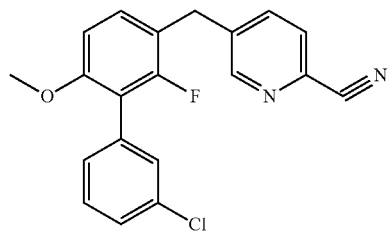

Synthesis of [5-(3'-Chloro-2-fluoro-6-methoxy-biphenyl-3-ylmethyl)-pyridin-2-ylmethyl]-carbamic acid tert-butyl

349 ester (P-355). Into a 20 mL vial was added I-33 (401 mg, 1.22 mmol), I-238 (336 mg, 1.46 mmol), $K_2CO_3$ (504 mg, 3.65 mmol), DME (5 mL), water (0.5 mL), ethanol (0.5 mL), and the suspension was degasses for 15 minutes. Tetrakis(triphenylphosphine)palladium(0) (141 mg, 0.12 mmol) was added and the reaction stirred at 80° C. for 16 hours. The reaction was diluted with water and extracted with ethyl acetate. The organics were concentrated and purified by flash column chromatography eluting with 15-20% ethyl acetate/hexanes to afford P-355 (64 mg, 15%) as a light-yellow oil. $^1$H NMR (400 MHz, $CDCl_3$) δ 8.62 (br s, 1H), 7.68-7.56 (m, 2H), 7.40-7.30 (m, 3H), 7.26-7.21 (m, 1H), 7.13 (t, J=8.4 Hz, 1H), 6.75 (d, J=8.3 Hz, 1H), 4.03 (br s, 2H), 3.78 (s, 3H) ppm. LC/MS=98.5%, 353.0 (APCI+).

Example 257

Preparation of P-344

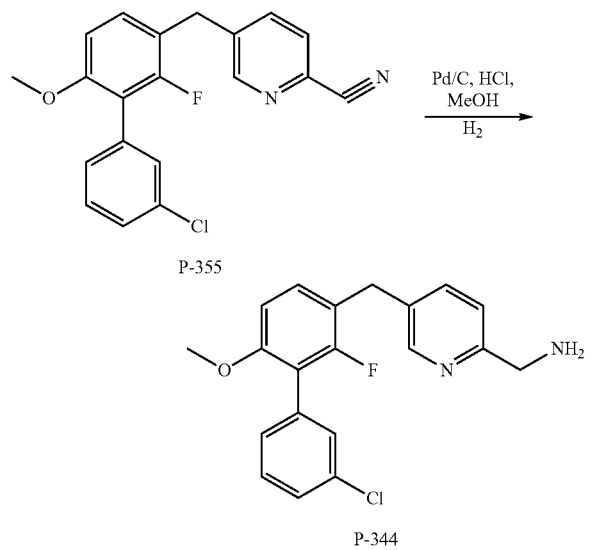

Synthesis of C-[5-(3'-Chloro-2-fluoro-6-methoxy-biphenyl-3-ylmethyl)-pyridin-2-yl]-methylamine (P-344). Into a 100 mL round bottom flask was added P-355 (0.55 g, 1.56 mmol), methanol (20 mL), concentrated HCl (0.65 mL, 7.79 mmol), and 10% Pd/C (100 mg). The suspension was stirred under a $H_2$ balloon for 18 hours, then filtered through Celite. The filtrate was concentrated. To the solid was added 1N aqueous NaOH and the product was extracted with dichloromethane. The dichloromethane was concentrated and purified by flash column chromatography eluting with 5-10% methanol/dichloromethane to give P-344 (89 mg, 16%) as a colorless oil. $^1$H NMR (400 MHz, DMSO-$d_6$) 8.55 (d, J=1.2 Hz, 1H), 8.32 (br s, 3H), 7.71 (dd, J=1.9, 7.9 Hz, 1H), 7.50-7.37 (m, 3H), 7.36 (d, J=5.4 Hz, 2H), 7.27 (d, J=6.6 Hz, 1H), 6.96 (d, J=8.6 Hz, 1H), 4.75 (br s, 2H), 4.14 (q, J=5.8 Hz, 2H), 4.01 (s, 2H), 3.73 (s, 3H) ppm. LC/MS=95.1%, 357.1 (APCI+).

350

Example 258

Preparation of P-367

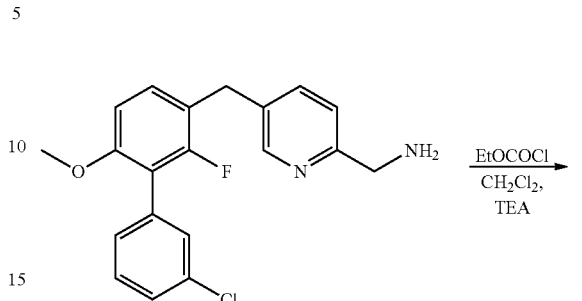

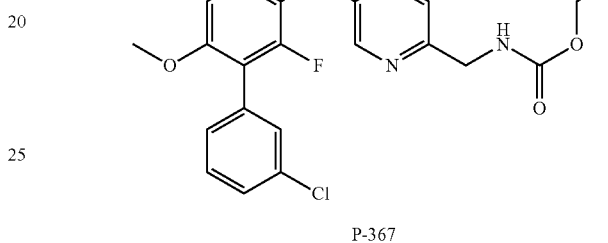

Synthesis of [5-(3'-Chloro-2-fluoro-6-methoxy-biphenyl-3-ylmethyl)-pyridin-2-ylmethyl]-carbamic acid ethyl ester (P-367). Into an 8 mL vial was added P-344 (43 mg, 0.12 mmol), dichloromethane (2 mL), triethylamine (33 uL, 0.24 mmol). The solution was cooled to 0° C. and ethyl chloroformate (20 mg, 0.18 mmol) was added. After 15 minutes at room temperature the solution was concentrated. The residue was purified by flash column chromatography eluting with 40-60% ethyl acetate to give 23 mg (54%) of P-367 as a white solid. $^1$H NMR (400 MHz, DMSO-$d_6$) 8.39 (d, J=1.5 Hz, 1H), 7.63 (t, J=6.0 Hz, 1H), 7.59 (dd, J=1.7, 8.1 Hz, 1H), 7.50-7.40 (m, 2H), 7.37 (s, 1H), 7.33 (t, J=8.7 Hz, 1H), 7.28 (d, J=6.6 Hz, 1H), 7.20 (d, J=7.9 Hz, 1H), 6.94 (d, J=8.6 Hz, 1H), 4.22 (d, J=6.2 Hz, 2H), 4.03-3.96 (m, 2H), 3.94 (s, 2H), 3.72 (s, 3H), 1.16 (t, J=7.1 Hz, 3H) ppm. LC/MS=100.0%, 429.1 (APCI+).

Example 259

Preparation of P-368

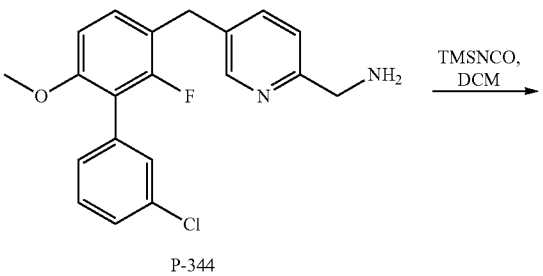

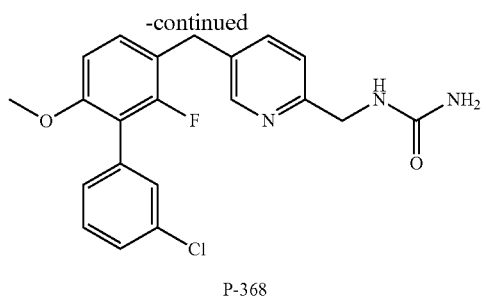

P-368

Synthesis of [5-(3'-Chloro-2-fluoro-6-methoxy-biphenyl-3-ylmethyl)-pyridin-2-ylmethyl]-urea (P-368). Into an 8 mL vial was added P-344 (43 mg, 0.12 mmol), dichloromethane (2 mL), and trimethylsilyl isocyanate (49 uL, 0.36 mmol). After 1 hour at 35° C., the solution was concentrated. The resulting solid was triturated with ether to afford P-368 (25 mg, 52%) as a white solid. $^1$H NMR (400 MHz, DMSO-d$_6$) 8.44 (s, 1H), 7.68 (d, J=7.8 Hz, 1H), 7.48-7.40 (m, 2H), 7.37 (s, 1H), 7.34 (t, J=8.9 Hz, 1H), 7.28 (d, J=7.6 Hz, 2H), 6.94 (d, J=8.6 Hz, 1H), 6.51 (br s, 1H), 5.64 (br s, 2H), 4.25 (d, J=5.0 Hz, 2H), 3.97 (s, 2H), 3.72 (s, 3H). LC/MS=96.4%, 400.1 (APCI+).

Example 260

Preparation of P-371

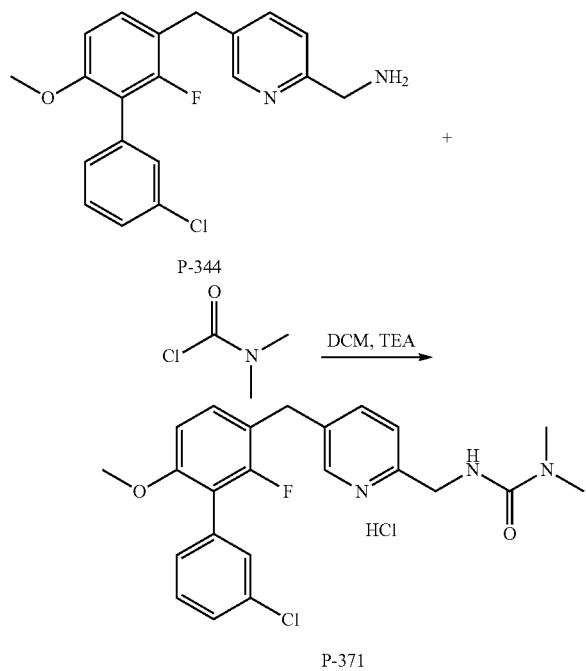

P-371

Synthesis of 3-[5-(3'-Chloro-2-fluoro-6-methoxy-biphenyl-3-ylmethyl)-pyridin-2-ylmethyl]-1,1-dimethyl-urea hydrochloride (P-371). Into an 8 mL vial was added P-344 (23 mg, 0.064 mmol), dichloromethane (1.5 mL), triethylamine (18 uL, 0.13 mmol) and the solution was cooled to 0° C. Dimethylcarbamyl chloride (9 uL, 0.097) was added and the reaction stirred for 18 hours at room temperature. The dichloromethane solution was washed with water and brine, and then concentrated. The residue was purified by flash column chromatography eluting with 5% methanol/dichloromethane. The colorless oil obtained was triturated with ether to obtain a white solid. The resulting solid was dissolved in 2 mL of 4.0 M HCl/dioxane and stirred for 2 hours at room temperature. The oil was treated with ether to form a solid, which was filtered to obtain P-371 (6.1 mg, 20%). $^1$H NMR (400 MHz, DMSO-d$_6$) 8.60 (s, 1H), 8.08 (d, J=7.4 Hz, 1H), 7.62 (d, J=8.1 Hz, 1H), 7.50-7.35 (m, 4H), 7.28 (d, J=6.4 Hz, 1H), 7.11 (br s, 1H), 6.97 (d, J=8.6 Hz, 1H), 4.41 (br s, 2H), 4.08 (s, 2H), 3.73 (s, 3H), 2.82 (s, 6H) ppm. LC/MS=100.0%, 428.1 (APCI+).

Example 261

Preparation of P-372

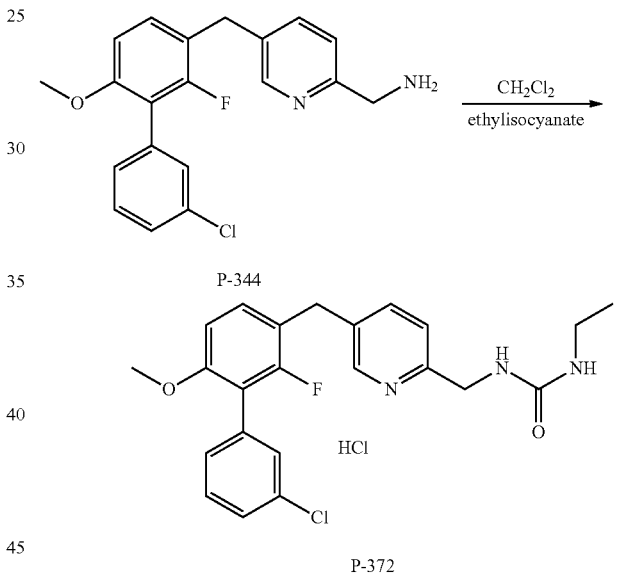

P-372

Synthesis of 1-[5-(3'-Chloro-2-fluoro-6-methoxy-biphenyl-3-ylmethyl)-pyridin-2-ylmethyl]-3-ethyl-urea (P-372). Into an 8 mL vial was added P-344 (23 mg, 0.064 mmol), dichloromethane (1.5 mL), and the solution was cooled to room temperature. Ethyl isocyanate (8 uL, 0.097 mmol) was added and the reaction was stirred for 18 hours at room temperature and then concentrated. To the resulting solid was added 4.0 M HCl/dioxane and the solution was stirred for 18 hours at room temperature and then concentrated. The oil which was obtained was treated with ether to form a solid, which was filtered to afford P-372 (15.1 mg, 50%) as a white solid. $^1$H NMR (400 MHz, DMSO-d$_6$) 8.63 (s, 1H), 8.14 (d, J=8.3 Hz, 1H), 7.63 (d, J=8.2 Hz, 1H), 7.51-7.33 (m, 4H), 7.28 (d, J=6.3 Hz, 1H), 6.98 (d, J=8.6 Hz, 1H), 6.62 (br s, 1H), 6.31 (br s, 1H), 4.42 (s, 2H), 4.10 (s, 2H), 3.74 (s, 3H), 3.01 (q, J=7.1 Hz, 2H), 0.99 (t, J=7.1 Hz, 3H) ppm. MS: 428.1 (APCI+).

Example 262

Preparation of P-373

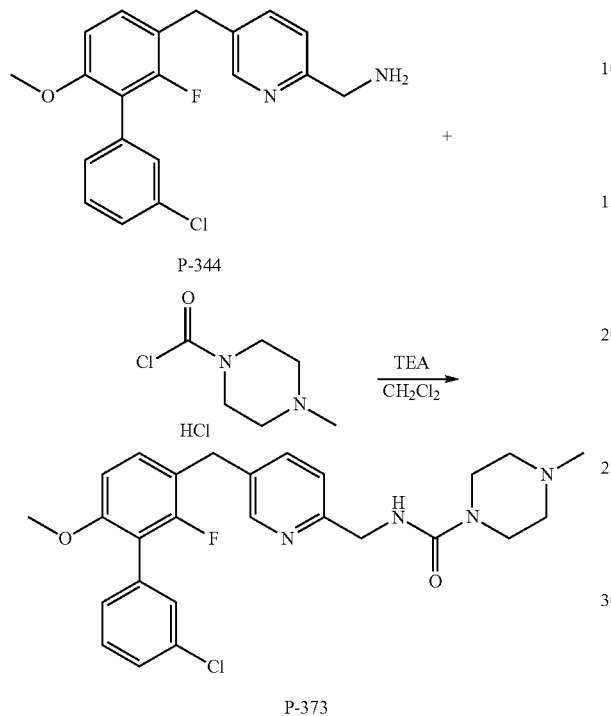

Example 263

Preparation of P-374

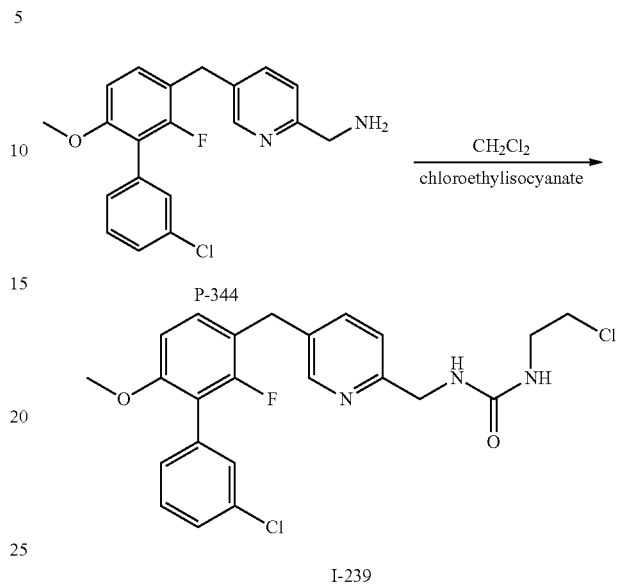

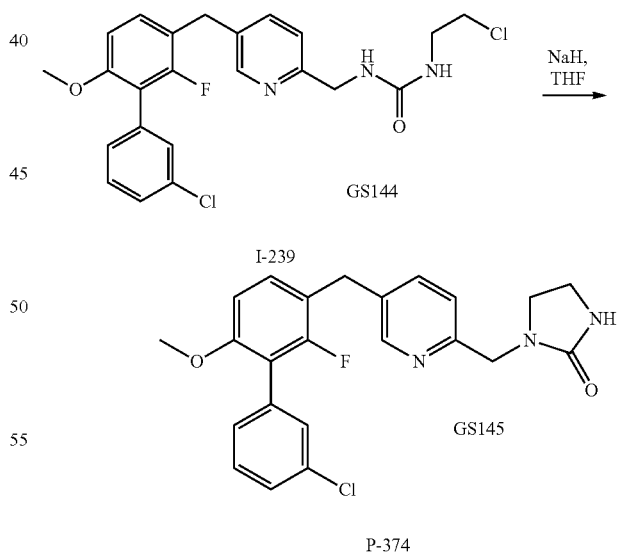

Synthesis of 1-(2-Chloro-ethyl)-3-[5-(3'-chloro-2-fluoro-6-methoxy-biphenyl-3-ylmethyl)-pyridin-2-ylmethyl]-urea (I-239). Into an 8 mL vial was added P-344 (63 mg, 0.177 mmol), dichloromethane (2 mL), and the reaction was cooled to 0° C. Chloroethyl isocyanate (19 mg, 0.177 mmol) was added and the reaction was stirred at room temperature for 1 hour and then concentrated to yield I-239 which was used as is.

Synthesis of 4-Methyl-piperazine-1-carboxylic acid [5-(3'-chloro-2-fluoro-6-methoxy-biphenyl-3-ylmethyl)-pyridin-2-ylmethyl]-amide (P-373). Into an 8 mL vial was added P-344 (23 mg, 0.064 mmol), dichloromethane (1.5 mL), triethylamine (18 uL, 0.13 mmol). The solution was cooled to 0° C. and 4-methyl-piperazine-1-carbonyl chloride (10 mg, 0.097 mmol) was added. After 18 hours at room temperature the reaction was washed with water, followed by brine. The organics were concentrated and purified by flash column chromatography eluting with 5-10% methanol/dichloromethane to afford 28 mg of semi-solid. The semi-solid was dissolved in 2 mL of 4.0M HCl/dioxane and stirred at room temperature for 18 hours, and then concentrated. Ether was added and a solid formed, which was filtered. To the solid was added 5N aqueous NaOH and the product was extracted with dichloromethane and then concentrated. Purification of the residue by flash column chromatography eluting with 10% methanol/dichloromethane afforded P-373 (9.6 mg, 31%) as a colorless oil. $^1$H NMR (400 MHz, DMSO-$d_6$) 8.38 (d, J=1.5 Hz, 1H), 7.57 (dd, J=2.0, 8.1 Hz, 1H), 7.48-7.39 (m, 2H), 7.37 (s, 1H), 7.32 (t, J=8.7 Hz, 1H), 7.28 (d, J=6.4 Hz, 1H), 7.17 (d, J=8.1 Hz, 1H), 7.09 (t, J=5.8 Hz, 1H), 6.94 (d, J=8.5 Hz, 1H), 4.26 (d, J=5.6 Hz, 2H), 3.93 (s, 2H), 3.72 (s, 3H), 3.17 (d, J=5.2 Hz, 4H), 2.29-2.20 (m, 4H), 2.16 (s, 3H) ppm. LC/MS=100.0%, 483.1 (APCI+).

Synthesis of 1-[5-(3'-Chloro-2-fluoro-6-methoxy-biphenyl-3-ylmethyl)-pyridin-2-ylmethyl]-imidazolidin-2-one (P-374). Into an 8 mL vial was added I-239 (82 mg, 0.177 mmol), THF (2 mL), and the suspension was cooled to 0° C. Sodium hydride (8 mg, 0.212 mmol) was added and the reaction was stirred at room temperature for 3 days. An additional 4 mg of sodium hydride was added and the reaction was stirred at 50° C. for 1 hour. Water was added and the product was extracted with ethyl acetate. The organics were concentrated and purified by flash column chromatography eluting with 25-50% acetone/dichloromethane to give P-374 (35 mg, 47%, 2 steps) as a white solid. $^1$H NMR (400 MHz, DMSO-$d_6$) 8.42 (d, J=1.5 Hz, 1H), 7.60 (dd, J=1.9, 7.9 Hz, 1H), 7.49-7.39 (m, 2H), 7.37 (s, 1H), 7.34 (t, J=8.7 Hz, 1H), 7.28 (d, J=6.7 Hz, 1H), 7.19 (d, J=7.9 Hz, 1H), 6.94 (d, J=8.6 Hz, 1H), 6.41 (s, 1H), 4.28 (s, 2H), 3.95 (s, 2H), 3.72 (s, 3H), 3.31-3.19 (m, 4H) ppm. LC/MS=100.0%, 426.1 (APCI+).

Example 264

Preparation of P-375

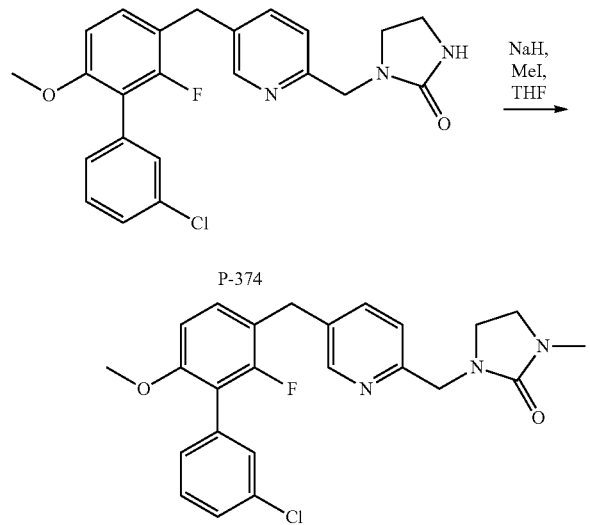

Synthesis of 1-[5-(3'-Chloro-2-fluoro-6-methoxy-biphenyl-3-ylmethyl)-pyridin-2-ylmethyl]-3-methyl-imidazolidin-2-one (P-375). Into an 8 mL vial was added P-374 (21 mg, 0.05 mmol), THF (1 mL) and the solution was cooled to 0° C. Sodium hydride (3 mg, 0.076 mmol) was added and after 15 minutes at room temperature, methyl iodide (6 uL, 0.101 mmoL) was added. The reaction was stirred for 30 minutes at room temperature and then 1 mL of water was added. The THF was evaporated and the product was extracted with ethyl acetate and concentrated. The residue was passed through a silica gel plug eluting with methanol, which afforded P-375 (18.1 mg, 82%) as a colorless oil. $^1$H NMR (400 MHz, DMSO-$d_6$) 8.42 (d, J=1.6 Hz, 1H), 7.60 (dd, J=2.0, 7.9 Hz, 1H), 7.50-7.39 (m, 2H), 7.37 (s, 1H), 7.34 (t, J=8.7 Hz, 1H), 7.28 (d, J=6.4 Hz, 1H), 7.19 (d, J=8.1 Hz, 1H), 6.94 (d, J=8.5 Hz, 1H), 4.31 (s, 2H), 3.95 (s, 2H), 3.72 (s, 3H), 3.24 (s, 4H), 2.67 (s, 3H) ppm. LC/MS=97.8%, 440.1 (APCI+).

Example 265

Preparation of P-520

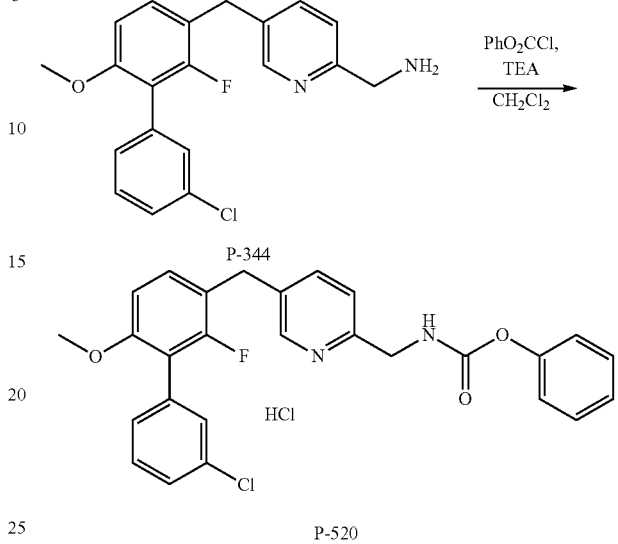

Synthesis of [5-(3'-Chloro-2-fluoro-6-methoxy-biphenyl-3-ylmethyl)-pyridin-2-ylmethyl]-carbamic acid phenyl ester (P-520). Into an 18 mL vial was added P-344 (128 mg, 0.36 mmol), TEA (0.10 mL, 0.72 mmol), and dichloromethane (3 mL). The solution was cooled to 0° C. and phenylchloroformate (68 uL, 0.54 mmol) was added. After stirring at room temperature for 15 minutes the reaction was concentrated. Purification by flash column chromatography (25%-75% EtOAc/hexanes) afforded P-520 (102 mg, 59%) as an off-white solid. (400 MHz, DMSO-$d_6$) 8.44 (s, 1H), 8.30 (t, J=5.9 Hz, 1H), 7.63 (dd, J=1.5, 7.9 Hz, 1H), 7.49-7.26 (m, 8H), 7.24-7.17 (m, 1H), 7.12 (d, J=7.9 Hz, 2H), 6.95 (d, J=8.6 Hz, 1H), 4.33 (d, J=6.0 Hz, 2H), 3.96 (s, 2H), 3.73 (s, 3H) ppm. LC/MS=100.0%, 477.1 (APCI+).

Example 266

Preparation of P-460

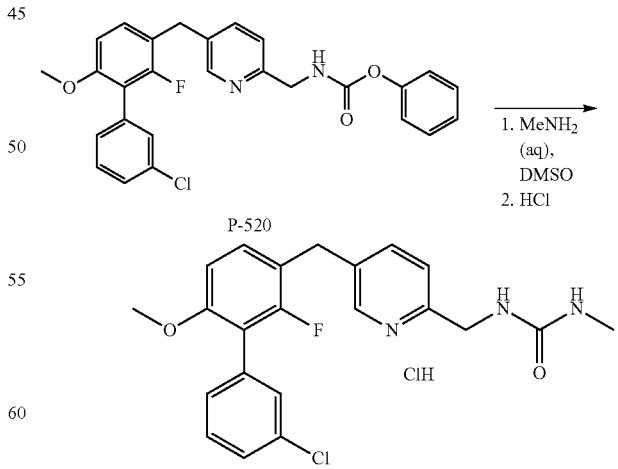

1-[5-(3'-Chloro-2-fluoro-6-methoxy-biphenyl-3-ylmethyl)-pyridin-2-ylmethyl]-3-methyl-urea hydrochloride (P-460). Into an 8 mL vial was added P-520 (84 mg, 0.18 mmol), DMSO (2 mL), and 40% aq. MeNH$_2$ (0.14 mL). After stirring for 30 minutes at room temperature, 5 mL of water was added. The product was extracted with EtOAc (4×2 mL) and the organics were concentrated. The white solid was triturated with ether to afford the free base compound. To the free base was added 4N HCl/dioxane (2 mL) and after stirring for 5 minutes at room temperature the solution was concentrated. The residue was triturated with ether to provide P-460 (42 mg, 53%) as a tan solid. $^1$H NMR (400 MHz, DMSO-d$_6$) 8.64 (s, 1H), 8.16 (d, J=7.9 Hz, 1H), 7.66 (d, J=8.2 Hz, 1H), 7.51-7.34 (m, 4H), 7.28 (d, J=6.4 Hz, 1H), 6.98 (d, J=8.6 Hz, 1H), 6.80 (br s, 1H), 6.30 (br s, 1H), 4.44 (s, 2H), 4.10 (s, 2H), 3.74 (s, 3H), 2.55 (s, 3H) ppm. LC/MS=97.5%, 414.0 (APCI+).

Example 267

Preparation of P-461

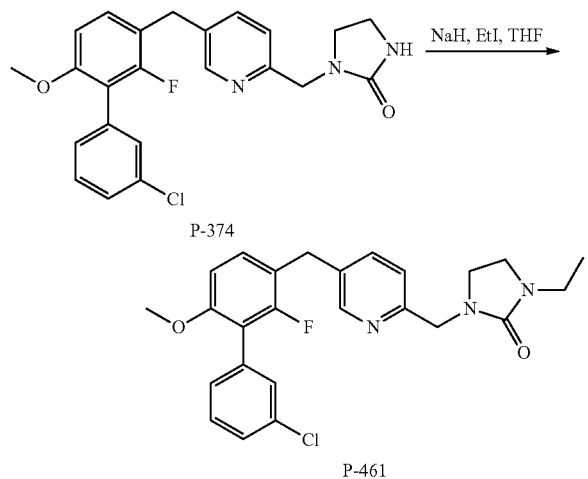

1-[5-(3'-Chloro-2-fluoro-6-methoxy-biphenyl-3-ylmethyl)-pyridin-2-ylmethyl]-3-ethyl-imidazolidin-2-one hydrochloride (P-461). Into an 18 mL vial was added P-374 (65 mg, 0.16 mmol), THF (3 mL), and the solution was cooled to 0° C. NaH (9 mg, 0.23 mmol) was added and the suspension was stirred at room temperature for 15 minutes. EtI (25 uL, 0.31 mmol) was added and the reaction was stirred for 1 hour at room temperature. Water was added and the product was extracted with EtOAc (3×3 mL). The organics were washed with water, brine, and concentrated. To the residue was added 2 mL of 4N HCl/dioxane. After stirring to dissolve, the solution was concentrated. The resulting residue was triturated with ether, filtered, washed with ether, and dried to give P-461 (51 mg, 65%) as a tan solid. $^1$H NMR (400 MHz, DMSO-d$_6$) 8.63 (br s, 2H), 8.07 (br s, 1H), 7.60 (d, J=7.9 Hz, 1H), 7.50-7.33 (m, 4H), 7.29 (d, J=5.8 Hz, 1H), 6.97 (d, J=8.3 Hz, 1H), 4.51 (s, 2H), 4.09 (br s, 2H), 3.74 (s, 3H), 3.57 (s, 2H), 3.31 (s, 2H), 3.19-3.10 (m, 2H), 1.10-0.97 (m, 3H) ppm. LC/MS=84.2%, 454.2 (APCI+).

Example 268

Preparation of P-462

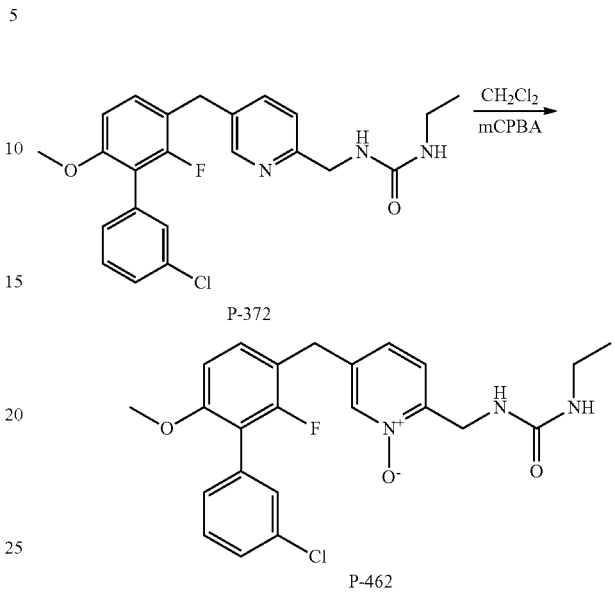

1-[5-(3'-Chloro-2-fluoro-6-methoxy-biphenyl-3-ylmethyl)-1-oxy-pyridin-2-ylmethyl]-3-ethyl-urea (P-462). Into an 18 mL vial was added P-372 (66 mg, 0.15 mmol), dichloromethane (4 mL), and the solution was cooled to 0° C. mCPBA (69 mg, 0.31 mmol) was added and the reaction was stirred at room temperature for 1 hour after which 5 mL of saturated aqueous NaHCO$_3$ was added. The layers were separated and the organic layer was washed sequentially with 5 mL each of saturated aqueous NaHCO$_3$, H$_2$O, and brine. The residue was then washed with 1N NaOH (2×5 mL), water (5 mL), and brine (5 mL). The product was dried over Na$_2$SO$_4$, filtered and concentrated to obtain P-462 (14.8 mg, 22%) as a white solid. $^1$H NMR (400 MHz, DMSO-d$_6$) 8.19 (s, 1H), 7.53-7.34 (m, 4H), 7.29 (d, J=6.6 Hz, 1H), 7.25-7.16 (m, 2H), 6.96 (d, J=8.6 Hz, 1H), 6.38 (t, J=6.0 Hz, 1H), 6.17 (t, J=5.4 Hz, 1H), 4.22 (d, J=6.2 Hz, 2H), 3.91 (s, 2H), 3.73 (s, 3H), 3.09-2.91 (m, 2H), 0.97 (t, J=7.2 Hz, 3H) ppm. LC/MS=100.0%, 444.1 (APCI+).

Example 269

Preparation of P-463

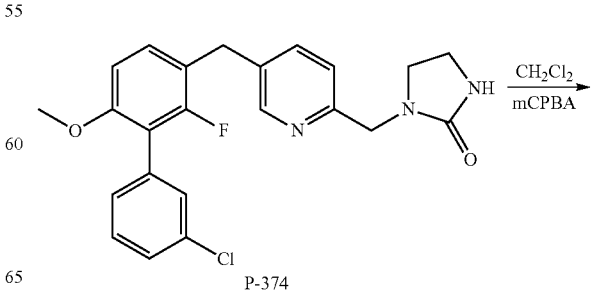

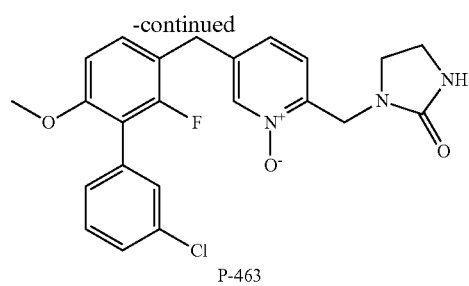

1-[5-(3'-Chloro-2-fluoro-6-methoxy-biphenyl-3-ylmethyl)-1-oxy-pyridin-2-ylmethyl]-imidazolidin-2-one (P-463). Into an 18 mL vial was added P-374 (62 mg, 0.15 mmol), dichloromethane (4 mL), and the solution was cooled to 0° C. mCPBA (82 mg, 0.36 mmol) was added and the reaction was stirred at room temperature for 1 hour after which 5 mL of aqueous 1N NaOH was added. The layers were separated and the aqueous layer was extracted with dichloromethane (2×3 mL). The organics were combined and washed with water (5 mL) and brine (5 mL) and then concentrated. The residue was taken up in 5 mL of EtOAc and it was washed with 5 mL of brine, dried over $Na_2SO_4$, and concentrated to a solid. The residue was triturated with ether to afford P-463 (23.5 mg, 35%) as a white solid. $^1$H NMR (400 MHz, DMSO-$d_6$) 8.23 (s, 1H), 7.49-7.34 (m, 4H), 7.32-7.16 (m, 3H), 6.96 (d, J=8.6 Hz, 1H), 6.56 (s, 1H), 4.31 (s, 2H), 3.93 (s, 2H), 3.73 (s, 3H), 3.45-3.36 (m, 2H), 3.32-3.25 (m, 2H) ppm. LC/MS=93.4%, 442.0 (APCI+).

Example 270

Preparation of P-465

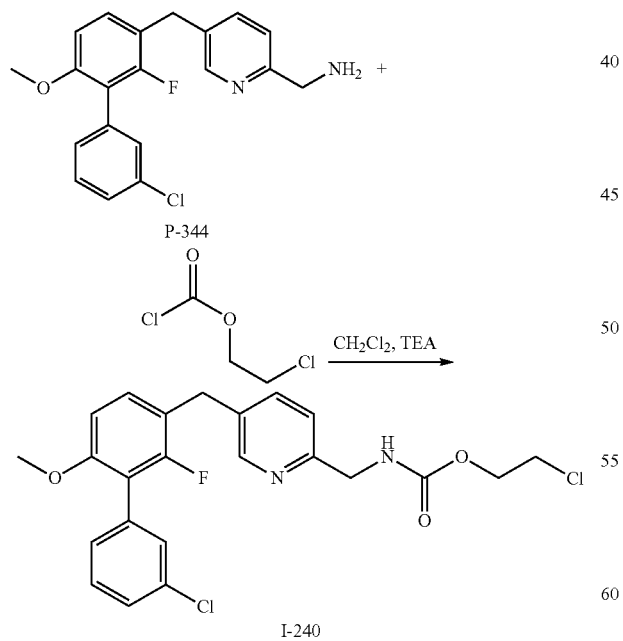

[5-(3'-Chloro-2-fluoro-6-methoxy-biphenyl-3-ylmethyl)-pyridin-2-ylmethyl]-carbamic acid 2-chloro-ethyl ester (I-240). Into an 18 mL vial was added P-344 (100 mg, 0.28 mmol), dichloromethane (4 mL), TEA (78 uL, 0.56 mmol), and after the solution was cooled to 0° C. 2-Chloroethyl chloroformate (43 uL, 0.42 mmol) was added. The reaction was stirred at room temperature for 18 hours and then 5 mL of water was added. The layers were separated and the aqueous was extracted with 5 mL more dichloromethane. The organics were combined, washed with 5 mL of water and 5 mL of brine, dried over $Na_2SO_4$, and then concentrated. The residue which was obtained was used as is in the next reaction.

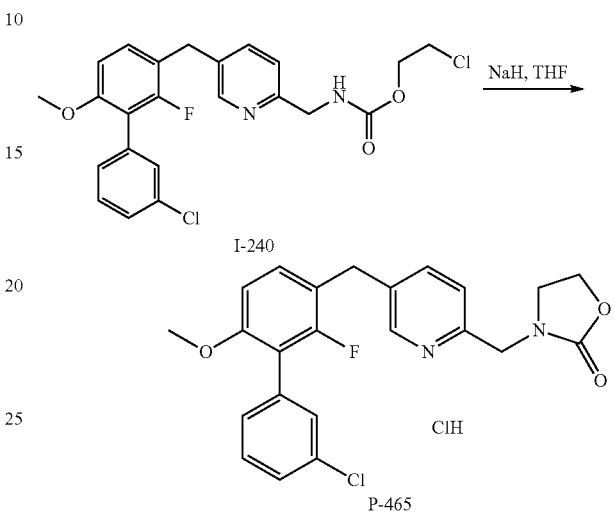

3-[5-(3'-Chloro-2-fluoro-6-methoxy-biphenyl-3-ylmethyl)-pyridin-2-ylmethyl]-oxazolidin-2-one hydrochloride (P-465). Into an 18 mL vial was added I-240 (0.28 mmol), THF (3 mL), and NaH (28 mg, 0.70 mmol). The reaction was stirred at room temperature for 18 hours, 50° C. for 4 hours, and then room temperature for 3 days. To the reaction was added 5 mL of water and the product was extracted with EtOAc. The organics were washed with brine and then dried over $Na_2SO_4$. The residue was purified by flash column chromatography eluting with 20%-50% acetone/hexanes. The free base which was obtained was dissolved in 1 mL of 4N HCl/dioxane and then concentrated. Compound P-465 was obtained as a tan solid (24.1 mg, 19% for 2 steps). $^1$H NMR (400 MHz, DMSO-$d_6$) 8.52 (s, 1H), 7.77 (br. s., 1H), 7.49-7.32 (m, 6H), 7.27 (br s, 1H), 6.96 (d, J=8.6 Hz, 1H), 4.47 (s, 2H), 4.35-4.24 (m, 2H), 4.01 (s, 2H), 3.73 (s, 3H), 3.57-3.50 (m, 2H) ppm. LC/MS=100.0%, 427.1 (APCI+).

Example 271

Preparation of P-521

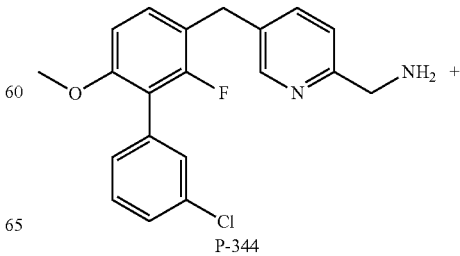

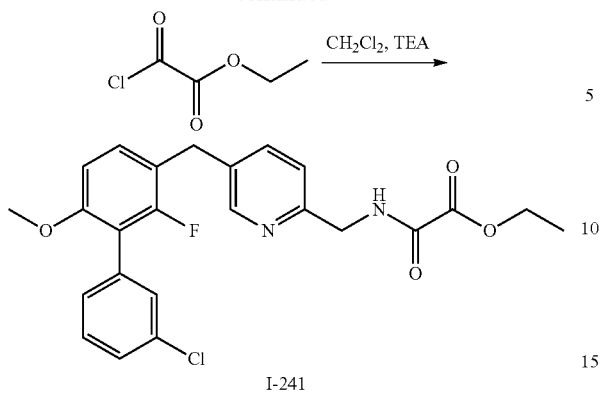

N-[5-(3'-Chloro-2-fluoro-6-methoxy-biphenyl-3-ylmethyl)-pyridin-2-ylmethyl]-oxalamic acid ethyl ester (I-241). Into an 18 mL vial was added P-344 (152 mg, 0.43 mmol), TEA (0.11 mL, 0.85 mmol), and dichloromethane (4 mL). The solution was cooled to 0° C. and ethyl chlorooxoacetate (71 uL, 0.64 mmoL) was added. After 20 minutes at room temperature the reaction was washed with brine and the organics were concentrated.

The semi-solid was triturated with 1:1 ether:EtOAc, filtered, and washed with EtOAc to provide I-241 (69 mg, 35%) as a gray-blue solid. $^1$H NMR (400 MHz, DMSO-$d_6$) 9.38 (t, J=6.0 Hz, 1H), 8.41 (s, 1H), 7.59 (dd, J=4.0, 8.0 Hz, 2H), 7.48-7.25 (m, 8H), 7.22 (d, J=8.1 Hz, 2H), 6.94 (d, J=8.6 Hz, 2H), 4.39 (d, J=6.0 Hz, 2H), 4.32-4.18 (m, 2H), 3.94 (s, 2H), 3.72 (s, 3H), 1.27 (t, J=7.1 Hz, 3H) ppm. LC/MS=97.9%, 457.0 (APCI+).

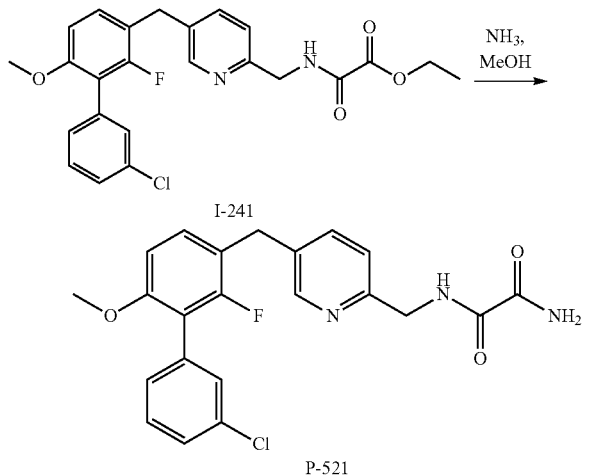

N-[5-(3'-Chloro-2-fluoro-6-methoxy-biphenyl-3-ylmethyl)-pyridin-2-ylmethyl]-oxalamide (P-521). Into an 8 mL vial was added I-241 (14.8 mg, 0.032 mmol) and 2 mL of 7N NH$_3$/MeOH. After stirring for 1 hour at room temperature, the solution was concentrated to afford P-521 (11.9 mg, 87%) as a tan solid. $^1$H NMR (400 MHz, DMSO-$d_6$) 9.15 (t, 1H), 8.41 (d, J=1.5 Hz, 1H), 8.08 (br s, 1H), 7.82 (br s, 1H), 7.59 (dd, J=1.9, 8.1 Hz, 1H), 7.48-7.25 (m, 5H), 7.19 (d, J=8.1 Hz, 1H), 6.94 (d, J=8.6 Hz, 1H), 4.39 (d, J=6.2 Hz, 2H), 3.94 (s, 2H), 3.72 (s, 3H) ppm. LC/MS=98.9%, 428.0 (APCI+).

Example 272

Preparation of I-145

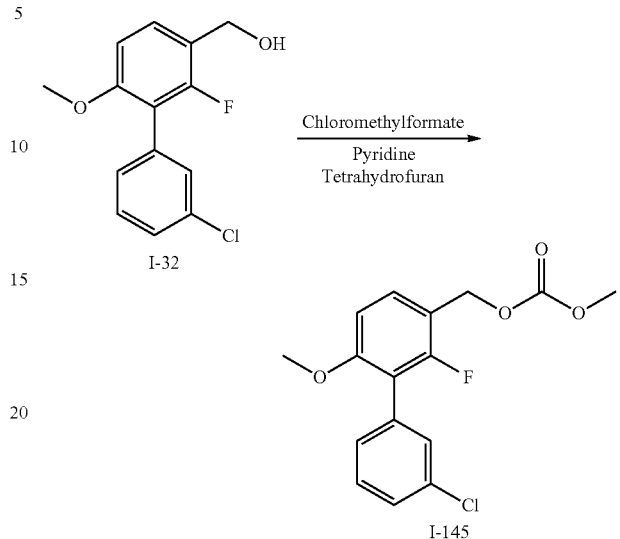

Synthesis of Carbonic acid 3'-chloro-2-fluoro-6-methoxy-biphenyl-3-ylmethyl ester methyl ester (I-145). A solution of (3'-Chloro-2-fluoro-6-methoxy-biphenyl-3-yl)-methanol (I-32, 3.00 g, 11.3 mmol) in pyridine (2.31 g, 29.3 mmol) and tetrahydrofuran (40 mL) was cooled to 0° C. in an ice water bath. The reaction vessel was purged with nitrogen and methyl chloroformate (2.34 g, 24.8 mmol) was added. The ice bath was removed and the reaction was stirred at room temperature overnight. The white suspension was adjusted to pH 2 by addition of 1 N aqueous hydrochloric acid (~25 mL) and the yellow biphasic solution was diluted with dichloromethane (200 mL) and water (150 mL). The layers were separated, and the aqueous layer was extracted with dichloromethane (2×100 mL). The dichloromethane extracts were combined, washed with water (2×200 mL) and brine (200 mL), dried over sodium sulfate, filtered, and the solvent removed under vacuum to give I-145 (3.84 g, quantitative yield).

$^1$H NMR (400 MHz, CDCl$_3$) 7.41-7.32 (m, 4H), 7.29-7.26 (m, 1H), 6.76 (dd, J=8.40 Hz, 0.80 Hz, 1H), 5.204 (s, 2H), 3.800 (s, 3H), 3.795 (s, 3H) ppm.

LCMS=98.2% purity. MS (APCI+)=249.0 (M−78), MS (APCI−)=249.0 (M−78).

Example 273

Preparation of P-376

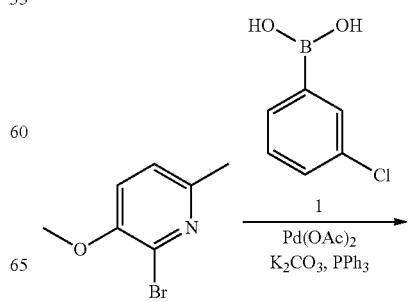

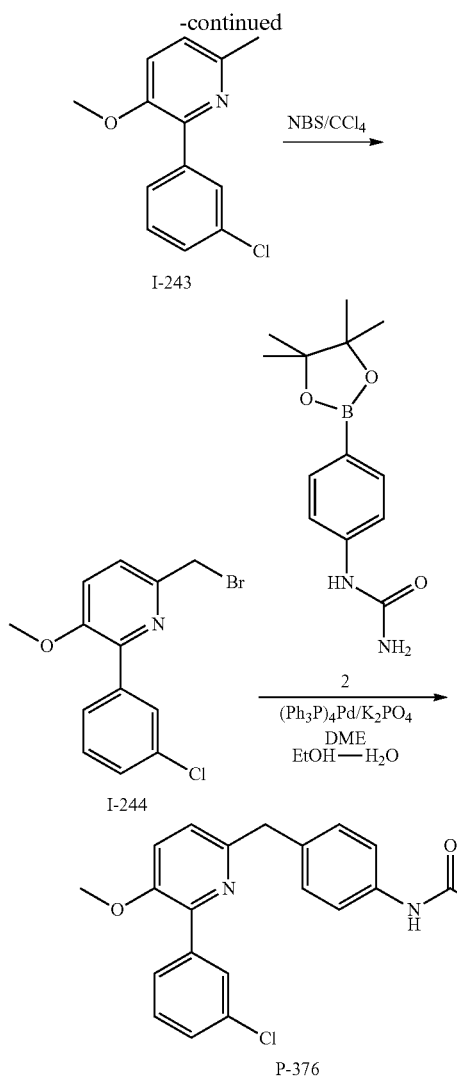

I-243

I-244

P-376

Synthesis of {4-[6-(3-chloro-phenyl)-5-methoxy-pyridin-2-ylmethyl]-phenyl}-urea (P-376). To I-244 (0.31 g, 1.0 mmol), [4-(4,4,5,5-Tetramethyl-[1,3,2]dioxaborolan-2-yl)-phenyl]-urea (0.39 g, 1.5 mmol), (PPh$_3$)$_4$Pd (0.12 g, 0.1 mmol) and K$_3$PO$_4$ (0.42 g, 2.0 mmol) was added DME (8 mL), and EtOH—H$_2$O (1:1, 4 mL). Ar gas was bubbled through the stirred reaction for 5 min. The reaction was stirred at 160° C. for 20 m using microwave oven (Biotage Intiator II). The reaction was cooled to room temperature, concentrated and H$_2$O and dichloromethane (50 mL each) were added. The organic layer was separated and the aqueous layer was extracted with dichloromethane (2×25 mL). The combined organic extracts were dried with Na$_2$SO$_4$, filtered, and concentrated. The residue was purified by silica gel column chromatography using 3-5% methanol in dichloromethane than triturated with 1:1 ethyl acetate in hexanes to afford 0.023 g (6%) of P-376 as off-white solid. $^1$H NMR (DMSO-d$_6$, 400 MHz): 8.42 (s, 1H), 7.84-7.93 (m, 2H), 7.4-7.54 (m, 3H), 7.3 (d, J=8.4 Hz, 2H), 7.22 (d, J=8.4 Hz, 1H), 7.14 (d, J=8.0 Hz, 2H), 5.77 (s, 2H), 3.99 (s, 2H), 3.83 (s, 3H) ppm; MS (APCI+): 368.0 (M+1), LC-MS: 92.5%.

Example 274

Preparation of P-379

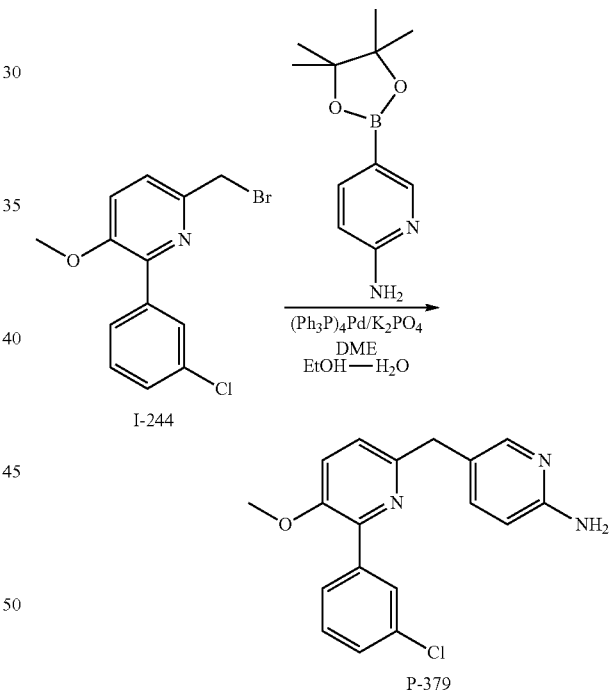

I-244

P-379

Synthesis of 2-(3-chloro-phenyl)-3-methoxy-6-methyl-pyridine (I-243): To 2-bromo-3-methoxy-6-methylpyridine (0.2 g, 1.0 mmol), 3-chlorophenylboronic acid (1) (0.19 g, 1.2 mmol), PPh$_3$ (0.13 g, 0.5 mmol), K$_2$CO$_3$ (0.06 g, 0.4 mmol) and Pd(OAc)$_2$ (0.03 g, 0.12 mmol) was added dioxane (3 mL), and EtOH—H$_2$O (1:1, 1.5 mL). Ar gas was bubbled through the stirred reaction for 5 min. The reaction was stirred at 180° C. for 15 m using microwave oven (Biotage Intiator II). The reaction was cooled to room temperature, concentrated, and H$_2$O and dichloromethane (40 mL each) were added. The organic layer was separated and the aqueous layer was extracted with dichloromethane (2×25 mL). The combined organic extracts were dried with Na$_2$SO$_4$, filtered, and concentrated. The residue was purified by silica gel column chromatography using 1:1 dichloromethane-hexanes then dichloromethane to afford 0.19 g (81%) of I-243 as a viscous liquid.

Synthesis of 6-bromomethyl-2-(3-chloro-phenyl)-3-methoxy-pyridine (I-244). To I-243 (1.02 g, 4.36 mmol) and NBS (0.78 g, 4.36 mmol) in CCl$_4$ (20 mL) was added benzoylperoxide (0.03 g, 0.12 mmol). The reaction was stirred at 80° C. under N$_2$ for 20 h. The reaction was cooled to room temperature and concentrated. The residue was dissolved in mixture of dichloromethane and hexanes (1:1, 8 mL) and purified by silica gel column chromatography using 1:1 dichloromethane-hexanes to afford 0.83 g (61%) of I-244 as a viscous liquid.

Synthesis of 5-[6-(3-chloro-phenyl)-5-methoxy-pyridin-2-ylmethyl]-pyridin-2-ylamine (P-379) To I-244 (0.1 g, 0.32 mmol), 5-(4,4,5,5-tetramethyl[1,3,2]dioxaborolan-2-yl)-pyridin-2-ylamine (0.08 g, 0.38 mmol), (PPh$_3$)$_4$Pd (0.04 g, 0.03 mmol) and K$_3$PO$_4$ (0.14 g, 0.64 mmol) was added DME (3 mL), and EtOH—H$_2$O (1:1, 1.54 mL). Ar gas was bubbled through the stirred reaction for 5 min. The reaction was stirred at 150° C. for 20 m using microwave oven (Biotage Intiator II). The reaction was cooled to room temperature, concentrated. The residue was purified by prep TLC using 70% ethyl acetate in hexanes to afford 0.06 g (55%) of P-379 as a viscous liquid. 1H NMR (CDCl$_3$, 400 MHz): 8.03 (d, J=1.6 Hz, 1H), 7.93-4-7.96 (m, 1H), 7.82-7.86 (m, 1H), 7.34-7.58

(m, 3H), 7.2 (d, J=8.4 Hz, 1H), 7.02 (d, J=8.8 Hz, 1H), 6.47 (dd, J=8.4, 0.8 Hz, 1H), 4.35 (s, 2H), 4.01 (s, 2H), 3.84 (s, 3H) ppm; MS (APCI+): 326.1 (M+1), LC-MS: 100%.

Example 275

Preparation of P-386

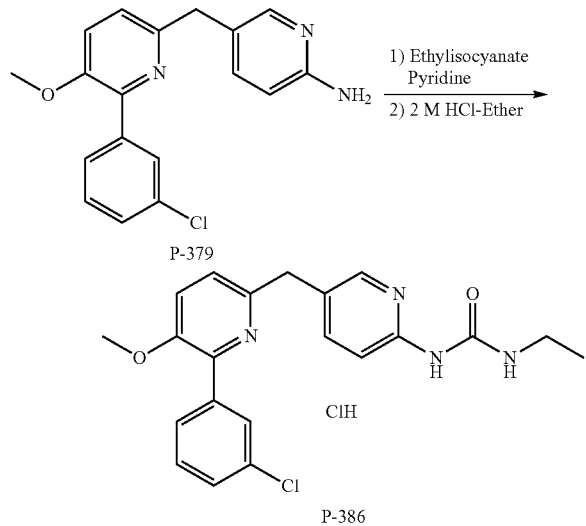

Synthesis of 1-{5-[6-(3-chloro-phenyl)-5-methoxy-pyridin-2-ylmethyl]-pyridin-2-yl}-3-ethyl-urea hydrochloride (P-386). To P-379 (0.05 g, 0.15 mmol) in pyridine (1.5 mL) was added ethylisocyanate (0.033 g, 0.46 mmol). The reaction was stirred at room temperature for 20 h. Water and ethyl acetate (20 mL each) were added. The organic layer was separated and the aqueous layer was extracted with ethyl acetate (2×10 mL). The combined organic extracts were washed with water (2×30 mL), brine (20 mL), dried with Na₂SO₄, filtered, and concentrated. The residue was dissolved in ether (2 mL), then 2M HCl in ether (0.5 ml) was added, stirred for 1 h. The ether layer was decanted, triturated with ether (2×2 mL), dried to afford 0.045 g (68%) of P-386 as light yellow solid. ¹H NMR (DMSO-d₆, 400 MHz): 10.03 (br s, 1H), 7.84-7.9 (m, 3H), 7.76 (br s, 1H), 7.58 (d, J=8.8 Hz, 1H), 7.44-7.5 (m, 2H), 7.34 (d, J=8.4 Hz, 1H), 7.30 (d, J=8.8 Hz, 1H), 4.08 (s, 2H), 3.85 (s, 3H), 3.15-3.23 (m, 2H), 1.08 (t, J=7.2 Hz, 3H) ppm; MS (APCI+): 397.1 (M+1), LC-MS: 99%, HPLC 97.9% pure.

Example 276

Preparation of P-099

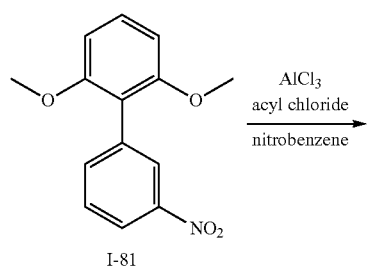

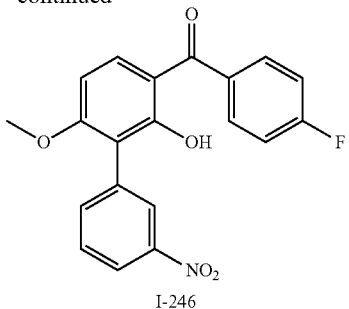

Synthesis of (4-Fluoro-phenyl)-(2-hydroxy-6-methoxy-3'-nitro-biphenyl-3-yl)-methanone (I-246). In an 8 mL vial equipped with a stir bar was placed nitrobenzene (1.0 mL) and AlCl₃ (92.7 mg, 0.695 mmol). After stirring for 5 minutes, 4-fluorobenzoyl chloride (83.2 µL, 0.695 mmol) was added and the mixture was allowed to stir for 1 hour at room temperature. Then, I-81 (150 mg, 0.579 mmol) was added and the reaction mixture was stirred at room temperature for 19 hours. The reaction mixture as quenched with water (25 mL) and extracted with EtOAc (2×30 mL). The extractions were combined, washed with brine (30 mL), dried (MgSO₄) and concentrated to a yellow solid. The crude material was triturated with Et₂O (5 mL) and the solid was collected by suction filtration. After the solid was washed with Et₂O, 64.5 mg of I-246 was isolated as a light yellow solid in 30% yield. MS (APCI-): 366.0 (M-1)

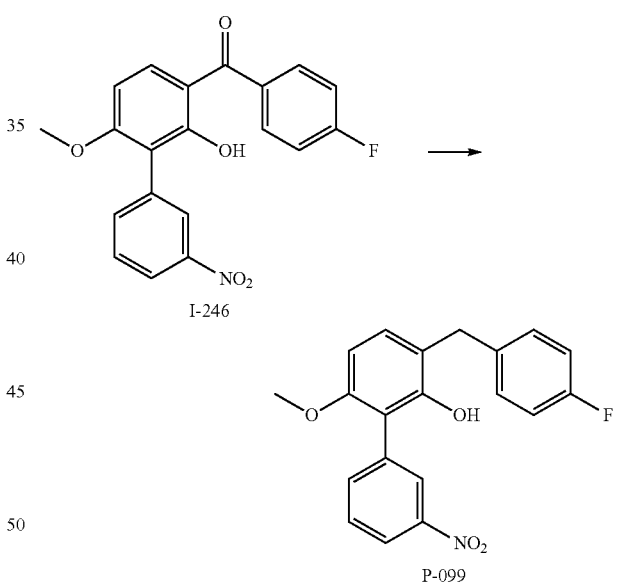

Synthesis of 3-(4-Fluoro-benzyl)-6-methoxy-3'-nitro-biphenyl-2-ol (P-099) In an 8 mL vial equipped with a stir bar was placed I-246 (60 mg, 0.163 mmol) and triethylsilane (350 µL). The mixture was cooled in an ice-water bath and then TFA (350 µL) was added. The reaction mixture was warmed to room temperature and reacted for 17 hours. After this time period, additional triethylsilane (1.1 mL) and TFA (1.1 mL) was introduced and the reaction mixture was heated to 60° C. in an oil bath for 24 hours. The reaction mixture was concentrated by a stream of N₂, quenched with water (20 mL) and extracted with dichloromethane (2×30 mL). The organic portions were combined, washed with brine (30 mL), dried (MgSO₄) and concentrated. The residue was purified by SiO₂ column chromatography utilizing 15% EtOAc/hexanes as the eluent to produce 18.9 mg of P-099 as a viscous, tan oil in 33% yield. $^1$H NMR (400 MHz, CDCl$_3$) δ 3.72 (s, 3H), 3.94 (s, 2H), 4.73 (s, 1H), 6.55 (d, J=8 Hz, 1H), 6.96-7.00 (m, 2H), 7.01 (d, J=8 Hz, 1H), 7.19-7.22 (m, 2H), 7.63 (t, J=7 Hz, 1H), 7.69 (dt, J=8, 2 Hz, 1H), 8.22-8.26 (m, 2H) ppm. MS (APCI−): 352.1 (M−1); LC-MS: 98%.

Example 277

Preparation of P-137

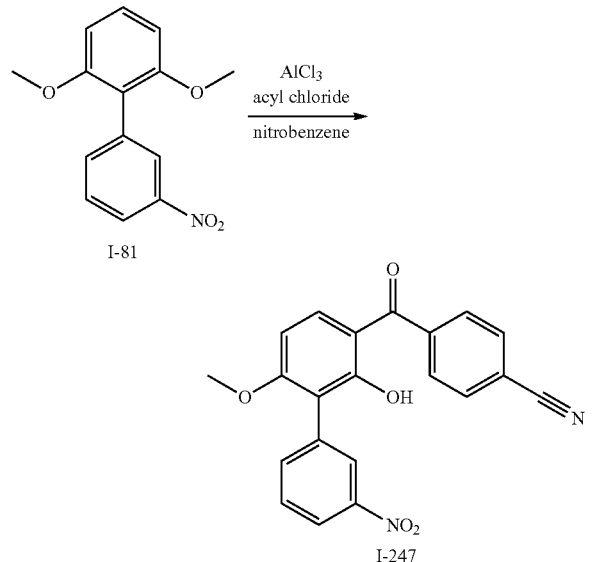

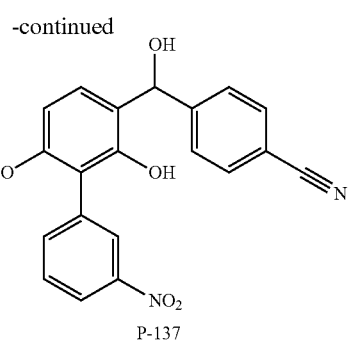

Synthesis of 4-[Hydroxy-(2-hydroxy-6-methoxy-3'-nitro-biphenyl-3-yl)-methyl]benzonitrile (P-137). In an 8 mL vial equipped with a stir bar was placed I-247 (20 mg, 0.0534 mmol), absolute EtOH (300 μL), anhydrous THF (400 μL) followed by NaBH$_4$ (40.5 mg, 1.07 mmol). The reaction mixture was stirred at room temperature for 17 hours. The reaction was quenched with water (20 mL) and extracted with dichloromethane (2×30 mL). The organic portions were combined, washed with brine (30 mL), dried (MgSO$_4$) and concentrated to produce 12.0 mg of P-137 as an off-white solid in 63% yield. $^1$H NMR (400 MHz, CDCl$_3$) δ 3.01 (d, J=3 Hz, 1H), 3.74 (s, 3H), 6.08 (m, 1H), 6.55 (d, J=8 Hz, 1H), 6.99 (d, J=9 Hz, 1H), 7.13 (s, 1H), 7.54 (d, J=8 Hz, 2H), 7.59 (t, J=8 Hz, 1H), 7.67 (d, J=8 Hz, 2H), 7.69-7.72 (m, 1H), 8.19-8.22 (m, 1H), 8.26-8.27 (m, 1H) ppm. MS (APCI−) δ 375.1 (M−1).

Example 278

Preparation of P-138

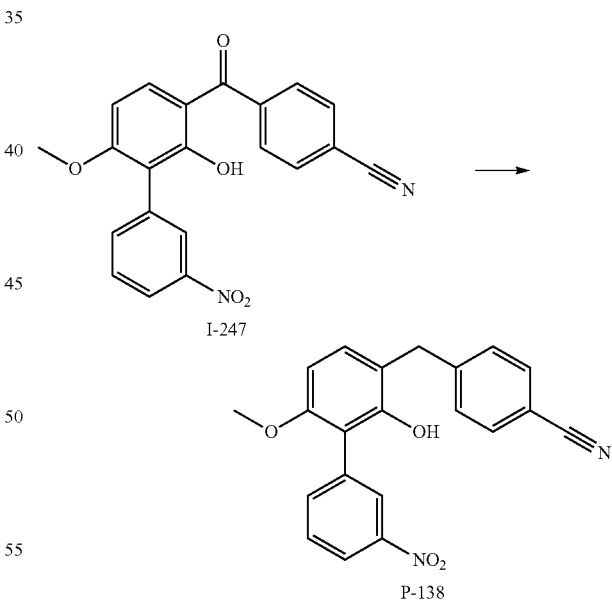

Synthesis of 4-(2-Hydroxy-6-methoxy-3'-nitro-biphenyl-3-carbonyl)-benzonitrile (I-247). In an 8 mL vial equipped with a stir bar was placed nitrobenzene (2.0 mL) and AlCl$_3$ (515 mg, 3.86 mmol). After stirring for 5 minutes, 4-cyanobenzoyl chloride (83.2 μL, 0.695 mmol) was added and the mixture was allowed to stir for 30 minutes at room temperature. Then, I-81 (200 mg, 0.771 mmol) was added and the reaction mixture was stirred at 60° C. for 17 hours. The reaction was quenched with 1M HCl (4 mL), water was added (20 mL) and then extracted with dichloromethane (2×30 mL). The organic portions were combined, washed with brine (30 mL), dried (MgSO$_4$) and concentrated. The material began to solidify which was increased by the addition of hexanes (4 mL). The solid was collected by suction filtration, washed with hexanes (3×1 mL) to produce 147 mg of I-247 as a light yellow solid in 51% yield. MS (APCI−): 373.1 (M−1); LC-MS: 91%.

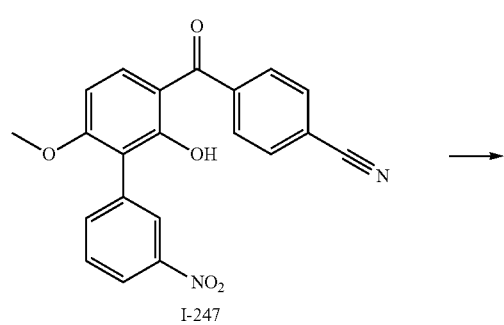

Synthesis of 4-(2-Hydroxy-6-methoxy-3'-nitro-biphenyl-3-ylmethyl)-benzonitrile (P-138). In an 8 mL vial equipped with a stir bar was placed I-247 (60 mg, 0.160 mmol) and triethylsilane (600 μL). The reaction mixture was cooled in an ice-water bath and then TFA (600 μL) was added. The mixture was heated to 70° C. for 23 hours. The reaction mixture was concentrated by a stream of N$_2$ followed by the addition of water (20 mL) and extraction with dichloromethane (2×30 mL). The organic portions were combined, washed with brine (30 mL), dried (MgSO$_4$) and concentrated. The residue was purified by SiO$_2$ column chromatography utilizing 25% EtOAc/hexanes as the eluent to produce 21.9 mg of P-138 as a pale yellow solid in 38% yield). $^1$H NMR (400 MHz, CDCl$_3$) δ 3.72 (s, 3H), 4.02 (s, 2H), 4.77 (s, 1H), 6.56 (d, J=8 Hz, 1H), 7.11 (d, J=8 Hz, 1H), 7.35 (d, J=9 Hz, 2H), 7.57 (d, J=8 Hz, 2H), 7.64-7.70 (m, 2H), 8.24-8.27 (m, 2H) ppm. MS (APCI–): 359.1 (M–1), LC-MS: >99%.

Example 279

Preparation of P-157

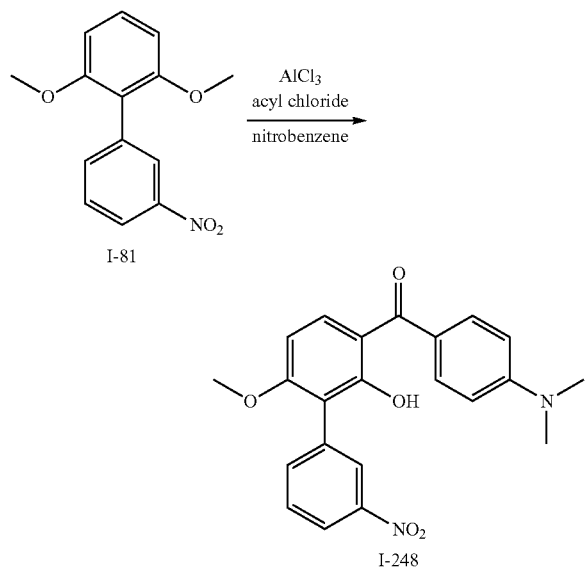

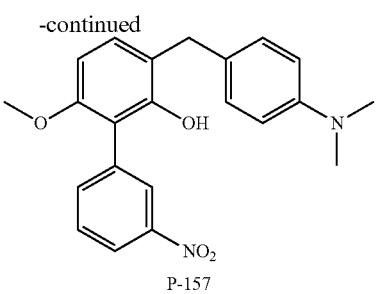

Synthesis of 3-(4-Dimethylamino-benzyl)-6-methoxy-3'-nitro-biphenyl-2-ol (P-157). In an 8 mL vial equipped with a stir bar was placed I-248 (165 mg, 0.420 mmol) and triethylsilane (1.6 mL). The reaction mixture was cooled in an ice-water bath and then TFA (1.6 mL) was added. The mixture was heated to 65° C. for 17 hours. The reaction mixture was concentrated by a stream of N$_2$ followed by the addition of water (25 mL) and extraction with dichloromethane (2×30 mL). The organic portions were combined, washed with brine (30 mL), dried (MgSO$_4$) and concentrated. The residue was purified by SiO$_2$ column chromatography utilizing 50% EtOAc/hexanes as the eluent to produce 52.4 mg of P-157 as a orange-red viscous oil in 33% yield. $^1$H NMR (400 MHz, CDCl$_3$) δ 2.91 (s, 6H), 3.73 (s, 3H), 3.90 (s, 2H), 4.86 (s, 1H), 6.55 (d, J=8 Hz, 1H), 6.69 (2, J=9 Hz, 2H), 7.11-7.15 (m, 3H), 7.57 (t, J=8 Hz, 1H), 7.70 (d, J=8 Hz, 1H), 8.17-8.20 (m, 1H), 8.25 (s, 1H) ppm. MS (APCI+): 379.1 (M+1); LC-MS: >99%.

Example 280

Preparation of P-173

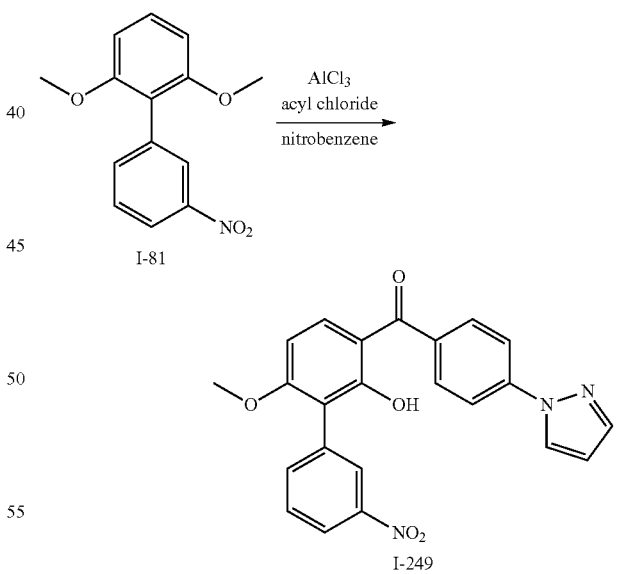

Synthesis of (4-Dimethylamino-phenyl)-(2-hydroxy-6-methoxy-3'-nitro-biphenyl-3-yl)-methanone (I-248). In an 8 mL vial equipped with a stir bar was placed nitrobenzene (2.5 mL) and AlCl$_3$ (773 mg, 5.80 mmol). After stirring for 5 minutes, 4-dimethylamino-benzoyl chloride (533 mg, 2.90 mmol) was added and the mixture was allowed to stir for 30 minutes at room temperature. Then, I-81 (300 mg, 1.16 mmol) was added and the reaction mixture was stirred at 60° C. for 23 hours. The reaction was quenched with 1M HCl (4 mL), water was added (20 mL) and then extracted with dichloromethane (2×30 mL). The organic portions were combined, washed with brine (30 mL), dried (MgSO$_4$) and concentrated. The residue was purified by SiO$_2$ column chromatography utilizing 10% EtOAc/hexanes as the eluent to produce 167 mg of I-248 as a yellow solid in 37% yield.

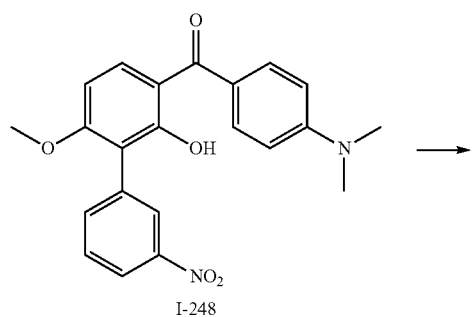

Synthesis of (2-Hydroxy-6-methoxy-3'-nitro-biphenyl-3-yl)-(4-pyrazol-1-yl-phenyl)-methanone (I-249). In an 8 mL vial equipped with a stir bar was placed nitrobenzene (2.4 mL) and AlCl$_3$ (515 mg, 3.86 mmol). After stirring for 5 minutes, 4-pyrazol-1-yl-benzoyl chloride (318 mg, 1.54 mmol) was added and the mixture was allowed to stir for 45 minutes at room temperature. Then, I-81 (250 mg, 0.964 mmol) was added and the reaction mixture was stirred at 60° C. for 17 hours. The reaction was quenched with 1M HCl (10 mL), water was added (15 mL) and then extracted with dichloromethane (2×30 mL). The organic portions were combined, washed with brine (30 mL), dried (MgSO$_4$) and concentrated. The residue was purified by SiO$_2$ column chromatography utilizing 50% EtOAc/hexanes as the eluent to produce 257 mg of I-249 as a yellow solid in 64% yield.

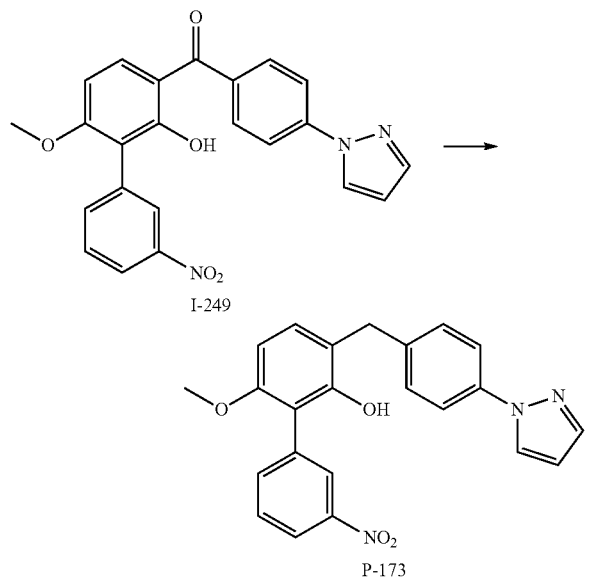

Synthesis of 6-Methoxy-3'-nitro-3-(4-pyrazol-1-yl-benzyl)-biphenyl-2-ol (P-173). In an 8 mL vial equipped with a stir bar was placed I-249 (150 mg, 0.361 mmol) and triethylsilane (1.3 mL, 8.14). The reaction mixture was cooled in an ice-water bath and then TFA (1.3 mL, 17.5 mmol) was added. The mixture was heated to 70° C. for 16 hours. The reaction mixture was concentrated by a stream of N$_2$ followed by the addition of water (20 mL) and extraction with dichloromethane (2×30 mL). The organic portions were combined, washed with brine (30 mL), dried (MgSO$_4$) and concentrated. The residue was purified by SiO$_2$ column chromatography utilizing 20% EtOAc/hexanes as the eluent to produce 105 mg of P-173 as a yellow viscous oil in 33% yield. $^1$H NMR (400 MHz, CDCl$_3$) δ 3.73 (s, 3H), 4.01 (s, 2H), 4.79 (s, 1H), 6.44-6.45 (m, 1H), 6.56 (d, J=8 Hz, 1H), 7.13 (d, J=8 Hz, 1H), 7.33 (d, J=8 Hz, 2H), 7.60-7.65 (m, 3H), 7.69-7.71 (m, 2H), 7.88 (d, J=3 Hz, 1H), 8.22-8.23 (m, 1H), 8.24-8.26 (m, 1H) ppm.

MS (APCI+): 402.1 (M+1); LC-MS: >99%.

Example 281

Preparation of P-174

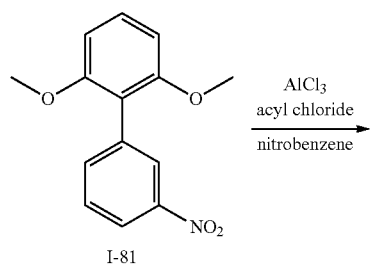

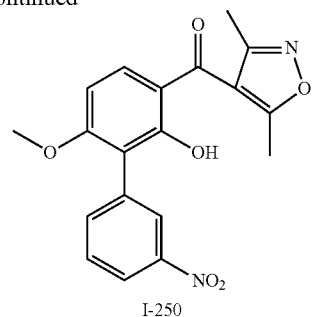

Synthesis of [4-(3,5-Dimethyl-isoxazol-4-yl)-phenyl]-(2-hydroxy-6-methoxy-3'-nitro-biphenyl-3-yl)-methanone (I-250) In an 8 mL vial equipped with a stir bar was placed nitrobenzene (2.4 mL) and AlCl$_3$ (515 mg, 3.86 mmol). After stirring for 5 minutes, 3,5-dimethyl-isoxazole-4-carbonyl chloride (246 mg, 1.54 mmol) was added and the mixture was allowed to stir for 45 minutes at room temperature. Then, I-81 (250 mg, 0.964 mmol) was added and the reaction mixture was stirred at 60° C. for 17 hours. The reaction was quenched with 1M HCl (10 mL), water was added (15 mL) and then extracted with dichloromethane (2×30 mL). The organic portions were combined, washed with brine (30 mL), dried (MgSO$_4$) and concentrated. The residue was purified by SiO$_2$ column chromatography utilizing 50% EtOAc/hexanes as the eluent to produce 194 mg of I-250 as a light brown solid in 55% yield.

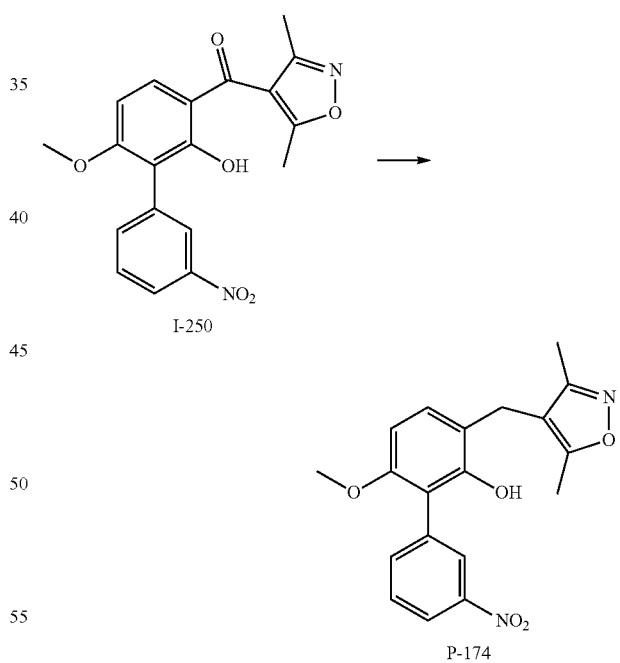

Synthesis of 3-[4-(3,5-Dimethyl-isoxazol-4-yl)-benzyl]-6-methoxy-3'-nitro-biphenyl-2-ol (P-174). In an 8 mL vial equipped with a stir bar was placed TFA (114 μL, 1.22 mmol) and anhydrous dichloromethane (450 μL). The solution was cooled to about −40 to −50° C. in an acetone-dry ice bath. Then NaBH$_4$ (46.2 mg, 1.22 mmol) was added portion wise over 5 minutes. The reaction mixture was warmed to 0° C. in an ice-water bath and then a solution of I-250 (45 mg, 0.122 mmol) in anhydrous dichloromethane (450 μL) was added drop wise over 5 minutes. The reaction mixture was warmed to room temperature and reacted for 18 hours. The reaction mixture was slowly quenched with water (20 mL) and extracted with dichloromethane (2×30 mL). The organic portions were combined, washed with brine (30 mL), dried (MgSO$_4$) and concentrated. The residue was purified by SiO$_2$ column chromatography utilizing 30% EtOAc/hexanes as the eluent to produce 16.9 mg of P-174 as a pale yellow viscous oil in 39% yield.

$^1$H NMR (400 MHz, CDCl$_3$) δ 2.16 (s, 3H), 2.32 (s, 3H), 3.62 (s, 2H), 3.71 (s, 3H), 4.84 (s, 1H), 6.51 (d, J=7 Hz, 1H), 6.95 (d, J=7 Hz, 1H), 7.66-7.70 (m, 2H), 8.24-8.28 (m, 2H) ppm. MS (APCI+): 355.1 (M+1); LC-MS: >99%.

Example 282

Preparation of P-180

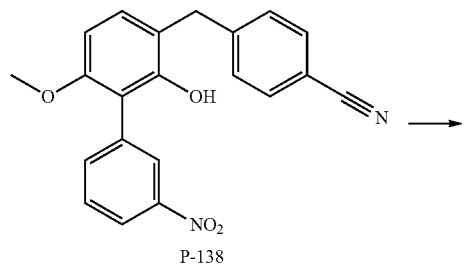

Synthesis of 4-(2-Hydroxy-6-methoxy-3'-nitro-biphenyl-3-ylmethyl)-benzaldehyde (P-180). In an 8 mL vial equipped with a stir bar was placed P-138 (105 mg, 0.291 mmol) and anhydrous THF (950 µL). The solution was cooled in an ice-water bath for 10 minutes and then DIBAL-H (1.0M in hexanes, 1.46 mL, 1.46 mmol) was added. The reaction mixture was warmed to room temperature and reacted for 17 hours. The reaction was cooled in an ice-water bath, quenched slowly with 1M HCl (4 mL) followed by the addition of water (20 mL) and extraction with dichloromethane (2×30 mL). The organic portions were combined, washed with brine (30 mL), dried (MgSO$_4$) and concentrated. The residue was purified by SiO$_2$ column chromatography utilizing 25% EtOAc/hexanes as the eluent to produce 32.4 mg of P-180 as an off-white solid in 31% yield. $^1$H NMR (400 MHz, CDCl$_3$) δ 3.72 (s, 3H), 4.05 (s, 2H), 4.76 (s, 1H), 6.57 (d, J=8 Hz, 1H), 7.13 (d, J=8 Hz, 1H), 7.42 (d, J=8 Hz, 2H), 7.63-7.70 (m, 2H), 7.81 (d, J=8 Hz, 2H), 8.24-8.26 (m, 2H), 9.97 (s, 1H) ppm. MS (APCI−): 362.1 (M−1); LC-MS: 99%.

Example 283

Preparation of P-183

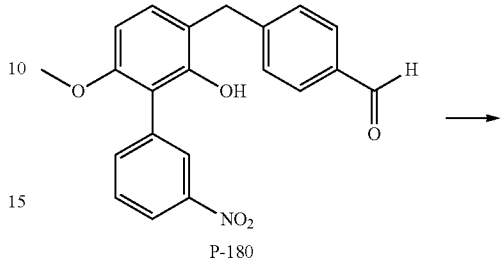

Synthesis of 3-(4-Hydroxymethyl-benzyl)-6-methoxy-3'-nitro-biphenyl-2-ol (P-183). In an 8 mL vial equipped with a stir bar was placed P-180 (23 mg, 0.0630 mmol) and anhydrous MeOH (250 µL). The mixture was cooled in an ice-water bath and then NaBH$_4$ (11.9 mg, 0.315 mmol) was added upon which the reaction mixture became a solution. The reaction was stirred for 22 hours at room temperature, quenched with 1M aqueous HCl (4 mL) and water (20 mL) and extracted with dichloromethane (2×30 mL). The organic portions were combined, washed with brine (30 mL), dried (MgSO$_4$) and concentrated. The residue was purified by SiO$_2$ column chromatography utilizing 50% EtOAc/hexanes as the eluent to produce 15.1 mg of P-183 as an orange viscous oil in 65% yield. $^1$H NMR (400 MHz, CDCl$_3$) δ 3.72 (s, 3H), 3.98 (s, 2H), 4.67 (s, 2H), 4.74 (s, 1H), 6.55 (d, J=9 Hz, 1H), 7.13 (d, J=9 Hz, 1H), 7.24-7.32 (m, 4H), 7.62 (t, J=8 Hz, 1H), 7.68-7.71 (m, 1H), 8.21-8.25 (m, 2H) ppm. MS (APCI+): 348.1 (M−17); LC-MS: >99%.

Example 284

Preparation of P-190

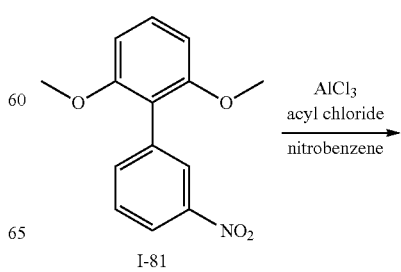

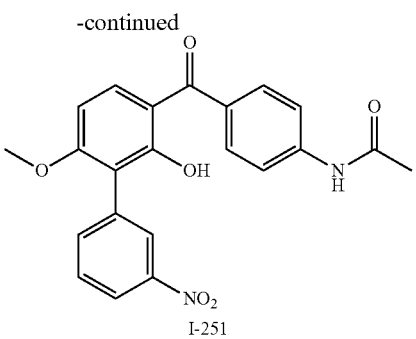

I-251

Synthesis of N-[4-(2-Hydroxy-6-methoxy-3'-nitro-biphenyl-3-carbonyl)-phenyl]-acetamide (I-251). In an 18 mL vial equipped with a stir bar was placed nitrobenzene (4.6 mL) and AlCl$_3$ (1.23 g, 9.24 mmol). After stirring for 5 minutes, 4-acetylamino-benzoyl chloride (913 mg, 4.62 mmol) was added and the mixture was allowed to stir for 30 minutes at room temperature. Then, I-81 (600 mg, 2.31 mmol) was added and the reaction mixture was stirred at 70° C. for 21 hours. The reaction was quenched with 1M aqueous HCl (10 mL), water was added (100 mL) and then extracted with dichloromethane (2×50 mL). The organic portions were combined, washed with brine (200 mL), dried (MgSO$_4$) and concentrated. The residue was triturated with Et$_2$O (35 mL), collected by suction filtration and washed with Et$_2$O (5×2 mL) to produce 333 mg of I-251 as a pale orange solid in 35% yield. MS (APCI+): 407.0 (M+1)

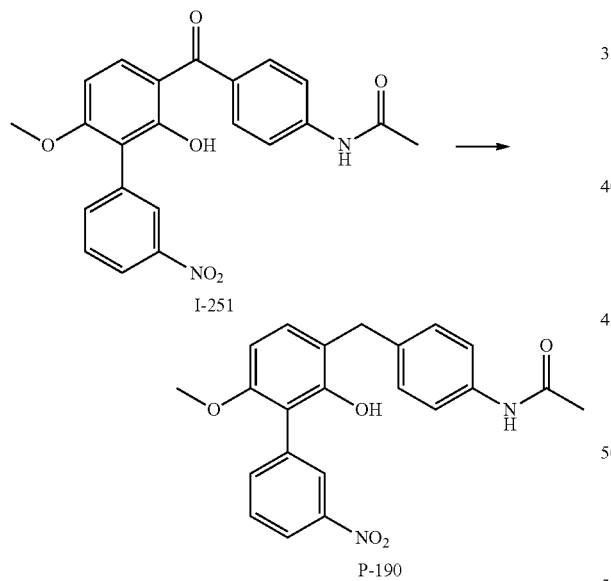

Synthesis of N-[4-(2-Hydroxy-6-methoxy-3'-nitro-biphenyl-3-ylmethyl)-phenyl]-acetamide (P-190). In an 8 mL vial equipped with a stir bar was placed I-251 (200 mg, 0.492 mmol) and triethylsilane (1.80 mL, 11.3). The reaction mixture was cooled in an ice-water bath and then TFA (1.80 mL, 24.6 mmol) was added. The mixture was heated to 70° C. for 18 hours. The reaction mixture was concentrated by a stream of N$_2$ followed by the addition of water (30 mL) and extraction with dichloromethane (2×30 mL). The organic portions were combined, washed with brine (30 mL), dried (MgSO$_4$) and concentrated. The crude material was purified by SiO$_2$ column chromatography utilizing 5% 1M NH$_3$ in MeOH/dichloromethane as the eluent to produce 36.6 mg of P-190 as a light yellow solid in 19% yield. $^1$H NMR (400 MHz, CDCl$_3$) δ 2.16 (s, 3H), 3.72 (s, 3H), 3.94 (s, 2H), 4.74 (s, 1H), 6.55 (d, J=9 Hz, 1H), 7.09 (bs, 1H), 7.7.11 (d, J=8 Hz, 1H), 7.20 (d, J=8 Hz, 2H), 7.42 (d, J=8 Hz, 2H), 7.62 (t, J=8 Hz, 1H), 7.68-7.70 (m, 1H), 8.21-8.25 (m, 2H) ppm. MS (APCI+): 393.1 (M+1); LC-MS: 93%.

Scheme 58.

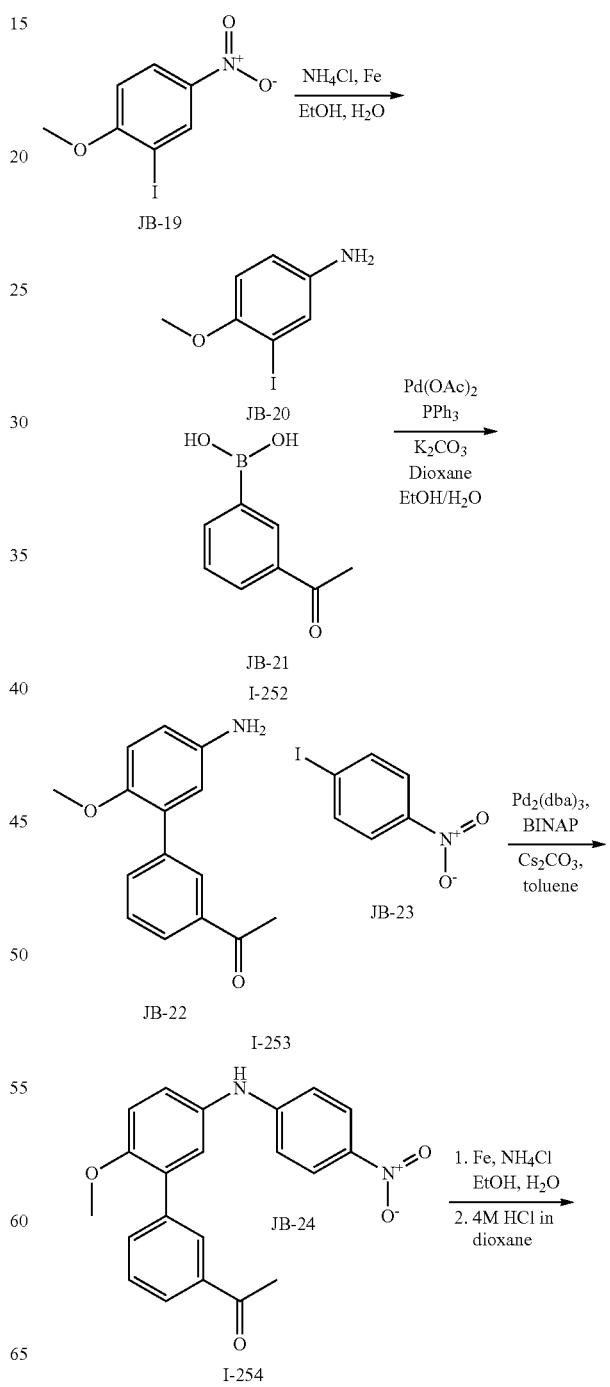

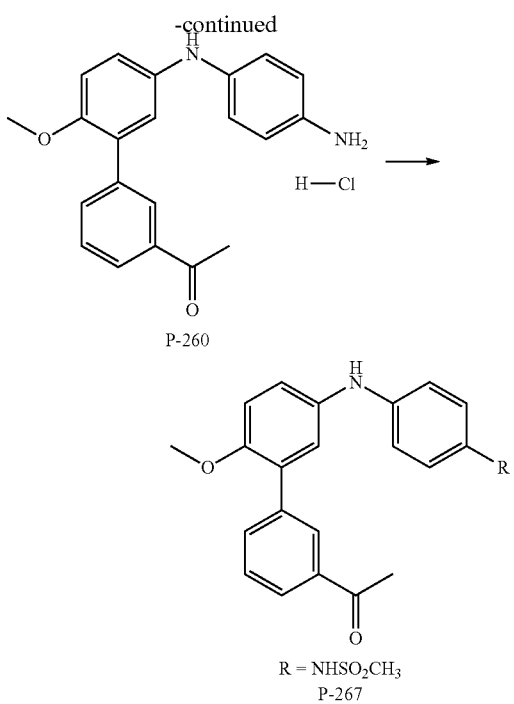

P-260

R = NHSO₂CH₃
P-267

Example 285

Preparation of P-260

Synthesis of 3-Iodo-4-methoxy-phenylamine (I-252). In a 3-neck 250 mL round-bottomed flask equipped with a stir bar, condenser and N₂ lines was placed iron powder (3.50 g, 62.7 mmol), ammonium chloride (4.88 g, 91.3 mmol), ethanol (72 mL) and water (23 mL). The mixture was heated to 85° C. and then 2-iodo-1-methoxy-4-nitro-benzene (5.0 g, 17.9 mmol) was added portion wise over a period of about 2 minutes. The mixture was allowed to stir at 85° C. for 2 hours and then filtered through Celite. The Celite was washed with EtOH (100 mL) and the filtrate was concentrated. To the concentrated material was added water (100 mL) and ethyl acetate (150 mL). The organic portion was removed and the aqueous portion was re-extracted with ethyl acetate (150 mL). The organic portions were combined, washed with brine (150 mL), dried (MgSO₄) and concentrated. The residue was purified by column chromatography utilizing 50% EtOAc/hexanes as the eluent to produce 3.92 g of I-252 as a brown semi-solid in 88% yield. MS (ESI+): 250.1 (M+1).

Synthesis of 1-(5'-Amino-2'-methoxy-biphenyl-3-yl)-ethanone (I-253). In a 3-neck 100 mL round-bottomed flask equipped with a condenser, stir bar and N2 lines was placed I-252 (2.92 g, 11.7 mmol), 3-acetylylphenylboronic acid (2.11 g, 12.9 mmol), potassium carbonate (4.85 g, 35.1 mmol), triphenylphosphine (921 mg, 3.51 mmol), 1,4-dioxane (23 mL), 50% aqueous ethanol (23 mL) followed by palladium (II) acetate (263 mg, 1.17 mmol). The mixture was heated to 90° C. for 16 hours and then cooled to room temperature. The palladium catalyst was removed via filtration and to the filtrate was added 1M aqueous HCl (50 mL) and water (50 mL). The aqueous portion was extracted with ethyl acetate (2×75 mL), the organic portions were combined, washed with brine (75 mL), dried (MgSO₄) and concentrated. The residue was purified by column chromatography utilizing 50% EtOAc/hexanes as the eluent to produce 1.18 g of I-253 as a pale orange oil in 42% yield. MS (APCI+): 242.0 (M+1).

Synthesis of 1-[2'-Methoxy-5'-(4-nitro-phenylamino)-biphenyl-3-yl]-ethanone (I-254). To a 40 mL vial equipped with a stir bar was placed 1-iodo-4-nitrobenzene (1.26 g, 5.07 mmol), cesium carbonate (2.20 g, 6.76 mmol), (±)-2,2'-bis (diphenylphosphino)-1,1'-binaphthalene (316 mg, 0.507 mmol), and a solution of I-253 (816 mg, 3.38 mmol) in toluene (13.5 mL). The mixture was stirred for 10 minutes and then tris(dibenzylideneacetone)dipalladium(0) (310 mg, 0.338 mmol) and the mixture was heated to 110° C. for 16 hours. The reaction was cooled to room temperature and then filtered through Celite. The filtrate was treated with water (40 mL), 1M HCl (40 mL) and then extracted with ethyl acetate (2×75 mL). The organic portions were combined, washed with brine (75 mL), dried (MgSO₄) and concentrated. The residue was purified by column chromatography utilizing 35% EtOAc/hexanes as the eluent to produce 277 mg of I-254 as a dark orange solid in 23% yield.

Synthesis of 1-[5'-(4-Amino-phenylamino)-2'-methoxy-biphenyl-3-yl]-ethanone hydrochloride (P-260). In an 18 mL vial equipped with a stir bar was placed iron powder (148 mg, 2.66 mmol), ammonium chloride (207 mg, 3.87 mmol), absolute EtOH (3.1 mL) and water (1.0 mL). The mixture was heated to 85° C. and then I-254 (275 mg, 0.759 mmol) was added and the mixture was heated for 2 hours. The reaction was cooled to room temperature, filtered through Celite and extracted with ethyl acetate (2×40 mL). The organic portions were combined, washed with brine (40 mL), dried (MgSO₄) and concentrated. The residue was purified by column chromatography utilizing 75% EtOAc/hexanes as the eluent to produce 207 mg of the free base as a dark orange oil in 82% yield. The free base was treated with 4.0 M HCl in 1,4-dioxane (1.0 mL) and stirred for 3 hours at room temperature. The reaction mixture was treated with diethyl ether (4 mL) and the solid was collected via suction filtration. After washing the solid with diethyl ether (3×2 mL), 20 mg of P-260 was isolated as a brown solid in 44% yield.

¹H NMR (400 MHz, DMSO-d₆) δ 2.61 (s, 3H), 3.75 (s, 3H), 4.63 (br s, 1H), 7.02-7.20 (m, 7H), 7.57 (t, J=8.0 Hz, 1H), 7.75 (d, J=8 Hz, 1H), 7.92 (d, J=8 Hz, 1H), 8.02 (t, J=2 Hz, 1H), 9.42 (br s, 3H) ppm. MS (APCI−): 366.9 (M−2)

Example 286

Preparation of P-267

Synthesis of N-[4-(3'-Acetyl-6-methoxy-biphenyl-3-ylamino)-phenyl]-methanesulfonamide (P-267). In an 8 mL vial equipped with a stir bar was placed P-260 (free base) (60.0 mg, 0.180 mmol), anhydrous dichloromethane (600 µL), pyridine (14.6 µL, 0.180 mmol), methanesulfonyl chloride (13.9 µL, 0.180 mmol). The reaction mixture was stirred at room temperature for 17 hours and then quenched with 1M aqueous HCl to pH 1-2. After adding water (20 mL), an extraction was performed with dichloromethane (2×30 mL), the organic portions were combined, washed with brine (30 mL), dried (MgSO₄) and concentrated. The residue was purified by column utilizing 10% acetone/dichloromethane as the eluent to produce 25 mg of P-267 as an off-white solid in 34% yield after drying in a high vacuum oven for 2 hours at 40° C.

¹H NMR (400 MHz, CDCl₃) δ 1.2.63 (s, 3H), 2.96 (s, 3H), 3.81 (s, 3H), 6.08 (br s, 1H), 6.91-6.98 (m, 3H), 7.11-7.14 (m, 4H), 7.51 (t, J=8 Hz, 1H), 7.72 (dt, J=8, 1 Hz, 1H), 7.92 (d, J=8 Hz, 1H), 8.10 (t, J=2 Hz, 1H) ppm. MS (APCI+): 411.1 (M+1) LC-MS: 97%.

Example 287

Preparation of P-261

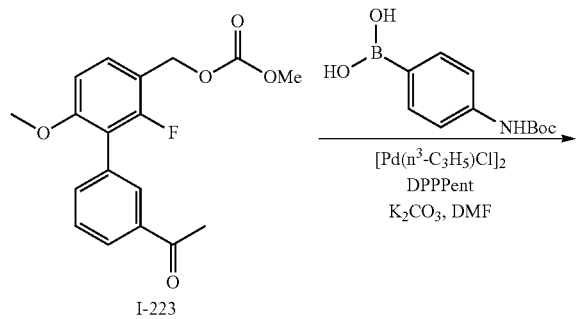

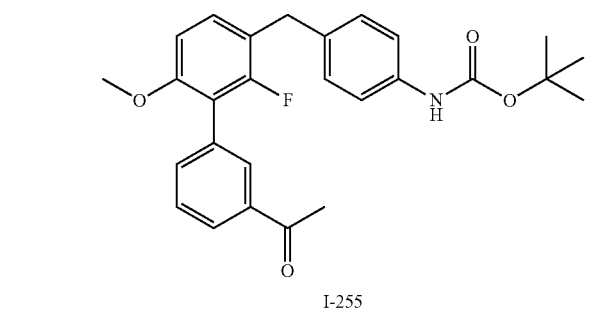

Synthesis of [4-(3'-Acetyl-2-fluoro-6-methoxy-biphenyl-3-ylmethyl)-phenyl]-carbamic acid tert-butyl ester (I-255). In an 8 mL vial equipped with a stir bar was placed I-223 (295 mg, 0.888 mmol), 4-[(tert-butoxycarbonyl)amino]-phenylboronic acid (232 mg, 0.977 mmol), potassium carbonate (270 mg, 1.95 mmol), 1,5-bis(diphenylphosphino)pentane (39.1 mg, 0.0888 mmol), allylpalladium(II) chloride dimer (16.2 mg, 0.0444 mmol) and dimethylformamide (1.5 mL). The reaction mixture was heated to 80° C. for 17 hours. In order to consume residual I-223, additional allylpalladium (II) chloride dimer (32.5 mg, 0.0888 mmol) and 1,5-bis(diphenylphosphino)pentane (78.2 mg, 0.178 mmol) were added and the reaction mixture was allowed to stir at 80° C. for 17 hours. The reaction mixture was filtered through Celite and to the filtrate was added water (40 mL) and a saturated ammonium chloride solution (40 mL). After an extraction with ethyl acetate (2×50 mL), the organic portions were combined, washed with brine (50 mL), dried (MgSO$_4$) and concentrated. The residue was purified by column chromatography utilizing 30% EtOAc/hexanes as the eluent to produce 365 mg of I-255 as a pale yellow solid in 91% yield.

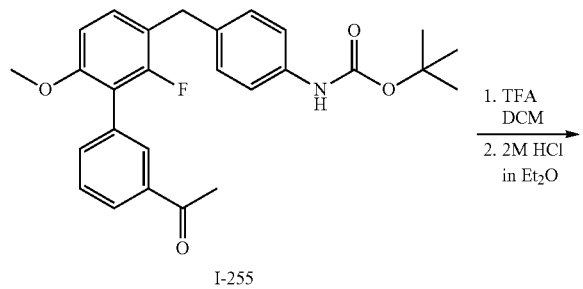

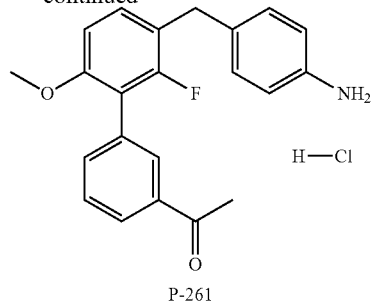

Synthesis of 1-[3'-(4-Amino-benzyl)-2'-fluoro-6'-methoxy-biphenyl-3-yl]-ethanone; hydrochloride (P-261). In an 8 mL vial equipped with a stir bar was placed I-255 (265 mg, 0.590 mmol), dichloromethane (2.0 ml) and trifluoroacetic acid (438 μL, 5.90 mmol). The reaction mixture was stirred at room temperature for 4 hours and then quenched to pH 7 with a saturated sodium bicarbonate solution. After the addition of water (30 mL) and extraction with dichloromethane (2×30 mL), the organic portions were combined, washed with brine (30 mL), dried (MgSO$_4$) and concentrated. The crude material was treated with diethyl ether (3 mL) and 2.0 M HCl in diethyl ether (1 mL) and allowed to stir at room temperature for 2 hours. The solid was collected an washed with diethyl ether (3×2 mL) to produce 139 mg of P-261 as a pale orange powder in 61% yield. $^1$H NMR (400 MHz, DMSO-d$_6$) δ 2.59 (s, 3H), 3.72 (s, 3H), 3.96 (s, 2H), 6.96 (d, J=8 Hz, 1H), 7.20-7.34 (m, 5H), 7.57 (d, J=5 Hz, 2H), 7.85 (bs, 1H), 7.94-7.97 (m, 1H) ppm. MS (APCI+): 350.1 (M+1-HCl).

Example 288

Preparation of P-269

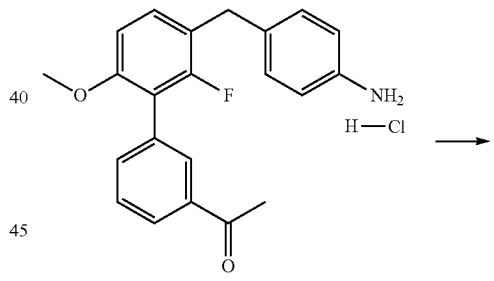

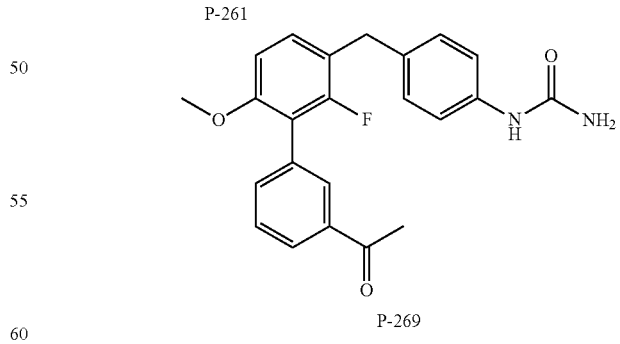

Synthesis of [4-(3'-Acetyl-2-fluoro-6-methoxy-biphenyl-3-ylmethyl)-phenyl]urea (P-269). In an 8 mL vial equipped with a stir bar was placed P-261 (31 mg, 0.0803 mmol), water (400 μL), acetic acid (200 μL) and sodium cyanate (20.9 mg, 0.321 mmol). The mixture was stirred at room temperature for 4 hours and then water (20 mL) was added followed by an extraction with dichloromethane (2×30 mL). The organic portions were combined, washed with a saturated sodium bicarbonate solution (30 mL) and brine (30 mL), dried (MgSO$_4$) and concentrated. The residue was purified by column chromatography utilizing 75% acetone/dichloromethane as the eluent to produce 18 mg of P-269 as an off-white solid in 56% yield. $^1$H NMR (400 MHz, CDCl$_3$) δ 2.62 (s, 3H), 3.75 (s, 3H), 3.95 (s, 2H), 4.59 (br s, 2H), 6.27 (br s, 1H), 6.72 (d, J=8 Hz, 1H), 7.11 (t, J=9 Hz, 1H), 7.21 (s, 4H), 7.52 (t, J=8 Hz, 1H), 7.60 (dd, J=9, 1 Hz, 1H), 7.95 (d, J=8 Hz, 1H), 7.99 (br s, 1H) ppm. MS (APCI+): 393.1 (M+1); LC-MS: 95%.

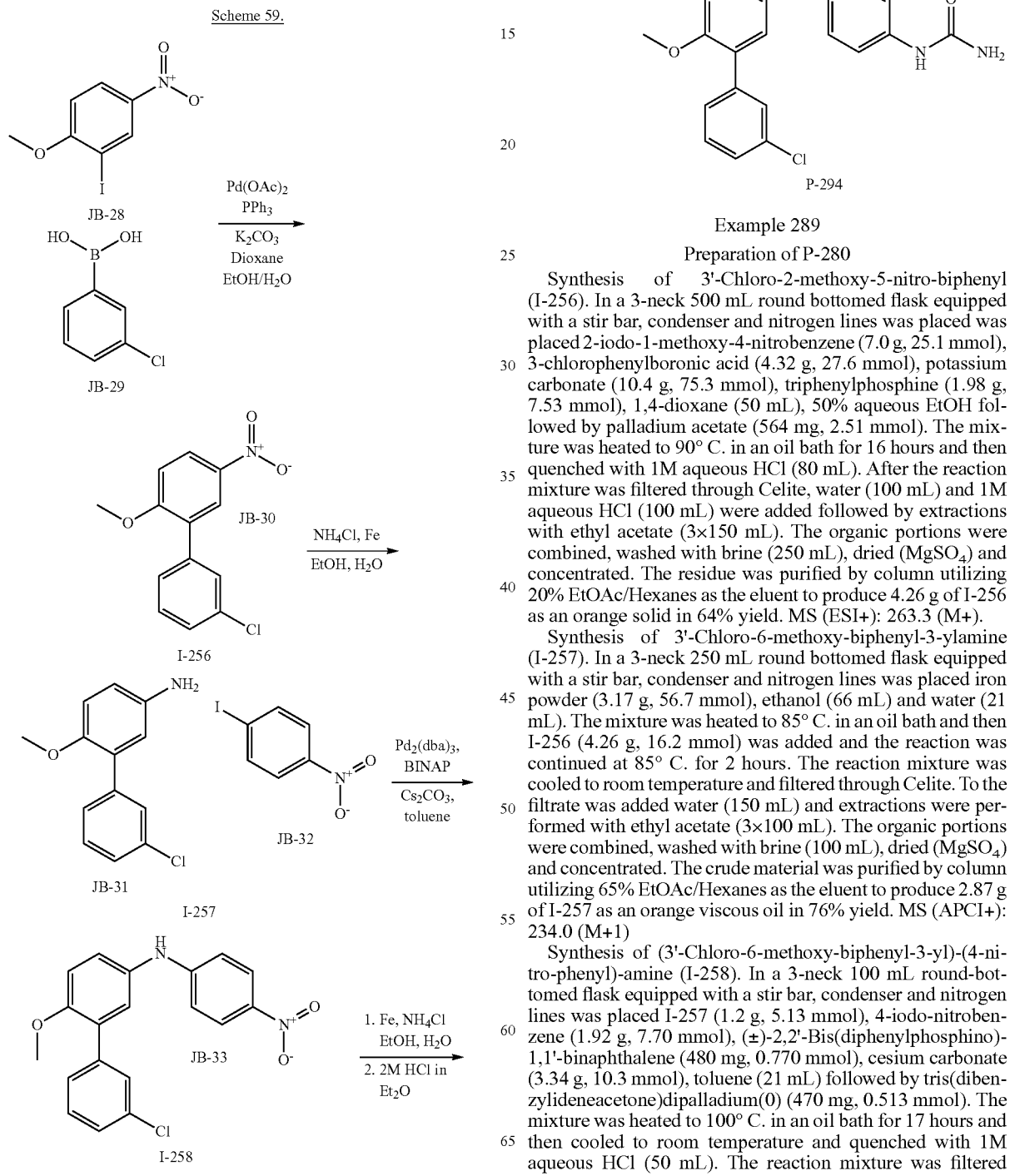

Example 289

Preparation of P-280

Synthesis of 3'-Chloro-2-methoxy-5-nitro-biphenyl (I-256). In a 3-neck 500 mL round bottomed flask equipped with a stir bar, condenser and nitrogen lines was placed was placed 2-iodo-1-methoxy-4-nitrobenzene (7.0 g, 25.1 mmol), 3-chlorophenylboronic acid (4.32 g, 27.6 mmol), potassium carbonate (10.4 g, 75.3 mmol), triphenylphosphine (1.98 g, 7.53 mmol), 1,4-dioxane (50 mL), 50% aqueous EtOH followed by palladium acetate (564 mg, 2.51 mmol). The mixture was heated to 90° C. in an oil bath for 16 hours and then quenched with 1M aqueous HCl (80 mL). After the reaction mixture was filtered through Celite, water (100 mL) and 1M aqueous HCl (100 mL) were added followed by extractions with ethyl acetate (3×150 mL). The organic portions were combined, washed with brine (250 mL), dried (MgSO$_4$) and concentrated. The residue was purified by column utilizing 20% EtOAc/Hexanes as the eluent to produce 4.26 g of I-256 as an orange solid in 64% yield. MS (ESI+): 263.3 (M+).

Synthesis of 3'-Chloro-6-methoxy-biphenyl-3-ylamine (I-257). In a 3-neck 250 mL round bottomed flask equipped with a stir bar, condenser and nitrogen lines was placed iron powder (3.17 g, 56.7 mmol), ethanol (66 mL) and water (21 mL). The mixture was heated to 85° C. in an oil bath and then I-256 (4.26 g, 16.2 mmol) was added and the reaction was continued at 85° C. for 2 hours. The reaction mixture was cooled to room temperature and filtered through Celite. To the filtrate was added water (150 mL) and extractions were performed with ethyl acetate (3×100 mL). The organic portions were combined, washed with brine (100 mL), dried (MgSO$_4$) and concentrated. The crude material was purified by column utilizing 65% EtOAc/Hexanes as the eluent to produce 2.87 g of I-257 as an orange viscous oil in 76% yield. MS (APCI+): 234.0 (M+1)

Synthesis of (3'-Chloro-6-methoxy-biphenyl-3-yl)-(4-nitro-phenyl)-amine (I-258). In a 3-neck 100 mL round-bottomed flask equipped with a stir bar, condenser and nitrogen lines was placed I-257 (1.2 g, 5.13 mmol), 4-iodo-nitrobenzene (1.92 g, 7.70 mmol), (±)-2,2'-Bis(diphenylphosphino)-1,1'-binaphthalene (480 mg, 0.770 mmol), cesium carbonate (3.34 g, 10.3 mmol), toluene (21 mL) followed by tris(dibenzylideneacetone)dipalladium(0) (470 mg, 0.513 mmol). The mixture was heated to 100° C. in an oil bath for 17 hours and then cooled to room temperature and quenched with 1M aqueous HCl (50 mL). The reaction mixture was filtered through Celite and to the filtrate was added water (50 mL)

followed by extractions with ethyl acetate (2×75 mL). The organic portions were combined, washed with brine (100 mL), dried (MgSO₄) and concentrated. The residue was purified by column utilizing 25% EtOAc/Hexanes as the eluent to produce 1.36 g of I-258 as a red-orange solid in 75% yield. MS (APCI+): 355.1 (M+1)

Synthesis of N-(3'-Chloro-6-methoxy-biphenyl-3-yl)-benzene-1,4-diamine; hydrochloride (P-280). In a 40 mL vial equipped with a stir bar was placed iron powder (330 mg, 5.92 mmol), ethanol (6.9 mL) and water (2.2 mL). The mixture was heated to 85° C. in an oil bath and then I-258 (600 mg, 1.69 mmol) was added and the reaction was continued at 85° C. for 2 hours. The reaction mixture was cooled to room temperature and filtered through Celite. To the filtrate was added water (50 mL) and extractions were performed with ethyl acetate (2×50 mL). The organic portions were combined, washed with brine (50 mL), dried (MgSO₄) and concentrated. The residue was purified by column utilizing 75% EtOAc/Hexanes as the eluent to produce 480 mg of the free base of P-280. To the free base was added Et₂O (4 mL) and 2.0 M HCl in Et₂O (2 mL) and the mixture was stirred at room temperature for 1 hour. The solid was collected, washed with Et₂O (10 mL) and dichloromethane (8 mL) and then dried in a high vacuum oven set at 35° C. for 2 hours to produce 355 mg of P-280 as a pale blue solid in 58% yield.

¹H NMR (400 MHz, DMSO-d₆) δ 3.75 (s, 3H), 7.02-7.21 (m, 7H), 7.38-7.45 (m, 3H), 7.51-7.53 (m, 1H), 9.97 (br s, 3H) ppm. MS (ESI+): 326.4 [(M+1)-HCl]. LC/MS: 92%.

Example 290

Preparation of P-294

Synthesis of [4-(3'-Chloro-6-methoxy-biphenyl-3-ylamino)-phenyl]-urea (P-294). In an 8 mL vial equipped with a stir bar was placed P-280 (150 mg, 0.415 mmol), water (2.4 mL), acetic acid (1.2 mL) and sodium cyanate (108 mg, 1.66 mmol). The mixture was stirred at room temperature for 72 hours and then water (20 mL) was added followed by an extraction with dichloromethane (2×30 mL). The organic portions were combined, washed with brine (30 mL), dried (MgSO₄) and concentrated. The residue was purified by column utilizing 40% acetone/dichloromethane as the eluent to produce 46 mg of P-294 as a light purple solid in 30% yield. ¹HNMR (400 MHz, DMSO-d₆) δ 3.71 (s, 3H), 5.67 (br s, 2H), 6.90-6.92 (m, 3H), 7.01 (s, 2H), 7.23 (d, J=9 Hz, 2H), 7.37-7.49 (m, 4H), 7.68 (s, 1H), 8.23 (br s, 1H) ppm. MS (APCI+): 368.1 (M+1); LC-MS: 95%.

Example 291

Preparation of P-281

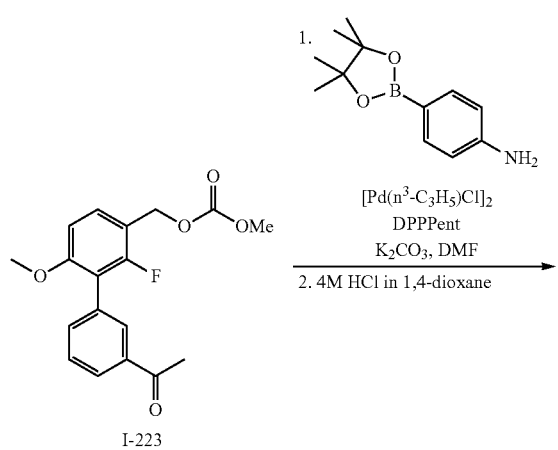

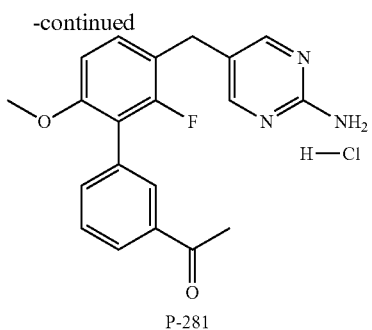

Synthesis of 1-[3'-(2-Amino-pyrimidin-5-ylmethyl)-2'-fluoro-6'-methoxy-biphenyl-3-yl]-ethanone hydrochloride (P-281). In an 18 mL vial equipped with a stir bar was placed I-223 (704 mg, 2.12 mmol), 5-(4,4,5,5-tetramethyl-[1,3,2]dioxaborolan-2-yl)-pyrimidin-2-ylamine (515 mg, 2.33 mmol), potassium carbonate (879 mg, 6.36 mmol), 1,5-bis(diphenylphosphino)pentane (280 mg, 0.636 mmol), allylpalladium(II) chloride dimer (116 mg, 0.318 mmol) and dimethylformamide (4.2 mL). The reaction mixture was heated to 70° C. for 65 hours. The reaction mixture was filtered through Celite and to the filtrate were added water (40 mL) and a saturated ammonium chloride solution (40 mL). After an extraction with ethyl acetate (2×50 mL), the organic portions were combined, washed with brine (50 mL), dried (MgSO₄) and concentrated. The residue was purified by column chromatography utilizing 20% acetone/dichloromethane (gradient elution increased to 30%, then 40% acetone/dichloromethane) as the eluent to produce 341 mg of P-281 an off-white solid in 46% yield. Then P-281 (20 mg, 0.0569 mmol) was treated with 1,4-dioxane (1 mL) and the mixture was heated to form a solution. To this solution was added 4.0M HCl in 1,4-dioxane (1 mL) and the mixture was stirred at room temperature for 3 hours. The solvent was removed via nitrogen stream and the resulting solid was triturated with diethyl ether (1 mL), collected via suction filtration and washed with diethyl ether (3×1 mL) to produce 12 mg of P-281HCl salt as a pale yellow solid in 55% yield. ¹H NMR (400 MHz, DMSO-d₆) δ 2.59 (s, 3H), 3.73 (s, 3H), 3.83 (s, 2H), 6.97 (d, J=8 Hz, 1H), 7.35 (t, J=9 Hz, 1H), 7.59 (d, J=6 Hz, 2H), 7.88 (bs, 1H), 7.95-7.97 (m, 1H), 8.36 (bs, 2H). MS (APCI+): 352.1 [(M+1)-HCl]; LC-MS: 98%.

Example 292

Preparation of P-284

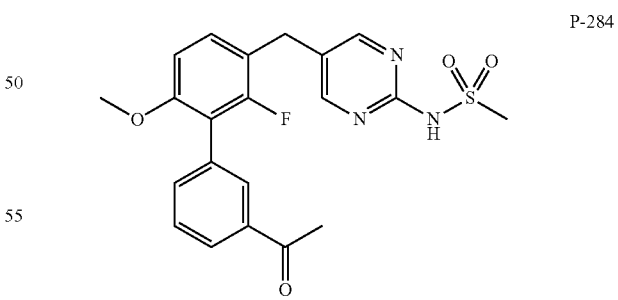

Synthesis of N-[5-(3'-Acetyl-2-fluoro-6-methoxy-biphenyl-3-ylmethyl)-pyrimidin-2-yl]-methanesulfonamide (P-284). In an 8 mL vial equipped with a stir bar was placed P-281 (free base) (70.0 mg, 0.199 mmol), pyridine (800 µL) and methane sulfonyl chloride (15.4 µL, 0.199 mmol). The reaction mixture was stirred at room temperature for 2 hours and then heated to 50° C. for 2 hours and then quenched with aqueous 1M HCl to pH 1-2. After adding water (20 mL), an extraction was performed with ethyl acetate (2×30 mL), the organic portions were combined, washed with brine (30 mL), dried (MgSO₄) and concentrated. The residue was purified by column utilizing 20% acetone/dichloromethane as the eluent to produce 29 mg of P-284 as a light yellow solid in 34% yield after drying in a high vacuum oven for 2 hours at 35° C. $^1$H NMR (400 MHz, CDCl₃) δ 2.62 (s, 3H), 3.44 (s, 3H), 3.77 (s, 3H), 3.91 (s, 2H), 6.76 (d, J=8 Hz, 1H), 7.158 (t, J=8 Hz, 1H), 7.53 (t, J=8 Hz, 1H), 7.59 (dd, J=8, 1 Hz, 1H), 7.95 (t, J=1 Hz, 1H), 7.97 (m, 1H), 8.51 (s, 2H), 9.85 (br s, 1H) ppm. MS (APCI+): 430.0 (M+1); LC-MS: 92%. HPLC: 97%.

Example 293

Preparation of P-315

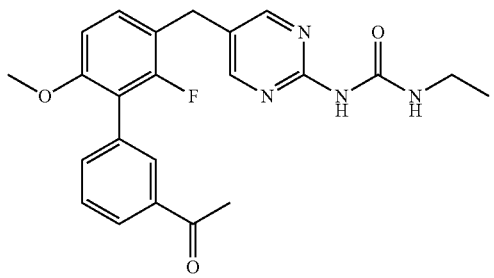

Synthesis of 1-[5-(3'-Acetyl-2-fluoro-6-methoxy-biphenyl-3-ylmethyl)-pyrimidin-2-yl]-3-ethyl-urea (P-315), In an 8 mL vial equipped with a stir bar was placed P-281 (free base) (80 mg, 0.228 mmol), pyridine (1.0 mL) and ethyl isocyanate (36.1 μL, 0.456 mmol). The reaction mixture was stirred at room temperature for 18 hours. TLC analysis indicated that the reaction mixture consisted of mostly starting materials. To the reaction mixture was added ethyl isocyanate (180 μL, 2.28 mmol) and the mixture was heated to 55° C. for 65 hours. The reaction mixture was quenched with water (3 mL) and the resulting solid was collected, washed with water (3×2 mL), ethyl acetate (3×1 mL) and dried in a high vacuum oven set at 40° C. for 4 hours to produce 59 mg of P-315 as a white solid in 61% yield. $^1$H NMR (400 MHz, DMSO-d₆) δ 1.09 (t, J=7 Hz, 3H), 2.59 (s, 3H), 3.18-3.26 (m, 2H), 3.73 (s, 3H), 3.90 (s, 2H), 6.97 (d, J=9 Hz, 1H), 7.36 (t, J=9 Hz, 1H), 7.57-7.59 (m, 2H), 7.88 (s, 1H), 7.94-7.97 (m, 1H), 8.46 (s, 2H), 8.91 (t, J=4 Hz, 1H), 9.61 (s, 1H) ppm. MS (APCI+): 423.1 (M+1); LC-MS: 94%, HPLC: 93%.

Example 294

Preparation of P-325

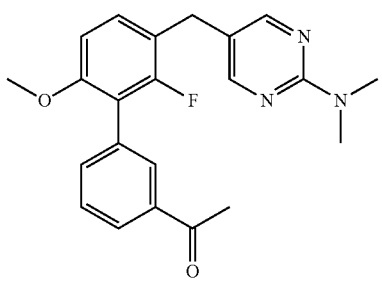

Synthesis of 1-[3'-(2-Dimethylamino-pyrimidin-5-ylmethyl)-2'-fluoro-6'-methoxy-biphenyl-3-yl]-ethanone (P-325). In an 8 mL vial equipped with a stir bar was placed I-223 (200 mg, 0.602 mmol), dimethyl-[5-(4,4,5,5-tetramethyl-[1,3,2]dioxaborolan-2-yl)-pyrimidin-2-yl]-amine (165 mg, 0.662 mmol), potassium carbonate (250 mg, 1.81 mmol), 1,5-bis(diphenylphosphino)pentane (79.6 mg, 0.181 mmol), allylpalladium(II) chloride dimer (33.0 mg, 0.0903 mmol) and dimethylformamide (1.2 mL). The reaction mixture was heated to 65° C. for 18 hours. The reaction mixture was filtered through Celite and to the filtrate were added water (40 mL) and a saturated ammonium chloride solution (40 mL). After an extraction with ethyl acetate (2×50 mL), the organic portions were combined, washed with brine (50 mL), dried (MgSO₄) and concentrated. The residue was purified by column chromatography utilizing 50% ethyl acetate/hexanes as the eluent to produce 90 mg of P-325 as a yellow solid in 39% yield. $^1$H NMR (400 MHz, DMSO-d₆) δ 2.59 (s, 3H), 3.07 (s, 6H), 3.72 (s, 3H), 3.77 (s, 2H), 6.94 (d, J=9 Hz, 1H), 7.30 (t, J=9 Hz, 1H), 7.58 (d, J=5 Hz, 2H), 7.87 (s, 1H), 7.94-7.96 (m, 1H), 8.24 (s, 2H) ppm. MS (APCI+): 380.1 (M+1); LC-MS: >99%.

Example 295

Preparation of P-362

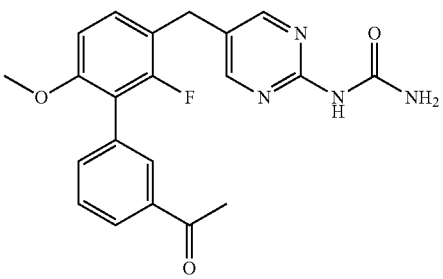

Synthesis of [5-(3'-Acetyl-2-fluoro-6-methoxy-biphenyl-3-ylmethyl)-pyrimidin-2-yl]-urea (P-362). In an 8 mL vial equipped with a stir bar was placed P-281 (free base) (30 mg, 0.0854 mmol), 1,4-dioxane (800 μL) pyridine (34.5 μL, 0.427 mmol) and trimethylsilyl isocyanate (57.8 μL, 0.427 mmol). The reaction mixture was heated to 90° C. for 18 hours and then water (15 mL) and 1M HCl (15 mL) were added followed by an extraction with dichloromethane (2×30 mL). The organic portions were combined and dried (MgSO₄) and concentrated. To the residue was added hexanes until cloudy and the resulting solid was collected, washed with hexanes (3×1 mL) and dried in a high vacuum oven set at 40° C. for 4 hours to produce 8 mg of P-362 as a pale yellow solid in 23% yield. $^1$H NMR (400 MHz, DMSO-d₆) δ 2.59 (s, 3H), 3.73 (s, 3H), 3.80 (s, 2H), 6.96 (d, J=9 Hz, 1H), 7.34 (t, J=9 Hz, 1H), 7.58-7.59 (m, 2H), 7.87 (s, 1H), 7.94-7.97 (m, 1H), 8.29 (s, 2H) ppm. LC-MS: >99%.

Example 296

Preparation of P-366

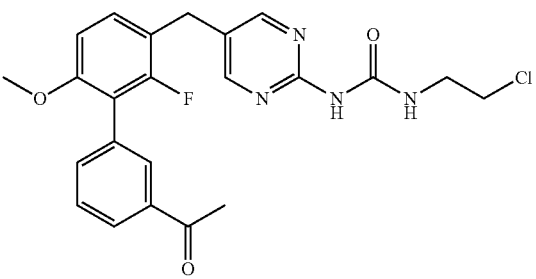

Synthesis of 1-[5-(3'-Acetyl-2-fluoro-6-methoxy-biphenyl-3-ylmethyl)-pyrimidin-2-yl]-3-(2-chloro-ethyl)-urea (P-366). In an 8 mL vial equipped with a stir bar was placed P-281 (free base) (70 mg, 0.199 mmol), chloroform (1.5 mL) and chloroethylisocyanate (17.0 µL, 0.199 mmol). The reaction mixture was heated to 65° C. for 18 hours. TLC analysis indicated a small amount of starting material was present. To the reaction mixture was added chloroethylisocyanate (50.90 µL, 0.597 mmol) and the mixture was stirred at 75° C. for 22 hours. The reaction was quenched with water (30 mL) and extracted with dichloromethane (2×30 mL). The organic portions were combined, washed with brine (30 mL), dried (MgSO$_4$) and concentrated. The residue was purified by column chromatography utilizing 15% acetone/dichlormethane and then recrystallized by dissolving the solid with dichloromethane (1 mL) and adding hexanes until cloudy. The solid was collected, washed with hexanes (3×1 mL) to produce 9 mg of P-366 as a white solid in 10% yield. $^1$H NMR (400 MHz, CDCl$_3$) δ 2.62 (s, 3H), 3.69-3.72 (m, 4H), 3.77 (s, 3H), 3.89 (s, 2H), 6.76 (d, J=8 Hz, 1H), 7.15 (t, J=9 Hz, 1H), 7.45 (s, 1H), 7.51-7.59 (m, 2H), 7.94-7.98 (m, 2H), 8.38 (s, 2H), 9.36 (br s, 1H) ppm. MS (APCI+): 457.1 (M+1).

Example 297

Preparation of P-288

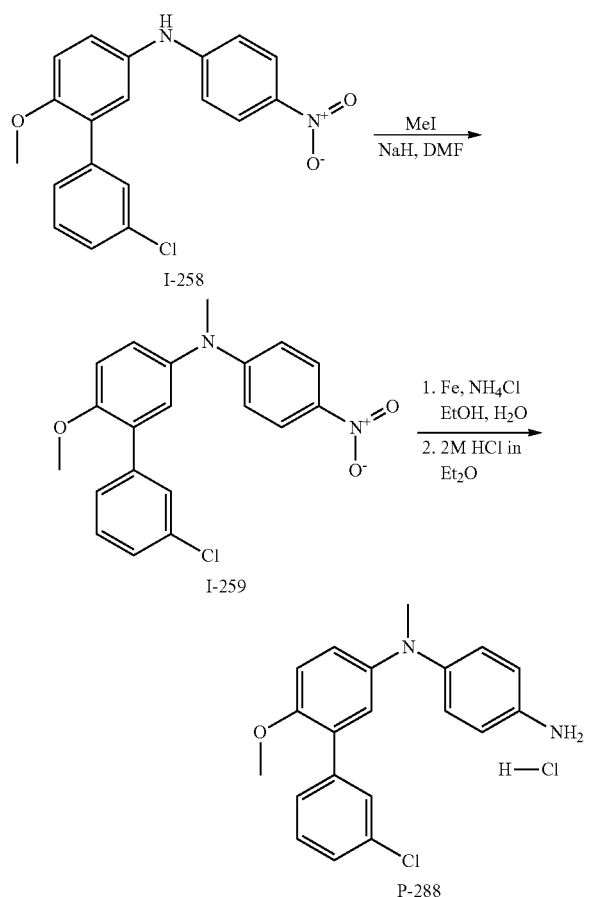

Synthesis of (3'-Chloro-6-methoxy-biphenyl-3-yl)-methyl-(4-nitro-phenyl)-amine (I-259), In a 40 mL vial equipped with a stir bar was placed I-258 (600 mg, 1.69 mmol), anhydrous DMF (6.8 mL), NaH (60%) (94.6 mg, 2.37 mmol) and methyl iodide (579 µL, 9.30 mmol). The reaction mixture was stirred at 50° C. for 17 hours and then quenched with water (30 mL) and a saturated ammonium chloride solution (30 mL). After extracting with EtOAc (2×50 mL), the extracts were combined, washed with brine (50 mL), dried (MgSO$_4$) and concentrated. The residue was purified by column utilizing 20% EtOAc/hexanes as the eluent to produce 490 mg of I-259 as a yellow-orange solid in 79% yield.

Synthesis of N-(3'-Chloro-6-methoxy-biphenyl-3-yl)-N-methyl-benzene-1,4-diamine; hydrochloride (P-288). In a 40 mL vial equipped with a stir bar was placed iron powder (260 mg, 4.66 mmol), ethanol (5.3 mL) and water (1.7 mL). The mixture was heated to 85° C. in an oil bath and then I-259 (490 mg, 1.33 mmol) was added and the reaction was continued at 85° C. for 2 hours. The reaction mixture was cooled to room temperature and filtered through Celite. To the filtrate was added water (50 mL) and extractions were performed with ethyl acetate (2×50 mL). The organic portions were combined, washed with brine (50 mL), dried (MgSO$_4$) and concentrated. The residue was purified by column utilizing 50% EtOAc/hexanes as the eluent to produce 376 mg of the free base of P-288 as an orange, viscous oil. To the free base was added Et$_2$O (5 mL) and 2.0 M HCl in Et$_2$O (3 mL) and the mixture was stirred at room temperature for 2 hours. The solid was collected, washed with Et$_2$O (6 mL) and dried in a high vacuum oven set at 40° C. for 3 hours to produce 225 mg of P-288 as a light brown solid in 54% yield. $^1$H NMR (400 MHz, DMSO-d$_6$) δ 3.25 (s, 3H), 3.79 (s, 3H), 6.85 (d, J=9 Hz, 2H), 7.12 (d, J=2 Hz, 1H), 7.15-7.21 (m, 4H), 7.38-7.44 (m, 3H), 7.52-7.54 (m, 1H), 9.84 (br s, 3H) ppm. MS (APCI+): 339.1 (M+1-HCl); LC-MS: 99%.

Example 298

Preparation of P-293

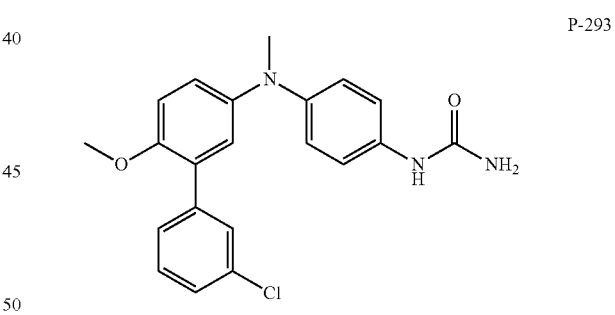

Synthesis of {4-[(3'-Chloro-6-methoxy-biphenyl-3-yl)-methyl-amino]-phenyl}-urea (P-293). In an 8 mL vial equipped with a stir bar was placed P-288 (100 mg, 0.266 mmol), water (1.6 mL), acetic acid (800 µL) and sodium cyanate (69.2 mg, 1.06 mmol). The mixture was stirred at room temperature for 72 hours and then water (30 mL) was added followed by an extraction with dichloromethane (2×30 mL). The organic portions were combined, washed with brine (30 mL), dried (MgSO$_4$) and concentrated. The residue was triturated with diethyl ether (2 mL) to produce 49 mg of P-293 as an off-white solid in 48% yield. $^1$H NMR (400 MHz, DMSO-d$_6$) δ 3.19 (s, 3H), 3.73 (s, 3H), 5.72 (br s, 2H), 6.87-6.89 (m, 3H), 6.94 (dd, J=9, 3 Hz, 1H), 7.04 (d, J=8 Hz, 1H), 7.28 (d, J=9 Hz, 2H), 7.36-7.43 (m, 3H), 7.48 (br s, 1H), 8.34 (br s, 1H) ppm. MS (APCI+): 382.1 (M+1); LC-MS: 98%.

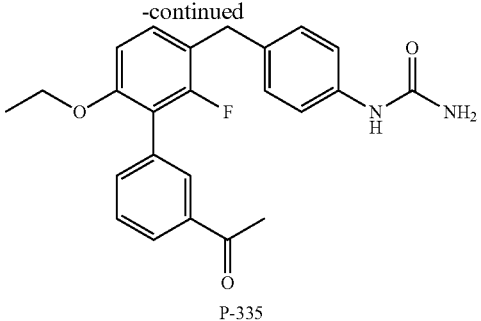

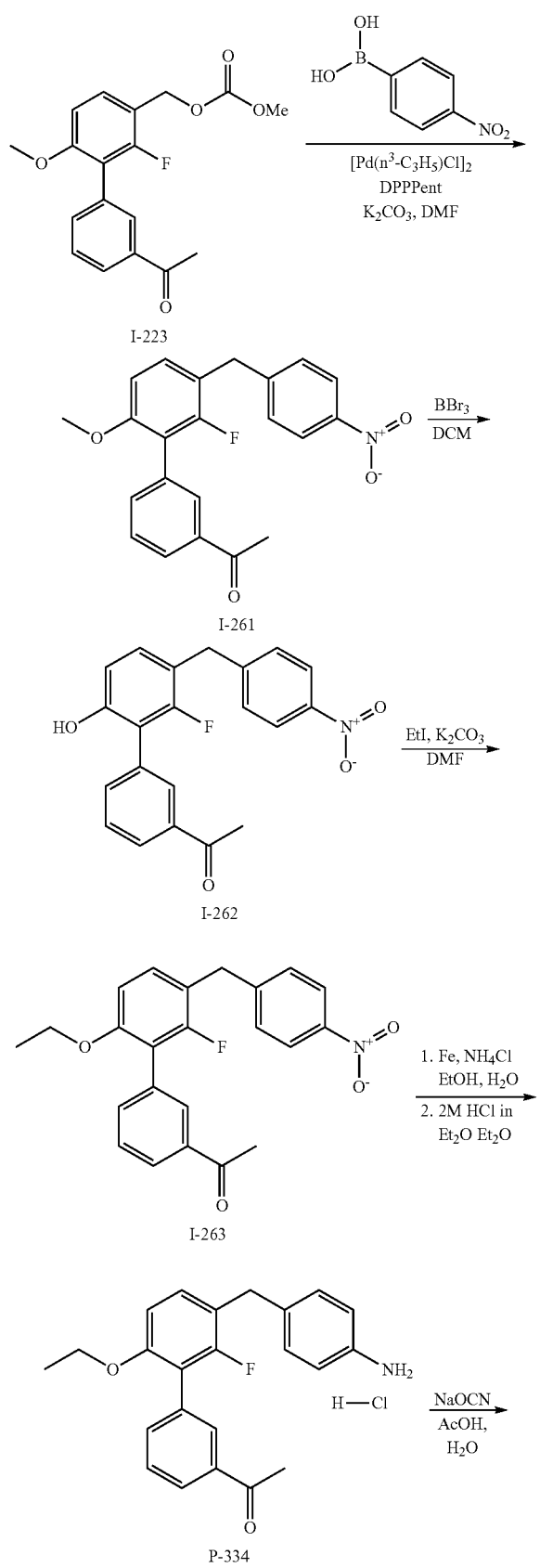

Example 299

Preparation of P-334

Synthesis of 1-[2'-Fluoro-6'-methoxy-3'-(4-nitro-benzyl)-biphenyl-3-yl]-ethanone (I-261) In an 18 mL vial equipped with a stir bar was placed I-223 (600 mg, 1.81 mmol), 4-nitrophenylboronic acid (332 mg, 1.99 mmol), potassium carbonate (750 mg, 5.43 mmol), 1,5-bis(diphenylphosphino)pentane (239 mg, 0.543 mmol), allylpalladium(II) chloride dimer (99.3 mg, 0.272 mmol) and dimethylformamide (3.6 mL). The reaction mixture was heated to 80° C. for 18 hours. The reaction mixture was filtered through Celite and to the filtrate were added water (40 mL) and a saturated ammonium chloride solution (40 mL). After an extraction with ethyl acetate (2×50 mL), the organic portions were combined, washed with brine (50 mL), dried ($MgSO_4$) and concentrated. The residue was purified by column chromatography utilizing 30% ethyl acetate/hexanes as the eluent to produce 410 mg of I-261 as a red-orange, wet solid in 60% yield.

MS (ESI−): 378.5 (M−1).

Synthesis of 1-[2'-Fluoro-6'-hydroxy-3'-(4-nitro-benzyl)-biphenyl-3-yl]-ethanone (I-262). In an 18 mL vial equipped with a stir bar was placed I-261 (351 mg, 0.925 mmol) and dichloromethane (3.0 mL). The solution was cooled to −78° C. in a dry-ice/acetone bath over 15 minutes and then boron tribromide (1.0M in dichloromethane) (2.78 mL, 2.78 mmol) was added and the vial was allowed to gradually warm to room temperature over a period of 2 hours. The reaction was poured into ice-water (40 mL) and then extracted with dichloromethane (2×30 mL). The organic portions were combined, washed with brine (50 mL), dried ($MgSO_4$) and concentrated to produce 274 mg of I-262 as a brown solid in 81% yield.

Synthesis of 1-[6'-Ethoxy-2'-fluoro-3'-(4-nitro-benzyl)-biphenyl-3-yl]-ethanone (I-263). In an 18 mL vial equipped with a stir bar was added I-262 (200 mg, 0.547 mmol), dimethylformamide (3.6 mL) and iodoethane (131 µL, 1.64 mmol). The mixture was stirred for 5 minutes and then potassium carbonate (227 mg, 1.64 mmol) was added and the reaction mixture was stirred at room temperature for 18 hours. The reaction mixture was quenched with water (30 mL) and acidified to pH 1 with 1M HCl. An extraction was performed with dichloromethane (2×30 mL) and the organic portions were combined, washed with brine (30 mL), dried ($MgSO_4$) and concentrated to produce 185 mg of I-263 as a red-orange oil in 86% yield.

Synthesis of 1-[3'-(4-Amino-benzyl)-6'-ethoxy-2'-fluoro-biphenyl-3-yl]-ethanone; hydrochloride (P-334). In an 18 mL vial equipped with a stir bar was placed iron powder (129 mg, 2.31 mmol), ethanol (5.6 mL) and water (850 µL). The mixture was heated to 85° C. in an oil bath and then I-263 (260 mg, 0.661 mmol) was added and the reaction was continued at 85° C. for 3 hours. The reaction mixture was cooled to room temperature and filtered through Celite. To the filtrate was added water (50 mL) and extractions were performed with ethyl acetate (2×50 mL). The organic portions were combined, washed with brine (50 mL), dried (MgSO$_4$) and concentrated. The residue was purified by column utilizing 40% EtOAc/hexanes as the eluent. To this purified material (free base) was added Et$_2$O (3 mL) and 2.0 M HCl in Et$_2$O (1.5 mL) and the mixture was stirred at room temperature for 1 hour. The solid was collected and dried in a high vacuum oven set at 40° C. for 3 hours to produce 46 mg of P-334 as an orange solid in 17% yield. $^1$H NMR (400 MHz, DMSO-d$_6$) δ 1.18 (t, J=7 Hz, 3H), 2.59 (s, 3H), 3.47 (br s, 2H), 3.96 (s, 2H), 4.03 (q, J=7 Hz, 2H), 6.94 (d, J=9 Hz, 1H), 7.20-7.32 (m, 5H), 7.55-7.62 (m, 2H), 7.91 (s, 1H), 7.94 (dt, J=7, 2 Hz, 1H) ppm.

MS (APCI+): 364.1 (M+1-HCl); LC-MS: 98%.

Example 300

Preparation of P-335

Synthesis of [4-(3'-Acetyl-6-ethoxy-2-fluoro-biphenyl-3-ylmethyl)-phenyl]-urea (P-335). In an 8 mL vial equipped with a stir bar was placed P-334 (38 mg, 0.0950 mmol), water (500 μL), acetic acid (250 μL) and sodium cyanate (24.7 mg, 0.380 mmol). The mixture was stirred at room temperature for 18 hours and then water (3 mL) was added and then the pH was adjusted to 6 with a saturated sodium bicarbonate solution. The resulting solid was collected and dried in a high vacuum oven set at 40° C. for 4 hours to produce 20 mg of P-335 as a pale orange solid in 53% yield. $^1$H NMR (400 MHz, CDCl$_3$) δ 1.27 (t, J=7 Hz, 3H), 2.62 (s, 3H), 3.94 (s, 2H), 3.99 (q, J=7 Hz, 2H), 4.65 (s, 2H), 6.40 (s, 1H), 6.70 (d, J=8 Hz, 1H), 7.078 (t, J=8 Hz, 1H), 7.21 (s, 4H), 7.50 (t, J=8 Hz, 1H), 7.62 (dd, J=8, 1 Hz, 1H), 7.94 (dt, J=8, 2 Hz, 1H), 8.03 (br s, 1H) ppm.

MS (APCI+): 407.1 (M+1); LC-MS: 94%.

Example 301

Preparation of P-340

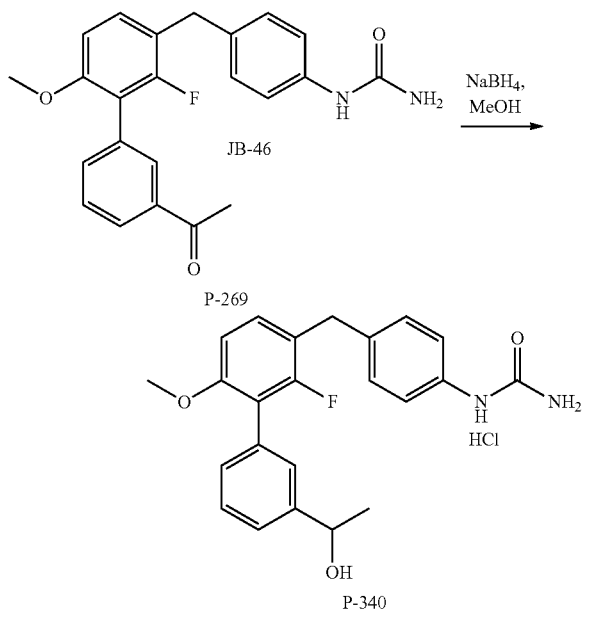

Synthesis of {4-[2-Fluoro-3'-(1-hydroxy-ethyl)-6-methoxy-biphenyl-3-ylmethyl]-phenyl}-urea (P-340). In an 8 mL vial equipped with a stir bar was placed P-269 (21 mg, 0.0535 mmol), methanol (200 μL) and sodium borohydride (6.1 mg, 0.161 mmol). The mixture was stirred at room temperature for 1 hour and then quenched with water (2 mL) and 1M aqueous HCl (4 mL). After stirring for 20 minutes, a saturated sodium bicarbonate solution was used to adjust the mixture to pH 7-8. After extracting with dichloromethane (2×30 mL), the organic portions were combined, dried (MgSO$_4$) and concentrated. The residue was purified via column chromatography utilizing 40% acetone/dichloromethane as the eluent produce 10 mg of P-340 as a white solid in 49% yield. $^1$H NMR (400 MHz, DMSO-d$_6$) δ 1.33 (d, J=6 Hz, 3H), 3.69 (s, 3H), 3.83 (s, 2H), 4.70-4.78 (m, 1H), 5.15 (d, J=4 Hz, 1H), 5.76 (s, 2H), 6.89 (d, J=9 Hz, 1H), 7.06 (d, J=8 Hz, 2H), 7.13 (d, J=7 Hz, 1H), 7.21 (t, J=9 Hz, 1H), 7.25-7.36 (m, 4H), 8.42 (s, 1H) ppm. MS (APCI+): 377.1 [(M+1)-18]; LC-MS: >99%.

Example 302

Preparation of P-381

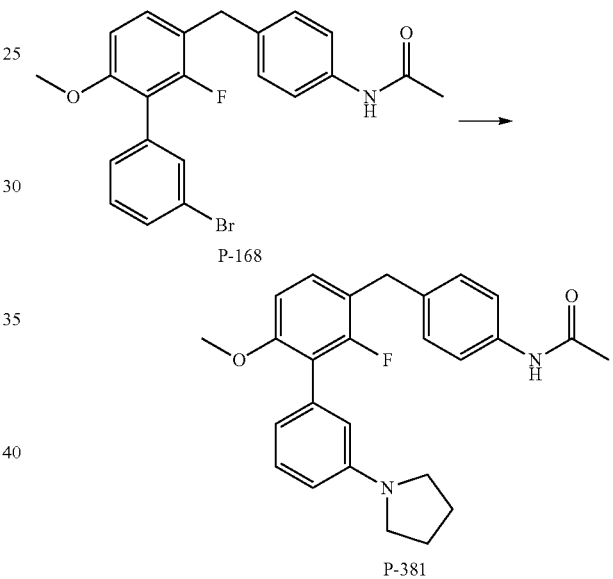

Synthesis of N-[4-(2-Fluoro-6-methoxy-3'-pyrrolidin-1-yl-biphenyl-3-ylmethyl)-phenyl]-acetamide (P-381). In an 8 mL vial equipped with a stir bar was placed P-168 (100 mg, 0.233 mmol), 1,4-dioxane (800 μL) and pyrrolidine (117 μL, 1.40 mmol). The mixture was degassed with nitrogen for 20 minutes and then dichlorobis(chloro tert-butyl phosphine) palladium (50.2 mg, 0.0932 mmol) was added. The mixture was heated to 85° C. for 20 hours and then filtered through Celite. The filtrate was treated with water (20 mL) and a saturated ammonium chloride solution (20 mL). After an extraction with ethyl acetate (2×30 mL), the organic portions were combined, washed with brine (30 mL), dried (MgSO$_4$) and concentrated. The residue was purified by column chromatography utilizing 20% acetone/dichloromethane as the eluent and to produce 31 mg of P-381 as a pale orange solid in 32% yield. $^1$H NMR (400 MHz, DMSO-d$_6$) δ 1.38 (d, J=14 Hz, 4H), 2.01 (s, 3H), 3.24 (m, 4H), 3.65 (s, 3H), 3.84 (s, 2H), 6.76 (d, 1H), 6.84 (d, J=8 Hz, 1H), 6.93 (t, J=8 Hz, 1H), 7.11 (d, J=8 Hz, 2H), 7.17 (t, J=8 Hz, 1H), 7.23 (br s, 1H), 7.30-7.32 (m, 1H), 7.48 (d, J=8 Hz, 2H), 9.83 (s, 1H) ppm. LC-MS: 92%.

Example 303

Preparation of P-390

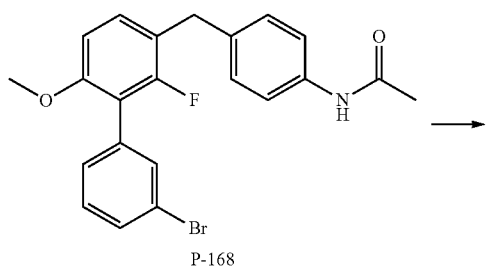

P-168

P-390

Synthesis of N-[4-(2-Fluoro-6-methoxy-3'-morpholin-4-yl-biphenyl-3-ylmethyl)-phenyl]-acetamide (P-390). In an 8 mL vial equipped with a stir bar was placed P-168 (80 mg, 0.187 mmol), sodium tert-butoxide (27.0 mg, 0.281 mmol), toluene (700 µL), morpholine (19.6 µL, 0.224 mmol) and 2,8,9-triisobutyl-2,5,8,9-tetraaza-1-phosphabicyclo[3.3.3]undecane (13.3 µL, 0.0374 mmol). The mixture was degassed with nitrogen for 15 minutes and then tris(dibenzylideneacetone)-dipalladium(0) (8.56 mg, 0.00935 mmol) was added. The mixture was heated to 90° C. for 18 hours and then filtered through Celite. The filtrate was treated with water (20 mL) and a saturated ammonium chloride solution (20 mL). After an extraction with ethyl acetate (2×30 mL), the organic portions were combined, washed with brine (30 mL), dried (MgSO$_4$) and concentrated. The residue was purified by column chromatography utilizing 10% acetone/dichloromethane as the eluent and to produce 21 mg of P-390 as an off white solid in 26% yield. $^1$H NMR (400 MHz, DMSO-d$_6$) δ 2.01 (s, 3H), 3.09 (t, J=5 Hz, 4H), 3.69 (s, 3H), 3.72 (t, J=5 Hz, 4H), 3.85 (s, 2H), 6.72 (d, J=7 Hz, 1H), 6.83 (br s, 1H), 6.87 (d, J=9 Hz, 1H), 6.92 (dd, J=8, 2 Hz, 1H), 7.13 (d, J=8 Hz, 2H), 7.18-7.27 (m, 2H), 7.47 (d, J=8 Hz, 2H), 7.69-7.80 (m, 1H) ppm. MS (APCI+): 435.1 (M+1); LC-MS: 95%.

Example 304

Preparation of P-385

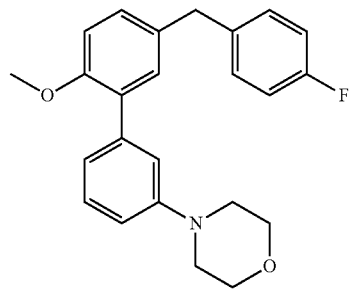

P-385

Synthesis of 4-[5'-(4-Fluoro-benzyl)-2'-methoxy-biphenyl-3-yl]-morpholine (P-385). In an 8 mL vial equipped with a stir bar was placed I-185 (200 mg, 0.678 mmol), 4-[3-(4,4,5,5-tetramethyl-[1,3,2]dioxaborolan-2-yl)-phenyl]-morpholine (216 mg, 0.746 mmol), potassium carbonate (281 mg, 2.03 mmol), triphenylphosphine (53.3 mg, 0.203 mmol), 1,4-dioxane (1.1 mL), 50% aqueous ethanol (1.1 mL) followed by palladium (II) acetate (15.2 mg, 0.0678 mmol). The mixture was heated to 90° C. for 18 hours and then cooled to room temperature. The palladium catalyst was removed via filtration through Celite. To the filtrate were added water (30 mL) and a saturated ammonium chloride solution (30 mL). After the aqueous portion was extracted with ethyl acetate (2×30 mL), the organic portions were combined, washed with brine (30 mL), dried (MgSO$_4$) and concentrated. The residue was purified by column chromatography utilizing 20% EtOAc/hexanes as the eluent and dried in a high vacuum oven set at 40° C. for 9 hours to produce 137 mg of P-385 as a yellow viscous oil in 54% yield. $^1$H NMR (400 MHz, CDCl$_3$) δ 3.18 (t, J=5 Hz, 4H), 3.78 (s, 3H), 3.87 (t, J=5 Hz, 4H), 3.92 (s, 2H), 6.87-7.01 (m, 5H), 7.04 (t, J=2 Hz, 1H), 7.09 (dd, J=8, 3 Hz, 1H), 7.12-7.17 (m, 3H), 7.30 (t, J=8 Hz, 1H) ppm. MS (APCI+): 378.1 (M+1); LC-MS: >99%

Example 305

Preparation of P-391

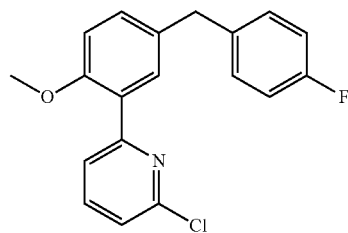

P-391

Synthesis of 2-Chloro-6-[5-(4-fluoro-benzyl)-2-methoxy-phenyl]-pyridine (P-391). In an 8 mL vial equipped with a stir bar was placed I-185 (250 mg, 0.847 mmol), 2-chloro-6-(4,4,5,5-tetramethyl-[1,3,2]dioxaborolan-2-yl)-pyridine (243 mg, 1.02 mmol), sodium tert-butoxide (122 mg, 1.27 mmol) and 1,4-dioxane. The mixture was degassed with nitrogen for 20 minutes and then dichlorobis(chloro tert-butyl phosphine)

palladium (122 mg, 0.127 mmol) was added. The mixture was heated to 90° C. for 18 hours and then filtered through Celite. The filtrate was treated with water (20 mL) and a saturated ammonium chloride solution (20 mL). After an extraction with ethyl acetate (2×30 mL), the organic portions were combined, washed with brine (30 mL), dried (MgSO$_4$) and concentrated. The residue was purified by column chromatography utilizing 10% ethyl acetate/hexanes as the eluent. The material was then recrystallized with diethyl ether and hexanes to produce 29 mg of P-391 as a white solid in 10% yield.

$^1$H NMR (400 MHz, CDCl$_3$) δ 3.84 (s, 3H), 3.96 (s, 2H), 6.91 (d, J=8 Hz, 1H), 6.94-6.98 (m, 2H), 7.12-7.17 (m, 2H), 7.23 (dd, J=8, 1 Hz, 1H), 7.64 (t, J=8 Hz, 1H), 7.69 (d, J=2 Hz, 1H), 7.79 (dd, J=8, 1 Hz, 1H) ppm. MS (APCI+): 328.0 (M+1); LC-MS: 97%.

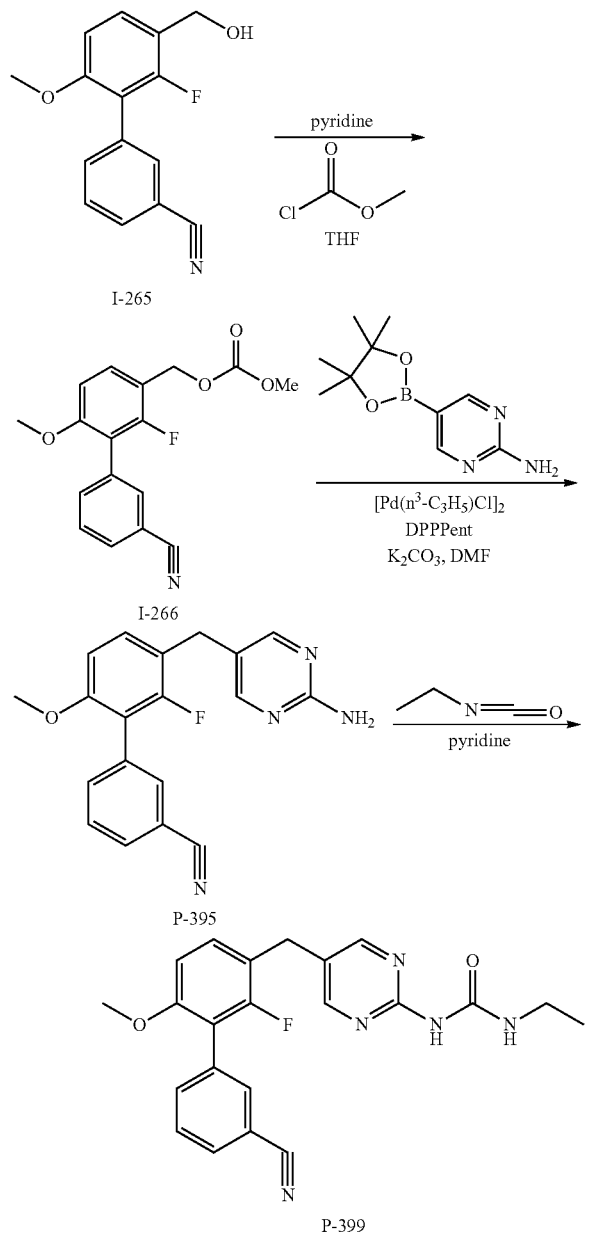

Scheme 61.

I-265

I-266

P-395

P-399

Example 306

Preparation of P-395

Synthesis of Carbonic acid 3'-cyano-2-fluoro-6-methoxy-biphenyl-3-ylmethyl ester methyl ester (I-266). In an 18 mL vial equipped with a stir bar was placed I-265 (465 mg, 1.81 mmol), anhydrous tetrahydrofuran (6.0 mL) and pyridine (381 μL, 4.71 mmol). The resulting clear solution was cooled in an ice water bath for 10 minutes and then methyl chloroformate (308 μL, 3.98 mmol) was added and reaction mixture was slowly warmed to room temperature and reacted for 17 hours. The reaction was acidified to pH 1 with 1M HCl, water (30 mL) was added followed by an extraction with dichloromethane (2×60 mL). The organic portions were combined, washed with brine (40 mL), dried (MgSO$_4$) and concentrated. After drying in a high vacuum oven for 2 hours at 45° C., 378 mg of I-266 was isolated as a light yellow in 66% yield.

Synthesis of 3'-(2-Amino-pyrimidin-5-ylmethyl)-2'-fluoro-6'-methoxy-biphenyl-3-carbonitrile (P-395). In an 8 mL vial equipped with a stir bar was placed I-266 (120 mg, 0.381 mmol), 5-(4,4,5,5-tetramethyl-[1,3,2]dioxaborolan-2-yl)-pyrimidin-2-ylamine (92.7 mg, 0.419 mmol), potassium carbonate (158 mg, 1.14 mmol), 1,5-bis(diphenylphosphino)pentane (50.3 mg, 0.114 mmol), allylpalladium(II) chloride dimer (20.9 mg, 0.0572 mmol) and dimethylformamide (1.3 mL). The reaction mixture was heated to 85° C. for 18 hours. The reaction mixture was filtered through Celite and to the filtrate were added water (30 mL) and a saturated ammonium chloride solution (30 mL). After an extraction with ethyl acetate (2×30 mL), the organic portions were combined, washed with brine (40 mL), dried (MgSO$_4$) and concentrated. The residue was purified by column chromatography utilizing 10% acetone/dichloromethane and then 30% acetone/dichloromethane as the eluent to produce 62 mg of P-395 as a pale yellow solid in 49% yield. $^1$H NMR (400 MHz, DMSO-d$_6$) δ 3.73 (s, 5H), 6.47 (s, 2H), 6.96 (d, J=8 Hz, 1H), 7.33 (t, J=9 Hz, 1H), 7.61-7.69 (m, 2H), 7.82-7.84 (m, 2H), 8.12 (s, 2H) ppm. MS (APCI+): 335.1 (M+1); LC-MS: 94%.

Example 307

Preparation of P-399

Synthesis of 1-[5-(3'-Cyano-2-fluoro-6-methoxy-biphenyl-3-ylmethyl)-pyrimidin-2-yl]-3-ethyl-urea (P-399). In an 8 mL vial equipped with a stir bar was placed P-395 (60 mg, 0.180 mmol), pyridine (600 μL) and ethyl isocyanate (71.2 μL, 0.900 mmol). The reaction mixture was stirred at room temperature for 18 hours. TLC analysis indicated that the reaction mixture consisted of about 50% starting materials. To the reaction mixture was added ethyl isocyanate (71.2 μL, 0.900 mmol) and the mixture was heated to 55° C. for 5 hours. The reaction mixture was quenched with water (4 mL) and the resulting solid was collected, washed with water (3×2 mL), ethyl acetate (3×2 mL) and dried in a high vacuum oven set at 40° C. for 18 hours to produce 36 mg of P-399 as a white solid in 49% yield. $^1$H NMR (400 MHz, DMSO-d$_6$) δ 1.09 (t, J=7 Hz, 3H), 3.19-3.25 (m, 2H), 3.74 (s, 3H), 3.89 (s, 2H), 6.98 (d, J=9 Hz, 1H), 7.39 (t, J=9 Hz, 1H), 7.61-7.70 (m, 2H), 7.83-7.85 (m, 2H), 8.46 (s, 2H), 8.91 (t, J=6 Hz, 1H), 9.611 (s, 1H) ppm. MS (APCI+): 406.1 (M+1); LC-MS: 92%.

Scheme 62

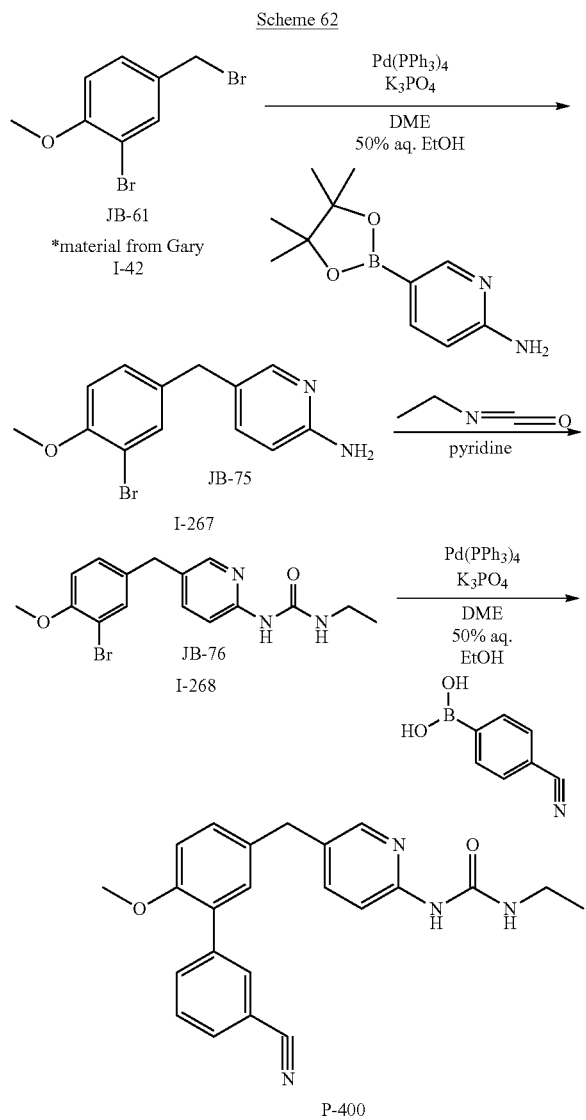

Example 308

Preparation of P-400

Synthesis of 5-(3-Bromo-4-methoxy-benzyl)-pyridin-2-ylamine (I-267) In a 40 mL vial equipped with a stir bar was placed I-42 (1.0 g, 3.57 mmol), 5-(4,4,5,5-tetramethyl-[1,3,2]dioxaborolan-2-yl)-pyridin-2-ylamine (865 mg, 3.93 mmol), potassium phosphate (tribasic) (1.52 g, 7.14 mmol), dimethoxyethane (6.0 mL) and 50% aqueous ethanol (6.0 mL). The mixture was degassed with nitrogen for 20 minutes and then add tetrakis(triphenylphosphine)palladium(0) (619 mg, 0.536 mmol). The mixture was heated to 60° C. for 4 hours and then the palladium catalyst was filtered off. To the filtrate were added water (50 mL) and a saturated ammonium chloride solution (50 mL). After extracting with ethyl acetate (2×60 mL), the organic portions were combined, washed with brine (50 mL), dried (MgSO₄) and concentrated. The residue was purified by column utilizing 10% acetone/dichloromethane, 30% acetone/dichloromethane, 40% acetone/dichloromethane as the eluent to produce 308 mg of I-267 as a yellow viscous oil in 29% yield. MS (APCI+): 295.0 (M+1); LC-MS: >99%.

Synthesis of 1-[5-(3-Bromo-4-methoxy-benzyl)-pyridin-2-yl]-3-ethyl-urea (I-268). In an 8 mL vial equipped with a stir bar was placed I-267 (300 mg, 1.02 mmol), pyridine (3.5 mL) and ethyl isocyanate (646 µL, 8.16 mmol). The reaction mixture was stirred at room temperature for 18 hours. The reaction mixture was quenched with water (30 mL) and 1M aqueous HCl (30 mL). After extracting with dichloromethane (2×60 mL), the organic portions were washed with 1M aqueous HCl (40 mL), brine (40 mL), dried (MgSO4) and concentrated. The crude sticky material was recrystallized with diethyl ether (2 mL), ethyl acetate (1 mL) and hexanes (700 µL). The resulting solid was collected by suction filtration and washed with diethyl ether (2×1 mL) to produce 49 mg of I-268 as an off-white solid in 13% yield. MS (APCI+): 366.0 (M+1); LC-MS: 98%.

Synthesis of 1-[5-(3'-Cyano-6-methoxy-biphenyl-3-ylmethyl)-pyridin-2-yl]-3-ethyl-urea (P-400). In an 8 mL vial equipped with a stir bar was placed I-268 (47 mg, 0.129 mmol), 3-cyanophenylboronic acid (22.7 mg, 0.155 mmol), potassium phosphate (tribasic) (54.8 mg, 0.258 mmol), dimethoxyethane (250 µL) and 50% aqueous ethanol (250 µL). The mixture was degassed with nitrogen for 15 minutes and then add tetrakis(triphenylphosphine)palladium(0) (14.9 mg, 0.0129 mmol). The mixture was heated to 85° C. for 18 hours and then the palladium catalyst was filtered off. To the filtrate were added water (20 mL) and a saturated ammonium chloride solution (20 mL). After extracting with ethyl acetate (2×30 mL), the organic portions were combined, washed with brine (30 mL), dried (MgSO₄) and concentrated. The residue was purified by column utilizing 15% acetone/dichloromethane as the eluent to produce 27 mg of P-400 as a white solid in 55% yield. ¹H NMR (400 MHz, DMSO-d₆) δ 1.07 (t, J=7 Hz, 3H), 3.13-3.20 (m, 2H), 3.75 (s, 3H), 3.84 (s, 2H), 7.07 (d, J=8 Hz, 1H), 7.23 (s, 1H), 7.25 (s, 1H), 7.55-7.62 (m, 3H), 7.77-7.82 (m, 1H), 7.90 (m, 1H), 8.10 (br s, 1H), 9.06 (s, 1H) ppm. MS (APCI+): 387.1 (M+1); LC-MS: 98%.

Example 309

Preparation of P-433

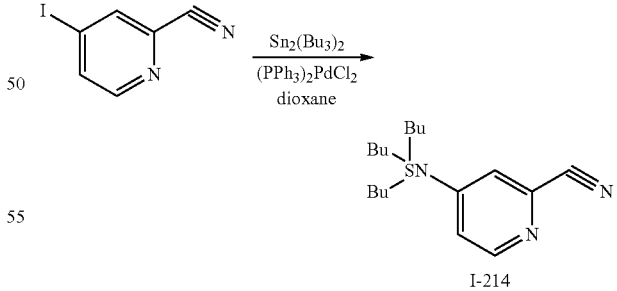

Synthesis of 4-Tributylstannanyl-pyridine-2-carbonitrile (I-214). In a 40 mL vial equipped with a stir bar was placed 4-iodo-pyridine-2-carbonitrile (1.26 g, 5.48 mmol), 1,4-dioxane (18 mL), and bis(tributyl)tin (3.32 mL, 6.58 mmol). After the reaction mixture was degassed with nitrogen for 15 minutes, bis(triphenylphosphine)-palladium(II) dichloride (192 mg, 0.274 mmol) was added. The reaction mixture was heated to 90° C. for 18 hours and then quenched with 2.2 M aqueous potassium fluoride (100 ml) in order to consume excess tin reagent. After stirring at room temperature for 2 hours, the mixture was filtered through Celite. To the filtrated was added water (50 mL), followed by extractions with ethyl acetate (5×100 mL). The organic portions were combined, washed with 2.2 M aqueous potassium fluoride (150 mL), water (150 mL) and brine (150 mL). After drying the organic portion with magnesium sulfate, the material was concentrated and purified by column chromatography utilizing 5% ethyl acetate/hexanes as the eluent to produce 1.24 g of I-214 as a colorless oil in 58% yield.

MS (APCI+): 394.0 (M+1)

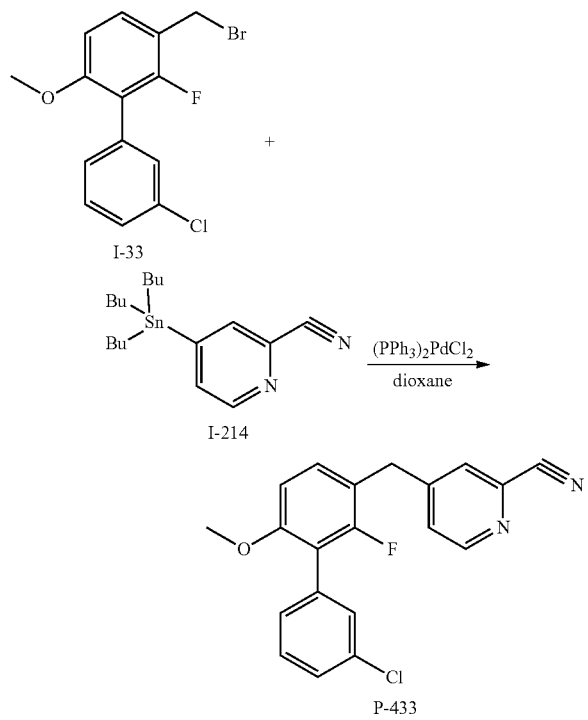

Synthesis of 4-(3'-Chloro-2-fluoro-6-methoxy-biphenyl-3-ylmethyl)-pyridine-2-carbonitrile (P-433). In an 18 mL vial equipped with a stir bar was placed I-33 (162 mg, 0.492 mmol), 1,4-dioxane (2.3 mL), and I-214 (232 mg, 0.590 mmol). After the reaction mixture was degassed with nitrogen for 20 minutes, bis(triphenylphosphine)-palladium(II) dichloride (17.3 mg, 0.0246 mmol) was added. The reaction mixture was heated to 80° C. for 18 hours. To the reaction mixture was added water (40 mL) followed by extractions with ethyl acetate (2×60 mL). The organic portions were combined, washed with brine (40 mL), dried (magnesium sulfate) and concentrated. The residue was purified by column chromatography utilizing 30% ethyl acetate/hexanes as the eluent to produce 102 mg of P-433 as an orange oil in 59% yield. $^1$H NMR (400 MHz, DMSO-d$_6$) δ 3.74 (s, 3H), 4.06 (s, 2H), 6.98 (d, J=9 Hz, 1H), 7.28-7.30 (m, 1H), 7.38-7.47 (m, 4H), 7.56 (d, J=5 Hz, 1H), 7.93 (s, 1H), 8.65 (d, J=5 Hz, 1H) ppm.

MS (APCI+): 354.0 (M+1); LC-MS: 97%.

Example 310

Preparation of P-437

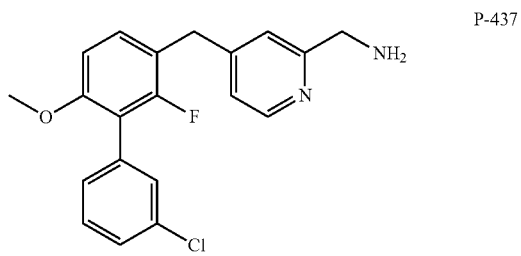 [SMILES: COc1ccc(Cc2ccnc(CN)c2)c(F)c1-c1cccc(Cl)c1]

Synthesis of C-[4-(3'-Chloro-2-fluoro-6-methoxy-biphenyl-3-ylmethyl)-pyridin-2-yl]-methylamine (P-437). In an 8 mL vial equipped with a stir bar was placed P-433 (95 mg, 0.269 mmol), methanol (2.8 mL), concentrated HCl (113 µL, 1.35 mmol), 10% palladium on activated carbon (19.0 mg), followed by attachment of a balloon of hydrogen. The mixture was allowed to stir at room temperature for 2 hours and then filtered through Celite. To the filtrate was added water (20 mL), the pH was adjusted to 10-11 with 1M NaOH, and extractions were done with ethyl acetate (2×60 mL). The organic portions were combined, washed with brine (50 mL), dried (magnesium sulfate) and concentrated. The residue was purified by column chromatography utilizing 10% methanol/dichloromethane to produce 14 mg of P-437 as a black, semi-solid in 14% yield. $^1$H NMR (400 MHz, DMSO-d$_6$) δ 3.17 (s, 2H), 3.74 (s, 3H), 3.78 (s, 2H), 3.95 (s, 2H), 6.96 (d, J=8 Hz, 1H), 7.06-7.07 (m, 1H), 7.28-7.47 (m, 6H), 8.37 (d, J=5 Hz, 1H) ppm. MS (APCI+): 358.0 (M+1); LC-MS: 96%.

Scheme 63

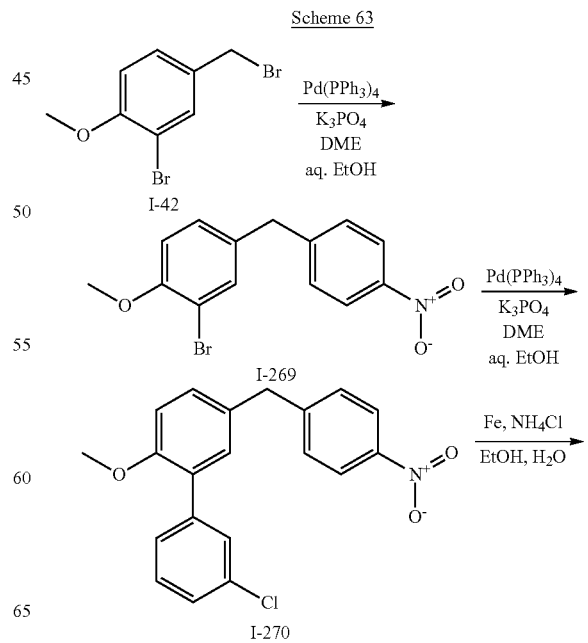

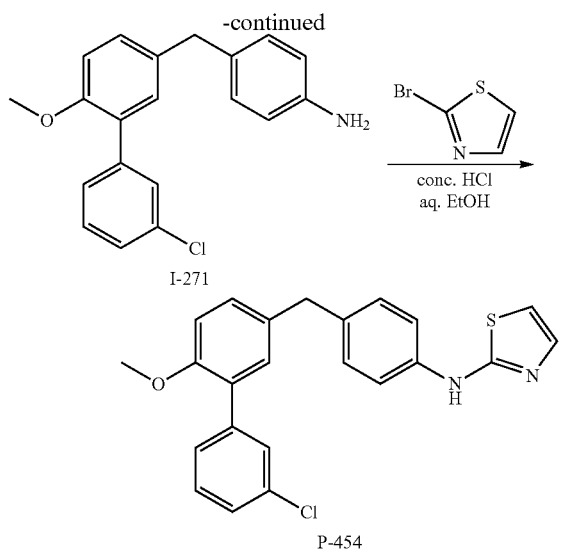

Example 311

Preparation of P-454

Synthesis of 2-Bromo-1-methoxy-4-(4-nitro-benzyl)-benzene (I-269). In a 100 mL round bottomed flask equipped with a stir bar was placed I-42 (2.0 g, 7.14 mmol), 4-nitrophenylboronic acid (2.27 g, 7.85 mmol), potassium phosphate (tribasic) (3.03 g, 14.3 mmol), dimethoxyethane (12 mL) and 50% aqueous ethanol (12 mL). The mixture was degassed with nitrogen for 20 minutes and then added tetrakis(triphenylphosphine)palladium(0) (825 mg, 0.714 mmol). The mixture was heated to 60° C. for 4 hours and then the palladium catalyst was filtered off. To the filtrate were added water (50 mL) and a saturated ammonium chloride solution (100 mL). After extracting with ethyl acetate (3×100 mL), the organic portions were combined, washed with brine (150 mL), dried (MgSO$_4$) and concentrated. The residue was purified by column utilizing 15% ethyl acetate/hexanes as the eluent to produce 1.06 g of I-269 as a pale yellow solid in 46% yield. MS (APCI−): 321.2 (M−1).

Synthesis of 3'-Chloro-2-methoxy-5-(4-nitro-benzyl)-biphenyl (I-270). In a 40 mL vial equipped with a stir bar was placed I-269 (960 mg, 2.98 mmol), 3-chlorophenylboronic acid (559 mg, 3.58 mmol),), potassium phosphate (tribasic) (1.27 g, 5.96 mmol), dimethoxyethane (5 mL) and 50% aqueous ethanol (5 mL) and tetrakis(triphenylphosphine)palladium(0) (344 mg, 0.298 mmol). The mixture was heated to 67° C. for 65 hours and then the palladium catalyst was filtered off. To the filtrate were added water (50 mL) and a saturated ammonium chloride solution (70 mL). After extracting with ethyl acetate (3×75 mL), the organic portions were combined, washed with brine (80 mL), dried (MgSO$_4$) and concentrated. The residue was purified by column utilizing 10% ethyl acetate/hexanes as the eluent to produce 1.05 g of I-270 as a yellow viscous oil in quantitative yield. MS (APCI−): 351.8 (M−2).

Synthesis of 4-(3'-Chloro-6-methoxy-biphenyl-3-ylmethyl)-phenylamine (I-271). In a 40 mL vial equipped with a stir bar was placed iron powder (586 mg, 10.5 mmol), ethanol (12 mL) and water (3.8 mL). The mixture was heated to 85° C. in an oil bath and then I-270 (1.05 g, 3.00 mmol) was added and the reaction was continued at 85° C. for 2 hours. The reaction mixture was cooled to room temperature and filtered through Celite. To the filtrate was added water (60 mL) and extractions were performed with ethyl acetate (2×60 mL). The organic portions were combined, washed with brine (60 mL), dried (MgSO$_4$) and concentrated to produce 862 mg of I-271 as a pale orange viscous oil in 89% yield. MS (APCI+): 324.1 (M+1); LC-MS: 97%.

Synthesis of [4-(3'-Chloro-6-methoxy-biphenyl-3-ylmethyl)-phenyl]-thiazol-2-yl-amine (P-454). In an 8 mL vial equipped with a stir bar was placed I-271 (70 mg, 0.216 mmol), 2-bromothiazole (38.5 μL, 0.432 mmol), 10% aqueous ethanol (1.1 mL) and concentrated hydrochloric acid (36.0 μL, 0.432 mmol). The mixture was heated to 95° C. for 18 hours and then combined with the reaction mixture from a 50 mg scale reaction of the exact same type. After water (30 mL) and 5% aqueous potassium carbonate (30 mL) were added, the aqueous portion was extracted with ethyl acetate (2×30 mL) and the organic portions were combined, washed with water (40 mL), brine (40 mL), dried (magnesium sulfate) and concentrated. The crude material was purified by column chromatography utilizing 3% acetone/dichloromethane as the eluent to produce 70 mg of P-454 as viscous, light yellow oil in 47% yield. $^1$H NMR (400 MHz, CDCl$_3$) δ 3.79 (s, 3H), 3.94 (s, 2H), 6.61 (d, J=4 Hz, 1H), 6.91 (d, J=8 Hz, 1H), 7.12-7.19 (m, 5H), 7.27-7.33 (m, 4H), 7.38 (dt, J=7, 2 Hz, 1H), 7.50 (t, J=2 Hz, 1H). MS (APCI+): 407.0 (M+1); LC-MS: 99%.

Example 312

Preparation of P-458

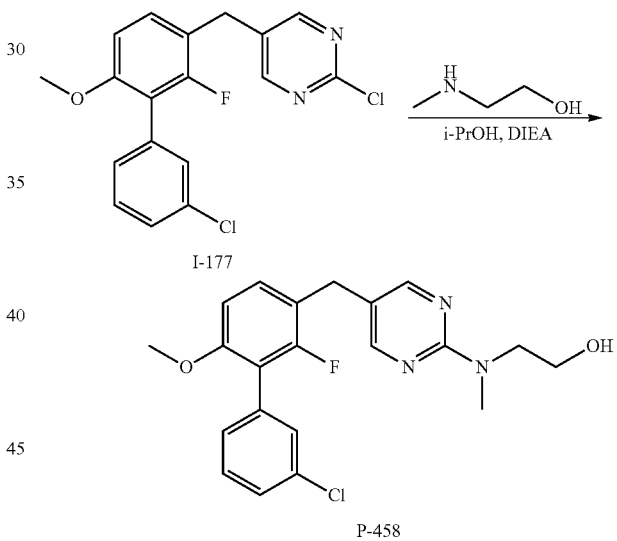

Synthesis of 2-{[5-(3'-Chloro-2-fluoro-6-methoxy-biphenyl-3-ylmethyl)-pyrimidin-2-yl]-methyl-amino}-ethanol (P-458). In an 8 mL vial equipped with a stir bar was placed I-177 (40 mg, 0.110 mmol), 2-(methylamino)-ethanol (13.2 μL, 0.165 mmol), isopropanol (600 μL) and diisopropylethylamine (57.5 μL, 0.330 mmol). The mixture was heated to 80° C. for 18 hours, combined with an identical 20 mg scale reaction and then treated with water (30 mL), 1M HCl (20 mL) and extracted with dichloromethane (2×50 mL). The organic portions were combined, washed with brine (50 mL), dried (magnesium sulfate) and concentrated. The residue was purified by silica gel column chromatography utilizing 10% acetone/dichloromethane as the eluent to produce 35 mg of P-458 as a colorless, viscous oil in 52% yield. $^1$H NMR (400 MHz, DMSO-d$_6$) δ 3.10 (s, 3H), 3.52-3.53 (m, 4H), 3.72 (s, 3H), 3.75 (s, 2H), 4.64 (t, J=5 Hz, 1H), 6.93 (d, J=8 Hz, 1H), 7.27-7.32 (m, 2H), 7.38 (s, 1H), 7.43-7.47 (m, 2H), 8.22 (s, 2H) ppm.

MS (APCI+): 402.0 (M+1); LC-MS: 99%.

Example 313
Preparation of P-467

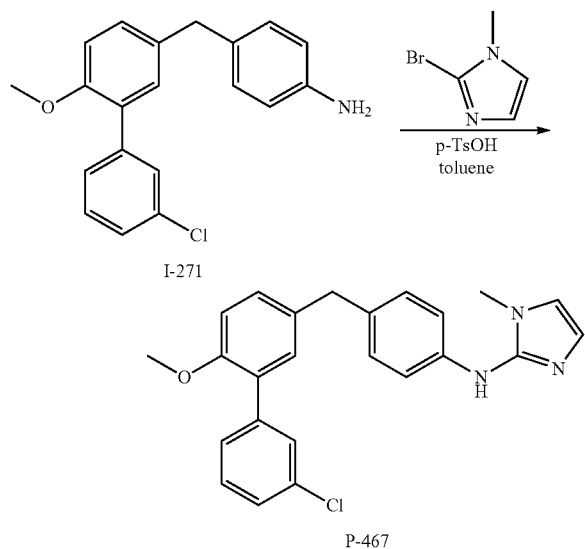

Scheme 64:

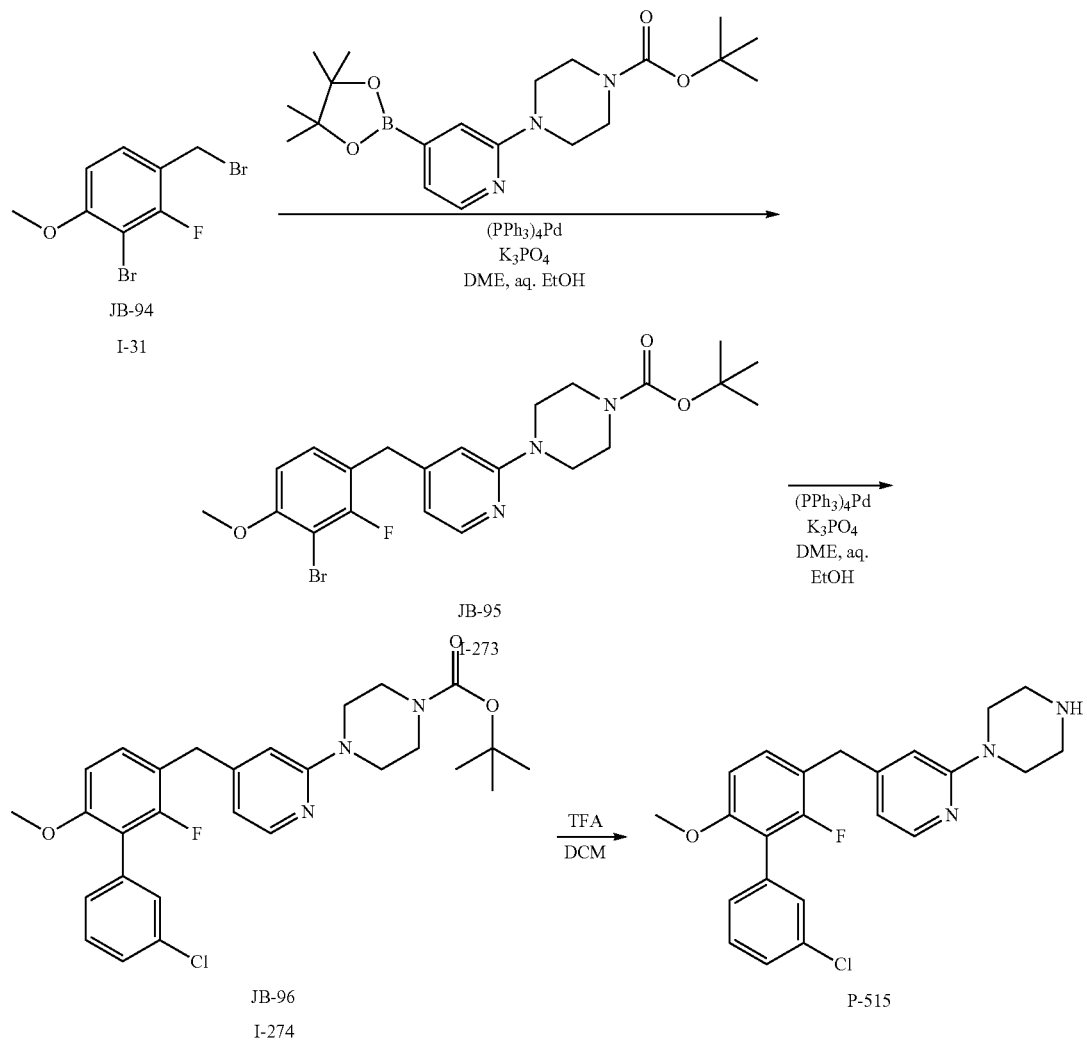

Synthesis of [4-(3'-Chloro-6-methoxy-biphenyl-3-ylmethyl)-phenyl]-(1-methyl-1H-imidazol-2-yl)-amine (P-467). In an 8 mL vial equipped with a stir bar was placed I-271 (150 mg, 0.463 mmol), 2-bromo-1-methyl-1H-imidazole (67.8 µL, 0.695 mmol), p-toluenesulfonic acid (106 mg, 0.556 mmol) and toluene (2.0 mL). The mixture was heated to 115° C. for 18 hours and then treated with water (30 mL) followed by adjustment to pH 10 with 5% aqueous potassium carbonate. After extracting with ethyl acetate (2×35 mL), the organic portions were combined, washed with brine (50 mL), dried (MgSO$_4$) and concentrated. The residue was purified by silica gel column chromatography utilizing 5% then 50% acetone/dichloromethane as the eluent to produce 89 mg of P-467 as a pale orange solid in 47% yield. $^1$H NMR (400 MHz, DMSO-d$_6$) δ 3.45 (s, 3H), 3.74 (s, 3H), 3.82 (s, 2H), 6.61 (d, J=2 Hz, 1H), 6.81 (d, J=2 Hz, 1H), 7.02-7.07 (m, 3H), 7.15 (d, J=2 Hz, 1H), 7.19 (dd, J=8, 2 Hz, 1H), 7.24 (d, J=8, 2 H), 7.35-7.44 (m, 3H), 7.48 (bs, 1H), 8.09 (s, 1H) ppm; MS (APCI+): 404.1 (M+1).

LC-MS: >99%.

Example 314

Preparation of P-515

Synthesis of 4-[4-(3-Bromo-2-fluoro-4-methoxy-benzyl)-pyridin-2-yl]-piperazine-1-carboxylic acid tert-butyl ester (I-273). In a 40 mL vial equipped with a stir bar was placed I-31 (642 mg, 2.15 mmol), 4-[4-(4,4,5,5-Tetramethyl-[1,3,2]dioxaborolan-2-yl)-pyridin-2-yl]-piperazine-1-carboxylic acid tert-butyl ester (922 mg, 2.37 mmol), potassium phosphate (tribasic) (913 mg, 4.30 mmol), dimethoxyethane (3.6 mL) and 50% aqueous ethanol (3.6 mL). After degassing with nitrogen for 15 minutes, tetrakis(triphenylphosphine)palladium(0) (248 mg, 0.215 mmol) was added. The mixture was heated to 60° C. for 5 hours and then the palladium catalyst was removed by filtering through Celite. To the filtrate were added water (50 mL) and a saturated ammonium chloride solution (50 mL). After extracting with ethyl acetate (3×75 mL), the organic portions were combined, washed with brine (75 mL), dried (MgSO$_4$) and concentrated. The residue was purified by column utilizing 35% ethyl acetate/hexanes as the eluent to produce 495 mg of I-273 as a yellow, viscous oil in 48% yield.

MS (APCI+): 480.0 (M+1);

Synthesis of 4-[4-(3'-Chloro-2-fluoro-6-methoxy-biphenyl-3-ylmethyl)-pyridin-2-yl]-piperazine-1-carboxylic acid tert-butyl ester (I-274). In a 18 mL vial equipped with a stir bar was placed I-273 (490 mg, 1.02 mmol), 3-chlorophenyl boronic acid (191 mg, 1.22 mmol), potassium phosphate (tribasic) (433 mg, 2.04 mmol), dimethoxyethane (2.0 mL) and 50% aqueous ethanol (2.0 mL). After degassing with nitrogen for 15 minutes, tetrakis(triphenylphosphine)palladium(0) (118 mg, 0.102 mmol) was added. The mixture was heated to 90° C. for 22 hours and then the palladium catalyst was removed by filtering through Celite. To the filtrate was added water (150 mL) followed by extractions with ethyl acetate (3×75 mL). The organic portions were combined, washed with brine (75 mL), dried (MgSO$_4$) and concentrated. The residue was purified by column utilizing 25% then 35% ethyl acetate/hexanes as the eluent to produce 360 mg of I-274 as a pale yellow solid in 69% yield. MS (APCI+): 512.1 (M+)

Synthesis of 1-[4-(3'-Chloro-2-fluoro-6-methoxy-biphenyl-3-ylmethyl)-pyridin-2-yl]-piperazine (P-515) In a 40 mL vial equipped with a stir bar was placed I-274 (360 mg, 0.703 mmol) and dichlormethane (2.3 mL). The solution was cooled in an ice-water bath for 10 minutes and then trifluoroacetic acid (522 µL, 7.03 mmol) was added. The solution was stirred at room temperature for 3 hours and then concentrated by a stream of nitrogen. To the oil was added water (50 mL), a saturated sodium bicarbonate solution (till pH 8) followed by extractions with dichloromethane (2×75 mL). The organic portions were combined, washed with brine (50 mL), dried (MgSO$_4$) and concentrated. The residue was purified by column utilizing 10%, 15% and then 20% methanol/dichloromethane as the eluent to produce 120 mg of P-515 as an off-white solid in 41% yield. $^1$H NMR (400 MHz, DMSO-d$_6$) δ 2.80 (t, J=5 Hz, 4H), 3.39 (t, J=5 Hz, 4H), 3.73 (s, 3H), 3.84 (s, 2H), 6.46 (d, J=5 Hz, 1H), 6.69 (s, 1H), 6.94 (d, J=8 Hz, 1H), 7.28 (bd, J=7 Hz, 1H), 7.32 (t, J=9 Hz, 1H), 7.36 (s, 1H), 7.41-7.47 (m, 2H), 7.98 (d, J=5 Hz, 1H) ppm. MS (APCI+): 412.1 (M+1); LC-MS: >99%.

Example 315

Preparation of P-518

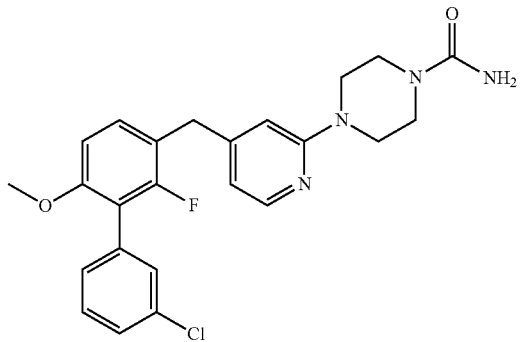

P-518

Synthesis of 4-[4-(3'-Chloro-2-fluoro-6-methoxy-biphenyl-3-ylmethyl)-pyridin-2-yl]-piperazine-1-carboxylic acid amide (P-518). In an 8 mL vial equipped with a stir bar was placed P-515 (50 mg, 0.121 mmol), water (800 µL), acetic acid (400 µL) and sodium cyanate (31.5 mg, 0.484 mmol). The mixture was stirred at room temperature for 18 hours and then water (30 mL) was added. After adjusting to pH 8 with a saturated sodium bicarbonate solution, the aqueous portion was extracted with dichloromethane (2×30 mL). The organic portions were combined, washed with brine (30 mL), dried (MgSO$_4$) and concentrated to produce an off-white solid. The residue was triturated with diethyl ether (1 mL), collected and dried in a high vacuum oven for 18 hours to produce 17 mg of P-518 as an off-white solid in 30% yield. $^1$H NMR (400 MHz, DMSO-d$_6$) δ 3.36-3.44 (m, 8H), 3.73 (s, 3H), 3.85 (s, 2H), 6.03 (s, 2H), 6.48 (d, J=5 Hz, 1H), 6.76 (s, 1H), 6.94 (d, J=9 Hz, 1H), 7.28 (d, J=7 Hz, 1H), 7.33 (t, J=9 Hz, 1H), 7.37 (s, 1H), 7.41-7.47 (m, 2H), 8.00 (d, J=5 Hz, 1H) ppm. MS (APCI+): 455.1 (M+1).

Example 316

Preparation of P-519

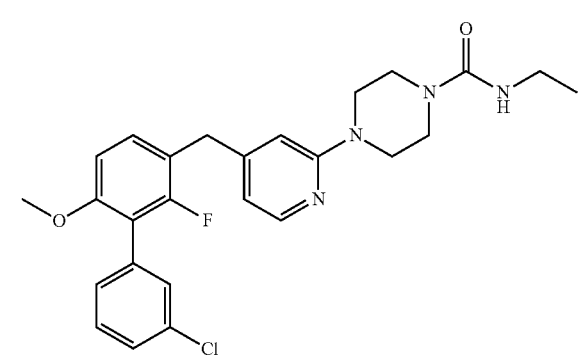

P-519

Synthesis of 4-[4-(3'-Chloro-2-fluoro-6-methoxy-biphenyl-3-ylmethyl)-pyridin-2-yl]-piperazine-1-carboxylic acid ethylamide (P-519). In an 8 mL vial equipped with a stir bar was placed P-515 (60 mg, 0.146 mmol), pyridine (500 µL) and ethyl isocyanate (92.5 µL, 1.17 mmol). The mixture was stirred at room temperature for 18 hours and then treated with water (20 mL) and a saturated sodium bicarbonate solution (20 mL). After extractions with dichloromethane (3×30 mL), the organic portions were combined, washed with 1M HCl (2×30 mL), brine (40 mL), dried (MgSO$_4$) and concentrated to produce an off-white solid. The crude material was triturated with diethyl ether (1 mL), collected and dried in a high vacuum oven for 18 hours to produce 22 mg of P-519 in 31% yield. $^1$H NMR (400 MHz, DMSO-d$_6$) δ 1.02 (t, J=4 Hz, 3H), 3.05-3.18 (m, 2H), 3.42 (br s, 4H), 3.53 (br s, 4H), 3.74 (s, 3H), 3.93 (s, 2H), 6.57 (m, 2H), 6.96 (d, J=8 Hz, 2H), 7.28 (d, J=7 Hz, 1H), 7.35-7.48 (m, 3H), 7.96 (d, J=5 Hz, 1H) ppm.

MS (APCI+): 483.1 (M+1); LC-MS: 98%.

Example 317

Preparation of P-527

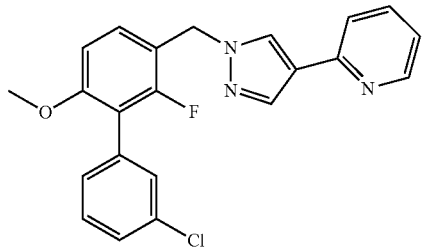

Synthesis of 2-[1-(3'-Chloro-2-fluoro-6-methoxy-biphenyl-3-ylmethyl)-1H-pyrazol-4-yl]-pyridine (P-527). In an 8 mL vial equipped with a stir bar was placed 2-(1H-pyrazol-4-yl)-pyridine (31.4 mg, 0.216 mmol), DMF (600 µL) and sodium hydride (60%) (11.9 mg, 0.296 mmol). The mixture was stirred at room temperature for 25 minutes and then a solution of I-33 (75 mg, 0.228 mmol) and DMF (600 µL) was added and the reaction mixture was stirred at room temperature for 18 hours. The reaction was quenched with water (40 mL) and extracted with dichloromethane (2×35 mL). The organic portions were combined, washed with brine (40 mL), dried (MgSO$_4$) and concentrated. The residue was purified by silica gel column chromatography utilizing 30% acetone/dichloromethane to produce 58 mg (65%) of P-527 as a colorless viscous oil.

$^1$H NMR (400 MHz, DMSO-d$_6$) δ 3.75 (s, 3H), 5.39 (s, 2H), 7.00 (d, J=9 Hz, 1H), 7.15-7.18 (m, 1H), 7.29-7.31 (m, 1H), 7.36 (d, J=9 Hz, 1H), 7.39 (s, 1H), 7.42-7.49 (m, 2H), 7.65 (dt, J=8, 1 Hz, 1H), 7.74 (td, J=8, 2 Hz, 1H), 8.03 (s, 1H), 8.36 (s, 1H), 8.48-8.50 (m, 1H) ppm. MS (APCI+): 394.1 (M+1); LC-MS: 92%.

Example 318

Preparation of P-528

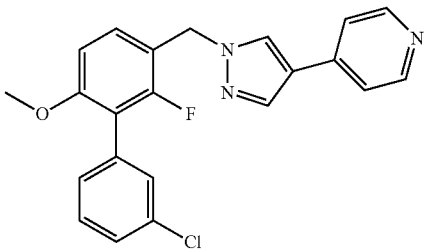

Synthesis of 4-[1-(3'-Chloro-2-fluoro-6-methoxy-biphenyl-3-ylmethyl)-1H-pyrazol-4-yl]-pyridine (P-528). In an 8 mL vial equipped with a stir bar was placed 4-(1H-pyrazol-4-yl)-pyridine (31.4 mg, 0.216 mmol), DMF (600 µL) and sodium hydride (60%) (11.9 mg, 0.296 mmol). The mixture was stirred at room temperature for 25 minutes and then a solution of I-33 (75 mg, 0.228 mmol) and DMF (600 µL) was added and the reaction mixture was stirred at room temperature for 18 hours. The reaction was quenched with water (40 mL) and extracted with dichloromethane (2×35 mL). The organic portions were combined, washed with brine (40 mL), dried (MgSO$_4$) and concentrated. The residue was purified by silica gel column chromatography utilizing 40% acetone/dichloromethane to produce 41 mg of P-528 as a white solid in 46% yield.

$^1$H NMR (400 MHz, DMSO-d$_6$) δ 3.75 (s, 3H), 5.38 (s, 2H), 7.00 (d, J=8 Hz, 1H), 7.30 (br d, J=7 Hz, 1H), 7.36 (d, J=9 Hz, 1H), 7.39 (s, 1H), 7.42-7.48 (m, 2H), 7.57-7.58 (m, 2H), 8.09 (s, 1H), 8.49 (m, 3H) ppm.

MS (APCI+): 394.1 (M+1); LC-MS: 90%.

Example 319

Preparation of P-544

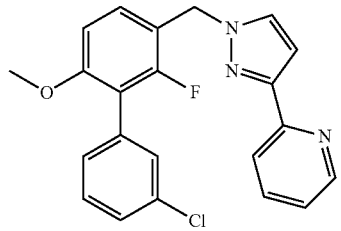

Synthesis of 2-[1-(3'-Chloro-2-fluoro-6-methoxy-biphenyl-3-ylmethyl)-1H-pyrazol-4-yl]-pyridine hydrochloride salt (P-544). In an 8 mL vial equipped with a stir bar was placed 2-(1H-pyrazol-3-yl)-pyridine (41.8 mg, 0.288 mmol), DMF (800 uL) and sodium hydride (15.8 mg, 0.394 mmol). The reaction mixture was stirred at room temperature for 25 minutes and then a solution of I-33 (100 mg, 0.303 mmol) in DMF (800 uL) was added and the reaction mixture was stirred at room temperature for 18 hours. The reaction was quenched with water (20 mL) and extracted with ethyl acetate (2×30 mL). The organic portions were combined, washed with brine (30 mL), dried (MgSO$_4$) and concentrated. The crude material was purified by silica gel column chromatography utilizing 15% acetone/dicholormethane as the eluent to produce 79 mg as a colorless, viscous oil. The hydrochloride salt was formed by treated the purified product with 1,4-dioxane (500 uL) and 4.0M HCl in 1,4-dioxane (500 uL). After stirring for 1 hour at room temperature the reaction mixture was concentrated and dried in a high vacuum oven set at 35° C. for 18 hours to provide 80 mg of P-544 as a white solid in 62% yield. $^1$H NMR (400 MHz, DMSO-d$_6$) δ 3.75 (s, 3H), 5.49 (s, 2H), 7.01 (d, J=8 Hz, 1H), 7.09 (s, 1H), 7.30 (br d, J=7 Hz, 1H), 7.36-7.40 (m, 2H), 7.43-7.49 (m, 2H), 7.59 (br s, 1H), 8.01 (d, J=2 Hz, 1H), 8.16 (bs, 2H), 8.65 (d, J=5 Hz, 1H) ppm. MS (APCI+): 394.1 (M+1-HCl); LC-MS: >99%.

Example 320

Preparation of P-545

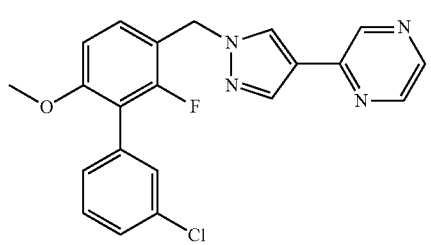

P-545

Synthesis of 2-[1-(3'-Chloro-2-fluoro-6-methoxy-biphenyl-3-ylmethyl)-1H-pyrazol-4-yl]-pyrazine (P-545). Same as procedure for P-544. Target compound crashed out of DMF with addition of water (6 mL), collect solid, wash with water (3×2 mL), dry in vacuum oven to afford 46 mg (35%) of P-545 as an off-white solid. $^1$H NMR (400 MHz, DMSO-$d_6$) δ 3.75 (s, 3H), 5.42 (s, 2H), 7.01 (d, J=8 Hz, 1H), 7.30 (br d, J=7 Hz, 1H), 7.39 (t, J=8 Hz, 2H), 7.43-7.48 (m, 2H), 8.14 (s, 1H), 8.41 (d, J=2 Hz, 1H), 8.50 (s, 1H), 8.54-8.55 (m, 1H), 8.99 (d, J=2 Hz, 1H) ppm. MS (APCI+): 395.1 (M+1); LC-MS: 99%.

Example 321

Preparation of P-546

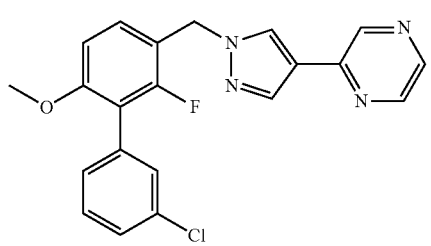

P-546

Synthesis of 4-[1-(3'-Chloro-2-fluoro-6-methoxy-biphenyl-3-ylmethyl)-1H-pyrazol-4-yl]-pyrimidine hydrochloride salt (P-546). Same as procedure for P-544. Purification was performed using 30% acetone/dichloromethane as the eluent. HCl salt formation provided 73 mg of P-546HCl salt as a white solid in 56% yield. $^1$H NMR (400 MHz, DMSO-$d_6$) δ 3.75 (s, 3H), 5.43 (s, 2H), 7.01 (d, J=8 Hz, 1H), 7.30 (br d, J=7 Hz, 1H), 7.39 (br s, 1H), 7.40-7.49 (m, 3H), 7.79 (dd, J=6, 1 Hz, 1H), 8.21 (s, 1H), 8.61 (s, 1H), 8.71 (br d, J=5 Hz, 1H), 9.07 (s, 1H) ppm. MS (APCI+): 395.1 (M+1-HCl); LC-MS: >99%.

Example 322

Preparation of P-549

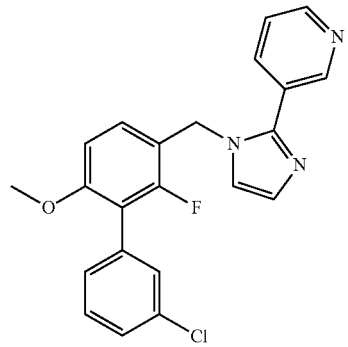

P-549

Synthesis of 3-[1-(3'-Chloro-2-fluoro-6-methoxy-biphenyl-3-ylmethyl)-1H-imidazol-2-yl]-pyridine hydrochloride salt (P-549). Same as procedure for P-544. Purification was performed using 5% methanol/dichloromethane as the eluent. HCl salt formation provided 14 mg of P-549 as a pale yellow solid in 11% yield. $^1$H NMR (400 MHz, DMSO-$d_6$) δ 3.74 (s, 3H), 5.47 (s, 2H), 6.96 (d, J=9 Hz, 1H), 7.21-7.23 (m, 1H), 7.28-7.31 (m, 2H), 7.44-7.46 (m, 2H), 7.67-7.70 (m, 1H), 7.88 (s, 2H), 8.23 (dt, J=8, 2 Hz, 1H), 8.85 (dd, J=5, 2 Hz, 1H), 8.94 (d, J=2 Hz, 1H) ppm.

MS (APCI+): 394.1 (M+1-HCl); LC-MS: >99%.

Example 323

Preparation of P-559

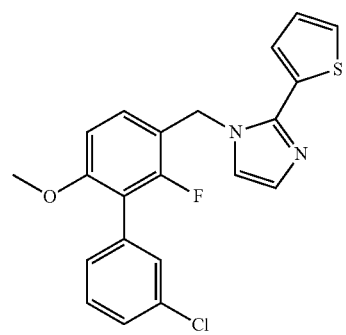

P-559

Synthesis of 1-(3'-Chloro-2-fluoro-6-methoxy-biphenyl-3-ylmethyl)-2-thiophen-2-yl-1H-imidazole hydrochloride salt (P-559). Same as procedure for P-544. Purification performed using 5% methanol/dichloromethane as the eluent. HCl salt formation provided 61 mg of P-559 in 46% yield. $^1$H NMR (400 MHz, DMSO-$d_6$) δ 3.75 (s, 3H), 5.52 (s, 2H), 6.84 (d, J=9 Hz, 1H), 7.18 (t, J=8 Hz, 1H), 7.27-7.28 (m, 1H), 7.31-7.34 (m, 1H), 7.37 (bs, 1H), 7.44-7.49 (m, 2H), 7.70-7.75 (m, 3H), 8.00 (br d, J=4 Hz, 1H) ppm. MS (APCI+): 399.1 (M+1-HCl); LC-MS: >99%.

Example 324

Preparation of P-551

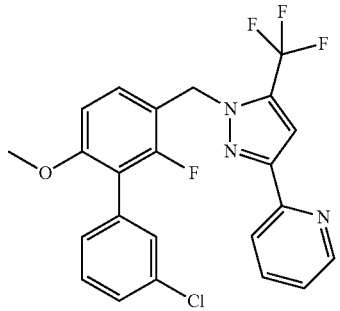

Synthesis of 2-[1-(3'-Chloro-2-fluoro-6-methoxy-biphenyl-3-ylmethyl)-5-trifluoromethyl-1H-pyrazol-3-yl]-pyridine hydrochloride salt (P-551). Same as procedure for P-544. Purification performed using 3% methanol/dichloromethane as the eluent. HCl salt formation provided 49 mg of P-551 as a white solid in 32% yield.

$^1$H NMR (400 MHz, DMSO-$d_6$) δ 3.75 (s, 3H), 5.58 (s, 2H), 7.01 (d, J=8 Hz, 1H), 7.26 (d, J=9 Hz, 1H), 7.28-7.30 (m, 1H), 7.38 (s, 1H), 7.44-7.48 (m, 3H), 7.50 (s, 1H), 7.94-8.06 (m, 2H), 8.64-8.66 (m, 1H) ppm. MS (APCI+): 462.1 (M+1-HCl); LC-MS: >99%.

Example 325

Preparation of P-552

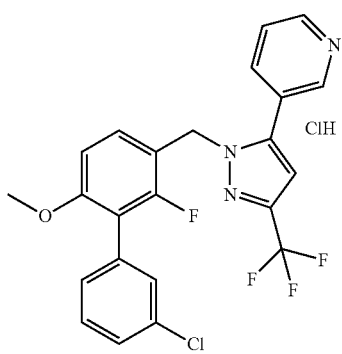

Synthesis of 3-[2-(3'-Chloro-2-fluoro-6-methoxy-biphenyl-3-ylmethyl)-5-trifluoromethyl-2H-pyrazol-3-yl]-pyridine hydrochloride salt (P-552). Same as procedure for P-544. Purification performed using 20% acetone/dichloromethane as the eluent. HCl salt formation provided 53 mg of P-552 as an off-white solid in 35% yield.

$^1$H NMR (400 MHz, DMSO-$d_6$) δ 3.75 (s, 3H), 5.58 (s, 2H), 7.01 (d, J=9 Hz, 1H), 7.27-7.31 (m, 2H), 7.37 (s, 1H), 7.43-7.49 (m, 2H), 7.72 (t, J=8 Hz, 2H), 8.48 (br d, J=8 Hz, 1H), 8.70 (dd, J=5, 1 Hz, 1H), 9.17 (d, J=2 Hz, 1H) ppm. MS (APCI+): 462.1 (M+1-HCl); LC-MS: 98%.

Example 326

Preparation of P-388

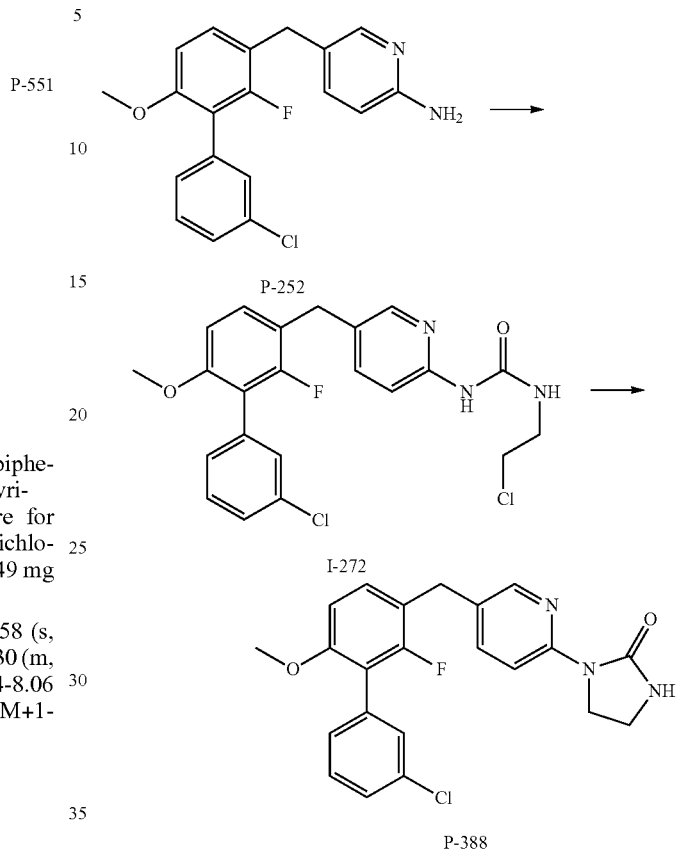

Synthesis of 1-(2-Chloro-ethyl)-3-[5-(3'-chloro-2-fluoro-6-methoxy-biphenyl-3-ylmethyl)-pyridin-2-yl]-urea (I-272). To a solution of P-252 (180 mg, 0.525 mol) in chloroform (4 mL) was added 2-chloroethylisocyanate (66.4 mg, 0.630 mmol) under nitrogen. The solution was stirred at room temperature for 48 h. Additional 2-chloroethylisocyanate (33.2 mg, 315 mmol) was added, and the reaction was stirred at 80° C. overnight. The solvent was removed under vacuum and the crude residue was purified by flash silica gel column chromatography (0-5% acetone in dichloromethane) to give I-272 (86.9 mg, 37% yield). $^1$H NMR (400 MHz, CDCl$_3$): 9.75 (s, 1H), 8.10 (m, 1H), 7.47-7.38 (m, 1H), 7.38-7.26 (m, 4H), 7.10 (t, J=8.4 Hz, 1H), 6.90 (s, 1H), 6.72 (d, J=9.2 Hz, 1H), 6.58 (d, J=8.4 Hz, 1H), 3.89 (s, 2H), 3.76 (s, 3H), 3.72-3.67 (m, 4H) ppm.

LCMS=55.1% purity. MS (APCI+)=448.0 (M).

Synthesis of 1-[5-(3'-Chloro-2-fluoro-6-methoxy-biphenyl-3-ylmethyl)-pyridin-2-yl]-imidazolidin-2-one (P-388). A suspension of I-272 (85.0 mg, 0.190 mmol) and sodium carbonate (60.3 mg, 0.569 mmol) in acetonitrile (2 mL) was stirred at reflux 21 h. The reaction was cooled to room temperature and the sodium carbonate removed by filtration. The solid was washed with ethyl acetate (3×5 mL) and the filtrate removed under vacuum. The residue was purified by silica gel preparatory thin layer chromatography eluting with 15% acetone in dichloromethane and using two developments, triturated in diethyl ether (2 mL), and filtered to give P-388 (11.8 mg, 15% yield) as a red pink powder. $^1$H NMR (400 MHz, CDCl$_3$) d: 8.09 (s, 1H), 7.43-7.28 (m, 5H), 7.08 (t, J=8.6 Hz, 1H), 6.97 (d, J=8.4 Hz, 1H), 6.69 (d, J=8.8 Hz, 1H), 4.42 (t, J=8.0 Hz, 2H), 3.88 (s, 2H), 3.82 (t, J=7.8 Hz, 2H), 3.75 (s, 3H) ppm. LCMS=95.9% purity. MS (APCI+)=412.1 (M+1).

Example 327

Preparation of I-275

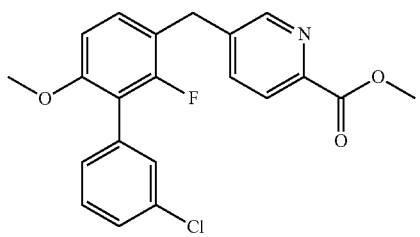

I-275

Synthesis of 5-(3'-Chloro-2-fluoro-6-methoxy-biphenyl-3-ylmethyl)-pyridine-2-carboxylic acid methyl ester (I-275). I-275 was synthesized from I-145 (516 mg, 1.59 mmol) and 2-methylcarboxypyridine-5-boronic acid pinocol ester (460 mg, 1.75 mmol) using the a similar procedure to P-252. The crude material was purified by flash silica gel column chromatography (0-5% acetone in dichloromethane) to give I-275 (381 mg, 62% yield) as an orange syrup. $^1$H NMR (400 MHz, CDCl$_3$): 8.65 (d, J=2.4 Hz, 1H), 8.06 (d, J=8.0 Hz, 1H), 7.66 (dd, J=8.0 Hz, 2.0 Hz, 1H), 7.37-7.33 (m, 3H), 7.26-7.24 (m, 1H), 7.11 (t, J=8.6 Hz, 1H), 6.73 (dd, J=8.6 Hz, 1.0 Hz, 1H), 4.04 (s, 2H), 4.00 (s, 3H), 3.77 (s, 3H) ppm. LCMS=96.8% purity. MS (APCI+)=386.0 (M+1).

Example 328

Preparation of I-276

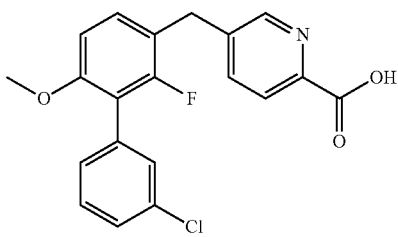

I-276

Synthesis of 5-(3'-Chloro-2-fluoro-6-methoxy-biphenyl-3-ylmethyl)-pyridine-2-carboxylic acid (I-276). To a solution of I-275 (317 mg, 0.822 mmol) in tetrahydrofuran (2.2 mL), methanol (2.2 mL), and water (2.2 mL) was added 1 N aqueous sodium hydroxide (1.64 mL, 1.64 mmol). The resultant solution was stirred at room temperature for 23 h. The pH was adjusted with glacial acetic acid to pH 4. Approximately three-fourths of the solvent was removed under vacuum, and the remaining suspension was diluted with water (10 mL). The suspension was extracted with dichloromethane (3×10 mL), and the combined extracts were dried over magnesium sulfate, filtered, and the solvent removed under vacuum to give I-276 (250.8 mg, 82% yield) as a beige solid.

$^1$H NMR (400 MHz, CDCl$_3$): 8.50 (m, 1H), 8.13 (d, J=7.6 Hz, 1H), 7.76-7.71 (m, 1H), 7.37-7.32 (m, 3H), 7.26-7.24 (m, 1H), 7.13 (t, J=8.6 Hz, 1H), 6.74 (d, J=8.8 Hz, 1H), 4.05 (s, 2H), 3.77 (s, 3H) ppm. MS (APCI+)=327.2 (M−44), MS (APCI−)=327.9 (M−44).

Example 329

Preparation of P-382

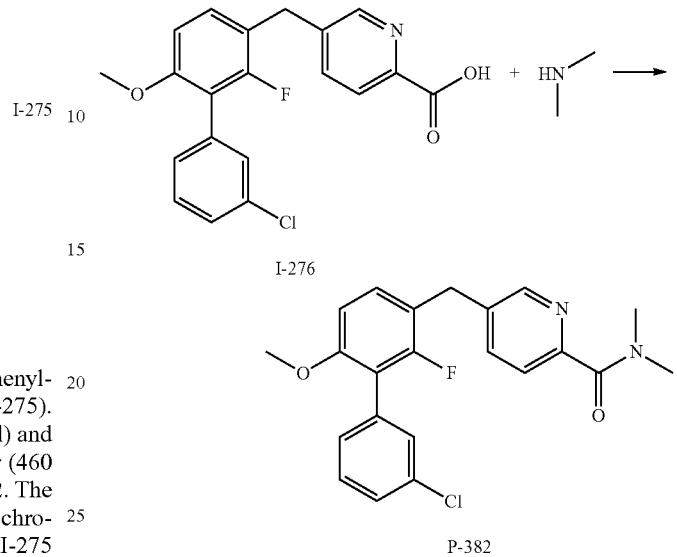

Synthesis of 5-(3'-Chloro-2-fluoro-6-methoxy-biphenyl-3-ylmethyl)-pyridine-2-carboxylic acid dimethylamide (P-382). A solution of I-276 (50.0 mg, 0.134 mmol), dimethyl amine (33% by weight in ethanol, 26.6 uL, 0.148 mmol), EDCI (28.4 mg, 0.148 mmol), and HOBt (20.0 mg, 0.148 mmol) was stirred at room temperature for 36 h. The solvent was removed under vacuum and the residue dissolved in ethyl acetate (5 mL). The organic solution was washed with water (5 mL), and the aqueous wash extracted with ethyl acteate (5 mL). The organic extracts were combined, washed with aqueous saturated sodium bicarbonate (10 mL), water (5 mL) and brine (5 mL), dried over sodium sulfate, filtered, and the solvent removed under vacuum. The crude yellow oil was purified by silica gel preparatory thin layer chromatography (dichloromethane) and dried under high vacuum at room temperature for 4 h to give P-382 (28.6 mg, 54% yield) as a clear syrup. $^1$H NMR (400 MHz, CDCl$_3$): 8.48 (s, 1H), 7.63-7.58 (m, 2H), 7.39-7.28 (m, 4H), 7.12 (t, J=8.4 Hz, 1H), 6.73 (d, J=8.4 Hz, 1H), 4.00 (s, 2H), 3.770 (s, 3H), 3.13 (s, 3H), 3.10 (s, 3H) ppm. LCMS=97.4% purity. MS (APCI+)=399.1 (M+1).

Example 330

Preparation of P-401

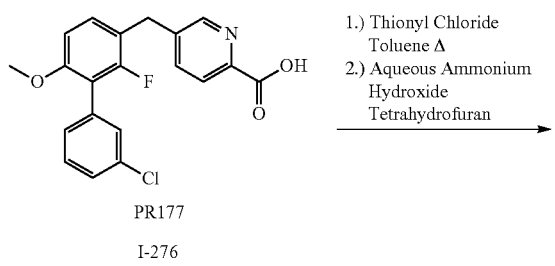

PR177

I-276

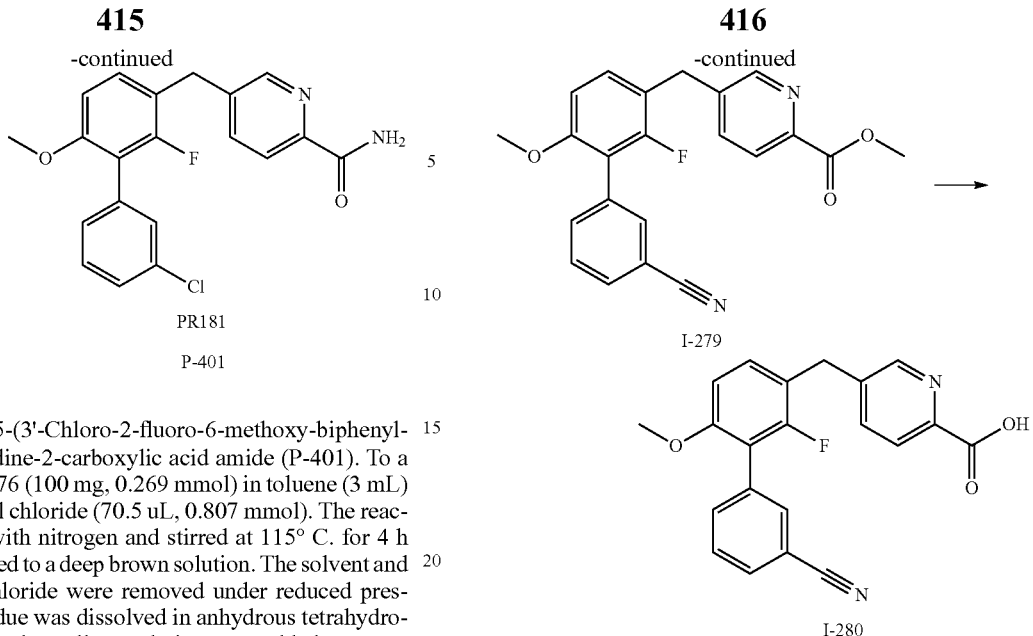

PR181
P-401

Synthesis of 5-(3'-Chloro-2-fluoro-6-methoxy-biphenyl-3-ylmethyl)-pyridine-2-carboxylic acid amide (P-401). To a suspension of I-276 (100 mg, 0.269 mmol) in toluene (3 mL) was added thionyl chloride (70.5 uL, 0.807 mmol). The reaction was sealed with nitrogen and stirred at 115° C. for 4 h over which it turned to a deep brown solution. The solvent and excess thionyl chloride were removed under reduced pressure, and the residue was dissolved in anhydrous tetrahydrofuran (3 mL). To the yellow solution was added aqueous concentrated ammonium hydroxide (5.8 uL, 0.807 mmoL) and the brown suspension was stirred at room temperature over night. The brown suspension was dissolved in ethyl acetate (50 mL) and water (50 mL). The two layers were separated, and the aqueous layer extracted with ethyl acetate (50 mL). The two organic extractions were combined, washed with water (50 mL), brine (50 mL), dried over sodium sulfate, filtered, and the solvent removed under vacuum to give crude product. The product was purified by silica gel silica gel preparatory thin layer chromatography (eluting with 10% acetone in dichoromethane) to give P-401 (42.0 mg, 42% yield) as an off-white solid. $^1$HNMR (400 MHz, DMSO-$d_6$) 8.54 (s, 1H), 8.04 (s, 1H), 7.96 (d, J=8.0 Hz, 1H), 7.78 (dd, J=8.0 Hz, 2.0 Hz, 1H), 7.57 (s, 1H), 7.45-7.35 (m, 4H), 7.28 (d, J=6.8 Hz, 1H), 6.96 (d, J=8.8 Hz, 1H), 4.06 (s, 2H), 3.73 (s, 3H) ppm. LCMS=100.0% purity. MS (APCI+)=371.0 (M+1).

Scheme 65

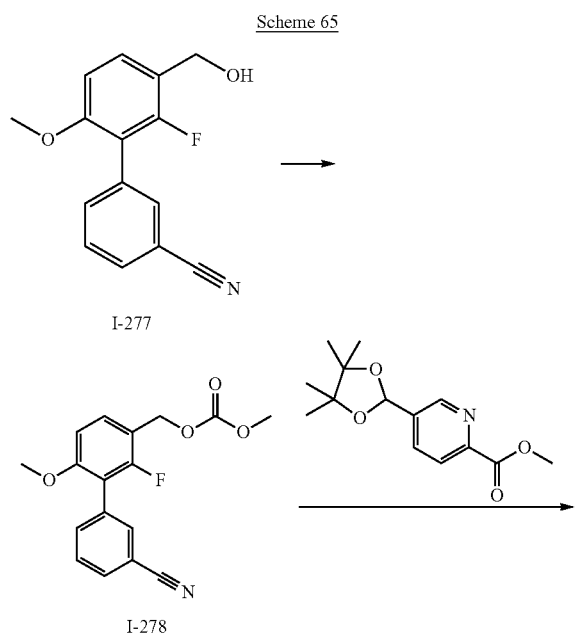

I-277

I-278

I-279

I-280

Example 331

Preparation of I-280

Synthesis of Carbonic acid 3'-cyano-2-fluoro-6-methoxy-biphenyl-3-ylmethyl ester methyl ester (I-278). I-278 was synthesized from 2'-fluoro-3'-hydroxymethyl-6'-methoxy-biphenyl-3-carbonitrile (500 mg, 1.94 mmol) using the same conditions as I-145 to give I-278 (466 mg, 75% yield) as a tacky white solid. $^1$H NMR (400 MHz, CDCl$_3$): 7.71 (m, 1H), 7.65-7.63 (m, 2H), 7.54-7.52 (m, 1H), 7.45-7.41 (m, 1H), 6.79 (d, J=9.2 Hz, 1H), 5.21 (s, 2H), 3.80 (s, 3H), 3.80 (s, 3H) ppm. LCMS=95.9% purity. MS (APCI−)=240.1 (M−75). MS (APCI+)=279.1 (M−32).

Synthesis of 5-(3'-Cyano-2-fluoro-6-methoxy-biphenyl-3-ylmethyl)-pyridine-2-carboxylic acid methyl ester (I-279). I-279 was synthesized from I-278 (440.0 mg, 1.40 mmol) and 2-methylcarboxypyridine-5-boronic acid pinocol ester (405 mg, 1.54 mmol) using the similar conditions to the preparation of P-252. The crude product was purified by trituration with diethyl ether (25 mL), filtered, and washed with diethyl ether (2×5 mL) to give I-279 (354 mg, 67% yield) as a yellow powder. $^1$H NMR (400 MHz, CDCl$_3$): 8.65 (d, J=2.0 Hz, 1H), 8.07 (d, J=8.0 Hz, 1H), 7.69-7.60 (m, 4H), 7.51 (t, J=7.8 Hz, 1H), 7.15 (t, J=8.6 Hz, 1H), 6.75 (d, J=8.8 Hz, 1H), 4.05 (s, 2H), 4.00 (s, 3H), 3.78 (s, 3H) ppm. LCMS=96.3% purity. MS (APCI+)=377.1 (M+1).

Synthesis of 5-(3'-Cyano-2-fluoro-6-methoxy-biphenyl-3-ylmethyl)-pyridine-2-carboxylic acid (I-280). A solution of I-279 (150 mg, 0.399 mmol) and 1 N aqueous sodium hydroxide (797 uL, 0.797 mmol) in methanol (1.5 mL), water (1.5 mL) and tetrahydrofuran (1.5 mL) was stirred at room temperature 11.5 h. Approximately one-half of the solvent was removed under vacuum and the remaining suspension was acidified with glacial acetic acid (2 mL). The suspension was diluted with water (50 mL), and extracted into dichloromethane (2×30 mL). The combined extracts were washed with brine (50 mL), dried over sodium sulfate, filtered, and the solvent removed under vacuum to give I-280 (109 mg, 76% yield) as a yellow foam.

Example 332

Preparation of P-415

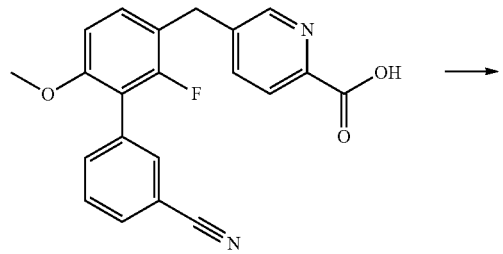

I-280

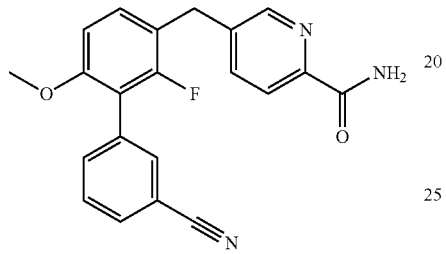

P-415

Synthesis of 5-(3'-Cyano-2-fluoro-6-methoxy-biphenyl-3-ylmethyl)-pyridine-2-carboxylic acid amide (P-415). P-415 was synthesized from I-280 (100 mg, 0.276 mmol) using the same conditions as for the preparation of P-401. The crude product was purified by silica gel preparatory thin layer chromatography (eluting with 25% acetone in dichloromethane), triturated with diethyl ether (5 mL), filtered, and washed with hexanes (2 mL) to give P-415 (10.0 mg, 10% yield) as a beige powder. $^1$H NMR (400 MHz, CDCl$_3$): 8.46 (m, 1H), 8.13 (d, J=8.00 Hz, 1H), 7.78 (s, 1H), 7.70-7.61 (m, 4H), 7.51 (t, J=7.8 Hz, 1H), 7.16 (t, J=8.6 Hz, 1H), 6.76 (d, J=8.4 Hz, 1H), 5.55 (s, 1H), 4.04 (s, 2H), 3.78 (s, 3H) ppm. LCMS purity=94.6%. MS (APCI+)=362.1 (M+1).

HPLC (254 nm); 92.23%. [Mobile Phase A and Mobile Phase B=Water and Acetonitrile, Symmetry C18, (250×4.6 mm, 5 um), Flow=1.0 mL/min, Inj. Wash=ACN, Inj. Vol.=10 uL. Retention time=24.17 min]

Example 333

Preparation of P-504

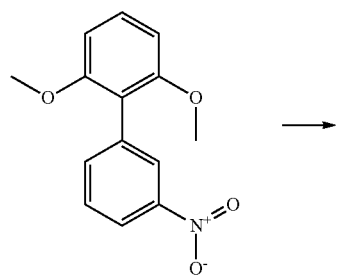

I-81

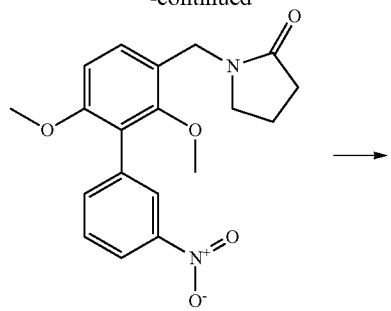

I-281

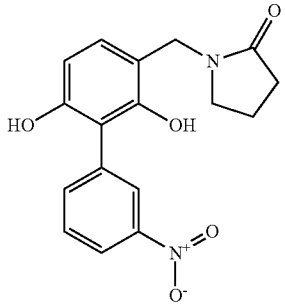

P-504

Synthesis 1-(2,6-Dimethoxy-3'-nitro-biphenyl-3-ylmethyl)-pyrrolidin-2-one (I-281). To a stirred solution of starting I-81 (1.93 mmol, 1.0 eq.) and 1-hydroxymethyl-pyrrolidin-2-one (1.93 mmol, 1.0 eq) in nitrobenzene at room temperature was added aluminum chloride (1.93 mmol, 1.0 eq). The resulting mixture was stirred at room temperature for 16 h. The reaction was diluted with water, and extracted with 2 portions of dichloromethane. The combined organics were washed with brine, dried over magnesium sulfate, and the filtrate concentrated in vacuo. The residue was purified via silica gel plug filtration, using a methanol/dichloromethane gradient as eluent to afford I-281 as a glassy solid in 72% yield. $^1$H NMR (400 MHz, CDCl$_3$) 2.03 (quintet, J=8.0, 7.6 Hz, 2H), 2.46 (dd, J=8.4, 8.0 Hz, 2H), 3.28 (s, 3H), 3.34 (dd, J=8.8, 6.8 Hz, 2H), 3.75 (s, 3H), 4.51 (s, 2H), 6.76 (d, J=8.4 Hz, 1H), 7.26 (d, J=8.4 Hz, 1H), 7.58 (dd, J=8.4, 7.6 Hz, 1H), 7.77 (dt, J=7.6, 1.2 Hz, 1H), 8.21 (ddd, J=8.0, 1.2, 0.8 Hz, 1H), 8.32 (dd, J=2.0, 1.6 Hz, 1H) ppm. LC/MS (100%): APCI (+) found: 357.1 (M+1); calc'd: 356.4 m/z.

Synthesis 1-(2,6-Dihydroxy-3'-nitro-biphenyl-3-ylmethyl)-pyrrolidin-2-one (P-504). To a stirred solution I-281 in dichloromethane at −70° C. was added 1 eq. of boron tribromide as a 1.0 M solution in dichloromethane. The resultant mixture was allowed to warm to room temperature. After 3 h, the reaction was again cooled to −70° C. and an additional 1 eq. of boron tribromide solution was added, and the reaction was allowed to warm to room temperature, and stir for 16 h. The reaction was cooled to −70° C., and excess (3.6 eq.) boron tribromide solution was added, and the reaction warmed to room temperature with stirring over 18 h. The reaction was quenched with water, and extracted with ethyl acetate. The combined extracts were washed successively with water and brine, and the dried (MgSO$_4$) solution was concentrated to afford P-504 as a tan solid in 59% yield.

$^1$H NMR, (400 MHz, DMSO-d$_6$): 1.96 (quintet, J=7.6 Hz, 2H), 2.33 (dd, J=8.4, 8.0 Hz, 2H), 3.43 (t, J=7.2 Hz, 2H), 4.27 (s, 2H), 6.48 (d, J=8.0 Hz, 1H), 7.04 (d, J=8.4 Hz, 1H), 7.65 (dd, J=8.8, 8.0 Hz, 1H), 7.78 (d, J=8.0 Hz, 1H), 8.12-8.14 (m, 2H), 9.45 (s, 1H), 9.55 (s, 1H) ppm. LC/MS (90.9%): APCI⁻ found: 327.1 (M−1); calc'd: 328.3 m/z.

Example 334

Preparation of P-504, I-282 and P-229

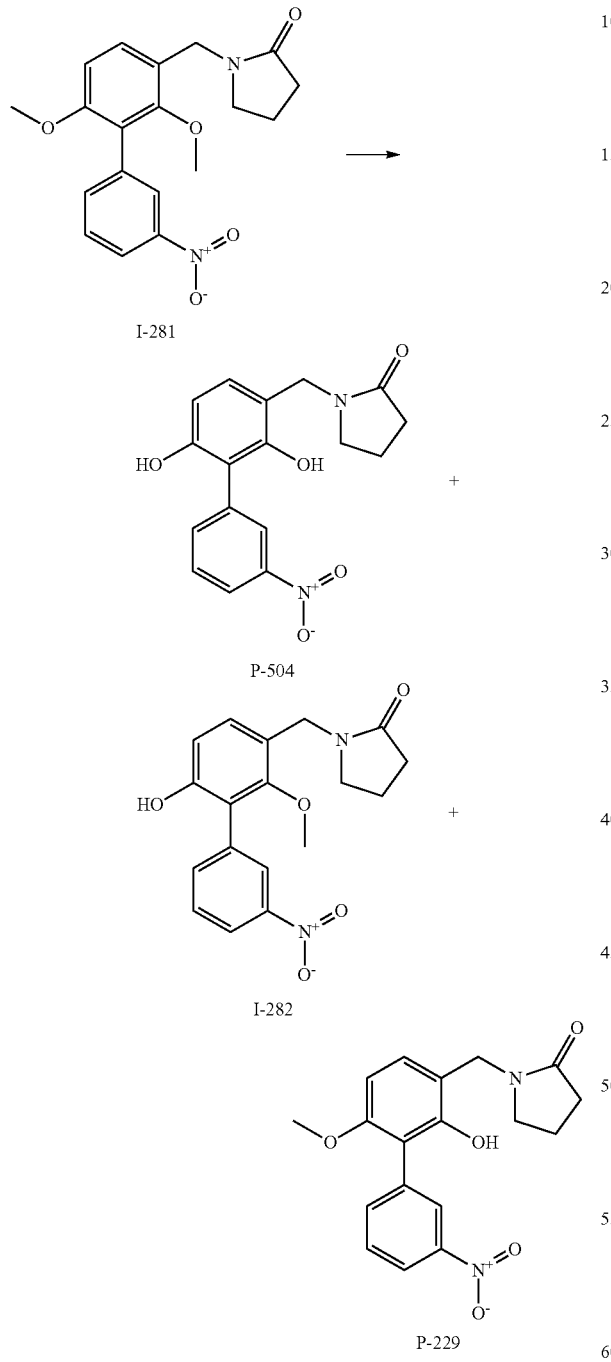

additional boron tribromide solution (1 eq.) was added over 1 min. The resultant solution was allowed to warm to room temperature, and stirred for 1 min, at which point, The reaction mixture was poured into ice water, and extracted with 3 portions of ethyl acetate. The combined extracts were washed with 3 portions of water, and brine. The solution was dried over magnesium sulfate, concentrated in vacuo, and the residue purified via preparatory thin layer chromatography using 30% acetone in hexanes to afford the above compounds; P-504, I-282, P-229.

I-282: $^1$H NMR (400 MHz, DMSO-d$_6$): 1.93 (quintet, J=7.6 Hz, 2H), 2.28 (dd, J=8.0, 7.6 Hz, 2H), 3.20 (s, 3H), 3.24-3.30 (M, 2H), 4.34 (s, 2H), 6.77 (d, J=8.4 Hz, 1H), 7.04 (d, J=8.4 Hz, 1H), 7.71 (dd, J=9.2, 7.6 Hz, 1H), 7.85 (dd, J=8.0, 1.6 Hz, 1H), 8.19-8.21 (M, 2H), 9.76 (s, 1H) ppm.

LC/MS (97%) APCI⁺ found: 343.1 (M+1); calc'd: 342.4 m/z

P-229: $^1$H NMR (400 MHz, DMSO-d$_6$): 1.96 (quintet, J=7.6 Hz, 2H), 2.33 (t, J=8.0 Hz, 2H), 3.44 (t, J=7.2 Hz, 2H), 3.68 (s, 3H), 4.32 (s, 2H), 6.65 (d, J=8.4 Hz, 1H), 7.22 (d, J=8.4 Hz, 1H), 7.67 (t, J=8.0 Hz, 1H), 7.73 (dt, J=7.6, 1.6, 1.2 Hz, 1H), 8.07 (m, 1H), 8.15 (ddd, J=8.4, 1.6, 1.2 Hz, 1H) 9.53 (s, 1H) ppm.

LC/MS (100%) APCI⁺ found: 343.1 (M+1); calc'd: 342.4 m/z

Example 335

Preparation of P-394

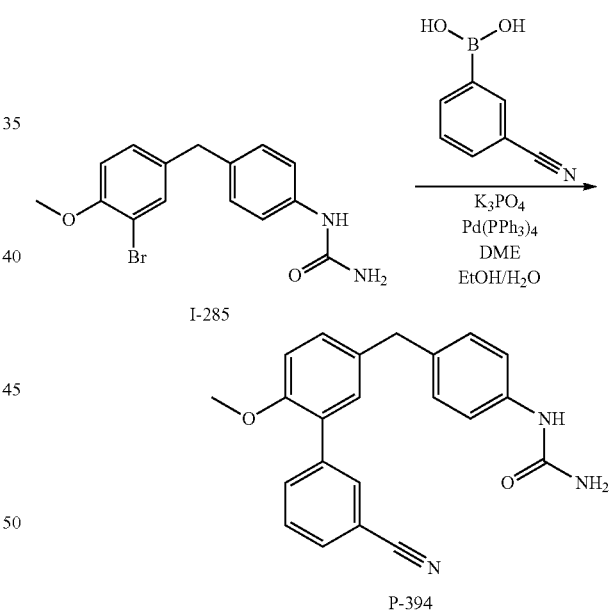

Synthesis of [4-(3'-Cyano-6-methoxy-biphenyl-3-ylmethyl)-phenyl]-urea (P-384). A suspension of I-285 (0.60 mmol, 1.0 eq), 3-cyanophenylboronic acid (1.2 mmol, 2 eq), potassium phosphate (1.2 mmol, 2 eq), and tetrakis(triphenylphosphine)palladium (0.06 mmol, 0.1 eq) in 5 mL of dimethoxyethane and 1.6 mL of 50% aqueous ethanol was degassed with nitrogen for 10 minutes. The resultant mixture was heated at 80° C. for 18 h and cooled to ambient temperature. The solids were removed by filtration and the cake washed with ethyl acetate. The filtrate washed with successive portions of water and brine, dried over magnesium sulfate, and filtered. The filtrate was concentrated under a stream of nitrogen to a volume of 5 mL, and the solids collected by (Demethylation of I-281: To a stirred solution of I-281 in dichloromethane at −70° C. was added a 1.0 M solution of boron tribromide in dichloromethane over 1 minute. The resultant solution was allowed to warm to room temperature and stirred overnight, at which point TLC analysis indicated no progress. The reaction was again cooled to −70° C., and filtration, washed with 2 portions of ethyl acetate, and dried in vacuo over ethyl acetate vapors for 3 h to afford the title compound, P-394, as a solid in 62% yield. $^1$H NMR, (400 MHz, DMSO-d$_6$): 3.75 (s, 3H), 3.83 (s, 2H), 5.76 (s, 2H), 7.04-7.10 (m, 3H), 7.20-7.22 (m, 2H), 7.27-7.29 (m, 2H), 7.60 (dd, J=8.0, 7.6 Hz, 1H), 7.77-7.80 (m, 2H), 7.89 (dd, J=1.6, 1.2 Hz, 1H), 8.40 (s, 1H) ppm. LC/MS=98.5% purity: APCI$^+$ found: 358.1 calc'd: 357.4 m/z Example 336

Preparation of P-421

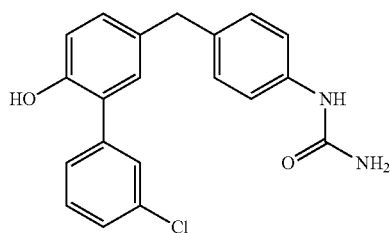

P-421

Synthesis of [4-(3'-Chloro-6-hydroxy-biphenyl-3-ylmethyl)-phenyl]-urea (P-421). To a suspension of P-378 (2.2 mmol, 1.0 eq.) in dichloromethane at −70° C. was added a 1.0 M solution of boron tribromide in dichloromethane (6.6 mmol, 3 eq) over 5 min. The resultant mixture was allowed to stir and warm to ambient temperature, and stirred for 20 min. The reaction was poured into ice water (100 mL), stirred for 30 min, filtered, and the cake washed with successive portions of water and hexanes. The solids were dried in vacuo over ethyl acetate vapors for 4 h to afford the title compound P-421, which was taken into further reactions as is. A portion of P-421 was further purified via chromatography on silica gel using acetone in dichloromethane as eluent, followed by trituration with dichloromethane to afford pure P-421 compound as a white solid.

$^1$H NMR (400 MHz, DMSO-d$_6$): 3.78 (s, 2H), 5.75 (s, 2H), 6.86 (d, J=8.0 Hz, 1H), 7.00 (dd, J=8.4, 2.4 Hz, 1H), 7.07 (d, J=8.4 Hz, 2H), 7.12 (d, J=2.4 Hz, 1H), 7.28 (d, J=8.4 Hz, 2H), 7.4 (m, 1H), 7.41 (dd, J=8.0, 7.6 Hz, 1H), 4.47 (m, 1H), 7.56 (m, 1H), 8.40 (s, 1H), 9.50 (s, 1H) ppm.

LC/MS=100% purity. APCI$^+$ found: 353.0 calc'd: 352.8 m/z

Example 337

Preparation of P-420

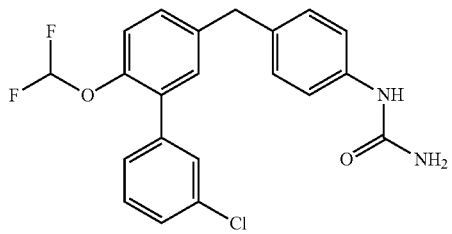

P-420

Synthesis of [4-(3'-Chloro-6-difluoromethoxy-2-fluoro-biphenyl-3-ylmethyl)-phenyl]-urea (P-420). To a solution of P-421 (0.992 mmol, 1.0 eq) in 10 mL of dimethylformamide was added sodium hydroxide (2.98 mmol, 3 eq), and the resultant suspension stirred 5 min. Sodium chlorodifluoroacetate (4.96 mmol, 5 eq) was added, and the mixture stirred at 50° C. for 18 h, and cooled to ambient temperature. Additional sodium hydroxide (2 mmol, 2 eq) and sodium chlorodifluoroacetate (3 mmol, 3 eq) were added, and the reaction stirred at 50° C. for an additional 5 h. The reaction was poured into 50 mL of water, and extracted with 3 portions of ethyl acetate. The combined organics were washed with successive portions of water and brine, dried over magnesium sulfate, filtered and concentrated. The residue was purified 3 times with flash column chromatography on silica gel, followed by prep TLC to afford the title compound, P-420, as a yellow solid. $^1$H NMR (400 MHz, DMSO-d$_6$): 3.89 (s, 2H), 5.76 (s, 2H), 7.10 (t, J=74.4 Hz, 1H), 7.12 (d, J=8.8 Hz, 2H), 7.22 (s, 1H), 7.27-7.31 (m, 3H), 7.33 (d, J=2.0 Hz, 1H), 7.39-7.50 (m, 4H), 8.41 (s, 1H) ppm.

LC/MS=98.1% purity. APCI$^+$ found: 403.0 calc'd: 402.8 m/z

Example 338

Preparation of P-468

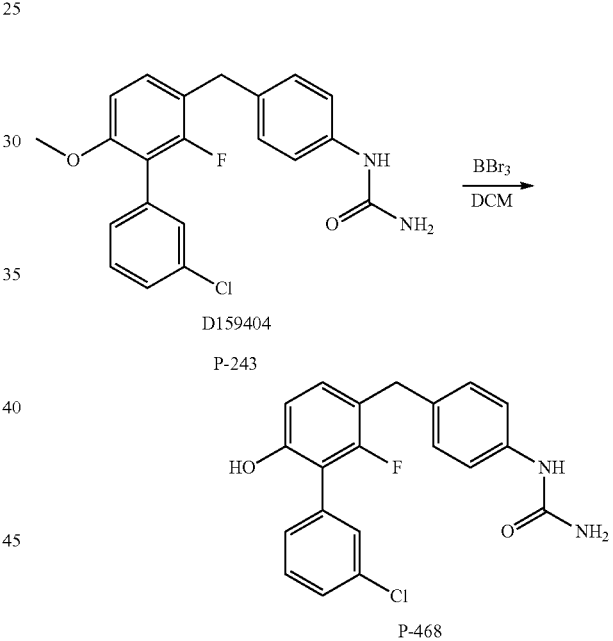

Synthesis of [4-(3'-Chloro-2-fluoro-6-hydroxy-biphenyl-3-ylmethyl)-phenyl]-urea (P-468). To a suspension of P-243 (3.9 mmol, 1.0 eq.) in dichloromethane at −70° C. was added a 1.0 M solution of boron tribromide in dichloromethane (12 mmol, 3 eq) over 30 sec. The resultant mixture was allowed to stir and warm to ambient temperature, and stirred for 1 h. The reaction was poured into ice water (75 mL), filtered, and the cake washed with successive portions of water and hexanes. The solids were dried in vacuo at 40-45° C. for 16 h to afford the title compound P-468, which was taken into further reactions as is. A portion of the title compound P-468 was further purified via chromatography on a silica gel using acetone in dichloromethane as eluent to afford pure P-468 title compound as a white solid. $^1$H NMR (400 MHz, DMSO-d$_6$): 3.78 (s, 2H), 5.76 (s, 2H), 6.73 (d, J=8.4 Hz, 1H), 7.04-7.08 (m, 3H), 7.28-7.33 (m, 3H), 7.38-7.46 (m, 3H), 8.41 (s, 1H), 9.82 (s, 1H) ppm. HPLC purity: 99.5%

423

Scheme 66. Preparation of I-286, I-287, I-150, I-147 and I-288

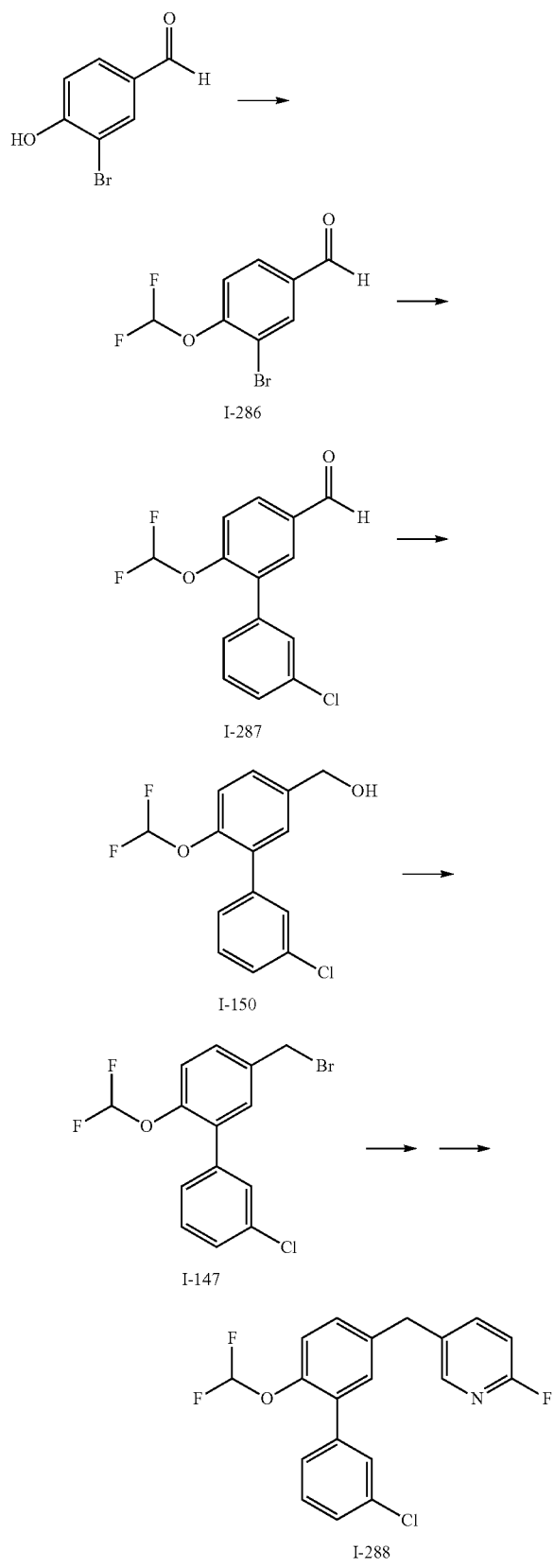

424

Example 339

Preparation of I-286, I-287, I-150, I-147 and I-288

Synthesis of 3-Bromo-4-difluoromethoxy-benzaldehyde (I-286). A suspension of 3-bromo-4-hydroxy-benzaldehyde (4.97 mmol; 1.0 eq.), cesium carbonate (7.46 mmol; 1.5 eq.) and sodium chlorodifluoroacetate was stirred at 65° C. for 5.5 h. The mixture was partitioned with ethyl acetate and water, and the aqueous portion extracted with diethyl ether. The combined extracts were washed with successive portions of water and brine, dried over magnesium sulfate, filtered and concentrated to afford the title compound, I-286, as a yellow oil. $^1$H NMR (400 MHz, DMSO-$d_6$): 7.49 (t, J=72.4 Hz, 3H), 7.54 (d, J=8.4 Hz, 1H), 8.00 (dd, J=8.4, 2.0 Hz, 1H), 8.26 (d, J=2.0 Hz, 1H), 9.96 (s, 1H) ppm.

Synthesis of 3'-Chloro-6-difluoromethoxy-biphenyl-3-carbaldehyde (I-287). A mixture of I-286 (7.98 mmol, 1.0 eq), 3-chlorophenylboronic acid (8.76 mmol, 1.1 eq), cesium carbonate (15.9 mmol, 2.0 eq) and palladium(II)acetate (0.40 mmol, 0.05 eq) in 20 mL of DMF was degassed with nitrogen for 5 min. The resulting suspension was heated to 50° C. for 2 h, cooled to ambient for 16 h, and additional palladium(II) acetate (0.40 mmol, 0.05 eq) added, and the reaction heated again to 50° C. for 2 h. The reaction was cooled to <30° C., and the solids removed by filtration. The filtrate was partitioned with ethyl acetate and water, and the aqueous portion extracted with ethyl acetate. The combined extracts were washed with successive portions of 5% lithium chloride, 0.5 N HCl, water and brine, dried over magnesium sulfate, filtered and concentrated to afford the title compound, I-287, as an oil in 98% yield. $^1$HNMR (400 MHz, DMSO-$d_6$): 7.40 (t, J=72.8 Hz, 1H), 7.49-7.62 (m, 5H), 8.02-8.04 (m, 2H), 10.04 (s, 1H) ppm.

Synthesis of (3'-Chloro-6-difluoromethoxy-biphenyl-3-yl)-methanol (I-150). To a solution of I-287 (6.8 mmol, 1.0 eq) in a mixture of 18 mL of THF and 6 mL of water at 0-5° C. was added sodium borohydride (10 mmol, 1.5 eq), and the resultant mixture stirred for 10 minutes. The reaction was diluted with 10 mL of water, and the pH adjusted to 8 with 15% ammonium chloride, and extracted with two portions of ethyl acetate. The combined organics were washed with successive portions of water and brine, dried over magnesium sulfate, filtered and concentrated to afford the title compound, I-150, in quantitative yield. $^1$H NMR (400 MHz, DMSO-$d_6$): 4.54 (d, J=5.6 Hz, 2H), 5.28 (t, J=5.2 Hz, 1H), 7.14 (t, J=74.0 Hz, 1H), 7.27 (d, J=8.8 Hz, 1H), 7.40 (s, 1H), 7.42-7.52 (m, 6H) ppm.

Synthesis of 5-Bromomethyl-3'-chloro-2-difluoromethoxy-biphenyl (I-147). To a solution of I-150 (3.5 mmol, 1.0 eq) in dichloromethane at 0-5° C. was added phosphorous tribromide (1.8 mmol, 0.5 eq), and the resulting solution was allowed to stir and warm naturally to ambient temperature over 2 h. To the reaction was added 15 mL of ice water, and the aqueous portion was extracted with 2 portions of ethyl acetate. The combined organics were washed with successive portions of saturated sodium bicarbonate, water and brine, dried over sodium sulfate, filtered and concentrated to afford the title compound, I-147 as an oil in 53% yield. $^1$H NMR (400 MHz, DMSO-$d_6$): 4.77 (s, 2H), 7.21 (t, J=74.0 Hz, 1H), 7.31 (d, J=8.4 Hz, 1H), 7.41-7.60 (m, 6H) ppm.

Synthesis of 5-(3'-Chloro-6-difluoromethoxy-biphenyl-3-ylmethyl)-2-fluoro-pyridine (I-288). A suspension of I-147 (1.7 mmol, 1.0 eq), 2-fluoropyridine-5-boronic acid (1.9 mmol, 1.1 eq), and potassium phosphate (3.4 mmol, 2.0 eq) in a mixture of dimethoxyethane (11 mL), and of 50% ethanol (5.4 mL) was degassed with nitrogen for 5 min. To the reaction was added tetrakis(triphenylphosphine)palladium (0.09 mmol, 0.05 eq), and the mixture was degassed further for 2 min. The suspension was heated to 65° C. for 1.5 h, cooled to ambient temperature, thiol functionalized silica gel (0.344 mmol) was added and stirred for 3 h. The solids were removed by filtration, the filtrate partition with ethyl acetate and water, and the aqueous extracted with ethyl acetate. The combined organics were washed with successive portions of water and brine, dried over magnesium sulfate, filtered and concentrated. The residue was purified via flash column chromatography on silica gel using acetone in hexanes as eluent to afford the title compound as an oil in 55% yield.

$^1$H NMR (400 MHz, DMSO-d$_6$): 4.03 (s, 2H), 7.12 (t, J=70.0 Hz, 1H), 7.11 (dd, J=8.4, 3.2 Hz, 1H), 7.25 (s, 1H), 7.31 (s, 1H), 7.36 (dd, J=6.4, 2.4 Hz, 1H), 7.41-7.52 (m, 6H), 7.90 (td, J=8.4, 2.4 Hz, 1H), 8.22 (d, J=2.4 Hz, 1H) ppm.

Example 340

Preparation of P-614

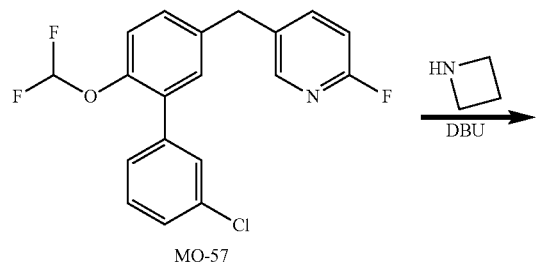

MO-57
I-288

P-614

Synthesis of 2-Azetidin-1-yl-5-(3'-chloro-6-difluoromethoxy-biphenyl-3-ylmethyl)-pyridine (P-614). A mixture of I-288 (0.404 mmol, 1.0 eq.) and azetidine (0.445 mmol; 1.1 eq.) in excess DBU was heated to 160° C. for 2.5 h, and allowed to cool to room temperature. The resultant mixture was partitioned with dichloromethane and 0.5N HCl, and the aqueous portion extracted with dichloromethane. The organics were washed with 0.5 N HCl and water, dried over magnesium sulfate, filtered and concentrated. The residue was purified by flash column chromatography on silica gel using acetone in dichloromethane as eluent to afford the title compound, P-614, as an oil in 32% yield.

$^1$H NMR (400 MHz, DMSO-d$_6$): 3.83-3.88 (m, 6H), 6.29 (d, J=8.0 Hz, 1H), 7.10 (t, J=74.0 Hz, 1H), 7.22 (s, 1H), 7.27-7.50 (m, 8H), 8.01 (d, J=2.0 Hz, 1H) ppm. LC/MS (99%)—found: 402.4 calc'd: 400.9 m/z.

Example 341

Preparation of P-422

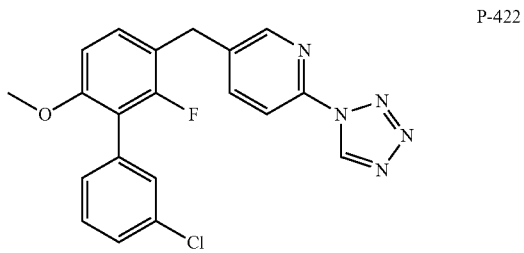 [SMILES: COc1ccc(Cc2ccc(-n3cnnn3)nc2)c(F)c1-c1cccc(Cl)c1]

P-422

Synthesis of 5-(3'-chloro-2-fluoro-6-methoxy-biphenyl-3-ylmethyl)-2-tetrazol-1-yl-pyridine (P-422). A suspension of P-252 (0.18 g, 0.53 mmol) and sodium azide (0.1 g, 1.58 mmol) in glacial acetic acid (5 mL) was added trimethylorthoformate (0.17 g, 1.58 mmol) was stirred at room temperature for 18. The reaction was diluted with cold water (60 mL), and basified with sat. NaHCO$_3$ solution. The suspension was extracted with dichloromethane (2×5 mL), washed with brine (10 ml), dried over Na$_2$SO$_4$, filtered, and concentrated under vacuum. The residue was purified by silica gel column chromatography using dichloromethane, than preparatory thin layer chromatography 40% ethyl acetate in hexanes to afford the free base of P-422 (0.13 g, 62% yield) as white solid. A portion of the free base of P-422 (0.04 g, 0.1 mmol) in ether (2 mL), then 2M HCl in ether (0.3 ml) was added, stirred for 4 h. The ether layer was decanted, triturated with ether (2×2 mL), dried to afford P-422 (0.03 g, 64% yield) as white solid. $^1$H NMR (400 MHz, DMSO-d$_6$): 10.13 (s, 1H), 8.58 (s, 1H), 8.0 (d, J=1.6 Hz, 1H), 7.36-7.48 (m, 4H), 7.26-7.34 (m, 1H), 6.98 (d, J=9.2 Hz, 1H), 4.11 (s, 2H), 3.74 (s, 3H) ppm; MS (APCI+): 368.0 (M+1), LC-MS: 100%.

Example 342

Preparation of P-434

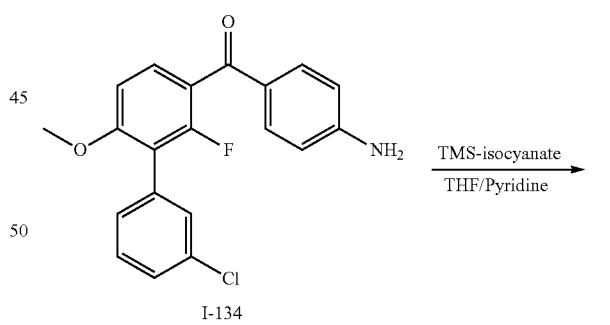

I-134

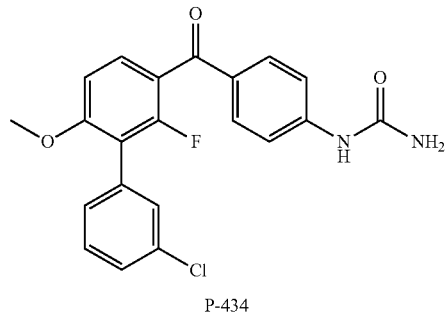

P-434

Synthesis of [4-(3'-chloro-2-fluoro-6-methoxy-biphenyl-3-carbonyl)-phenyl]-urea (P-434). To I-134 (0.14 g, 0.36 mmol) in THF (2.0 mL) was added pyridine (0.5 mL) and trimethylsilylisocyanate (0.06 g, 0.54 mmol). The reaction was stirred at room temperature for 90 h, and concentrated under vacuum. The residue was then triturated with 1:1 dichloromethane-hexanes (5 mL), and dried to afford P-434 (0.16 g, 98% yield) as off-white solid. $^1$H NMR (400 MHz, DMSO-$d_6$): 9.08 (br s, 1H), 7.34-7.78 (m, 8H), 7.14 (d, J=8.4 Hz, 2H), 6.09 (s, 2H), 3.85 (s, 3H) ppm. MS (APCI+): 399 (M+1), LC-MS: 100%

Example 343

Preparation of P-441

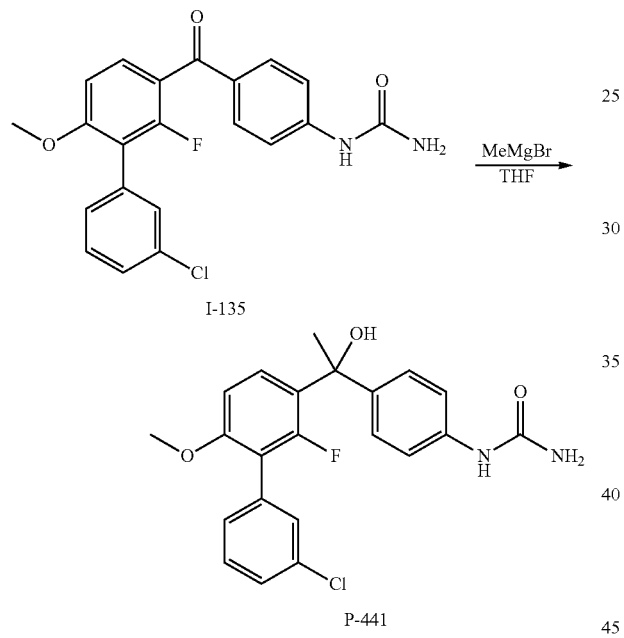

Synthesis of {4-[1-(3'-chloro-2-fluoro-6-methoxy-biphenyl-3-yl)-1-hydroxy-ethyl]-phenyl}-urea (P-441). To I-135 (0.06 g, 0.15 mmol) in THF (10.0 mL) was added methylmagnesium bromide (3M solution in diethyl ether, 0.2 mL, 0.6 mmol). The reaction was stirred at room temperature for 4 h, cooled to 0° C., and quenched with saturated ammonium chloride solution (3 mL). The reaction was extracted with ethyl acetate (2×60 mL), washed with brine (40 ml), dried over Na$_2$SO$_4$, filtered, and concentrated. The residue was purified by preparatory thin layer chromatography using 6% methanol-in dichloromethane to afford P-441 (0.04 g, 61% yield) as white solid.

$^1$H NMR (400 MHz, DMSO-$d_6$): 8.42 (s, 1H), 7.70 (t, J=8.8 Hz, 1H), 7.14-7.42 (m, 7H), 6.96 (d, J=8.4 Hz, 2H), 5.76 (s, 2H), 5.60 (s, 1H), 3.74 (s, 3H), 1.82 (s, 3H) ppm. MS (APCI+): 397 (M−16), LC-MS: 99.0%.

Example 344

Preparation of P-532

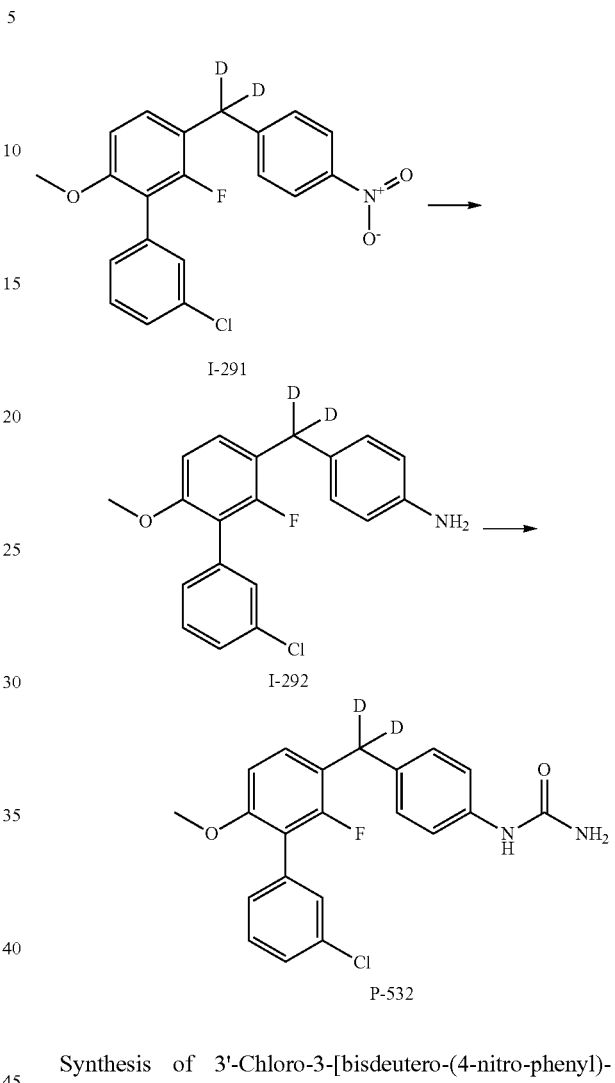

Synthesis of 3'-Chloro-3-[bisdeutero-(4-nitro-phenyl)-methyl]-2-fluoro-6-methoxy-biphenyl (I-291). A solution of (3'-Chloro-2-fluoro-6-methoxy-biphenyl-3-yl)-(4-nitro-phenyl)-methanone (500 mg, 1.30 mmol) in dichloromethane (10 mL) was purged with nitrogen. Trifluoroacetic acid (2.49 mL, 32.40 mmol) was added and the reaction cooled to 0° C. in an ice water bath. To the solution was added sodium borodeuteride (543 mg, 12.96 mmol) portion wise over 45 min. The reaction was stirred for 20 h, allowing to warm to room temperature. The reaction was neutralized with saturated aqueous sodium bicarbonate (25 mL) to pH 7.5, and extracted with ethyl acetate (50 mL). The extract was washed with water (2×25 mL) and brine (25 mL), dried over sodium sulfate, and the solvent removed under reduced pressure to give crude I-291. The product was purified by flash silica gel column chromatography eluting with 20% ethyl acetate in hexanes to give I-291 (157 mg, 32% yield) as a white powder. $^1$H NMR (400 MHz, DMSO-$d_6$): 8.18-8.15 (m, 2H), 7.52-7.37 (m, 5H), 7.29-7.27 (m, 1H), 6.97 (d, J=8.8 Hz, 1H), 3.74 (s, 3H) ppm.

Synthesis of 4-[(3'-Chloro-2-fluoro-6-methoxy-biphenyl-3-yl)-bisduetero-methyl]-phenylamine (I-292). A suspension of I-291 (140 mg, 0.375 mmol), iron powder (73.2 mg, 1.31 mmol) and solid ammonium chloride (102 mg, 1.91 mmol) in ethanol (1.5 mL) and water (500 uL) was heated to 105° C. for 1 h. The solvent was removed under vacuum, the residue suspended in water (20 mL), and extracted with ethyl acetate (2×20 mL). The combined organic extracts were washed with water (2×20 mL) and brine (20 mL), dried over magnesium sulfate, and the solvent removed under vacuum to give crude I-292. The product was purified by flash silica gel column chromatography to give I-292 (103 mg, 30.0% yield) as an orange oil. $^1$H NMR (400 MHz, CDCl$_3$): 7.39 (m, 1H), 7.36-7.26 (m, 3H), 7.07 (t, J=8.6 Hz, 1H), 7.03-7.00 (m, 2H), 6.68 (dd, J=8.4 Hz, 1.2 Hz, 1H), 6.65-6.61 (m, 2H), 3.74 (s, 3H), 3.57 (s, 2H) ppm.

Synthesis of {4-[(3'-Chloro-2-fluoro-6-methoxy-biphenyl-3-yl)-bisduetero-methyl]-phenyl}-urea (P-532). A solution of I-292 (80 mg, 0.233 mmol) and sodium cyanate (30.2 mg, 0.465 mmol) in water (4 mL) and glacial acetic acid (2 mL) was stirred at room temperature for 2 h. The reaction basified with saturated aqueous sodium bicarbonate (25 mL), and extracted with dichloromethane (2×30 mL). The extract was dried over magnesium sulfate and the solvent removed under vacuum to give crude product. The crude product was purified by silica gel preparatory thin layer chromatography eluting with 5% acetone in dichloromethane to give P-532 (35.4 mg, 39% yield) as a white powder. $^1$H NMR (400 MHz, DMSO-d$_6$): 8.42 (s, 1H), 7.47-7.41 (m, 2H), 7.36 (s, 1H), 7.30-7.24 (m, 4H), 7.07 (d, J=8.8 Hz, 2H), 6.92 (d, J=9.2 Hz, 1H), 5.76 (s, 2H), 3.72 (s, 3H) ppm. LCMS=100.0% purity MS (APCI+)=387.1 (M+1); HPLC (254 nm); 98.747%. [Mobile Phase A and Mobile Phase B=Water and Acetonitrile, Symmetry C18, (250×4.6 mm, 5 um), Flow=1.0 mL/min, Inj. Wash=ACN, Inj. Vol.=10 uL. Retention time=27.89 min]

Example 345

Preparation of P-402

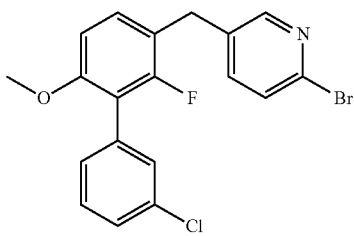

P-402

Synthesis of 2-Bromo-5-(3'-chloro-2-fluoro-6-methoxybiphenyl-3-ylmethyl)-pyridine (P-402). A solution of I-33 (400 mg, 1.21 mmol) and 2-bromopyridine-5-boronic acid (282 mg, 1.39 mmol) in 1,2-dimethoxyethane (12 mL) was degassed with a nitrogen stream for 10 minutes. To the solution was added potassium phosphate (770 mg, 3.63 mmol), ethanol (2.5 mL), water (2.5 mL), and tetrakis(triphenylphosphine)palladium(0) (140 mg, 0.12 mmol) and the reaction was stirred under nitrogen for 2 h. The ethanol and dimethoxyethane were removed under vacuum, and the aqueous solution extracted with ethyl acetate (3×20 mL). The combined organic extracts were washed with water (10 mL) and brine (10 mL), dried over sodium sulfate, and the solvent removed under vacuum. The crude product was purified by flash silica gel column chromatography eluting with 10% ethyl acetate in hexanes, followed by silica gel preparatory thin layer chromatography eluting with 15% ethyl acetate in hexanes to give P-402 (243 mg, 49% yield). $^1$H NMR (CDCl$_3$, 400 MHz): 8.27 (s, 1H), 7.24-7.41 (m, 6H), 7.09 (t, J=8.6 Hz, 1H), 6.72 (d, J=8.4 Hz, 1H), 3.91 (s, 2H), 3.76 (s, 3H) ppm. Calc. 406.68; APCI$^+$ (M+1): 407.9, 96%.

Example 346

Preparation of P-469

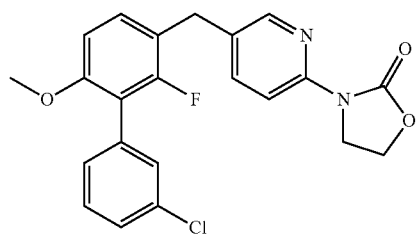

P-469

Synthesis of 3-[5-(3'-Chloro-2-fluoro-6-methoxy-biphenyl-3-ylmethyl)-pyridin-2-yl]-oxazolidin-2-one (P-469). A solution of P-402 (100 mg, 0.246 mmol) and 2-oxazolidinone (21.4 mg, 0.246 mmol) in dioxane (1 mL) and water (7 uL) was degassed with a nitrogen stream for 15 min. To the solution was added sodium tert-butoxide (33.0 mg, 0.344 mmol), xantphos (8.5 mg, 0.0148 mmol), and palladium(II) acetate (1.65 mg, 0.00737 mmol), and the reaction was heated to 100° C. with stirring for 20 h. Additional 2-oxazolidinone (21.4 mg, 0246 mmol), sodium tert-butoxide (33.0 mg, 0.344 mmol), xantphos (8.5 mg, 0.0148 mmol), and palladium(II) acetate (1.65 mg, 0.00737 mmol) were added, and reacted stirred at reflux overnight. The reaction was diluted with water (10 mL) and extracted with ethyl acetate (25 mL). The organic extract was washed with water (25 mL), brine (25 mL), dried over sodium sulfate, and the solvent removed under vacuum. The residue was purified by silica gel preparatory thin layer chromatography (10% ethyl acetate in hexanes×2, 35% ethyl acetate in hexanes×4) to give crude product. To the crude oil was added diethyl ether (2 mL) and 2 N hydrochloric acid in diethyl ether. The suspension was stirred for 2 h, and filtered to give P-469 (22.9 mg, 21% yield) as a yellow powder. $^1$H NMR (400 MHz, DMSO-d$_6$): 8.27 (d, J=2.4 Hz, 1H), 8.00 (d, J=8.8 Hz, 1H), 7.68 (dd, J=8.6 Hz, 2.6 Hz, 1H), 7.48-7.27 (m, 6H), 6.94 (d, J=8.8 Hz, 1H), 4.44 (t, J=8.0 Hz, 2H), 4.14 (t, J=8.0 Hz, 2H), 3.73 (s, 3H).

LCMS purity=97.43%. MS (APCI+)=413.0 (M+1).

Example 347

Preparation of P-470

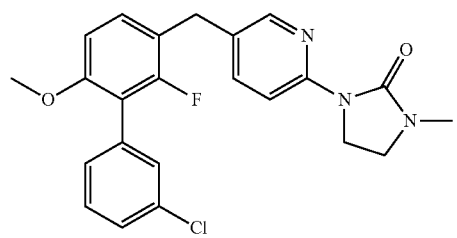

P-470

Synthesis of 1-[5-(3'-Chloro-2-fluoro-6-methoxy-biphenyl-3-ylmethyl)-pyridin-2-yl]-3-methyl-imidazolidin-2-one (P-470). A solution of P-402 (115 mg, 0.283 mmol), 1-methyl-imidazolidin-2-one (56.7 mg, 0.566 mmol), and xantphos (9.0 mg, 0.0170 mmol) in dioxane (1 mL) was degassed under a nitrogen stream for 15 min. To the solution was added sodium tert-butoxide (38.0 mg, 0.396 mmol), water (7 uL), and palladium(II) acetate (1.90 mg, 0.00848 mmol) under nitrogen. The reaction was stirred at 100° C. for 24 h. The reaction was diluted with water (30 mL), and extracted with ethyl acetate (2×30 mL). The organic extracts were combined, washed with water (30 mL) and brine (30 mL), dried over sodium sulfate, and the solvent removed under vacuum. The crude product was purified by silica gel thin layer chromatography eluting with 40% ethyl acetate in hexanes and developed 6 times to give P-470 (76.1 mg, 63% yield).

$^1$H NMR (400 MHz, CDCl$_3$) δ 8.21 (d, J=8.8 Hz, 1H), 8.15 (d, J=2.4 Hz, 1H), 7.49-7.27 (m, 5H), 7.08 (t, J=8.6 Hz, 1H), 6.69 (dd, J=9.8 Hz, 1.0 Hz, 1H), 4.02 (t, J=8.0 Hz, 2H), 3.90 (s, 2H), 3.75 (s, 3H), 3.46 (t, J=8.0 Hz, 2H), 2.90 (s, 3H) ppm.

Example 348

Preparation of P-423

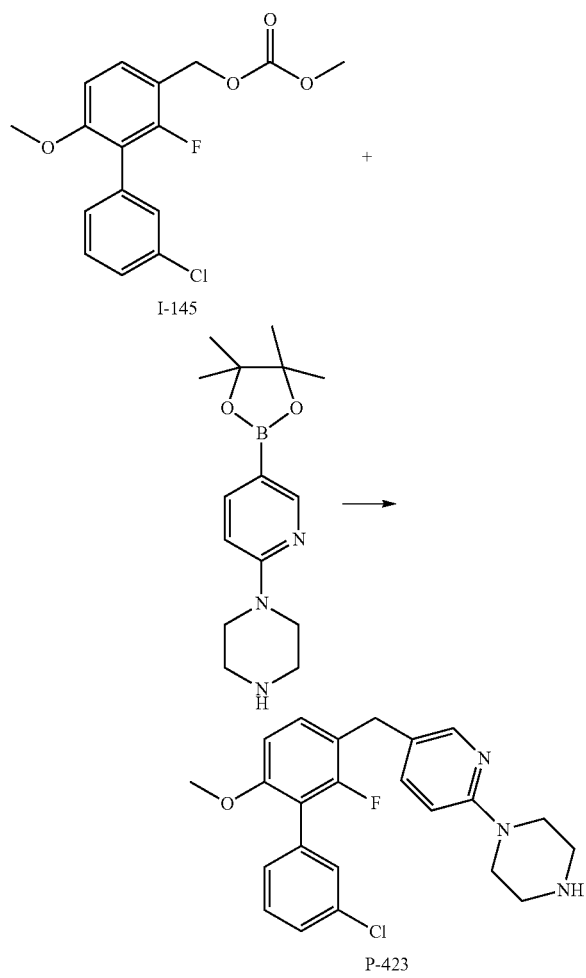

Synthesis of 1-[5-(3'-chloro-2-fluoro-6-methoxy-biphenyl-3-ylmethyl)-pyridin-2-yl]-piperazine (P-423). To carbonic acid 3'-chloro-2-fluoro-6-methoxy-biphenyl-3-ylmethyl ester methyl ester (0.2 g, 0.62 mmol), 1-[5-(4,4,5,5-tetramethyl-[1,3,2]dioxaborolan-2-yl)-pyridin-2-yl]-piperazine (0.2 g, 0.68 mmol), bis-diphenylphosphinopentane (0.08 g, 0.18 mmol), potassium carbonate (0.26 g, 1.85 mmol) and allyl palladium (II) chloride dimer (0.034 g, 0.09 mmol) was added dimethyl formamide (6 mL). The reaction was degassed with an argon stream for 10 min. The reaction was stirred at 85° C. for 18 h. The reaction was cooled to room temperature, poured onto crushed ice-water (150 mL), filtered, washed with water, dried over sodium sulfate, filtered, and the solvent removed under vacuum. The residue was purified by silica gel column chromatography using 10% methanol in dichloromethane to afford P-423 (0.05 g, 18% yield) as light brown gummy solid.

$^1$H NMR (400 MHz, DMSO-d$_6$): 3.20 (br s, 3H) 3.55-3.99 (m, 10H), 6.95 (d, J=8.59 Hz, 1H), 7.11 (br s, 1H), 7.23-7.39 (m, 3H), 7.39-7.55 (m, 2H), 7.69 (br s, 1H), 8.02 (s, 1H), 9.33 (br s, 2H) ppm. Calc. 411.9; APCI$^+$ (M+1): 412.1, 97%.

Example 349

Preparation of P-514

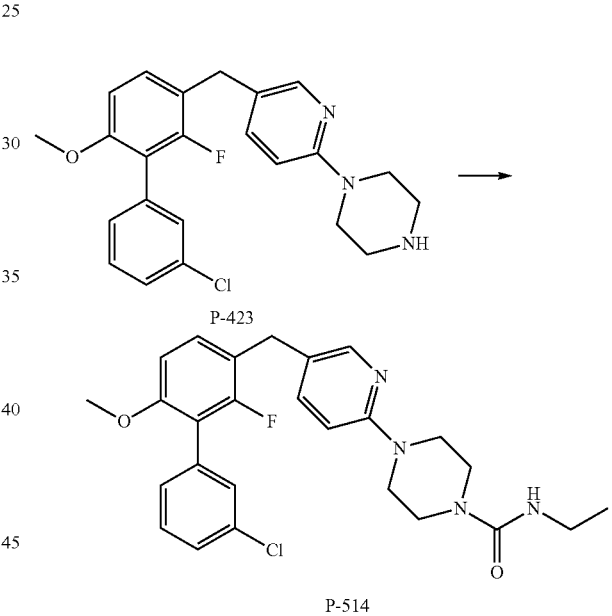

Synthesis of 4-[5-(3'-chloro-2-fluoro-6-methoxy-biphenyl-3-ylmethyl)-pyridin-2-yl]-piperazine-1-carboxylic acid ethylamide hydrochloride (P-514). To P-423 (0.05 g, 0.11 mmol) in pyridine (1.5 mL) was added ethylisocyanate (0.023 g, 0.33 mmol). The reaction was stirred at room temperature for 20 h, and concentrated under vacuum. The residue was purified by preparative thin layer chromatography using 5% methanol in dichloromethane to give crude material. The solid was dissolved in diethyl ether (2 mL), then 2M HCl in diethyl ether (0.5 ml) was added, the reaction stirred for 1 h, and concentrated under vacuum to afford P-514 (0.035 g, 58% yield) as light yellow solid.

$^1$H NMR (400 MHz, DMSO-d$_6$): 8.20-8.26 (m, 1H), 7.93 (s, 1H), 7.74 (br s, 1H), 7.4-7.48 (m, 2H), 7.26-7.38 (m, 3H), 7.21 (br s, 1H), 6.95 (d, J=8.0 Hz, 1H), 6.59 (br s, 1H), 3.89 (s, 2H), 3.73 (s, 3H), 3.40-3.75 (m, 8H), 3.01-3.16 (m, 2H), 1.00-1.08 (m, 3H) ppm. MS (APCI+): 483.1 (M+1), LC-MS: 99.1%.

Scheme 67: Synthesis of P-564

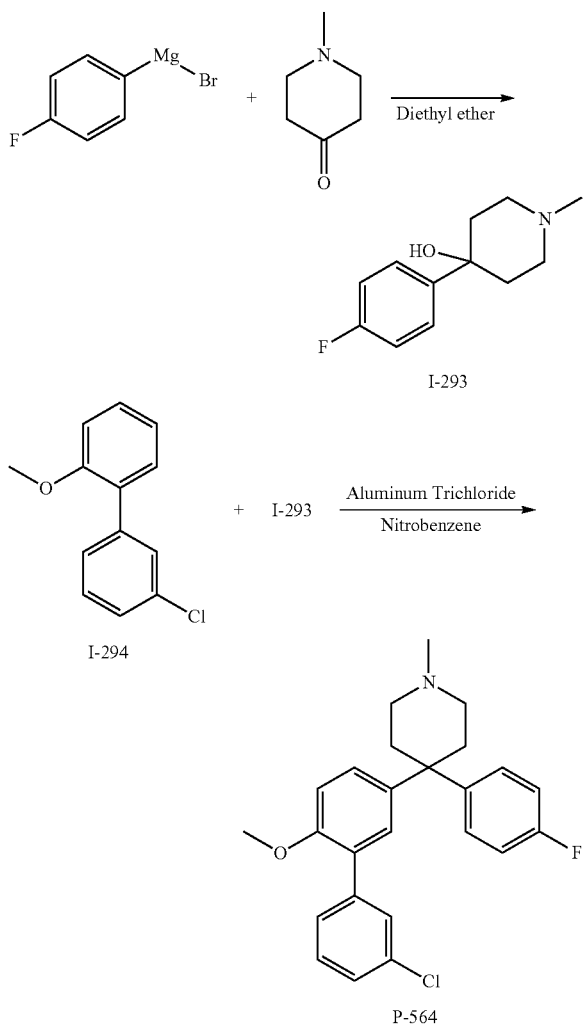

Example 350

Preparation of P-564

Synthesis of 4-(4-Fluoro-phenyl)-1-methyl-piperidin-4-ol (I-293). A solution of N-methyl-piperidin-4-one (1.50 g, 13.3 mmol) in diethyl ether (10 mL) was degassed under a nitrogen stream. The solution was cooled to 0° C. in an salt ice bath. To the stirring solution was added 4-fluorophenylmagnesium bromide (1.74 g, 14.6 mmol) dropwise over 5 min. A solid formed partway through the addition, and additional diethyl ether was added (2 mL). The reaction was then stirred at 0° C. for 2 h. To the suspension was added aqueous ammonium chloride (15 mL). The biphasic solution was diluted with ethyl acetate (40 mL) and additional saturated aqueous ammonium chloride (20 mL). The layer was separated, and the organic extract washed with brine (50 mL), dried over sodium sulfate, filtered, and the solvent removed under vacuum to give I-293 (965 mg, 32% yield) as a brown powder. The product was taken on without further purification. $^1$H NMR (400 MHz, DMSO-$d_6$): 7.51-7.48 (m, 2H), 7.13-7.09 (m, 2H), 4.80 (s, 1H), 2.52-2.53 (m, 3H), 2.36-2.30 (m, 2H), 2.19 (s, 3H), 1.94-1.87 (m, 2H), 1.57-1.54 (m, 2H) ppm.

Synthesis of 4-(3'-Chloro-6-methoxy-biphenyl-3-yl)-4-(4-fluoro-phenyl)-1-methyl-piperidine (P564). To nitrobenzene (2 mL) was added a solution of I-293 (286 mg, 1.37 mmol) in dimethylformamide (1.5 mL). The reaction was stirred under a nitrogen atmosphere, cooled of 0° C. in an ice-water bath, and aluminum trichloride (304 mg, 2.28 mmol) was added. The reaction was stirred at 0° C. for 30 min over the time which the solution turned from orange to purple. To the solution was added I-294 (250 mg, 1.14 mmol) in dimethyl formamide (0.5 mL). The solution was stirred for 2 h allowing to warm to room temperature. The reaction was diluted with ethyl acetate (50 mL), washed with saturated aqueous ammonium chloride (50 mL), water (50 mL), and brine (50 mL), dried over sodium sulfate, decanted, and the solvent removed under vacuum. The residue was dissolved in ethyl acetate (50 mL), and extracted into 4N aqueous hydrochloric acid (50 mL). The aqueous extract was basified to pH 9 with solid sodium bicarbonate, and the product extracted with ethyl acetate (3×50 mL), and the solvent removed under vacuum. The product was purified by flash silica gel column chromatography eluting with 10% ethyl acetate in hexanes. The impure product was diluted with dichloromethane, dried over sodium sulfate, filtered, and the solvent removed under vacuum. The residue was suspended in diethyl ether, filtered, and the mother liquor removed under vacuum to give P-564 (109 mg, 23% yield) as a yellow orange powder. $^1$H NMR (400 MHz, CDCl$_3$): 7.46-7.46 (s, 1H), 7.32-7.26 (m, 3H), 7.24-7.20 (m, 2H), 7.16-7.15 (m, 2H), 6.99-6.94 (m, 2H), 6.90-6.87 (m, 1H), 3.78 (s, 3H), 2.46 (m, 8H), 2.24 (s, 3H) ppm. LCMS=96.14% purity MS[APCI+]=410.1 (M+1), Scheme 68: Synthsis of P-516

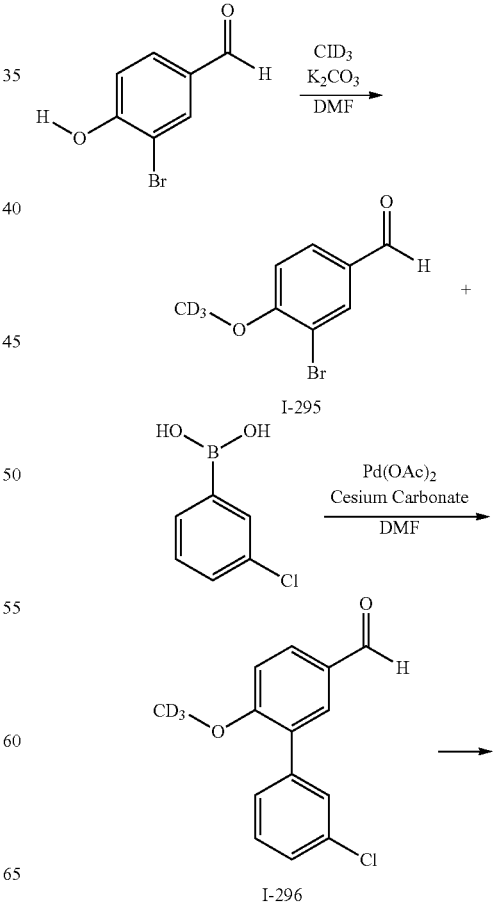

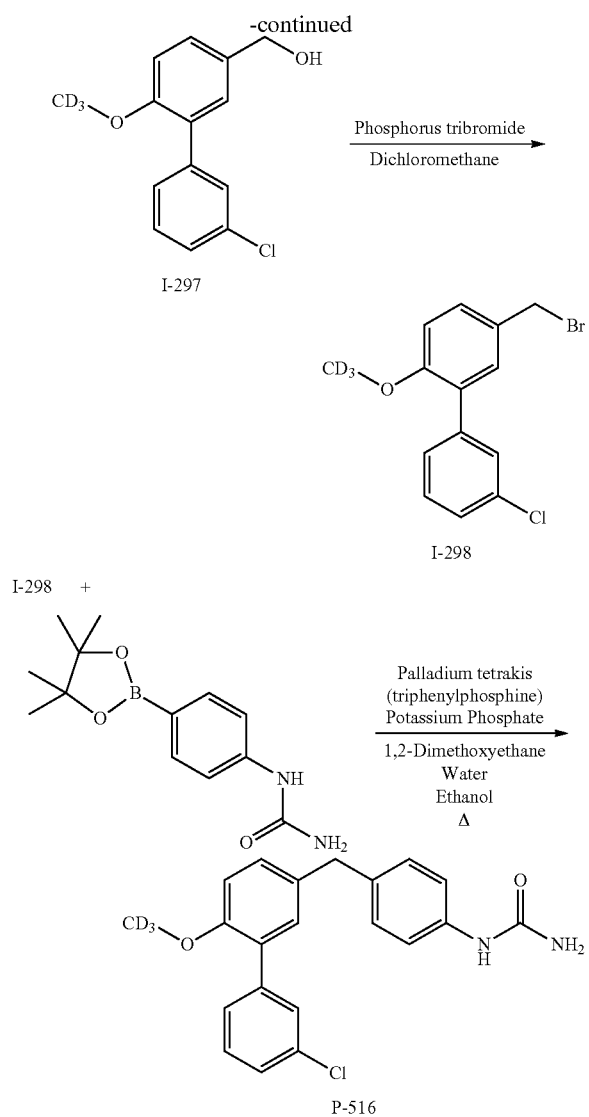

Example 351

Preparation of P-516

Synthesis of 3-Bromo-4-trideuteromethoxy-benzaldehyde (I-295). A suspension of 3-bromo-4-hydroxy-benzaldehyde (15.0 g, 74.6 mmol) and solid potassium carbonate (10.3 g, 74.6 mmol) in dimethylformamide (150 mL) was stirred at room temperature for 15 min. To the suspension was added trideuteromethyl iodide (21.6 g, 149.2 mmol) and the reaction was stirred at room temperature for 60 h. The reaction was diluted with water (1000 mL) and extracted with ethyl acetate (2×600 mL). The combined organic extracts were washed with brine (1000 mL), dried over sodium sulfate, and the solvent removed under vacuum to give I-295 (16.33 g) as a gummy beige solid which was taken on without further purification. $^1$H NMR (400 MHz, DMSO-$d_6$) d: 9.86 (s, 1H), 8.10 (d, J=2.0 Hz, 1H), 7.94 (dd, J=8.4 Hz, 2.0 Hz, 1H), 7.32 (d, J=8.8 Hz, 1H) ppm.

Synthesis of 3'-Chloro-6-trideuteromethoxy-biphenyl-3-carbaldehyde (I-296). A suspension of I-296 (10.0 g, 45.9 mmol) and 3-chlorophenylboronic acid (7.90 g, 50.45 mmol) in dimethyl formamide (225 mL) and 1 N aqueous cesium carbonate (45 mL) was degassed with a nitrogen stream for 30 min. To the suspension was added palladium(II) acetate (1.04 g, 4.59 mmol) and the reaction was stirred at 50° C. overnight. The suspension was filtered through celite and washed with dimethyl formamide (100 mL). The solution was diluted with water (1000 mL), and extracted with ethyl acetate (2×600 mL). The combined extracts were washed with brine (500 mL), dried over sodium sulfate, decanted, and the solvent removed under vacuum. The crude brown product was purified by flash silica gel column chromatography eluting with 15% acetone in hexanes to give I-296 (10.29 g, 90% yield) as a clear oil which solidified to a yellow powder. $^1$H NMR (400 MHz, DMSO-$d_6$): 9.94 (s, 1H), 7.96 (dd, J=8.4 Hz, 1.6 Hz, 1H), 7.86 (d, J=2.0 Hz, 1H), 7.58 (s, 1H), 7.49-7.44 (m, 3H), 7.35 (d, J=8.4 Hz, 1H) ppm.

Synthesis of (3'-Chloro-6-trideuteromethoxy-biphenyl-3-yl)-methanol (I-297). A solution of I-296 (9.75 g, 39.05 mmol) in tetrahydrofuran (75 mL) and water (75 mL) was cooled to 0° C. in an ice water bath. Over 5 minutes was added solid sodium borohydride (2.22 g, 58.58 mmol). The reaction was stirred, allowing to warm to room temperature over 3 h. The reaction was diluted with ethyl acetate (250 mL), washed with water (125 mL), and the aqueous wash extracted with ethyl acetate (250 mL). The combined extracts were washed with brine, dried over sodium sulfate, and the solvent removed under vacuum to give product. The crude material was dried under high vacuum to give I-297 (9.01 g, 92% yield) as a pale yellow oil.

Synthesis of 5-Bromomethyl-3'-chloro-2-trideuteromethoxy-biphenyl (I-298). A solution of I-297 (9.00 g, 35.76 mmol) and phosphorus tribromide (4.84 g, 17.9 mmol) in dichloromethane (50 mL) was stirred at 0° C. and allowed to warm to room temperature with stirring for 18.5 h. The reaction was cooled in an ice water bath and 150 mL water was added. The reaction was extracted with dichloromethane (2×100 mL). The combined extracts were washed with aqueous saturated sodium bicarbonate (250 mL) and brine (100 mL), dried over magnesium sulfate, filtered, and the solvent removed under vacuum to give I-298 (10.5 g, 92% yield). $^1$H NMR (400 MHz, DMSO-$d_6$): 7.51-7.40 (m, 6H), 7.12 (d, J=8.8 Hz, 1H), 4.75 (s, 2H) ppm.

Synthesis of [5-(3'-Chloro-6-trideuteromethoxy-biphenyl-3-ylmethyl)-pyridin-2-yl]-urea (P-516). A suspension of I-298 (5.00 g, 15.89 mmol), 1-(uriedo)phenylboronic acid pinacol ester (4.16 g, 15.89 mmol), and solid potassium phosphate (6.75 g, 31.79 mmol), in 1,2-dimethoxyethane (40 mL), water (10 mL), and ethyl alcohol (10 mL), was degassed with a nitrogen stream for 15 minutes. To the suspension was added palladium tetrakis(triphenylphosphine) (3.67 g, 3.18 mmol) and the reaction was stirred overnight for 17 h. The suspension was diluted with ethyl acetate (250 mL), washed with water (200 mL) and brine (100 mL), dried over sodium sulfate, filtered, and the solvent was removed under vacuum. The crude dark red gum was dissolved in 100 mL DCM, and silica-thiol (10 g) was added. The suspension was stirred at room temperature overnight. The suspension was filtered and the solvent removed under vacuum. The crude material was purified by flash silica gel column chromatography (10% isopropyl alcohol in dichloromethane), and dried under high vacuum overnight to give P-516 (1.20 g, 20% yield) as a white powder. $^1$H NMR (400 MHz, DMSO-$d_6$): 7.48-7.47 (m, 1H), 7.44-7.35 (m, 3H), 7.29-7.27 (m, 2H), 7.20-7.15 (m, 2H), 7.10-7.07 (m, 2H), 7.03 (d, J=8.4 Hz, 1H), 3.83 (s, 2H) ppm. LCMS=94.2% purity. MS (ESI+)=370.4 (M+1).

HPLC (254 nm); 97.000%. [Mobile Phase A and Mobile Phase B=Water and Acetonitril, Symmetry C18, (250×4.6 mm, 5 um), Flow=1.0 mL/min, Inj. Wash=ACN, Inj. Vol.=10 uL. Retention time=26.69 min]

Scheme 69.

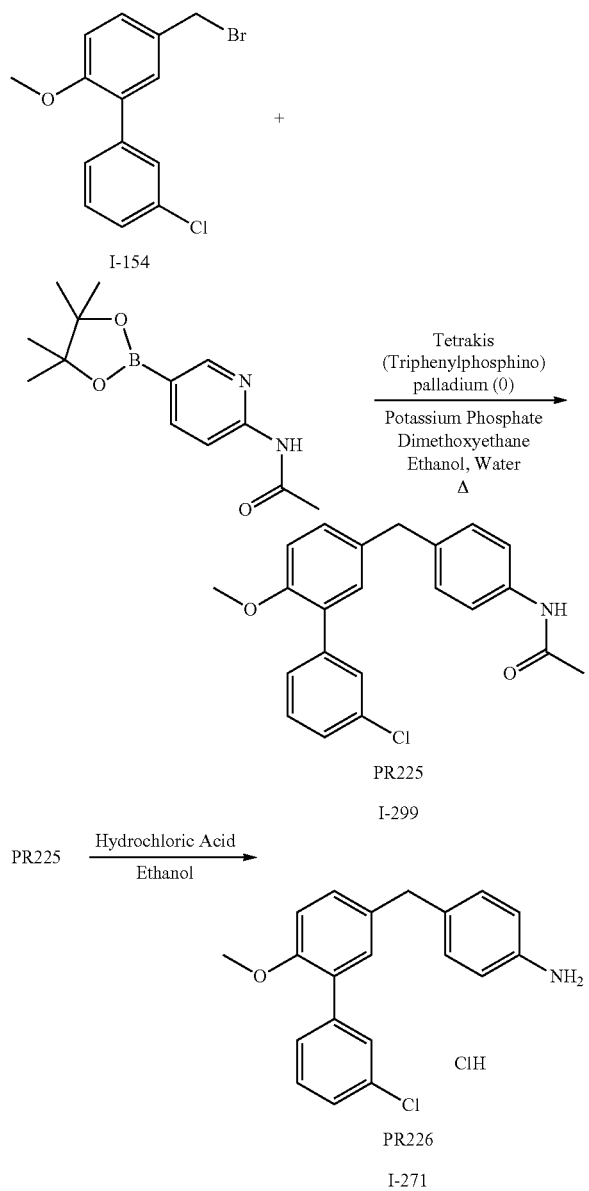

Example 352

Preparation of I-299 and I-271

N-[4-(3'-Chloro-6-methoxy-biphenyl-3-ylmethyl)-phenyl]-acetamide (I-299) A solution of I-154 (3.90 g, 12.5 mmol) and 2-acetimidopyridine-5-boronic acid pinocol ester (3.60 g, 13.8 mmol) in 1,2-dimethoxyethane (100 mL) was degassed with a nitrogen stream for 15 min. To the solution was adde ethanol (12.5 mL), water (12.5 mL), solid potassium phosphate (5.30 g, 25.0 mmol), and degassing was continued for 20 min. To the resulting suspension, triphenyl phosphine (985 mg, 3.78 mmol) and palladium(II)acetate (281 mg, 1.25 mmol) were added under nitrogen. The suspension was heated to 85° C. with stirring for 4 h. The reaction was diluted with ethyl acetate (500 mL), washed with water (2×250 mL) and brine (250 mL), dried over sodium sulfate, decanted, and the solvent removed under vacuum. The crude material was purified by flash silica gel column chromatography eluting with 40% ethyl acetate in hexanes to give I-299 (2.20 g, 48% yield) as a yellow oil. $^1$H NMR. (400 MHz, DMSO-d$_6$): 7.49 (t, J=1.8 Hz, 1H), 7.42-7.28 (m, 5H), 7.16-7.10 (m, 5H), 6.89 (d, J=8.4 Hz, 1H), 3.92 (s, 2H), 3.79 (s, 3H), 2.16 (s, 3H) ppm.

4-(3'-Chloro-6-methoxy-biphenyl-3-ylmethyl)-phenylamine hydrochloride salt (I-271). A solution of I-299 (2.20 g, 6.01 mmol) in ethanol (90 mL) and concentrated aqueous hydrochloric acid (90 mL) was stirred at room temperature for 1 h, and heated to 80° C. for an additional 2 h. The reaction was diluted with water (500 m), basified to pH 9 with solid sodium bicarbonate, and extracted with ethyl acetate (3×250 mL). The combined extracts were washed with water (250 mL) and brine (250 mL), dried over sodium sulfate, decanted, and the solvent removed under vacuum. The crude product was stirred in 2 N hydrogen chloride in ethyl ether (15 mL) for 3 h at room temperature. The suspension was filtered to give I-271 (1.55 g, 80% yield) as a beige powder.

$^1$H NMR (400 MHz, DMSO-d$_6$) d: 9.95 (br s, 2H), 7.49-7.34 (m, 6H), 7.25-7.20 (m, 4H), 7.05 (d, J=8.4 Hz, 1H), 3.94 (s, 2H), 3.74 (s, 3H) ppm.

LCMS=94.5% purity. MS (APCI+)=324.1 (M+1)

Example 353

Preparation of P-129

Synthesis of (2-Hydroxy-6-methoxy-3'-nitro-biphenyl-3-yl)-isoxazol-5-yl-methanone (P-129). Nitrobenzene (1 mL) and AlCl$_3$ (154 mg, 1.15 mmol) were placed in an 8 mL vial with a stir bar and stirred at room temperature for 10 min. Isoxazole-5-carbonyl chloride (151 mg, 1.15 mmol) was added and the solution was allowed to stir at room temperature for another 30 minutes. Then adding I-81 (250 mg, 0.96 mmol) was added and the resulting solution was stirred at room temperature for 20 hours and heating for 1 hour. The reaction mixture was diluted with ethyl acetate (90 mL) washed with water, brine and dried over Na$_2$SO$_4$. After filtration and removal of solvent, the residue was purified by silica gel column chromatography with ethyl acetate/hexane to yield 100 mg (32%) of P-129. $^1$H NMR (400 MHz, CDCl$_3$) 3.91 (s, 3H) 6.71-6.78 (m, 1H) 7.10-7.15 (m, 1H) 7.52-7.64 (m, 1H) 7.57-7.64 (m, 1H), 7.72-7.77 (m, 1H) 8.21-8.30 (m, 1H) 8.44-8.47 (m, 1H), 8.48-8.53 (m, 1H), 12.62 (s, 1H) ppm.

Example 354

Preparation of P-130

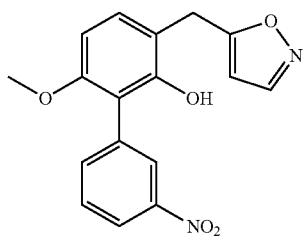

Synthesis of 3-isoxazol-5-ylmethyl-6-methoxy-3'-nitro-biphenyl-2-ol (P-130). Compound P-129 (80 mg, 0.24 mmol) was diluted with TFA (2 mL) and cooled to −20° C. NaBH$_4$ was added slowly and then the solution was purge with N$_2$ for 2 minutes. The reaction mixture was stirred at room temperature for 20 hours under N$_2$. The reaction was quenched with ice/water (20 mL) and the pH was adjusted to ~6 using saturated aqueous NaHCO$_3$. The solution was extracted with ethyl acetate (2×30 mL) and the combined ethyl acetate extracts were washed with brine and dried over Na$_2$SO$_4$. After filtration and removal of solvent, the residue was purified by preparative chromatography plate with 30% ethyl acetate/hexanes to yield 52 mg of compound (P-130). $^1$H NMR (400 MHz, CDCl$_3$) 3.73 (s, 3H), 4.12 (s, 2H), 4.89 (s, 1H), 5.99 (s, 1H), 6.57 (d, J=8.59 Hz, 1H), 7.20 (d, J=8.59 Hz, 1H), 7.63-7.73 (m, 2H), 8.14 (s, 1H), 8.22-8.29 (m, 2H) ppm. LC-MS (APCI+): 327.1 (M+1).

Example 355

Preparation of P-133

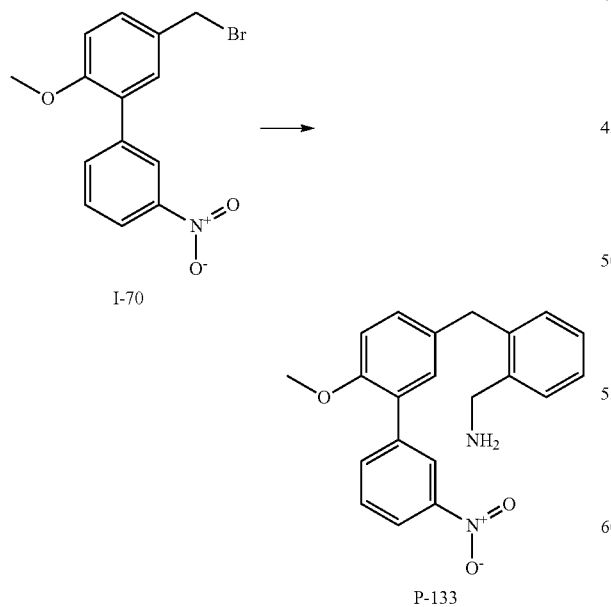

Synthesis of 3-(6-Methoxy-3'-nitro-biphenyl-3-ylmethyl)-benzylamine (P-133). A reaction mixture of compound I-70 (300 mg, 0.93 mmol), 2-[2-(4,4,5,5-tetramethyl-[1,3,2]dioxaborolan-2-yl)-benzyl]-isoindole-1,3-dione (338 mg, 0.93 mmol), triphenylphosphine (73 mg, 0.28 mmol), K$_3$PO$_4$ (394 mg, 1.86 mmol), Pd(OAc)$_2$ (20.8 mg, 0.09 mmol) in 1,2-dimethoxyethane (8 mL), ethanol (0.8 mL) and water (0.8 mL) was stirred at 80° C. for 20 hours under Ar. The reaction mixture was diluted with ethyl acetate (40 mL), washed with water, brine and dried over Na$_2$SO$_4$. After filtration and removal of solvent, the residue was purified by silica gel column chromatography with ethyl acetate/hexane to yield 370 mg of product that was reacted with hydrazine hydrate (0.11 mL, 2.34 mmol) in ethanol (10 mL). The reaction mixture was stirred at 80° C. for 2 hours. The mixture was filtered and the filtrate was concentrated. The resulting residue was triturated with diethyl ether to obtain 150 mg (77%) of compound P-133. $^1$H NMR (400 MHz, CDCl$_3$) 1.45 (br s, 2H), 3.80 (s, 3H), 3.86 (s, 2H), 4.07 (s, 2H), 6.92 (d, J=8.0 Hz, 1H), 7.08-7.31 (m, 5H), 7.37 (d, J=7.0 Hz, 1H), 7.53 (t, J=8.0 Hz, 1H), 7.80 (d, J=7.8 Hz, 1H) 8.15 (dd, J=8.2, 1.34 Hz, 1H) 8.38 (s, 1H) ppm. LC-MS (APCI+): 349.1 (M+1) 100%.

Example 356

Preparation of P-158

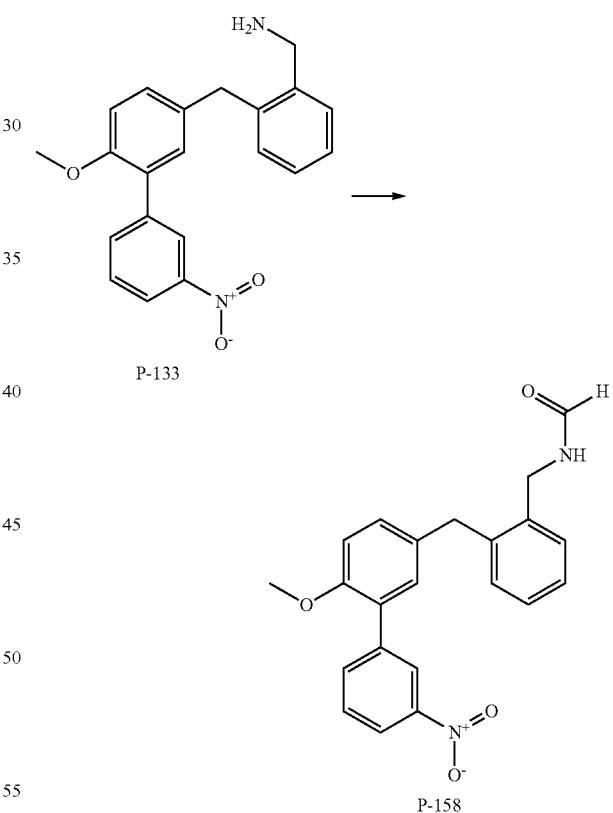

Synthesis of N-[2-(6-Methoxy-3'-nitro-biphenyl-3-ylmethyl)-benzyl]-formamide (P-158). Formic acid (0.18 mL, 4.57 mmol) was added to acetic anhydride (0.42 mL, 4.57 mmol) at 0° C. Then reaction mixture was heated at 50° C. for 2 hours. 0.3 mL of the above mixture was added dropwise into the DCM (1 mL) solution of P-133 (50 mg, 0.14 mmol) at −30° C. and then stirred at −10° C. 30 minutes then room temperature 20 hours. The reaction mixture was diluted with ethyl acetate, washed with water, brine and dried over Na$_2$SO$_4$. After removal of solvent, the residue was purified by

441

2 g silica gel column chromatography with ethyl acetate/hexane as eluent to give 53 mg of product P-158. Yield: 100%. $^1$H NMR (400 MHz, CDCl$_3$) ppm 3.81 (s, 3H) 4.05 (s, 2H) 4.50 (d, J=5.77 Hz, 2H) 5.50 (br. s., 1H) 6.93 (d, J=8.99 Hz, 1H) 7.03-7.14 (m, 2H) 7.16-7.35 (m, 4H) 7.54 (t, J=7.98 Hz, 1H) 7.80 (d, J=7.51 Hz, 1H) 8.13-8.19 (m, 2H) 8.37 (s, 1H) LC-MS (APCI+): 349.1 (M+1) 98.2%.

Example 357

Preparation of P-501

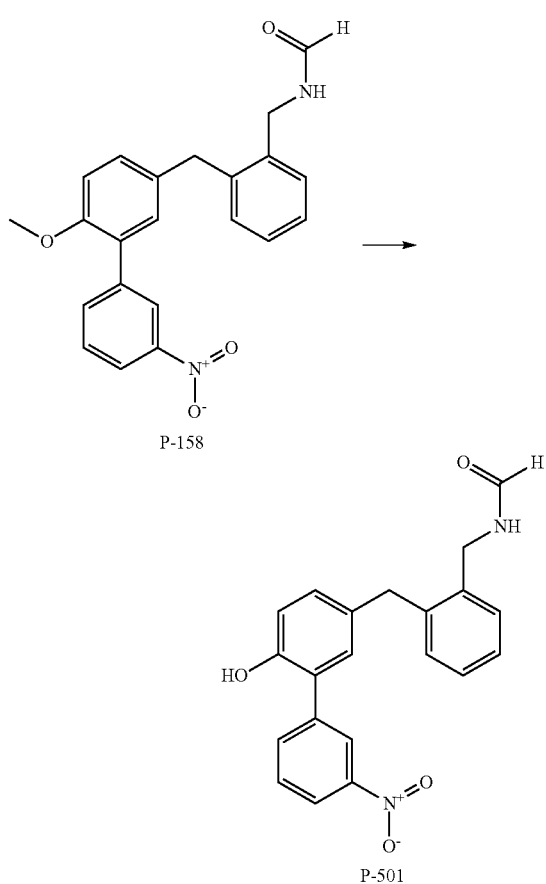

Synthesis of N-[2-(6-Hydroxy-3'-nitro-biphenyl-3-ylmethyl)-benzyl]-formamide ((P-501). To a mixture of compound P-158 (30 mg, 0.08 mmol) in dichloromethane (2 mL), was added BBr$_3$ (1M in dichloromethane, 0.24 mL, 0.24 mmol) at −78° C. under N$_2$. The reaction mixture was stirred at −78° C. to room temperature and room temperature overnight. The reaction mixture was diluted with water and extracted with ethyl acetate (3×6 mL). The ethyl acetate extracts were washed with water, brine, and dried over Na$_2$SO$_4$. After filtration and removal of solvent, the residue was purified by preparative chromatography plate with 2% methanol (7M NH$_3$)/dichloromethane (two developments) to give 20 mg (69%) of compound P-501. $^1$H NMR (400 MHz, CDCl$_3$) 4.03 (s, 2H), 4.49 (d, J=5.6 Hz, 2H), 5.52 (br s, 1H), 6.83-6.90 (m, 1H), 6.98-7.10 (m, 2H), 7.19-7.33 (m, 4H), 7.58 (t, J,=, 7.9 Hz, 1H), 7.84 (d, J,=, 7.5 Hz, 1H), 8.12-8.22 (m, 2H), 8.39 (s, 1H) ppm; LC-MS (APCI+): 363.1 (M+1) 100%.

Example 358

Preparation of P-160

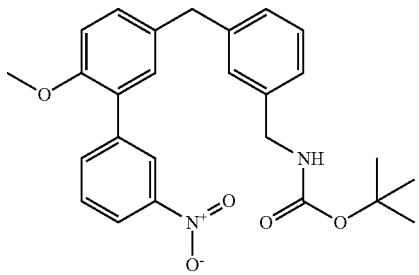

Synthesis of [3-(6-Methoxy-3'-nitro-biphenyl-3-ylmethyl)-benzyl]-carbamic acid tert-butyl ester (11×6) (P-160). A reaction mixture of compound I-70 (400 mg, 1.24 mmol), 3-(n-Boc-aminomethyl)phenylboronic acid (312 mg, 1.24 mmol), triphenylphosphine (98 mg, 0.37 mmol), K$_3$PO$_4$ (526 mg, 2.48 mmol), Pd(OAc)$_2$ (27.8 mg, 0.12 mmol) in 1,2-dimethoxyethane (10 mL), ethanol (1 mL) and water (1 mL) was stirred at 80° C. 20 hours under Ar. The reaction mixture was diluted with ethyl acetate (40 mL), washed with water, brine and dried over Na$_2$SO$_4$. After removal of solvent, the residue was purified by silica gel column chromatography with ethyl acetate/hexane to yield 200 mg of product P-160. Yield: 36% $^1$H NMR (400 MHz, CDCl$_3$) ppm 1.44 (s, 9H) 3.81 (s, 3H) 3.97 (s, 2H) 4.28 (br. s., 2H) 4.80 (br. s., 1H) 6.94 (d, J=8.32 Hz, 1H) 7.05-7.22 (m, 5H) 7.22-7.30 (m, 1H) 7.54 (t, J=7.98 Hz, 1H) 7.83 (d, J=7.65 Hz, 1H) 8.16 (dd, J=8.25, 1.14 Hz, 1H) 8.39 (s, 1H); LC-MS (APCI−): 448.2 (M−1) 100%.

Example 359

Preparation of P-161

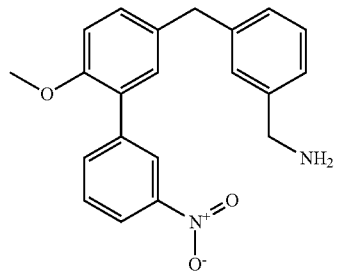

Synthesis of 3-(6-Methoxy-3'-nitro-biphenyl-3-ylmethyl)-benzylamine (P-161). To a mixture of compound P-160 (53 mg, 0.12 mmol) in dichloromethane (2 mL), was added TFA (3 mL). The reaction mixture was stirred at room temperature. for 1 h. After removal of most solvent, the residue was dissolved in dichloromethane (5 mL) and washed with saturated aqueous NaHCO$_3$ (2×10 mL), water, brine and dried over Na$_2$SO$_4$. After filtration and removal of solvent, the residue was purified by preparative chromatography plate with 2% methanol (7M NH$_3$)/dichloromethane to yield 30 mg (73%) of compound P-161. $^1$H NMR (400 MHz, CDCl$_3$) 3.81

(s, 3H), 3.84 (s, 2H), 3.98 (s, 2H), 6.94 (d, J=8.3 Hz, 1H), 7.09 (d, J=7.51 Hz, 1H), 7.13-7.23 (m, 4H), 7.22-7.31 (m, 1H), 7.54 (t, J=7.98 Hz, 1H), 7.83 (d, J=7.78 Hz, 1H), 8.11-8.20 (m, 1H), 8.39 (s, 1H) ppm; LC-MS (APCI+): 349.1 (M+1) 100%.

Example 360

Preparation of P-179

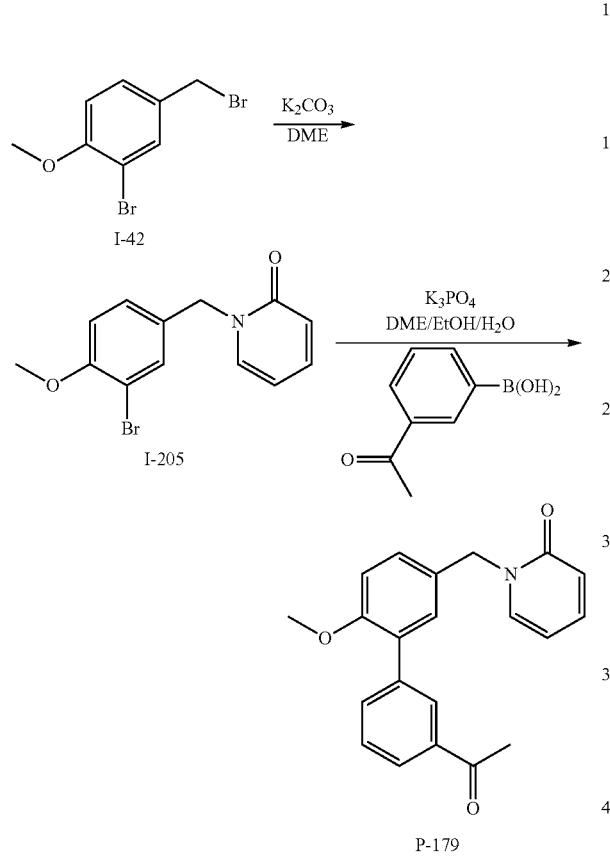

1-(3-Bromo-4-methoxy-benzyl)-1H-pyridin-2-one (I-205). A reaction mixture of compound I-42 (550 mg, 1.96 mmol), pyridin-2-ol (170 mg, 1.78 mmol), K₂CO₃ (538 mg, 3.89 mmol) in 1,2-dimethoxyethane (5 mL) was stirred at 80° C. for 20 hours under Ar. The reaction mixture was diluted with dichloromethane (15 mL), washed with water, brine and dried over Na₂SO₄. After filtration and removal of solvent, the residue was purified by silica gel column chromatography with ethyl acetate/hexanes to yield 230 mg (39%) of I-205.

Synthesis of 1-(3'-Acetyl-6-methoxy-biphenyl-3-ylmethyl)-1H-pyridin-2-one (P-179). A reaction mixture of compound I-205 (100 mg, 0.35 mmol), 3-acetylphenyl boronic acid (58 mg, 0.35 mmol), triphenylphosphine (18 mg, 0.07 mmol), K₂CO₃ (145 mg, 1.05 mmol), Pd(OAc)₂ (9.5 mg, 0.04 mmol) in 1,2-dimethoxyethane (3 mL), ethanol (0.5 mL) and water (0.5 mL) was stirred at 80° C. for 20 hours under Ar. The reaction mixture was diluted with ethyl acetate (15 mL), washed with water, brine and dried over Na₂SO₄. After filtration and removal of solvent, the residue was purified by preparative chromatography plate with 2% methanol (7M NH₃)/dichloromethane to give 52 mg (46%) of compound P-179. ¹H NMR (400 MHz, CDCl₃) 2.63 (s, 3H), 3.80 (s, 3H), 5.13 (s, 2H), 6.10-6.18 (m, 1H), 6.55-6.64 (m, 1H), 6.96 (d, J=8.5 Hz, 1H), 7.27-7.37 (m, 4H), 7.45-7.53 (m, 1H), 7.69 (d, J=7.8 Hz, 1H), 7.92 (d, J=7.8 Hz, 1H), 8.07 (s, 1H) ppm. LC-MS (APCI+): 334.1 (M+1).

Example 361

Preparation of P-172

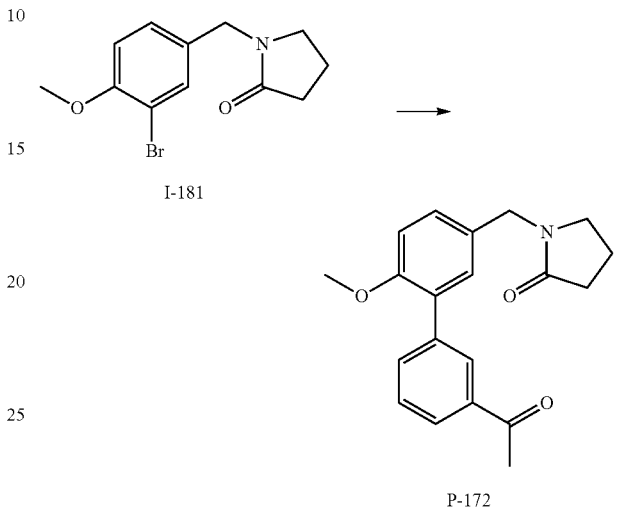

1-(3'-Acetyl-6-methoxy-biphenyl-3-ylmethyl)-pyrrolidin-2-one (P172). A reaction mixture of compound I-181 (120 mg, 0.42 mmol), 3-acetylphenyl boronic acid (69.2 mg, 0.42 mmol), triphenylphosphine (22 mg, 0.08 mmol), K₂CO₃ (174 mg, 1.26 mmol), Pd(OAc)₂ (9.5 mg, 0.04 mmol) in 1,2-dimethoxyethane (4 mL), ethanol (0.5 mL) and water (0.5 mL) was stirred at 80° C. for 20 hours under Ar. The reaction mixture was diluted with ethyl acetate (15 mL), washed with water, brine and dried over Na₂SO₄. After filtration and removal of solvent, the residue was purified by preparative chromatography plate with 2% methanol (7M NH₃)/dichloromethane to give 48 mg (34%) of compound P-172. ¹H NMR (400 MHz, CDCl₃) 1.93-2.06 (m, 2H), 2.44 (t, J=8.1 Hz, 2H), 2.64 (s, 3H), 3.30 (t, J=7.0 Hz, 2H), 3.81 (s, 3H), 4.45 (s, 2H), 6.96 (d, J=8.4 Hz, 1H), 7.20 (d, J=2.1 Hz, 1H), 7.22-7.29 (m, 1H), 7.45-7.56 (m, 1H), 7.71 (d, J=7.8 Hz, 1H), 7.92 (d, J=7.8 Hz, 1H), 8.09 (s, 1H) ppm. LC-MS (APCI+): 324.1 (M+1).

Example 362

Preparation of P-241

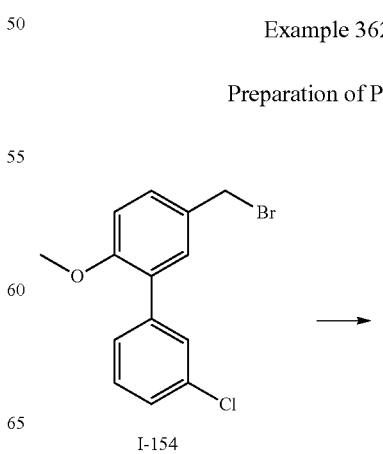

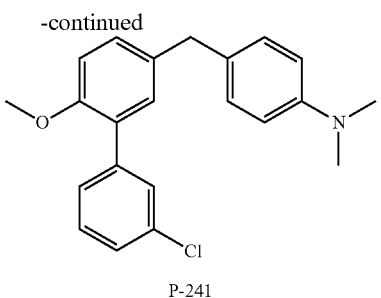

P-241

Synthesis of [4-(3'-Chloro-6-methoxy-biphenyl-3-ylmethyl)-phenyl]-dimethyl-amine (P-241). A reaction mixture of compound I-154 (200 mg, 0.64 mmol), 4-(dimethylamino) phenylboronic acid (138 mg, 0.83 mmol), triphenylphosphine (34 mg, 0.12 mmol), $K_2CO_3$ (132 mg, 0.96 mmol), $Pd(OAc)_2$ (14.0 mg, 0.06 mmol) in 1,2-dimethoxyethane (2 mL), ethanol (0.25 mL) and water (0.25 mL) was stirred at 80° C. for 3.5 hours under Ar. The reaction mixture was diluted with water (10 mL) and extract with ethyl acetate (3×5 mL), washed with brine and dried over $Na_2SO_4$. After filtration and removal of solvent, the residue was purified by silica gel column chromatography with ethyl acetate/hexane to yield 140 mg of product P-241 as the free base. This residue was dissolved in ether (3 mL) and stir for 0.5 hour, followed by adding 2M HCl solution in ether (3 mL) and the solution was stirred for another 2 hours. Removal of the solvent provided P-241HCl salt (120 mg, 77%) as a white solid.

$^1$H NMR (400 MHz, CDCl$_3$) 3.14 (s, 6H), 3.80 (s, 3H), 3.99 (s, 2H), 6.92 (d, J=8.3 Hz, 1H), 7.08 (d, J=2.0\ Hz, 1H), 7.09-7.14 (m, 1H), 7.27-7.39 (m, 5H), 7.48 (s, 1H), 7.67 (d, J=8.3 Hz, 2H), 14.64 (br s. 1H) ppm.

Example 363

Preparation of P-246

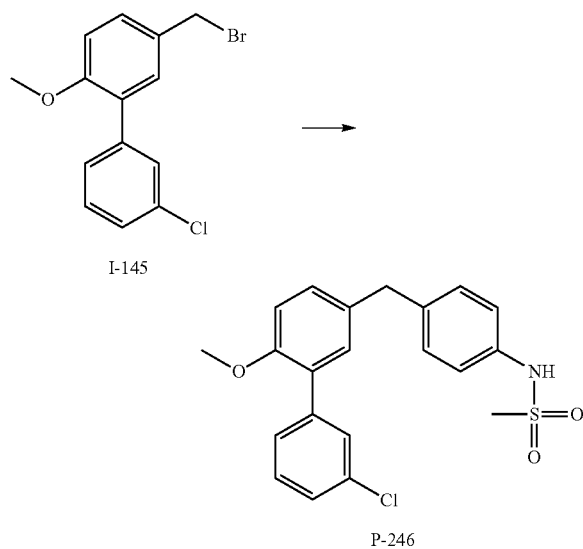

Synthesis of N-[4-(3'-Chloro-6-methoxy-biphenyl-3-ylmethyl)-phenyl]-methanesulfonamide (P-246). A reaction mixture of compound I-145 (300 mg, 0.96 mmol), 4-(N-phenyl-methanesulfonamide)boronic acid (228 mg, 0.96 mmol), triphenylphosphine (75 mg, 0.29 mmol), $K_3PO_4$ (407 mg, 0.92 mmol), $Pd(OAc)_2$ (22.0 mg, 0.10 mmol) in 1,2-dimethoxyethane (4 mL), ethanol (0.5 mL) and water (0.5 mL) was stirred at 80° C. for 16 hours under Ar. The reaction mixture was diluted with water (20 mL) and extract with ethyl acetate (3×5 mL), washed with brine and dried over $Na_2SO_4$. After filtration and removal of solvent, the residue was purified by silica gel column chromatography with ethyl acetate/ hexanes as eluent to give 46 mg (16%) of P-246. $^1$H NMR (400 MHz, CDCl$_3$) 2.99 (s, 3H) 3.79 (s, 3H) 3.94 (s, 2H) 6.20 (br. s., 1H) 6.91 (d, J=8.32 Hz, 1H) 7.08-7.17 (m, 4H) 7.16-7.22 (m, 2H) 7.27-7.34 (m, 2H) 7.35-7.41 (m, 1H) 7.48 (s, 1H)

Example 364

Preparation of P-476

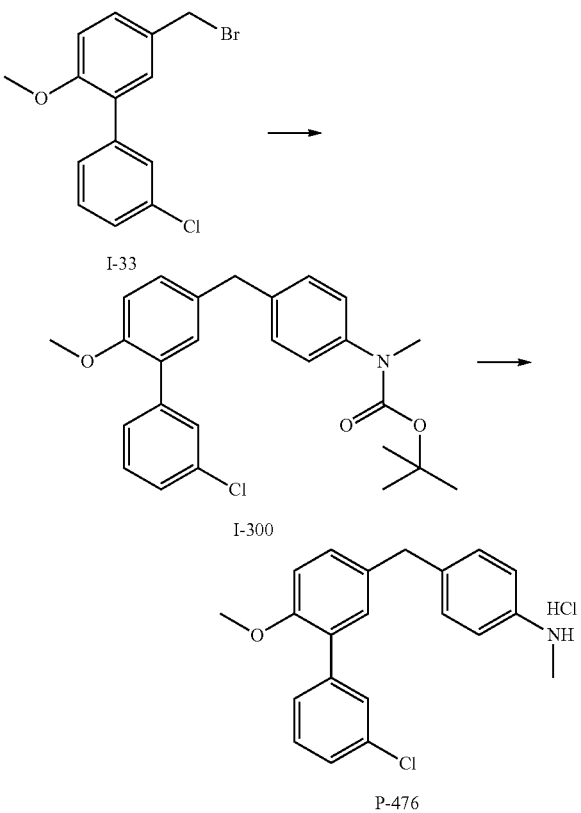

Synthesis of [4-(3'-Chloro-6-hydroxy-biphenyl-3-ylmethyl)-phenyl]-methyl-carbamic acid tert-butyl ester (I-300). A reaction mixture of compound I-33 (300 mg, 0.96 mmol), methyl-[4-(4,4,5,5-tetramethyl-[1,3,2]dioxaborolan-2-yl)-phenyl]-carbamic acid tert-butyl ester (417 mg, 1.25 mmol), triphenylphosphine (52 mg, 0.20 mmol), $K_3PO_4$ (414 mg, 2.0 mmol), $Pd(OAc)_2$ (52.0 mg, 0.20 mmol) in 1,2-dimethoxyethane (4 mL), ethanol (0.5 mL) and water (0.5 mL) was stirred at 80° C. for 3 hours under Ar. The reaction mixture was diluted with water (10 mL) and extract with ethyl acetate (3×5 mL), washed with brine and dried over $Na_2SO_4$. After filtration and removal of solvent, the residue was purified by silica gel column chromatography with ethyl acetate/hexane as eluent to give 340 mg (81%) of product I-300.

Synthesis of [4-(3'-Chloro-6-methoxy-biphenyl-3-ylmethyl)-phenyl]-methyl-amine hydrochloric acid (P-476). I-300 (90 mg, 0.21 mmol) was dissolved in dichloromethane (1 mL) and then TFA (1 mL) was added and the mixture was stirred at room temperature 0.5 hour. followed by removal TFA in vacuo. The material was acidified with aqueous 1M HCl to pH=2 and extracted with ether (3×3 mL). The aqueous layer was then basified with aqueous 2M $Na_2CO_3$ to pH=9 and then extracted with ethyl acetate (3×3 mL) and the combined extracts were concentrated. The residue was dissolved in ether (3 mL) and 2M HCl solution in ether (3 mL) was added and the mixture was allowed to stir for 2 hours. The solid was vacuum filtered to afford 32 mg (41%, two steps) of P-476 as a white solid. $^1$H NMR (400 MHz, $CDCl_3$) 2.98 (s, 3H), 3.79 (s, 3H), 3.95 (s, 2H), 6.90 (d, J=8.3 Hz, 1H), 7.04-7.12 (m, 2H), 7.27-7.39 (m, 5H), 7.45-7.54 (m, 3H), 11.47 (br s, 2H) ppm.

Example 365

Preparation of P-247

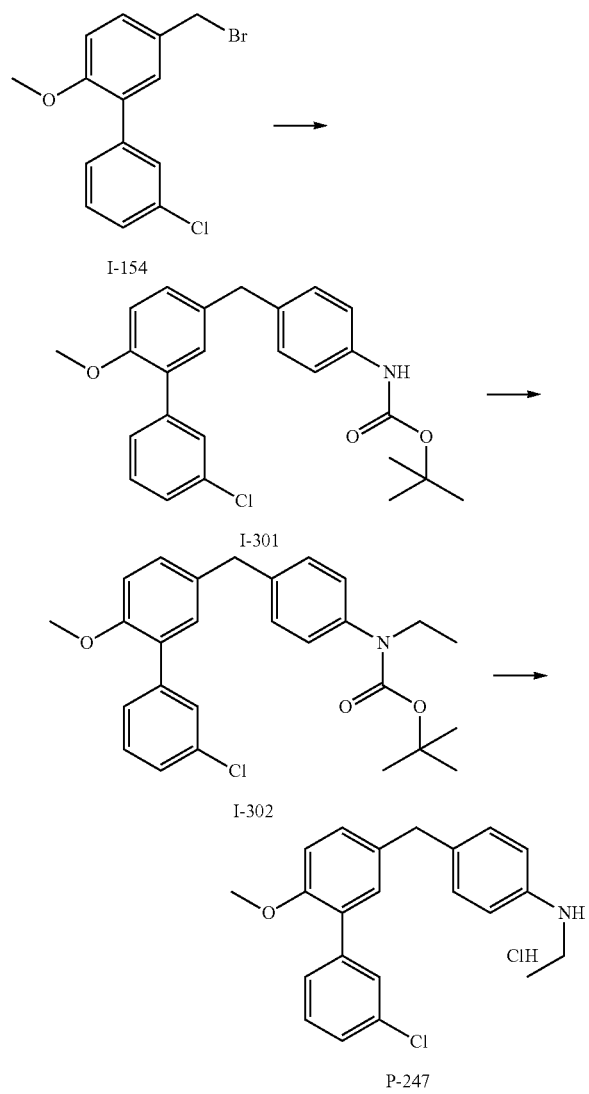

Synthesis of [4-(3'-Chloro-6-methoxy-biphenyl-3-ylmethyl)-phenyl]-carbamic acid tert-butyl ester (I-301). A reaction mixture of compound I-154 (300 mg, 0.96 mmol), 4-(N-Boc-amino)phenylboronic acid (228 mg, 0.96 mmol), triphenylphosphine (75 mg, 0.29 mmol), $K_3PO_4$ (407 mg, 1.92 mmol), $Pd(OAc)_2$ (22.0 mg, 0.10 mmol) in 1,2-dimethoxyethane (4 mL), ethanol (0.5 mL) and water (0.5 mL) was stirred at 80° C. for 3 hours under Ar. The reaction mixture was diluted with water (20 mL) and extract with ethyl acetate (3×5 mL), washed with brine and dried over $Na_2SO_4$. After filtration and removal of solvent, the residue was purified by silica gel column chromatography with ethyl acetate/hexane to yield 200 mg (50%) of product I-301.

Synthesis of [4-(3'-Chloro-6-methoxy-biphenyl-3-ylmethyl)-phenyl]-ethyl-carbamic acid tert-butyl ester (I-302) I-301 (140 mg, 0.33 mmol) was dissolved in 2 mL of DMF and stirred for 10 minutes under $N_2$; then NaH was added. Once effervescence had ceased. ethyl iodide was added and the reaction mixture was stirred at room temperature for 2 hours and quenched with 20 mL of water. The mixture was extracted with ethyl acetate (3×5 mL), and the combined organic extracts were washed with brine and dried over $Na_2SO_4$. After filtration and removal of solvent, 120 mg (81%) of I-302 was collected.

Synthesis of [4-(3'-Chloro-6-methoxy-biphenyl-3-ylmethyl)-phenyl]-ethylamine; HCl salt (P-247). Compound I-302 (120 mg, 0.27 mmol) was dissolved in dichloromethane (1 mL) and then added TFA (1 mL) was added The mixture was stirred at room temperature for 0.5 hour. The mixture was cincentrated and the residue was dissolved in ether (2 mL) and 2M HCl solution in ether (2 mL) was added and the mixture was allowed to stir for another 2 hours. The solid was vacuum filtered to afford 30 mg (29%, two steps) of P-247 as white solid. $^1$H NMR (400 MHz, $CDCl_3$) 1.32-1.43 (m, 3H), 3.32 (br s, 2H), 3.79 (s, 3H), 3.94 (s, 2H), 6.90 (d, J=8.3 Hz, 1H), 7.03-7.14 (m, 2H), 7.23-7.39 (m, 5H), 7.44-7.55 (m, 3H), 11.40 (br. s., 1H) ppm.

Example 366

Preparation of P-477

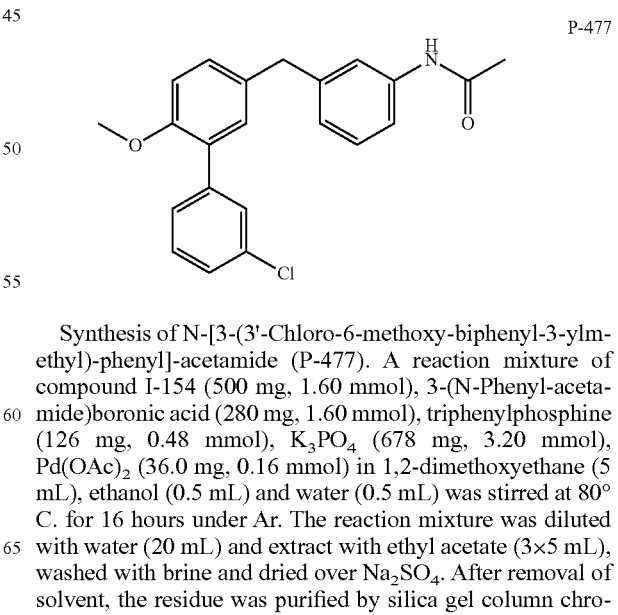

Synthesis of N-[3-(3'-Chloro-6-methoxy-biphenyl-3-ylmethyl)-phenyl]-acetamide (P-477). A reaction mixture of compound I-154 (500 mg, 1.60 mmol), 3-(N-Phenyl-acetamide)boronic acid (280 mg, 1.60 mmol), triphenylphosphine (126 mg, 0.48 mmol), $K_3PO_4$ (678 mg, 3.20 mmol), $Pd(OAc)_2$ (36.0 mg, 0.16 mmol) in 1,2-dimethoxyethane (5 mL), ethanol (0.5 mL) and water (0.5 mL) was stirred at 80° C. for 16 hours under Ar. The reaction mixture was diluted with water (20 mL) and extract with ethyl acetate (3×5 mL), washed with brine and dried over $Na_2SO_4$. After removal of solvent, the residue was purified by silica gel column chromatography with ethyl acetate/hexane and methanol/dichloromethane to yield 178 mg (30%) of P-477) $^1$H NMR (400 MHz, CDCl$_3$) 2.11-2.23 (m, 3H), 3.79 (s, 3H), 3.94 (s, 2H), 6.90 (d, J=8.32 Hz, 1H), 6.95 (d, J=7.51 Hz, 1H), 7.04-7.09 (m, 1H), 7.09-7.16 (m, 2H), 7.19-7.34 (m, 4H), 7.34-7.42 (m, 2H), 7.50 (s, 1H) ppm.

Example 367

Preparation of P-255

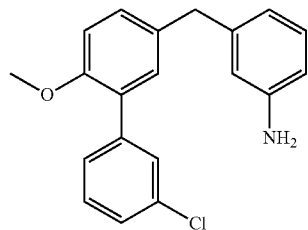

P-255

Synthesis of 3-(3'-Chloro-6-methoxy-biphenyl-3-ylmethyl)-phenylamine (P-255). To a 24 mL vial was placed P-477 (80 mg, 0.22 mmol), concentrated HCl (4 mL) and EtOH (4 mL) and the reaction mixture was stirred at 85° C. over night. White solid was formed upon cooling to room temperature. To the vial was added H$_2$O (10 mL) and the mixture was stirred at room temperature for 20 minutes then filtered to yield 75 mg (95%) of P-255. $^1$H NMR (400 MHz, CDCl$_3$) 3.77 (s, 3H), 3.96 (s, 2H), 6.84-6.96 (m, 1H), 7.03-7.14 (m, 2H), 7.16-7.44 (m, 7H), 7.50 (s, 1H), 10.50 (br s, 2H) ppm.

Example 368

Preparation of P-270

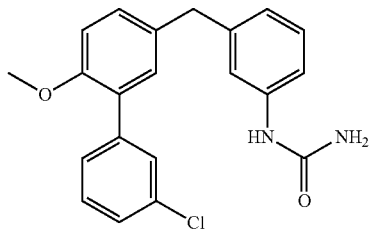

P-270

Synthesis of [3-(3'-Chloro-6-methoxy-biphenyl-3-ylmethyl)-phenyl]-urea (P-270). To a 24 mL vial was placed P-255 (60 mg, 0.17 mmol), NaOCN (21.7 mg, 0.33 mmol), AcOH (1 mL) and H$_2$O (2 mL). The reaction mixture was stirred at room temperature over night. The white solid formed was filtered to yield 54 mg. (87%) of P-270. $^1$H NMR (400 MHz, DMSO-d$_6$) 3.74 (s, 3H), 3.86 (s, 2H), 5.76 (s, 2H), 6.78 (m, 1H), 7.04 (d, J=8 Hz, 1H), 7.11 (t, J=8 Hz, 1H), 7.17-7.20 (m, 3H), 7.23-7.25 (m, 1H), 7.35-7.43 (m, 3H), 7.48 (m, 1H), 8.43 (s, 1H) ppm.

Example 369

Preparation of P-271

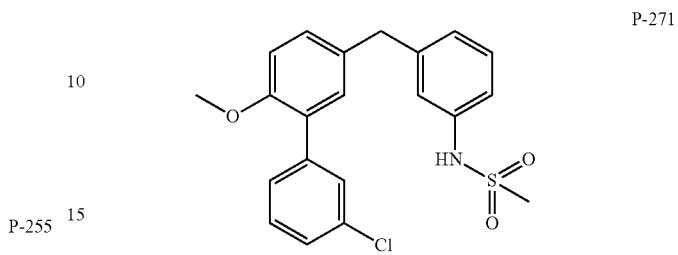

P-271

Synthesis of N-[3-(3'-Chloro-6-methoxy-biphenyl-3-ylmethyl)-phenyl]-methanesulfonamide (P-271). To a 4 mL vial was added P-255 (60 mg, 0.17 mmol), followed by pyridine (2 mL) then methanesulfonyl chloride (13 µL) at 0° C. The resulting solution was allowed to stir at room temperature overnight. The reaction mixture was diluted with water (10 mL) and extracted with ethyl acetate (3×5 mL). The combined organics were concentrated under vacuum, and the residue was purified by silica gel column chromatography with methanol/dichloromethane to yield 36.7 mg (55%) of P-271). $^1$H NMR (400 MHz, CDCl$_3$) 2.98 (s, 3H), 3.79 (s, 3H), 3.94 (s, 2H), 6.53 (s, 1H), 6.91 (d, J=8.4 Hz, 1H), 6.99-7.17 (m, 5H), 7.22-7.35 (m, 3H), 7.34-7.41 (m, 1H), 7.48 (s, 1H) ppm.

Example 370

Preparation of P-282

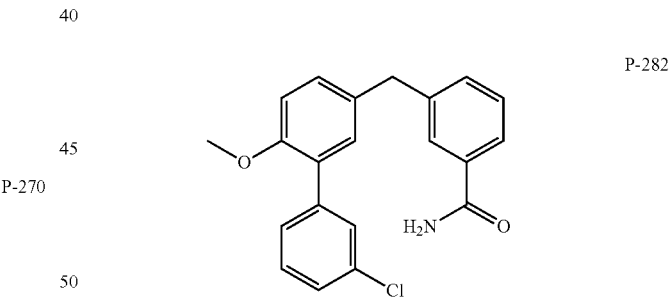

P-282

Synthesis of 3-(3'-Chloro-6-methoxy-biphenyl-3-ylmethyl)-benzamide (P-282).

A reaction mixture of compound I-154 (200 mg, 0.64 mmol), 3-benzamid boronic acid (129 mg, 0.96 mmol), triphenylphosphine (50 mg, 0.20 mmol), K$_3$PO$_4$ (271 mg, 1.28 mmol), Pd(OAc)$_2$ (14.0 mg, 0.06 mmol) in 1,2-dimethoxyethane (2.5 mL), ethanol (0.25 mL) and water (0.25 mL) was stirred at 80° C. overnight under Ar. The reaction mixture was diluted with water (10 mL) and extracted with ethyl acetate (3×3 mL), and the combined organic extracts were washed with brine and dried over Na$_2$SO$_4$. After filtration and removal of solvent, the residue was purified by silica gel column chromatography eluting with ethyl acetate/hexane and dichloromethane to yield 108 mg (48%) of P-282).

¹H NMR (400 MHz, CDCl₃) 3.78 (s, 3H), 3.99 (s, 2H), 6.12 (br s, 2H), 6.89 (d, J=8.32 Hz, 1H), 7.08-7.15 (m, 2H), 7.23-7.39 (m, 5H), 7.48 (s, 1H), 7.57-7.64 (m, 1H), 7.69 (s, 1H) ppm.

Example 371

Preparation of P-303

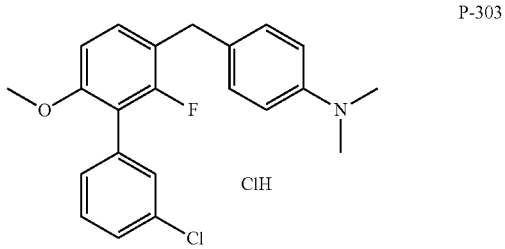

P-303

Synthesis of [4-(3'-Chloro-2-fluoro-6-methoxy-biphenyl-3-ylmethyl)-phenyl]-dimethyl-amine (P-303). A reaction mixture of compound I-33 (100 mg, 0.30 mmol), 4-N,N-dimethylphenylboronic acid (60 mg, 0.36 mmol), K₃PO₄ (127 mg, 0.60 mmol) in 1,2-dimethoxyethane (4 mL), ethanol (0.5 mL) and water (0.5 mL) was purged with argon for 5 minutes before adding palladium tetrakis(triphenylphosphine) (18 mg, 0.02 mmol) and then stirred at 80° C. overnight under argon. The reaction mixture was diluted with water (10 mL) and extracted with ethyl acetate (3×3 mL). The combined organic extracts were washed with brine and dried over Na₂SO₄. After filtration and removal of solvent, the residue was purified by silica gel column chromatography with ethyl acetate/hexane and methanol/ethyl acetate as eluent to give free base P-303. P-303 was dissolved in ether (2 mL) and HCl (2M in ether) was added and the resulting solution was then stirred for 30 minutes. Filtration of the mixture afforded 53 mg (43%) of P-303HCl salt. ¹H NMR (400 MHz, CDCl₃) 2.91 (s, 6H), 3.74 (s, 3H), 3.87 (s, 2H), 6.62-6.74 (m, 3H), 7.01-7.13 (m, 3H), 7.24-7.36 (m, 3H), 7.40 (s, 1H) ppm.

Example 372

Preparation of P-310

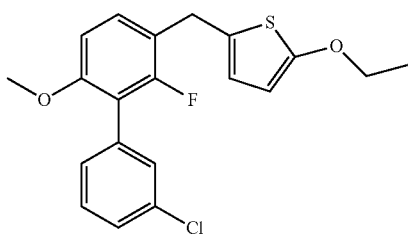

P-310

Synthesis of 2-(3'-Chloro-2-fluoro-6-methoxy-biphenyl-3-ylmethyl)-5-ethoxythiophene (P-310). A reaction mixture of compound I-33 (100 mg, 0.30 mmol), 4-ethoxythiophene boronic acid (50 mg, 0.36 mmol), K₃PO₄ (127 mg, 0.60 mmol) in 1,2-dimethoxyethane (4 mL), ethanol (0.5 mL) and water (0.5 mL) was purged with Ar for 5 minutes before adding palladium tetrakis(triphenylphosphine) (18 mg, 0.02 mmol) and then stirred at 80° C. over night under Ar. The reaction mixture was diluted with water (10 mL) and extract with ethyl acetate (3×3 mL). The combined organic extracts were washed with brine and dried over Na₂SO₄. After filtration and removal of solvent, the residue was purified by silica gel column chromatography with ethyl acetate/hexanes and methanol/ethyl acetate as eluent to give 40 mg (35%) of P-310. ¹H NMR (400 MHz, CDCl₃) δ 1.39 (t, J=8 Hz, 3H), 3.74 (s, 3H), 3.89 (2, 2 H), 4.00 (q, 2H), 6.80 (m, 1H), 7.05-7.40 (m, 7H) ppm.

Example 373

Preparation of P-311

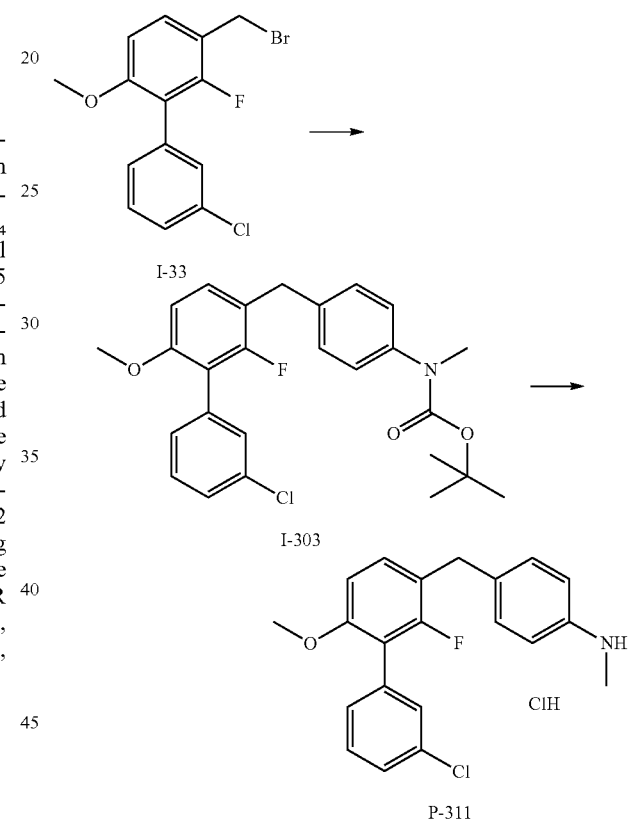

Synthesis of [4-(3'-Chloro-2-fluoro-6-methoxy-biphenyl-3-ylmethyl)-phenyl]-methyl-carbamic acid tert-butyl ester (I-303). A reaction mixture of compound I-33 (300 mg, 0.91 mmol), methyl-[4-(4,4,5,5-tetramethyl-[1,3,2]dioxaborolan-2-yl)-phenyl]-carbamic acid tert-butyl ester (240 mg, 1.09 mmol), palladium tetrakis(triphenylphosphine) (53 mg, 0.05 mmol), K₃PO₄ (380 mg, 1.82 mmol) in 1,2-dimethoxyethane (10 mL), ethanol (1 mL) and water (1 mL) was purged with argon for 5 minutes before adding palladium tetrakis(triphenylphosphine) (53 mg, 0.05 mmol) and then stirred at 80° C. for 2 hours under argon. The reaction mixture was diluted with water (10 mL) and extract with ethyl acetate (3×5 mL). The combined organic extracts were washed with brine and dried over Na₂SO₄. After filtration and removal of solvent, the residue was purified by silica gel column chromatography with ethyl acetate/hexane as eluent to give 240 mg (60%) of I-303.

Synthesis of [4-(3'-Chloro-2-fluoro-6-methoxy-biphenyl-3-ylmethyl)-phenyl]-methyl-amine (P-311). I-303 (240 mg, 0.21 mmol) was dissolved in dichloromethane (1 mL) and then TFA (1 mL) was added and the mixture was stirred at room temperature for 0.5 hour. The solvent was removed and the residue was diluted with ether (3 mL) and HCl (2M in ether) (2 mL) and the mixture was stirred at room temperature for 2 hours. The resulting solids were filtered to provide 130 mg (70%) of P-311HCl salt. $^1$H NMR (400 MHz, CDCl$_3$) 2.99 (br s, 3H), 3.76 (s, 3H), 3.95 (s, 2H), 6.71 (d, J=8.5 Hz, 1H), 7.07 (t, J=8.5 Hz, 1H), 7.27-7.40 (m, 6H), 7.47-7.55 (m, 2H), 11.46 (br s, 1H) ppm.

Example 374

Preparation of P-326

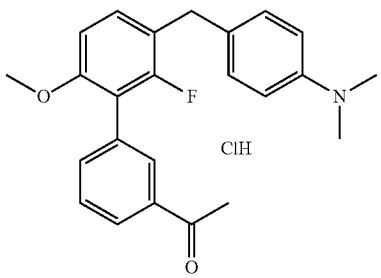

Synthesis of 1-[3'-(4-Dimethylamino-benzyl)-2'-fluoro-6'-methoxy-biphenyl-3-yl]-ethanone (P-326). In an 24 mL vial equipped with a stir bar was placed I-223 (150 mg, 0.45 mmol), 4-(dimethylamino)phenylboronic acid (89.1 mg, 0.54 mmol), potassium carbonate (136 mg, 0.99 mmol), 1,5-bis(diphenylphosphino)pentane (60 mg, 0.14 mmol), allylpalladium(II) chloride dimer (26 mg, 0.07 mmol) and dimethylformamide (3 mL). The reaction mixture was heated to 80° C. over night under N$_2$. The reaction mixture was filtered through celite and to the filtrate was added water (10 mL). After extraction with ethyl acetate (3×10 mL), the organic portions were combined, washed with brine (50 mL), dried (Na$_2$SO$_4$), filtered and concentrated. The residue was purified by column chromatography utilizing EtOAc/hexanes as the eluent to give free base product. Conversion of the free base product to HCl salt was accomplished by dissolving the free base in ether (2 mL) and then HCl (2N in ether) was added and the resulting mixture was stirred for 0.5 hour. The resulting solids were filtered to provide 66.2 mg (39%) of P-326HCl salt. $^1$H NMR (400 MHz, CDCl$_3$) 2.62 (s, 3H), 2.91 (s, 6H), 3.74 (s, 3H), 3.88 (s, 2H), 6.70 (d, J=8.6 Hz, 3H), 7.04-7.14 (m, 3H), 7.47-7.55 (m, 1H), 7.54-7.64 (m, 1H), 7.94 (d, J=7.8 Hz, 1H), 8.00 (s, 1H) ppm.

Example 375

Preparation of P-332

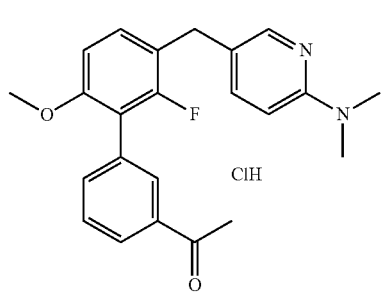

Synthesis of 1-[3'-(6-Dimethylamino-pyridin-3-ylmethyl)-2'-fluoro-6'-methoxy-biphenyl-3-yl]-ethanone (P-332). In an 24 mL vial equipped with a stir bar was placed I-223 (150 mg, 0.45 mmol), 6-(dimethylamino)pyridin-3-ylboronic acid (155 mg, 0.54 mmol), potassium carbonate (136 mg, 0.99 mmol), 1,5-bis(diphenylphosphino)pentane (60 mg, 0.14 mmol), allylpalladium(II) chloride dimer (26 mg, 0.07 mmol) and dimethylformamide (3 mL). The reaction mixture was heated to 80° C. overnight under N$_2$. The reaction mixture was filtered through Celite and to the filtrate was added water (10 mL). After extraction with ethyl acetate (3×10 mL), the organic portions were combined, washed with brine (50 mL), dried (Na$_2$SO$_4$), filtered and concentrated. The residue was purified by column chromatography utilizing EtOAc/hexanes as the eluent to give free base product. Conversion of the free base product to HCl salt was accomplished by dissolving it in dichloromethane (1 mL) and then adding HCl (2N in ether) and stir 0.5 hour. After filtration, 100 mg (59 5) of P-332HCl salt was obtained.

$^1$H NMR (400 MHz, CDCl$_3$) δ 3.40 (br s, 6H), 3.77 (s, 3H), 3.85 (s, 2H); 6.7-8.1 (m, 9H).

Table of 1H NMR Spectra

| | | |
|---|---|---|
| P-008 | 1H NMR (CDCl3, 400 MHz): d = 3.87 (3H, s), 3.97 (2H, s), 6.97 (1H, d, J = 8.4 Hz), 7.12-7.15 (3H, m), 7.17 (1H, dd, J = 8.4 and 8.4 Hz), 7.55 (1H, dd, J = 8 and 8 Hz), 7.82 (1H, m), 8.17 (1H, m), 8.38 (1H, m), 8.51 (2H, m). | |
| P-011 | 1H NMR (CDCl3, 400 MHz): d = 3.84 (3H, s), 3.98 (2H, s), 6.98 (1H, d, J = 8.8 Hz), 7.13 (2H, m), 7.19 (1H, d, J = 2.8 Hz), 7.22 (1H, dd, J = 8 and 2 Hz), 7.61 (1H, m), 7.80 (1H, m), 7.84 (1H, m), 8.52 (2H, m). | |
| P-013 | 1H NMR (400 MHz, DMSO-d6) d ppm 3.75-3.87 (m, 3 H) 4.11 (s, 2 H) 7.16 (d, J = 8.46 Hz, 1 H) 7.43 (d, J = 8.33 Hz, 1 H) 7.48-7.60 (m, 2 H) 7.76 (d, J = 9.40 Hz, 1 H) 7.90 (s, 1 H) 7.96 (d, J = 9.27 Hz, 1 H) 8.00-8.10 (m, 2 H) | LCMS = purity. APCI(−) = 372 (M + 14). 94.9% |
| P-028 | 1H NMR (CDCl3, 400 MHz): d = 3.82 (3H, s), 5.00 (2H, s), 6.91 (1H, m), 6.98 (1H, d, J = 8.4 Hz), 7.08-7.15 (2H, m), 7.22 (1H, m), 7.34 (1H, m), 7.40 (1H, dd, J = 8.4 and 2 Hz), 7.56 (1H, dd, J = 8.4 and 8.4 Hz), 7.79 (1H, m), 8.18 (1H, m), 8.37 (1H, m). | |
| P-046 | $^1$H NMR (400 MHz, CDCl$_3$): 3.82 (s, 3H), 3.95 (s, 3H), 5.32 (s, 2H), 6.98 (d, J = 8.5 Hz, 1H), 7.17 (dd, J = 10.5, 8.7 Hz, 1H), 7.21-7.32 (m, 2H), 7.64 (ddd, J = 8.4, 4.6, 2.4 Hz, 1H), 7.97 (s, 1 H), 8.03 (dd, J = 7.0, 2.3 Hz, 1 H), 8.07 (s, 1 H) ppm. | APCI$^+$ (M + 1): 342., 100% |
| P-048 | 1H NMR (CDCl3, 400 MHz): d = 8.06 (s, 1 H), 7.97 (s, 1 H), 7.89-7.96 (m, 1 H), 7.45-7.52 (m, 1 H), 7.32 (dd, J = 8.5, 2.3 Hz, 1 H), 7.19-7.28 (m, 2 H), 6.99 (d, J = 8.5 Hz, 1 H), 5.31 (s, 2 H), 3.93 (s, 3 H), 3.80 (s, 3 H) | Calc. 341.3; APCI$^+$ (M + 1): 342, 100% |

Table of 1H NMR Spectra

| | | |
|---|---|---|
| P-049 | 1H NMR (CDCl3, 400 MHz): d = 8.31 (Brs, 1 H), 8.21-8.25 (m, 1 H), .7.85-7.89 (m, 2 H), 7.57-7.74 (m, 3 H), 7.12-7.17 (m, 2 H), .6.93 (d, J = 8.8 Hz, 1 H), 3.89 (s, 3 H) | Calc. 369.33; APCI− (M): 369, 100% |
| P-050 | 1H NMR (CDCl3, 400 MHz): d = 8.30 (s, 1 H), 8.19-8.22 (m, 1 H), 7.73 (dd, J = 7.7, 1.3 Hz, 1 H), 7.57 (t, J = 8.0 Hz, 1 H), 7.10-7.21 (m, 3 H), 6.98 (t, J = 8.7 Hz, 1 H), 6.74 (d, J = 7.6 Hz, 2 H), 3.95 (s, 2 H), 3.77 (s, 3 H) | Calc. 355.34; APCI− (M): 355, 100% |
| P-051 | 1H NMR (400 MHz, CDCl$_3$): 3.79 (s, 3H), 6.12 (br. s., 1H), 6.82 (d, J = 8.7 Hz, 1H), 7.04 (t, J = 8.7 Hz, 2H), 7.40 (dd, J = 8.5, 5.5 Hz, 2H), 7.47 (t, J = 8.6 Hz, 1 H), 7.50-7.64 (m, 1H), 7.70 (s, 1H), 8.22 (s, 1H), 8.27 (s, 1 H) ppm. | Calc. 371.34; APCI+ (M − OH): 354, 94% |
| P-054 | 1H NMR (CDCl3, 400 MHz): d = 3.79 (3H, s), 4.19 (2H, s), 6.90 (1H, d, J = 9.2 Hz), 6.98 (1H, d, J = 8.8 Hz), 7.04 (2H, m), 7.27 (2H, m), 7.64 (1H, dd, J = 8 and 8 Hz), 7.89 (1H, m), 8.28 (1H, m), 8.39 (1H, m). | |
| P-057 | 1H NMR (CDCl3, 400 MHz): d = 4.19 (2H, s), 6.45 (1H, t, J = 72 Hz), 7.02 (2H, m), 7.13 (1H, d, J = 8.4 Hz), 7.27 (2H, m), 7.55 (1H, d, J = 8.4 Hz), 7.62 (1H, dd, J = 8 and 8 Hz), 8.29 (2H, m), 8.79 (1H, m). | |
| P-060 | 1H NMR (CDCl3, 400 MHz): d = 3.82 (3H, s), 5.32 (2H, s), 6.98 (1H, d, J = 8.4 Hz), 7.15-7.22 (3H, m), 7.28 (1H, m), 7.31-7.36 (1H, m), 7.97 (1H, s), 8.07 (1H, s). | |
| P-061 | 1H NMR (CDCl3, 400 MHz): d = 3.83 (3H, s), 5.32 (2H, s), 6.98 (1H, d, J = 8.8 Hz), 7.13 (2H, m), 7.19 (1H, m), 7.28 (1H, m), 7.97 (1H, s), 8.07 (1H, s). | |
| P-063 | 1H NMR (CDCl3, 400 MHz): d = 3.82 (3H, s), 5.33 (2H, s), 6.99 (1H, d, J = 8 Hz), 7.25-7.30 (2H, m), 7.46-7.68 (3H, m), 7.74 (1H, m), 7.97 (1H, s), 8.08 (1H, s). | |
| P-078 | 1H NMR (CDCl3, 400 MHz): d = 1.71-1.77 (m, 1H), 2.19-2.23 (m, 1H), 2.33-2.37 (m, 1H), 2.54-2.58 (m, 1H), 2.68-2.71 (m, 1H), 2.85-2.91 (m, 1H), 3.63 (s, 2H), 3.82 (s, 3H), 4.33-4.36 (m, 1H), 6.95 (d, J = 8 Hz, 1H), 7.268 (s, J = 3.4 Hz, 1H), 7.31 (dd, J = 8, 2 Hz, 1H), 7.5 (t, 1H), 7.56 (d, J = 8 Hz, 1H), 7.71 (d, J = 8 Hz, 1H), 7.78 (s, 1H). | MS (APCI+): 352 (M + 1), LCMS: 97.55% |
| P-083 | 1H NMR (CDCl3, 400 MHz): d = 3.34-3.47 (t, 2H), 3.82 (s, 3H), 4.29-4.33 (t, 2H), 4.42 (s, 2H), 6.98 (d, J = 8.4 Hz, 1H), 7.22 (d, J = 2.4 Hz, 1H), 7.3 (dd, J = 8.4, 2.4 Hz, 1H), 7.52 (t, 1H), 7.59 (d, J = 8 Hz, 1H), 7.68 (d, J = 8 Hz, 1H), 7.77 (s, 1H). | MS (ESI+): 352 (M + 1), LCMS: 94% |
| P-095 | 1H NMR (DMSO-d6, 400 MHz): d = 8.19-8.24 (m, 2 H), 8.00 (br. s., 1 H), 7.82-7.90 (m, 2 H), 7.74 (t, J = 8.0 Hz, 1 H), 7.50 (d, J = 8.8 Hz, 1 H), 7.29-7.39 (m, 2H), 7.08 (d, J = 8.4 Hz, 1 H)), 3.81 (s, 3 H), 3.16 ppm (s, 3 H) | Calc. 383.38; APCI− (M − 1): 382; (M − 2): 381, |
| P-096 | 1H NMR (DMSO-d6, 400 MHz): d = 8.18-8.25 (m, 2 H), 7.73-7.85 (m, 4 H), 7.65 (d, J = 9.1 Hz, 2 H), 7.40-7.51 (m, 2 H), 6.85 (d, J = 9.2 1 H), 3.84 (s, 3 H) | Calc. 369.35; APCI− (M − 2): 367, |
| P-097 | 1H NMR (CDCl3, 400 MHz): d = 8.33 (br, s, 1 H), 8.17-8.21 (m, 1 H), 7.76-7.79 (m, 1 H), 7.56 (t, J = 8.0 Hz, 1H), 7.16-7.20 (m, 1 H), 7.11 (d, J = 8.5 Hz, 1 H), 6.95-7.01 (m, 2 H), 6.73 (d, J = 8.8 Hz, 1 H), 3.96 (s, 2 H), 3.73 (s, 3 H), 3.13 (s, 3 H) | |
| P-098 | 1H NMR (CDCl3, 400 MHz): d = 716-7.26 (m, 3 H), 7.03 (t, J = 8.8 Hz, 1 H), 6.96 (t, J = 8.8 Hz, 2 H), 6.78 (d, J = 7.6, 1 H), 6.67-6.71 (m, 3 H), 3.92 (s, 2 H), 3.74 (s, 3 H) | Calc. 325.3; ESI+ (M + 1): 326 95%. |
| P-106 | 1H NMR (400 MHz, CDCl3) d ppm 8.48 (s, 1 H) 8.11-8.36 (m, 4 H) 7.47-7.73 (m, 4 H) 7.02-7.23 (m, 2 H) 6.55 (d, J = 8.5 Hz, 1 H) 6.44-6.59 (m, 1 H) 3.96 (s, 2 H) 3.72 (s, 3 H) | |
| P-110 | 1H NMR (DMSO-d6, 400 MHz): d = 1.45 (9H, s), 3.77 (3H, s), 3.90 (2H, s), 7.10 (1H, d, J = 8.4 Hz), 7.28 (2H, m), 7.60 (1H, dd, J = 8.4 and 2 Hz), 7.70 (2H, m), 7.92 (1H, m), 8.18 (2H, m), 8.28 (1H, m), 9.62 (1H, s). | |
| P-111 | 1H NMR (CDCl3, 450 MHz): d = 3.81 (3H, s), 3.84 (2H, s), 4.32 (2H, br), 6.46 (1H, d, J = 8.5 Hz), 7.12 (1H, d, J = 2.5 Hz), 7.17 (1H, dd, J = 8.5 and 2.5 Hz), 7.25 (1H, m), 7.54 (1H, dd, J = 8 and 8 Hz), 7.97 (1H, m), 8.16 (1H, m), 8.38 (1H, m). | |
| P-112 | 1H NMR (CDCl3, 500 MHz): d = 1.50 (9H, s), 3.80 (3H, s), 3.93 (2H, s), 6.40 (1H, br), 6.92 (1H, d, J = 8.5 Hz), 7.12 (3H, m), 7.17 (1H, dd, J = 8.5 and 2.5 Hz), 7.28 (1H, m), 7.53 (1H, dd, J = 8 and 8 Hz), 7.81 (1H, m), 8.15 (1H, m), 8.38 (1H, m). | |
| P-113 | 1H NMR (CDCl3, 500 MHz): d = 3.80 (3H, s), 3.87 (2H, s), 6.63 (2H, m), 6.92 (1H, d, J = 8.5 Hz), 6.99 (2H, m), 7.14 (1H, d, J = 2 Hz), 7.18 (1H, dd, J = 8.5 and 2.5 Hz), 7.53 (1H, dd, J = 8 and 8 Hz), 7.81 (1H, m), 8.15 (1H, m), 8.38 (1H, m). | |
| P-114 | 1H NMR (CDCl3, 500 MHz): d = 2.16 (3H, s), 3.81 (3H, s), 3.94 (2H, s), 6.93 (1H, d, J = 8.5 Hz), 7.07 (1H, br), 7.13-7.18 (4H, m), 7.41 (2H, d, J = 8.5 Hz), 7.53 (1H, dd, J = 8 and 8 Hz), 7.81 (1H, m), 8.15 (1H, m), 8.38 (1H, m). | |
| P-116 | 1H NMR (CDCl3, 400 MHz): d = 8.25-8.28 (m, 2 H), 7.72 (d, J = 8.0 Hz, 1 H), 7.62 (t, J = 8.0 Hz, 1 H), 7.7.16-7.21 (m, 3 H), 6.98-7.05 (m, 3 H), 6.36 (t, J = 112 Hz, 1 H), 4.00 (s, 2 H), | Calc. 391.33; APCI− (M): 391, |
| P-121 | 1H NMR (CDCl3, 500 MHz): d = 3.39 (6H, s), 3.82 (3H, s), 4.02 (2H, s), 6.96 (1H, d, J = 8.5 Hz), 7.17 (1H, d, J = 2 Hz), 7.20 (1H, dd, J = 8.5 and 2 Hz), 7.26-7.30 (4H, m), 7.55 (1H, dd, J = 8 and 8 Hz), 7.83 (1H, m), 8.17 (1H, m), 8.39 (1H, m). | |
| P-122 | 1H NMR (CDCl3, 400 MHz): d = 2.68 (2H, m), 2.80 (2H, m), 3.80 (3H, s), 3.95 (2H, s), 6.93 (1H, d, J = 8 Hz), 7.12-7.18 (4H, m), 7.35 (1H, br), 7.41 (2H, d, J = 8 Hz), 7.53 (1H, dd, J = 8 and 8 Hz), 7.81 (1H, m), 8.15 (1H, m), 8.37 (1H, m). | |
| P-123 | 1H NMR (DMSO-d6, 400 MHz): d = 2.93 (3H, s), 3.77 (3H, s), 3.90 (2H, s), 7.08-7.13 (3H, m), 7.21-7.29 (4H, m), 7.70 (1H, dd, J = 8 and 8 Hz), 7.92 (1H, m), 8.17 (1H, m), 8.27 (1H, m), 9.60 (1H, br). | |
| P-125 | 1H NMR (400 MHz, CDCl3) d ppm 8.20-8.27 (m, 2 H) 8.06 (d, J = 1.7 Hz, 1 H) 7.58-7.73 (m, 2 H) 7.46 (dd, J = 8.5, 2.3 Hz, 1 H) 7.10 (d, J = 8.5 Hz, 1 H) 6.68 (d, J = 8.5 Hz, 1 H) 6.54 (d, J = 8.5 Hz, 1 H) 4.79 (s, 1 H) 3.91 (s, 3 H) 3.88 (s, 2 H) 3.71 (s, 3 H) | |
| P-126 | 1H NMR (400 MHz, CDCl3) d ppm 8.30 (d, J = 2.1 Hz, 2 H) 8.19-8.28 (m, 2 H) 7.62-7.70 (m, 2 H) 7.52 (dd, J = 8.2, 2.4 Hz, 1 H) 7.22 (d, J = 8.2 Hz, 1 H) 7.12 (d, J = 8.5 Hz, 1 H) 6.55 (d, J = 8.5 Hz, 1 H) 4.85 (s, 1 H) 3.93 (s, 2 H) 3.72 (s, 3 H) | |

| | Table of 1H NMR Spectra | |
|---|---|---|
| P-127 | 1H NMR (CDCl3, 400 MHz): d = 8.30 (br, s, 1 H), 8.19-8.21 (m, 1 H), 7.74 (d, J = 8.0 Hz, 1 H), 7.58 (t, J = 8.0 Hz, 1 H), 7.24 (t, J = 8.4 Hz, 1 H), 7.75 (d, J = 8.4 Hz, 1 H), 3.78 (s, 3 H), 3.62-3.69 (m, 4 H), 2.03-2.15 (s, 2 H), 1.90-1.99 (m, 1 H), 1.65-1.72 (M, 1 H) | Calc. 347.4; APCI⁻ (M) 347, 99% |
| P-136 | 1H NMR (DMSO-d6, 400 MHz): d = 8.23 (ddd, J = 8.2, 2.3, 1.1 Hz, 4 H), 8.15 (s, 4 H), 7.83 (d, J = 1.2 Hz, 2 H), 7.81 (d, J = 1.2 Hz, 3 H), 7.71-7.77 (m, 4 H), 7.28-7.40 (m, 13 H), 7.19-7.26 (m, 8 H), 7.00 (s, 4 H), 3.97 ppm (s, 8 H) | |
| P-139 | 1H NMR (CDCl3, 400 MHz): d = 7.55 (br, s 1 H), 7.46-7.48 (m, 1 H), 7.25-7.33 (m, 2 H), 7.15-7.19 (m, 2 H), 7.07 (t, J = 6.8 Hz, 1 H), 6.95-6.99 (m, 2 H), 6.69 (dd, J = 6.8, 0.8 Hz, 1 H), 3.92 (s., 2 H), 3.44 (s, 3 H) | |
| P-142 | 1H NMR (CDCl3, 400 MHz): d = 3.81 (3H, s), 3.91 (2H, s), 4.63 (1H, s), 6.76 (2H, m), 6.93 (1H, d, J = 8 Hz), 7.07 (2H, m), 7.13-7.19 (2H, m), 7.53 (1H, dd, J = 8 and 8 Hz), 7.82 (1H, m), 8.15 (1H, m), 8.38 (1H, m). | |
| P-143 | 1H NMR (CDCl3, 400 MHz): d = 1.46 (9H, s), 3.80 (3H, s), 3.91 (2H, d, J = 6 Hz), 3.93 (2H, s), 6.92 (1H, d, J = 8 Hz), 7.12-7.18 (4H, m), 7.42 (2H, d, J = 8 Hz), 7.53 (1H, dd, J = 8 and 8 Hz), 7.81 (1H, m), 8.15 (1H, m), 8.16 (1H, br), 8.37 (1H, m). | |
| P-144 | 1H NMR (DMSO-d6, 400 MHz): d = 2.86 (6H, s), 3.77 (3H, s), 3.92 (2H, s), 4.14 (2H, s), 7.09 (1H, d, J = 8 Hz), 7.23-7.28 (4H, m), 7.54 (2H, d, J = 8 Hz), 7.70 (1H, dd, J = 8 and 8 Hz), 7.92 (1H, d, J = 8 Hz), 8.18 (1H, m), 8.27 (1H, m), 10.0 (1H, br), 10.87 (1H, s). | |
| P-145 | 1H NMR (DMSO-d6, 400 MHz): d = 3.75 (2H, br), 3.77 (3H, s), 3.91 (2H, s), 7.09 (1H, d, J = 8 Hz), 7.23-7.28 (4H, m), 7.50 (2H, d, J = 8 Hz), 7.70 (1H, dd, J = 8 and 8 Hz), 7.92 (1H, m), 8.16 (3H, br), 8.18 (1H, m), 8.27 (1H, m). | |
| P-146 | 1H NMR (DMSO-d6, 400 MHz): d = 1.39 (1H, m), 1.65-1.85 (5H, m), 2.82-2.92 (4H, m), 3.28-3.45 (4H, m), 3.77 (3H, s), 3.90 (2H, s), 7.20 (2H, d, J = 8 Hz), 7.23-7.26 (2H, m), 7.50 (2H, d, J = 8 Hz), 7.70 (1H, dd, J = 8 and 8 Hz), 7.92 (1H, m), 8.19 (1H, m), 8.26 (1H, m), 9.69 (1H, br), 10.18 (1H, s). | |
| P-148 | 1H NMR (METHANOL-d4, 400 MHz): d = 8.16 (s, 2 H), 7.65 (d, J = 8.0 Hz, 2 H), 7.33 (s, 5 H), 7.36 (s, 6 H), 6.92 (s, 3 H), 4.07 (s, 5 H), 3.78 (s, 7 H), 0.00 ppm (s, 10 H) | |
| P-149 | 1H NMR (400 MHz, CDCl3) d ppm 8.30 (s, 1 H) 8.19 (dd, J = 8.2, 1.2 Hz, 1 H) 7.75 (d, J = 7.6 Hz, 1 H) 7.52-7.63 (m, 1 H) 7.38 (s, 1 H) 7.07 (d, J = 8.3 Hz, 1 H) 6.52 (d, J = 8.5 Hz, 1 H) 4.87 (d, J = 5.2 Hz, 2 H) 3.75 (s, 3 H) | |
| P-150 | 1H NMR (400 MHz, METHANOL-d4) d ppm 8.13-8.20 (m, 1 H) 8.12 (s, 1 H) 8.04 (d, J = 2.0 Hz, 1 H) 7.57-7.70 (m, 3 H) 7.11 (d, J = 8.5 Hz) 6.80 (d, J = 8.5 Hz, 1 H) 6.60 (d, J = 8.5 Hz, 1 H) 4.56-4.61 (m, 2 H) 3.91 (s, 1 H) 3.68 (s, 1 H) 3.44-3.50 (m, 5 H) 2.89 (s, 2 H) | |
| P-152 | 1H NMR (CDCl3, 400 MHz): d = 8.26-8.30 (m, 2 H), 8.19-8.23 (m., 1 H), 7.69-7.73 (m, 1 H), 7.58 (t, J = 8.4 Hz, 1 H), 7.49 (dd, J = 8.2, 2.5 Hz, 1 H), 7.25 (d, J = 8.0 Hz, 1 H), 7.15 (t, J = 8.6 Hz, 1 H), 6.76 (d, J = 8.4 Hz, 1 H), 3.96 (s, 2 H), 3.78 (s, 3 H) | Calc. 372.8; APCI⁺ (M + 1): 373, 99% |
| P-159 | 1H NMR (DMSO-d6, 400 MHz): d = 2.67 (2H, t, J = 7 Hz), 3.06 (2H, m), 3.77 (3H, s), 3.90 (2H, s), 7.09 (1H, d, J = 8.8 Hz), 7.20 (2H, d, J = 8 Hz), 7.23-7.26 (2H, m), 7.50 (2H, d, J = 8.8 Hz), 7.70 (1H, dd, J = 8 and 8 Hz), 7.76 (3H, br), 7.92 (1H, m), 8.18 (1H, m), 8.26 (1H, m), 10.10 (1H, s). | |
| P-164 | 1H NMR (CDCl3, 400 MHz): d = 2.91 (6H, s), 3.42 (2H, br), 3.81 (3H, s), 3.93 (2H, s), 4.45 (2H, br), 6.85 (2H, m), 6.93 (1H, d, J = 8.8 Hz), 7.11-7.19 (4H, m), 7.54 (1H, dd, J = 8 and 8 Hz), 7.82 (1H, d, J = 8 Hz), 8.15 (1H, m), 8.37 (1H, m), 13.0 (1H, br). | |
| P-165 | 1H NMR (CDCl3, 400 MHz): d = 1.81 (4H, br), 2.65 (4H, br), 2.92 (2H, t, J = 6 Hz), 3.80 (3H, s), 3.91 (2H, s), 4.10 (2H, t, J = 6 Hz), 6.85 (2H, d, J = 8 Hz), 6.93 (1H, d, J = 8 Hz), 7.20-7.19 (4H, m), 7.52 (1H, dd, J = 8 and 8 Hz), 7.82 (1H, m), 8.15 (1H, m), 8.38 (1H, m). | |
| P-166 | 1H NMR (CDCl3, 400 MHz): d = 1.45 (2H, m), 1.60 (4H, m), 2.50 (4H, br), 2.76 (2H, t, J = 6 Hz), 3.80 (3H, s), 3.91 (2H, s), 4.08 (2H, t, J = 6 Hz), 6.83 (2H, m), 6.92 (1H, d, J = 8 Hz), 7.10 (2H, d, J = 8 Hz), 7.14-7.19 (2H, m), 7.52 (1H, dd, J = 8 and 8 Hz), 7.82 (1H, m), 8.15 (1H, m), 8.38 (1H, m). | |
| P-168 | 1H NMR (CDCl3, 400 MHz): d = 7.26 (s, 13 H), 3.92 (s, 3 H), 3.75 (s, 6 H), 2.16 (s, 5 H), 1.54 ppm (s, 11 H) | |
| P-171 | 1H NMR (CDCl3, 400 MHz): d = 2.56 (4H, m), 2.78 (2H, t, J = 6 Hz), 3.72 (2H, t, J = 5 Hz), 3.80 (3H, s), 3.91 (2H, s), 4.08 (2H, t, J = 6 Hz), 6.84 (2H, d, J = 8 Hz), 6.92 (1H, d, J = 8 Hz), 7.08-7.19 (4H, m), 7.52 (1H, dd, J = 8 and 8 Hz), 7.82 (1H, m), 8.15 (1H, m), 8.38 (1H, m). | |
| P-175 | 1H NMR (METHANOL-d4, 400 MHz): d = 7.23 (s, 9 H), 4.40 (s, 4 H), 3.94 (s, 7 H), 3.78 (s, 5 H), 2.92 ppm (s, 10 H) | |
| P-177 | 1H NMR (400 MHz, METHANOL-d4) d ppm 8.26 (d, J = 1.9 Hz, 1 H) 8.18 (dd, J = 8.0, 1.3 Hz, 1 H) 8.12 (s, 1 H) 7.54-7.76 (m, 4 H) 7.37 (d, J = 8.2 Hz, 1 H) 7.17 (d, J = 8.5 Hz, 1 H) 6.63 (d, J = 8.6 Hz, 1 H) 4.00 (s, 3 H) 3.98 (s, 2 H) 3.69 (s, 2 H) | |
| P-178 | 1H NMR (400 MHz, METHANOL-d4) d ppm 8.18-8.26 (m, 2 H) 8.00 (d, J = 4.3 Hz, 1 H) 7.78 (dd, J = 9.3, 8.2 Hz, 2 H) 7.61-7.71 (m, 1 H) 7.32 (d, J = 8.6 Hz, 1 H) 7.17 (dd, J = 7.4, 5.0 Hz, 1 H) 6.94 (d, J = 8.6 Hz, 1 H) 4.16 (s, 2 H) 3.78 (s, 3 H) | |
| P-181 | 1H NMR (DMSO-d6, 400 MHz): d = 8.43 (s, 3 H), 8.16 (s, 3 H), 7.74 (d, J = 7.9 Hz, 3 H), 7.30 (d, J = 8.6 Hz, 8 H), 7.08 (d, J = 8.3 Hz, 6 H), 5.77 (s, 5 H), 3.86 (s, 6 H), 3.32 (s, 4 H), 2.54 (s, 1 H), 1.06 ppm (t, J = 7.0 Hz, 2 H) | |
| P-185 | 1H NMR (400 MHz, METHANOL-d4) d ppm 8.03-8.19 (m, 1 H) 7.56-7.67 (m, 1 H) 7.49-7.58 (m, 1 H) 7.29-7.48 (m, 5 H) 7.00 (d, J = 8.6 Hz, 1 H) 4.24 (s, 2 H) 3.78 (s, 3 H) | |
| P-186 | 1H NMR (CDCl3, 400 MHz): d = 1.98-2.04 (m, 2H), 2.42-2.46 (t, 2H), 3.28-3.32 (t, 2H), 3.82 (s, 3H), 4.45 (s, 2H), 6.96 (d, J = 8.4 Hz, 1H), 7.22 (d, J = 2.4 Hz, 1H), 7.25 (dd, J = 8.4, 2.4 Hz, 1H), 7.56 (t, J = 8 Hz, 1H), 7.69 (d, J = 8 Hz, 1H), 8.04 (d, J = 8 Hz, 1H), 8.24 (s, 1H), 8.47 (s, 1H) | |
| P-187 | 1H NMR (CDCl3, 400 MHz): d = 7.25-7.41 (m, 4 H), 7.16-7.19 (m, 2 H), 7.07 (t, J = 8.4 Hz, 1 H), 6.97 (t, J = 8.4 Hz, 2 H), 6.71 (d, J = 8.4 Hz, 1 H), 3.93 (s, 2 H), 3.75 (s, 3 H) | |
| P-194 | 1H NMR (DMSO-d6, 400 MHz): d = 2.00 (3H, s), 3.76 (3H, s), 5.04 (2H, s), 6.95 (2H, m), 7.01 (1H, d, J = 8.8 Hz), 7.35 (1H, m), 7.41 (1H, dd, J = 8 and 8 Hz), 7.48 (2H, m), 7.51-7.54 (2H, m), 7.57-7.60 (1H, m), 9.78 (1H, s). | |

Table of 1H NMR Spectra

| | | |
|---|---|---|
| P-197 | 1H NMR (CDCl3, 400 MHz): d = 2.32 (s, 3H), 3.81 (s, 3H), 5.26 (s, 2H), 6.85 (d, J = 9.2 Hz, 1H), 6.96 (d, J = 8.4 Hz, 1H), 7.04 (d, J = 9.2 Hz, 1H), 7.44 (d, J = 2.4 Hz, 1H), 7.5 (dd, J = 8.4, 2.4 Hz, 1H), 7.52-7.56 (t, 1H), 7.81-7.84 (m, 1H), 8.15-8.18 (m, 1H), 8.39 (s, 1H). | MS (APCI+): 352 (M + 1), LCMS: 100% |
| P-199 | 1H NMR (CDCl3, 400 MHz): d = 3.43 (2H, br), 3.78 (3H, s), 5.01 (2H, s), 6.64 (2H, m), 6.77 (1H, d, J = 8.8 Hz), 6.83 (2H, m), 7.30 (1H, d, J = 8 Hz), 7.34 (1H, m), 7.42 (1H, dd, J = 8 and 8 Hz), 7.48 (1H, m), 7.56 (1H, m). | |
| P-200 | 1H NMR (CDCl3, 400 MHz): d = 7.52-7.56 (m, 2 H), 7.48 (dt, J = 7.6, 1.7 Hz, 2 H), 7.25-7.34 (m, 7 H), 7.19-7.24 (m, 5 H), 7.07-7.17 (m, 7 H), 6.69-6.73 (m, 3 H), 6.31 (s, 2 H), 3.94 (s, 5 H), 3.76 (s, 7 H), 2.99 (s, 7 H), 1.55 ppm (s, 4 H) | |
| P-202 | 1H NMR (CDCl3, 400 MHz): d = 2.96 (3H, s), 3.79 (3H, s), 5.07 (2H, s), 6.38 (1H, s), 6.79 (1H, J = 8.8 Hz), 6.98 (2H, m), 7.20 (2H, m), 7.30 (1H, d, J = 8 Hz), 7.34 (1H, m), 7.42 (1H, dd, J = 8 and 8 Hz), 7.50 (1H, m), 7.56 (1H, m). | |
| P-204 | 1H NMR (CDCl3, 400 MHz): d = 3.83 (overlap, 6), 5.17 (s, 2H), 6.88 (s, 2H), 6.96 (d, J = 8.4 Hz, 1H), 7.46 (d, J = 2.4 Hz, 1H), 7.5 (dd, J = 8.4, 2.4 Hz, 1H), 7.51-7.57 (t, 1H), 7.82-7.85 (m, 1H), 8.15-8.18 (m, 1H), 8.39 (dd, J = 2 Hz, 1H) | MS (APCI+): 368 (M + 1), LCMS: 100% |
| P-205 | 1H NMR (CDCl3, 400 MHz): d = 3.81 (s, 3H), 5.31 (s, 2H), 6.92 (dd, J = 9.2, 1.6 Hz, 1H), 6.96 (d, J = 9.2 Hz, 1H), 7.15 (dd, J = 9.6, 4 Hz, 1H), 7.4 (d, J = 2 Hz, 1H), 7.5 (dd, J = 8.4, 2.4 Hz, 1H), 7.52-7.56 (t, 1H), 7.76 (dd, J = 4, 1.6 Hz, 1H), 7.81-7.84 (m, 1H), 8.15-8.18 (m, 1H), 8.39 (dd, 1H) | MS (APCI+): 338 (M + 1), LCMS: 96% |
| P-206 | 1H NMR (CDCl3, 400 MHz): d = 3.81 (overlap, 6), 5.17 (s, 2H), 6.1 (t, 1H), 6.57 (dd, J = 7.6, 1.6 Hz, 1H), 6.94 (dd, J = 7.6, 1.6 Hz, 1H)), 6.96 (d, J = 8.4 Hz, 1H), 7.33 (d, J = 2.4 Hz, 1H), 7.39 (dd, J = 8.4, 2.4 Hz, 1H), 7.51-7.57 (t, 1H), 7.79-7.81 (m, 1H), 8.15-8.18 (m, 1H), 8.37 (dd, J = 2 Hz, 1H) | MS (APCI+): 367 (M + 1), LCMS: 100% |
| P-216 | 1H NMR (CDCl3, 400 MHz): d = 3.74 (3H, s), 3.89 (2H, s), 4.61 (1H, s), 6.68 (1H, dd, J = 8.4 and 1 Hz), 6.75 (2H, m), 7.07 (1H, dd, J = 8 and 8 Hz), 7.09 (2H, m), 7.26-7.36 (3H, m), 7.39 (1H, m). | |
| P-217 | 1H NMR (CDCl3, 400 MHz): d = 3.74 (3H, s), 3.91 (2H, s), 4.72 (1H, br), 6.65-6.71 (3H, m), 6.81 (1H, d, J = 8 Hz), 7.09 (1H, dd, J = 8.4 and 8.4 Hz), 7.15 (1H, dd, J = 7.6 and 7.6 Hz), 7.26-7.36 (3H, m), 7.39 (1H, m). | |
| P-219 | 1H NMR (CDCl3, 400 MHz): d = 2.57 (4H, m), 2.78 (2H, t, J = 6 Hz), 3.72 (4H, m), 3.74 (3H, s), 3.90 (2H, s), 4.08 (2H, t, J = 6 Hz), 6.68 (1H, dd, J = 8.4 and 1 Hz), 6.83 (2H, m), 7.07 (1H, dd, J = 8.4 and 8.4 Hz), 7.13 (2H, m), 7.26-7.36 (3H, m), 7.39 (1H, m). | |
| P-220 | 1H NMR (CDCl3, 400 MHz): d = 2.56 (4H, m), 2.78 (2H, t, J = 6 Hz), 3.72 (4H, m), 3.75 (3H, s), 3.92 (2H, s), 4.08 (2H, t, J = 6 Hz), 6.69 (1H, d, J = 8 Hz), 6.71-6.78 (2H, m), 6.83 (1H, d, J = 8 Hz), 7.11 (1H, dd, J = 8.4 and 8.4 Hz), 7.19 (1H, dd, J = 8 and 8 Hz), 7.26-7.36 (3H, m), 7.39 (1H, m). | |
| P-221 | 1H NMR (CDCl3, 400 MHz): d = 3.75 (3H, s), 3.96 (2H, s), 4.96 (2H, br), 6.69 (1H, dd, J = 8 and 1 Hz), 7.05 (2H, m), 7.09 (1H, dd, J = 8.4 and 8.4 Hz), 7.22 (2H, m), 7.26-7.36 (3H, m), 7.39 (1H, m). | |
| P-222 | 1H NMR (CDCl3, 400 MHz): d = 3.75 (3H, s), 3.96 (2H, s), 4.98 (2H, br), 6.69 (1H, d, J = 8.8 Hz), 6.99 (2H, m), 7.07-7.12 (2H, m), 7.26-7.36 (4H, m), 7.39 (1H, m). | |
| P-225 | 1H NMR (400 MHz, CDCl3) d ppm 8.21 (br. s., 1 H) 7.93 (br. s., 1 H) 7.35 (d, J = 9.7 Hz, 4 H) 7.00 (br. s., 2 H) 6.75 (br. s., 1 H) 4.27 (br. s., 2 H) 3.78 (s, 3 H) | |
| P-226 | 1H NMR (400 MHz, CDCl3) d ppm 8.29 (d, J = 1.9 Hz, 1 H) 7.48 (dd, J = 8.2, 2.3 Hz, 1 H) 7.28-7.39 (m, 3 H) 7.20-7.29 (m, 2 H) 7.10 (t, J = 8.5 Hz, 1 H) 6.72 (d, J = 8.6 Hz, 1 H) 3.94 (s, 2 H) 3.76 (s, 3 H) | |
| P-227 | 1H NMR (CDCl3, 400 MHz): d = 7.29-7.41 (m, 7 H), 7.26 (s, 8 H), 7.18-7.29 (m, 4 H), 7.07-7.18 (m, 7 H), 6.72 (s, 2 H), 6.26 (s, 2 H), 3.94 (s, 4 H), 3.76 (s, 7 H), 2.99 (s, 7 H), 1.54 ppm (s, 3 H) | |
| P-228 | 1H NMR (CDCl3, 400 MHz): d = 7.37-7.43 (m, 7 H), 7.33 (d, J = 9.7 Hz, 5 H), 7.26 (s, 9 H), 7.07 (s, 4 H), 6.70 (s, 3 H), 3.92 (s, 5 H), 3.75 (s, 7 H), 2.16 (s, 6 H), 1.54 ppm (s, 5 H) | |
| P-231 | 1H NMR (DMSO-d6, 400 MHz): d = 2.03 (3H, s), 3.77 (3H, s), 5.05 (2H, s), 6.71 (1H, m), 7.01 (1H, d, J = 8 Hz), 7.10 (1H, m), 7.19 (1H, dd, J = 8 and 8 Hz), 7.32 (1H, m), 7.37 (1H, m), 7.42 (1H, m), 7.44-7.49 (2H, m), 7.55 (1H, dd, J = 8.8 and 8.8 Hz).. | |
| P-232 | 1H NMR (CDCl3, 400 MHz): d = 3.65 (2H, s), 3.77 (3H, s), 5.04 (2H, s), 6.29-6.34 (2H, m), 6.41 (1H, m), 6.67 (1H, d, J = 8 Hz), 7.06 (1H, dd, J = 8 and 8 Hz), 7.27-7.37 (3H, m), 7.40-7.45 (2H, m). | |
| P-233 | 1H NMR (DMSO-d6, 400 MHz): d = 2.00 (3H, s), 3.73 (3H, s), 3.89 (2H, s), 6.92 (2H, m), 7.19 (1H, dd, J = 8 and 8 Hz), 7.28 (2H, m), 7.38 (2H, m), 7.44 (3H, m), 9.85 (1H, s). | |
| P-234 | 1H NMR (DMSO-d6, 400 MHz): d = 3.73 (3H, s), 3.92 (2H, s), 6.88-7.02 (4H, m), 7.22-7.38 (4H, m), 7.40-7.48 (2H, m). | |
| P-235 | CDCl3, 3.83 (s, 3H), 5.04 (s, 2H), 6.99 (d, J = 8.4 Hz, 1H), 7.27 (d, J = 2 Hz, 1H), 7.3-7.36 (m, 4H), 7.49 (s, 1H), 7.68 (d, J = 3.2 Hz, 1H), 8.54 (d, J = 3.2 Hz, 1H) | MS (APCI+): 406 (M + 1), LCMS: 90% |
| P-237 | 1H NMR (DMSO-d6, 400 MHz): d = 7.73 (s, 2 H), 7.17 (s, 9 H), 5.47 (s, 4 H), 4.12 (s, 4 H), 3.92 (s, 5 H), 3.74 (s, 7 H), 2.09 ppm (s, 8 H) | |
| P-242 | 1H NMR (CDCl3, 400 MHz): d = 3.75 (3H, s), 3.87 (2H, s), 5.91 (2H, s), 6.68-6.74 (4H, m), 7.09 (1H, dd, J = 8 and 8 Hz), 7.26-7.36 (3H, m), 7.39 (1H, br). | |
| P-249 | 1H NMR (CDCl3, 400 MHz): d = 7.52 (s, 2 H), 7.20-7.31 (m, 14 H), 7.09-7.16 (m, 5 H), 3.95 (s, 4 H), 3.76 (s, 5 H), 2.99 (s, 5 H), 2.62 (s, 5 H), 2.05 (s, 2 H), 1.54 (s, 4 H), 1.26 ppm (s, 2 H) | |
| P-250 | 1H NMR (CDCl3, 400 MHz): d = 7.26 (s, 11 H), 7.18 (s, 7 H), 6.71 (s, 2 H), 6.13 (s, 2 H), 3.92 (s, 4 H), 3.75 (s, 6 H), 3.28 (s, 4 H), 1.56 (s, 7 H), 1.14 ppm (t, J = 7.2 Hz, 5 H) | |
| P-256 | 1H NMR (DMSO-d6, 400 MHz): d = 3.73 (3H, s), 3.88 (2H, s), 6.75 (1H, m), 6.85 (1H, br), 6.95 (1H, d, J = 8 Hz), 7.24 (1H, d, J = 8 Hz), 7.26-7.33 (2H, m), 7.37 (1H, br), 7.40-7.48 (2H, m). | |

| | Table of 1H NMR Spectra |
|---|---|
| P-257 | 1H NMR (CDCl3, 400 MHz): d = 3.77 (3H, s), 3.98 (2H, s), 6.74 (1H, d, J = 8 Hz), 6.85 (1H, dd, J = 8.8 and 1.6 Hz), 6.97 (1H, d, J = 1.6 Hz), 7.13 (1H, dd, J = 8 and 8 Hz), 7.27 (1H, m), 7.32-7.36 (2H, m), 7.38 (1H, m), 8.01 (1H, d, J = 8.8 Hz), 10.62 (1H, s). |
| P-259 | 1H NMR (400 MHz, DMSO-d6) d ppm 13.83 (br. s., 1 H) 8.03 (br. s., 2 H) 7.75-7.87 (m, 2 H) 7.40-7.49 (m, 2 H) 7.26-7.40 (m, 3 H) 6.97 (dd, J = 8.7, 5.8 Hz, 2 H) 3.85 (s, 2 H) 3.74 (s, 3 H) |
| P-262 | 1H NMR (DMSO-d6, 400 MHz): d = 3.72 (3H, s), 3.78 (2H, s), 6.12 (2H, s), 6.58 (1H, d, J = 8.8 Hz), 6.62 (1H, s), 6.92 (1H, d, J = 8.8 Hz), 7.23-7.30 (2H, m), 7.37 (1H, s), 7.40-7.48 (2H, m), 7.68 (1H, d, J = 8 Hz), 7.91 (1H, s), 9.84 (1H, s). |
| P-263 | 1H NMR (CDCl3, 400 MHz): d = 3.76 (3H, s), 3.98 (2H, s), 6.71 (1H, d, J = 8 Hz), 6.95 (1H, d, J = 8.4 Hz), 7.04 (1H, d, J = 8 Hz), 7.07 (1H, s), 7.10 (1H, dd, J = 8.4 and 8.4 Hz), 7.28 (1H, m), 7.31-7.36 (2H, m), 7.38 (1H, m), 8.03 (1H, br). |
| P-264 | 1H NMR (CDCl3, 400 MHz): d = 2.98 (3H, s), 3.75 (3H, s), 3.89 (2H, s), 6.23 (2H, br), 6.71 (1H, d, J = 8.4 Hz), 6.80 (1H, m), 6.82 (1H, s), 7.11 (1H, dd, J = 8.4 and 8.4 Hz), 7.17 (1H, d, J = 8 Hz), 7.26-7.40 (4H, m). |
| P-265 | 1H NMR (CDCl3, 400 MHz): d = 3.03 (3H, s), 3.28 (3H, s), 3.76 (3H, s), 3.95 (2H, s), 6.72 (1H, d, J = 8 Hz), 6.97 (1H, br), 7.12 (1H, dd, J = 8.4 and 8.4 Hz), 7.18-7.22 (2H, m), 7.26-7.28 (1H, m), 7.31-7.40 (3H, m), 7.61 (1H, d, J = 8.8 Hz). |
| P-273 | 1H NMR (DMSO-d6, 400 MHz): d = 10.49 (s, 3 H), 8.14 (br. s., 7 H), 7.51 (d, J = 8.5 Hz, 5 H), 7.43 (s, 5 H), 7.21 (s, 6 H), 6.94 (s, 3 H), 3.90 ppm (s, 5 H) |
| P-274 | 1H NMR (CDCl3, 400 MHz): d = 3.78 (3H, s), 4.01 (2H, s), 6.74 (1H, d, J = 8.8 Hz), 7.05 (1H, d, J = 9.2 Hz), 7.08-7.14 (2H, m), 7.24-7.28 (1H, m), 7.32-7.38 (3H, m), 7.53 (1H, dd, J = 8 and 8 Hz). |
| P-275 | 1H NMR (DMSO-d6, 400 MHz): d = 3.73 (3H, s), 3.98 (2H, s), 4.01 (2H, br), 6.95 (1H, d, J = 8.8 Hz), 7.10-7.16 (2H, m), 7.25-7.28 (1H, m), 7.37-7.38 (2H, m), 7.42-7.49 (3H, m), 8.25 (3H, br). |
| P-278 | 1H NMR (400 MHz, DMSO-d6) d ppm 8.45 (s, 2 H) 7.24-7.50 (m, 6 H) 6.96 (d, J = 8.6 Hz, 1 H) 3.85 (s, 2 H) 3.74 (s, 3 H) |
| P-279 | 1H NMR (400 MHz, DMSO-d6) d ppm 7.98 (br. s., 1 H) 7.75-7.85 (m, 2 H) 7.37-7.49 (m, 3 H) 7.24-7.36 (m, 2 H) 6.95 (t, J = 8.1 Hz, 2 H) 4.03 (q, J = 6.8 Hz, 2 H) 3.84 (s, 2 H) 1.19 (t, J = 6.9 Hz, 3 H) |
| P-285 | 1H NMR (DMSO-d6, 400 MHz): d = 3.72 (3H, s), 3.82 (2H, s), 6.93 (1H, d, J = 8.8 Hz), 7.10 (1H, d, J = 8.4 Hz), 7.21 (1H, d, J = 8 Hz), 7.26-7.37 (4H, m), 7.41-7.46 (2H, m), 8.68 (3H, br). |
| P-286 | 1H NMR (CDCl3, 400 MHz): d = 2.85 (3H, s), 3.76 (3H, s), 3.95 (2H, s), 4.35 (2H, d, J = 6.4 Hz), 4.61 (1H, br), 6.72 (1H, dd, J = 8.4 and 1.2 Hz), 6.94 (1H, d, J = 11.2 Hz), 7.02 (1H, dd, J = 8 and 1.2 Hz), 7.10 (1H, dd, J = 8.4 and 8.4 Hz), 7.25-7.28 (2H, m), 7.30-7.35 (2H, m), 7.38 (1H, m). |
| P-287 | 1H NMR (DMSO-d6, 400 MHz): d = 3.72 (3H, s), 3.92 (2H, s), 4.15 (2H, d, J = 6 Hz), 5.52 (2H, s), 6.33 (1H, m), 6.93 (1H, d, J = 8.8 Hz), 6.90-7.04 (2H, m), 7.20-7.38 (4H, m), 7.41-7.46 (2H, m). |
| P-289 | 1H NMR (DMSO-d6, 400 MHz): d = 10.57 (s, 2 H), 8.90 (br. s., 4 H), 7.51 (d, J = 8.5 Hz, 4 H), 7.41-7.47 (m, 4 H), 7.21 (d, J = 8.5 Hz, 4 H), 6.94 (s, 2 H), 3.90 (s, 8 H), 3.72 (s, 6 H), 2.61 (s, 6 H), 0.00 ppm (s, 6 H) |
| P-290 | 1H NMR (400 MHz, DMSO-d6) d ppm 13.34-13.96 (m, 1 H) 7.91-8.04 (m, 3 H) 7.74-7.90 (m, 3 H) 7.59 (d, J = 4.7 Hz, 2 H) 7.35 (t, J = 8.7 Hz, 1 H) 6.97 (dd, J = 8.7, 2.5 Hz, 2 H) 3.86 (s, 2 H) 2.60 (s, 3 H) |
| P-291 | 1H NMR (400 MHz, DMSO-d6) d ppm 8.41 (s, 2 H) 7.24-7.50 (m, 5 H) 6.95 (d, J = 8.6 Hz, 1 H) 3.83 (s, 2 H) 3.74 (s, 3 H) |
| P-292 | 1H NMR (400 MHz, CDCl3) d ppm 8.49 (s, 2 H) 7.29-7.42 (m, 3 H) 7.14 (t, J = 8.5 Hz, 1 H) 6.74 (d, J = 8.5 Hz, 1 H) 3.90 (s, 2 H) 3.77 (s, 3 H) 3.44 (s, 3 H) |
| P-295 | 1H NMR (CDCl3, 400 MHz): d = 3.77 (3H, s), 3.95 (2H, s), 5.50 (1H, s), 6.72 (1H, dd, J = 8.4 Hz), 6.82 (1H, m), 6.88 (1H, d, J = 8 Hz), 7.10 (1H, dd, J = 8.4 and 8.4 Hz), 7.27 (1H, m), 7.33-7.39 (3H, m), 7.42 (1H, d, J = 8 Hz). |
| P-296 | 1H NMR (DMSO-d6, 400 MHz): d = 3.73 (3H, s), 3.87 (2H, s), 3.88 (2H, m), 6.74 (2H, m), 6.94 (2H, m), 7.20 (1H, d, J = 8 Hz), 7.27-7.32 (2H, m), &.35 (1H, s), 7.42-7.48 (2H, m), 7.94 (3H, br), 10.01 (1H, s). |
| P-297 | 1H NMR (400 MHz, CDCl3) d ppm 8.12 (s, 2 H) 7.90-8.00 (m, 2 H) 7.47-7.65 (m, 2H) 7.24 (d, J = 8.9 Hz, 1 H) 7.13 (t, J = 8.6 Hz, 1 H) 6.75 (d, J = 8.6 Hz, 1 H) 3.90 (s, 2 H) 3.76 (s, 3 H) 3.11 (s, 3 H) 2.62 (s, 3 H) |
| P-299 | 1H NMR (CDCl3, 400 MHz): d = 2.84 (3H, s), 3.75 (3H, s), 3.90 (2H, s), 4.28 (2H, d, J = 6.4 Hz), 4.82 (1H, br), 5.81 (1H, s), 6.69 (1H, s), 6.71 (1H, d, J = 8.4 Hz), 6.78 (1H, d, J = 8 Hz), 7.08 (1H, d, J = 8.8 Hz), 7.11 (1H, d, J = 8 Hz), 7.27 (1H, m), 7.32-7.35 (2H, m), 7.38 (1H, m). |
| P-300 | 1H NMR (acetone-d6, 400 MHz): d = 1.90 (3H, s), 3.79 (3H, s), 3.98 (2H, s), 4.35 (2H, d, J = 5.6 Hz), 6.93 (1H, d, J = 8.8 Hz), 6.98 (1H, d, J = 11.2 Hz), 7.05 (1H, d, J = 8 Hz), 7.27-7.34 (3H, m), 7.38-7.46 (3H, m). |
| P-301 | 1H NMR (CDCl3, 400 MHz): d = 3.72 (3H, s), 3.85 (2H, s), 4.14 (2H, d, J = 5.2 Hz), 4.71 (2H, br), 5.41 (1H, br), 6.64-6.68 (2H, m), 6.76 (1H, s), 6.90 (1H, d, J = 8 Hz), 7.08 (1H, dd, J = 8.4 and 8.4 Hz), 7.24-7.32 (3H, m), 7.37 (1H, s). |
| P-302 | 1H NMR (CDCl3, 400 MHz): d = 2.00 (3H, s), 3.74 (3H, s), 3.89 (2H, s), 4.28 (2H, d, J = 6.8 Hz), 6.25 (1H, br), 6.66-6.71 (2H, m), 6.80 (1H, d, J = 1.6 Hz), 6.97 (1H, d, J = 8 Hz), 7.11 (1H, dd, J = 8.4 and 8.4 Hz), 7.26-7.35 (3H, m), 7.38 (1H, s). |
| P-313 | 1H NMR (CDCl3, 400 MHz): d = 2.17 (3H, s), 3.96 (2H, s), 6.31 (1H, t, 73 Hz), 6.97 (1H, d, J = 8.8 Hz), 7.08 (1H, br), 7.12 (1H, d, J = 8.4 Hz), 7.18 (2H, d, J = 8.4 Hz), 7.31 (2H, m), 7.42 (2H, d, J = 8 Hz), 7.51-7.54 (2H, m). |
| P-316 | 1H NMR (DMSO-d6, 400 MHz): d = 3.93 (2H, s), 5.78 (2H, s), 7.17 (1H, t, 73 Hz), 7.10 (2H, d, J = 8.4 Hz), 7.17 (1H, d, J = 8.4 Hz), 7.31 (2H, d, J = 8.4 Hz), 7.43 (1H, dd, J = 8.4 and 8.4 Hz), 7.78 (1H, d, J = 8.4 Hz), 7.86 (1H, m), 8.23 (1H, s), 8.29 (1H, m), 8.44 (1H, s). |

Table of 1H NMR Spectra

| | |
|---|---|
| P-317 | 1H NMR (DMSO-d6, 400 MHz): d = 4.00 (2H, s), 7.14 (1H, t, 73 Hz), 7.12-7.20 (3H, m), 7.29 (2H, d, J = 8.4 Hz), 7.36 (1H, m), 7.40-7.4 (2H, m), 7.55 (1H, m), 7.62 (1H, m), 9.20-9.80 (3H, br). |
| P-318 | 1H NMR (400 MHz, DMSO-d6) d ppm 13.27 (br. s., 1 H) 8.58-8.75 (m, 1 H) 7.63-7.87 (m, 3 H) 7.36-7.51 (m, 3 H) 7.20-7.41 (m, 2 H) 6.97 (t, J = 9.9 Hz, 1 H) 3.87 (s, 2 H) 3.28-3.41 (m, 2 H) 1.20 (t, J = 7.2 Hz, 3 H) |
| P-322 | 1H NMR (DMSO-d6, 400 MHz): d = 1.18 (3H, t, J = 7 Hz), 2.00 (3H, s), 3.86 (2H, s), 4.01 (2H, q, J = 7 Hz), 6.90 (1H, d, J = 8 Hz), 7.13 (2H, d, J = 8.4 Hz), 7.23 (1H, dd, J = 8.4 and 8.4 Hz), 7.33-7.40 (2H, m), 7.47 (2H, d, J = 8.4 Hz), 7.52-7.56 (2H, m), 9.85 (1H, s). |
| P-323 | 1H NMR (DMSO-d6, 400 MHz): d = 3.90 (2H, s), 5.77 (2H, s), 7.13 (1H, t, 73 Hz), 7.09 (2H, d, J = 8.4 Hz), 7.11 (1H, d, J = 9.2 Hz), 7.31 (2H, d, J = 9.2 Hz), 7.37 (2H, d, J = 8.4 Hz), 7.43 (2H, dd, J = 8 and 8 Hz), 7.57 (1H, s), 7.63 (1H, m), 8.44 (1H, s). |
| P-329 | 1H NMR (CDCl3, 400 MHz): d = 1.99 (3H, s), 2.62 (3H, s), 3.76 (3H, s), 3.94 (2H, s), 4.43 (2H, d, J = 5.6 Hz), 5.73 (1H, br), 6.73 (1H, d, J = 8.4 Hz), 6.91 (1H, d, J = 8 Hz), 6.99 (1H, d, J = 8 Hz), 7.12 (1H, dd, J = 8.4 and 8.4 Hz), 7.26 (1H, m), 7.51 (1H, m), 7.60 (1H, m), 7.94 (1H, m), 7.99 (1H, m). |
| P-330 | 1H NMR (DMSO-d6, 400 MHz): d = 2.59 (3H, s), 3.72 (3H, s), 3.94 (2H, s), 4.15 (2H, d, J = 5.6 Hz), 5.51 (2H, br), 6.35 (1H, t, J = 5.6 Hz), 6.94 (1H, d, J = 8.4 Hz), 7.00-7.04 (2H, m), 7.22 (1H, dd, J = 8 and 8 Hz), 7.32 (1H, dd, J = 8.8 and 8.8 Hz), 7.57 (2H, m), 7.86 (1H, s), 7.95 (1H, m). |
| P-336 | 1H NMR (CDCl3, 400 MHz): d = 7.99 (s, 2 H), 7.93-7.96 (m, 1H), 7.58-7.61 (m, 1 H), 7.51 (t, J = 7.6 Hz, 1 H), 7.31 (dd, J = 7.6, 2.4 Hz, 1 H), 7.09 (t, J = 8.4 Hz, 1 H), 6.71 (d, J = 8.4 Hz, 1 H), 6.35 (d, J = 8.8 Hz, 1 H), 4.47 (br, s, 1 H), 3.82 (s, 2 H), 3.74 (s, 3 H), 2.90 (d, J = 4.4 Hz, 3 H), 2.62 (s, 3 H). Calc. 364.4; APCI+ (M + 1): 365, 98% |
| P-337 | 1H NMR (DMSO-d6, 400 MHz): d = 9.08 (s, 1 H), 8.06 (br, s, 2 H), 7.93-7.96 (m, 1 H), 7.87 (br, s, 1 H), 7.58 (d, J = 5.2 Hz, 2 H), 7.53 (dd, J = 8.8, 2.4 Hz, 1 H), 7.30 t, J = 9.2 Hz, 1 H), 7.26 (d, J = 8.8 Hz, 1 H), 6.95 (d, J = 8.8 Hz, 1 H), 3.87 (s, 2 H), 3.72 (s, 3 H), 3.13-3.20 (m, 2 H), 2.59 (s, 3 H), 1.07 (t, J = 7.2 Hz, 3 H). Calc. 364.4; APCI+ (M + 1): 365, 98% |
| P-339 | 1H NMR (DMSO-d6, 400 MHz): d = 8.78 ((br. s, 1 H), 7.97 (br, s, 1 H), 7.86 (s, 1 H), 7.73-7.76 (m, 2 H), 7.58-7.59 (m, 2 H), 7.35 (t, J = 8.8 Hz, 1 H), 6.96-7.02 (m, 2 H), 3.88 (s, 2 H), 3.73 (s, 3 H), 3.35-3.39 (m, 2H), 2.59 (s, 3 H), 1.19 (t, J = 7.2 Hz, 3 H). Calc. 378.36; APCI+ (M + 1): 379.1, 100% |
| P-345 | 1H NMR (CDCl3, 400 MHz): d = 8.09-8.15 (m, 2 H), 7.94-7.98 (m, 2 H), 7.86 (br, s, 1 H), 7.50-7.60 (m, 3 H), 7.10 (t, J = 8.8 Hz, 1 H), 6.73 (d, J = 8.8 Hz, 1 H), 3.93 (s, 2 H), 3.76 (s, 3 H), 2.62 (s, 3 H), 2.19 (s, 3 H). Calc. 392.43; APCI+ (M + 1): 393, >95% |
| P-357 | 1H NMR (400 MHz, CDCl3) d ppm 1.31 (t, J = 7.11 Hz, 3 H) 3.76 (s, 3 H) 3.90 (s, 2 H) 4.23 (q, J = 7.16 Hz, 2 H) 6.70 (d, J = 8.32 Hz, 1 H) 7.08 (t, J = 8.59 Hz, 1 H) 7.29-7.42 (m, 4 H) 7.48-7.60 (m, 2 H) 7.88 (d, J = 8.45 Hz, 1 H) 8.14 (d, J = 1.48 Hz, 1 H) |
| P-359 | 1H NMR (400 MHz, CDCl3) d ppm 1.21 (t, J = 6.98 Hz, 3 H) 1.27-1.33 (m, 3 H) 3.76 (s, 3 H) 3.93 (s, 2 H) 3.99 (q, J = 7.02 Hz, 2 H) 4.23 (q, J = 7.11 Hz, 2 H) 6.71 (d, J = 8.59 Hz, 1 H) 7.11 (t, J = 8.52 Hz, 1 H) 7.27-7.42 (m, 4 H) 7.45-7.56 (m, 2 H) 8.28 (d, J = 1.21 Hz, 1 H) |
| P-387 | 1H NMR (CDCl3, 400 MHz): d = 8.09-8.15 (m, 2 H), 7.81 (br, s, 1 H), 7.55-7.55 (m, 1 H), 7.31-7.38 (m, 3 H), 7.24-7.26 (m, 1 H), 7.08 (d, J = 8.8 Hz, 1 H), 6.71 (d, J = 8.4 Hz, 1 H), 3.91 (s, 2 H), 3.76 (s, 3 H), 2.19 (s, 3 H). : Calc. 384.84; APCI+ (M + 1): 385, 100% |
| P-392 | 1H NMR (400 MHz, CDCl3) d ppm 3.78 (s, 3 H) 3.94 (s, 2 H) 6.75 (d, J = 8.45 Hz, 1 H) 7.13 (t, J = 8.52 Hz, 1 H) 7.31-7.40 (m, 3 H) 8.50 (s, 2 H) |
| P-407 | 1H NMR (DMSO-d6, 400 MHz): d = 11.85 (s, 1 H), 8.47 (s, 1 H), 8.14 (dd, J = 9.2, 2.0 Hz, 1 H), 8.07 (br, a,, 1 H), 7.73 (d, J = 8.4 Hz, 1 H), 7.61-7.65 (m, 1 H), 7.26-7.45 (m, 5H), 6.95 (d, J = 8.4 Hz, 1 H), 6.42 (d, J = 10.0 Hz, 1 H), 3.96 (s, 2 H), 3.72 (s, 3 H). Calc. 420.86; APCI+ (M + 1): 421, 94.1% |
| P-410 | 1H NMR (CDCl3, 400 MHz): d = 8.91 (d, J = 2.4 Hz, 1 H), 8.61 (s, 1 H), 8.17 (dd, J = 8.0, 2.4 Hz, 1 H), 7.63-7.65 (m, 1 H), 7.57 (d, J = 8.0 Hz, 1 H), 7.24-7.39 (m, 5 H), 7.15 (t, J = 8.4 Hz, 1 H), 6.73 (d, J = 8.8 Hz, 1 H), 4.02 (s, 2 H), 3.77 (s, 3 H). : Calc. 483.77; APCI+ (M + 1): 485, 96% |
| P-411 | 1H NMR (CDCl3, 400 MHz): d = 7.90 (br. s, 1 H), 7.39 (s, 1 H), 7.25-7.35 (m, 4 H), 7.07 (d, J = 8.6 Hz, 1 H), 6.70 (d, J = 8.8 Hz, 1 H), 6.44 (d, J = 8.8 Hz, 1 H), 5.02 (br, s, 1 H), 3.77-3.80 (m, 4 H), 3.75 (s, 3 H), 3.48-3.51 (m., 2 H). Calc. 386.86; APCI+ (M + 1): 387, 100% |
| P-412 | 1H NMR (CDCl3, 400 MHz): d = 9.13 (s, 1 H), 8.03 (s, 1 H), 8.08 (s, 1 H), 7.82 (d, J = 8.8 Hz, 1 H), 7.72 (dd, J = 8.4, 2.4 Hz, 1 H), 7.38 (s, 1 H), 7.26-7.35 m, 3 H), 7.14 (t, J = 8.4 Hz, 1 H), 6.74 (d, J = 8.0 Hz, 1 H), 4.02 (s, 2 H), 3.77 (s, 3 H). Calc. 394.84; APCI+ (M + 1): 395, 100% |
| P-416 | 1H NMR (400 MHz, CDCl3) d ppm 3.70-3.81 (m, 3 H) 4.88 (br. s., 2 H) 6.72 (d, J = 8.59 Hz, 1 H) 7.27-7.41 (m, 5 H) 7.65 (d, J = 12.08 Hz, 1 H) 9.34 (s, 1 H) |
| P-418 | 1H NMR (400 MHz, CDCl3) d ppm 3.81 (s, 3 H) 6.80 (d, J = 8.86 Hz, 1 H) 6.99-7.18 (m, 4 H) 7.30 (d, J = 7.25 Hz, 1 H) 7.33-7.39 (m, 2 H) 7.41 (s, 1 H) 7.47 (dd, J = 8.45, 5.50 Hz, 2 H) 7.55 (t, J = 8.59 Hz, 1 H) |
| P-419 | 1H NMR (400 MHz, CDCl3) d ppm 3.76 (s, 3 H) 6.50-6.64 (m, 3 H) 6.95 (t, J = 8.65 Hz, 2 H) 7.14 (t, J = 8.59 Hz, 1 H) 7.21-7.30 (m, 3 H) 7.31-7.37 (m, 2 H) 7.37-7.42 (m, 1 H) |
| P-424 | 1H NMR (CDCl3, 400 MHz): d = 7.71 (s, 1 H), 7.58 (s, 1 H), 7.39 (br, s, 1 H), 7.21-7.435 (m, 6 H), 6.75 (d, J = 6.8 Hz, 1 H), 6.68 (d, J = 6.4 Hz, 2 H), 5.33 (s, 2 H), 3.77 (s, 3 H), Calc. 407.88; APCI+ (M + 1): 408, 98% |
| P-431 | 1H NMR (CDCl3, 400 MHz): d = 8.09 (s, 1 H), 7.25-7.39 (m, 5 H), 7.08 (t, J = 8.4 Hz, 1 H), 6.68 (d, J = 8.4 Hz, 1 H), 6.60 (d, J = 8.4 Hz, 1 H), 4.17 (q, J = 7.1 Hz, 2 H), 3.84 (s, 2 H), 3.74 (s, 3 H), 3.48-3.60 (m., 8 H), 1.28 (t, J = 7.2 Hz, 3 H),) Calc. 483.97; APCI+ (M + 1): 484, 93% |
| P-432 | 1H NMR (DMSO-d6, 400 MHz): d = 7.96 (s, 1 H), 7.69 (br, s, 1 H), 7.27-7.48 (m, 5 H), 7.06-7.16 (br, s, 1 H), 6.94 (d, J = 8.8 Hz, 1 H), 6.44-6.64 (m, 2 H), 3.44-4.66 (m, 18 H). Calc. 454; APCI+ (M): 454, 93% |
| P-435 | 1H NMR (DMSO-d6, 400 MHz): d = 8.49 (s, 1 H), 8.10 (s, 1 H), 7.80 (s, 1 H), 7.24-7.47 (m, 9 H), 7.00 (d, J = 8.8 Hz, 1 H), 5.80 (s, 2 H), 5.33 (s, 2 H), 3.74 (s, 3 H). Calc. 450.9; APCI+ (M + 1): 451, 93.8% |

-continued

Table of 1H NMR Spectra

| | | |
|---|---|---|
| P-436 | 1H NMR (CDCl3, 400 MHz): d = 7.76 (s, 1 H), 7.65 (s, 1 H), 7.23-7.42 (m, 9 H), 6.75 (d, J = 8.4 Hz, 1 H), 6.17 (s, 1 H), 5.34 (s, 2 H), 4.61 (br, s, 1 H), 3.77 (s, 3 H), 3.31 (q, J = 7.2 Hz, 2 H), 1.15 (t, J = 7.2 Hz, 3 H) | Calc. 478.96; APCI+ (M + 1): 479, 100% |
| P-451 | 1H NMR (CDCl3, 400 MHz): d = 8.35 (s, 1 H), 8.24-8.28 (m, 1 H), 7.78 (d, J = 7.6 Hz, 1 H), 7.65 (t, J = 8.0 Hz, 1 H), 7.16-7.21 (m, 2 H), 7.06 (t, J = 8.4 Hz, 1 H), 6.94 (t, J = 8.8 Hz, 2 H), 4.91 (s, 1 H), 3.94 (s, 2 H) | |
| P-453 | 1H NMR (400 MHz, CD3OD): 3.76 (s, 3 H), 4.02 (s, 2 H), 6.87 (d, J = 8.6 Hz, 1 H), 7.17-7.35 (m, 5 H), 7.34-7.45 (m, 3 H), 7.45-7.53 (m, 1 H) ppm. | |
| P-471 | 1H NMR (CDCl3, 400 MHz): d = 7.52 (s, 4 H), 7.30-7.39 (m, 7 H), 7.26 (s, 10 H), 7.14 (s, 4 H), 4.47 (s, 3 H), 3.79 (s, 11 H), 1.25 (s, 7 H), 0.07 ppm (s, 2 H) | Calc. 399.9; APCI+ (M − NH2): 383, 100% |
| P-496 | 1H NMR (CDCl3, 400 MHz): d = 7.57-7.63 (m, 2 H), 7.34-7.40 (m, 2 H), 7.15-7.19 (m, 2 H), 7.02 (t, J = 8.4 Hz, 1 H), 6.55-7.02 (m, 2 H), 6.72 (dd, J = 8.4, 1.2 Hz, 1 H), 4.97 (br. s., 1 H), 3.91 (s, 3 H) | Calc. 375.22; APCI− (M): 375 100% |
| P-497 | 1H NMR (CDCl3, 400 MHz): d = 7.55 (br, s 1 H), 7.46-7.48 (m, 1 H), 7.25-7.33 (m, 2 H), 7.15-7.19 (m, 2 H), 7.07 (t, J = 6.8 Hz, 1 H), 6.95-6.99 (m, 2 H), 6.69 (dd, J = 6.8, 0.8 Hz, 1 H), 3.92 (s., 2 H), 3.44 (s, 3 H) | |
| P-498 | 1H NMR (CDCl3, 400 MHz): d = 3.80 (3H, s), 3.90 (2H, s), 4.70 (1H, s), 6.76 (2H, m), 6.93 (1H, d, J = 8 Hz), 7.06 (2H, m), 7.12-7.19 (2H, m), 7.52 (1H, dd, J = 8 and 8 Hz), 7.81 (1H, m), 8.14 (1H, m), 8.38 (1H, m). | |
| P-499 | 1H NMR (400 MHz, CDCl3) d ppm 8.29 (s, 2 H) 8.03 (d, J = 2.0 Hz, 1 H) 7.62-7.79 (m, 2 H) 7.48 (dd, J = 8.5, 2.3 Hz, 1 H) 7.02 (d, J = 8.3 Hz, 1 H) 6.70 (d, J = 8.5 Hz, 1 H) 6.51 (d, J = 8.2 Hz, 1 H) 3.91 (s, 3 H) 3.87 (s, 2 H) | |
| P-500 | 1H NMR (400 MHz, CDCl3) d ppm 8.21-8.37 (m, 3 H) 7.64-7.80 (m, 2 H) 7.52 (dd, J = 8.2, 2.3 Hz, 1 H) 7.23 (d, J = 8.2 Hz, 1 H) 7.03 (d, J = 8.3 Hz, 1 H) 6.52 (d, J = 8.3 Hz, 1 H) 4.87-4.94 (m, 1 H) 4.83 (s, 1 H) 3.92 (s, 2 H) | |
| P-502 | 1H NMR (DMSO-d6, 400 MHz): d = 8.14 (s, 2 H), 7.74 (d, J = 8.0 Hz, 2 H), 7.36 (s, 2 H), 7.21 (s, 7 H), 6.99 (s, 2 H), 4.31 (d, J = 5.8 Hz, 4 H), 3.94 (s, 7 H), 3.75 (s, 5 H), 3.38 (d, J = 7.0 Hz, 3 H), 2.80 (s, 11 H), 1.09 ppm (t, J = 7.0 Hz, 2 H) | |
| P-505 | 1H NMR (400 MHz, DMSO-d6) d ppm 10.31 (br. s., 1 H) 10.12 (br. s., 1 H) 7.63 (br. s., 3 H) 7.39-7.49 (m, 3 H) 7.24-7.35 (m, 4 H) 7.21 (br. s., 2 H) 6.83 (d, J = 8.5 Hz, 1 H) 4.43 (br. s., 2 H) 2.05 (s, 3 H) | |
| P-507 | 1H NMR (400 MHz, DMSO-d6) d ppm 7.91-8.00 (m, 2 H) 7.87 (s, 1 H) 7.76-7.84 (m, 2 H) 7.59 (d, J = 4.8 Hz, 2 H) 7.35 (t, J = 8.8 Hz, 1 H) 6.97 (dd, J = 8.7, 5.8 Hz, 2 H) 3.86 (s, 2 H) 3.73 (s, 3 H) 2.60 (s, 3 H) | |
| P-517 | 1H NMR (400 MHz, DMSO-d6) d ppm 3.77 (s, 3 H) 5.39 (s, 2 H) 7.07 (d, J = 8.59 Hz, 1 H) 7.28-7.64 (m, 5 H) 7.77 (br. s., 1 H) 8.18 (s, 1 H) 8.52 (br. s., 1 H) 8.66 (br. s., 1 H) 9.11 (s, 1 H) | |
| P-574 | 1H NMR (CDCl3, 400 MHz): d = 8.22 (d, J = 2.8 Hz, 1 H), 7.65 (dd, J = 8.8, 2.4 Hz, 1 H), 7.28-7.45 (m, 5 H), 6.76 (d, J = 6.8 Hz, 1 H), 6.70 (d, J = 7.2 Hz, 1 H), 5.37 (s, 2 H), 3.79 (s, 3 H). | |
| P-575 | 1H NMR (CDCl3, 400 MHz): d = 8.22 (d, J = 9.2 Hz, 2 H), 7.26-7.42 (m, 5 H), 7.05 (d, J = 9.3 Hz, 2 H), 6.81 (d, J = 8.4 Hz, 1 H), 5.18 (s, 2 H), 3.81 (s, 3 H). | Calc. 387.8; APCI− (M − 1): 386, 100% |
| P-576 | 1H NMR (CDCl3, 400 MHz): d = 9.70 (br. S, 2 H), 7.56 (t, J = 8.8 Hz, 1 H), 7.24-7.50 (m, 6 H), 7.12 (d, J = 8.8 Hz, 2 H), 7.01 (d, J = 8.8 Hz, 1 H), 5.10 (s, 2 H), 3.77 (s, 3 H). | Calc. 357.8; APCI+ (M + 1): 358, 97.4% |
| P-583 | 1H NMR (DMSO-d6, 400 MHz): d = 8.17 (d, J = 8.4 Hz, 2 H), 7.69 (d, J = 8.4 Hz, 2 H), 7.35-7.48 (m, 6 H), 7.08 (d, J = 8.4 Hz, 1 H), 6.15 (s, 1 H), 3.75 (s, 3 H). | Calc. 370.8; APCI+ (M − OH): 353, 97.7% |
| P-584 | 1H NMR (DMSO-d6, 400 MHz): d = 8.42 (s, 1 H), 7.26-7.47 (m, 8 H), 7.20 (d, J = 8.4 Hz, 2 H), 7.05 (d, J = 8.4 Hz, 1 H), 5.76 (s, 2 H), 5.67 (s, 1 H), 3.74 (s, 3 H). | |
| P-585 | 1H NMR (CDCl3, 400 MHz): d = 8.14 (d, J = 2.8 Hz, 1 H), 7.24-7.41 (m, 7 H), 6.80 (dd, J = 7.2, 2.4 Hz, 1 H), 5.11 (s, 2 H), 3.80 (s, 3 H) | Calc. 378.2; APCI+ (M): 378, 100% |
| P-586 | 1H NMR (CDCl3, 400 MHz): d = 7.95 (dd, J = 3.2, 0.8 Hz, 1 H), 7.26-7.43 (m, 5 H), 7.20 (dd, J = 8.9, 3.0 Hz, 1 H), 6.75 (d, J = 8.4 Hz, 1 H), 6.26 (dd, J = 8.9, 0.5 Hz, 1 H), 5.02 (s, 2 H), 3.98 (t, J = 7.3 Hz, 4 H), 3.79 (s, 3 H), 2.36 (quin, J = 7.3 Hz, 2 H). | Calc. 398.89; APCI+ (M + 1): 399, 99% |
| P-589 | 1H NMR (DMSO-d6, 400 MHz): d = 8.32 (s, 1 H), 7.43-7.55 (m, 3 H), 7.40 (s, 1 H), 7.27-7.33 (s, 3 H), 7.01 (d, J = 8.4 Hz, 1 H), 6.90 (d, J = 9.0 Hz, 2 H), 5.70 (s, 2 H), 5.02 (s, 2 H), 3.76 (s, 3 H) | Calc. 400.8; APCI+ (M + 1): 401, 100% |
| P-594 | 1H NMR (CDCl3, 400 MHz): d = 7.27-7.45 (m, 6 H), 7.09 (br. s., 1 H), 6.94 (d, J = 9.2 Hz, 2 H), 6.78 (d, J = 8.8 Hz, 1 H),), 5.06 (s, 2 H), 3.79 (s, 3 H), 2.15 (s, 3 H). | Calc. 399.85; APCI+ (M + 1): 400, 95% |
| P-603 | 1H NMR (CDCl3, 400 MHz): d = 8.20 (d, J = 5.6 Hz, 1 H), 7.52 (br. s., 1 H), 7.32-7.41 (m, 5 H), 7.01 (d, J = 8.4 Hz, 1 H), 6.92 (d, J = 2.1 Hz, 1 H), 6.82 (dd, J = 5.8, 2.2 Hz, 1 H), 5.06 (s, 2 H), 3.84 (s, 3 H). | Calc. 360.24; APCI+ (M): 360, 97% |
| P-604 | 1H NMR (CDCl3, 400 MHz): d = 8.21 (d, J = 5.8 Hz, 1 H), 7.26-7.42 (m, 5 H), 6.94 (d, J = 2.1 Hz, 1 H), 6.79-6.87 (m, 2 H), 5.12 (s, 2 H), 3.81 (s, 3 H). | Calc. 378.23; APCI+ (M): 378, 99% |
| P-607 | 1H NMR (CDCl3, 400 MHz): d = 8.01 (d, J = 6.4 Hz, 1 H), 7.52 (br. s., 1 H), 7.29-7.41 (m, 5 H), 7.00 (d, J = 8.4 Hz, 1 H), 6.23 (dd, J = 6.0, 2.0 Hz, 1 H), 5.89 (d, J = 2.0 Hz, 1 H), 5.03 (s, 2 H), 3.83 (s, 3 H), 3.41-3.45 (m, 4 H), 1.97-2.05 (m, 4 H). | |
| P-608 | 1H NMR (CDCl3, 400 MHz): d = 8.01 (d, J = 6.4 Hz, 1 H), .7.28-7.45 (m, 4 H), 6.79 (d, J = 8.8 Hz, 1 H), 6.23 (dd, J = 6.0, 2.4 Hz, 1 H), 5.90 (d, J = 2.0 Hz, 1 H), 5.10 (s, 2 H), 3.79 (s, 3 H), 3.41-3.45 (m, 4 H), 1.97-2.05 (m, 4 H). | |

Table of 1H NMR Spectra

P-620   1H NMR (CDCl3, 400 MHz): d = 2.16 (3H, s), 3.90 (2H, s), 4.95 (1H, s), 6.71 (1H, d, J = 9.2 Hz),
7.02 (1H, dd, J = 8.4 and 8.4 Hz), 7.07 (1H, br), 7.17 (2H, d, J = 8.4 Hz), 7.34-7.37 (2H, m),
7.41 (1H, d, J = 8.4 Hz), 7.55-7.59 (2H, m).

We claim:

1. A compound of formula

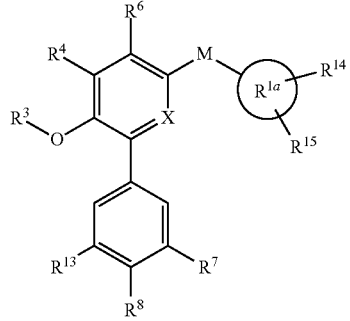

or salt thereof wherein $R^{1a}$ is phenyl;

$R^{14}$ is chosen from —CH$_2$NHC(=O)NH$_2$, —NHC(=O)NH$_2$, —NHC(=O)NHEt, —CH$_3$, —CH$_2$CF$_3$, —CH$_2$NHC(=O)CH$_3$, —NHCH$_3$, —NHEt, —NH(tBoc), —CHO, —NHC(=O)NHCH$_2$CH$_2$Cl, —NHSO$_2$NH$_2$, —N(CH$_3$)$_2$, —NH$_2$, —COOH, —C(=O)NH$_2$, —CH$_2$C(=O)NH$_2$, —CH$_2$COOH, —CH$_2$COOEt, —CN, —OCH$_3$, —OC(=O)NH$_2$, —NH(CH$_3$)C(=O)NH$_2$, halogen, —CH$_2$NHC(=O)OEt, —NHSO$_2$CH$_3$, —N(SO$_2$CH$_3$)$_2$, —NHC(=O)OCH$_3$, —OH, —CH$_2$NHC(=O)N(CH$_3$)$_2$, —CH$_2$NH$_2$, —CH$_2$OH, —CH$_2$CH$_2$OH, —SO$_2$NH$_2$, —NHC(=O)NHCH$_2$COOH, —CH$_2$NHCHO, —NHC(=O)NHCH$_2$COOEt, —COOCH$_3$, —COOEt, —NHC(=O)NH(CH$_2$)$_3$COOEt, —NHC(=O)NH(CH$_2$)$_2$COOEt, —NH(Et)C(=O)OEt, —NHC(=O)NH(CH$_2$)$_2$COOH, —CH$_2$NHSO$_2$CH$_3$, —OEt, —NHC(=O)CH$_2$N(CH$_3$)$_2$, —NHC(=O)NH(CH$_2$)$_3$COOH, —NHC(=O)CH$_2$NH$_2$, —NHC(=O)CH$_2$CH$_2$NH$_2$, —NHC(=O)CH$_2$NH(tBoc), —OCH$_2$CH$_2$N(CH$_3$)$_2$, —OCH$_2$CH$_2$OCH$_3$, 3'-nitro-6-methoxybiphenyl-3-yl-methyl, tetrahydroimidazol-2-on-1-yl, 3-methyltetrahydroimidazol-2-one-1-yl, pyrazol-1-yl,

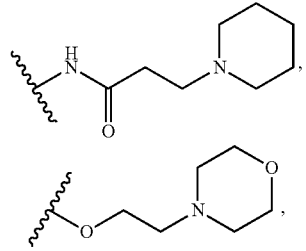

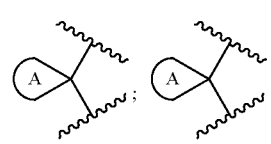

and residues of amino acids, amino acid amides, protected residues of amino acids, protected residues of amino acid amides, N-methylated amino acids and N-methylated amino acid amides, wherein said amino acid is selected from the group consisting of alanine, arginine, asparagine, aspartic acid, cysteine, glutamic acid, glutamine, glycine, histidine, isoleucine, leucine, lysine, methionine, ornithine, phenylalanine, proline, selenocysteine, serine, threonine, tryptophan, tyrosine, and valine;

$R^{15}$ is chosen from H, NO$_2$, OH, NH$_2$, and —NHSO$_2$NH$_2$; or $R^{15}$ together with $R^{14}$ forms methylene dioxy;

$R^3$ is chosen from —C(=O)NH$_2$, —(C$_1$-C$_6$)alkyl, halo(C$_1$-C$_6$)alkyl, —(C$_1$-C$_6$)alkyl-R$^{30}$, —(C$_2$-C$_6$)alkyl-R$^{31}$, and saturated 4- or 5-membered heterocycle optionally substituted with methyl;

$R^{30}$ is chosen from —C(=O)NH$_2$ and 4- or 5-membered heterocycle optionally substituted with methyl;

$R^{31}$ is chosen from (C$_1$-C$_4$)alkoxy, amino, hydroxy, (C$_1$-C$_6$)alkylamino and di(C$_1$-C$_6$)alkylamino;

$R^4$ is chosen from H and F;

$R^6$ is chosen from H, (C$_1$-C$_6$)alkyl and halogen;

X is N, N→O, or C—R$^5$;

$R^5$ is chosen from H, halogen, OH, (C$_1$-C$_6$)alkyl, (C$_1$-C$_6$)alkoxy, CF$_3$, CN, NH$_2$, CH$_2$OH, CH$_2$NH$_2$ and C≡CH;

M is chosen from —C(R$^{20}$)(R$^{21}$)—, —O—, —NR$^{22}$—, —S(O)$_n$—, —C(=O)—, —C(R$^{20}$)(R$^{21}$)C(R$^{20}$)(R$^{21}$)—, —C(R$^{20}$)=C(R$^{21}$)—, —C(R$^{20}$)(R$^{21}$)—O—, —C(R$^{20}$)(R$^{21}$)—NR$^{22}$—, —C(R$^{20}$)(R$^{21}$)—S(O)$_n$—, —C(R$^{20}$)(R$^{21}$)—C(=O)—, —O—C(R$^{20}$)(R$^{21}$)—, —NR$^{22}$—C(R$^{20}$)(R$^{21}$)—, —S(O)$_n$—C(R$^{20}$)(R$^{21}$)—, —C(=O)—C(R$^{20}$)(R$^{21}$)— and is a five or six-membered ring optionally substituted with methyl;

n is zero, one or two; and $R^{20}$, $R^{21}$ and $R^{22}$ are selected independently in each occurrence from H and (C$_1$-C$_4$)alkyl;

$R^7$ is chosen from hydrogen, halogen, nitro, cyano, halo($C_1$-$C_6$)alkyl, hydroxy, ($C_1$-$C_6$)alkoxy, ($C_1$-$C_6$)oxaalkyl, carboxy, ($C_1$-$C_6$)alkoxycarbonyl, aminocarbonyl (—$CONH_2$), ($C_1$-$C_6$)alkylaminocarbonyl, acyl, hydroxy($C_1$-$C_6$)alkyl, halo($C_1$-$C_6$)alkoxy, amino($C_1$-$C_6$)alkyl, ($C_1$-$C_6$)alkylamino, di[($C_1$-$C_6$)alkyl]amino, mercapto, ($C_1$-$C_6$)alkylthio, ($C_1$-$C_6$)alkylsulfinyl, ($C_1$-$C_6$)alkylsulfonyl, ($C_1$-$C_6$)alkylsulfonamido, acylamino, amidino, phenyl, benzyl, monocyclic heterocyclyl, phenoxy, benzyloxy, and monocyclic heteroaryloxy; and $R^8$ and $R^{13}$ are chosen independently from H and F, wherein all of $R^7$, $R^8$, and $R^{13}$ may not be hydrogen.

2. A compound or salt according to claim 1 wherein X is N or N→O.

3. A compound or salt according to claim 1 wherein X is $CR^5$.

4. A compound or salt according to claim 1 wherein M is chosen from —$CH_2$—, —CH(OH)—, —C[($CH_3$)(OH)]—, —C[($CH_3$)($NH_2$)]—, —C(═O)—, —O—, —NH—, —N($CH_3$)—, —S(O)$_n$—, —$CH_2$NH—, —$CH_2CH_2$—, —CH═CH—, —$CH_2$S(O)$_n$—, —$CH_2$O— and

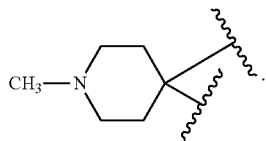 [SMILES: *C1(*)CCN(C)CC1 ; "."]

5. A compound or salt according to claim 1, wherein $R^8$ and $R^{13}$ are H and $R^7$ is chosen from fluoro, chloro, bromo, nitro, cyano, acetyl, trifluoromethyl, methoxy, trifluoromethoxy, oxadiazolyl, tetrazolyl, methylthio, methanesulfinyl, methanesulfonyl, methansulfonamido, methoxymethyl, hydroxyethyl, and morpholinyl.

6. A compound or salt according to claim 1 wherein $R^7$ is chosen from halogen, nitro, acetyl, hydroxyethyl, amino, methylthio, trifluoromethyl, methoxymethyl, methoxycarbonyl, trifluoromethoxy, cyano and 1,3,4-thiadiazol-2-yl.

7. A compound or salt according to claim 1 wherein $R^5$ is fluoro, H, CN or OH.

8. A compound or salt according to claim 1 wherein $R^3$ is methyl or fluoromethyl.

9. A compound or salt of formula:

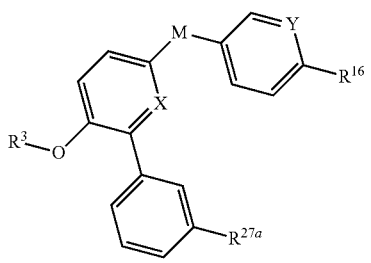

wherein $R^3$ is methyl or fluorinated methyl;
Y is CH;
X is N, N→O, or C—$R^5$;
$R^5$ is chosen from H, halogen, OH, ($C_1$-$C_6$)alkyl, ($C_1$-$C_6$)alkoxy, $CF_3$, CN, $NH_2$, $CH_2OH$, $CH_2NH_2$ and C≡CH;
M is chosen from —C($R^{20}$)($R^{21}$)—, —O—, —$NR^{22}$—, —S(O)$_n$—, —C(═O)—, —C($R^{20}$)($R^{21}$)C($R^{20}$)($R^{21}$), —C($R^{20}$)═C($R^{21}$)—, —C($R^{20}$)($R^{21}$)—O—, —C($R^{20}$)($R^{21}$)—$NR^{22}$—, —C($R^{20}$)($R^{21}$)—S(O)$_n$—, —C($R^{20}$)($R^{21}$)—C(═O)—, —O—C($R^{20}$)($R^{21}$)—, —$NR^{22}$—C($R^{20}$)($R^{21}$)—, —S(O)$_n$—C($R^{20}$)($R^{21}$)—, —C(═O)—C($R^{20}$)($R^{21}$)— and

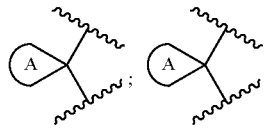

is a five or six-membered ring optionally substituted with methyl;

n is zero, one or two and $R^{20}$, $R^{21}$ and $R^{22}$ are selected independently in each occurrence from H and ($C_1$-$C_4$)alkyl;

$R^{27a}$ is chosen from halogen, cyano, acetyl, methylthio, nitro and trifluoromethyl; and $R^{16}$ is chosen from —$NR^{17}$C(═O)$NR^{18}R^{19}$, halogen, acetamide, carbamate, and

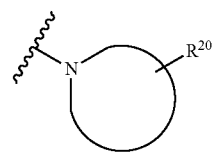

wherein

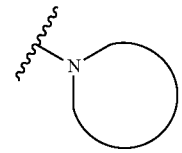 [SMILES: *N(C)C]

is a 4-7 membered ring heterocycle attached through its nitrogen;

$R^{17}$, and $R^{18}$ are independently chosen from H, ($C_1$-$C_6$)alkyl and halo($C_1$-$C_6$)alkyl;

$R^{19}$ is chosen from H, ($C_1$-$C_6$)alkyl, halo($C_1$-$C_6$)alkyl, —[($C_1$-$C_6$)alkyl]COOH, and —[($C_1$-$C_6$)alkyl]COO($C_1$-$C_6$)alkyl; and $R^{20}$ is chosen from a carboxylic acid, a carboxamide, a carboxylic ester, a primary, secondary or tertiary alcohol and a primary, secondary or tertiary amine.

10. A compound or salt according to claim 9 wherein

X is CH, CF or N—O;

M is —$CH_2$— or —S—;

$R^{27a}$ is chosen from chloro, cyano, acetyl and methylthio; and $R^{16}$ is chosen from —$NR^{17}$C(═O)$NR^{18}R^{19}$, halogen, —$NHCOCH_3$, —$NHCOOC(CH_3)_3$,

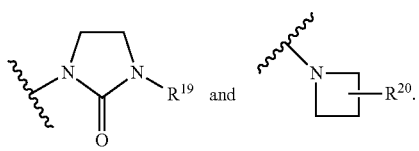

11. A compound or salt according to claim 10 wherein Y is CH; M is —$CH_2$—; $R^{27a}$ is chloro; and $R^{16}$ is —$NR^{17}C(=O)NR^{18}R^{19}$.

12. A compound or salt according to claim 11 wherein $R^{16}$ is —$NR^{17}C(=O)NR^{18}R^{19}$ and $R^{17}$, $R^{18}$ and $R^{19}$ are all hydrogen.

13. A salt of a compound of claim 1 wherein the salt is a pharmaceutically acceptable salt.

14. A pharmaceutical composition comprising a pharmaceutically acceptable carrier and a compound or pharmaceutically acceptable salt according to claim 1.

15. A pharmaceutical composition comprising
 (a) a pharmaceutically acceptable carrier;
 (b) a compound or pharmaceutically acceptable salt according to claim 1; and
 (c) a second agent chosen from cholinesterase inhibitors, NMDA antagonists, calpain inhibitors and antioxidants.

16. A pharmaceutical composition according to claim 15 wherein said second agent is chosen from tacrine, huperzine, donepezil, lanicemine, remacemide, neramexane, memantine, vitamin E and coenzyme Q10.

17. A compound or salt according to claim 1 wherein $R^3$ is chosen from —$CH_3$, —$CH_2CH_3$, —$CF_3$, —$CHF_2$ and —$CH_2F$.

18. A compound or salt according to claim 1 wherein $R^5$ is chosen from H, —F, —OH, —$CH_3$, —$OCH_3$, —$CF_3$, —CN, —$NH_2$ and —CCH.

19. A compound or salt according to claim 1 wherein $R^7$ is chosen from halogen, nitro, acetyl, hydroxyethyl, —$SCH_3$, methoxycarbonyl, —$SOCH_3$, —$SO_2CH_3$, —$OCH_3$, —$OCF_3$, —CN, —$CF_3$, and —$CH_2OCH_3$.

20. A pharmaceutical composition comprising a pharmaceutically acceptable carrier and a compound or pharmaceutically acceptable salt according to claim 9.

21. A pharmaceutical composition comprising
 (a) a pharmaceutically acceptable carrier;
 (b) a compound or pharmaceutically acceptable salt according to claim 9; and
 (c) a second agent chosen from cholinesterase inhibitors, NMDA antagonists, calpain inhibitors and antioxidants.

22. A pharmaceutical composition according to claim 21 wherein said second agent is chosen from tacrine, huperzine, donepezil, lanicemine, remacemide, neramexane, memantine, vitamin E and coenzyme Q10.

* * * * *